US007465730B2

(12) United States Patent
Anker et al.

(10) Patent No.: US 7,465,730 B2
(45) Date of Patent: Dec. 16, 2008

(54) TREATMENT OF NEUROPATHIC PAIN WITH 6H-PYRROLO[3,4-D]PYRIDAZINE COMPOUNDS

(75) Inventors: Naomi Burke Anker, Boston, MA (US); Jeannie M. Arruda, San Diego, CA (US); Brian Thomas Campbell, San Diego, CA (US); Benito Munoz, San Diego, CA (US); Petpiboon Prasit, San Diego, CA (US); Brian A. Stearns, San Diego, CA (US); Tao Hu, San Diego, CA (US)

(73) Assignee: Merck & Co. Inc., Rahway, NJ (US)

( * ) Notice: Subject to any disclaimer, the term of this patent is extended or adjusted under 35 U.S.C. 154(b) by 229 days.

(21) Appl. No.: 10/520,962

(22) PCT Filed: Jul. 8, 2003

(86) PCT No.: PCT/US03/21493

§ 371 (c)(1), (2), (4) Date: Nov. 28, 2005

(87) PCT Pub. No.: WO2004/006836

PCT Pub. Date: Jan. 22, 2004

(65) Prior Publication Data

US 2006/0154929 A1    Jul. 13, 2006

Related U.S. Application Data

(60) Provisional application No. 60/394,734, filed on Jul. 11, 2002.

(51) Int. Cl.
*A01N 43/58* (2006.01)
*A61K 31/5025* (2006.01)
*C07D 487/06* (2006.01)

(52) U.S. Cl. .................................. 514/252; 544/236
(58) Field of Classification Search ....................... None
See application file for complete search history.

(56) References Cited

U.S. PATENT DOCUMENTS 5,622,948 A    4/1997  Dunn et al.
6,063,783 A    5/2000  Pineiro et al.

OTHER PUBLICATIONS

The Merck Manual of Diagnosis and Therapy, Seventeenth Edition, published 1999 by Merck Research Laboratories, edited by Beers and Berkow, pp. 1371-1372.*
Merriam-Webster's Collegiate Dictionary, Tenth Edition, published by Merriam-Webster Incorporated, p. 924.*
Uchida et al., "Synthetic Approaches to Fused Heteroaromatic Compounds by the Condensation Reactions of Functional Pyrroles (1)" Journal of Heterocyclic Chemistry (1978) vol. 15, pp. 241-248.*
Rips et al., "Friedel-Crafts Acylations of 1-Phenyl-2,5-dimethylpyrrole and 1,2-Diphenyl-5-methylpyrrole", Journal of Organic Chemistry, 1959, 24, pp. 551-554.

* cited by examiner

*Primary Examiner*—Shaojia Anna Jiang
*Assistant Examiner*—Eric S Olson
(74) *Attorney, Agent, or Firm*—Sylvia A. Ayler; William Krovatin

(57) ABSTRACT

6H-pyrrolo[3,4-d]pyridazine compounds and methods of their use of as ligands of voltage gated calcium channels (VGCC), useful in the treatment of neuropathic pain, and psychiatric and mood disorders such as, for example, schizophrenia, anxiety, depression, panic, and bipolar disorder, as well as in the treatment of pain, Parkinson's disease, cognitive dysfunction, epilepsy, circadian rhythm disorders, drug addiction, drug abuse, drug withdrawal and other.

3 Claims, No Drawings ural filing under 35 USC 371 of PCT/US03/
TREATMENT OF NEUROPATHIC PAIN WITH 6H-PYRROLO[3,4-D]PYRIDAZINE COMPOUNDS

RELATED APPLICATION DATA

This is a National filing under 35 USC 371 of PCT/US03/21493, filed Jul 8, 2003, which claims priority from U.S. Ser. No. 60/394,734, filed Jul. 11, 2002.

BACKGROUND OF THE INVENTION

1. Field of the Invention

The present invention is directed 6H-pyrrolo[3,4-d]pyridazine compounds and method of their use. In particular, this invention is directed to a method of use of 6H-pyrrolo[3,4-d]pyridazine compounds in the treatment of neuropathic pain.

2. Related Background

A major mechanism in many physiological processes, including neurotransmission in the mammalian nervous system, is the opening and closing of voltage gated calcium channels ("VGCC"), also known as voltage sensitive calcium channels ("VSCC"). Such VGCC are formed by the assembly of subunit classes such as alpha 1 and alpha 2. One subunit in the alpha 2 class is the $\alpha_2\delta$ subunit. The activity of the calcium channel can be modulated by the activities of the component subunits. For example, gabapentin is known to bind with high affinity to the $\alpha_2\delta$ subunit. Four isoforms of this $\alpha_2\delta$ protein are known and gabapentin binds with high affinity to 2 of these ($\alpha_2\delta$-1 and $\alpha_2\delta$-2). The relative importance of these two activities in accounting for the efficacy and adverse effects of gabapentin is not known. Compounds that display high-affinity binding to the $\alpha_2\delta$ subunit of voltage gated calcium channels have been shown to be efficacious for the treatment of, for example, neuropathic pain. See, *J. Biol. Chem.*, 271 (10):5768-5776(1996) and *J. Med. Chem.*, 41:1838-1845 (1998). Nonetheless, if one isoform is more controlling of the channel modulation, while the other is less, then compounds that are selective to the controlling isoform are likely to be more efficacious and display fewer side-effects.

Thus, it is desirable to identify other compounds that display high-affinity binding to the $\alpha_2\delta$ subunit of voltage gated calcium channels to provide new medicines in the treatment of neuropathic pain. Further, such compounds can be useful in the treatment of psychiatric and mood disorders such as, for example, schizophrenia, anxiety, depression, bipolar disorders, and panic, as well as in the treatment of pain, Parkinson's disease, cognitive dysfunction, epilepsy, circadian rhythm and sleep disorders—such as shift-work induced sleep disorder and jet-lag, drug addiction, drug abuse, drug withdrawal and other diseases.

International Patent Publication No. WO 01/88101 describes a cell line for the expression of an $\alpha_2\delta2$ calcium channel subunit.

6-Methyl-6H-pyrrolo[3,4-d]pyridazine is described in MM. J. Duflos et al., *Tetrahedron Lett.*, 3453-3454(1973). 1,4,5,7-tetramethyl-6-phenyl-6H-pyrrolo [3,4-d]pyridazine, 1,4,5-trimethyl-6,7-diphenyl-6H-pyrrolo[3,4-d]pyridazine, 5,7-dimethyl-1,4,6-triphenyl-6H-pyrrolo[3,4-d]pyridazine, 5-methyl-1,4,6,7-tetraphenyl-6H-pyrrolo[3,4-d]pyridazine, 1,4-bis-(4-methoxy-phenyl)-5,7-dimethyl-6-phenyl-6H-pyrrolo[3,4-d]pyridazine, 1,4-bis-(4-methoxy-phenyl)-5-methyl-6,7-diphenyl-6H-pyrrolo[3,4-d]pyridazine, and 1,4-diethyl-5,7-dimethyl-6-phenyl-6H-pyrrolo[3,4-d]pyridazine are described in R. Rips et al., *J. Org. Chem.*, 24:551-554 (1959). 1,4,5,7-Tetramethyl-6H-pyrrolo[3,4-d]pyridazine, N-(1,4,5,7-tetramethyl-pyrrolo[3,4-d]pyridazin-6-yl)-benzamide, 1,4,5,7-tetramethyl-pyrrolo[3,4-d]pyridazin-6-ylamine picrate, and 1,4,5,7-tetramethyl-pyrrolo[3,4-d]pyridazin-6-ylamine are described in W. L. Mosby, *J. Chem. Soc.*, 3997-4003(1957). 5,7-Dimethyl-6-phenyl-6H-pyrrolo [3,4-d]pyridazine is described in R. Rips et al., *J. Org. Chem.*, 24:372-374(1959).

5,7-Dimethyl-2-phenacyl-6H-pyrrolo[3,4-d]pyridazinium bromide (also known as 5,7-dimethyl-2-(2-oxo-2-phenyl-ethyl)-6H-pyrrolo[3,4-d]pyridazin-2-ium bromide) and 2-(2-methoxycarbonylvinyl)-5,7-dimethyl-6H-pyrrolo[3,4-d]pyridazinium tetrafloroborate are described in F. Fuentes-Rodriguez et al., *J. Chem. Res. Miniprint*, 11:2901-2914(1987). 5,7-Diphenyl-6H-pyrrolo[3,4-d]pyridazine is described in T. Hernandez et al., *J. Chem. Soc., Perkins Trans.*, 1:899-902(1985), and F. F. Rodriguez et al., *J. Chem. Res. Miniprint*, 11:3001-3001(1987). 5,6,7-Trimethyl-6H-pyrrolo[3,4-d]pyridazine is described in T. Hernandez et al., *J. Chem. Soc., Perkin Trans.*, 1:899-902(1985), F. Fuentes-Rodriguez et al., *J. Chem. Res. Miniprint*, 11:2901-2914(1987), and R. von Kreher et al., *Agnew Chem.*, 82:958 (1970).

1,4-Diphenyl-7,8,9,10-tetrahydro-pyridazino[4,5-a]indolizine (also known as 1,4-diphenyl-5,6,7,8-tetrahydro-2,3,8a-triaza-fluorene) and 5-methyl-1,4-diphenyl-7,8,9,10-tetrahydro-pyridazino[4,5-a]indolizine (also known as 9-methyl-1,4-diphenyl-5,6,7,8-tetrahydro-2,3,8a-triazafluorene) are described in T. Uchida et al., *J. Heterocycl. Chem.*, 15:1303-1307(1978). 6-Benzyl-1,4-diphenyl-5-p-tolyl-6, H-pyrrolo[3,4-d]pyridazine 6-benzyl-5-(2-chlorophenyl)-1,4-diphenyl-6H-pyrrolo[3,4-d]pyridazine, 1,4,5,6,7-pentaphenyl-6H-pyrrolo[3,4-d]pyridazine,6,7,10,11-tetraphenyl-pyridazino[4',5':3,4]pyrrolo[1,2-a]quinoxaline (also known as 6,7,10,11-tetraphenyl-5,8,9,11a-tetraazabenzo[a]fluorene), 11-(4-nitro-phenyl)-6,7,10-triphenyl-pyridazino[4'.5':3,4]pyrrolo[1,2-a]quinoxaline (also known as 11-(4-nitro-phenyl)6,7,10-triphenyl-5,8,9,11a-tetraazabenzo[a]fluorene), and 6-benzyl-1,4,5-triphenyl-6H-pyrrolo [3,4-d]pyridazine are described in T. Uchida et al., *J. Heterocycl. Chem.*, 15:241-248(1978).

9,12-Diphenyl-pyridazino[4',5':3,4]pyrrolo[2,1-a]isoquinoline, 5-methylsulfanyl-1,4,6,7-tetraphenyl-6H-pyrrolo [3,4-d]pyridazine, and 1,4,6,7-tetraphenyl-6H-pyrrolo[3,4-d]pyridazine-5-carboxylic acid ethyl ester are described in K. T. Potts et al., *J. Org. Chem.*, 42:1639-1644(1977). 7,10-Diphenyl-pyridazino[4',5':3,4]pyrrolo[1,2-a]quinoline, and 11,14-diphenyl-pyridazino[4',5':3,4]pyrrolo[1,2-f]phenanthridine (also known as 9,12-diphenyl-10,11,13a-triaza-indeno[1,2-l]phenanthrene) are described in K. T. Potts et al.,*J. Org. Chem.*, 44:977-979(1979).

1-Oxo-7-oxy-6b,11b-dihydro(pyridazino[4',5'-c]-pyrrolo) [2,1-c]benzoxazine-1,4 (also known as 11-hydroxy-5-oxa-8,9,11a-triaza-benzo[a]fluoren-6-one) is described in Kumashiro et al., *Nippon Kagaku Zasshi.*, 82:1072-1074 (1961). 10-Methyl-1,4-diphenyl-8,9-dihydro-7H-benzo(ef) pyridazino[4,5-a]cycl[3.3.2]azine, and 11-methyl-1,4-diphenyl-7,8,9,10-tetrahydrocyclohepta(ef)pyridazino[4,5-a]cycl [3.3.2]azine are described in M. Noguchi et al., *J. Heterocycl. Chem.*, 22:1049-1053(1985).

1,4-Dichloro-5,6,7-trimethyl-6H-pyrrolo[3,4-d]pyridazine, 1-chloro-4ethoxy-5,6,7-trimethyl-6H-pyrrolo[3,4-d]pyridazine, 1-chloro-5,6,7-trimethyl-6H-pyrrolo[3,4-d]pyridazinium chloride, 1-ethoxy-2,5,6,7-tetramethyl-6H-pyrrolo[3,4-d]pyridazinium tetrafluoroborate, 1-ethoxy-5,6,7-trimethyl-2H,6H-pyrrolo[3,4-d]pyridazinium tetrafluoroborate, 1-ethoxy-3-ethyl-5,6,7-trimethyl-6H-pyrrolo[3,4-d]pyridazinium tetrafluoroborate,and 1-ethoxy-5,6, 7-trimethyl-6H-pyrrolo[3,4-d]pyridazine are described in S. Inel et al., *Tetrahedron,* 40:3979-3986(1984).

5-Cyano-1,4-dimethylpyridazino[4,5-a]indolizine (also known as 1,4-dimethyl-2,3,8a-triaza-fluorene-9-carbonitrile), 1,4-dimethyl-6-phenyl-2,3,8a-triaza-fluorene-9-carbonitrile, 6-benzolyl-1,4-dimethyl-2,3,8a-triaza-fluorene-9-carbonitrile, 6-benzyl-1,4-diphenyl-2,3,8a-triaza-fluorene-9-carbonitrile, and 1,4,6-trimethyl-2,3,8a-triaza-fluorene-9-carbonitrile are described in K. Matsumoto et al., *J. Heterocycl. Chem.,* 25:1793-1801(1988). 5-Cyano-1,4-diphenylpyridazino[4,5-a]indolizine (also known as 1,4-diphenyl-2,3,8a-triaza-fluorene-9-carbonitrile) is described in K. Matsumoto et al., *J. Heterocycl. Chem.,* 25:1793-1801 (1988), and K. Matsumoto et al., *Heterocycles,* 20:1525-1529 (1983). 6-Methyl-1,4-diphenyl-2,3,8a-triaza-fluorene-9-carbonitrile, 6-benzoyl-1,4-diphenyl-2,3,8a-triaza-fluorene-9-carbonitrile, and 1,4,6-triphenyl-2,3,8a-triaza-fluorene-9-carbonitrile are described in K. Matsumoto et al., *J. Heterocycl. Chem.,* 25:1793-1801(1988), K. Matsumoto et al., *Heterocycles,* 34:2239-2242(1992), K. Matsumoto et al., *Heterocycles,* 20:1525-1529(1983), and K. Matsumoto et al., *Can. J. Chem.,* 71:529-533(1993). 5,7-Dimethyl-1,4-diphenyl-2,3,8a-triaza-fluorene-9-carbonitrile, and 9,12-diphenyl-pyridazino[4',5':3,4]pyrrolo[2,1-a]isoquinoline-8-carbonitrile are described in K. Matsumoto et al., *Heterocycles,* 34:2239-2242(1992), and K. Matsumoto et al., *Can. J. Chem.,* 71:529-533(1993).

Dimethyl 3,12,13,17-tetramethyl-$7^2,7^3$-diazabenzo[g] porphyrin-2,18-dipropionate is described in I. A. Chaudhry et al., *Aust. J. Chem.,* 35:1185-11201(1982).5,6-Dihydro-2,3-dimethoxypyridazino[4',5':3,4]pyrrolo[2,1-a]isochinolin-9-ol, 5,6-dihydro-2,3-dimethoxypyridazino[4',5':3,4]pyrrolo[2,1-a]isochinolin-9-ol-hydrochloride, and 3-methyl-6,9-diphenylthiazolo[3',2':1,2]pyrrolo[3,4-d]pyridine (also known as 1-methyl-4,7-diphenyl-3-thia-5,6,8a-triaza-cyclopenta[a]indene) are described in W. Losel et al., *Chem. Ber.,* 118:413-427 (1985). 1,4-Diphenylpyridazino[4',5':3,4]pyrrolo[2,1-b]benzothiazole (also known as 1,4-diphenyl-5-thia-2,3,9b-triaza-indeno[2,1-a]indene) is described in N. Abe et al., *Bull. Chem. Soc. Japan,* 55:200-203(1982).

Nevertheless, there is a need to identify 6H-pyrrolo[3,4-d] pyridazine compounds that display high-affinity binding—particularly selective binding—to the $\alpha_2\delta$ subunit of voltage gated calcium channels to provide new medicines in the treatment of neuropathic pain, as well as psychiatric and mood disorders such as, for example, schizophrenia, anxiety, depression, bipolar disorders, and panic, as well as in the treatment of pain, Parkinson's disease, cognitive dysfunction, epilepsy, circadian rhythm and sleep disorders—such as shift-work induced sleep disorder and jet-lag, drug addiction, drug abuse, drug withdrawal and other diseases.

SUMMARY OF THE INVENTION

The present invention is directed to a method of use of 6H-pyrrolo[3,4-d]pyridazine compounds in the treatment of neuropathic pain. The present invention is also directed to the use of 6H-pyrrolo[3,4-d]pyridazine compounds in the treatment of psychiatric and mood disorders such as, for example, schizophrenia, anxiety, depression, bipolar disorders, and panic, as well as in the treatment of pain, Parkinson's disease, cognitive dysfunction, epilepsy, circadian rhythm and sleep disorders—such as shift-work induced sleep disorder and jet-lag, drug addiction, drug abuse, drug withdrawal and other diseases. The present invention is also directed to novel 6H-pyrrolo[3,4-d]pyridazine compounds that selectively bind to $\alpha_2\delta$-1 subunit of Ca channels.

DETAILED DESCRIPTION OF THE INVENTION

A method of treatment of neuropathic pain, and treatment of psychiatric and mood disorders such as, for example, schizophrenia, anxiety, depression, bipolar disorders, and panic, as well as the treatment of pain, Parkinson's disease, cognitive dysfunction, epilepsy, circadian rhythm and sleep disorders—such as shift-work induced sleep disorder and jet-lag, drug addiction, drug abuse, and drug withdrawal of the present invention comprising a step of administering an effective amount of a compound represented by Formula (I):

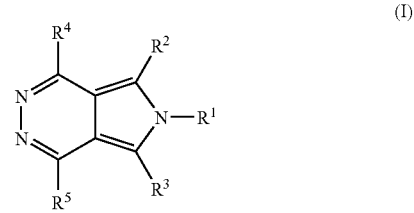

(I)

or a pharmaceutically acceptable salt thereof, wherein $R^1$ is —$C_{0-6}$alkyl-aryl, —$C_{0-6}$alkyl-heteroaryl, —$C_{0-6}$alkyl-$C_{3-6}$cycloalkyl, or —$C_{0-6}$alkyl-heteroC$_{3-7}$cycloalkyl, optionally substituted with 1-6 independent halogen, —CN; $NO_2$, —$C_{1-6}$alkyl, —$C_{0-6}$alkyl-$C_{3-6}$cycloalkyl, —$C_{0-6}$alkyl-heteroC$_{3-7}$cycloalkyl, —$OR^6$, —$NR^6R^7$, —$C(=NR^6)$ $NR^7R^8$, —$N(-NR^{88}R^6)NR^7R^8$, —$NR^6COR^7$, —$NR^6CO_2R^7$, —$NR^6SO_2R^{88}$, —$NR^6CONR^7R^8$, —$SR^{88}$, —$SOR^{88}$, —$SO_2R^{88}$, —$SO_2NR^6R^7$, —$COR^6$, —$CO_2R^6$, —$CONR^6R^7$, —$C(=NR^6)R^7$, or —$C(=NOR^6)R^7$ substituents;

$R^2$, $R^4$, $R^3$, and $R^5$ each independently is —$C_{0-6}$alkyl, —$C_{0-6}$alkyl-aryl, —$C_{0-6}$alkyl-heteroaryl, —$C_{0-6}$alkyl-$C_{3-6}$cycloalkyl, or —$C_{0-6}$alkyl-heteroC$_{3-7}$cycloalkyl, optionally substituted with 1-6 independent halogen, —CN, $NO_2$, —$C_{1-6}$ alkyl, —$OR^6$, —$NR^6R^7$, —$C(=NR^6)NR^7R^8$, —$N(-NR^{88}R^6)NR^7R^8$, —$NR^6COR^7$, —$NR^6CO_2R^7$, —$NR^6SO_2R^{88}$, —$NR^6CONR^7R^8$, —$SR^{88}$, —$SOR^{88}$, —$SO_2R^{88}$, —$SO_2NR^6R^7$, —$COR^6$, —$CO_2R^6$, —$CONR^6R^7$, —$C(=NR^6)R^7$, or —$C(=NOR^6)R^7$ substituents;

$R^6$, $R^7$, $R^8$, and $R^{88}$ each independently is —$C_{0-6}$alkyl, —$C_{3-7}$cycloalkyl, heteroaryl, or aryl; optionally substituted with 1-5 independent halogen, —CN, —$C_{1-6}$alkyl, —O($C_{0-6}$ alkyl), —O($C_{3-7}$cycloalkyl), —O(aryl), —N($C_{0-6}$alkyl)($C_{0-6}$ alkyl), —N($C_{0-6}$alkyl)($C_{3-7}$cycloalkyl), or —N($C_{0-6}$alkyl) (aryl) substituents; and provided that the compound is not selected from the following table:

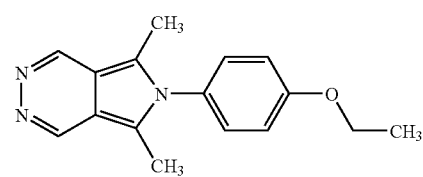

-continued

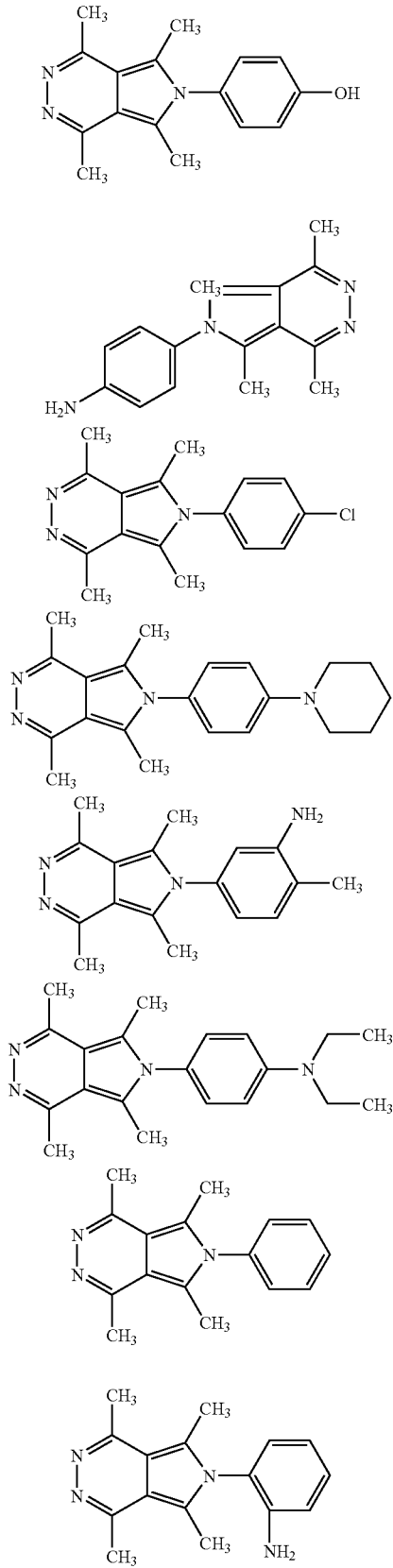

-continued

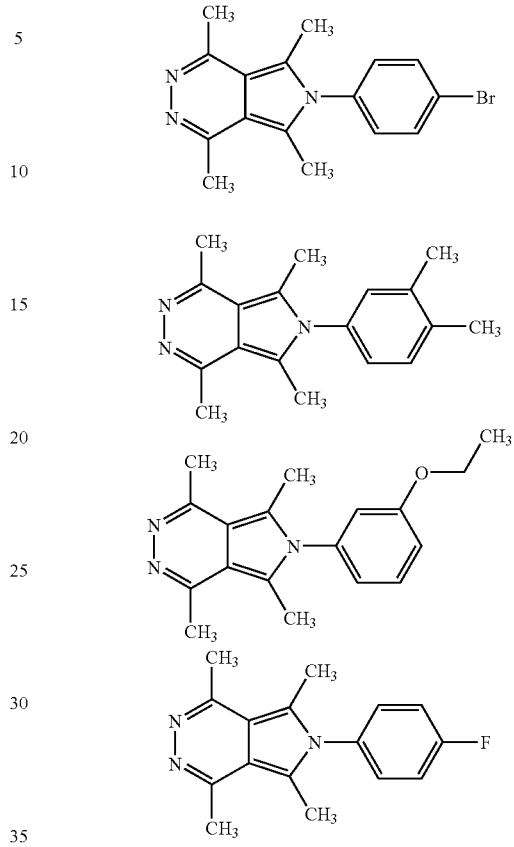

In one aspect, the method of this invention administers an effective amount of a compound represented by Formula (I), or a pharmaceutically acceptable salt thereof, wherein $R^1$ is —$C_{0-6}$alkyl-aryl optionally substituted with 1-6 independent halogen, —CN, $NO_2$, —$C_{1-6}$alkyl, —$C_{0-6}$alkyl-$C_{3-6}$cycloalkyl, —$C_{0-6}$alkyl-hetero$C_{3-7}$cycloalkyl, —$OR^6$, —$NR^6R^7$, —C(=$NR^6$)$NR^7R^8$, —N(—$NR^{88}R^6$)$NR^7R^8$, —$NR^6COR^7$, —$NR^6CO_2R^7$, —$NR^6SO_2R^{88}$, —$NR^6CONR^7R^8$, —$SR^{88}$, —$SOR^{88}$, —$SO_2R^{88}$, —$SO_2NR^6R^7$, —$COR^6$, —$CO_2R^6$, —$CONR^6R^7$, —C(=$NR^6$)$R^7$, or —C(=$NOR^6$)$R^7$ substituents;

$R^2$, $R^4$, $R^3$, and $R^5$ each independently is —$C_{0-6}$alkyl, —$C_{0-6}$alkyl-aryl, —$C_{0-6}$alkyl-heteroaryl, —$C_{0-6}$alkyl-$C_{3-6}$cycloalkyl, or —$C_{0-6}$alkyl-hetero$C_{3-7}$cycloalkyl, optionally substituted with 1-6 independent halogen, —CN, $NO_2$, —$C_{1-6}$ alkyl, —$OR^6$, —$NR^6R^7$, —C(=$NR^6$)$NR^7R^8$, —N(—$NR^{88}R^6$)$NR^7R^8$, —$NR^6COR^7$, —$NR^6CO_2R^7$, —$NR^6SO_2R^{88}$, —$NR^6CONR^7R^8$, —$SR^{88}$, —$SOR^{88}$, —$SO_2R^{88}$, —$SO_2NR^6R^7$, —$COR^6$, —$CO_2R^6$, —$CONR^6R^7$, —C(=$NR^6$)$R^7$, or —C(=$NOR^6$)$R^7$ substituents;

$R^6$, $R^7$, $R^8$, and $R^{88}$ each independently is —$C_{0-6}$alkyl, —$C_{3-7}$cycloalkyl, heteroaryl, or aryl; optionally substituted with 1-5 independent halogen, —CN, —$C_{1-6}$alkyl, —O($C_{0-6}$ alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) substituents; and provided that the compound is not selected from the following table:

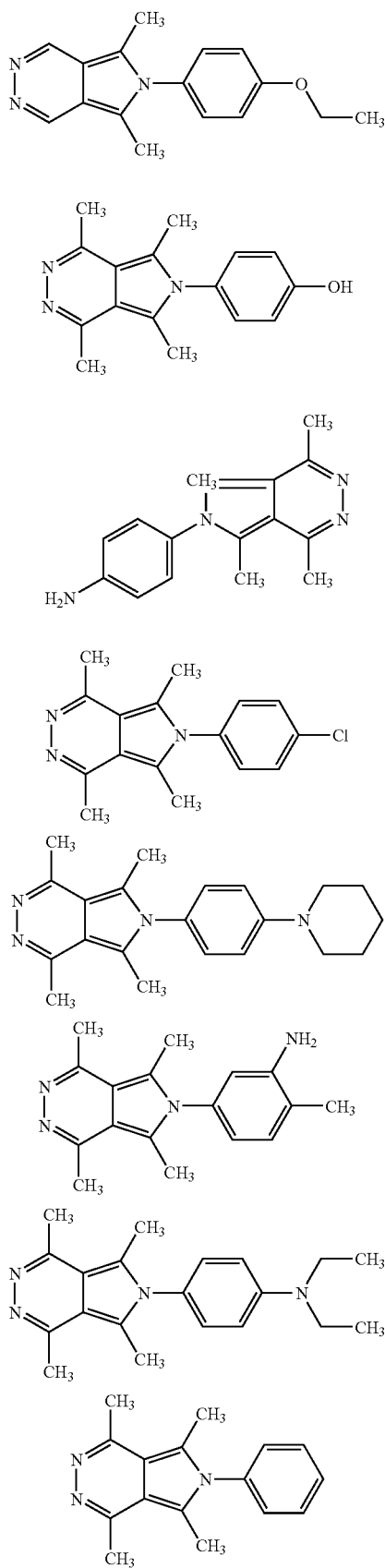

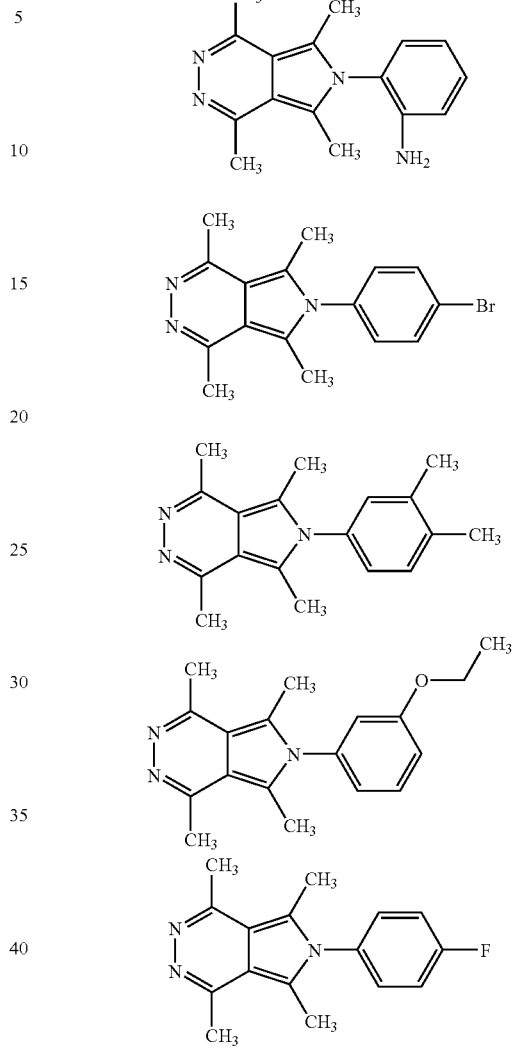

-continued

In an embodiment of this one aspect, the method of this invention administers an effective amount of a compound represented by Formula (I), or a pharmaceutically acceptable salt thereof, wherein $R^1$ is —$C_{0-6}$alkyl-phenyl optionally substituted with 1-6 independent halogen, —CN, $NO_2$, —$C_{1-6}$alkyl, —$C_{0-6}$alkyl-$C_{3-6}$cycloalkyl, —$C_{0-6}$alkyl-hetero$C_{3-7}$cycloalkyl, —$OR^6$, —$NR^6R^7$, —$C(=NR^6)NR^7R^8$, —$N(-NR^{88}R^6)NR^7R^8$, —$NR^6COR^7$, —$NR^6CO_2R^7$, —$NR^6SO_2R^{88}$, —$NR^6CONR^7R^8$, —$SR^{88}$, —$SOR^{88}$, —$SO_2R^{88}$, —$SO_2NR^6R^7$, —$COR^6$, —$CO_2R^6$, —$CONR^6R^7$, —$C(=NR^6)R^7$, or —$C(=NOR^6)R^7$ substituents;

$R^2$, $R^4$, $R^3$, and $R^5$ each independently is —$C_{0-6}$alkyl, —$C_{0-6}$alkyl-aryl, —$C_{0-6}$alkyl-heteroaryl, —$C_{0-6}$alkyl-$C_{3-6}$cycloalkyl, or —$C_{0-6}$alkyl-hetero$C_{3-7}$cycloalkyl, optionally substituted with 1-6 independent halogen, —CN, $NO_2$, —$C_{1-6}$ alkyl, —$OR^6$, —$NR^6R^7$, —$C(=NR^6)NR^7R^8$, —$N(-NR^{88}R^6)NR^7R^8$, —$NR^6COR^7$, —$NR^6CO_2R^7$, —$NR^6SO_2R^{88}$, —$NR^6CONR^7R^8$, —$SR^{88}$, —$SOR^{88}$, —$SO_2R^{88}$, —$SO_2NR^6R^7$, —$COR^6$, —$CO_2R^6$, —$CONR^6R^7$, —$C(=NR^6)R^7$, or —$C(=NOR^6)R^7$ substituents;

$R^6$, $R^7$, $R^8$, and $R^{88}$ each independently is —$C_{0-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) substituents; and provided that the compound is not selected from the following table:

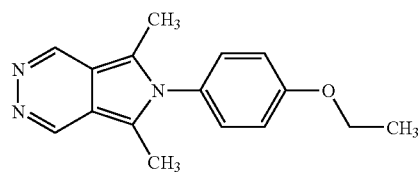
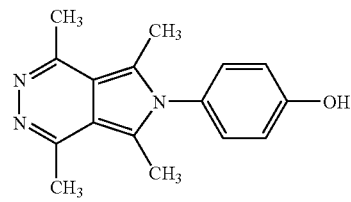
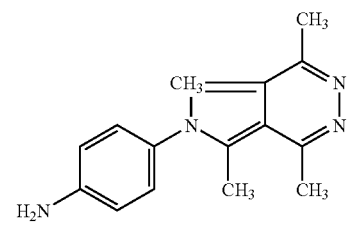
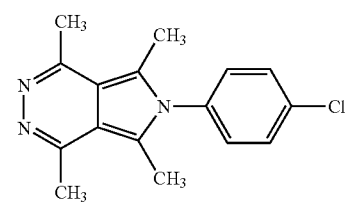
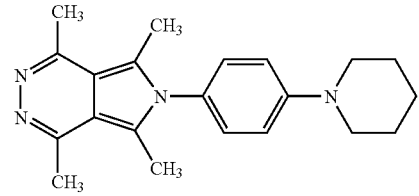
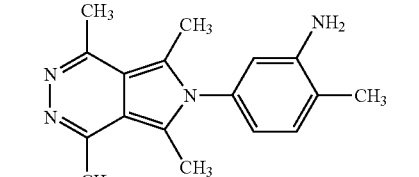
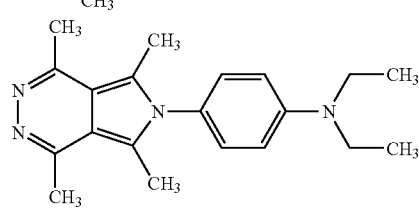
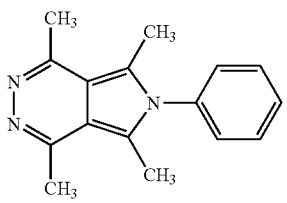
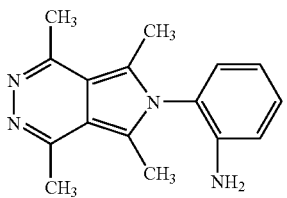
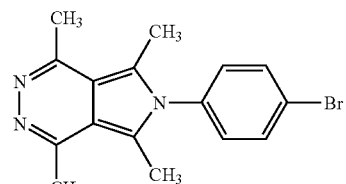
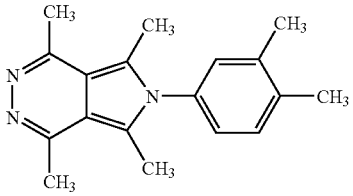
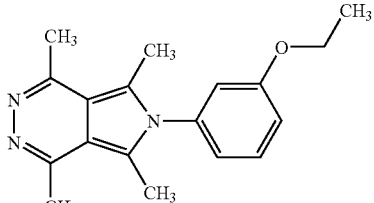
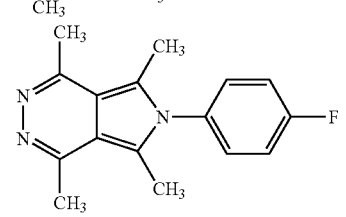

In another embodiment of this one aspect, the method of this invention administers an effective amount of a compound represented by Formula (I), or a pharmaceutically-acceptable salt thereof, wherein $R^1$ is —$C_{0-6}$alkyl-phenyl optionally substituted with 1-6 independent halogen, —CN, $NO_2$, —$C_{1-6}$alkyl, —$C_{0-6}$alkyl-$C_{3-6}$cycloalkyl, —$C_{0-6}$alkyl-hetero$C_{3-7}$cycloalkyl, —$OR^6$, —$NR^6R^7$, —C(=$NR^6$)$NR^7R^8$, —N(—$NR^{88}R^6$)$NR^7R^8$, —$NR^6COR^7$, —$NR^6CO_2R^7$, —$NR^6SO_2R^{88}$, —$NR^6CONR^7R^8$, —$SR^{88}$, —$SOR^{88}$, —$SO_2R^{88}$, —$SO_2NR^6R^7$, —$COR^6$, —$CO_2R^6$, —$CONR^6R^7$, —C(=$NR^6$)$R^7$, or —C(=$NOR^6$)$R^7$ substituents;

$R^2$, $R^4$, $R^3$, and $R^5$ each independently is —$C_{0-6}$alkyl or —$C_{0-6}$alkyl-phenyl, optionally substituted with 1-6 independent halogen, —CN, $NO_2$, —$C_{1-6}$alkyl, —$OR^6$, —$NR^6R^7$, —C(=NR⁶)NR⁷R⁸, —N(—NR⁸⁸R⁶)NR⁷R⁸, —NR⁶COR⁷, —NR⁶CO₂R⁷, —NR⁶SO₂R⁸⁸, —NR⁶CONR⁷R⁸, —SR⁸⁸, —SOR⁸⁸, —SO₂R⁸⁸, —SO₂NR⁶R⁷, —COR⁶, —CO₂R⁶, —CONR⁶R⁷, —C(=NR⁶)R⁷, or —C(=NOR⁶)R⁷ substituents;

R⁶, R⁷, R⁸, and R⁸⁸ each independently is —C₀₋₆alkyl, —C₃₋₇cycloalkyl, heteroaryl, or aryl; optionally substituted with 1-5 independent halogen, —CN, —C₁₋₆alkyl, —O(C₀₋₆ alkyl), —O(C₃₋₇cycloalkyl), —O(aryl), —N(C₀₋₆alkyl)(C₀₋₆ alkyl), —N(C₀₋₆alkyl)(C₃₋₇cycloalkyl), or —N(C₀₋₆alkyl)(aryl) substituents; and provided that the compound is not selected from the following table:

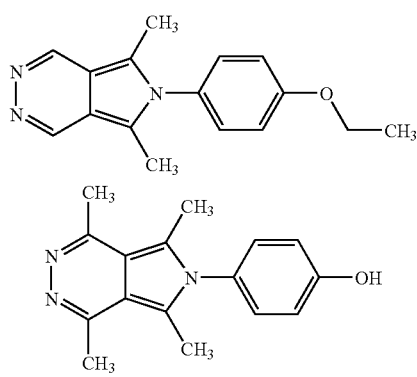

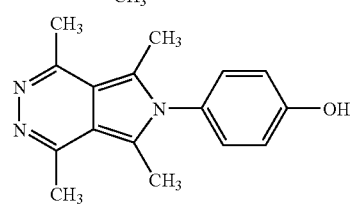

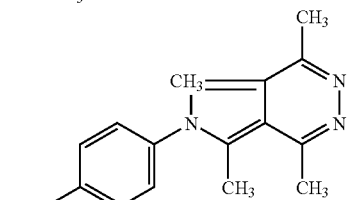

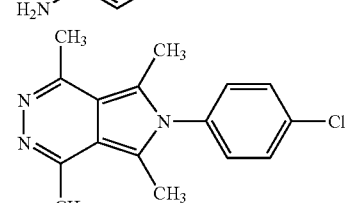

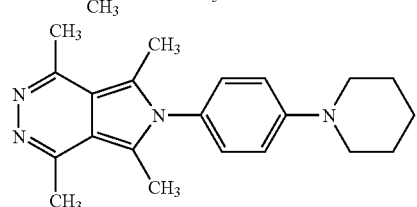

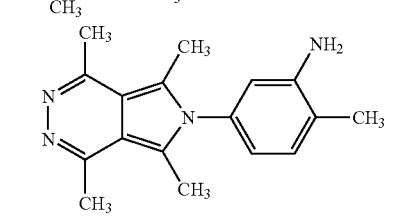

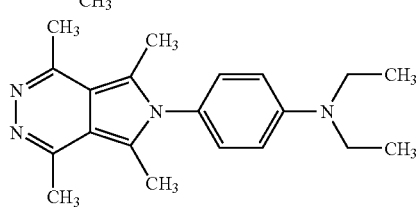

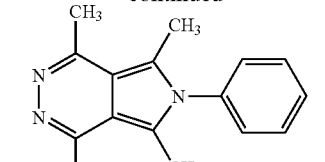

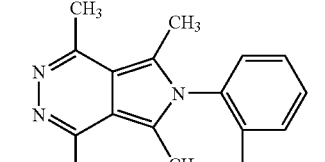

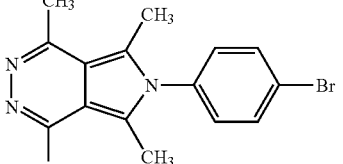

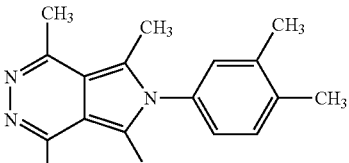

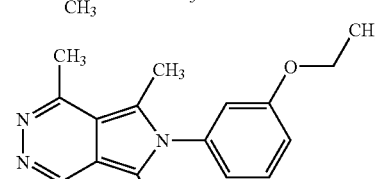

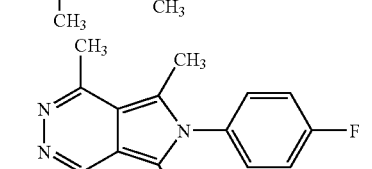

In another aspect, this invention is directed to a compound represented by Formula (I):

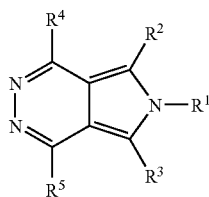

(I)

or a pharmaceutically acceptable salt thereof, wherein

R¹ is —C₀₋₆alkyl-aryl, —C₀₋₆alkyl-heteroaryl, —C₀₋₆alkyl-C₃₋₆cycloalkyl, or —C₀₋₆alkyl-heteroC₃₋₇cycloalkyl, optionally substituted with 1-6 independent halogen, —CN, NO₂, —C₁₋₆alkyl, —C₀₋₆alkyl-C₃₋₆cycloalkyl, —C₀₋₆alkylheteroC$_{3-7}$cycloalkyl, —OR$^6$, —NR$^6$R$^7$, —C(=NR$^6$)NR$^7$R$^8$, —N(—NR$^{88}$R$^6$)NR$^7$R$^8$, —NR$^6$COR$^7$, —NR$^6$CO$_2$R$^7$, —NR$^6$SO$_2$R$^{88}$, —NR$^6$CONR$^7$R$^8$, —SR$^{88}$, —SOR$^{88}$, —SO$_2$R$^{88}$, —SO$_2$NR$^6$R$^7$, —COR$^6$, —CO$_2$R$^6$, —CONR$^6$R$^7$, —C(=NR$^6$)R$^7$, or —C(=NOR$^6$)R$^7$ substituents;

R$^2$, R$^4$, R$^3$, and R$^5$ each independently is —C$_{0-6}$alkyl, —C$_{0-6}$alkyl-aryl, —C$_{0-6}$alkyl-heteroaryl, —C$_{0-6}$alkyl-C$_{3-6}$cycloalkyl, or —C$_{0-6}$alkyl-heteroC$_{3-7}$cycloalkyl, optionally substituted with 1-6 independent halogen, —CN, NO$_2$, —C$_{1-6}$ alkyl, —OR$^6$, —NR$^6$R$^7$, —C(=NR$^6$)NR$^7$R$^8$, —N(—NR$^{88}$R$^6$)NR$^7$R$^8$, —NR$^6$COR$^7$, —NR$^6$CO$_2$R$^7$, —NR$^6$SO$_2$R$^{88}$, —NR$^6$CONR$^7$R$^8$, —SR$^{88}$, —SOR$^{88}$, —SO$_2$R$^{88}$, —SO$_2$NR$^6$R$^7$, —COR$^6$, —CO$_2$R$^6$, —CONR$^6$R$^7$, —C(=NR$^6$)R$^7$, or —C(=NOR$^6$)R$^7$ substituents;

R$^6$, R$^7$, R$^8$, and R$^{88}$ each independently is —C$_{0-6}$alkyl, —C$_{3-7}$cycloalkyl, heteroaryl, or aryl; optionally substituted with 1-5 independent halogen, —CN, —C$_{1-6}$alkyl, —O(C$_{0-6}$alkyl), —O(C$_{3-7}$cycloalkyl), —O(aryl), —N(C$_{0-6}$alkyl)(C$_{0-6}$alkyl), —N(C$_{0-6}$alkyl)(C$_{3-7}$cycloalkyl), or —N(C$_{0-6}$alkyl)(aryl) substituents; provided that the compound is not 6-methyl-6H-pyrrolo[3,4-d]pyridazine,
1,4,5,7-tetramethyl-6-phenyl-6H-pyrrolo[3,4-d]pyridazine,
1,4,5-trimethyl-6,7-diphenyl-6H-pyrrolo[3,4-d]pyridazine,
5,7-dimethyl-1,4,6-triphenyl-6H-pyrrolo[3,4-d]pyridazine,
5-methyl-1,4,6,7-tetraphenyl-6H-pyrrolo[3,4-d]pyridazine,
1,4-bis-(4-methoxy-phenyl)-5,7-dimethyl-6-phenyl-6H-pyrrolo[3,4-d]pyridazine,
1,4-bis-(4-methoxy-phenyl)-5-methyl-6,7-diphenyl-6H-pyrrolo[3,4-d]pyridazine,
1,4-diethyl-5,7-dimethyl-6-phenyl-6H-pyrrolo[3,4-d]pyridazine,
1,4,5,7-tetramethyl-6H-pyrrolo[3,4-d]pyridazine,
N-(1,4,5,7-tetramethyl-pyrrolo[3,4-d]pyridazin-6-yl)7benzamide,
1,4,5,7-tetramethyl-pyrrolo[3,4-d]pyridazin-6-ylamine picrate,
1,4,5,7-tetramethyl-pyrrolo[3,4-d]pyridazin-6-ylamine,
5,7-dimethyl-6-phenyl-6H-pyrrolo[3,4-d]pyridazine,
5,7-dimethyl-2-phenacyl-6H-pyrrolo[3,4-d]pyridazinium bromide,
2-(2-methoxycarbonylvinyl)-5,7-dimethyl-6H-pyrrolo[3,4-d]pyridazinium tetrafloroborate
5,7-diphenyl-6H-pyrrolo[3,4-d]pyridazine,
5,6,7-trimethyl-6H-pyrrolo[3,4-d]pyridazine,
1,4diphenyl-7,8,9,10-tetrahydro-pyrrolo[4,5-a]indolizine,
5-methyl-1,4-diphenyl-7,8,9,10-tetrahydro-pyridazino[4,5-a]indolizine,
6-benzyl-1,4-diphenyl-5-p-tolyl-6H-pyrrolo [3,4-d]pyridazine,
6-benzyl-5-(2-chloro-phenyl)-1,4-diphenyl-6H-pyrrolo[3,4-d]pyridazine.
1,4,5,6,7-pentaphenyl-6H-pyrrolo[3,4-d]pyridazine,
6,7,10,11-tetraphenyl-pyridazino[4',5':3,4]pyrrolo[1,2-a]quinoxaline,
11-(4-nitro-phenyl)-6,7,10-triphenyl-pyridazino[4',5':3,4]pyrrolo[ 1,2-a]quinoxaline,
6-benzyl-1,4,5-triphenyl-6H-pyrrolo[3,4-d]pyridazine,
9,12-diphenyl-pyridazino[4',5':3,4]pyrrolo[2,1-a]isoquinoline,
5-methylsulfanyl-1,4,6,7-tetraphenyl-6H-pyrrolo[3,4-d]pyridazine,
1,4,6,7-tetraphenyl-6H-pyrrolo[3,4-d]pyridazine-5-carboxylic acid ethyl ester,
7,10-diphenyl-pyridazino[4',5':3,4]pyrrolo[1,2-a]quinoline,
11,14-diphenyl-pyridazino[4',5':3,4]pyrrolo[1,2-f]phenanthridine,
1-oxo-7-oxy-6b,11b-dihydro(pyridazino[4',5'-c]-pyrrolo)[2.1-c]benzoxazine-1,4,
10-methyl-1,4-diphenyl-8,9-dihydro-7H-benzo(ef)pyridazino[4,5-a]cycl[3.3.2]azine,
11-methyl-1,4-diphenyl-7,8,9,10-tetrahydrocyclohepta(ef)pyridazino[4,5-a]cycl[3.3.2]azine,
1,4-dichloro-5,6,7-trimethyl-6H-pyrrolo[3,4-d]pyridazine,
1-chloro-4-ethoxy-5,6,7-trimethyl-6H-pyrrolo[3,4-d]pyridazine,
1-chloro-5,6,7-trimethyl-6H-pyrrolo[3,4-d]pyridazinium chloride,
1-ethoxy-2,5,6,7-tetramethyl-6H-pyrrolo[3,4-d]pyridazinium tetrafluoroborate,
1-ethoxy-5,6,7-trimethyl-2H,6H-pyrrolo[3,4-d]pyridazinium tetrafluoroborate,
1-ethoxy-3-ethyl-5,6,7-trimethyl-6H-pyrrolo[3,4-d]pyridazinium tetrafluoroborate,
1-ethoxy-5,6,7-trimethyl-6H-pyrrolo[3,4-d]pyridazine,
5-cyano-1,4-dimethylpyridazino[4,5-a]indolizine,
1,4-dimethyl-6-phenyl-2,3,8a-triaza-fluorene-9-carbonitrile,
6-benzolyl-1,4-dimethyl-2,3,8a-triaza-fluorene-9-carbonitrile,
6-benzyl-1,4-diphenyl-2,3,8a-triaza-fluorene-9-carbonitrile,
1,4,6-trimethyl-2,3,8a-triaza-fluorene-9-carbonitrile,
5-cyano-1,4-diphenylpyridazino[4,5-a]indolizine,
6-methyl-1,4diphenyl-2,3,8a-triaza-fluorene-9-carbonitrile,
6-benzoyl-1,4-diphenyl-2,3,8a-triaza-fluorene-9-carbonitrile,
1,4,6-triphenyl-2,3,8a-triaza-fluorene-9-carbonitrile,
5,7-dimethyl-1,4-diphenyl-2,3,8a-triaza-fluorene-9-carbonitrile,
9,12-diphenyl-pyridazino[4',5':3,4]pyrrolo[2,1-a]isoquinoline-8-carbonitrile,
dimethyl 3,12,13,17-tetramethyl-7$^2$,7$^3$-diazabenzo[g]porphyrin-2,18-dipropionate,
5,6-dihydro-2,3-dimethoxypyridazino[4',5':3,4]pyrrolo[2,1-a]isochinolin-9-ol,
5,6-dihydro-2,3-dimethoxypyridazino[4',5':3,4]pyrrolo[2,1-a]isochinolin-9-ol-hydrochloride,
3-methyl-6,9-diphenylthiazolo[3',2':1,2]pyrrolo[3,4-d]pyridine, or
1,4-diphenylpyridazino[4',5':3,4]pyrrolo[2,1-b]benzothiazole;
and the compound is not selected from the following table:

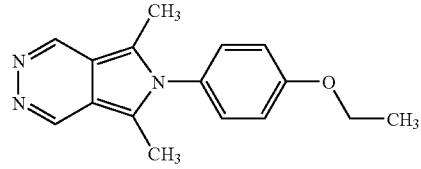

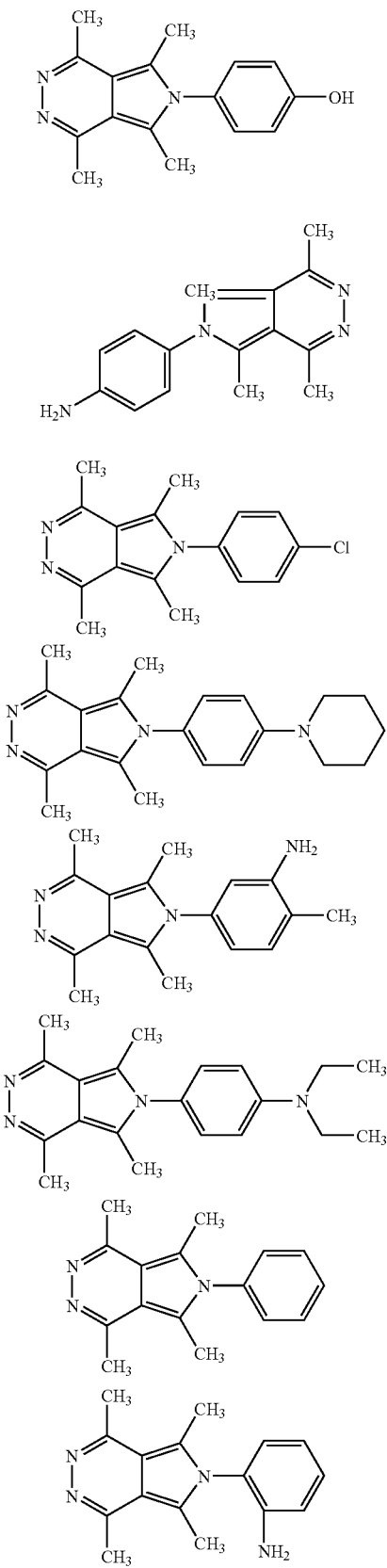
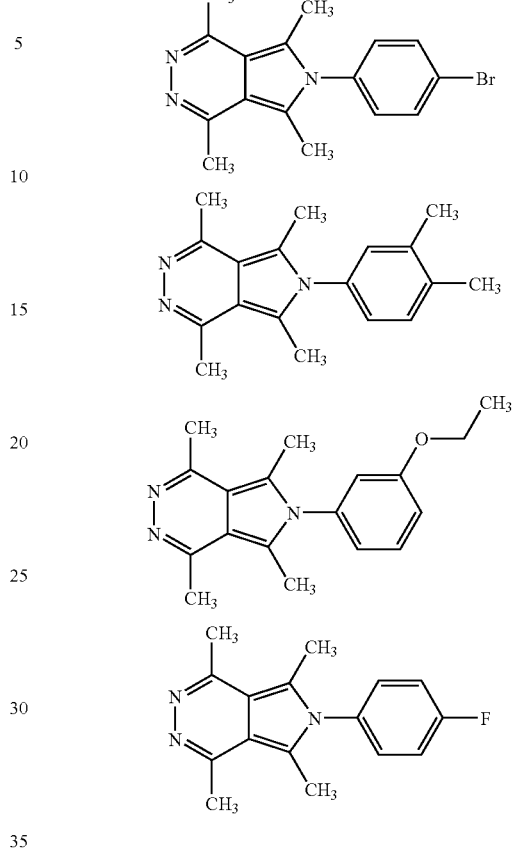

As used herein, "alkyl" as well as other groups having the prefix "alk" such as, for example, alkoxy, alkanoyl, alkenyl, alkynyl and the like, means carbon chains which may be linear or branched or combinations thereof. Examples of alkyl groups include methyl, ethyl, propyl, isopropyl, butyl, sec- and tert-butyl, pentyl, hexyl, heptyl and the like. "Alkenyl", "alkynyl" and other like terms include carbon chains containing at least one unsaturated C—C bond.

The term "cycloalkyl" means carbocycles containing no heteroatoms, and includes mono-, bi- and tricyclic saturated carbocycles, as well as fused ring systems. Such fused ring systems can include one ring that is partially or fully unsaturated such as a benzene ring to form fused ring systems such as benzofused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, indenyl, fluorenyl, 1,2,3,4-tetrahydronaphalene and the like. Similarly, "cycloalkenyl" means carbocycles containing no heteroatoms and at least one non-aromatic C—C double bond, and include mono-, bi- and tricyclic partially saturated carbocycles, as well as benzofused cycloalkenes. Examples of cycloalkenyl include cyclohexenyl, indenyl, and the like.

The term "aryl" means an aromatic substituent which is a single ring or multiple rings fused together. When formed of multiple rings, at least one of the constituent rings is aromatic. The preferred aryl substituents are phenyl and naphthyl groups.

The term "cycloalkyloxy" unless specifically stated otherwise includes a cycloalkyl group connected by a short $C_{1-2}$alkyl length to the oxy connecting atom.

The term "$C_{0-6}$alkyl" includes alkyls containing 6, 5, 4, 3, 2, 1, or no carbon atoms. An alkyl with no carbon atoms is a hydrogen atom substituent when the alkyl is a terminal group and is a direct bond when the alkyl is a bridging group.

The term "hetero" unless specifically stated otherwise includes one or more O, S, or N atoms. For example, heterocycloalkyl and heteroaryl include ring systems that contain one or more O, S, or N atoms in the ring, including mixtures of such atoms. The hetero atoms replace ring carbon atoms. Thus, for example, a heterocyclo$C_5$alkyl is a five-member ring containing from 4 to no carbon atoms. Examples of heteroaryls include pyridinyl, quinolinyl, isoquinolinyl, pyridazinyl, pyrimidinyl, pyrazinyl, quinoxalinyl, furyl, benzofuryl, dibenzofuryl, thienyl, benzthienyl, pyrrolyl, indolyl, pyrazolyl, indazolyl, oxazolyl, benzoxazolyl, isoxazolyl, thiazolyl, benzothiazolyl, isothiazolyl, imidazolyl, benzimidazolyl, oxadiazolyl, thiadiazolyl, triazolyl, and tetrazolyl. Examples of heterocycloalkyls include azetidinyl, pyrrolidinyl, piperidinyl, piperazinyl, morpholinyl, tetrahydrofuranyl, imidazolinyl, pyrolidin-2-one, piperidin-2-one, and thiomorpholinyl.

The term "hetero$C_{0-4}$alkyl" means a heteroalkyl containing 3, 2, 1, or no carbon atoms. However, at least one heteroatom must be present. Thus, as an example, a hetero$C_{0-4}$alkyl having no carbon atoms but one N atom would be a —NH— if a bridging group and a —NH$_2$ if a terminal group. Analogous bridging or terminal groups are clear for an O or S heteroatom.

The term "amine" unless specifically stated otherwise includes primary, secondary and tertiary amines substituted with $C_{0-6}$alkyl.

The term "carbonyl" unless specifically stated otherwise includes a $C_{0-6}$alkyl substituent group when the carbonyl is terminal.

The term "halogen" includes fluorine, chlorine, bromine and iodine atoms.

The term "optionally substituted" is intended to include both substituted and unsubstituted. Thus, for example, optionally substituted aryl could represent a pentafluorophenyl or a phenyl ring. Further, optionally substituted multiple moieties such as, for example, alkylaryl are intended to mean that the aryl and the alkyl groups are optionally substituted. If only one of the multiple moieties is optionally substituted then it will be specifically recited such as "an alkylaryl, the aryl optionally substituted with halogen or hydroxyl."

Compounds described herein contain one or more double bonds and may thus give rise to cis/trans isomers as well as other conformational isomers. The present invention includes all such possible isomers as well as mixtures of such isomers.

Compounds described herein can contain one or more asymmetric centers and may thus give rise to diastereomers and optical isomers. The present invention includes the use of all such possible diastereomers as well as their racemic mixtures, their substantially pure resolved enantiomers, all possible geometric isomers, and pharmaceutically acceptable salts thereof. The above Formula I is shown without-a definitive stereochemistry at certain positions. The present invention includes the use of all stereoisomers of Formula I and pharmaceutically acceptable salts thereof. Further, mixtures of stereoisomers as well as isolated specific stereoisomers are also included. During the course of the synthetic procedures used to prepare such compounds, or in using racemization or epimerization procedures known to those skilled in the art, the products of such procedures can be a mixture of stereoisomers.

The term "pharmaceutically acceptable salts" refers to salts prepared from pharmaceutically acceptable non-toxic bases or acids. When the compound used in the present invention is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound used in the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric, and tartaric acids.

The pharmaceutical compositions used of 2H-pyrrolo[3,4-c]pyridazine compounds of the present invention comprise a compound represented by Formula I (or pharmaceutically acceptable salts thereof) as an active ingredient, a pharmaceutically acceptable carrier and optionally other therapeutic ingredients or adjuvants. Such additional therapeutic ingredients include, for example, i) opiate agonists or antagonists, ii) calcium channel antagonists, iii) 5HT receptor agonists or antagonists iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) GABA-A receptor modulators, x) dopamine agonists or antagonists, xi) selective serotonin reuptake inhibitors ("SSRI") and/or selective serotonin and norepinephrine reuptake inhibitors ("SSNRI"), xii) tricyclic antidepressant drugs, xiv) norepinephrine modulators, xv) L-DOPA, xvi) buspirone, xvii) lithium, xviii) valproate, ixx) neurontin (gabapentin), xx) olanzapine, xxi) nicotinic agonists or antagonists including nicotine, xxii) muscarinic agonists or antagonists, xxiii) heroin substituting drugs such as methadone, levo-alpha-acetylmethadol, buprenorphine and naltrexone, and xxiv) disulfiram and acamprosate. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Creams, ointments, jellies, solutions, or suspensions containing the compound of Formula I can be employed for topical use. Mouth washes and gargles are included within the scope of topical use for the purposes of this invention.

Dosage levels from about 0.01 mg/kg to about 140 mg/kg of body weight per day are useful in the treatment of psychiatric and mood disorders such as, for example, schizophrenia, anxiety, depression, panic, bipolar disorders, and circadian disorders, as well as being useful in the treatment of pain which are responsive to calcium channel modulation, or alternatively about 0.5 mg to about 7 g per patient per day. For example, schizophrenia, anxiety, depression, and panic may be effectively treated by the administration of from about 0.01 mg to 75 mg of the compound per kilogram of body weight per day, or alternatively about 0.5 mg to about 3.5 g per patient per day. Pain may be effectively treated by the administration of from about 0.01 mg to 125 mg of the compound per kilogram of body weight per day, or alternatively about 0.5 mg to about 5.5 g per patient per day. Further, it is understood that the calcium channel modulating compounds of this invention can be administered at prophylactically effective dosage levels to prevent the above-recited conditions.

The amount of active ingredient that may be combined with the carrier materials to produce a single dosage form will vary depending upon the host treated and the particular mode of administration. For example, a formulation intended for the oral administration to humans may conveniently contain from about 0.5 mg to about 5 g of active agent, compounded with an appropriate and convenient amount of carrier material which may vary from about 5 to about 95 percent of the total composition. Unit dosage forms will generally contain between from about 1 mg to about 1000 mg of the active ingredient, typically 25 mg, 50 mg, 100 mg, 200 mg, 300 mg, 400 mg, 500 mg, 600 mg, 800 mg or 1000 mg.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In practice, the compounds used represented by Formula I, or pharmaceutically acceptable salts thereof, of this invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions used in the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compound represented by Formula I, or pharmaceutically acceptable salts thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions used in this invention may include a pharmaceutically acceptable carrier and a compound or a pharmaceutically acceptable salt of Formula I. The compounds of Formula I, or pharmaceutically acceptable salts thereof, can also be included in pharmaceutical compositions in combination with one or more other therapeutically active compounds.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet Or capsule preferably containing from about 0.1 mg to about 500 mg of the active ingredient. Thus, a tablet, cachet, or capsule conveniently contains 0.1 mg, 1 mg, 5 mg, 25 mg, 50 mg, 100 mg, 200 mg, 300 mg, 400 mg, or 500 mg of the active ingredient taken one or two tablets, cachets, or capsules, once, twice, or three times daily.

Pharmaceutical compositions used in the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions used in the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), vegetable oils, and suitable mixtures thereof.

Pharmaceutical compositions used in the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or pharmaceutically acceptable salts thereof, via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions used in this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in moulds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

The compounds and pharmaceutical compositions used in this invention have been found to exhibit biological activity as calcium channel ligands. Accordingly, another aspect of the invention is the treatment in mammals of, for example, schizophrenia, anxiety, depression, panic, bipolar disorders, circadian rhythm and sleep disorders, pain, Parkinson's disease, cognitive dysfunction, epilepsy, drug addiction, drug abuse and drug withdrawal—maladies that are amenable to amelioration through modulation of the calcium channel—by the administration of an effective amount of the compounds of this invention. The term "mammals" includes humans, as well as other animals such as, for example, dogs, cats, horses, pigs, and cattle. Accordingly, it is understood that the treatment of mammals other than humans is the treatment of clinical correlating afflictions to those above recited examples that are human afflictions.

Further, as described above, the compound used in this invention can be utilized in combination with other therapeutic compounds. In particular, the combinations of the calcium channel modulating compound used in this invention can be advantageously used in combination with i) opiate agonists or antagonists, ii) mGluR5 antagonists, iii) 5HT receptor agonists or antagonists iv) sodium channel antagonists, v) NMDA receptor agonists or antagonists, vi) COX-2 selective inhibitors, vii) NK1 antagonists, viii) non-steroidal anti-inflammatory drugs ("NSAID"), ix) GABA-A receptor modulators, x) dopamine agonists or antagonists, xi) selective serotonin reuptake inhibitors ("SSRI") and/or selective serotonin and norepinephrine reuptake inhibitors ("SSNRI"), xii) tricyclic antidepressant drugs, xiii) norepinephrine modulators, xiv) L-DOPA, xv) buspirone, xvi) lithium, xvii) valproate, xviii) neurontin (gabapentin), xix) olanzapine, xx) nicotinic agonists or antagonists including nicotine, xxi) muscarinic agonists or antagonists, xxii) heroin substituting drugs such as methadone, levo-alpha-acetylmethadol, buprenorphine and naltrexone, and xxiii) disulfiram and acamprosate.

The abbreviations used herein have the following tabulated meanings. Abbreviations not tabulated below have their meanings as commonly used unless specifically stated otherwise.

| | |
|---|---|
| Ac | acetyl |
| AIBN | 2,2'-azobis(isobutyronitrile) |
| BINAP | 1,1'-bi-2-naphthol |
| Bn | benzyl |
| cAMP | cyclic adenosine-3',5'-monophosphate |
| DAST | (diethylamino)sulfur trifluoride |
| DEAD | diethyl azodicarboxylate |
| DBU | 1,8-diazabicyclo[5.4.0]undec-7-ene |
| DIBAL | diisobutylaluminum hydride |
| DMAP | 4-(dimethylamino)pyridine |
| DMF | N,N-dimethylformamide |
| Dppf | 1,1'-bis(diphenylphosphino)-ferrocene |
| EDCI | 1-(3-dimethylaminopropyl)-3-ethylcarbodiimide hydrochloride |
| $Et_3N$ | triethylamine |
| GST | glutathione transferase |
| HMDS | hexamethyldisilazide |
| LDA | lithium diisopropylamide |
| m-CPBA | metachloroperbenzoic acid |
| MMPP | monoperoxyphthalic acid |
| MPPM | monoperoxyphthalic acid, magnesium salt $6H_2O$ |
| Ms | methanesulfonyl = mesyl = $SO_2Me$ |
| Ms0 | methanesulfonate = mesylate |
| NBS | N-bromo succinimide |
| NSAID | non-steroidal anti-inflammatory drug |
| o-Tol | ortho-tolyl |
| OXONE ® | $2KHSO_5 \cdot KHSO_4 \cdot K_2SO_4$ |
| PCC | pyridinium chlorochromate |
| $Pd_2(dba)_3$ | Bis(dibenzylideneacetone) palladium(0) |
| PDC | pyridinium dichromate |
| PDE | Phosphodiesterase |
| Ph | Phenyl |
| Phe | Benzenediyl |
| PMB | para-methoxybenzyl |
| Pye | Pyridinediyl |
| r.t. | room temperature |
| Rac. | Racemic |
| SAM | aminosulfonyl or sulfonamide or $SO_2NH_2$ |
| SEM | 2-(trimethylsilyl)ethoxymethoxy |
| SPA | scintillation proximity assay |
| TBAF | tetra-n-butylammonium fluoride |
| Th | 2- or 3-thienyl |
| TFA | trifluoroacetic acid |
| TFAA | trifluoroacetic acid anhydride |
| THF | Tetrahydrofuran |
| Thi | Thiophenediyl |
| TLC | thin layer chromatography |
| TMS-CN | trimethylsilyl cyanide |
| TMSI | trimethylsilyl iodide |
| Tz | 1H (or 2H)-tetrazol-5-yl |
| XANTPHOS | 4,5-Bis-diphenylphosphanyl-9,9-dimethyl-9H-xanthene |
| $C_3H_5$ | Allyl |

| ALKYL GROUP ABBREVIATIONS | |
|---|---|
| Me = | Methyl |
| Et = | ethyl |
| n-Pr = | normal propyl |
| i-Pr = | isopropyl |
| n-Bu = | normal butyl |
| i-Bu = | isobutyl |
| s-Bu = | secondary butyl |
| t-Bu = | tertiary butyl |
| c-Pr = | cyclopropyl |
| c-Bu = | cyclobutyl |
| c-Pen = | cyclopentyl |
| c-Hex = | cyclohexyl |

Assays Demonstrating Biological Activity

The compounds of this invention were tested by the following assays.

Membrane Preparation:

A710 (HEK293 co-expressing α1b, α2δ, β3) cultured in T250 flask were harvested and washed once with buffer A (20 mM HEPES 10 mM EDTA pH=7.4). The pellet was homogenized in buffer A using a Polytron for 20s. After centrifugation for 10 min, the resulting pellet was washed once with the same buffer and twice with buffer B (20 mM HEPES 0.1 mM EDTA pH=7.4). The final pellet was resuspended in the same buffer and aliquoted and stored at −70° C. Protein contents was measured by the Biorad D C method with bovine serum albumin used as standard.

[$^3$H]-GABApentin Binding:

After thawing, the membranes were washed one time with buffer C (50 mM TRIS pH=7.1) and resuspended in ice cold assay buffer (20 mM HEPES pH=7.4), to have a final protein concentration of 50 µg of protein/well. For the competitive binding experiments, the membranes were incubated with 7 nM [$^3$H]-GABApentin for 1 h at rt in the absence or the presence of at least 11 concentrations of the compounds to be tested. The non-specific binding was measured in the presence of 100 µM GABApentin. At the end of the incubation, the suspension was filtered onto 96 well Whatmann GF/B filter plate (Packard) and washed 3 times with ice-cold assay buffer. The plate was dried and 50 µL of microscint 20 (Packard) was added in each well. The plate was sealed and was counted using a Packard Topcount. The plate was counted (2 min) in normal cpm count mode and transforms in DPM with a constant quench correction.

The compounds of this invention displayed efficacy in the above model by $IC_{50}$ values of less than 10 µM. The compounds the following table, however, gave $IC_{50}$ values of more than 10 µM:

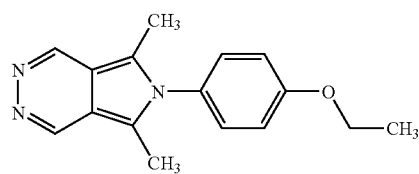

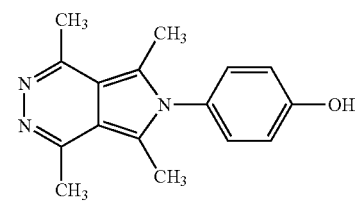

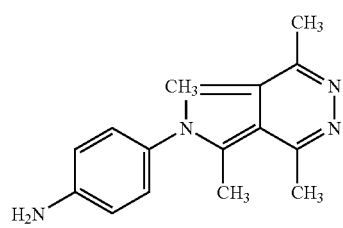

-continued

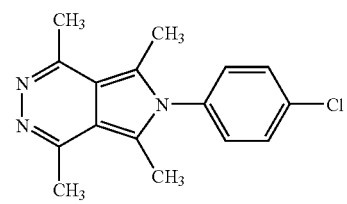

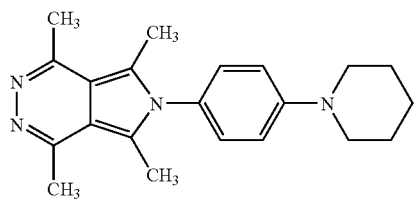

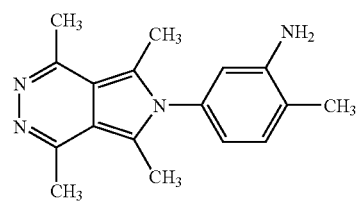

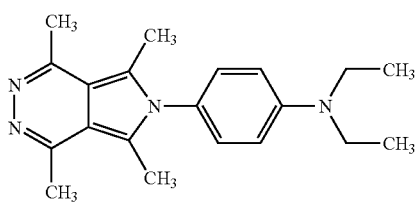

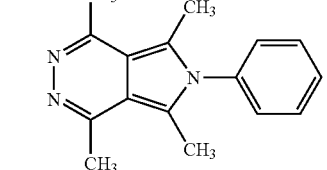

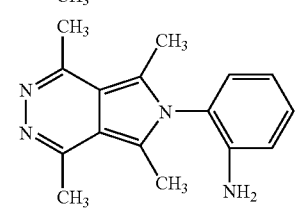

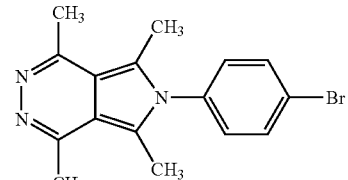

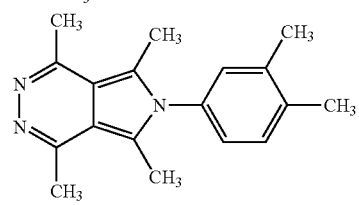

-continued

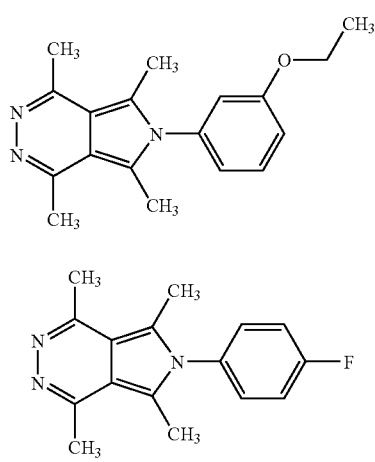

Spinal Nerve Ligation Model (Chung Model):

The spinal nerve ligation model of neuropathic pain was used to assess the effects of test compounds on nerve injury-induced tactile allodynia (S. H. Kim and J. M. Chung, *Pain* 50:355-363(1992)). Male Sprague Dawley rats (175-200 g) received unilateral tight ligation of the left L5/L6 spinal nerves distal to the dorsal root ganglion using 4-0 silk suture. Behavioral-nociceptive testing occurred 7-14 days following spinal nerve ligation by placing the rats in chambers on a wire mesh. Rats were tested for tactile allodynia (decreased hindpaw withdrawal threshold to non-noxious punctate stimulation) by applying a series of calibrated von Frey filaments to the plantar aspect of the left hindpaw ipsilateral to the site of nerve injury. The mean 50% hindpaw withdrawal threshold (g.) was determined using the Dixon "up-down" non-parametric test (Chaplan et al., *J. Neurosci. Methods,* 53:55-63 (1994)). Rats that displayed a pre-drug withdrawal threshold >4 g were not considered allodynic and were excluded from the study. Following determination of pre-drug withdrawal thresholds, rats received either an i.p. or p.o. injection of test compound. The effect of the test compound on tactile allodynia was determined over time by measuring hindpaw withdrawal thresholds 30, 60, 90, 120 min post-injection. In above model, EXAMPLE 1 produced a 65% effect after i.p. dosing at 30 mg/kg, EXAMPLE 50 produced a 100% effect after i.p. dosing at 20 mg/kg, EXAMPLE 115 produced a 60% effect after i.p. dosing at 30 mg/kg i.p.

The examples that follow are intended as an illustration of certain preferred embodiments of the invention and no limitation of the invention is implied.

Unless specifically stated otherwise, the experimental procedures were performed under the following conditions. All operations were carried out at room or ambient temperature—that is, at a temperature in the range of 18-25° C. Evaporation of solvent was carried out using a rotary evaporator under reduced pressure (600-4000 pascals: 4.5-30 mm Hg) with a bath temperature of up to 60° C. The course of reactions was followed by thin layer chromatography (TLC) and reaction times are given for illustration only. Melting points are uncorrected and 'd' indicates decomposition. The melting points given are those obtained for the materials prepared as described. Polymorphism may result in isolation of materials with different melting points in some preparations. The structure and purity of all final products were assured by at least one of the following techniques: TLC, mass spectrometry, nuclear magnetic resonance (NMR) spectrometry or microanalytical data. When given, yields are for illustration only. When given, NMR data is in the form of delta ($\delta$) values for major diagnostic protons, given in parts per million (ppm) relative to tetramethylsilane (TMS) as internal standard, determined at 300 MHz, 400 MHz or 500 MHz using the indicated solvent. Conventional abbreviations used for signal shape are: s. singlet; d. doublet; t. triplet; m. multiplet; br. broad; etc. In addition, "Ar" signifies an aromatic signal. Chemical symbols have their usual meanings; the following abbreviations are used: v (volume), w (weight), b.p. (boiling point), m.p. (melting point), L (liter(s)), mL (milliliters), g (gram(s)), mg (milligrams(s)), mol (moles), mmol (millimoles), eq (equivalent(s)).

Methods of Synthesis

Compounds of the present invention can be prepared according to the following methods. The substituents are the same as in Formula I except where defined otherwise.

EXAMPLES 1-47

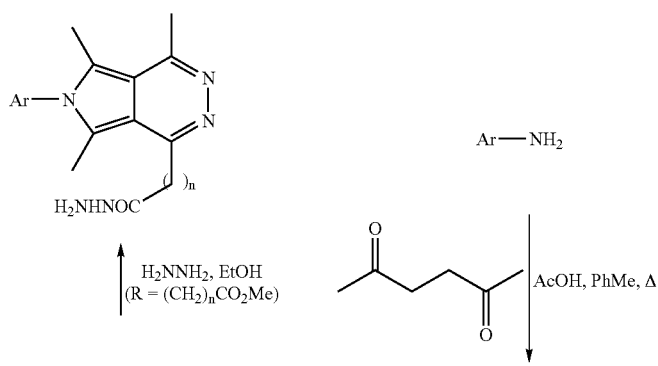

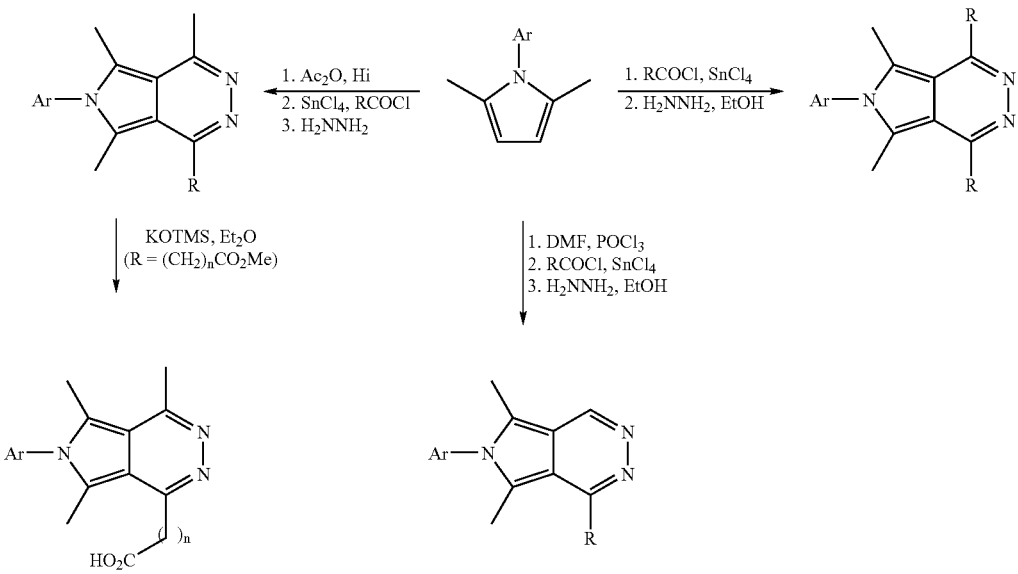
EXAMPLES 48-84
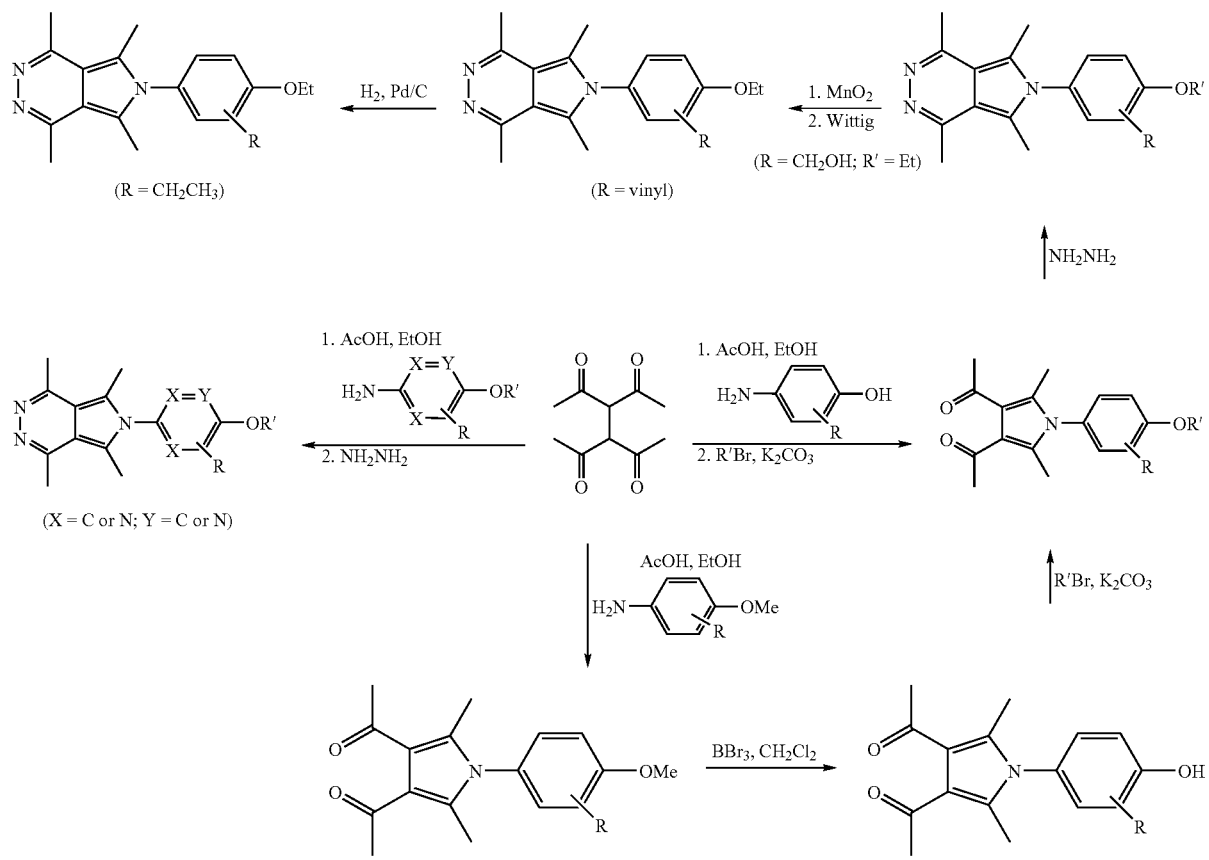

EXAMPLES 85-370
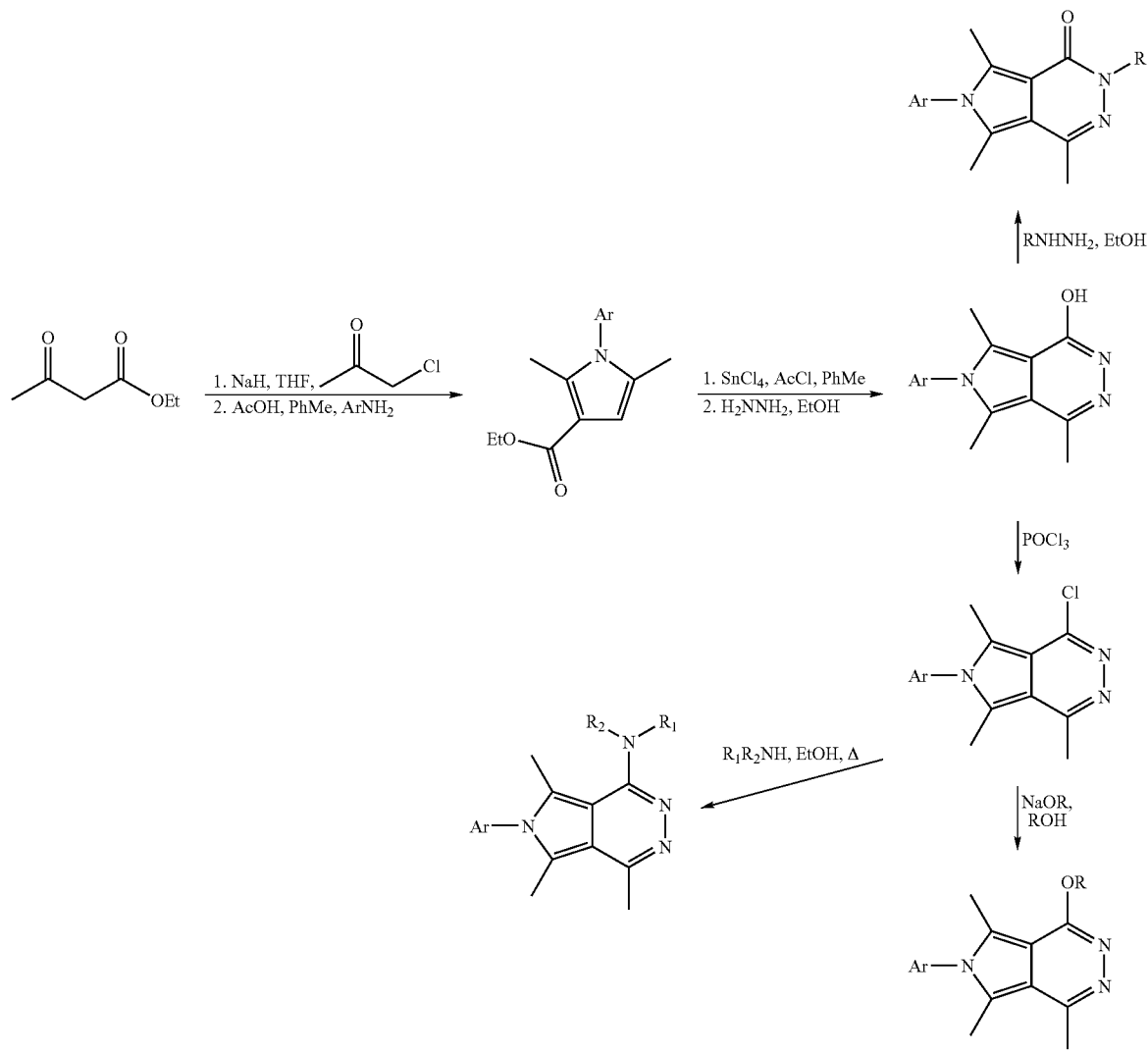
EXAMPLE 1
6-(4-ethoxyphenyl)-1-(4-methoxyphenyl)-4,5,7-trimethyl-6H-pyrrolo[3,4-d]pyridazine
EXAMPLE 371
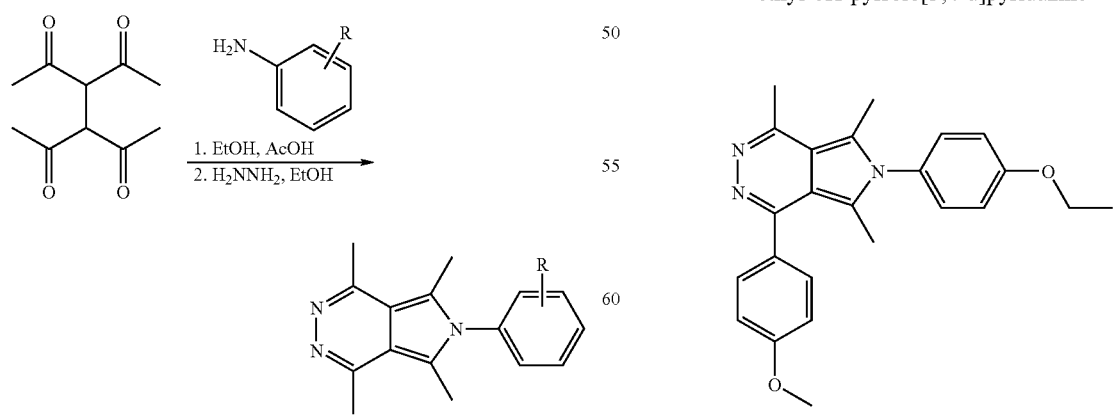

To a solution of acetonyl acetone (11.7 mL, 100 mmol) and toluene (750 mL) was added p-phenetidine (12.9 mL, 100 mmol) and glacial acetic acid (1 mL). The mixture was heated at reflux overnight. After cooling to rt, the mixture was concentrated in vacuo and purified by column chromatography on silica gel (15% EtOAc/hexanes) to give 2,5-dimethyl-1-(4-ethoxyphenyl)pyrrole as a pale yellow solid: $^1$H NMR (CDCl$_3$, 500 MHz) δ 7.13-7.10 (m, 2H), 6.97-6.94 (m, 2H), 5.88 (br s, 2H), 4.08 (q, 2H), 2.02 (s, 6H), 1.46 (t, 3H); MS (ESI) 216 (M+H)$^+$.

Acetic anhydride (8.5 mL, 89 mmol) and hydriodic acid (0.48 mL, 6.3 mmol) were added to 2,5-dimethyl-1-(4-ethoxyphenyl)pyrrole (8.0 g, 37 mmol) under nitrogen and the resulting mixture maintained at 100° C. overnight. After cooling to rt, the mixture was diluted with 1N NaOH (200 mL), extracted with EtOAc (2×200 mL), and the combined extracts washed with brine (200 mL), dried (MgSO$_4$), filtered, concentrated in vacuo, and purified by flash chromatography on silica gel (15% EtOAc/hexanes) to give 3-acetyl-2,5-dimethyl-1-(4-ethoxyphenyl)pyrrole as a tan solid: $^1$H NM (CDCl$_3$, 500 MHz) δ 7.08-7.04 (m, 2H), 6.99-6.96 (m, 2H), 6.30 (s, 1H), 4.08 (q, 2H), 2.41 (s, 3H), 2.29 (s, 3H), 1.97 (s, 3H), 1.45 (t, 3H); MS (ESI) 258 (M+H)$^+$.

To a solution of 3-acetyl-2,5-dimethyl-1-(4-ethoxyphenyl) pyrrole (200 mg, 0.78 mmol) and toluene (4 mL) at 0° C. was added dropwise SnCl$_4$ (0.94 mL, 0.94 mmol, 1.0M solution in CH$_2$Cl$_2$) and p-anisoyl chloride (160 mg, 0.94 mmol). The mixture was allowed to warm to rt and heated at 50° C. overnight. After cooling to rt, the mixture was diluted with 1N NaOH (15 mL), extracted with EtOAc (2×15 mL), and the combined extracts washed with brine (15 mL), dried (MgSO$_4$), filtered, concentrated in vacuo, and purified by flash chromatography (0-33% EtOAc/hexanes). The resulting residue was dissolved in EtOH (5 mL) and hydrazine (0.5 mL). The solution was stirred at 50° C. overnight, cooled to rt, and concentrated in vacuo to give 6-(4-ethoxyphenyl)-1-(4-methoxyphenyl)-4,5,7-trimethyl-6H-pyrrolo[3,4-d]pyridazine as a light yellow solid: $^1$H NMR (CDCl$_3$, 500 MHz) δ 7.57-7.54 (m, 2H), 7.12-7.09 (m, 2H), 7.05-7.03 (m, 2H), 6.99-6.97 (m, 2H), 4.11 (q, 2H), 3.85 (s, 3H), 2.90 (s, 3H), 2.49 (s, 3H), 1.94 (s, 3H), 1.47 (t, 3H); MS (ESI) 388 (M+H)$^+$.

EXAMPLE 2

1,4-diethyl-5,7-dimethyl-6-(4-ethoxyphenyl)-6H-pyrrolo[3,4-d]pyridazine

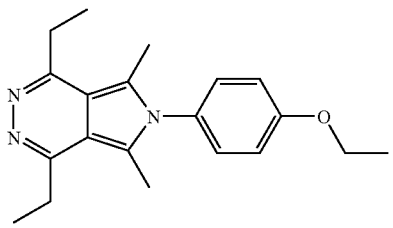

To a solution of 2,5-dimethyl-1-(4-ethoxyphenyl)pyrrole (EXAMPLE 1) (1.0 g, 4.7 mmol) and toluene (15 mL) at 0° C. was added dropwise SnCl$_4$ (4.7 mL, 4.7 mmol, 1.0M solution in CH$_2$Cl$_2$) and propionyl chloride (0.40 mL, 4.7 mmol). The mixture was warmed to rt and then heated at 50° C. overnight. After cooling to rt, the mixture was quenched with 1N NaOH (50 mL), extracted with EtOAc (2×50 mL), the combined extracts washed with brine (50 mL), dried (MgSO$_4$), filtered, concentrated in vacuo, and purified by flash chromatography on silica gel (0-25% EtOAc/hexanes). The resulting residue was dissolved in EtOH (10 mL) and hydrazine (0.1 mL). The resulting solution was maintained at 50° C. overnight, cooled to rt, and concentrated in vacuo to give 1,4-diethyl-5,7-dimethyl-6-(4-ethoxyphenyl)-6H-pyrrolo[3,4-d]pyridazine as a light yellow solid: $^1$H NMR (CDCl$_3$, 500 MHz) δ 7.13-7.10 (m, 2H), 7.06-7.03 (m, 2H), 4.12 (q, 2H), 3.11 (q, 4H), 2.40 (s, 6H), 1.48 (t, 3H), 1.39 (t, 6H); MS (ESI) 324 (M+H)$^+$.

EXAMPLE 3

6-(4-ethoxyphenyl)-1-ethyl-4,5,7-trimethyl-6H-pyrrolo[3,4-d]pyridazine

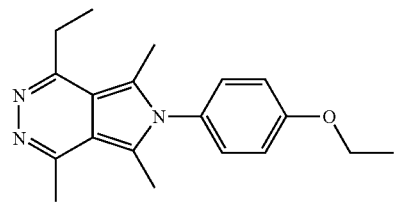

Utilizing the general procedure outlined in EXAMPLE 1, 3-acetyl-2,5-dimethyl-1-(4-ethoxyphenyl)pyrrole (200 mg, 0.78 mmol) and propionyl chloride (0.08 mL, 0.94 mmol) reacted to give 6-(4-ethoxyphenyl)-1-ethyl-4,5,7-trimethyl-6H-pyrrolo[3,4-d]pyridazine as a light yellow solid: $^1$H NMR (CDCl$_3$, 500 MHz) δ 7.13-7.11 (m, 2H), 7.08-7.05 (m, 2H), 4.13 (q, 2H), 3.15 (q, 2H), 2.85 (s, 3H), 2.45 (s, 3H), 2.42 (s, 3H), 1.49 (t, 3H), 1.40 (t, 3H); MS (ESI) 310 (M+H)$^+$.

EXAMPLE 4

6-(4-ethoxyphenyl)-1-phenyl-4,5,7-trimethyl-6H-pyrrolo[3,4-d]pyridazine

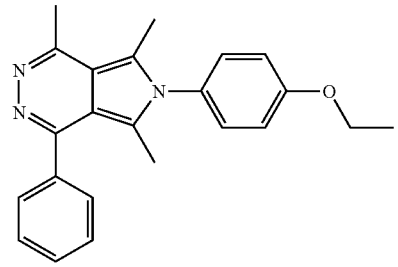

To a solution of 2,5-dimethyl-1-(4-ethoxyphenyl)pyrrole (EXAMPLE 1) (1.0 g, 4.7 mmol) and toluene (15 mL) at 0° C. was added dropwise SnCl$_4$ (4.7 mL, 4.7 mmol, 1.0M solution in CH$_2$Cl$_2$) and benzoyl chloride (0.54 mL, 4.7 mmol). The mixture was warmed to rt and heated at 50° C. overnight. After cooling to rt, the mixture was diluted with 1N NaOH (50 mL), extracted with EtOAc (2×50 mL), the combined extracts washed with brine (50 mL), dried MgSO$_4$), filtered, concentrated in vacuo, and purified by flash chromatography on silica gel (0-25% EtOAc/hexanes) to give 3-benzoyl-2,5-dimethyl-1-(4ethoxyphenyl)pyrrole as a tan solid: $^1$H NMR (CDCl$_3$, 500 MHz) δ 7.84-7.82 (m, 2H), 7.52-7.43 (m, 3H), 7.14-7.12 (m, 2H), 7.01-6.98 (m, 2H), 6.18 (s, 1H), 4.10 (q, 2H), 2.33 (s, 3H), 1.98 (s, 3H), 1.47 (t, 3H). MS (ESI) 320 (M+H)$^+$.

To a solution of 3-benzoyl-2,5-dimethyl-1-(4-ethoxyphenyl)pyrrole (201 mg, 0.63 mmol) and toluene (5 mL) at 0° C. was added dropwise SnCl$_4$ (0.76 mL, 0.76 mmol, 1.0M solution in CH$_2$Cl$_2$) and acetyl chloride (0.06 mL, 0.76 mmol).

The mixture was warmed to rt overnight, quenched with 1N NaOH (10 mL), extracted with EtOAc (2×20 mL), the combined extracts washed with brine (50 mL), dried (MgSO$_4$), filtered, concentrated in vacuo, and purified by flash chromatography on silica gel (0-33% EtOAc/hexanes). The resulting residue was dissolved in EtOH (5 mL) and hydrazine (0.1 mL). The solution was stirred at rt overnight and concentrated in vacuo to give 6-(4-ethoxyphenyl)-1-phenyl-4,5,7-trimethyl-6H-pyrrolo[3,4-d]pyridazine as a tan solid: $^1$H NMR (CDCl$_3$, 500 MHz) δ 7.62-7.59 (m, 2H), 7.47-7.44 (m, 3H), 7.12-7.09 (m, 2H), 7.05-7.02 (m, 2H), 4.11 (q, 2H), 2.89 (s, 3H), 2.49 (s, 3H), 1.87 (s, 3H), 1.47 (t, 3H). MS (ESI) 358 (M+H)$^+$.

EXAMPLE 5

6-(4-ethoxyphenyl)-1-(3-methoxyphenyl)-4,5,7-trimethyl-6H-pyrrolo[3,4-d]pyridazine

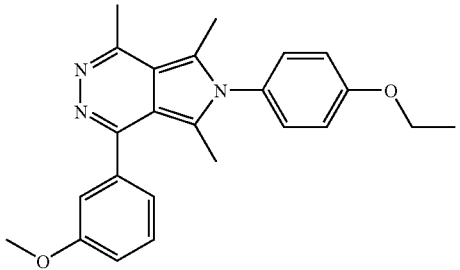

Utilizing the general procedure in EXAMPLE 1, 3-acetyl-2,5-dimethyl-1-(4-ethoxyphenyl)pyrrole (200 mg, 0.78 mmol) and m-anisoyl chloride (0.13 mL, 0.94 mmol) reacted to give 6-(4-ethoxyphenyl)-1-(3-methoxyphenyl)-4,5,7-trimethyl-6H-pyrrolo[3,4-d]pyridazine as a light yellow solid: $^1$H NMR (CDCl$_3$, 500 MHz) δ 7.38-7.33 (m, 1H), 7.18-7.14 (m, 2H), 7.13-7.08 (m, 2H), 7.07-7.02 (m, 2H), 7.01-6.97 (m, 1H), 4.11 (q, 2H), 3.84 (s, 3H), 2.96 (s, 3H), 2.51 (s, 3H), 1.92 (s, 3H), 1.47 (t, 3H); MS (ESI) 388 (M+H)$^+$.

EXAMPLE 6

6-(4-ethoxyphenyl)-1-(3-benzyl)-4,5,7-trimethyl-6H-pyrrolo[3,4-d]pyridazine

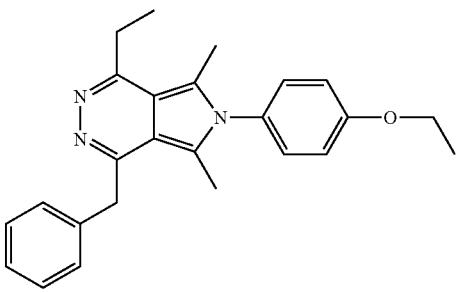

Utilizing the general procedure in EXAMPLE 1, 3-acetyl-2,5-dimethyl-1-(4-ethoxyphenyl)pyrrole (200 mg, 0.78 mmol) and phenacetyl chloride (0.16 mL, 0.94 mmol) reacted to give 6-(4-ethoxyphenyl)-1-(3-benzyl)4,5,7-trimethyl-6H-pyrrolo[3,4-d]pyridazine as a light yellow solid: $^1$H NMR (CDCl$_3$, 500 MHz) δ 7.38-7.33 (m, 1H), 7.18-7.14 (m, 3H), 7.13-7.08 (m, 2H), 7.07-7.02 (m, 2H), 7.01-6.97 (m, 1H), 4.51 (s, 2H), 4.11 (q, 2H), 3.84 (s, 3H), 2.96 (s, 3H), 2.51 (s, 3H), 1.92 (s, 3H), 1.47 (t, 3H); MS (ESI) 372 (M+H)$^+$.

EXAMPLE 7

1-(4chlorophenyl)-6-(4-ethoxyphenyl)-4,5,7-trimethyl-6H-pyrrolo[3,4-d]pyridazine

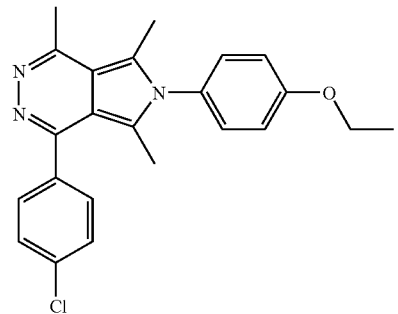

Utilizing the general procedure outlined in EXAMPLE 1, 3-acetyl-2,5-dimethyl-1-(4-ethoxyphenyl)pyrrole (200 mg, 0.78 mmol) and 4-chlorobenzoyl chloride (0.14 mL, 0.94 mmol) reacted to give 1-(4-chlorophenyl)-6-(4-ethoxyphenyl)-4,5,7-trimethyl-6H-pyrrolo[3,4-d]pyridazine as a light yellow solid: $^1$H NMR (CDCl$_3$, 500 MHz) δ 7.58-7.53 (m, 2H), 7.46-7.41 (m, 2H), 7.14-7.08 (m, 2H), 7.07-7.02 (m, 2H), 4.11 (q, 2H), 2.94 (s, 3H), 2.51 (s, 3H), 1.91 (s, 3H), 1.48 (t, 3H); MS (ESI) 392 (M+H)$^+$.

EXAMPLE 8

6-(4-ethoxyphenyl)-1-(2-methoxyphenyl)-4,5,7-trimethyl-6H-pyrrolo[3,4-d]pyridazine

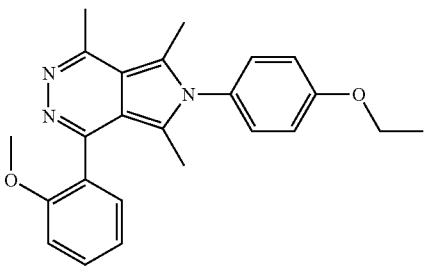

Utilizing the general procedure outlined in EXAMPLE 1, 3-acetyl-2,5-dimethyl-1-(4-ethoxyphenyl)pyrrole (200 mg, 0.78 mmol) and o-anisoyl chloride (0.14 mL, 0.94 mmol) reacted to give 6-(4-ethoxyphenyl)-1-(2-methoxyphenyl)4,5,7-trimethyl-6H-pyrrolo[3,4-d]pyridazine as a light yellow solid: $^1$H NMR (CDCl$_3$, 500 MHz) δ 7.47-7.41 (m, 1H), 7.39-7.34 (m, 1H), 7.17-7.12 (m, 1H), 7.10-7.01 (m, 4H), 7.00-6.95 (m, 1H), 4.10 (q, 2H), 3.73 (s, 3H), 2.96 (s, 3H), 2.49 (s, 3H), 1.77 (s, 3H), 1.47 (t, 3H); MS (ESI) 388 (M+H)$^+$.

EXAMPLE 9

1-(3chlorophenyl)-6-(4-ethoxyphenyl)4,5,7-trimethyl-6H-pyrrolo[3,4-d]pyridazine

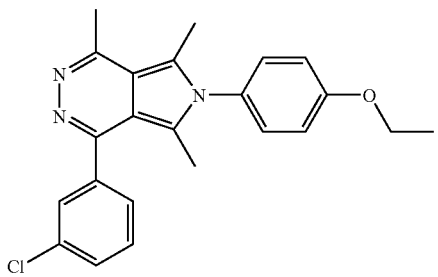

Utilizing the general procedure outlined in EXAMPLE 1, 3-acetyl-2,5-dimethyl-1-(4-ethoxyphenyl)pyrrole (200 mg, 0.78 mmol) and 3-chlorobenzoyl chloride (0.12 mL, 0.94 mmol) reacted to give 1-(3-chlorophenyl)-6-(4-ethoxyphenyl)-4,5,7-trimethyl-6H-pyrrolo[3,4-d]pyridazine as a light yellow solid: $^1$H NMR (CDCl$_3$, 500 MHz) δ 7.62-7.58 (m, 1H), 7.53-7.48 (m, 1H), 7.44-7.37 (m, 2H), 7.14-7.09 (m, 2H), 7.07-7.03 (m, 2H), 4.11 (q, 2H), 2.97 (s, 3H), 2.51 (s, 3H), 1.91 (s, 3H), 1.47 (t, 3H); MS (ESI) 392 (M+H)$^+$.

EXAMPLE 10

1-(2-chlorophenyl)-6-(4-ethoxyphenyl)-4,5,7-trimethyl-6H-pyrrolo[3,4-d]pyridazine

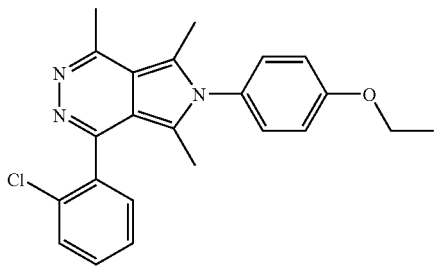

Utilizing the general procedure outlined in EXAMPLE 1, 3-acetyl-2,5-dimethyl-1-(4-ethoxyphenyl)pyrrole (200 mg, 0.78 mmol) and 2-chlorobenzoyl chloride (0.12 mL, 0.94 mmol) reacted to give 1-(2-chlorophenyl)-6-(4-ethoxyphenyl)-4,5,7-trimethyl-6H-pyrrolo[3,4-d]pyridazine as a light yellow solid: $^1$H NMR (CDCl$_3$, 500 MHz) δ 7.48-7.43 (m, 2H), 7.40-7.34 (m, 2H), 7.17-7.12 (m, 1H), 7.08-6.99 (m, 3H), 4.10 (q, 2H), 2.93 (s, 3H), 2.50 (s, 3H), 1.74 (s, 3H), 1.46 (t, 3H); MS (ESI) 392 (M+H)$^+$.

EXAMPLE 11

6-(4-ethoxyphenyl)-1-(4-methylphenyl)-4,5,7-trimethyl-6H-pyrrolo[3,4-d]pyridazine

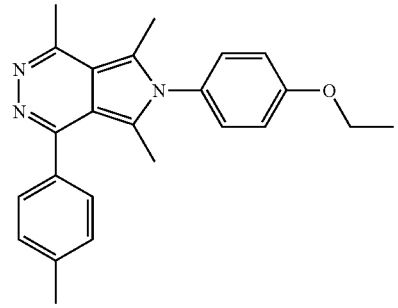

Utilizing the general procedure outlined in EXAMPLE 1, 3-acetyl-2,5-dimethyl-1-(4-ethoxyphenyl)pyrrole (214 mg, 0.83 mmol) and p-toluoyl chloride (0.13 mL, 1.0 mmol) reacted to give 6-(4-ethoxyphenyl)-1-(4-methylphenyl)-4,5,7-trimethyl-6H-pyrrolo[3,4-d]pyridazine as a yellow solid: $^1$H NMR (CDCl$_3$, 500 MHz) δ 7.50 (d, 2H), 7.26 (d, 2H), 7.12-7.10 (m, 2H), 7.05-7.03 (m, 2H), 4.11 (q, 2H), 2.93 (s, 3H), 2.50 (s, 3H), 2.41 (s, 3H), 1.91 (s, 3H), 1.47 (t, 3H); MS ESI) 372 (M+H)$^+$.

EXAMPLE 12

6-(4-ethoxyphenyl)-1-(4-ethylphenyl)-4,5,7-trimethyl-6H-pyrrolo[3,4-d]pyridazine

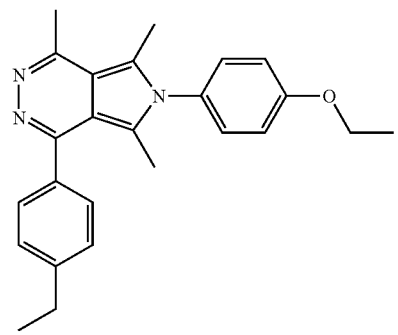

Utilizing the general procedure outlined in EXAMPLE 1, 3-acetyl-2,5-dimethyl-1-(4-ethoxyphenyl)pyrrole (214 mg, 0.83 mmol) and 4-ethylbenzoyl chloride (0.15 mL, 1.0 mmol) reacted to give 6-(4-ethoxyphenyl)-1-(4-ethylphenyl)-4,5,7-trimethyl-6H-pyrrolo[3,4-d]pyridazine as a yellow solid: $^1$H NMR (CDCl$_3$, 500 MHz) δ 7.54-7.51 (m, 2H), 7.29-7.25 (m, 2H), 7.12-7.09 (m, 2H), 7.06-7.03 (m, 2H), 4.11 (q, 2H), 2.93 (s, 3H), 2.71 (q, 2H), 2.50 (s, 3H), 1.91 (s, 3H), 1.47 (t, 3H), 1.26 (t, 3H); MS (ESI) 386 (M+H)$^+$.

EXAMPLE 13

1-(1-cyclopentethyl)-6-(4-ethoxyphenyl)-4,5,7-trimethyl-6H-pyrrolo[3,4-d]pyridazine

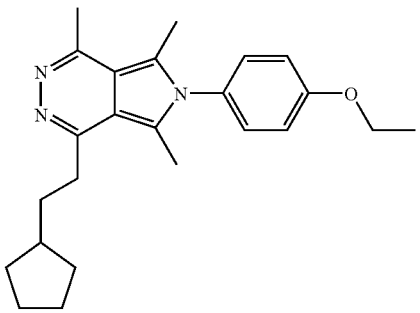

Utilizing the general procedure outlined in EXAMPLE 1, 3-acetyl-2,5-dimethyl-1-(4-ethoxyphenyl)pyrrole (257 mg, 1.0 mmol) and 3-cyclopentylpropionyl chloride (0.18 mL, 1.2 mmol) reacted to give 1-(1-cyclopentylethyl)-6-(4-ethoxyphenyl)-4,5,7-trimethyl-6H-pyrrolo[3,4-d]pyridazine as a white solid: $^1$H NMR (CDCl$_3$, 500 MHz) δ 7.13-7.09 (m, 2H), 7.07-7.03 (m, 2H), 4.11 (q, 2H), 3.09 (dd, 2H), 2.77 (s, 3H), 2.42 (s, 3H), 2.40 (s, 3H), 1.98-1.89 (m, 1H), 1.87-1.77 (m, 4H), 1.63-1.56 (m, 2H), 1.55-1.47 (m, 2H), 1.48 (t, 3H), 1.20-1.15 (m, 2H); MS (ESI) 378 (M+H)$^+$.

EXAMPLE 14

1-(4-ethoxyphenyl)-6-(4-ethoxyphenyl)-4,5,7-trimethyl-6H-pyrrolo[3,4-d]pyridazine

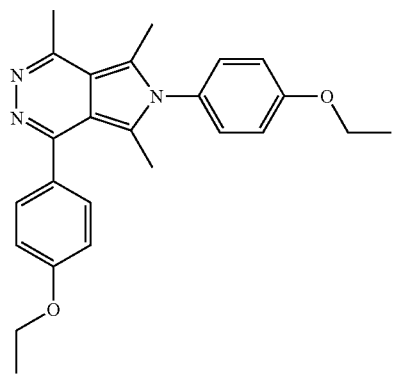

Utilizing the general procedure outlined in EXAMPLE 1, 3-acetyl-2,5-dimethyl-1-(4-ethoxyphenyl)pyrrole (214 mg, 0.83 mmol) and 4-ethoxybenzoyl chloride (185 mg, 1.0 mmol) reacted to give 1-(4-ethoxyphenyl)-6-(4-ethoxyphenyl)-4,5,7-trimethyl-6H-pyrrolo[3,4-d]pyridazine as a white solid: $^1$H NMR (CDCl$_3$, 500 MHz) δ 7.55 (d, 2H), 7.12-7.09 (m, 2H), 7.05-7.03 (m, 2H), 6.97 (d, 2H), 4.14-4.06 (m, 4H), 2.93 (s, 3H), 2.50 (s, 3H), 1.94 (s, 3H), 1.47 (t, 3H), 1.43 (t, 3H); MS (ESI) 402 (M+H)$^+$.

EXAMPLE 15

1-(cyclopropyl)-6-(4-ethoxyphenyl)-4,5,7-trimethyl-6H-pyrrolo[3,4-d]pyridazine

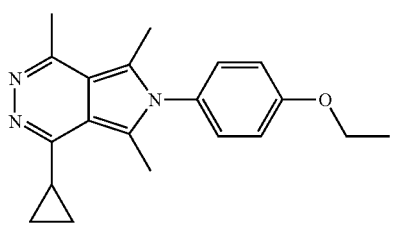

Utilizing the general procedure outlined in EXAMPLE 1, 3-acetyl-2,5-dimethyl-1-(4-ethoxyphenyl)pyrrole (257 mg, 1.0 mmol) and cyclopropanecarbonyl chloride (0.11 mL, 1.2 mmol) reacted to give 1-(cyclopropyl)-6-(4-ethoxyphenyl)-4,5,7-trimethyl-6H-pyrrolo[3,4-d]pyridazine as a white solid: $^1$H NMR (CDCl$_3$, 500 MHz) δ 7.14-7.10 (m, 2H), 7.07-7.03 (m, 2H), 4.12 (q, 2H), 2.76 (s, 3H), 2.52 (s, 3H), 2.42 (s, 3H), 2.38 (quintet, 1H), 1.49 (t, 3H), 1.34-1.32 (m, 2H), 0.99-0.96 (m, 2H); MS (ESI) 322 (M+H)$^+$.

EXAMPLE 16

6-(4-ethoxyphenyl)-1-(2-methylpropyl)-4,5,7-trimethyl-6H-pyrrolo[3,4-d]pyridazine

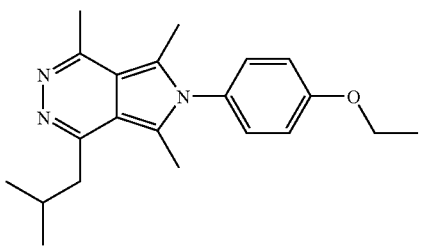

Utilizing the general procedure outlined in EXAMPLE 1, 3-acetyl-2,5-dimethyl-1-(4-ethoxyphenyl)pyrrole (257 mg, 1.0 mmol) and isovaleryl chloride (0.15 mL, 1.2 mmol) reacted to give 6-(4-ethoxyphenyl)-1-(2-methylpropyl)-4,5,7-trimethyl-6H-pyrrolo[3,4-d]pyridazine as a white solid: $^1$H NMR (CDCl$_3$, 500 MHz) δ 7.12-7.09 (m, 2H), 7.06-7.03 (m, 2H), 4.12 (q, 2H), 2.94 (d, 2H), 2.78 (s, 3H), 2.42 (s, 3H), 2.38 (s, 3H), 2.18-2.10 (m, 1H), 1.48 (t, 3H), 1.01 (d, 6H); MS (ESI) 338 (M+H)$^+$.

EXAMPLE 17

1-(cyclopentyl)-6-(4-ethoxyphenyl)-4,5,7-trimethyl-6H-pyrrolo[3,4-d]pyridazine

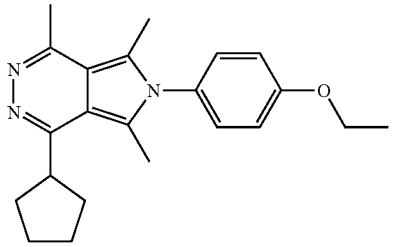

Utilizing the general procedure outlined in EXAMPLE 1, 3-acetyl-2,5-dimethyl-1-(4-ethoxyphenyl)pyrrole (257 mg, 1.0 mmol) and cyclopentanecarbonyl chloride (0.15 mL, 1.2 mmol) reacted to give 1-(cyclopentyl)-6-(4-ethoxyphenyl)4,5,7-trimethyl-6H-pyrrolo[3,4-d]pyridazine as a white solid: $^1$H NMR (CDCl$_3$, 500 MHz) δ 7.12-7.09 (m, 2H), 7.06-7.02 (m, 2H), 4.12 (q, 2H), 3.67 (quintet, 1H), 2.77 (s, 3H), 2.42 (s, 6H), 2.26-2.19 (m, 2H), 2.02-1.93 (m, 2), 1.92-1.84 (m, 2H) 1.70-1.63 (m, 2H), 1.48 (t, 3H); MS (ESI) 350 (M+H)$^+$.

EXAMPLE 18

1-(cyclopentylmethyl)-6-(4-ethoxyphenyl)-4,5,7-trimethyl-6H-pyrrolo[3,4-d]pyridazine

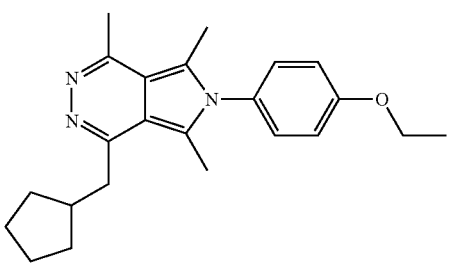

Utilizing the general procedure outlined in EXAMPLE 1, 3-acetyl-2,5-dimethyl-1-(4-ethoxyphenyl)pyrrole (257 mg, 1.0 mmol) and cyclopentylacetyl chloride (176 mg, 1.2 mmol) reacted to give 1-(cyclopentylmethyl)-6-(4-ethoxyphenyl)-4,5,7-trimethyl-6H-pyrrolo[3,4-d]pyridazine as a white solid: $^1$H NMR (CDCl$_3$, 500 MHz) δ 7.13-7.09 (m, 2H), 7.06-7.02 (m, 2H), 4.12 (q, 2H), 3.08 (d, 2H), 2.78 (s, 3H), 2.42 (s, 3H), 2.40 (s, 3H), 2.41-2.32 (m, 1H), 1.79-1.72 (m, 2H), 1.70-1.62 (m, 2H) 1.55-1.46 (m, 2H), 1.48 (t, 3H), 1.44-1.37 (m, 2H); MS (ESI) 364 (M+H)$^+$.

EXAMPLE 19

1-(cyclohexyl)-6-(4-ethoxyphenyl)-4,5,7-trimethyl-6H-pyrrolo[3,4-d]pyridazine

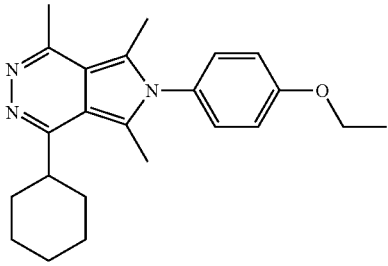

Utilizing the general procedure outlined in EXAMPLE 1, 3-acetyl-2,5-dimethyl-1-(4-ethoxyphenyl)pyrrole (257 mg, 1.0 mmol) and cyclohexanecarbonyl chloride (0.16 mL, 1.2 mmol) reacted to give 1-(cyclohexyl)-6-(4-ethoxyphenyl)-4,5,7-trimethyl-6H-pyrrolo[3,4-d]pyridazine as a white solid: $^1$H NMR (CDCl$_3$, 500 MHz) δ 7.12-7.08 (m, 2H), 7.06-7.02 (m, 2H), 4.12 (q, 2H), 3.14 (tt, 1H), 2.77 (s, 3H), 2.41 (s, 3H), 2.39 (s, 3H), 2.04-1.98 (m, 2H), 1.95-1.82 (m, 4H), 1.78-1.72 (m, 1H) 1.48 (t, 3H), 1.44-1.34 (m, 3H); MS (ESI) 364 (M+H)$^+$.

EXAMPLE 20

6-(4-ethoxyphenyl)-1-pentyl-4,5,7-trimethyl-6H-pyrrolo[3,4-d]pyridazine

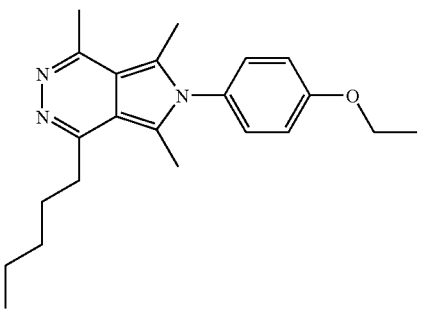

Utilizing the general procedure outlined in EXAMPLE 1, 3-acetyl-2,5-dimethyl-1-(4-ethoxyphenyl)pyrrole (257 mg, 1.0 mmol)-and hexanoyl chloride (0.17 mL, 1.2 mmol) reacted to give 6-(4-ethoxyphenyl)-1-penyl-4,5,7-trimethyl-6H-pyrrolo[3,4-d]pyridazine as a white solid: $^1$H NMR (CDCl$_3$, 500 MHz) δ 7.13-7.09 (m, 2H), 7.06-7.03 (m, 2H), 4.12 (q, 2H), 3.06 (dd, 2H), 2.77 (s, 3H), 2.42 (s, 3H), 2.39 (s, 3H), 1.81-1.75 (m, 2H), 1.50-1.44 (m, 2), 1.48 (t, 3H), 1.42-1.34 (m, 2H), 0.89 (t, 3H); MS (ESI) 352 (M+H)$^+$.

EXAMPLE 21

6-(4-ethoxyphenyl)-1-(4-fluorophenyl)-4,5,7-trimethyl-6H-pyrrolo[3,4-d]pyridazine

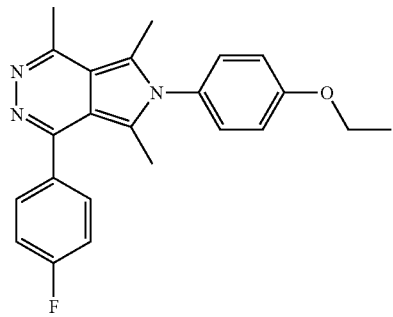

Utilizing the general procedure outlined in EXAMPLE 1, 3-acetyl-2,5-dimethyl-1-(4-ethoxyphenyl)pyrrole (214 mg, 0.83 mmol) and 4-fluorobenzoyl chloride (0.12 mL, 1.0 mmol) reacted to give 6-(4-ethoxyphenyl)-1-(4-fluorophenyl)-4,5,7-trimethyl-6H-pyrrolo[3,4-d]pyridazine as a yellowish solid: $^1$H NMR (CDCl$_3$, 500 MHz) δ 7.62-7.58 (m, 2H), 7.18-7.08 (m, 4H), 7.07-7.03 (m, 2H), 4.11 (q, 2H), 2.95 (s, 3H), 2.51 (s, 3H), 1.91 (s, 3H), 1.48 (t, 3H); MS (ESI) 376 (M+H)$^+$.

EXAMPLE 22

6-(4-ethoxyphenyl)-1-(2,2,4-trimethylpentyl)-4,5,7-trimethyl-6H-pyrrolo[3,4-d]pyridazine

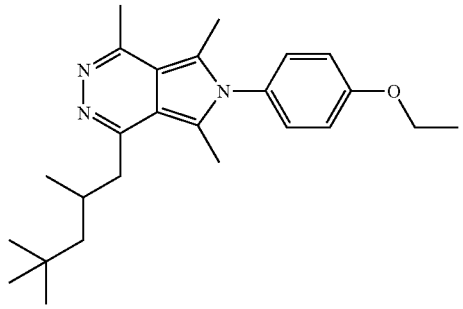

Utilizing the general procedure outlined in EXAMPLE 1, 3-acetyl-2,5-dimethyl-1-(4-ethoxyphenyl)pyrrole (257 mg, 1.0 mmol) and 3,5,5-trimethylhexanoyl chloride (0.23 mL, 1.2 mmol) reacted to give 6-(4-ethoxyphenyl)-1-(2,2,4-trimethylpentyl)4,5,7-trimethyl-6H-pyrrolo[3,4-d]pyridazine as a white solid:
$^1$H NMR (CDCl$_3$, 500 MHz) δ 7.14-7.08 (m, 2H), 7.06-7.03 (m, 2H), 4.12 (q, 2H), 2.99 (dd, 1H), 2.92 (dd, 1H), 2.78 (s, 3H), 2.42 (s, 3H), 2.40 (s, 3H), 2.15 (quintet, 1H), 1.53 (dd, 1H), 1.49 (t, 3H), 1.21 (dd, 1H), 1.02 (d, 3H), 0.82 (s, 9H); MS (ESI) 394 (M+H)$^+$.

EXAMPLE 23

6-(4-ethoxyphenyl)-1-(1-phenylethyl)-4,5,7-trimethyl-6H-pyrrolo[3,4-d]pyridazine

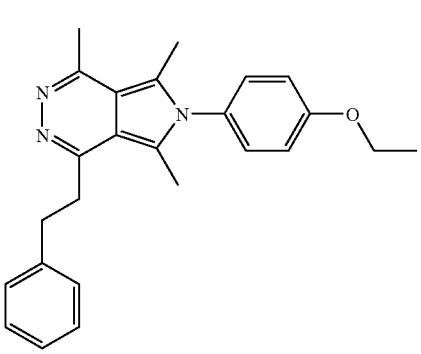

Utilizing the general procedure outlined in EXAMPLE 1, 3-acetyl-2,5-dimethyl-1-(4-ethoxyphenyl)pyrrole (257 mg, 1.0 mmol) and hydrocinnamoyl chloride (0.18 mL, 1.2 mmol) reacted to give 6-(4-ethoxyphenyl)-1-(1-phenylethyl)-4,5,7-trimethyl-6H-pyrrolo[3,4-d]pyridazine as a white solid: $^1$H NMR (CDCl$_3$, 500 MHz) δ 7.31-7.26 (m, 4H), 7.22-7.18 (m, 1H), 7.12-7.09 (m, 2H), 7.06-7.04 (m, 2H), 4.12 (q, 2H), 3.38 (dd, 2H), 3.15 (dd, 2H), 2.79 (s, 3H), 2.43 (s, 3H), 2.41 (s, 3H), 1.48 (t, 3H); MS (ESI) 386 (M+H)$^+$.

EXAMPLE 24

1-(2,2-dimethylpropyl)-6-(4-ethoxyphenyl)-4,5,7-trimethyl-6H-pyrrolo[3,4-d]pyridazine

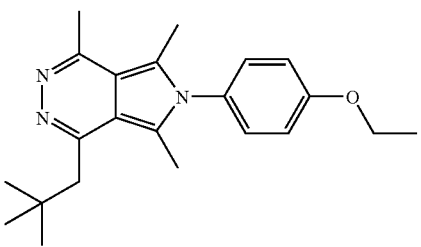

Utilizing the general procedure outlined in EXAMPLE 1, 3-acetyl-2,5-dimethyl-1-(4-ethoxyphenyl)pyrrole (257 mg, 1.0 mmol) and tert-butylacetyl chloride (0.17 mL, 1.2 mmol) reacted to give 1-(2,2-dimethylpropyl)-6-(4-ethoxyphenyl)4,5,7-trimethyl-6H-pyrrolo[3,4-d]pyridazine as a white solid: $^1$H NMR (CDCl$_3$, 500 MHz) δ 7.12-7.08 (m, 2H), 7.06-7.02 (m, 2H), 4.12 (q, 2H), 3.03 (s, 2H), 2.79 (s, 3H), 2.43 (s, 3H), 2.42 (s, 3H), 1.48 (t, 3H), 1.06 (s, 9H); MS (ESI) 352 (M+H)$^+$.

EXAMPLE 25

6-(4-ethoxyphenyl)-1-(4-methoxyphenylmethyl)-4,5,7-trimethyl-6H-pyrrolo[3,4-d]pyridazine

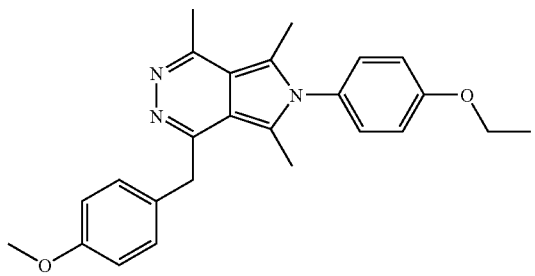

Utilizing the general procedure outlined in EXAMPLE 1, 3-acetyl-2,5-dimethyl-1-(4-ethoxyphenyl)pyrrole (257 mg, 1.0 mmol) and 4-methoxyphenylacetyl chloride (0.19 mL, 1.2 mmol) reacted to give 6-(4-ethoxyphenyl)-1-(4-methoxyphenylmethyl)-4,5,7-trimethyl-6H-pyrrolo[3,4-d]pyridazine as a white solid: $^1$H NMR (CDCl$_3$, 500 MHz) δ 7.16 (d, 2H), 7.05-6.98 (m, 4H), 6.76 (d, 2H), 4.39 (s, 2H), 4.09 (q, 2H), 3.74 (s, 3H), 2.81 (s, 3H), 2.41 (s, 3H), 2.19 (s, 3H), 1.46 (t, 3H); MS (ESI) 402 (M+H)$^+$.

EXAMPLE 26

6-(4-ethoxyphenyl)-1-(4-(trifluoromethoxy)phenyl)-4,5,7-trimethyl-6H-pyrrolo[3,4-d]pyridazine hydrochloride

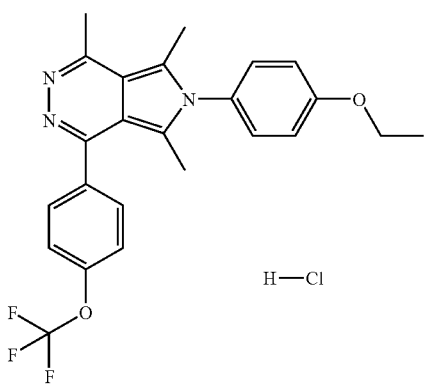

Utilizing the general procedure outlined in EXAMPLE 1, 3-acetyl-2,5-dimethyl-1-(4-ethoxyphenyl)pyrrole (214 mg, 0.83 mmol) and 4-(trifluoromethoxy)benzoyl chloride (0.16 mL, 1.0 mmol) reacted to give the product which was taken up in hot ether, precipitated with HCl in ether, and filtered to give 6-(4-ethoxyphenyl)-1-(4-(trifluoromethoxy)phenyl)-4,5,7-trimethyl-6H-pyrrolo[3,4-d]pyridazine as a yellow solid: $^1$H NMR (d$_6$-DMSO, 500 MHz) δ 7.86 (d, 2H), 7.62 (d, 2H), 7.38 (d, 2H), 7.21 (d, 2H), 4.14 (q, 2H), 3.14 (s, 3H), 2.60 (s, 3H), 1.94 (s, 3H), 1.38 (t, 3H); MS (ESI) 442 (M+H)$^+$.

EXAMPLE 27

6-(4-ethoxyphenyl)-1-(3-methoxyphenylmethyl)-4,5,7-trimethyl-6H-pyrrolo[3,4-d]pyrdazine

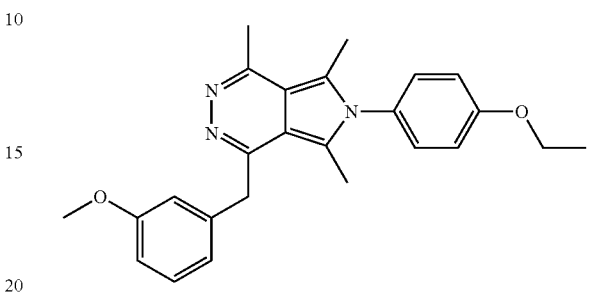

Utilizing the general procedure outlined in EXAMPLE 1, 3-acetyl-2,5-dimethyl-1-(4-ethoxyphenyl)pyrrole (257 mg, 1.0 mmol) and 3-methoxyphenylacetyl chloride (0.19 mL, 1.2 mmol) reacted to give 6-(4-ethoxyphenyl)-1-(3-methoxyphenylmethyl)4,5,7-trimethyl-6H-pyrrolo[3,4-d]pyridazine as a white solid: $^1$H NMR (CDCl$_3$, 500 MHz) δ 7.15 (dd, 1H), 7.06-7.03 (m, 2H), 7.02-6.98 (m, 2H), 6.83 (d, 1H), 6.80 (s, 1H), 6.71 (d, 1H), 4.43 (s, 2H), 4.09 (q, 2H), 3.72 (s, 3H), 2.81 (s, 3H), 2.42 (s, 3H), 2.20 (s, 3H), 1.46 (t, 3H); MS (ESI) 402 (M+H)$^+$.

EXAMPLE 28

1-(4-bromophenyl)-6-(4-ethoxyphenyl)-4,5,7-trimethyl-6H-pyrrolo[3,4-d]pyridazine hydrochloride

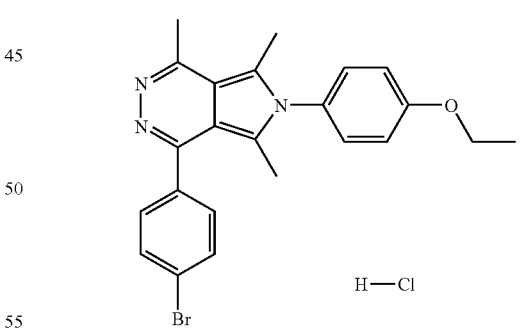

Utilizing the general procedure outlined in EXAMPLE 1, 3-acetyl-2,5-dimethyl-1-(4-ethoxyphenyl)pyrrole (214 mg, 0.83 mmol) and p-bromobenzoyl chloride (220 mg, 1.0 mmol) reacted to give the product which was taken up in hot ether, precipitated with HCl in ether, and filtered to give 1-(4-bromophenyl)-6-(4-ethoxyphenyl)-4,5,7-trimethyl-6H-pyrrolo[3,4-d]pyridazine hydrochloride as a yellow solid: $^1$H NMR (DMSO-d$_6$, 500 MHz) δ 7.83 (d, 2H), 7.66 (d, 2H), 7.37 (d, 2H), 7.20 (d, 2H), 4.14 (q, 2H), 3.12 (s, 3H), 2.59 (s, 3H), 1.94 (s, 3H), 1.38 (t, 3H); MS (ESI) 437 (M+H)$^+$.

EXAMPLE 29

1-(2,4-dimethoxyphenyl)-6-(4-ethoxyphenyl)-4,5,7-trimethyl-6H-pyrrolo[3,4-d]pyridazine hydrochloride

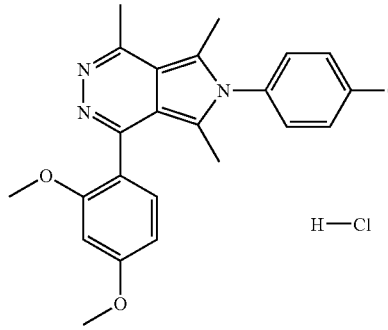

Utilizing the general procedure outlined in EXAMPLE 1, 3-acetyl-2,5-dimethyl-1-(4-ethoxyphenyl)pyrrole (214 mg, 0.83 mmol) and 2,4-dimethoxybenzoyl chloride (201 mg, 1.0 mmol) reacted to give the product which was taken up in hot ether, precipitated with HCl in ether, and filtered to give 1-(2,4-dimethoxyphenyl)-6-(4-ethoxyphenyl)-4,5,7-trimethyl-6H-pyrrolo[3,4-d]pyridazine hydrochloride as a yellow solid: $^1$H NMR (DMSO-$d_6$, 500 MHz) δ 7.41-7.30 (m, 3H), 7.18 (d, 2H), 6.80-6.73 (m, 2H), 4.14 (q, 2H), 3.87 (s, 3H), 3.76 (s, 3H), 3.03 (br s, 3H), 2.54 (s, 3H), 1.87 (s, 3H), 1.38 (t, 3H); MS (ESI) 418 (M+H)$^+$.

EXAMPLE 30

1-(4-biphenyl)-6-(4-ethoxyphenyl)-4,5,7-trimethyl-6H-pyrrolo[3,4-d]pyridazine

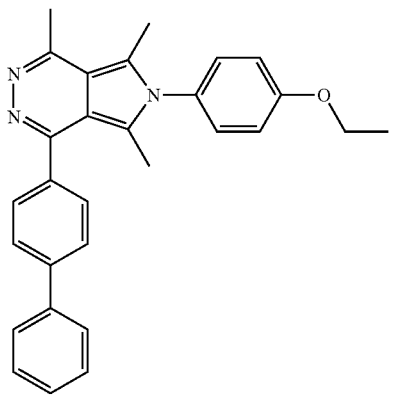

Utilizing the general procedure outlined in EXAMPLE 1, 3-acetyl-2,5-dimethyl-1-(4-ethoxyphenyl)pyrrole (214 mg, 0.83 mmol) and 4-biphenylcarbonyl chloride (217 mg, 1.0 mmol) reacted to give 1-(4-biphenyl)-6-(4-ethoxyphenyl)4,5,7-trimethyl-6H-pyrrolo[3,4-d]pyridazine as a yellow solid: $^1$H NMR (CDCl$_3$, 500 MHz) δ 7.73-7.64 (m, 4H), 7.60 (d, 2H), 7.45 (t, 2H), 7.35 (t, 1H), 7.11 (d, 2H), 7.03 (d, 2H), 4.11 (q, 2H), 2.87 (s, 3H), 2.49 (s, 3H), 1.95 (s, 3H), 1.47 (t, 3H); MS (ESI) 434 (M+H)$^+$.

EXAMPLE 31

4-[6-(4-ethoxyphenyl)-4,5,7-trimethyl-6H-pyrrolo[3,4-d]pyridazin-1-yl]-butyric acid methyl ester

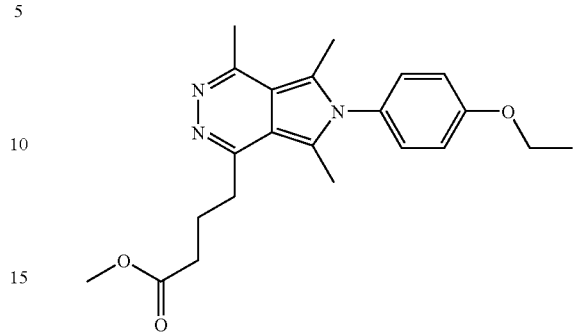

Utilizing the general procedure outlined in EXAMPLE 1, 3-acetyl-2,5-dimethyl-1-(4-ethoxyphenyl)pyrrole (771 mg, 3.0 mmol) and methyl 5-chloro-5-oxovalerate (0.63 mL, 4.5 mmol) reacted to give 5-[4-acetyl-2,5-dimethyl-1-(4-ethoxyphenyl)-1H-pyrrol-3-yl]-5-oxo-pentanoic acid methyl ester as a white solid: $^1$H NMR (CDCl$_3$, 500 MHz) δ 7.05 (d, 2H), 6.98 (d, 2H), 4.08 (q, 2H), 3.65 (s, 3H), 2.75 (t, 2H), 2.41 (s, 3H), 2.40 (t, 2H), 2.11 (s, 3H), 2.01 (s, 3H), 2.00 (quintet, 2H), 1.45 (t, 3H); MS (ESI) 386 (M+H)$^+$.

To a solution of 5-[4-acetyl-2,5-dimethyl-1-(4-ethoxyphenyl)-1H-pyrrol-3-yl]-5-oxo-pentanoic acid methyl ester (250 mg, 0.65 mmol) in ethanol (1 mL) was added a 1.0M solution of hydrazine in ethanol (0.72 mL, 0.72 mmol). The solution was stirred overnight at rt and concentrated in vacuo to give 4-[6-(4-ethoxyphenyl)-4,5,7-trimethyl-6H-pyrrolo[3,4-d]pyridazin-1-yl]-butyric acid methyl ester as a white solid: $^1$H NMR (CDCl$_3$, 500 MHz) δ 7.11-7.08 (m, 2H), 7.05-7.03 (m, 2H), 4.11 (q, 2H), 3.63 (s, 3H), 3.12 (t, 2H), 2.77 (s, 3H), 2.51 (t, 2H), 2.41 (s, 3H), 2.40 (s, 3H), 2.14 (quintet, 2H), 1.47 (t, 3H); MS (ESI) 382 (M+H)$^+$.

EXAMPLE 32

4-[6-(4-ethoxyphenyl)-4,5,7-trimethyl-6H-pyrrolo[3,4-d]pyridazin-1-yl]propionic acid methyl ester

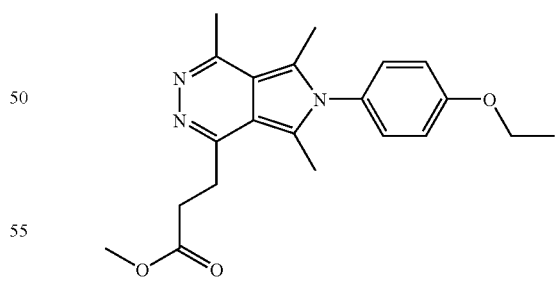

Utilizing the general procedure outlined in EXAMPLE 1, 3-acetyl-2,5-dimethyl-1-(4-ethoxyphenyl)pyrrole (771 mg, 3.0 mmol) and methyl 4-chloro-4-oxobutyrate (0.56 mL, 4.5 mmol) reacted to give 4-[4-acetyl-2,5-dimethyl-1-(4-ethoxyphenyl)-1H-pyrrol-3-yl]4-oxo-butyric acid methyl ester as a white solid: $^1$H NMR (CDCl$_3$, 500 MHz) δ 7.06 (d, 2H), 6.98 (d, 2H), 4.08 (q, 2H), 3.67 (s, 3H), 3.03 (t, 2H), 2.74 (t, 2H), 2.41 (s, 3H), 2.11 (s, 3H), 2.06 (s, 3H), 1.45 (t, 3H); MS (ESI) 372 (M+H)$^+$.

To a solution of 4-[4-acetyl-2,5-dimethyl-1-(4-ethoxyphenyl)-1H-pyrrol-3-yl]-4-oxo-butyric acid methyl ester (250 mg, 0.67 mmol) in ethanol (1 mL) was added a 1.0M solution of hydrazine in ethanol (0.74 mL, 0.74 mmol). The solution was stirred overnight at rt and concentrated in vacuo to give 4-[6-(4-ethoxyphenyl)-4,5,7-trimethyl-6H-pyrrolo[3,4-d]pyridazin-1-yl]-propionic acid methyl ester as a white solid: $^1$H NMR (CDCl$_3$, 500 MHz) δ 7.11-7.08 (m, 2H), 7.06-7.03 (m, 2H), 4.12 (q, 2H), 3.70 (s, 3), 3.43 (t, 2H), 3.00 (t, 2H), 2.79 (s, 3H), 2.44 (s, 3H), 2.42 (s, 3H), 1.48 (t, 3H); MS (ESI) 368 (M+H)$^+$.

EXAMPLE 33

1-(cyclopropyl)-6-(2,4-dimethoxyphenyl)-4,5,7-trimethyl-6H-pyrrolo[3,4-d]pyridazine

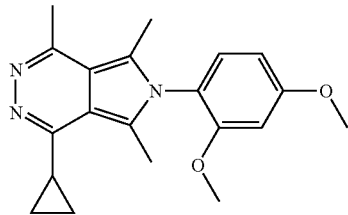

Utilizing the general procedure outlined in EXAMPLE 1, acetonyl acetone (5.88 mL, 50 mmol) and 2,4-dimethoxyaniline (7.12 mL, 50 mmol) reacted to give 1-(2,4-dimethoxyphenyl)-2,5-dimethylpyrrole as a tan solid: $^1$H NMR (CDCl$_3$, 500 MHz) δ 7.08 (dd, 1H), 6.59 (d, 1H), 6.55 (dd, 1H), 5.90 (s, 2H), 3.91 (s, 3H), 3.80 (s, 3H), 1.97 (s, 6H); MS (ESI) 232 (M+H)$^+$.

Utilizing the general procedure outlined in EXAMPLE 1, 1-(2,4-dimethoxyphenyl)-2,5-dimethylpyrrole (2.31 g, 10 mmol), acetic anhydride (5 mL), and hydriodic acid (0.13 mL, 1.7 mmol) reacted to give 3-acetyl-1-(2,4dimethoxyphenyl)-2,5-dimethylpyrrole as a tan solid: $^1$H NMR (CDCl$_3$, 500 MHz) δ 7.02 (dd, 1H), 6.59 (d, 1H), 6.55 (dd, 1H), 6.32 (s, 1H), 3.90 (s, 3H), 3.76 (s, 3H), 2.42 (s, 3H), 2.25 (s, 3H), 1.93 (s, 3H); MS (ESI) 274 (M+H)$^+$.

To a solution of 3-acetyl-1-(2,4-dimethoxyphenyl)-2,5-dimethylpyrrole (273 mg, 1.0 mmol) in toluene (5 mL) at −78° C. was added 3-cyclopropanecarbonyl chloride (0.11 mL, 1.2 mmol) followed by dropwise addition of a 1.0M solution of tin(IV) chloride in CH$_2$Cl$_2$ (1.2 mL, 1.2 mmol). The reaction was allowed to warm to room temp overnight. The solution was diluted with 0.25M NaOH, extracted with EtOAc, the organic layer washed with brine, dried over MgSO$_4$, filtered, concentrated in vacuo, and purified by flash chromatography (10-25% EtOAc/hexanes) to give the dione (MS (ESI) 342 (M +H)$^+$). The dione was taken up in ethanol (5 mL) and excess hydrazine (0.1 mL) was added. The solution was stirred at 40° C. overnight, poured into water, and filtered to give 1-(cyclopropyl)-6-(2,4-dimethoxyphenyl)-4,5,7-trimethyl-6H-pyrrolo[3,4-d]pyridazine as a white solid: $^1$H NMR (CDCl$_3$, 500 MHz) δ 7.03 (dd, 1H), 6.66-6.56 (m, 2H), 3.90 (s, 3H), 3.75 (s, 3H), 2.75 (s, 3H), 2.47 (s, 3H), 2.39 (quintet, 1H), 2.38 (s, 3H), 1.35-1.28 (m, 2H), 0.97 (dd, 2H); MS (ESI) 338 (M+H)$^+$.

EXAMPLE 34

6-(2,4-dimethoxyphenyl)-1-(4-methylphenl)-4,5,7-trimethyl-6H-pyrrolo[3,4-d]pyridazine hydrochloride

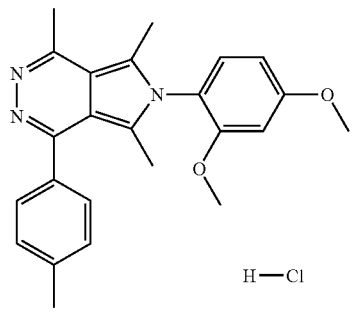

Utilizing the general procedure outlined in EXAMPLE 33, 3-acetyl-1-(2,4-dimethoxyphenyl)-2,5-dimethylpyrrole (273 mg, 1.0 mmol) and p-toluoyl chloride (0.27 mL, 2.0 mmol) reacted to give the product as a clear oil which was taken up in ether, precipitated with HCl in ether, and filtered to give 6-(2,4-dimethoxyphenyl)-1-(4-methylphenyl)-4,5,7-trimethyl-6H-pyrrolo[3,4-d]pyridazine hydrochloride as a yellow solid: $^1$H NMR (DMSO-d$_6$, 500 MHz) δ 7.58-7.51 (m, 2H), 7.45-7.37 (m, 2H), 7.33 (dd, 1H), 6.92 (d, 1H), 6.79 (dd, 1H), 3.90 (s, 3H), 3.77 (s, 3H), 3.08 (br s, 3H), 2.50 (br s, 3H), 2.44 (s, 3H), 1.90 (s, 3H); MS (ESI) 388 (M+H)$^+$.

EXAMPLE 35

6-(2,4-dimethoxyphenyl)-1-(4-methoxyphenyl)-4,5,7-trimethyl-6H-pyrrolo[3,4-d]pyridazine hydrochloride

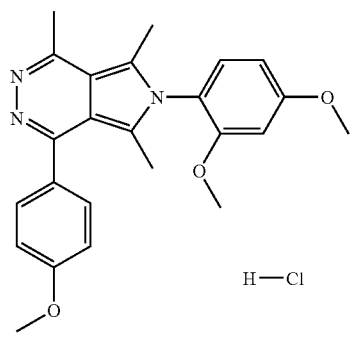

Utilizing the general procedure outlined in EXAMPLE 33, 3-acetyl-1-(2,4-dimethoxyphenyl)-2,5-dimethylpyrrole (273 mg, 1.0 mmol) and p-anisoyl chloride (0.28 mL, 2.0 mmol) reacted to give the product as a clear oil which was taken up in ether, precipitated with HCl in ether, and filtered to give 6-(2,4-dimethoxyphenyl)-1-(4-methoxyphenyl)-4,5,7-trimethyl-6H-pyrrolo[3,4-d]pyridazine hydrochloride as a yellow solid: $^1$H NMR (DMSO-d$_6$, 500 MHz) δ 7.58-7.51 (m, 2H), 7.45-7.37 (m, 2H), 7.33 (dd, 1H), 6.92 (d, 1H), 6.79 (dd, 1H), 3.90 (s, 3H), 3.87 (s 3H), 3.77 (s, 3H), 3.08 (br s, 3H), 2.50 (s, 3H), 2.00 (s, 3H); MS (ESI) 404 (M+H)$^+$.

EXAMPLE 36

1-(cyclopropyl)-6-(4-ethoxy-2-methylphenyl)-4,5,7-trimethyl-6H-pyrrolo[3,4-d]pyridazine

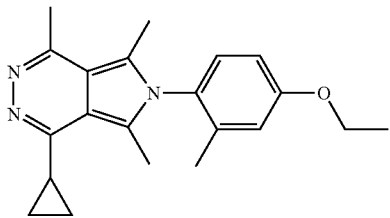

Utilizing the general procedure outlined in EXAMPLE 1, acetonyl acetone (5.88 mL, 50 mmol) and o-cresol (6.12, 50 mmol) reacted to give 1-(4-hydroxy-2-methylphenyl)-2,5-dimethylpyrrole as a colorless oil: $^1$H NMR (CDCl$_3$, 500 MHz) δ 7.05 (d, 1H), 6.80 (d, 1H), 6.75 (dd, 1H), 5.96 (s, 2H), 5.10 (br s, 1H), 1.96 (s, 6H), 1.92 (s, 3H); MS (ESI) 202 (M+H)$^+$.

To a solution of 1-(4-hydroxy-2-methylphenyl)-2,5-dimethylpyrrole (~50 mmol) in acetonitrile (300 mL) was added potassium carbonate (55 mmol) and an excess of bromoethane (>100 mmol). The reaction mixture was stirred at 50° C. overnight, cooled to room temperature, and partitioned between EtOAc and water. The organic layer was washed with brine, dried over MgSO$_4$, filtered, concentrated in vacuo, and purified by column chromatography (15% EtOAc/hexanes) to give 2,5-dimethyl-1-(4-ethoxy-2-methylphenyl)pyrrole as a colorless oil: $^1$H NMR (CDCl$_3$, 500 MHz) δ 7.07 (d, 1H), 6.84 (d, 1H), 6.79 (dd, 1H), 5.90 (s, 2H), 4.07 (q, 2H), 1.92 (s, 6H), 1.90 (s, 3H), 1.45 (t, 3H; MS (ESI) 230 (M+H)$^+$.

Utilizing the general procedure outlined in EXAMPLE 1, 2,5-dimethyl-1-(4-ethoxy-2-methylphenyl)pyrrole (2.29 g, 10 mmol), acetic anhydride (5 mL), and hydriodic acid (0.13 mL, 1.7 mmol) reacted to give 3-acetyl-2,5-dimethyl-1-(4-ethoxy-2-methylphenyl)pyrrole as a tan solid: $^1$H NMR (CDCl$_3$, 500 MHz) δ 6.99 (d, 1H), 6.85 (d, 1H), 6.79 (dd, 1H), 6.32 (s, 1H), 4.06 (q, 2H), 2.42 (s, 3H), 2.22 (s, 3H), 1.89 (s, 3H), 1.88 (s, 3H), 1.44 (t, 3H); MS (ESI) 272 (M+H)$^+$.

Utilizing the general procedure outlined in EXAMPLE 1, 3-acetyl-2,5-dimethyl-1-(4-ethoxy-2-methylphenyl)pyrrole (271 mg, 1.0 mmol) and 3-cyclopropanecarbonyl chloride (0.11 mL, 1.2 mmol) reacted to give 1-(cyclopropyl)-6-(4-ethoxy-2-methylphenyl)-4,5,7-trimethyl-6H-pyrrolo[3,4-d]pyridazine as a white solid: $^1$H NMR (CDCl$_3$, 500 MHz) δ 7.03 (d, 1H), 6.92 (d, 1H), 6.88 (dd, 2H), 4.10 (q, 2H), 2.76 (s, 3H), 2.45 (s, 3H), 2.38 (quintet, 1H), 2.35 (s, 3H), 1.83 (s, 3H), 1.47 (t, 3H), 1.39-1.31 (m, 2H), 0.98 (dd, 2H); MS (ESI) 336 (M+H)$^+$.

EXAMPLE 37

6-(4-ethoxy-2-methylphenyl)-1-(4-methylphenyl)-4,5,7-trimethyl-6H-pyrrolo[3,4-d]pyridazine hydrochloride

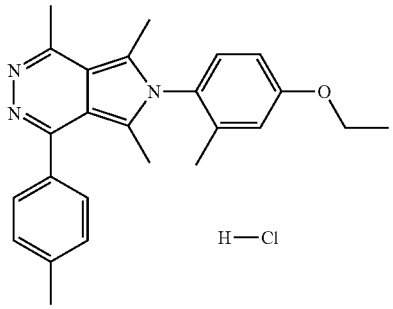

Utilizing the general procedure outlined in EXAMPLE 36, 3-acetyl-2,5-dimethyl-1-(4-ethoxy-2-methylphenyl)pyrrole (271 mg, 1.0 mmol) and p-toluoyl chloride (0.27 mL, 2.0 mmol) reacted to give the product as a clear oil which was taken up in ether, precipitated with HCl in ether, and filtered to give 6-(4-ethoxy-2-methylphenyl)-1-(4-methylphenyl)-4,5,7-trimethyl-6H-pyrrolo[3,4-d]pyridazine hydrochloride as a yellow solid: $^1$H NMR (DMSO-d$_6$, 500 MHz) δ 7.63-7.59 (m, 2H), 7.47-7.39 (m, 2H), 7.24 (d, 1H), 7.13 (d, 1H), 7.03 (dd, 1H), 4.12 (q, 2H), 3.09 (br s, 3H), 2.51 (br s, 3H), 2.44 (s, 3H), 1.89 (s, 3H), 1.83 (s, 3H), 1.37 (t, 3H); MS (ESI) 386 (M+H)$^+$.

EXAMPLE 38

6-(4-ethoxy-2-methylphenyl)-1-(4-methoxyphenyl)-4,5,7-trimethyl-6H-pyrrolo[3,4-d]pyridazine hydrochloride

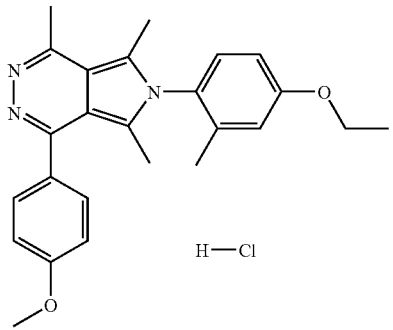

Utilizing the general procedure outlined in EXAMPLE 36, 3-acetyl-2,5-dimethyl-1-(4-ethoxy-2-methylphenyl)pyrrole (271 mg, 1.0 mmol) and p-anisoyl chloride (0.28 mL, 2.0 mmol) reacted to give the product as a clear oil which was taken up in ether, precipitated with HCl in ether, and filtered to give 6-(4-ethoxy-2-methylphenyl)-1-(4-methoxyphenyl)-4,5,7-trimethyl-6H-pyrrolo[3,4-d]pyridazine hydrochloride as a yellow solid: $^1$H NMR (DMSO-d$_6$, 500 MHz) δ 7.63-7.59 (m, 2H), 7.47-7.39 (m, 2H), 7.24 (d, 1H), 7.13 (d, 1H), 7.03 (dd, 1H), 4.12 (q, 2H), 3.87 (s, 3H), 3.09 (br s, 3H), 2.51 (br s, 3H), 2.44 (s, 3H), 1.89 (s, 3H), 1.37 (t, 3H); MS (ESI) 404 (M+H)$^+$.

EXAMPLE 39

6-(3-chloro-4-ethoxyphenyl)-1-(cyclopropyl)-4,5,7-trimethyl-6H-pyrrolo[3,4-d]pyridazine hydrochloride

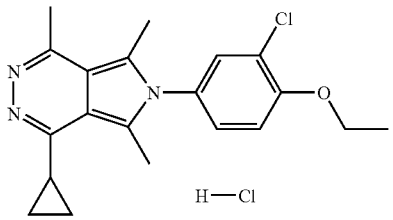

Utilizing the general procedure outlined in EXAMPLE 1, acetonyl acetone (0.83 mL, 7.0 mmol) and 4-amino-2-chlorophenol (1.0 g, 7.0 mmol) reacted to give 1-(3-chloro-4-hydroxyphenyl)-2,5-dimethylpyrrole as a brown solid: $^1$H NMR (CDCl$_3$, 500 MHz) δ 7.22 (d, 1H), 7.10 (d, 1H), 7.05 (dd, 1H), 5.88 (s, 2H), 5.66 (br s, 1H), 2.03 (s, 6H); MS (ESI) 222 (M+H)$^+$.

Using the general procedure outlined in EXAMPLE 1, 1-(3-chloro-4-hydroxyphenyl)-2,5-dimethylpyrrole (1.11 g, 5 mmol) and an excess of bromoethane (1.0 mL) reacted to give 1-(3-chloro-4-ethoxyphenyl)-2,5-dimethylpyrrole as a tan solid: $^1$H NMR (CDCl$_3$, 500 MHz) δ 7.27 (d, 1H), 7.08 (dd, 1H), 6.99 (dd, 1H), 5.89 (s, 2H), 4.18 (q, 2H), 2.04 (s, 6H), 1.53 (t, 3H); MS (ESI) 250 (M+H)$^+$.

Utilizing the general procedure outlined in EXAMPLE 1, 1-(3-chloro-4-ethoxyphenyl)-2,5-dimethylpyrrole (1.21 g, 4.8 mmol), acetic anhydride (5 mL), and hydriodic acid (0.07 mL, 0.83 mmol) reacted to give 3-acetyl-1-(3-chloro-4-ethoxyphenyl)-2,5-dimethylpyrrole as a tan solid: $^1$H NMR (CDCl$_3$, 500 MHz) δ 7.21 (d, 1H), 7.04-6.98 (m, 2H), 6.29 (s, 1H), 4.17 (q, 2H), 2.41 (s, 3H), 2.30 (s, 3H), 1.98 (s, 3H), 1.52 (t, 3H); MS (ESI) 292 (M+H)$^+$.

Utilizing the general procedure outlined in EXAMPLE 1, 3-acetyl-1-(3-chloro-4-ethoxyphenyl)-2,5-dimethylpyrrole (291 mg, 1.0 mmol) and 3-cyclopropanecarbonyl chloride (0.18 mL, 2.0 mmol) reacted to give the product as a clear oil which was taken up in ether, precipitated with HCl in ether, and filtered to give 6-(3-chloro-4-ethoxyphenyl)-1-(cyclopropyl)-4,5,7-trimethyl-6H-pyrrolo[3,4-d]pyridazine hydrochloride as a yellow solid: $^1$H NMR (DMSO-d$_6$, 500 MHz) δ 7.70 (s, 1H), 7.46-7.41 (m, 2H), 4.26 (q, 2), 2.99 (br s, 3H), 2.67-2.61 (m, 1H), 2.58 (s, 3H), 2.52 (s, 3H), 1.43 (t, 3H), 1.28-1.12 (m, 4H); MS (ESI) 356 (M+H)$^+$.

EXAMPLE 40

6-(3-chloro-4-ethoxyphenyl)-1-(4-methylphenyl)-4,5,7-trimethyl-6H-pyrrolo[3,4-d]pyridazine hydrochloride

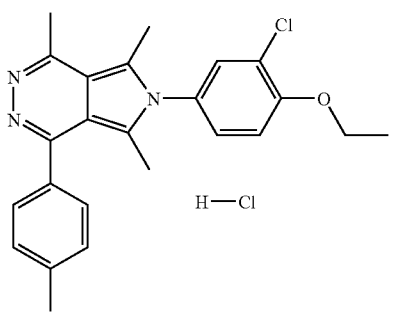

Utilizing the general procedure outlined in EXAMPLE 39, 3-acetyl-1-(3-chloro-4-ethoxyphenyl)-2,5-dimethylpyrrole (291 mg, 1.0 mmol) and p-toluoyl chloride (0.27 mL, 2.0 mmol) reacted to give the product as a clear oil which was taken up in ether, precipitated with HCl in ether, and filtered to give 6-(3-chloro-4-ethoxyphenyl)-1-(4-methylphenyl)-4,5,7-trimethyl-6H-pyrrolo[3,4-d]pyridazine hydrochloride as a green solid: $^1$H NMR (DMSO-d$_6$, 500 MHz) δ 7.71 (d, 1H), 7.63-7.57 (m, 2H), 7.45-7.39 (m, 4H), 4.25 (q, 2H), 3.08 (br s, 3H), 2.44 (s, 3H), 1.96 (s, 3H), 1.41 (t, 3H); MS (ESI) 406 (M+H)$^+$.

EXAMPLE 41

1-(cyclopropyl)-6-(4-ethoxy-2-methoxyphenyl)4,5,7-trimethyl-6H-pyrrolo[3,4-d]pyridazine hydrochloride

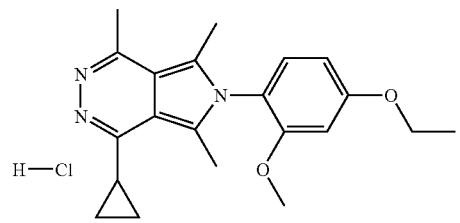

To a solution of 3-acetyl-1-(2,4-dimethoxyphenyl)-2,5-dimethylpyrrole (2.73 g, 10 mmol) (EXAMPLE 33) in CH$_2$Cl$_2$ at rt (75 mL) was added a 1.0M solution of boron tribromide in CH$_2$Cl$_2$ (15 mL, 15 mmol) and the reaction monitored by LC. After complete consumption of the starting material, the reaction was carefully quenched with saturated NaHCO$_3$ and partitioned between EtOAc and water. The organic layer was washed with brine, dried over MgSO$_4$, filtered, concentrated in vacuo, and purified by flash chromatography to give 3-acetyl-2,5-dimethyl-1-(4-hydroxy-2-methoxyphenyl)pyrrole as a tan solid: $^1$H NMR (CDCl$_3$, 500 MHz) δ 6.92 (d, 1H), 6.61 (d, 1H), 6.54 (dd, 1H), 6.32 (s, 1H), 3.72 (s, 3H), 2.44 (s, 3H), 2.26 (s, 3H), 1.93 (s, 3H), 1.69 (br s, 1H); MS (ESI) 260 (M+H)$^+$.

Using the general procedure outlined in EXAMPLE 1, 3-acetyl-2,5-dimethyl-1-(4-hydroxy-2-methoxyphenyl)pyrrole (1.37 g, 5.3 mmol) and an excess of bromoethane (2.0 mL) reacted to give 3-acetyl-2,5-dimethyl-1-(4-ethoxy-2-methoxyphenyl)pyrrole as a tan solid: $^1$H NMR (CDCl$_3$, 500 MHz) δ 6.99 (d, 1H), 6.59 (d, 1H), 6.53 (dd, 1H), 6.31 (s, 1H), 4.08 (q, 2H), 3.74 (s, 3H), 2.41 (s, 3H), 2.25 (s, 3H), 1.93 (s, 3H), 1.46 (t, 3H); MS (ESI) 288 (M+H)$^+$.

Utilizing the general procedure outlined in EXAMPLE 1, 3-acetyl-2,5-dimethyl-1-(4-ethoxy-2-methoxyphenyl)pyrrole (241 mg, 0.84 mmol) and 3-cyclopropanecarbonyl chloride (0.10 mL, 1.0 mmol) reacted to give the product which was taken up in ether, precipitated with HCl in ether, and filtered to give 1-(cyclopropyl)-6-(4-ethoxy-2-methoxyphenyl)-4,5,7-trimethyl-6H-pyrrolo[3,4-d]pyridazine hydrochloride as a yellow solid: $^1$H NMR (DMSO-d$_6$, 500 MHz) δ 7.29 (d, 1H), 6.92 (d, 1H), 6.79 (dd, 2H), 4.18 (q, 2H), 3.77 (s, 3H), 3.45 (br s, 3H), 2.99 (br s, 3H), 2.64 (m, 1H), 2.46 (s, 3H), 1.40 (t, 3H), 1.20-1.12 (m, 4H); MS (ESI) 352 (M+H)$^+$.

EXAMPLE 42

6-(4-ethoxy-2-methoxyphenyl)-1-(4-methylphenyl)-4,5,7-trimethyl-6H-pyrrolo[3,4-d]pyridazine hydrochloride

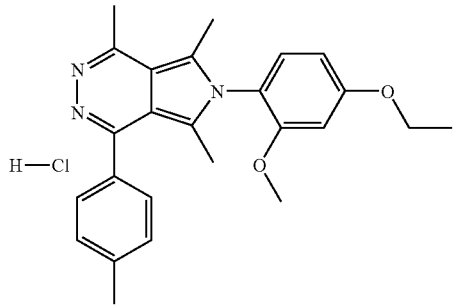

Utilizing the general procedure outlined in EXAMPLE 1, 3-acetyl-2,5-dimethyl-1-(4-ethoxy-2-methoxyphenyl)pyrrole (EXAMPLE 34) (241 mg, 0.84 mmol) and p-toluoyl chloride (0.13 mL, 1.0 mmol) reacted to give the product as a clear oil which was taken up in ether, precipitated with HCl in ether, and filtered to give 6-(4-ethoxy-2-methoxyphenyl)-1-(4-methylphenyl)-4,5,7-trimethyl-6H-pyrrolo[3,4-d]pyridazine hydrochloride as a yellow solid: $^1$H NMR (DMSO-$d_6$, 500 MHz) δ 7.59-7.53 (m, 2H), 7.46-7.42 (m, 2H), 7.28 (d, 1H), 6.88 (d, 1H), 6.76 (dd, 1H), 4.15 (q, 2H), 3.75 (s, 3H), 3.56 (br s, 3H), 3.10 (br s, 3H), 2.43 (s, 3H), 1.89 (s, 3H), 1.38 (t, 3H); MS (ESI) 402 (M+H)$^+$.

EXAMPLE 43

6-(4-ethoxy-2-methoxyphenyl)-1-(4-methoxyphenyl)-4,5,7-trimethyl-6H-pyrrolo[3,4-d]pyridazine hydrochloride

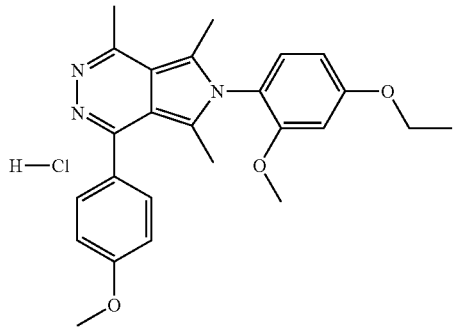

Utilizing the general procedure outlined in EXAMPLE 1, 3-acetyl-2,5-dimethyl-1-(4-ethoxy-2-methoxyphenyl)pyrrole (EXAMPLE 35) (241 mg, 0.84 mmol) and p-anisoyl chloride (0.15 mL, 1.0 mmol) reacted to give the product as a clear oil which was taken up in ether, precipitated with HCl in ether, and filtered to give 6-(4-ethoxy-2-methoxyphenyl)-1-(4-methoxyphenyl)-4,5,7-trimethyl-6H-pyrrolo[3,4-d]pyridazine hydrochloride as a yellow solid: $^1$H NMR (DMSO-$d_6$, 500 MHz) δ 7.69-7.62 (m, 2H), 7.29 (d, 1H), 7.19-7.13 (m, 2H), 6.90 (d, 1H), 6.77 (dd, 1H), 4.16 (q, 2H), 3.87 (s, 3H), 3.76 (s, 3H), 3.65 (br s, 3H), 3.05 (br s, 3H), 1.93 (s, 3H), 1.38 (t, 3H); MS (ESI) 418 (M+H)$^+$.

EXAMPLE 44

4-[6-(4-ethoxyphenyl)-4,5,7-trimethyl-6H-pyrrolo[3,4-d]pyridazin-1-yl]-butyric acid hydrazide

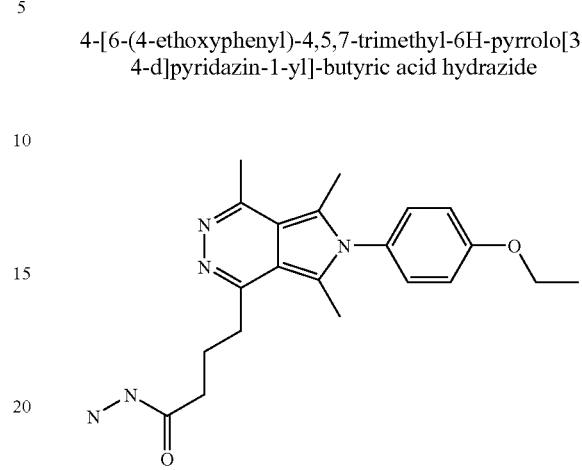

To a solution of 5-[4-acetyl-2,5-dimethyl-1-(4-ethoxyphenyl)-1H-pyrrol-3-yl]-5-oxo-pentanoic acid methyl ester (100 mg, 0.26 mmol) (EXAMPLE 31) in ethanol (1 mL) was added excess hydrazine (0.1 mL). The solution was stirred overnight at 50° C. and concentrated in vacuo to give 4-[6-(4-ethoxyphenyl)-4,5,7-trimethyl-6H-pyrrolo[3,4-d]pyridazin-1-yl]-butyric acid hydrazide as a white solid: $^1$H NMR (CDCl$_3$, 500 MHz) δ 9.04 (br s, 1H), 7.12-7.09 (m, 2H), 7.06-7.03 (m, 2H), 4.11 (q, 2H), 3.78 (br s, 2H), 3.15 (t, 2H), 2.78 (s, 3H), 2.43 (s, 3H), 2.41 (s, 3H), 2.32 (t, 2H), 2.18-2.12 (m, 2H), 1.48 (t, 3H); MS (ESI) 382 (M+H)$^+$.

EXAMPLE 45

4-[6-(4-ethoxyphenyl)-4,5,7-trimethyl-6H-pyrrolo[3,4-d]pyridazin-1-yl]-butyric acid potassium salt

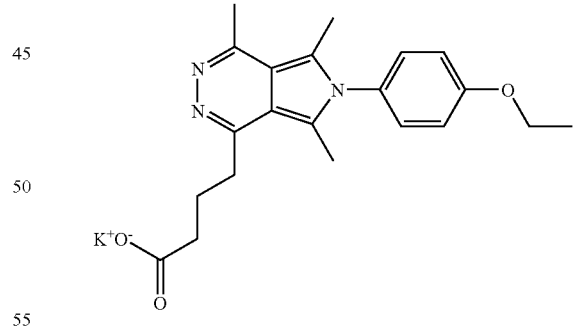

To a solution of 4-[6-(4-ethoxyphenyl)-4,5,7-trimethyl-6H-pyrrolo[3,4-d]pyridazin-1-yl]-butyric acid methyl ester (104 mg, 0.27 mmol) (EXAMPLE 31) in THF (3 mL) was added potassium trimethylsilanoate (57 mg, 0.4 mmol). The mixture was stirred overnight and filtered to give 4-[6-(4-ethoxyphenyl)-4,5,7-trimethyl-6H-pyrrolo[3,4-d]pyridazin-1-yl]-butyric acid potassium salt as a tan solid: $^1$NMR (DMSO-$d_6$, 500 MHz) δ 7.27 (d, 2H), 7.12 (d, 2H), 4.12 (q, 2H), 2.90 (t, 2H), 2.64 (s, 3H), 2.37 (s, 3H), 2.36 (s, 3H), 1.91 (t, 2H), 1.80-1.75 (m, 2H), 1.37 (t, 3H); MS (ESI) 368 (M+H)$^+$.

EXAMPLE 46

4-[6-(4-ethoxyphenyl)-4,5,7-trimethyl-6H-pyrrolo[3,4-d]pyridazin-1-yl]-propionic acid hydrazide

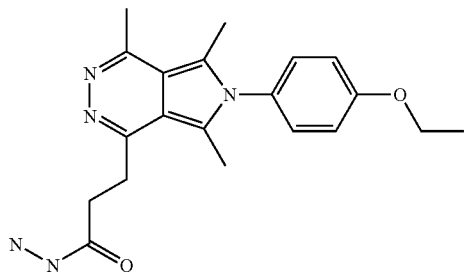

Utilizing the general procedure outlined in EXAMPLE 44, 4-[4-acetyl-2,5-dimethyl-1-(4-ethoxyphenyl)-1H-pyrrol-3-yl]-4oxo-butyric acid methyl ester (100 mg, 0.27 mmol) (EXAMPLE 32) and excess hydrazine (0.1 mL) reacted to give 4-[6-(4-ethoxyphenyl)-4,5,7-trimethyl-6H-pyrrolo[3,4-d]pyridazin-1-yl]-propionic acid hydrazide as a white solid: $^1$H NMR (CDCl$_3$, 500 MHz) δ 8.62 (br s, 1H), 7.13-7.08 (m, 2H), 7.07-7.04 (m, 2H), 4.12 (q, 2H), 3.49 (t, 2H), 3.09 (br s, 2H), 2.91 (t, 2H), 2.83 (s, 3H), 2.46 (s, 3H), 2.44 (s, 3), 1.49 (t, 3H); MS (ESI) 368 (M+H)$^+$.

EXAMPLE 47

4-[6-(4-ethoxyphenyl)-4,5,7-trimethyl-6H-pyrrolo[3,4-d]pyridazin-1-yl]-propionic acid potassium salt

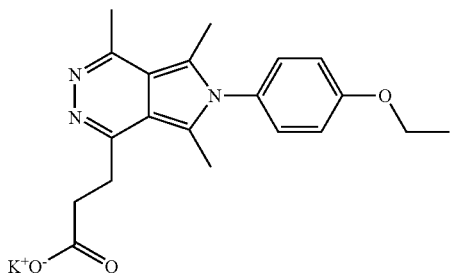

Utilizing the general procedure outlined in EXAMPLE 45, 4-[6-(4-ethoxyphenyl)-4,5,7-trimethyl-6H-pyrrolo[3,4-d]pyridazin-1-yl]-propionic acid methyl ester (100 mg, 0.27 mmol) (EXAMPLE 32) and potassium trimethylsilanoate (57 mg, 0.4 mmol) reacted to give 4-[6-(4-ethoxyphenyl)-4,5,7-trimethyl-6H-pyrrolo[3,4-d]pyridazin-1-yl]-propionic acid potassium salt as a tan solid: $^1$H NMR (DMSO-d$_6$, 500 MHz) δ 7.27 (d, 2H), 7.12 (d, 2H), 4.12 (q, 2H), 3.09 (dd, 2H), 2.63 (s, 3H), 2.36 (s, 3H), 2.35 (s, 3H), 2.15 (dd, 2H), 1.37 (t, 3H); MS (ESI) 354 (M+H)$^+$.

EXAMPLE 48

1,4,5,7-tetramethyl-6-[4-(trifluoromethoxy)phenyl]-6H-pyrrolo[3,4-d]pyridazine

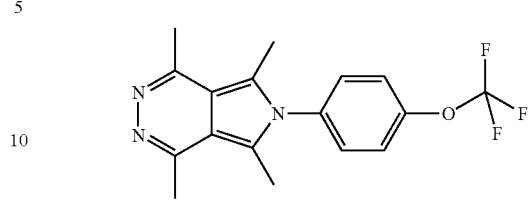

A solution of 1,1,2,2-tetraacetylethane (250 mg, 1.26 mmol) and 4-trifluoromethoxy aniline (170 μL, 1.26 mmol) was refluxed in EtOH (5 mL)/AcOH (1%) for 48 h. Hydrazine (100 μL, 3.15 mmol) was added and the mixture was refluxed for 1 h. The reaction mixture was poured into ice water (50 mL). The resulting precipitate was filtered and dried under vacuum to afford 1,4,5,7-tetramethyl-6-[4-(trifluoromethoxy)phenyl]-6H-pyrrolo[3,4-d]pyridazine as a tan solid: $^1$H NMR (CDCl$_3$, 500 MHz) δ 7.42 (d, 2H), 7.25 (d, 2H), 2.81 (s, 6H), 2.41 (s, 6H); MS (ESI) 336 (M+H)$^+$.

EXAMPLE 49

6-(4-isopropylphenyl)-1,4,5,7-tetramethyl-6H-pyrrolo[3,4-d]pyridazine

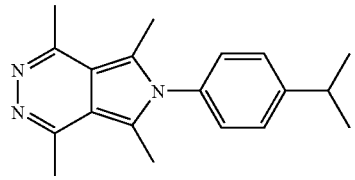

Utilizing the general procedure outlined in EXAMPLE 48, 1,1,2,2-tetraacetylethane (250 mg, 1.26 mmol) and 4-isopropyl aniline (172 μL, 1.26 mmol) reacted to give 6-(4-isopropylphenyl)-1,4,5,7-tetramethyl-6H-pyrrolo[3,4-d]pyridazine as a tan solid: $^1$H NMR (CDCl$_3$, 500 MHz) δ 7.40 (d, 2H), 7.07 (d, 2H), 3.01-2.97 (m, 1H) 2.83 (s, 6H), 2.41 (s, 6H) 1.28 (d, 6H); MS (ESI) 294 (M+H)$^+$.

EXAMPLE 50

6-(4-ethoxy)-1,4,5,7-tetramethyl-6H-pyrrolo[3,4-d]pyridazine

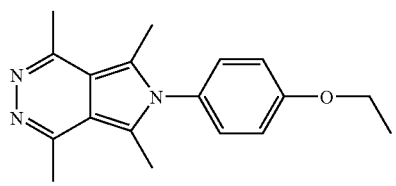

Utilizing the general procedure outlined in EXAMPLE 48, 1,1,2,2-tetraacetylethane (250 mg, 1.26 mmol) and p-phenetidine (172 μL, 1.26 mmol) reacted to give 6-(4-ethoxyphenyl)-1,4,5,7-tetramethyl-6H-pyrrolo[3,4-d]pyridazine as a tan solid: $^1$H NMR (CDCl$_3$, 500 MHz) δ 7.41-7.39 (d, 2H), 7.07-7.06 (d, 2H), 4.07 (q, 2H), 2.83 (s, 6H), 2.41 (s, 6H) 1.45 (t, 6H); MS (ESI) 294 (M+H)⁺.

EXAMPLE 51

6-(2-ethoxy)-1,4,5,7-tetramethyl-6H-pyrrolo[3,4-d]pyridazine

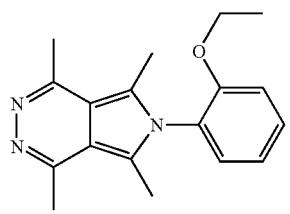

Utilizing the general procedure outlined in EXAMPLE 48, 1,1,2,2-tetraacetylethane (250 mg, 1.26 mmol) and o-phenetidine (172 μL, 1.26 mmol) reacted to give 6-(2-ethoxyphenyl)-1,4,5,7-tetramethyl-6H-pyrrolo[3,4-d]pyridazine as a tan solid: ¹H NMR (CDCl₃, 500 MHz) δ 7.41-7.39 (d, 2H), 7.07-7.06 (d, 2H), 4.12 (q, 2H), 2.83 (s, 6H), 2.41 (s, 6H) 1.55 (t, 6H); MS (ESI) 294 (M+H)⁺.

EXAMPLE 52

6-(4-hydroxyphenyl)-1,4,5,7-tetramethyl-6H-pyrrolo[3,4-d]pyridazine

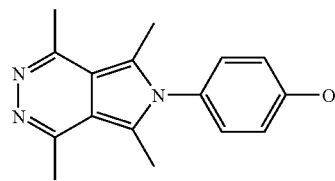

Utilizing the general procedure outlined in EXAMPLE 48, 1,1,2,2-tetraacetylethane (250 mg, 1.26 mmol) and 4-aminophenol (172 μL, 1.26 mmol) reacted to give 6-(4-hydroxyphenyl)-1,4,5,7-tetramethyl-6H-pyrrolo[3,4-d]pyridazine as a tan solid: ¹H NMR (CDCl₃, 500 MHz) δ 7.41-7.39 (d, 2H), 7.07-7.06 (d, 2H), 2.83 (s, 6H), 2.41 (s, 6H); MS (ESI) 266 (M+H)⁺.

EXAMPLE 53

6-(4-isopropylphenyl)-1,4,5,7-tetramethyl-6H-pyrrolo[3,4-d]pyridazine

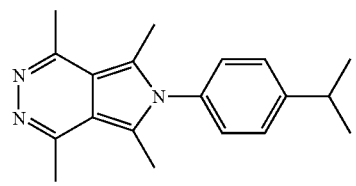

Utilizing the general procedure outlined in Example 48, 1,1,2,2-tetraacetylethane (250 mg, 1.26 mmol) and 4-isopropyl aniline (172 μL, 1.26 mmol) reacted to give 6-(4-isopropylphenyl)-1,4,5,7-tetramethyl-6H-pyrrolo[3,4-d]pyridazine as a tan solid. ¹H NM (CDCl₃, 500 MHz) δ 7.41-7.39 (d, 2H), 7.07-7.06 (d, 2H), 3.01-2.97 (m, 1H) 2.83 (s, 6H), 2.41 (s, 6H) 1.28-1.27 (d, 6H). MS 294 (M+H).

EXAMPLE 54

6-(6-Ethoxy-pyridin-3-yl)-1,4,5,7-tetramethyl-6H-pyrrolo[3,4-d]pyridazine

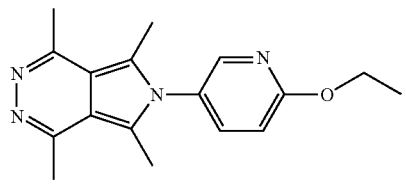

Utilizing the general procedure outlined in Example 48, 1,1,2,2-tetraacetylethane (200 mg, 1.0 mol) and 6-ethoxy-pyridin-3-yl amine (140 mg, 1.0 mmol) reacted to give 6-(6-Ethoxy-pyridin-3-yl)-1,4,5,7-tetramethyl-6H-pyrrolo[3,4-d]pyridazine as a pale yellow solid: ¹H NMR (CDCl₃, 500 MHz) δ 8.04 (s, 1H), 7.41 (d, 1H), 6.93 (d, 1H), 4.46 (q, 1H), 2.80 (s, 6H), 2.45 (s, 6H), 1.46 (t, 3H); MS (ESI) 297 (M+H)⁺.

EXAMPLE 55

6-(5-Ethoxy-pyrazin-2-yl)-1,4,5,7-tetramethyl-6H-pyrrolo[3,4-d]pyridazine

Utilizing the general procedure outlined in Example 48, 1,1,2,2

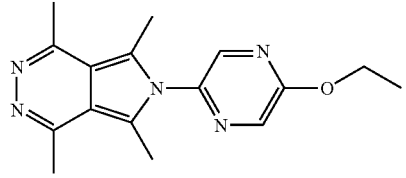

-tetraacetylethane (200 mg, 1.0 mol) and 5-ethoxy-pyrazin-2-yl amine (130 mg, 1.0 mmol) reacted to give 6-(5-ethoxy-pyrazin-2-yl)-1,4,5,7-tetramethyl-6H-pyrrolo[3,4-d]pyridazine as light yellow solid: ¹H NMR (CDCl₃, 500 MHz) δ 8.27 (s, 1H), 8.11 (s, 1H), 4.50 (q, 1H), 2.80 (s, 6H), 2.48 (s, 6H), 1.50 (t, 3H); MS (ESI) 298 (M+H)⁺.

EXAMPLE 56

1,4,5,7-Tetramethyl-6-(5-propoxy-pyridin-2-yl)-6H-pyrrolo[3,4-d]pyridazine

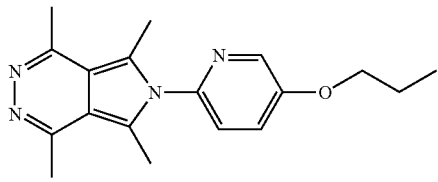

Utilizing the general procedure outlined in Example 48, 1,1,2,2-tetraacetylethane (100 mg, 0.5 mol) and 5-ethoxy-pyrazin-2-yl amine (80 mg, 0.5 mmol) reacted to give 1,4,5,7-tetramethyl-6-(5-propoxy-pyridin-2-yl)-6H-pyrrolo[3,4-d]pyridazine as yellow solid: $^1$H NMR (CDCl$_3$, 500 MHz) δ 8.35 (s, 1H), 7.44 (d, 1H), 7.22 (d, 1H), 4.08 (t, 2H), 2.80 (s, 6H), 2.45 (s, 6H), 1.89 (q, 2H), 1.10 (t, 3H); MS (ESI) 311 (M+H)$^+$.

EXAMPLE 57

2-Chloro-4-(1,4,5,7-tetramethyl-pyrrolo[3,4-d]pyridazin-6-yl)-phenol

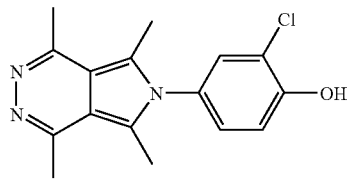

Utilizing the general procedure outline in Example 48, 1,1,2,2-tetraacetylethane (200 mg, 1.0 mol) and 4-amino-2-chloro-phenol amine (144 mg, 1.0 mmol) reacted to give 1-[4-acetyl-1-(3-chloro-4-hydroxy-phenyl)-2,5-dimethyl-1H-pyrrol-3-yl]-ethanone as yellow solid: MS (ESI) 306 (M+H)$^+$.

To a solution of 1-[4-acetyl-1-(3-chloro-4-hydroxy-phenyl)-2,5-dimethyl-1H-pyrrol-3-yl]-ethanone (340 mg, 1.0 mmol) was added hydrazine (50 μL). After stirring at rt for 1 h, the reaction mixture was poured into ice water (25 mL). The resulting precipitate was filtered, washed with diethyl ether (20 mL), and then dried under vacuum to afford 2-chloro-4-(1,4,5,7-tetramethyl-pyrrolo[3,4-d]pyridazin-6-yl)-phenol as a pale yellow solid: $^1$H NMR (CD$_3$OD, 500 MHz) δ 7.34 (br s, 1H), 7.08 (m, 2H), 2.83 (s, 6H), 2.52 (s, 6H); MS (ESI) 302 (M+H)$^+$.

EXAMPLE 58

6-(2,4-Dimethoxy-phenyl)-1,4,5,7-tetramethyl-6H-pyrrolo[3,4-d]pyridazine

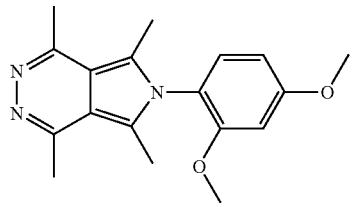

Utilizing the general procedure outlined in Example 48, 1,1,2,2-tetraacetylethane (400 mg, 2.0 mol), 2,4-dimethoxyaniline (305 mg, 2.0 mmol) and hydrazine (200 μL) reacted to give 1,4,5,7-tetramethyl-6-(4-propoxy-phenyl)-6H-pyrrolo[3,4-d]pyridazine as yellow solid: $^1$H NMR (CDCl$_3$, 500 MHz) δ 7.06 (d, 1H), 6.67 (m, 2H), 3.89 (s, 3H), 3.78 (s, 3H), 2.80 (s, 6H), 2.40 (s, 6H); MS (ESI) 312 (M+H)$^+$.

EXAMPLE 59

6-(4-Isopropoxy-phenyl)-1,4,5,7-tetramethyl-6H-pyrrolo[3,4-d]pyridazine

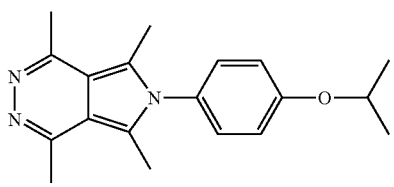

Utilizing the general procedure outlined in Example 48, 1,1,2,2-tetraacetylethane (100 mg, 0.5 mol), 2,4-dimethoxyaniline (76 mg, 0.5 mmol) and hydrazine (50 μL) reacted to give 6-(4-Isopropoxy-phenyl)-1,4,5,7-tetramethyl-6H-pyrrolo[3,4-d]pyridazine as yellow solid: $^1$H NMR (CDCl$_3$, 500 MHz) δ 7.12 (d, 2H), 7.07 (d, 2H), 4.68 (m, 1H), 2.86 (s, 6H), 2.47 (s, 6H), 1.45 (d, 6H); MS (ESI) 310 (M+H)$^+$.

EXAMPLE 60

1,4,57-Tetramethyl-6-(4-trifluoromethoxy-phenyl)-6H-pyrrolo[3,4-d]pyridazine

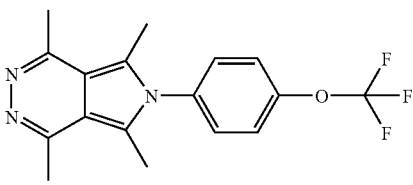

Utilizing the general procedure outlined in Example 48, 1,1,2,2-tetraacetylethane (200 mg, 1.0 mol), 2-methyl-4-(trifluoromethoxy) aniline (191 mg, 1.0 mmol) and hydrazine (50 μL) reacted to give 1,4,5,7-Tetramethyl-6-(4-trifluoromethoxy-phenyl)-6H-pyrrolo[3,4-d]pyridazine as light yellow solid: ¹H NMR (CDCl₃, 500 MHz) δ 8.27 (s, 1H), 8.11 (s, 1H), 4.50 (q, 1H), 2.80 (s, 6H), 2.48 (s, 6H), 1.50 (t, 3H); MS (ESI) 298 (M+H)⁺; MS (ESI) 350 (M+H)⁺.

EXAMPLE 61

2-Methyl-4-(1,4,5,7-tetramethyl-pyrrolo[3,4-d]pyridazin-6-yl)-phenol

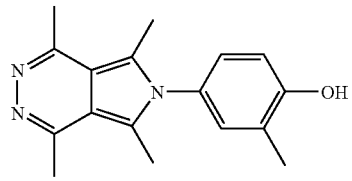

Utilizing the general procedure outlined in Example 48, 1,1,2,2-tetraacetylethane (400 mg, 2.0 mol) and 4-amino-o-cresol (250 mg, 2.0 mmol) reacted to give 1-[4-acetyl-1-(4-hydroxy-3-methyl-phenyl)-2,5-dimethyl-1H-pyrrol-3-yl]-ethanone as yellow solid: MS (ESI) 286 (M+1)⁺.

To a solution of 1-[4-acetyl-1-(4-hydroxy-3-methyl-phenyl)-2,5-dimethyl-1H-pyrrol-3-yl]-ethanone (100 mg, 0.32 mmol) in ethanol (5 mL) was added hydrazine (20 μL). After stirring at rt for 1 h, the reaction mixture was poured into ice water (25 mL). The resulting precipitate was filtered, washed with diethyl ether (20 mL), and then dried under vacuum to afford 2-methyl-4-(1,4,5,7-tetramethyl-pyrrolo[3,4-d]pyridazin-6-yl)-phenol as a pale yellow solid: ¹H NMR (CD₃OD, 500 MHz) δ 7.09 (d, 1H), 7.03 (s, 1H), 6.97 (d, 1H), 3.00 (s, 6H), 2.59 (s, 6H), 2.34 (s, 3H); MS (ESI) 282 (M+H)⁺.

EXAMPLE 62

6-(2,3-Dihydro-benzo[1,4]dioxin-6-yl)-1,4,5,7-tetramethyl-6H-pyrrolo[3,4-d]pyridazine

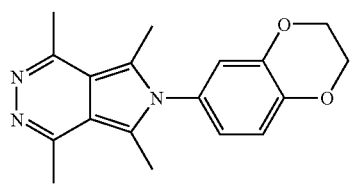

Utilizing the general procedure outlined in Example 48, 1,1,2,2-tetraacetylethane (200 mg, 1.0 mol), 5-ethoxypyrazin-2-yl amine (151 mg, 1.0 mmol) and hydrazine (50 μL) reacted to give 6-(2,3-Dihydro-benzo[1,4]dioxin-6-yl)-1,4,5,7-tetramethyl-6H-pyrrolo[3,4-d]pyridazine as light yellow solid: ¹H NMR (CDCl₃, 500 MHz) δ 7.06 (d, 1H), 6.76 (s, 1H), 6.70 (d, 1H), 4.36 (br m, 4H), 2.83 (s, 6H); MS (ESI) 310 (M+H)⁺.

EXAMPLE 63

3-Methyl-4-(1,4,5,7-tetramethyl-pyrrolo[3,4-d]pyridazin-6-yl)-phenol

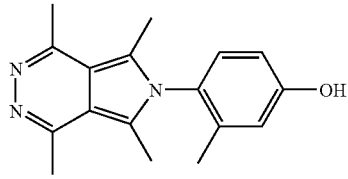

Utilizing the general procedure outlined in Example 48, 1,1,2,2-tetraacetylethane (200 mg, 1.0 mol) and 4-amino-3-methyl-phenol (123 mg, 1.0 mmol) reacted to give 1-[4-acetyl-1-(4-hydroxy-2-methyl-phenyl)-2,5-dimethyl-1H-pyrrol-3-yl]-ethanone as a brown solid: MS (ESI) 306 (M+H)⁺.

Utilizing the general procedure outlined in Example 48, 1-[4-acetyl-1-(3-chloro-4-hydroxy-phenyl)-2,5-dimethyl-1H-pyrrol-3-yl]-ethanone (323 mg, 1.0 mmol) and hydrazine (50 μL) reacted to afford 3-methyl-4-(1,4,5,7-tetramethyl-pyrrolo[3,4-d]pyridazin-6-yl)-phenol as brown solid: ¹H NMR (CDCl₃, 500 MHz) δ 7.34 (br s, 1H), 7.08 (m, 2H), 2.83 (s, 6H), 2.52 (s, 6H); MS (ES) 302 (M+H)⁺.

EXAMPLE 64

6-(3-Chloro-4-ethoxy-phenyl)-1,4,5,7-tetramethyl-6H-pyrrolo[3,4-d]pyridazine

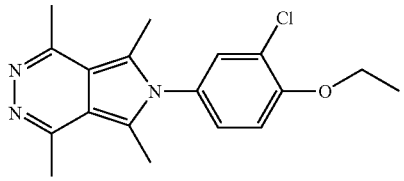

To a solution of 1-[4-acetyl-1-(3-chloro-4-hydroxy-phenyl)-2,5-dimethyl-1H-pyrrol-3-yl]-ethanone (prepared as outline in Example 57; 80 mg, 0.27 mmol) in 3 mL of dry DMF was added bromoethane (54 mg, 0.5 mmol) and K₂CO₃ powder (50 mg). The resulting reaction mixture was warmed to 50° C. and stirred for 1 h. It was quenched by addition of 20 mL of H₂O, extracted with diethyl ether (20 mL×2). The combined organic extracts were washed with brine (50 mL), dried (MgSO₄), filtered, and concentrated in vacuo to afford 1-[4-acetyl-1-(3-chloro-4-ethoxy-phenyl)-2,5-dimethyl-1H-pyrrol-3-yl]-ethanone: MS (ESI) 302 (M+H)⁺.

Utilizing the general procedure outlined in Example 48, 1-[4-acetyl-1-(3-chloro-4-ethoxy-phenyl)-2,5-dimethyl-1H-pyrrol-3-yl]-ethanone and hydrazine reacted to give 6-(3-Chloro-4-ethoxy-phenyl)-1,4,5,7-tetramethyl-6H-pyrrolo[3,4-d]pyridazine as yellow solid: ¹H NMR (CD₃OD, 500 MHz) δ 7.47 (s, 1H), 7.32 (d, 1H), 7.25 (d, 1H), 4.27 (q, 2H), 2.79 (s, 6H), 2.48 (s, 6H), 1.53 (t, 3H); MS (ESI) 330 (M+H)⁺.

EXAMPLE 65

6-(4-Ethoxy-2-methyl-phenyl)-1,4,5,7-tetramethyl-6H-pyrrolo[3,4-d]pyridazine

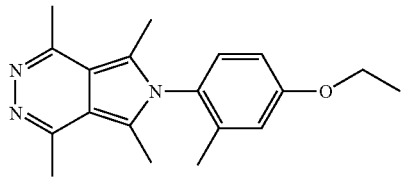

To a solution of 1-[4-acetyl-1-(4-hydroxy-2-methyl-phenyl)-2,5-dimethyl-1H-pyrrol-3-yl]-ethanone (prepared as outline in Example 63; 56 mg, 0.20 mmol) in 2 mL of dry DMF was added bromoethane (100 μL) and $K_2CO_3$ powder (50 mg). The resulting reaction mixture was warmed to 50° C. and stirred for 1 h. It was quenched by addition of 20 mL of $H_2O$, extracted with diethyl ether (20 mL×2). The combined organic extracts were washed with brine (50 mL), dried ($MgSO_4$), filtered, and concentrated in vacuo to afford 1-[4-acetyl-1-(4-ethoxy-2-methyl-phenyl)-2,5-dimethyl-1H-pyrrol-3-yl]-ethanone: MS (ESI) 314 $(M+H)^+$.

Utilizing the general procedure outlined in Example 48, 1-[4-acetyl-1-(4-ethoxy-2-methyl-phenyl)-2,5-dimethyl-1H-pyrrol-3-yl]-ethanone and hydrazine reacted to give 6-(4-ethoxy-2-methyl-phenyl)-1,4,5,7-tetramethyl-6H-pyrrolo[3,4-d]pyridazine as light yellow solid: $^1H$ NMR ($CDCl_9$, 500 MHz) δ 7.06 (d, 1H), 6.94 (s, 1H), 6.90 (m, 1H), 4.12 (q, 2H), 2.81 (s, 6H), 2.38 (s, 6H), 1.80 (s, 3H), 1.50 (t, 3H); MS (ESI) 310 $(M+H)^+$.

EXAMPLE 66

6-[4-(2-Fluoro-ethoxy)-2-methyl-phenyl]-1,4,5,7-tetramethyl-6H-pyrrolo[3,4-d]pyridazine

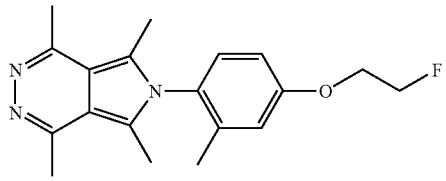

As outlined in Example 65, 1-[4-acetyl-1-(4-hydroxy-2-methyl-phenyl)-2,5-dimethyl-1H-pyrrol-3-yl]-ethanone (20 mg) reacted with 1-bromo-2-fluoro ethane (50 μL), in the presence of $K_2CO_3$ powder (50 mg), to afford 1-{4-acetyl-1-[4-(2-fluoro-ethoxy)-2-methyl-phenyl]-2,5-dimethyl-1H-pyrrol-3-yl}-ethanone: MS (ESI) 332 $(M+H)^+$. Utilizing the general procedure outlined in Example 48, 1-[4-acetyl-1-(4-ethoxy-2-methyl-phenyl)-2,5-dimethyl-1H-pyrrol-3-yl]-ethanone and hydrazine reacted to give 6-[4-(2-fluoro-ethoxy)-2-methyl-phenyl]-1,4,5,7-tetramethyl-6H-pyrrolo[3,4-d]pyridazine as light yellow solid: $^1H$ NMR ($CDCl_3$, 500 MHz) δ 7.06 (d, 1H), 6.94 (s, 1H), 6.90 (m, 1H), 4.12 (q, 2H), 2.81 (s, 6H), 2.38 (s, 6H), 1.80 (s, 3H), 1.50 (t, 3H); MS (ESI) 310 $(M+H)^+$.

EXAMPLE 67

1,4,5,7-Tetramethyl-6-(4-propoxy-phenyl)-6H-pyrrolo[3,4-d]pyridazine

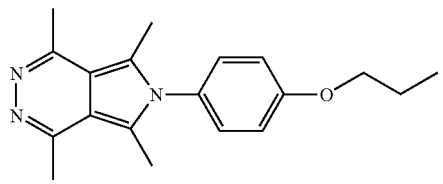

As outlined in Example 65, 1-[4-acetyl-1-(4-hydroxy-2-methyl-phenyl)-2,5-dimethyl-1H-pyrrol-3-yl]-ethanone (Example 52, 20 mg) reacted with 1-bromo-propane (100 μL), in the presence of $K_2CO_3$ powder (50 mg), to afford 1-[4-acetyl-2,5-dimethyl-1-(4-propoxy-phenyl)-1H-pyrrol-3-yl]-ethanone: MS (ESI) 328 $(M+H)^+$. Utilizing the general procedure outlined in Example 48, 1-[4-acetyl-2,5-dimethyl-1-(4-propoxy-phenyl)-1H-pyrrol-3-yl]-ethanone and hydrazine reacted to give 1,4,5,7-Tetramethyl-6-(4-propoxy-phenyl)-6H-pyrrolo[3,4-d]pyridazine as light yellow solid: $^1H$ NMR ($CDCl_3$, 500 MHz) δ 7.04 (d, 1H), 6.95 (br s, 1H), 6.91 (d, 1H), 4.03 (t, 2H), 2.85 (s, 6H), 2.42 (s, 6H), 1.86 (q, 2H), 1.79 (s, 3H), 1.09 (t, 3H); MS (ESI) 328 $(M+H)^+$.

EXAMPLE 68

6-(4-Allyloxy-phenyl)-1,4,5,7-tetramethyl-6H-pyrrolo[3,4-d]pyridazine

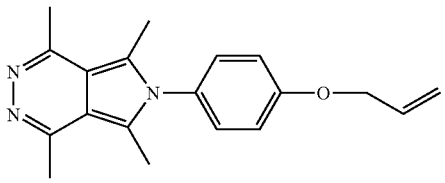

As in Example 65, 1-[4-acetyl-1-(4-hydroxy-2-methyl-phenyl)-2,5-dimethyl-1H-pyrrol-3-yl]-ethanone (Example 52, 20 mg) reacted with allyl bromide (50 μL), in the presence of $K_2CO_3$ (50 mg), to afford 1-[4-acetyl-1-(4-allyloxy-phenyl)-2,5-dimethyl-1H-pyrrol-3-yl]-ethanone: MS (ESI) 326 $(M+H)^+$. Utilizing the general procedure outlined in Example 48, 1-[4-acetyl-1-(4-allyloxy-phenyl)-2,5-dimethyl-1H-pyrrol-3-yl]-ethanone (20 mg) and hydrazine (50 μL) reacted to give 6-(4-allyloxy-phenyl)-1,4,5,7-tetramethyl-6H-pyrrolo[3,4-d]pyridazine as light yellow solid: $^1H$ NMR ($CDCl_3$, 500 MHz) δ 7.04 (m, 1H), 6.98 (s, 1H), 6.94 (m, 1H), 6.13 (m, 1H), 5.52 (d, 1H), 5.39 (d, 1H), 4.64 (d, 2H), 2.81 (s, 6H), 2.35 (s, 6H), 1.84 (s, 3H); MS (ESI) 322 $(M+H)^+$.

EXAMPLE 69

6-(4-ethoxy-3-methyl-phenyl)-1,4,5,7-tetramethyl-6H-pyrrolo[3,4-d]pyridazine

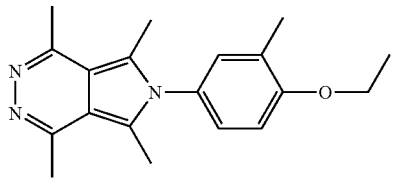

To a solution of 1-[4-acetyl-1-(4-hydroxy-3-methyl-phenyl)-2,5-dimethyl-1H-pyrrol-3-yl]-ethanone (prepared as in Example 61) (90 mg, 0.32 mmol) in 3 mL of dry DMF was added bromoethane (108 mg, 1.0 mmol) and $K_2CO_3$ powder (50 mg). The resulting reaction mixture was warmed to 50° C. and stirred for 1 h. It was quenched by addition of 20 mL of $H_2O$, extracted with diethyl ether (20 mL×2). The combined organic extracts were washed with brine (50 mL), dried ($MgSO_4$), filtered, and concentrated in vacuo to afford 1-[4-acetyl-1-(4-ethoxy-3-methyl-phenyl)-2,5-dimethyl-1H-pyrrol-3-yl]-ethanone: MS (ESI) 314 (M+H)$^+$.

Utilizing the general procedure outlined in Example 48, 1-[4-acetyl-1-(3-chloro-4-ethoxy-phenyl)-2,5-dimethyl-1H-pyrrol-3-yl]-ethanone (99 mg, 0.32 mmol) and hydrazine (50 μL) reacted to give 6-(4-ethoxy-3-methyl-phenyl)-1,4,5,7-tetramethyl-6H-pyrrolo[3,4-d]pyridazine as yellow solid: $^1$H NMR (CD$_3$OD, 500 MHz) δ 6.96 (m, 3H), 4.15 (q, 2H), 2.80 (s, 6H), 2.49 (s, 6H), 2.32 (s, 3H), 1.52 (t, 3H); MS (ESI) 310 (M+H)$^+$.

EXAMPLE 70

6-(4-Ethoxy-2-methoxy-phenyl)-1,4,5,7-tetramethyl-6H-pyrrolo[3,4-d]pyridazine

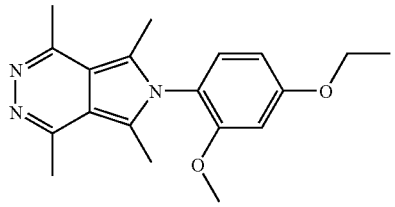

Utilizing the general procedure outlined in Example 48, 1,1,2,2-tetraacetylethane (400 mg, 2.0 mol), 2,4-dimethoxyaniline (305 mg, 2.0 mmol) reacted to give 1-[4-acetyl-1-(2,4-dimethoxy-phenyl)-2,5-dimethyl-1H-pyrrol-3-yl]-ethanone as yellow solid: MS (ESI) 316 (M+H)$^+$.

To a stirring solution of crude 1-[4-acetyl-1-(4-ethoxy-2-methoxy-phenyl)-2,5-dimethyl-1H-pyrrol-3-yl]-ethanone prepared as above (90 mg, 0.3 mmol) in 5.0 mL of $CH_2Cl_2$ at 0° C. was added BBr$_3$ (1.0 M in $CH_2Cl_2$, 0.9 mL, 0.9 mmol). After 1 h at 0° C., it was warmed to rt and stirred for an additional 2 h before it was quenched with saturated aq. NaHCO$_3$ solution (5 mL). It was extracted with EtOAc (2×10 mL), and the combined organic extracts were washed with dried with MgSO$_4$, filtered, and concentrated in vacuo to afford the crude product as a yellow oil. This crude material was purified by automated chromatography on silica gel (using 20-50%EtOAc/hexanes gradient) to give the major product 1-[4-acetyl-1-(4-hydroxy-2-methoxy-phenyl)-2,5-dimethyl-1H-pyrrol-3-yl]-ethanone as pale yellow oil: MS (ESI) 302 (M+H)$^+$; In this reaction, small amount (~10%) of minor product 1-[4-acetyl-1-(2,4-dihydroxy-phenyl)-2,5-dimethyl-1H-pyrrol-3-yl]-ethanone was also isolated as clear colorless oil: MS (ESI) 288 (M+H)$^+$.

Utilizing the general procedure outlined in Example 65, 1-[4-acetyl-1-(4-hydroxy-2-methoxy-phenyl)-2,5-dimethyl-1H-pyrrol-3-yl]-ethanone (70 mg, 2.3 mmol) reacted with bromoethane (300 μL, excess), in the presence of $K_2CO_3$ (50 mg), to afford 1-[4-acetyl-1-(4-ethoxy-2-methoxy-phenyl)-2,5-dimethyl-1H-pyrrol-3-yl]-ethanone: MS (ESI) 330 (M+H)$^+$.

Utilizing the general procedure outlined in Example 48, 1-[4-acetyl-1-(4-ethoxy-2-methoxy-phenyl)-2,5-dimethyl-1H-pyrrol-3-yl]-ethanone (60 mg) and hydrazine (50 μL) reacted to give 6-(4-Ethoxy-2-methoxy-phenyl)-1,4,5,7-tetramethyl-6H-pyrrolo[3,4-d]pyridazine as light yellow solid: $^1$H NMR (CDCl$_3$, 500 MHz) δ 7.06 (d, 1H), 6.66 (m, 2H), 4.05 (q, 2H), 3.86 (s, 3H), 2.84 (s, 6H), 2.41 (s, 6H), 1.25 (t, 3H); MS (ESI) 326 (M+H)$^+$

EXAMPLE 71

6-(2,4-diethoxy-phenyl)-1,4,5,7-tetramethyl-6H-pyrrolo[3,4-d]pyridazine

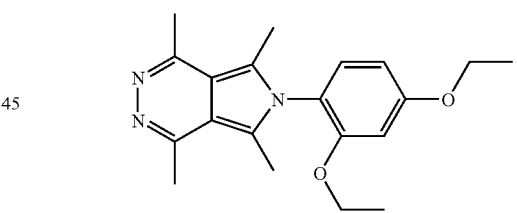

Utilizing the general procedure outlined in Example 65, 1-[4-acetyl-1-(2,4dihydroxy-phenyl)-2,5-dimethyl-1H-pyrrol-3-yl]-ethanone prepared as in Example 70 (12 mg, 0.4 mmol) reacted with bromoethane (30 μL, excess), in the presence of $K_2CO_3$ (10 mg), to afford 1-[4-acetyl-1-(2,4-diethoxy-phenyl)-2,5-dimethyl-1H-pyrrol-3-yl]-ethanone: MS (ESI) 344 (M+H)$^+$. Utilizing the general procedure outlined in Example 48, 1-[4-acetyl-1-(2,4-diethoxy-phenyl)-2,5-dimethyl-1H-pyrrol-3-yl]-ethanone (4 mg) and hydrazine (5 μL) reacted to give 6-(2,4-diethoxy-phenyl)-1,4,5,7-tetramethyl-6H-pyrrolo[3,4-d]pyridazine as off-white solid: $^1$H NMR (CDCl$_3$, 500 MHz) δ 7.03 (d, 1H), 6.67 (s, 1H), 6.64 (d, 1H), 4.15 (q, 1H), 4.04 (q, 1H), 2.89 (br s, 6H), 2.43 (s, 6H), 1.49 (t, 3H, 1.26 (t, 3H); MS (ESI) 340 (M+H)$^+$.

EXAMPLE 72

6-(2-ethoxy-4-methoxy-phenyl)-1,4,5,7-tetramethyl-6H-pyrrolo[3,4-d]pyridazine

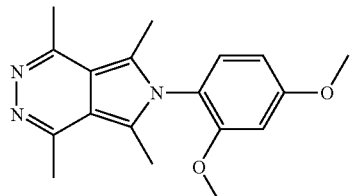

To a stirring solution of 1-[4-acetyl-1-(2,4-dimethoxy-phenyl)-2,5-dimethyl-1H-pyrrol-3-yl]-ethanone prepared as in Example 70 (1580 mg, 0.5 mmol) in 2.0 mL of dry DMF at rt was added sodium ethanethiolate (80%, Aldrich; 210 mg, 2.0 mmol). After 20 min at rt, it was heated to 120° C. and stirred for an additional 2 h before it was quenched with 1N HCl (5 mL). It was extracted with EtOAc (2×10 mL), and the combined organic extracts were washed with dried with MgSO$_4$, filtered, and concentrated in vacuo to afford the crude product as a yellow oil. This crude material was purified by automated chromatography on silica gel (using an 20-50% EtOAc/hexanes gradient) to give the major product 1-[4-acetyl-1-(2-hydroxy-4-methoxy-phenyl)-2,5-dimethyl-1H-pyrrol-3-yl]-ethanone as pale yellow oil: MS (ESI) 302 (M+H)$^+$.

Utilizing the general procedure outlined in Example 65, 1-[4-acetyl-1-(2-hydroxy-4-methoxy-phenyl)-2,5-dimethyl-1H-pyrrol-3-yl]-ethanone (70 mg, 2.3 mmol) reacted with bromoethane (300 μL, excess), in the presence of K$_2$CO$_3$ (50 mg), to afford 1-[4-acetyl-1-(2-ethoxy-4-methoxy-phenyl)-2,5-dimethyl-1H-pyrrol-3-yl]-ethanone: MS (ESI) 330 (M+H)$^+$. Utilizing the general procedure outlined in Example 48, 1-[4-acetyl-1-(4-ethoxy-2-methoxy-phenyl)-2,5-dimethyl-1H-pyrrol-3-yl]-ethanone (60 mg) and hydrazine (50 μL) reacted to give 6-(2-ethoxy-4-methoxy-phenyl)-1,4,5,7-tetramethyl-6H-pyrrolo[3,4-d]pyridazine as light yellow solid: $^1$H NMR (CDCl$_3$, 500 MHz) δ 7.04 (d, 1H), 6.68 (s, 1H), 6.64 (d, 1H), 4.15 (q, 1H), 3.78 (s, 3H), 2.81 (s, 6H), 2.40 (s, 6H), 1.51 (t, 3H); MS (ESI) 326 (M+H)$^+$.

EXAMPLE 73

6-(4-Ethoxy-2,3-dimethyl-phenyl)-1,4,5,7-tetramethyl-6H-pyrrolo[3,4-d]pyridazine

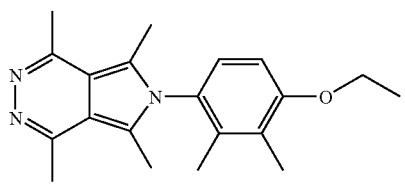

Utilizing the general procedure outlined in Example 48, 1,1,2,2-tetraacetylethane (300 mg, 1.5 mol) and 4-amino-2.3-xylenol (206 mg, 1.5 mmol) reacted to give 1-[4-acetyl-1-(4-hydroxy-2,3-dimethyl-phenyl)-2,5-dimethyl-1H-pyrrol-3-yl]-ethanone as yellow solid: MS (ESI) 300 (M+H)$^+$.

Utilizing the general procedure outlined in Example 65, 1-[4-acetyl-1-(4-hydroxy-2,3-dimethyl-phenyl)-2,5-dimethyl-1H-pyrrol-3-yl]-ethanone (100 mg, 0.3 mmol) reacted with bromoethane (300 μL, excess), in the presence of K$_2$CO$_3$ (50 mg), to afford 1-[4-acetyl-1-(4-ethoxy-2,3-dimethyl-phenyl)-2,5-dimethyl-1H-pyrrol-3-yl]-ethanone: MS (ESI) 328 (M+H)$^+$. Utilizing the general procedure outlined in Example 48, 1-[4-acetyl-1-(4-ethoxy-2,3-dimethyl-phenyl)-2,5-dimethyl-1H-pyrrol-3-yl]-ethanone (108 mg, 0.3) and hydrazine (50 μL) reacted to give 6-(4-Ethoxy-2,3-dimethyl-phenyl)-1,4,5,7-tetramethyl-6H-pyrrolo[3,4-d]pyridazine as off-white solid: $^1$H NMR (CDCl$_3$, 500 MHz) δ 6.92 (d, 1H), 6.86 (d, 1H), 4.14 (q, 2H), 2.83 (s, 6H), 2.36 (s, 6H), 2.28 (s, 3H), 1.72 (s, 3H), 1.52 (t, 3H); MS (ESI) 324 (M+H)$^+$.

EXAMPLE 74

6-(4-Ethoxy-2,5-dimethyl-phenyl)-1,4,5,7-tetramethyl-6H-pyrrolo[3,4-d]pyridazine Utilizing the general procedure outlined in Example 481, 1,1,2,2

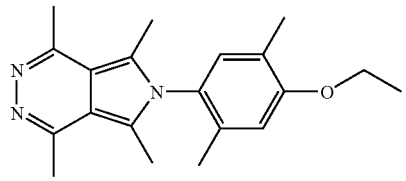

-tetraacetylethane (200 mg, 1.0 mol) and 4-amino-2,5-dimethylphenol (138 mg, 1.0 mmol) reacted to give 1-[4-acetyl-1-(4-hydroxy-2,5-dimethyl-phenyl)-2,5-dimethyl-1H-pyrrol-3-yl]-ethanone as yellow solid: MS (ESI) 300 (M+H)$^+$.

Utilizing the general procedure outlined in Example 7, 1-[4-acetyl-1-(4-hydroxy-2,5-dimethyl-phenyl)-2,5-dimethyl-1H-pyrrol-3-yl]-ethanone (100 mg, 0.3 mmol) reacted with bromoethane (300 μL, excess), in the presence of K$_2$CO$_3$ (50 mg), to afford 1-[4-acetyl-1-(4-ethoxy-2,5-dimethyl-phenyl)-2,5-dimethyl-1H-pyrrol-3-yl]-ethanone: MS (ESI) 328 (M+H)$^+$. Utilizing the general procedure outlined in Example 48, 1-[4-acetyl-1-(4-ethoxy-2,5-dimethyl-phenyl)-2,5-dimethyl-1H-pyrrol-3-yl]-ethanone (108 mg, 0.3) and hydrazine (50 μL) reacted to give 6-(4-Ethoxy-2,3-dimethyl-phenyl)-1,4,5,7-tetramethyl-6H-pyrrolo[3,4-d]-pyridazine as an off-white solid: $^1$H NMR (CDCl$_3$, 500 MHz) δ 6.88 (s, 1H), 6.77 (s, 1H), 4.14 (q, 2H), 2.85 (s, 6H), 2.39 (s, 6H), 2.26 (s, 3H), 1.83 (s, 3H, 1.50 (t, 3H); MS (ESI) 324 (M+H)$^+$.

EXAMPLE 75

6-(4-Ethoxy-2-fluoro-phenyl)-1,4,5,7-tetramethyl-6H-pyrrolo[3,4-d]pyridazine

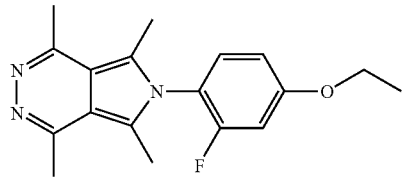

To a solution of 3-fluoro-4-nitrophenol (1.57 g, 10.0 mmol) in 20 mL of dry DMF was added bromoethane (540 mg, 5.0 mmol) and K$_2$CO$_3$ powder (500 mg). The resulting reaction mixture was warmed to 50° C. and stirred for 1 h. It was quenched by addition of 20 mL of H$_2$O, extracted with diethyl ether (100 mL×2). The combined organic extracts were washed with brine (50 mL), dried (MgSO$_4$), filtered, and concentrated in vacuo to afford 4-ethoxy-2-fluoro-1-nitrobenzene as a pale yellow oil: MS (ESI) 186 (M+H)$^+$.

To a solution of 4-ethoxy-2-fluoro-1-nitro benzene (1.0 g, 5.4 mmol) in absolute EtOH (25 mL) at rt was added 250 mg of Pd/C (Aldrich, 10 wt. % on activated carbon), followed by slow addition of hydrazine hydrate (2.5 mL). The resulting reaction mixture was refluxed at 90° C. for 30 min. It then cooled to rt, filtered through Celite, and then concentrated in vacuo to afford 4-ethoxy-2-fluoro-phenyl amine as a pale yellow oil: MS (ESI) 156 (M+H)$^+$.

Utilizing the general procedure outlined in Example 48, 1,1,2,2-tetraacetylethane (200 mg, 1.0 mol), 4-ethoxy-2-fluoro-phenyl amine (155 mg, 1.0 mmol) and hydrazine (50 µL) reacted to give 6-(4-ethoxy-2-fluoro-phenyl)-1,4,5,7-tetramethyl-6H-pyrrolo[3,4-d]pyridazine as yellow solid: $^1$H NMR (CDCl$_3$, 500 MHz) δ 7.13 (t, 1H), 6.88 (m, 2H), 4.16 (q, 2H), 2.82 (s, 6H), 2.46 (s, 6H), 1.53 (t, 3H); MS (ESI) 314 (M+H)$^+$.

EXAMPLE 76

6-(4-Ethoxy-2-methylsulfanyl-phenyl)-1,4,5,7-tetramethyl-6H-pyrrolo[3,4-d]pyridazine

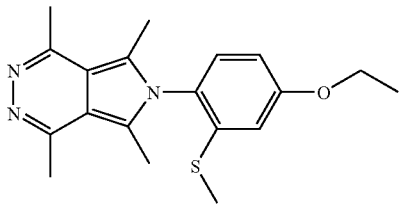

To a solution of 4-Ethoxy-2-fluoro-1-nitro benzene prepared as in Example 75 (185 mg, 1.0 mmol) in 2 mL of dry DMF was added NaSMe (84 mg, 1.20 mmol). The resulting reaction mixture was warmed to 50° C. and stirred for 1 h. It was quenched by addition of 20 mL of H$_2$O. The precipitate was filtered, washed with H$_2$O and dried under vacuum to afford 4-ethoxy-2-methylsulfanyl-1-nitro-benzene as yellow oil: MS (ESI) 211 (M+H)$^+$.

To a solution of 4-ethoxy-2-methylsulfanyl-1-nitro-benzene (1.0 g, 5.4 mmol) in absolute EtOH (25 mL) at rt was added 40 mg of Pd/C (Aldrich, 10 wt. % on active carbon), followed by slow addition of hydrazine hydrate (0.5 mL). The resulting reaction mixture was refluxed at 90° C. for 3 h. It then cooled to rt, filtered through Celite, and then concentrated in vacuo to afford 4-ethoxy-2-methylsulfanyl-phenyl amine as a pale yellow oil: MS (ESI) 184 (M+H)$^+$.

Utilizing the general procedure outlined in Example 48, 1,1,2,2-tetraacetylethane (200 mg, 1.0 mol), 4-ethoxy-2-methylsulfanyl-phenyl amine (140 mg, 0.8 mmol) and hydrazine (50 µL) reacted to give 6-(4-Ethoxy-2-methylsulfanyl-phenyl)-1,4,5,7-tetramethyl-6H-pyrrolo[3,4-d]pyridazine as yellow solid: $^1$H NMR (CDCl$_3$, 500 MHz) δ 7.05 (d, 1H), 6.88 (s, 1H), 6.82 (d, 1H), 4.16 (q, 2H), 2.81 (s, 6H), 2.42 (s, 6H), 1.53 (t, 3H); MS (ESI) 342 (M+H)$^+$.

EXAMPLE 77

6-(4-Ethoxy-2-vinyl-phenyl)-1,4,5,7-tetramethyl-6H-pyrrolo[3,4-d]pyridazine

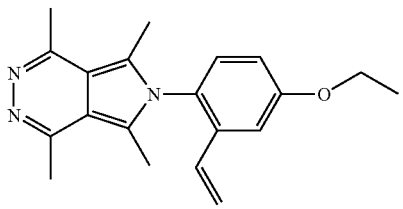

To a solution of 3-hydroxymethyl-4-nitro-phenol (510 mg, 3.0 mmol) in 5 mL of dry DMF was added bromoethane (540 mg, 5.0 mmol) and K$_2$CO$_3$ powder (500 mg). The resulting reaction mixture was warmed to 50° C. and stirred for 1 h. It was quenched by addition of 20 mL of H$_2$O, extracted with diethyl ether (2×20 mL). The combined organic extracts were washed with brine (50 mL), dried (MgSO$_4$), filtered, and concentrated in vacuo to afford (5-ethoxy-2-nitro-phenyl)-methanol as a pale yellow oil: $^1$H NMR (CDCl$_3$, 500 MHz) δ 8.20 (d, 1H), 7.36 (s, 1H), 6.89 (m, 1H), 5.00 (s, 2H), 4.16 (q, 2H), 2.57 (br t, 1H), 1.49 (t, 3H).

To a solution of (5-ethoxy-2-nitro-phenyl)-methanol (592 mg, 3.0 mmol) in absolute EtOH (20 mL) at rt was added 150 mg of Pd/C (Aldrich, 10 wt. % on active carbon), followed by slow addition of hydrazine hydrate (1.5 mL). The resulting reaction mixture was refluxed at 90° C. for 1 h. It was then cooled to rt, filtered through Celite, and then concentrated in vacuo to afford crude (2-amino-5-ethoxy-phenyl)-methanol as a pale yellow oil: MS (ESI) 168 (M+H)$^+$.

A solution of 1,1,2,2-tetraacetylethane (600 mg, 3.0 mol) and (2-amino-5-ethoxy-phenyl)-methanol (496 mg, 3.0 mmol) was refluxed in EtOH (10 mL)/AcOH (1%) for 14 h. It was cooled to rt, and anhydrous hydrazine (200 µL, 6.3 mmol) was added. After stilling at rt for 1 h, the reaction mixture was poured into ice water (50 mL). The resulting precipitate was filtered, washed with diethyl ether (20 mL), and then dried under vacuum to afford [5-ethoxy-2-(1,4,5,7-tetramethyl-pyrrolo[3,4-δ]pyridazin-6-yl)-phenyl]-methanol as a pale yellow solid: 1H NMR (CDCl$_3$, 500 MHz) δ 7.24 (s, 1H), 6.98 (m, 2H), 4.62 (s, 2H), 4.16 (q, 2H), 2.66 (s, 6H), 2.41 (s, 6H), 1.50 (t, 3H); MS (ESI) 327 (M+H)$^+$.

To a solution of [5-ethoxy-2-(1,4,5,7-tetramethyl-pyrrolo[3,4-d]pyridazin-6-yl)-phenyl]-methanol (70 mg, 2.3 mmol) in CH$_2$Cl$_2$ (10 mL) at rt was added MnO$_2$ (200 mg, excess). The resulting reaction mixture was stirred at rt for 2 h before if was filtered through Celite, and eluted with CH$_2$Cl$_2$ (20 mL×2). The eluant was collected and concentrated in vacuo to afford 5-ethoxy-2-(1,4,5,7-tetramethyl-pyrrolo[3,4-δ]pyridazin-6-yl)-benzaldehyde as a yellow solid: $^1$H NMR (CDCl$_3$, 500 MHz) δ 10.56 (s, 1H), 7.71 (s, 1H), 7.40 (d, 1H), 7.20 (d, 1H), 4.28 (q, 2H), 2.86 (s, 6H), 2.45 (s, 6H), 1.58 (t, 3H); MS (ESI) 325 (M+H)$^+$.

A suspension of methyltriphenylphosphonium bromide (178 mg, 0.5 mmol) in 3.0 mL of THF at rt was treated with n-BuLi (1.6 M in Hexane, 280 µL, 0.45 mmol) dropwise. After 5 min at rt, it was warmed to 50° C. and stirred for 30 min, and then cooled back to rt to give the in situ generated ylide solution. Part of this reaction solution (2.0 mL) was transferred to another reaction flask containing 5-ethoxy-2-(1,4,5,7-tetramethyl-pyrrolo[3,4-δ]pyridazin-6-yl)-benzaldehyde (32 mg, 0.1 mol) and 0.5 mL of THF under $N_2$ atmosphere. The resulting reaction mixture was stirred at rt for 3 h before it was quenched with $H_2O$ and extracted with diethyl ether (2×10 mL). All organic extracts were combined, dried ($MgSO_4$), filtered, and concentrated in vacuo to afford crude product as yellow oil. It was purified by preparative TLC plate (20×20 cm, 0.5 mm layer thickness, eluted with 7% $CH_2Cl_2$/MeOH) to give pure 6-(4-ethoxy-2-vinyl-phenyl)-1,4,5,7-tetramethyl-6H-pyrrolo[3,4-δ]pyridazine as a pale yellow solid: $^1$H NMR (CDCl$_3$, 500 MHz) δ 7.26 (s, 1H), 7.06 (d, 1H), 6.98 (d, 1H), 5.79 (dd, 1H), 5.77 (d, 1H), 5.24 (d, 2H), 4.15 (q, 2H), 2.81 (s, 6H), 2.37 (s, 6H), 1.52 (t, 3H); MS (ESI) 323 (M+H)$^+$.

EXAMPLE 78

6-(4-Ethoxy-2-ethyl-phenyl)-1,4,5,7-tetramethyl-6H-pyrrolo[3,4-d]pyridazine

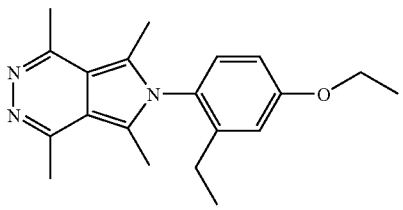

To a solution of 6-(4-ethoxy-2-vinyl-phenyl)-1,4,5,7-tetramethyl-6H-pyrrolo[3,4-d]pyridazine (30 mg, 3.0 mmol) in 3 mL of ethanol was added anhydrous hydrazine (20 μL). The resulting reaction solution was refluxed at 90° C. for 90 min. It was allowed to warm to rt and directly condensed in vacuo to afford 6-(4-Ethoxy-2-ethyl-phenyl)-1,4,5,7-tetramethyl-6H-pyrrolo[3,4-d]pyridazine as a light yellow solid: $^1$H NMR (CDCl$_3$, 500 MHz) δ 7.00 (m, 2H), 6.89 (m, 1H), 4.15 (q, 2H), 2.82 (s, 6H), 2.38 (s, 6H), 2.10 (q, 2H), 1.52 (t, 3H), 1.08 (t, 3H); MS (ESI) 324 (M+H)$^+$.

EXAMPLE 79

6-(4-Ethoxy-2,6-dimethyl-phenyl)-1,4,5,7-tetramethyl-6H-pyrrolo[3,4-d]pyridazine

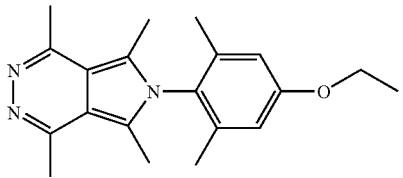

Utilizing the general procedure outlined in Example 77, 4-nitro-3,5-dimethyl-phenol was converted to 4-ethoxy-2,6-dimethyl-phenylamine in two step. This crude amine was use directly in the next reaction without further purification.

Utilizing the general procedure outlined in Example 48, 1,1,2,2-tetraacetylethane (308 mg, 1.56 mol), 4-ethoxy-2,6-dimethyl-phenylamine (250 mg, 1.0 mmol) and hydrazine (100 μL) reacted to give 6-(4-ethoxy-2,6-dimethyl-phenyl)-1,4,5,7-tetramethyl-6H-pyrrolo[3,4-d]-pyridazine as yellow solid: $^1$H NM (CDCl$_3$, 500 MHz) δ 6.81 (s, 1H), 6.75 (s, 1H), 4.04 (q, 2H), 2.82 (s, 6H), 2.44 (s, 6H), 2.47 (s, 3H), 2.35 (s, 6H), 1.79 (s, 3H), 1.88 (t, 3H), ; MS (ESI) 324 (M+H)$^+$.

EXAMPLE 80

[5-Ethoxy-2-(1,4,5,7-tetramethyl-pyrrolo[3.4-d]pyridazin-6-yl)-phenyl]-methanol

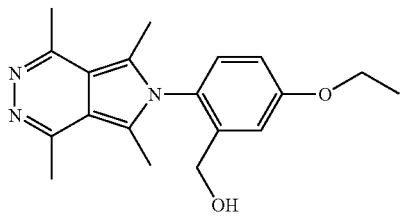

To a solution of 3-hydroxymethyl-4-nitro-phenol (510 mg, 3.0 mmol) in 5 mL of dry DMF was added bromoethane (540 mg, 5.0 mmol) and $K_2CO_3$ powder (500 mg). The resulting reaction mixture was warmed to 50° C. and stirred for 1 h. It was quenched by addition of 20 mL of $H_2O$, extracted with diethyl ether (2×20 mL). The combined organic extracts were washed with brine (50 mL), dried ($MgSO_4$), filtered, and concentrated in vacuo to afford (5-ethoxy-2-nitro-phenyl)-methanol as a pale yellow oil: $^1$H NMR (CDCl$_3$, 500 MHz ) δ 8.20 (d, 1H), 7.36 (s, 1H), 6.89 (m, 1H), 5.00 (s, 2H), 4.16 (q, 2H), 2.57 (br t, 1H), 1.49 (t, 3H).

To a solution of (5-ethoxy-2-nitro-phenyl)-methane (592 mg, 3.0 mmol) in absolute EtOH (20 mL) at rt was added 150 mg of Pd/C (Aldrich, 10 wt. % on activated carbon), followed by slow addition of hydrazine hydrate (1.5 mL). The resulting reaction mixture was refluxed at 90° C. for 1h. It then cooled to rt, filtered through Celite, and then concentrated in vacuo to afford crude (2-amino-5-ethoxy-phenyl)-methanol as a pale yellow oil: MS (ESI) 168 (M+H)$^+$.

A solution of 1,1,2,2-tetraacetylethane (600 mg, 3.0 mol) and (2-amino-5-ethoxy-phenyl)-methanol (496 mg, 3.0 mmol) was refluxed in EtOH (10 mL)/AcOH (1%) for 14 h. It was cooled to rt, and anhydrous hydrazine (200 μL, 6.3 mmol) was added. After stirring at rt for 1 h, the reaction mixture was poured into ice water (50 mL). The resulting precipitate was filtered, washed with diethyl ether (20 mL), and then dried under vacuum to afford [5-ethoxy-2-(1,4,5,7-tetramethyl-pyrrolo[3,4-d]pyridazin-6-yl)-phenyl]-methanol as a pale yellow solid: $^1$H NMR (CDCl$_3$, 500 MHz) δ 7.22 (s, 1H), 6.95 (m, 2H), 4.40 (s, 2H), 4.16 (q, 2H), 2.66 (s, 6H), 2.41 (s, 6H), 1.50 (t, 3H); MS (ESI) 326 (M+H)$^+$.

EXAMPLE 81

[2-Ethoxy-5-(1,4,5,7-tetramethyl-pyrrolo[3.4-d]pyridazin-6-yl)-phenyl]-methanol

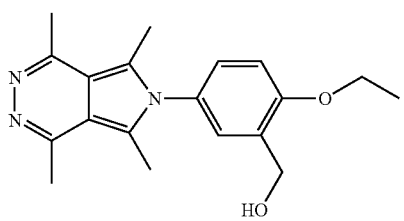

Utilizing the general procedure outlined in Example 77, 2-hydroxymethyl-4-nitro-phenol was converted to afford (5-amino-2-ethoxy-phenyl)-methanol in two step. This crude amine was use directly in the next reaction without further purification.

Utilizing the general procedure outlined in Example 48, 1,1,2,2-tetraacetylethane (308 mg, 1.56 mol), (5-amino-2-ethoxy-phenyl)-methanol (250 mg, 1.0 mmol) and hydrazine (100 µL) reacted to give [2-ethoxy-5-(1,4,5,7-tetramethyl-pyrrolo[3,4-d]pyridazin-6-yl)-phenyl]-methanol as yellow solid: $^1$H NMR (CDCl$_3$, 500 MHz) δ 7.24 (s, 1H), 7.08-7.01 (m, 2H), 4.81 (s, 2H), 4.18 (q, 2H), 2.77 (s, 6H), 2.43 (s, 6H), 1.51 (t, 3H); MS (ESI) 326 (M+H)$^+$.

EXAMPLE 82

5-Ethoxy-2-(1,4,5,7-tetramethyl-pyrrolo[3,4-d]pyridazin-6-yl)-benzaldehyde

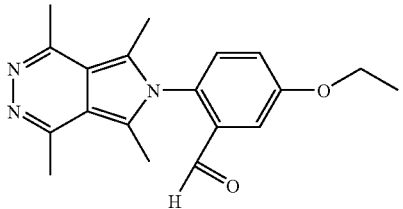

To a solution of [5-ethoxy-2-(1,4,5,7-tetramethyl-pyrrolo[3,4-d]pyridazin-6-yl)-phenyl]-methanol (prepared as described in Example 81; 70 mg, 2.3 mmol) in CH$_2$Cl$_2$ (10 mL) at rt was added MnO$_2$ (200 mg, excess). The resulting reaction mixture was stirred at rt for 2 h before if was filtered through Celite, and eluted with CH$_2$Cl$_2$ (2×20mL). The eluant was collected and concentrated in vacuo to afford 5-ethoxy-2-(1,4,5,7-tetramethyl-pyrrolo[3,4δ]pyridazin-6-yl)-benzaldehyde as a yellow solid: $^1$H NMR (CDCl$_3$, 500 MHz) δ 10.55 (s, 1H), 7.70 (s, 1H), 7.40 (d, 1H), 7.20 (d, 1H), 4.30 (s, 2H), 2.87 (s, 6H), 2.45 (s, 6H), 1.57 (t, 3H); MS (ESI) 324 (M+H)$^+$.

EXAMPLE 83

2-Ethoxy-5-(1,4,5,7-tetramethyl-pyrrolo[3,4-d]pyridazin-6-yl)-benzaldehyde

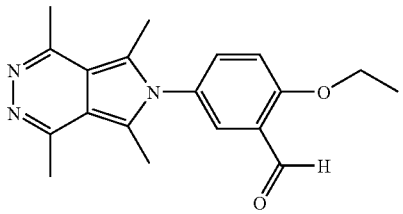

Utilizing the general procedure outlined in Example 82, [5-ethoxy-2-(1,4,5,7-tetramethyl-pyrrolo[3,4-d]pyridazin-6-yl)-phenyl]-methanol (prepared as described in Example 81; 100 mg, 0.3 mmol) reacted with MnO$_2$ (200 mg, excess) to afford 2-ethoxy-5-(1,4,5,7-tetramethyl-pyrrolo[3,4-d]pyridazin-6-yl)-benzaldehyde as a yellow solid: $^1$H NMR (CDCl$_3$, 500 MHz) δ 9.20 (s, 1H), 7.57 (s, 1H), 7.34 (d, 1H), 7.24 (d, 1H), 4.20 (q, 2H), 2.90 (s, 6H), 2.42 (s, 6H), 1.51 (t, 3H); MS (ESI) 324 (M+H)$^+$.

EXAMPLE 84

6-(4-ethoxy-2-nitrophenyl)-1,4,5,7-tetramethyl-6H-pyrrolo[3,4d]pyridazine hydrochloride

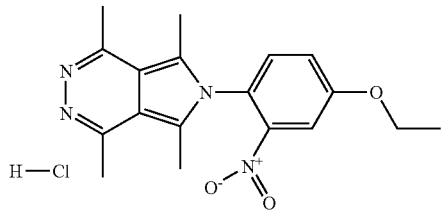

To a solution of acetonyl acetone (1.95 mL, 16.5 mmol) in acetic acid (100 mL) was added 4-ethoxy-2-nitroaniline (3.0 g, 16.5 mmol) and the red mixture heated at reflux overnight. After cooling to rt, the now black solution was poured into water and extracted with EtOAc (2×200mL). The combined organic layers were washed with brine, dried over MgSO$_4$, filtered, and concentrated in vacuo to an oil. Purification by flash chromatography (10% EtOAc/hexanes) gave 2,5-dimethyl-1-(4-ethoxy-2-nitrophenyl)pyrrole as a red oil: $^1$H NMR (CDCl$_3$, 500 MHz) δ 7.46 (d, 1H), 7.27 (t, 1H), 7.19 (dd, 1H), 5.91 (s, 2H), 4.15 (q, 1H), 1.96 (s, 6H), 1.50 (t, 3H); MS (ESI) 261 (M+H)$^+$.

To a solution of 2,5-dimethyl-1-(4-ethoxy-2-nitrophenyl) pyrrole (3.10 g, 11.9 mmol) in CH$_2$Cl$_2$ (80 mL) at 0° C. was added acetyl chloride (2.13 mL, 30 mmol) followed by dropwise addition of tin(IV) chloride (3.51mL, 30 mmol). The solution was allowed to warm to rt overnight followed by heating at reflux for an addition 24 hours. After cooling to rt, the reaction was diluted with 0.25 M NaOH, extracted with EtOAc, the organic layer washed with brine, dried over MgSO$_4$, filtered, concentrated in vacuo, and purified by flash chromatography (20-75% EtOAc/hexanes) to give 3,4-diacetyl-2,5-dimethyl-1-(4-ethoxy-2-nitrophenyl)pyrrole as a green solid (MS (ESI) 345 (M+H)$^+$; the major product being monoacylation). The solid was taken up in ethanol (10 mL), an excess of hydrazine (0.1 mL) added, and the solution heated at 50° C. After 3 hours, the reaction was poured over ice, filtered, taken up in hot ether, precipitated with HCl in ether, and filtered to give 6-(4-ethoxy-2-nitrophenyl)-1,4,5,7-tetramethyl-6H-pyrrolo[3,4-d]pyridazine hydrochloride as a tan solid: $^1$H NMR (DMSO-d$_6$, 500 MHz) δ 7.93 (d, 1H), 7.68-7.61 (m, 2H), 4.29 (q, 1H), 3.02 (br s, 3H), 2.82 (br s, 3H), 2.46 (s, 6H), 1.42 (t, 3H); MS (ESI) 341 (M+H)$^+$.

EXAMPLE 85

6-(4-ethoxyphenyl)-N,4,5,7-tetramethyl-6H-pyrrolo[3,4-d]pyridazin-1-amine

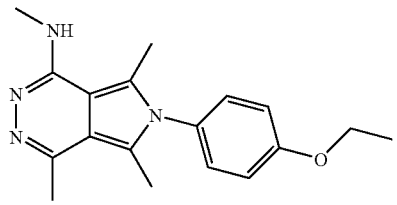

To a slurry of NaH (2.6 g, 66 mmol, 60% dispersion in mineral oil) and THF (200 mL) at 0° C. was added ethyl acetoacetate (7.8 mL, 60 mmol) dropwise. After 15 min, α-chloroacetone (5.2 mL, 66 mmol) was added and the resulting solution allowed to warm to rt over 12 h. The reaction mixture was partitioned between MTBE and water, the water layer extracted with MTBE (2×50 mL), and the combined extracts dried (MgSO$_4$), and concentrated under reduced pressure to afford, after automated chromatography on silica gel (using an EtOAc/hexanes gradient), ethyl 2-acetyl-4-oxopentanoate as a colorless oil.

Ethyl 2-acetyl-4-oxopentanoate (6.37 g, 34.2 mmol) was dissolved in 20 mL of EtOH. p-Phenetidine (4.70 g, 34.2 mmol) was added as well as several drops of AcOH and heated at reflux for 15 h. The reaction mixture was allowed to cool to rt and then concentrated under reduced pressure. The resulting brown oil was dissolved in CH$_2$Cl$_2$ (20 mL) and washed with saturated aqueous NaHCO$_3$ (3×50 mL) dried (MgSO$_4$) and concentrated. The resulting crude ethyl 1-(4-ethoxyphenyl)-2,5-dimethyl-1H-pyrrole-3-carboxylate was taken on without further purification. MS (ESI) 288 (M+H)$^+$.

In an oven-dried flask, ethyl 1-(4-ethoxyphenyl)-2,5-dimethyl-1H-pyrrole-3-carboxylate (9.32 g, 32.5 mmol) combined with toluene (100 mL), acetyl chloride (2.8 mL, 39.3 mmol), and SnCl$_4$ (4.67 mL, 29.3 mmol). The reaction mixture was stirred at rt for 4 h. The reaction was quenched by the addition of 1N NaOH (added until pH 12 was reached) and the aqueous layer extracted with CH$_2$Cl$_2$ (2×200 mL) and Et$_2$O (2×100 mL). The combined organic extracts were dried (MgSO$_4$) and concentrated in vacuo. The resulting crude (ethyl-4-acetyl-1-(4-ethoxyphenyl)-2,5-dimethyl-1H-pyrrole-3-carboxylate) was of sufficient purity for further reactions. MS (ESI) 330 (M+H)$^+$.

A solution of ethyl-4-acetyl-1-(4-ethoxyphenyl)-2,5-dimethyl-1H-pyrrole-3-carboxylate (7.50 g, 22.8 mmol) and EtOH (75 mL) was placed in a resealable reaction vessel. Hydrazine (2 mL, 64 mmol) and AcOH (~1 mL) were added, the tube closed, and heated to 80° C. for 12 h. The resulting slurry was allowed to cool to rt and poured into ice water (50 mL). The resulting white solid (6-(4-ethoxyphenyl)4,5,7-trimethyl-2,6-dihydro-1H-pyrrolo[3,4-d]pyridazin-1-one) was filtered and dried under vacuum for 8 h. MS (ESI) 298 (M+H)$^+$.

A solution of POCl$_3$ (15 mL) and 6-(4-ethoxyphenyl)4,5,7-trimethyl-2,6-dihydro-1H-pyrrolo[3,4-d]pyridazin-1-one (1.5 g) were combined and heated at reflux for 48 h. The reaction mixture was allowed to cool to rt, and was quenched by the careful addition of water (50 mL) followed by a saturated aqueous solution NaHCO$_3$ (50 mL). The reaction mixture was extracted with CH$_2$Cl$_2$ (5×50 mL), and the combined organic extracts were dried (MgSO$_4$) and concentrated under reduced pressure to yield 1-chloro-6-(4-ethoxyphenyl)-4,5,7-trimethyl-6H-pyrrolo[3,4-d]pyridazine as a yellow/green solid. MS (ESI) 316 (M+H)$^+$.

To a Personal Chemistry Microwave Synthesizer microwave vial was combined 1-chloro-6-(4-ethoxyphenyl)-4,5,7-trimethyl-6H-pyrrolo[3,4-d]pyridazine (200 mg, 0.64 mmol), MeNH$_2$ (1 mL, 40% in H$_2$O), and EtOH (1 mL). The vial was sealed and heated at 120° C. for 12 min. The reaction mixture was poured into water to afford crude 6-(4-ethoxyphenyl)-N,4,5,7-tetramethyl-6H-pyrrolo[3,4-d]pyridazin-1-amine. Purification by reverse phase preparative HPLC using a YMC CombiPrep Pro C$_{18}$20×100 column (Gradient: 5%-100% Acetonitrile in a H$_2$O+0.1% TFA solution over 10 min, retention time: 6.1 min) afforded pure 6-(4-ethoxyphenyl)-N,4,5,7-tetramethyl-6H-pyrrolo[3,4-d]pyridazin-1-amine as a colorless solid: $^1$H NMR (CDCl$_3$, 500 MHz) δ 7.05-7.12 (m, 4H), 4.16 (q, 2H), 3.20 (s, 3H), 2.69 (s, 3H), 2.43 (s, 3H), 2.39 (s, 3H), 1.51 (t, 3H); MS (ESI) 311 (M+H)$^+$.

EXAMPLE 86

6-(4-ethoxyphenyl)-N,N,4,5,7-pentamethyl-6H-pyrrolo[3,4-d]pyridazin-1-amine

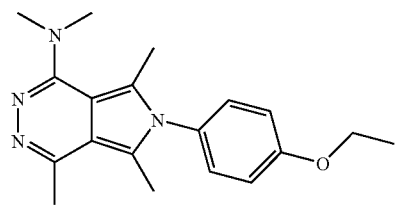

Utilizing the general procedure outlined in EXAMPLE 85, 1-chloro-6-(4-ethoxyphenyl)-4,5,7-trimethyl-6H-pyrrolo[3,4-d]pyridazine and Me$_2$N (1 mL, 40% solution in H$_2$O) reacted to give 6-(4-ethoxyphenyl)-N,N,4,5,7-pentamethyl-6H-pyrrolo[3,4-d]pyridazin-1-amine: $^1$H NMR (CDCl$_3$, 500 MHz) δ 7.06-7.15 (m, 4H), 4.15 (q, 2H), 3.08 (s, 6H), 2.78 (s, 3H), 2.50 (s, 2H), 2.44 (s, 2H), 1.51-1.52 (s, 3H); MS (ESI) 325 (M+H)$^+$.

EXAMPLE 87

6-(3,5-dibromo-4-ethoxyphenyl)-1-aminomethyl-4,5,7-trimethyl-6H-pyrrolo[3,4-d]pyridazine

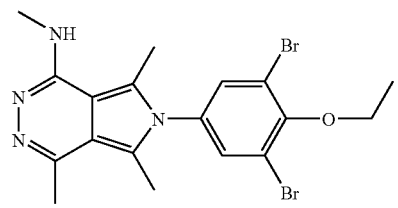

Utilizing the procedure outlined in Example 85, ethyl 2-acetyl-4-oxopentanoate (6.37 g, 34.2 mmol) was dissolved in 20 mL of EtOH. 2,6-dibromo-4-aminophenol (11.6g, 34.2mmol) were reacted to afford ethyl 1-(3,5-dibromo-4-hydroxyphenyl)-2,5-dimethyl-1H-pyrrole-3-carboxylate was taken on without further purification. MS (ESI) 418 (M+H)$^+$.

Crude ethyl 1-(3,5-dibromo-4-hydroxyphenyl)-2,5-dimethyl-1H-pyrrole-3-carboxylate was mixed with Cs$_2$CO$_3$ (11.4 g, 35 mmol), bromoethane (7.50 g, 70.0 mmol), and MeCN (150 mL) and heated at 50 ° C. for 4 hr. Standard aqueous workup afforded, after purification on silica gel (utilizing an ethyl acetate/hexanes gradient) ethyl 1-(3,5-dibromo-4-ethoxyphenyl)-2,5-dimethyl-1H-pyrrole-3-carboxylate as a reddish solid. MS (ESI) 446 (M+H)$^+$. This compound was processed as in example 85 to afford 6-(3,5-dibromo-4-ethoxyphenyl)-N,4,5,7-tetramethyl-6H-pyrrolo[3,4-d]pyridazin-1-amine as a colorless solid: $^1$H NMR (CDCl$_3$, 500 MHz) δ 7.41 (s, 2H), 4.19 (q, 2H), 3.13 (s, 3H), 2.62 (s, 3H), 2.59 (s, 3H), 2.40 (s, 3H), 1.54 (t, 3H); MS (ESI) 469 (M+H)$^+$.

EXAMPLE 88

6-(4-ethoxyphenyl)-1-(4-methoxyphenyl)amino-4,5,7-trimethyl-6H-pyrrolo[3,4-d]pyridazine

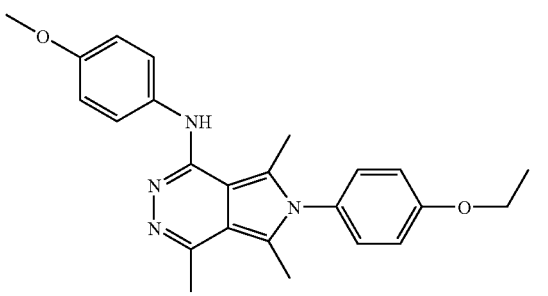

Utilizing the general procedure outlined in EXAMPLE 85, 1-chloro-6-(4-ethoxyphenyl)-4,5,7-trimethyl-6H-pyrrolo[3,4-d]pyridazine and p-anisidine (0.40 mg, 0.32 mmol) reacted to give 6-(4-ethoxyphenyl)-1-hydrazino-4,5,7-trimethyl-6H-pyrrolo[3,4-d]pyridazine: $^1$H NMR (CDCl$_3$, 500 MHz) δ 7.32 (d, 2H), 7.08 (d, 2H), 7.06 (d, 2H), 6.91 (d, 2H), 4.12 (q, 2H), 3.81 (s, 3H), 2.69 (s, 3H), 2.55 (s, 3H), 1.50 (t, 3H); MS (ESI) 403 (M+H)$^+$.

EXAMPLE 89

6-(4-ethoxyphenyl)-1-aminophenyl-4.5.7-trimethyl-6H-pyrrolo[3,4-d]pyridazine

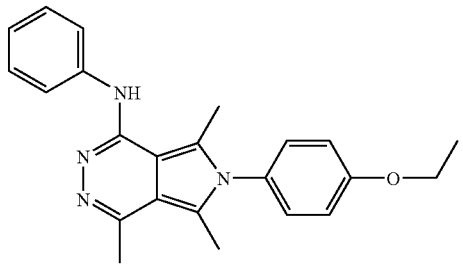

Utilizing the general procedure outlined in EXAMPLE 85, 1-chloro-6-(4-ethoxyphenyl)-4,5,7-trimethyl-6H-pyrrolo[3,4-d]pyridazine and aniline (0.36 mg 0.32 mmol) reacted to give 6-(4-ethoxyphenyl)-1-hydrazino-4,5,7-trimethyl-6H-pyrrolo[3,4-d]pyridazine: $^1$H NMR (CDCl$_3$, 500 MHz) δ 7.33-7.36 (m, 3H), 6.65-7.13 (m, 6H), 4.14 (q, 2H), 2.42 (s, 3H), 2.37 (s, 3H), 2.32 (s, 3H) 1.52 (t, 3H); MS (ESI) 403 (M+H)$^+$.

EXAMPLE 90

6-(4-ethoxyphenyl)-1-(4-methylphenyl)amino-4,5,7-trimethyl-6H-pyrrolo[3,4-d]pyridazine

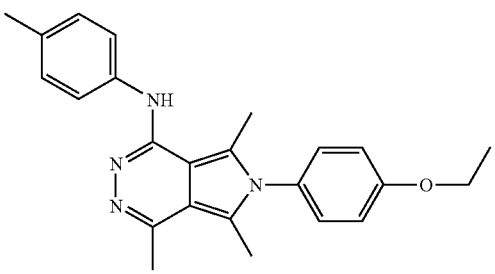

Utilizing the general procedure outlined in EXAMPLE 85, 1-chloro-6-(4-ethoxyphenyl)4,5,7-trimethyl-6H-pyrrolo[3,4-d]pyridazine and 4-methylaniline (0.40 mg, 0.32 mmol) reacted to give 6-(4-ethoxyphenyl)-1-hydrazino-4,5,7-trimethyl-6H-pyrrolo[3,4-d]pyridazine: $^1$H NMR (CDCl$_3$, 500 MHz) δ 7.50 (d, 2H), 7.17 (d, 2H), 7.16 (d, 2H), 6.99 (d, 2H), 4.16 (q, 2H), 2.81 (s, 3H), 2.34 (s, 3H), 2.27 (s, 3H), 2.21 (s, 3H), 1.52 (t, 3H); MS (ESI) 423 (M+H)$^+$.

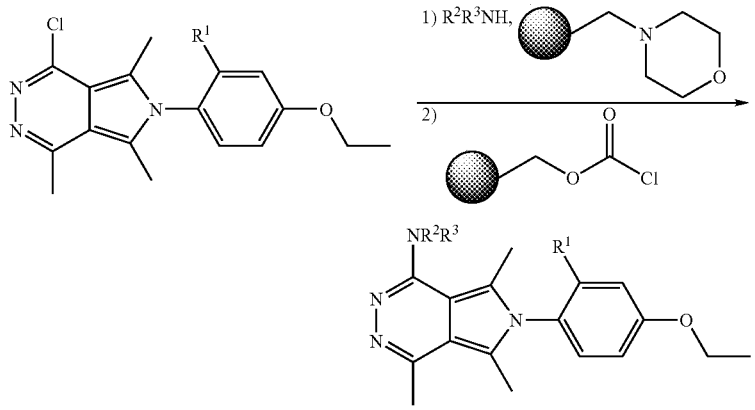

EXAMPLES 91-367

Example 91-367 were synthesized in library mode. 1-Chloro-6-(4-ethoxyphenyl)-4,5,7-trimethyl-6H-pyrrolo[3,4-d]pyridazine (50 mg per vessel) or 1-Chloro-6-(2-methoxy-4-ethoxyphenyl)-4,5,7-trimethyl-6H-pyrrolo[3,4-d]pyridazine (prepared as in example 85 utilizing 2-methoxy-4-ethoxy aniline) (50 mg per vessel), and polystyrene resin-bound N-methylmorpholine (1.1 eq.) were dry loaded into reaction vessels. Amines (2 eq.) in pyridine (1 mL) was added to the vessels. The vessels were capped and sealed. The reactions were heated to 100 ° C. and agitated overnight. Additional polystyrene resin-bound N-methylmorpholine (2 eq.), polystyrene resin-bound chloroformate (2 eq.), and chloroform (4 mL) were added. The resulting suspension was agitated at 50 ° C. overnight. The reaction solutions were collected by filtration, concentrated and dried in GeneVac. The products were analyzed by LCMS.

| Example | Name | Structure | MS (ESI) |
|---|---|---|---|
| Example 91 | 6-(4-ethoxy-2-methoxyphenyl)-N-(1H-indol-5-ylmethyl)-4,5,7-trimethyl-6H-pyrrolo[3,4-d]pyridazin-1-amine | 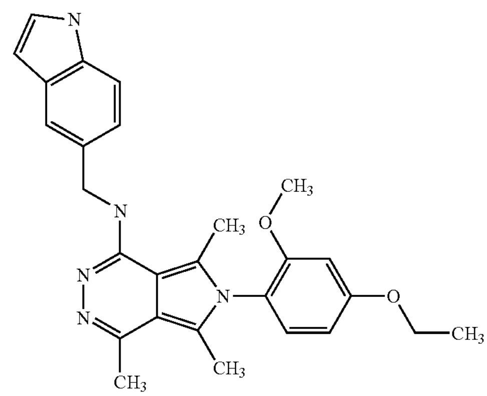 | 457 |
| Example 92 | N-benzyl-6-(4-ethoxy-2-methoxyphenyl)-4,5,7-trimethyl-6H-pyrrolo[3,4-d]pyridazin-1-amine | 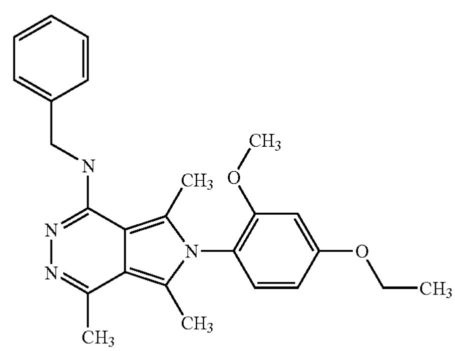 | 418 |
| Example 93 | N-(1,3-dihydro-2-benzofuran-5-yl)-6-(4-ethoxy-2-methoxyphenyl)-4,5,7-trimethyl-6H-pyrrolo[3,4-d]pyridazin-1-amine | 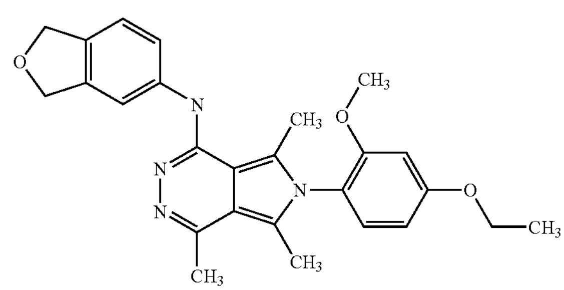 | 446 |

-continued

| Example | Name | Structure | MS (ESI) |
|---|---|---|---|
| Example 94 | 1-(4-{[6-(4-ethoxy-2-methoxyphenyl)-4,5,7-trimethyl-6H-pyrrolo[3,4-d]pyridazin-1-yl]amino}phenyl)imidazolidin-2-one | 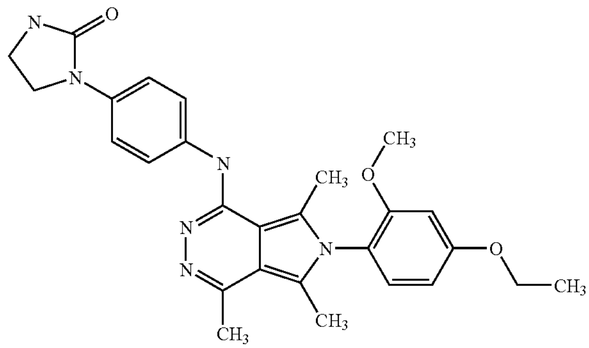 | 488 |
| Example 95 | 6-(4-ethoxy-2-methoxyphenyl)-N-(3-methoxyphenyl)-4,5,7-trimethyl-6H-pyrrolo[3,4-d]pyridazin-1-amine | 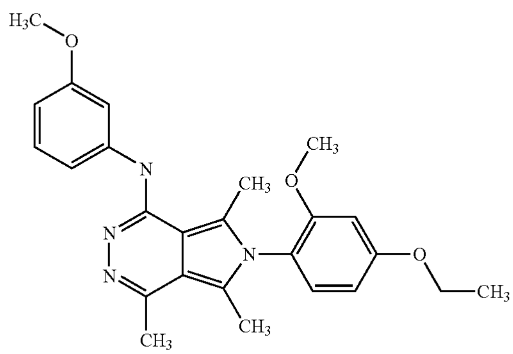 | 434 |
| Example 96 | 6-(4-ethoxy-2-methoxyphenyl)-N-(3-isopropylphenly)-4,5,7-trimethyl-6H-pyrrolo[3,4-d]pyridazin-1-amine | 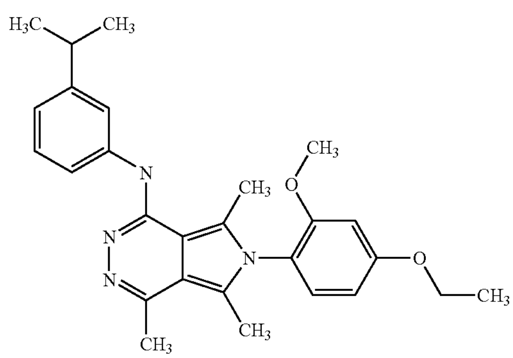 | 446 |
| Example 97 | N-(3,5-dimethoxyphenyl)-6-(4-ethoxy-2-methoxyphenyl)-4,5,7-trimethyl-6H-pyrrolo[3,4-d]pyridazin-1-amine | 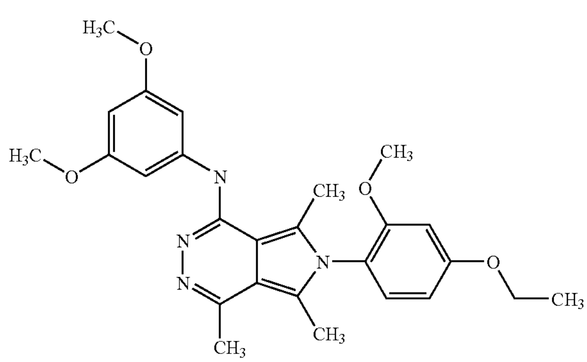 | 464 |

| Example | Name | Structure | MS (ESI) |
|---|---|---|---|
| Example 98 | 6-(4-ethoxy-2-methoxyphenyl)-4,5,7-trimethyl-N-phenyl-6H-pyrrolo[3,4-d]pyridazin-1-amine | 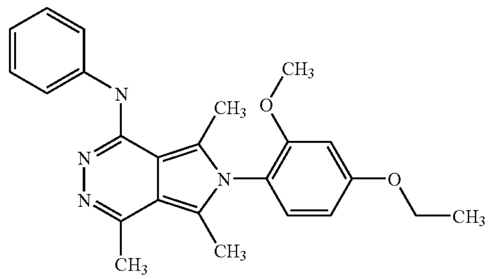 | 404 |
| Example 99 | 6-(4-ethoxy-2-methoxyphenyl)-4,5,7-trimethyl-N-(3-pyridin-3-ylpropyl)-6H-pyrrolo[3,4-d]pyridazin-1-amine | 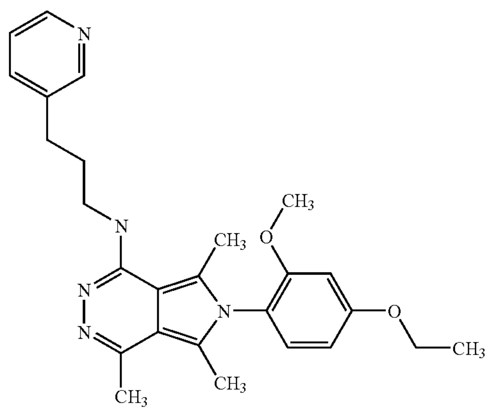 | 447 |
| Example 100 | 6-(4-ethoxy-2-methoxyphenyl)-4,5,7-trimethyl-N-(2-pyridin-2-ylethyl)-6H-pyrrolo[3,4-d]pyridazin-1-amine | 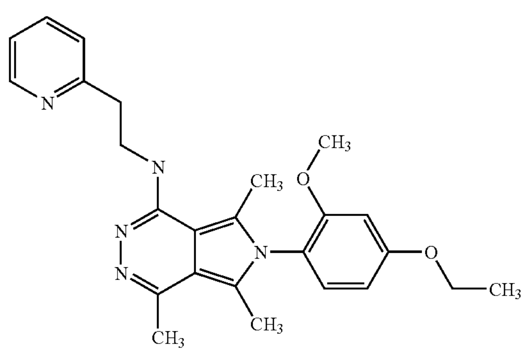 | 433 |
| Example 101 | 6-(4-ethoxy-2-methoxyphenyl)-N-isopropyl-4,5,7-trimethyl-6H-pyrrolo[3,4-d]pyridazin-1-amine | 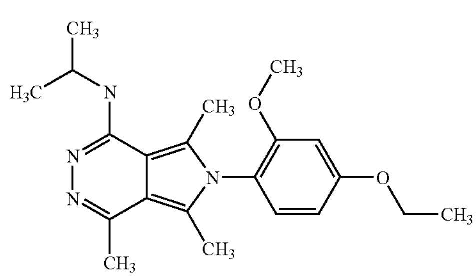 | 369 |

-continued

| Example | Name | Structure | MS (ESI) |
|---|---|---|---|
| Example 102 | 6-(4-ethoxy-2-methoxyphenyl)-4,5,7-trimethyl-N-[4-(methylthio)phenyl]-6H-pyrrolo[3,4-d]pyridazin-1-amine | 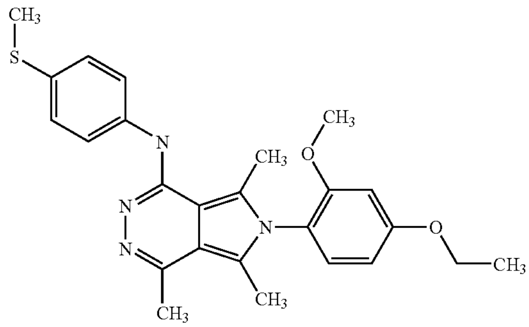 | 450 |
| Example 103 | 6-(4-ethoxy-2-methoxyphenyl)-4,5,7-trimethyl-N-(4-methylbenzyl)-6H-pyrrolo[3,4-d]pyridazin-1-amine | 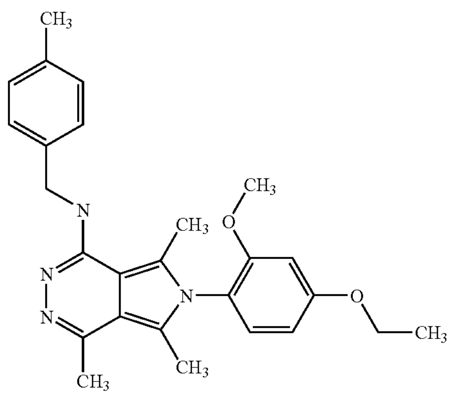 | 432 |
| Example 104 | 6-(4-ethoxy-2-methoxyphenyl)-4,5,7-trimethyl-N-(pyridin-3-ylmethyl)-6H-pyrrolo[3,4-d]pyridazin-1-amine | 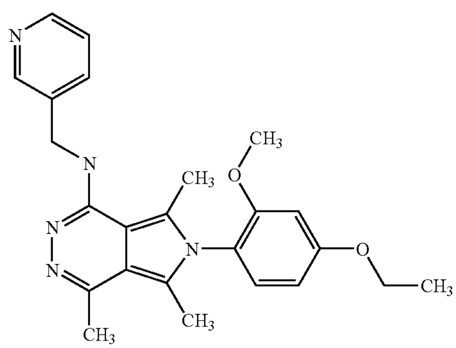 | 419 |
| Example 105 | 6-(4-ethoxy-2-methoxyphenyl)-N-(2,4,5,6,7,8-hexahydrocyclohepta[c]pyrazol-3-ylmethyl)-4,5,7-trimethyl-6H-pyrrolo[3,4-d]pyridazin-1-amine | 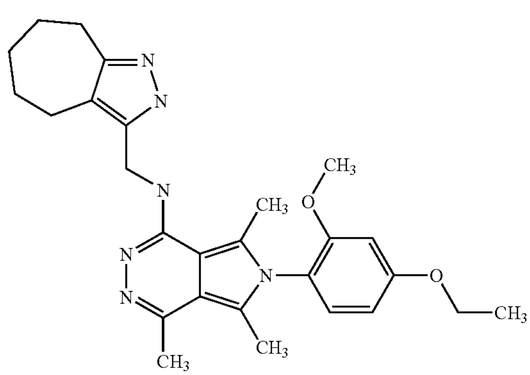 | 476 |

-continued

| Example | Name | Structure | MS (ESI) |
|---|---|---|---|
| Example 106 | 4-(2-{[6-(4-ethoxy-2-methoxyphenyl)-4,5,7-trimethyl-6H-pyrrolo[3,4-d]pyridazin-1-yl]amino}ethyl)phenol | 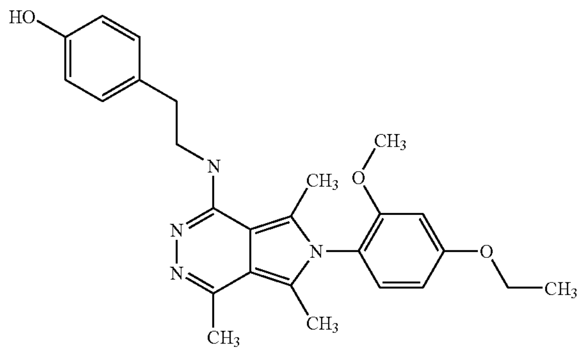 | 448 |
| Example 107 | N-(3-{[6-(4-ethoxy-2-methoxyphenyl)-4,5,7-trimethyl-6H-pyrrolo[3,4-d]pyridazin-1-yl]amino}phenyl)acetamide | 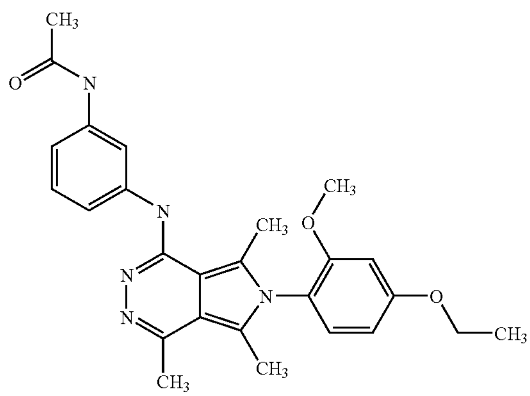 | 461 |
| Example 108 | 6-(4-ethoxy-2-methoxyphenyl)-N-(3-fluoro-4-methylphenyl)-4,5,7-trimethyl-6H-pyrrolo[3,4-d]pyridazin-1-amine | 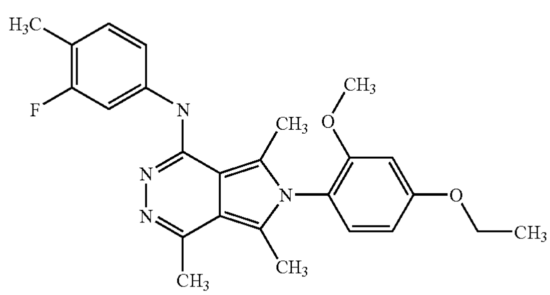 | 436 |
| Example 109 | 1-[6-(4-ethoxy-2-methoxyphenyl)-4,5,7-trimethyl-6H-pyrrolo[3,4-d]pyridazin-1-yl]piperidine-4-carboxamide | 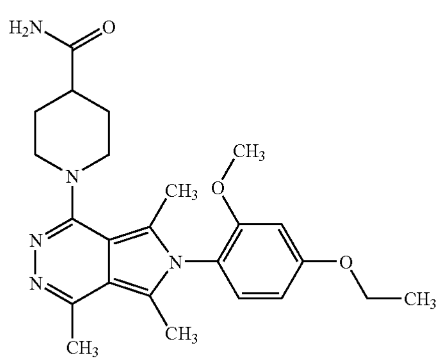 | 439 |

| Example | Name | Structure | MS (ESI) |
|---|---|---|---|
| Example 110 | 6-(4-ethoxy-2-methoxyphenyl)-4,5,7-trimethyl-N-(pyridin-2-ylmethyl)-6H-pyrrolo[3,4-d]pyridazin-1-amine | 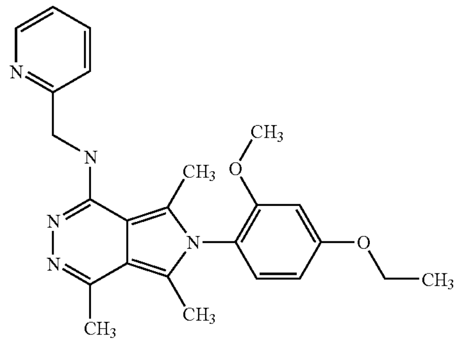 | 419 |
| Example 111 | N-butyl-6-(4-ethoxy-2-methoxyphenyl)-4,5,7-trimethyl-6H-pyrrolo[3,4-d]pyridazin-1-amine | 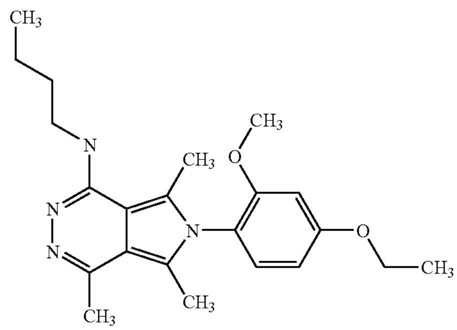 | 384 |
| Example 112 | N-(3,4-dimethoxybenzyl)-6-(4-ethoxy-2-methoxyphenyl)-4,5,7-trimethyl-6H-pyrrolo[3,4-d]pyridazin-1-amine | 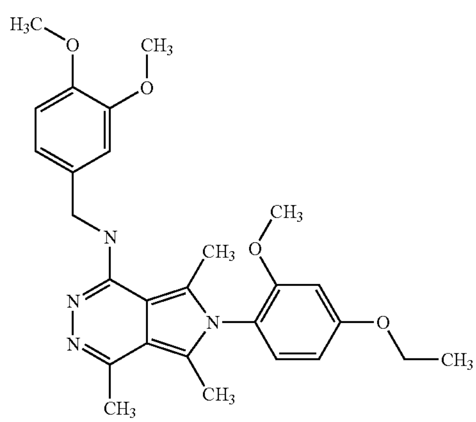 | 478 |
| Example 113 | N-(cyclohexylmethyl)-6-(4-ethoxy-2-methoxyphenyl)-4,5,7-trimethyl-6H-pyrrolo[3,4-d]pyridazin-1-amine | 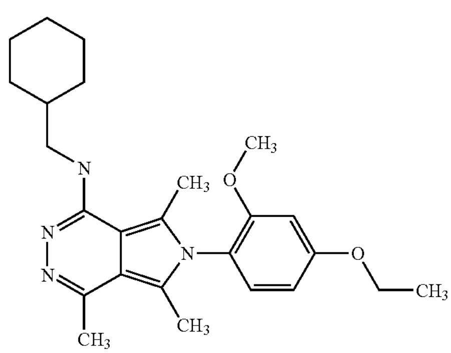 | 424 |

| Example | Name | Structure | MS (ESI) |
|---|---|---|---|
| Example 114 | 6-(4-ethoxy-2-methoxyphenyl)-4,5,7-trimethyl-N-(tetrahydrofuran-2-ylmethyl)-6H-pyrrolo[3,4-d]pyridazin-1-amine | 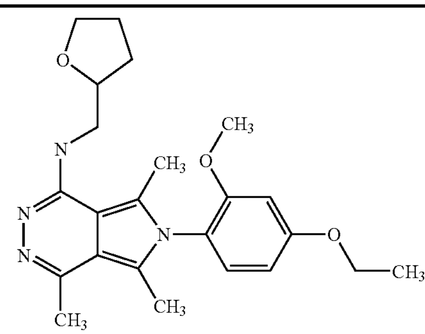 | 412 |
| Example 115 | N-(2,3-dihydro-1H-inden-1-yl)-6-(4-ethoxy-2-methoxyphenyl)-4,5,7-trimethyl-6H-pyrrolo[3,4-d]pyridazin-1-amine | 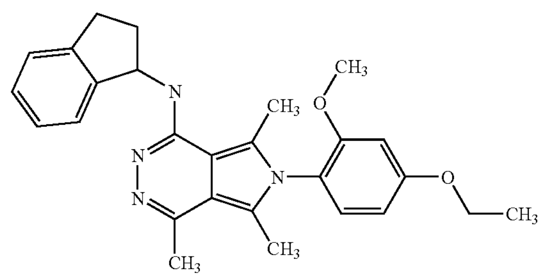 | 444 |
| Example 116 | 6-(4-ethoxy-2-methoxyphenyl)-N-(4-methoxyphenyl)-4,5,7-trimethyl-6H-pyrrolo[3,4-d]pyridazin-1-amine | 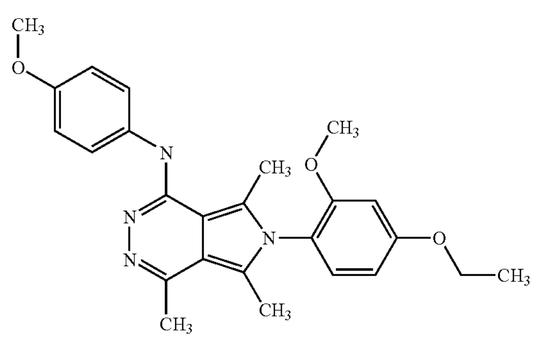 | 434 |
| Example 117 | 6-(4-ethoxy-2-methoxyphenyl)-4,5,7-trimethyl-N-(2-methylbenzyl)-6H-pyrrolo[3,4-d]pyridazin-1-amine | 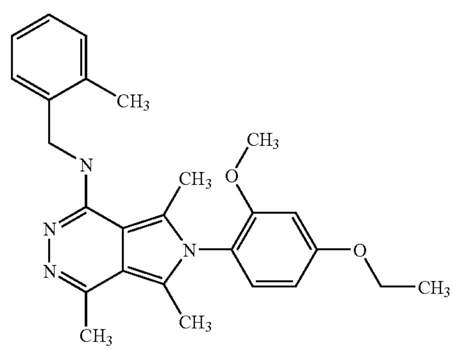 | 432 |

-continued

| Example | Name | Structure | MS (ESI) |
|---|---|---|---|
| Example 118 | 6-(4-ethoxy-2-methoxyphenyl)-4,5,7-trimethyl-N-(3-phenylpropyl)-6H-pyrrolo[3,4-d]pyridazin-1-amine | 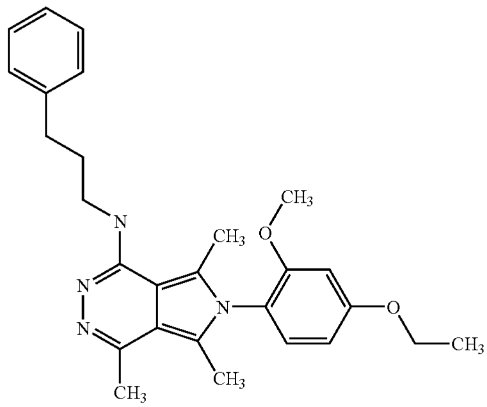 | 446 |
| Example 119 | N-(2,3-dihydro-1H-inden-2-ylmethyl)-6-(4-ethoxy-2-methoxyphenyl)-4,5,7-trimethyl-6H-pyrrolo[3,4-d]pyridazin-1-amine | 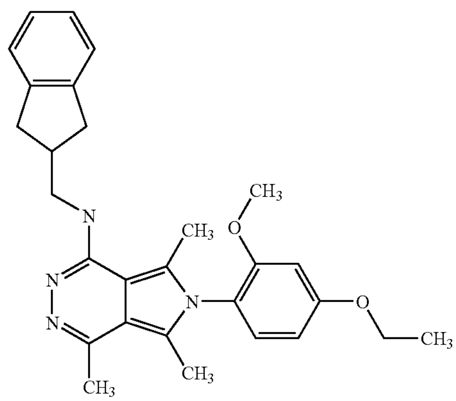 | 458 |
| Example 120 | 6-(4-ethoxy-2-methoxyphenyl)-N-1H-indazol-6-yl-4,5,7-trimethyl-6H-pyrrolo[3,4-d]pyridazin-1-amine | 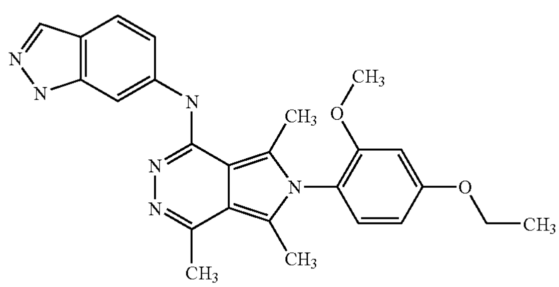 | 444 |
| Example 121 | 6-(4-ethoxy-2-methoxyphenyl)-4,5,7-trimethyl-N-(1-phenylethyl)-6H-pyrrolo[3,4-d]pyridazin-1-amine | 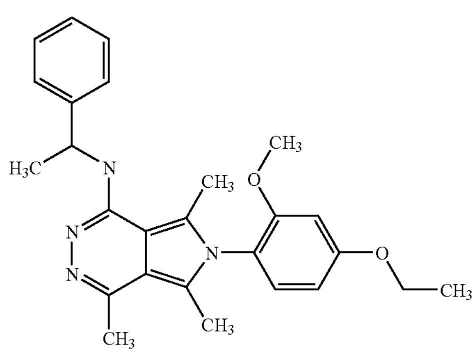 | 432 |

| Example | Name | Structure | MS (ESI) |
|---|---|---|---|
| Example 122 | 6-(4-ethoxyphenyl)-N-1H-indol-5-yl-4,5,7-trimethyl-6H-pyrrolo[3,4-d]pyridazin-1-amine | 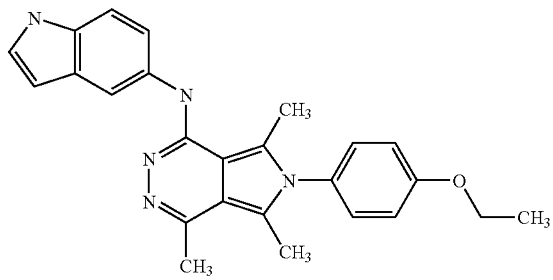 | 413 |
| Example 123 | 6-(4-ethoxy-2-methoxyphenyl)-4,5,7-trimethyl-N-(2-methyl-1,3-benzothiazol-6-yl)-6H-pyrrolo[3,4-d]pyridazin-1-amine | 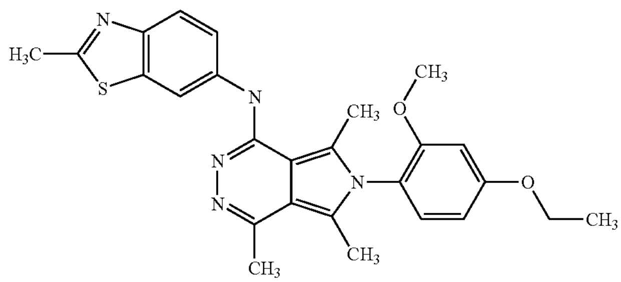 | 475 |
| Example 124 | N-cyclopentyl-6-(4-ethoxy-2-methoxyphenyl)-4,5,7-trimethyl-6H-pyrrolo[3,4-d]pyridazin-1-amine | 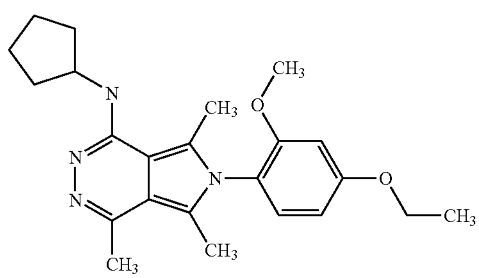 | 396 |
| Example 125 | 6-(4-ethoxy-2-methoxyphenyl)-4,5,7-trimethyl-N-(2-phenylpropyl)-6H-pyrrolo[3,4-d]pyridazin-1-amine | 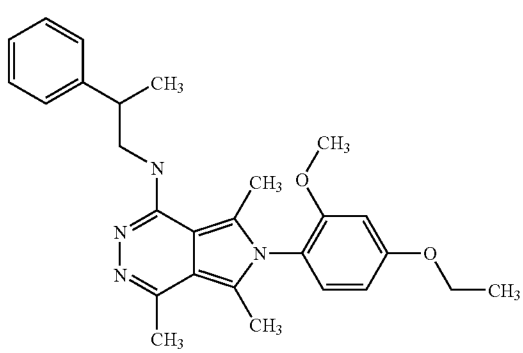 | 446 |

| Example | Name | Structure | MS (ESI) |
|---|---|---|---|
| Example 126 | 6-(4-ethoxy-2-methoxyphenyl)-4,5,7-trimethyl-N-(4-phenylbutyl)-6H-pyrrolo[3,4-d]pyridazin-1-amine | 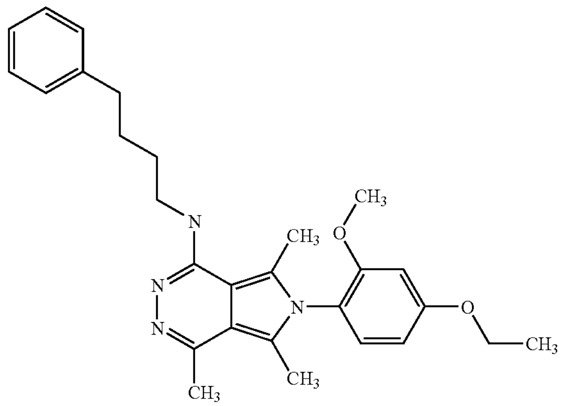 | 460 |
| Example 127 | 6-(4-ethoxy-2-methoxyphenyl)-N-[(1-ethyl-1H-pyrazol-4-yl)methyl]-4,5,7-trimethyl-6H-pyrrolo[3,4-d]pyridazin-1-amine | 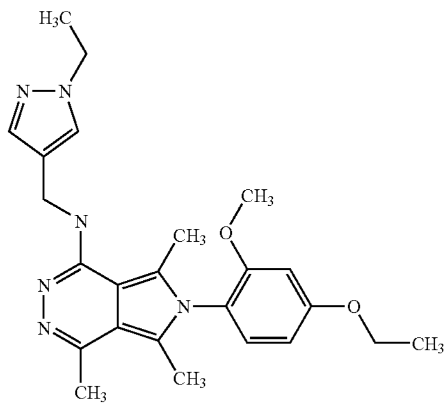 | 436 |
| Example 128 | 6-(4-ethoxyphenyl)-4,5,7-trimethyl-N-(5,6,7,8-tetrahydro-1,8-naphthyridin-2-ylmethyl)-6H-pyrrolo[3,4-d]pyridazin-1-amine | 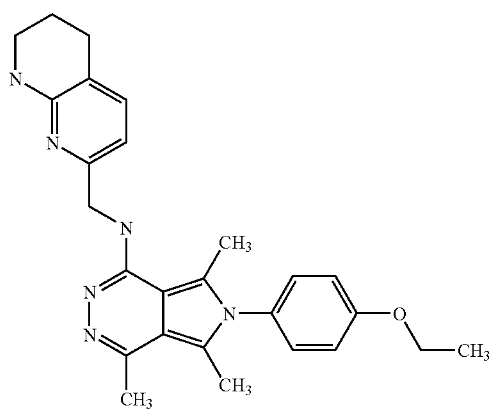 | 444 |
| Example 129 | 6-(4-ethoxy-2-methoxyphenyl)-4,5,7-trimethyl-N-[2-(tetrahydro-2H-pyran-2-yl)ethyl]-6H-pyrrolo[3,4-d]pyridazin-1-amine | 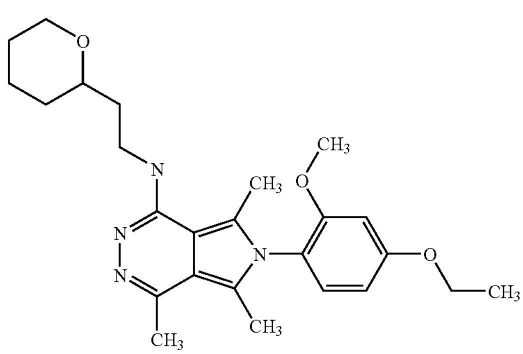 | 440 |

-continued

| Example | Name | Structure | MS (ESI) |
|---|---|---|---|
| Example 130 | 6-(4-ethoxy-2-methoxyphenyl)-N-(3-methoxybenzyl)-4,5,7-trimethyl-6H-pyrrolo[3,4-d]pyridazin-1-amine | 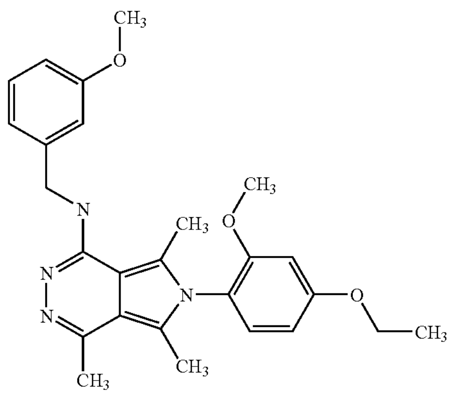 | 448 |
| Example 131 | N-(3,4-dimethoxyphenyl)-6-(4-ethoxy-2-methoxyphenyl)-4,5,7-trimethyl-6H-pyrrolo[3,4-d]pyridazin-1-amine | 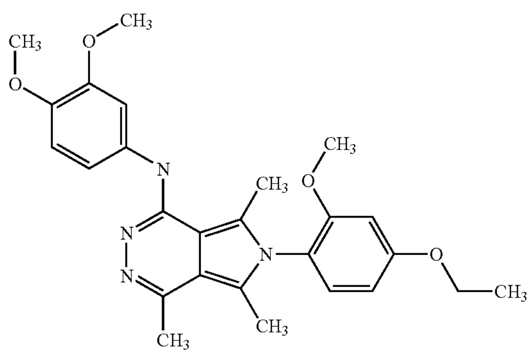 | 464 |
| Example 132 | 6-(4-ethoxy-2-methoxyphenyl)-N-2H-indazol-5-yl-4,5,7-trimethyl-6H-pyrrolo[3,4-d]pyridazin-1-amine | 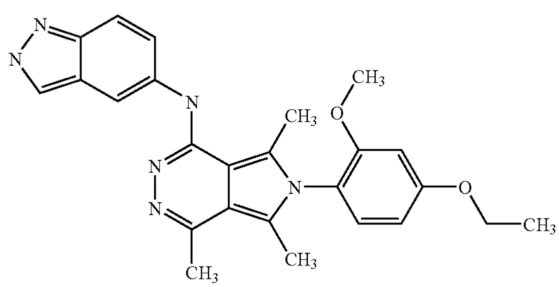 | 444 |
| Example 133 | 6-(4-ethoxy-2-methoxyphenyl)-4,5,7-trimethyl-N-(3-methylbenzyl)-6H-pyrrolo[3,4-d]pyridazin-1-amine | 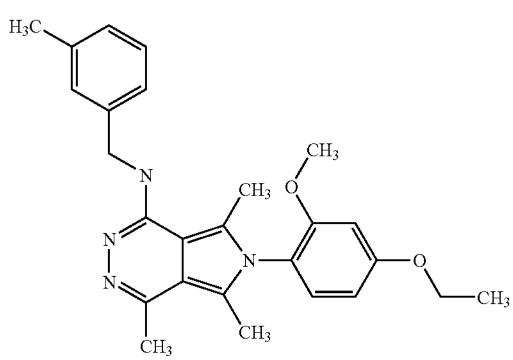 | 432 |

-continued

| Example | Name | Structure | MS (ESI) |
|---|---|---|---|
| Example 134 | 6-(4-ethoxy-2-methoxyphenyl)-4,5,7-trimethyl-N-(spiro[2.5]oct-1-ylmethyl)-6H-pyrrolo[3,4-d]pyridazin-1-amine | 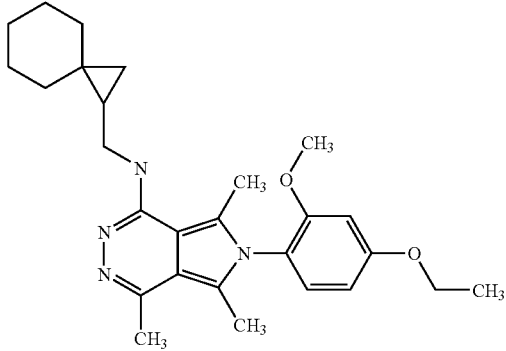 | 450 |
| Example 135 | N-(2,2-dimethoxyethyl)-6-(4-ethoxy-2-methoxyphenyl)-4,5,7-trimethyl-6H-pyrrolo[3,4-d]pyridazin-1-amine | 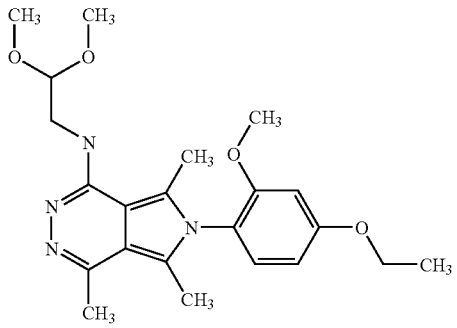 | 416 |
| Example 136 | 6-(4-ethoxy-2-methoxyphenyl)-N-(2-furylmethyl)-4,5,7-trimethyl-6H-pyrrolo[3,4-d]pyridazin-1-amine | 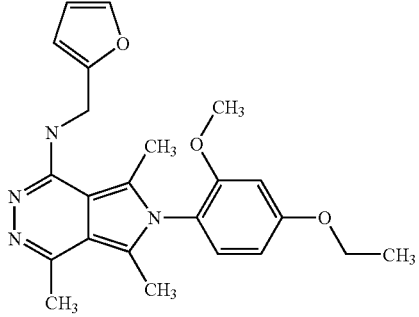 | 407 |
| Example 137 | 6-(4-ethoxy-2-methoxyphenyl)-N-1H-indol-5-yl-4,5,7-trimethyl-6H-pyrrolo[3,4-d]pyridazin-1-amine | 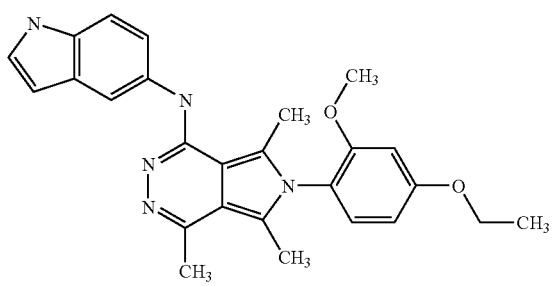 | 443 |

-continued

| Example | Name | Structure | MS (ESI) |
|---|---|---|---|
| Example 138 | 6-(4-ethoxy-2-methoxyphenyl)-4,5,7-trimethyl-N-[(1-methylpiperidin-4-yl)methyl]-6H-pyrrolo[3,4-d]pyridazin-1-amine | 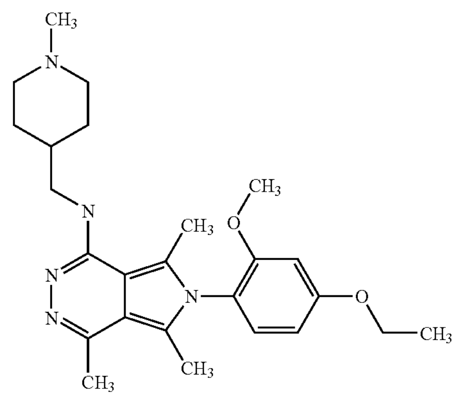 | 439 |
| Example 139 | 6-(4-ethoxy-2-methoxyphenyl)-4,5,7-trimethyl-N-(1-phenylpiperidin-4-yl)-6H-pyrrolo[3,4-d]pyridazin-1-amine | 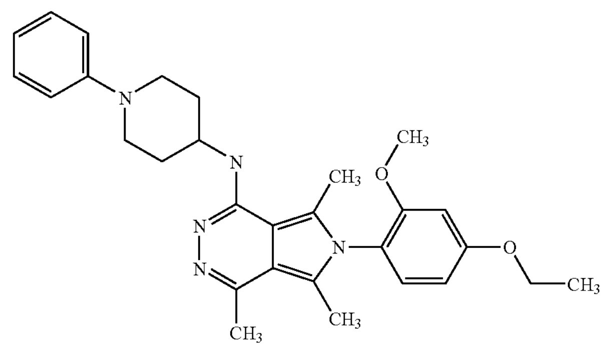 | 487 |
| Example 140 | 6-(4-ethoxy-2-methoxyphenyl)-4,5,7-trimethyl-N-(2-phenylethyl)-6H-pyrrolo[3,4-d]pyridazin-1-amine | 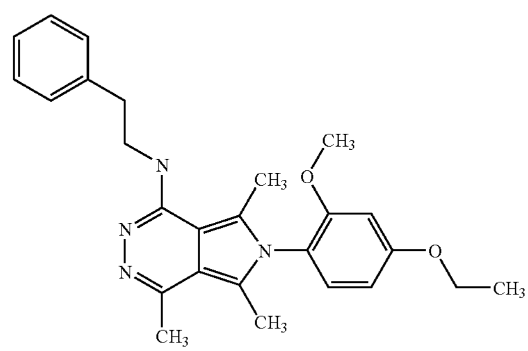 | 432 |
| Example 141 | 1-(4-{[6-(4-ethoxy-2-methoxyphenyl)-4,5,7-trimethyl-6H-pyrrolo[3,4-d]pyridazin-1-yl]amino}phenyl)-3-methylimidazolidin-2-one | 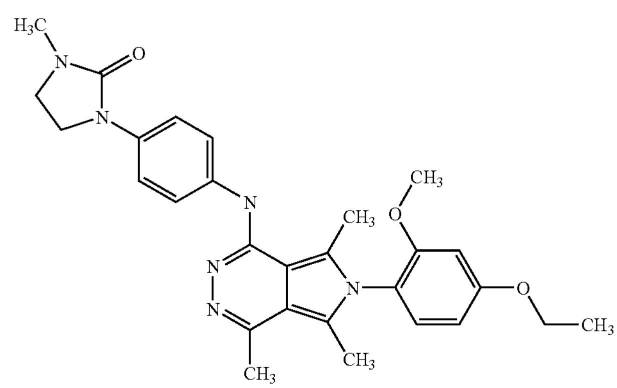 | 502 |

-continued

| Example | Name | Structure | MS (ESI) |
|---|---|---|---|
| Example 142 | 6-(4-ethoxy-2-methoxyphenyl)-4,5,7-trimethyl-N-[1-methyl-2-(1H-1,2,4-triazol-1-yl)ethyl]-6H-pyrrolo[3,4-d]pyridazin-1-amine | 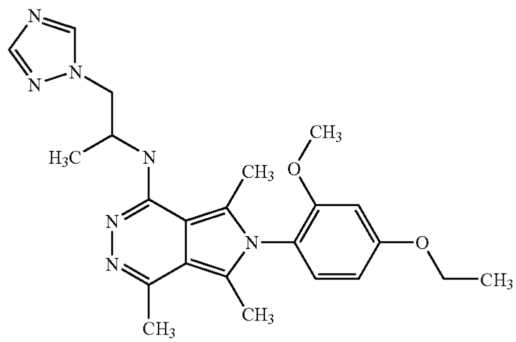 | 437 |
| Example 143 | N-(2-ethoxybenzyl)-6-(4-ethoxy-2-methoxyphenyl)-4,5,7-trimethyl-6H-pyrrolo[3,4-d]pyridazin-1-amine | 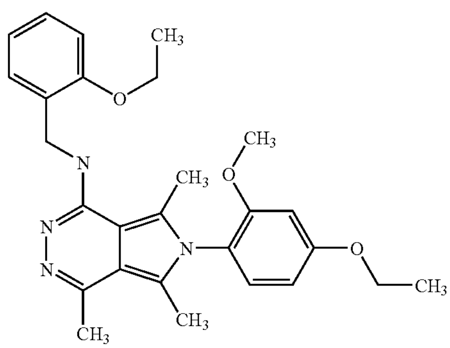 | 462 |
| Example 144 | 4-[6-(4-ethoxy-2-methoxyphenyl)-4,5,7-trimethyl-6H-pyrrolo[3,4-d]pyridazin-1-yl]-2,3,4,5-tetrahydro-1,4-benzoxazepine | 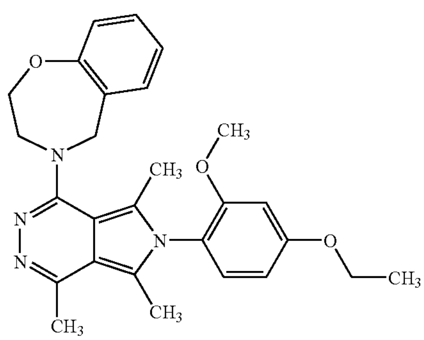 | 460 |
| Example 145 | 6-(4-ethoxy-2-methoxyphenyl)-4,5,7-trimethyl-N-[2-(1H-pyrazol-1-yl)ethyl]-6H-pyrrolo[3,4-d]pyridazin-1-amine | 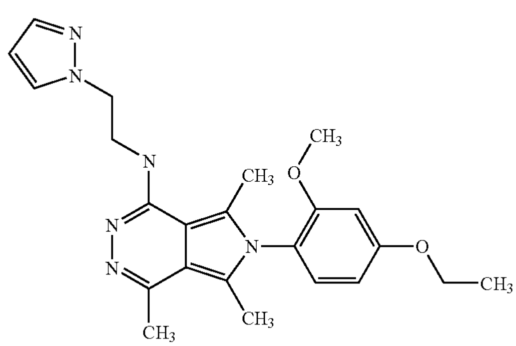 | 422 |

| Example | Name | Structure | MS (ESI) |
|---|---|---|---|
| Example 146 | N-(4-chlorobenzyl)-6-(4-ethoxy-2-methoxyphenyl)-4,5,7-trimethyl-6H-pyrrolo[3,4-d]pyridazin-1-amine | 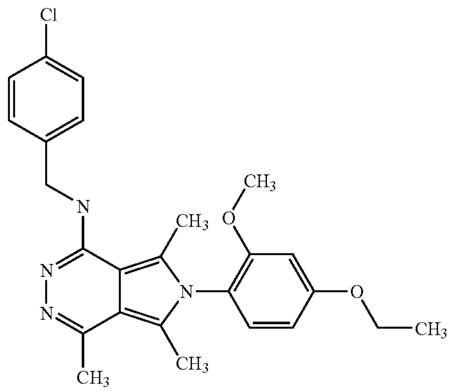 | 452 |
| Example 147 | 6-(4-ethoxyphenyl)-N-1H-indazol-5-yl-4,5,7-trimethyl-6H-pyrrolo[3,4-d]pyridazin-1-amine | 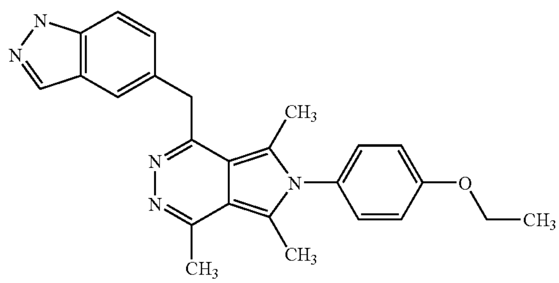 | 413 |
| Example 148 | 6-(4-ethoxy-2-methoxyphenyl)-4,5,7-trimethyl-N-[3-(trifluoromethyl)benzyl]-6H-pyrrolo[3,4-d]pyridazin-1-amine | 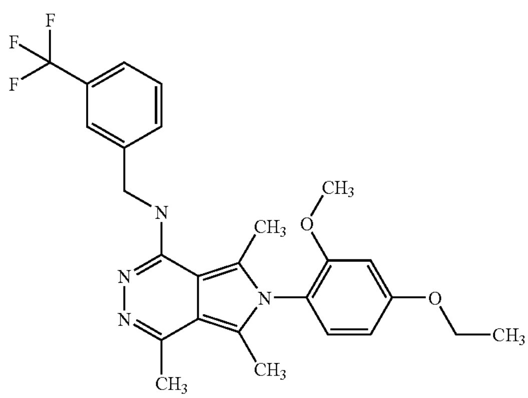 | 486 |
| Example 149 | (3-{[6-(4-ethoxy-2-methoxyphenyl)-4,5,7-trimethyl-6H-pyrrolo[3,4-d]pyridazin-1-yl]amino}phenyl)methanol | 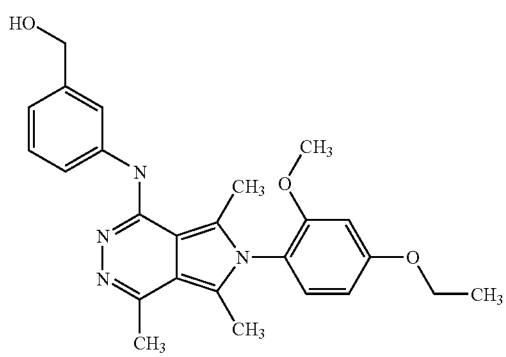 | 434 |

-continued

| Example | Name | Structure | MS (ESI) |
| --- | --- | --- | --- |
| Example 150 | 6-(4-ethoxy-2-methoxyphenyl)-4,5,7-trimethyl-N-(2-methyl-1,3-benzothiazol-5-yl)-6H-pyrrolo[3,4-d]pyridazin-1-amine | 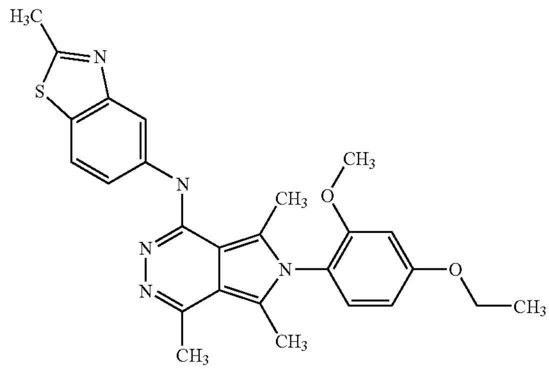 | 475 |
| Example 151 | N-(3-chlorobenzyl)-6-(4-ethoxyphenyl)-4,5,7-trimethyl-6H-pyrrolo[3,4-d]pyridazin-1-amine | 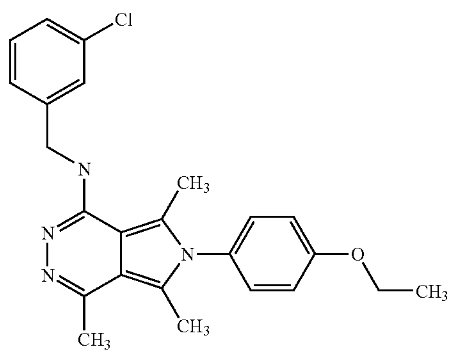 | 422 |
| Example 152 | 6-(4-ethoxy-2-methoxyphenyl)-4,5,7-trimethyl-N-[(1-methylpyrrolidin-3-yl)methyl]-6H-pyrrolo[3,4-d]pyridazin-1-amine | 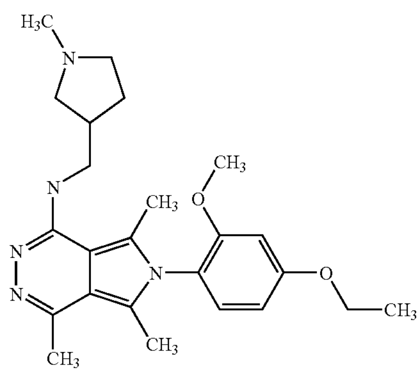 | 425 |
| Example 153 | 6-(4-ethoxy-2-methoxyphenyl)-N-[2-(3-methoxyphenyl)ethyl]-4,5,7-trimethyl-6H-pyrrolo[3,4-d]pyridazin-1-amine | 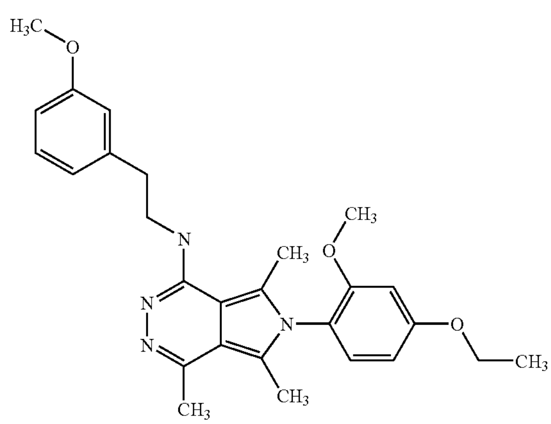 | 462 |

-continued

| Example | Name | Structure | MS (ESI) |
|---------|------|-----------|----------|
| Example 154 | 6-(4-ethoxy-2-methoxyphenyl)-4,5,7-trimethyl-N-[(1-methyl-1H-pyrazol-4-yl)methyl]-6H-pyrrolo[3,4-d]pyridazin-1-amine | 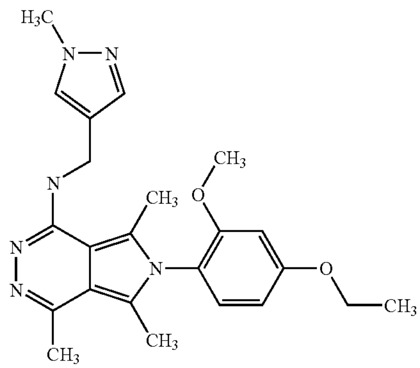 | 422 |
| Example 155 | 6-(4-ethoxy-2-methoxyphenyl)-4,5,7-trimethyl-N-(pyrazolo[1,5-a]pyridin-7-ylmethyl)-6H-pyrrolo[3,4-d]pyridazin-1-amine | 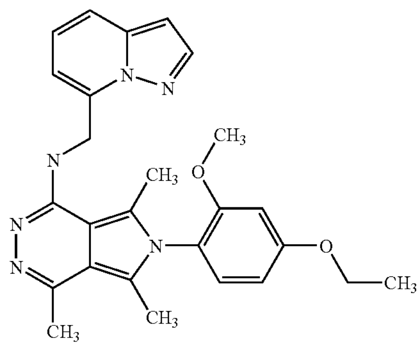 | 458 |
| Example 156 | 6-(4-ethoxy-2-methoxyphenyl)-4,5,7-trimethyl-N-(4-phenoxyphenyl)-6H-pyrrolo[3,4-d]pyridazin-1-amine | 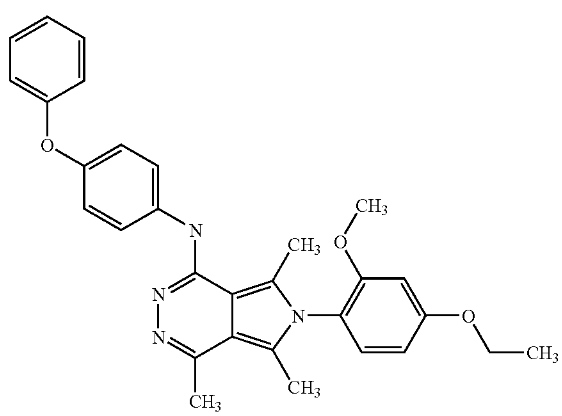 | 496 |
| Example 157 | N'-[6-(4-ethoxy-2-methoxyphenyl)-4,5,7-trimethyl-6H-pyrrolo[3,4-d]pyridazin-1-yl]-N,N-dimethylbenzene-1,4-diamine | 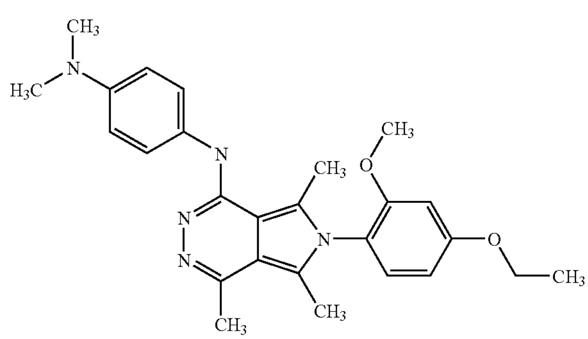 | 447 |

-continued

| Example | Name | Structure | MS (ESI) |
|---|---|---|---|
| Example 158 | 6-(4-ethoxy-2-methoxyphenyl)-N-(3-isopropoxyphenyl)-4,5,7-trimethyl-6H-pyrrolo[3,4-d]pyridazin-1-amine | 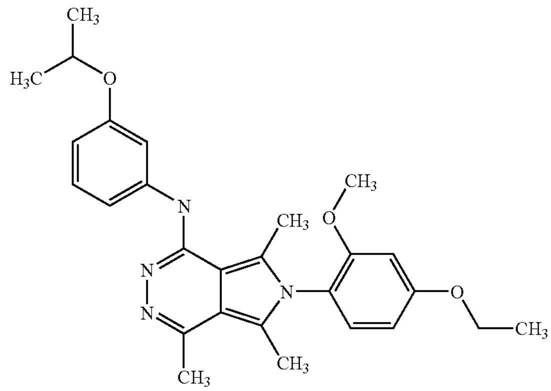 | 462 |
| Example 159 | 6-(4-ethoxy-2-methoxyphenyl)-N-(2-methoxyethyl)-4,5,7-trimethyl-6H-pyrrolo[3,4-d]pyridazin-1-amine | 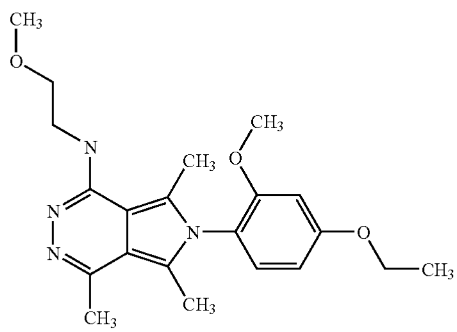 | 385 |
| Example 160 | N-(3-chloro-4-methylphenyl)-6-(4-ethoxy-2-methoxyphenyl)-4,5,7-trimethyl-6H-pyrrolo[3,4-d]pyridazin-1-amine | 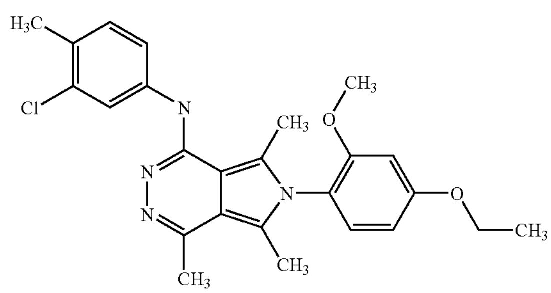 | 452 |
| Example 161 | 6-(4-ethoxy-2-methoxyphenyl)-4,5,7-trimethyl-N-[2-(1-methylpyrrolidin-2-yl)ethyl]-6H-pyrrolo[3,4-d]pyridazin-1-amine | 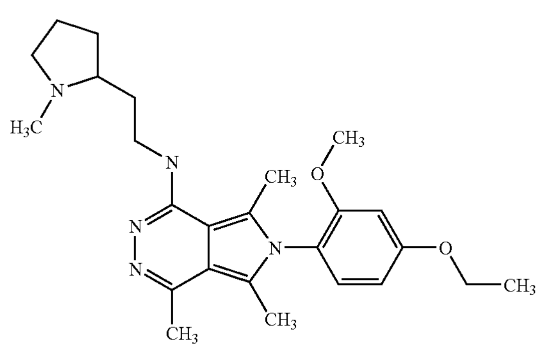 | 439 |

-continued

| Example | Name | Structure | MS (ESI) |
|---|---|---|---|
| Example 162 | N-[2-(3-chlorophenyl)ethyl]-6-(4-ethoxy-2-methoxyphenyl)-4,5,7-trimethyl-6H-pyrrolo[3,4-d]pyridazin-1-amine | 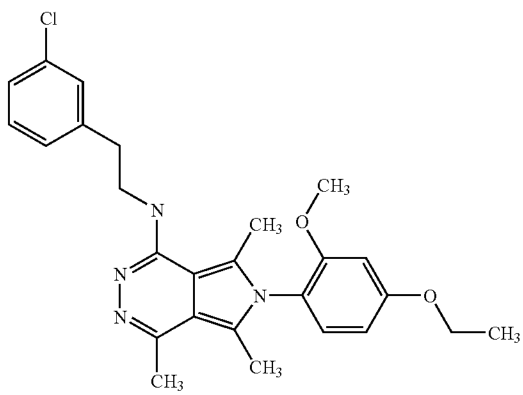 | 466 |
| Example 163 | N-(2,3-dihydro-1,4-benzodioxin-6-yl)-6-(4-ethoxy-2-methoxyphenyl)-4,5,7-trimethyl-6H-pyrrolo[3,4-d]pyridazin-1-amine | 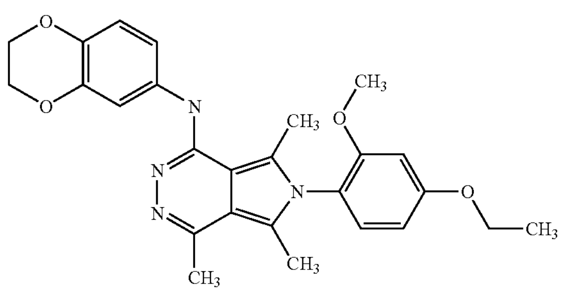 | 462 |
| Example 164 | N-cyclobutyl-6-(4-ethoxy-2-methoxyphenyl)-4,5,7-trimethyl-6H-pyrrolo[3,4-d]pyridazin-1-amine | 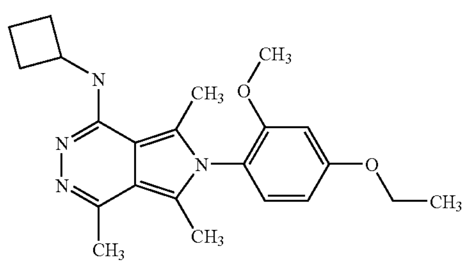 | 381 |
| Example 165 | N-(3,4-dihydro-1H-isochromen-1-ylmethyl)-6-(4-ethoxy-2-methoxyphenyl)-4,5,7-trimethyl-6H-pyrrolo[3,4-d]pyridazin-1-amine | 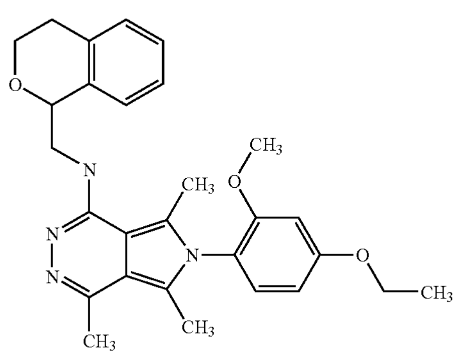 | 474 |

-continued

| Example | Name | Structure | MS (ESI) |
|---|---|---|---|
| Example 166 | 6-(4-ethoxy-2-methoxyphenyl)-4,5,7-trimethyl-N-(3-morpholin-4-ylpropyl)-6H-pyrrolo[3,4-d]pyridazin-1-amine | 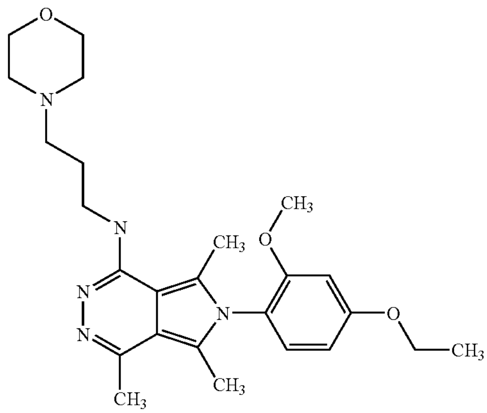 | 455 |
| Example 167 | 6-(4-ethoxy-2-methoxyphenyl)-4,5,7-trimethyl-N-(2-pyrazin-2-ylethyl)-6H-pyrrolo[3,4-d]pyridazin-1-amine | 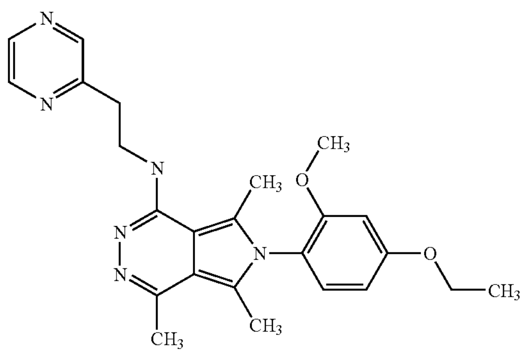 | 434 |
| Example 168 | 7-chloro-4-[6-(4-ethoxy-2-methoxyphenyl)-4,5,7-trimethyl-6H-pyrrolo[3,4-d]pyridazin-1-yl]-2,3,4,5-tetrahydro-1,4-benzoxazepine | 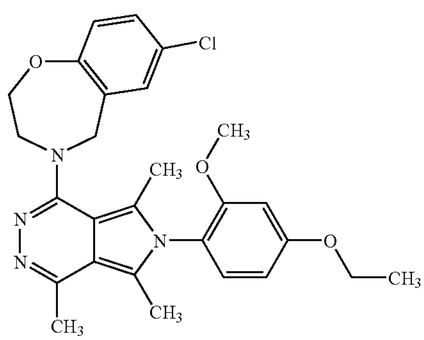 | 494 |
| Example 169 | 6-(4-ethoxy-2-methoxyphenyl)-N-[2-(4-methoxyphenyl)ethyl]-4,5,7-trimethyl-6H-pyrrolo[3,4-d]pyridazin-1-amine | 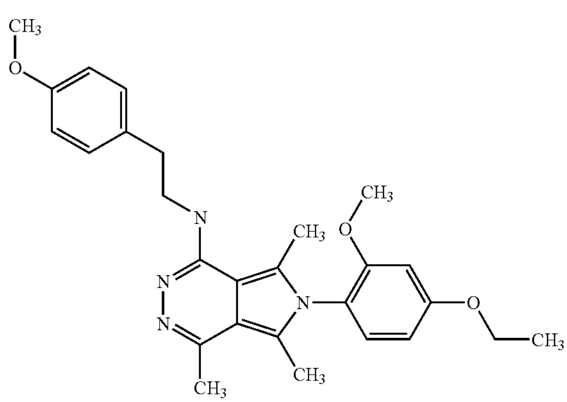 | 462 |

-continued

| Example | Name | Structure | MS (ESI) |
|---|---|---|---|
| Example 170 | 6-(4-ethoxy-2-methoxyphenyl)-4,5,7-trimethyl-N-[3-(methylthio)phenyl]-6H-pyrrolo[3,4-d]pyridazin-1-amine | 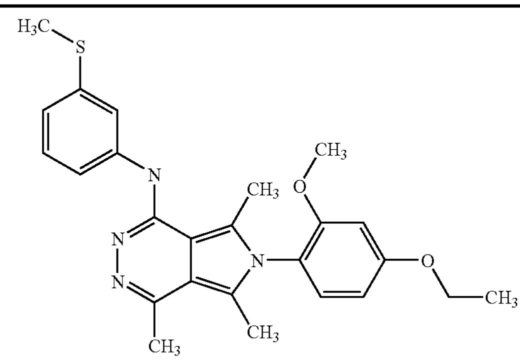 | 450 |
| Example 171 | N-(1-benzylpiperidin-4-yl)-6-(4-ethoxy-2-methoxyphenyl)-4,5,7-trimethyl-6H-pyrrolo[3,4-d]pyridazin-1-amine | 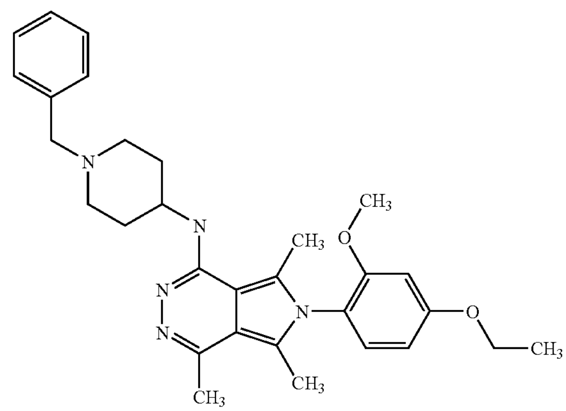 | 501 |
| Example 172 | 6-(4-ethoxy-2-methoxyphenyl)-N-(3-fluorobenzyl)-4,5,7-trimethyl-6H-pyrrolo[3,4-d]pyridazin-1-amine | 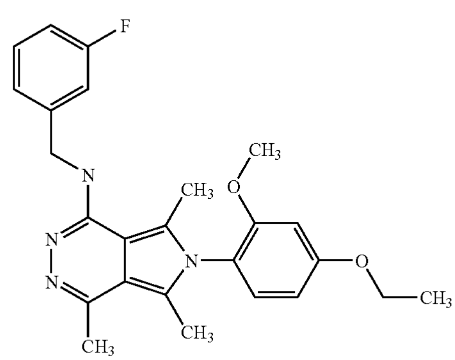 | 436 |
| Example 173 | N-cyclopropyl-6-(4-ethoxy-2-methoxyphenyl)-4,5,7-trimethyl-6H-pyrrolo[3,4-d]pyridazin-1-amine | 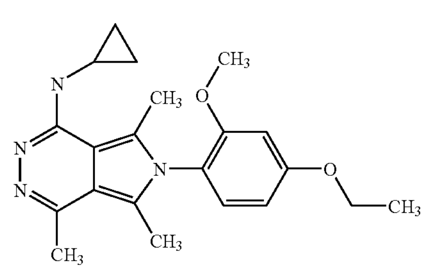 | 367 |

-continued

| Example | Name | Structure | MS (ESI) |
|---------|------|-----------|----------|
| Example 174 | (3aR,9bR)-2-[6-(4-ethoxy-2-methoxyphenyl)-4,5,7-trimethyl-6H-pyrrolo[3,4-d]pyridazin-1-yl]-2,3,3a,4,5,9b-hexahydro-1H-benzo]e]isoindole | Chiral | 484 |
| Example 175 | 6-(4-ethoxy-2-methoxyphenyl)-N-(3-ethylphenyl)-4,5,7-trimethyl-6H-pyrrolo[3,4-d]pyridazin-1-amine | 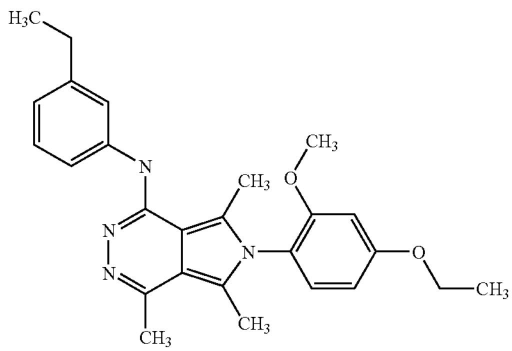 | 432 |
| Example 176 | N-(3,5-dimethylphenyl)-6-(4-ethoxy-2-methoxyphenyl)-4,5,7-trimethyl-6H-pyrrolo[3,4-d]pyridazin-1-amine | 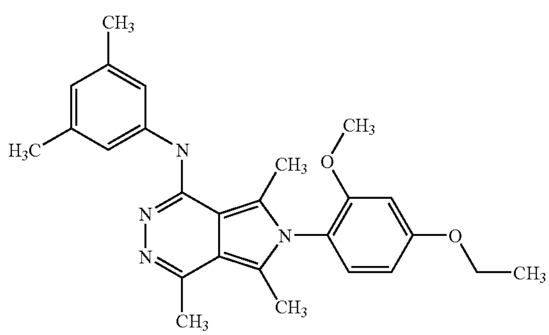 | 432 |
| Example 177 | 6-(4-ethoxy-2-methoxyphenyl)-4,5,7-trimethyl-N-(2-morpholin-4-ylethyl)-6H-pyrrolo[3,4-d]pyridazin-1-amine | 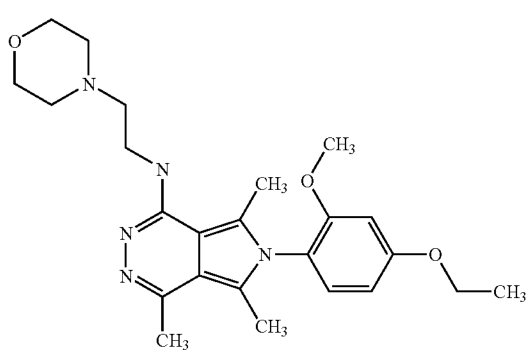 | 441 |

-continued

| Example | Name | Structure | MS (ESI) |
|---|---|---|---|
| Example 178 | 6-(4-ethoxy-2-methoxyphenyl)-1,5,7-trimethyl-4-(4-phenyl-1,4-diazepan-1-yl)-6H-pyrrolo[3,4-d]pyridazine | 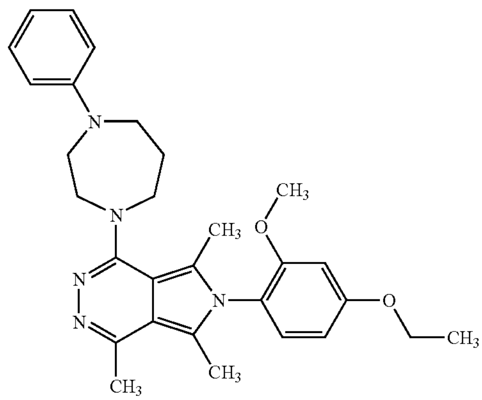 | 487 |
| Example 179 | 6-(4-ethoxy-2-methoxyphenyl)-4,5,7-trimethyl-N-[4-(trifluoromethoxy)phenyl]-6H-pyrrolo[3,4-d]pyridazin-1-amine | 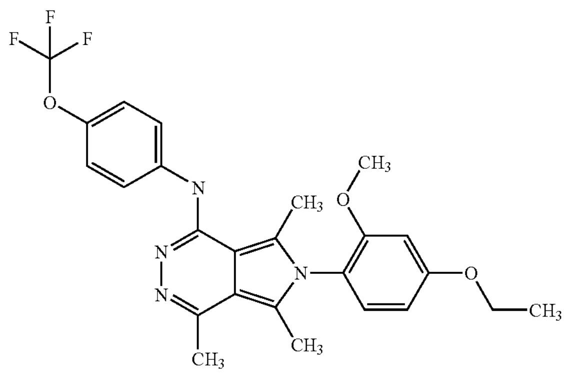 | 487 |
| Example 180 | 6-(4-ethoxy-2-methoxyphenyl)-N-(2-methoxybenzyl)-4,5,7-trimethyl-6H-pyrrolo[3,4-d]pyridazin-1-amine | 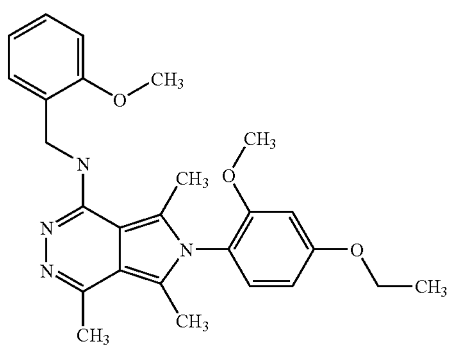 | 448 |
| Example 181 | 3-benzyl-7-[6-(4-ethoxy-2-methoxyphenyl)-4,5,7-trimethyl-6H-pyrrolo[3,4-d]pyridazin-1-yl]-5,6,7,8-tetrahydroimidazo[1,2-a]pyrazine | 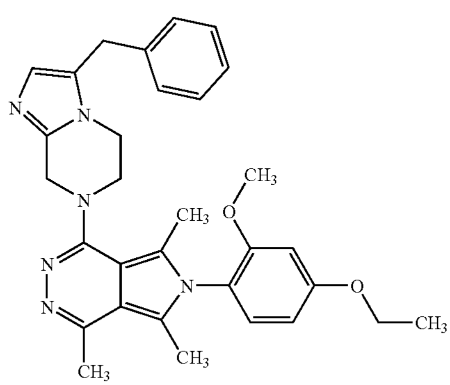 | 524 |

-continued

| Example | Name | Structure | MS (ESI) |
|---|---|---|---|
| Example 182 | N'-[6-(4-ethoxy-2-methoxyphenyl)-4,5,7-trimethyl-6H-pyrrolo[3,4-d]pyridazin-1-yl]-N,N-diethylpropane-1,3-diamine | 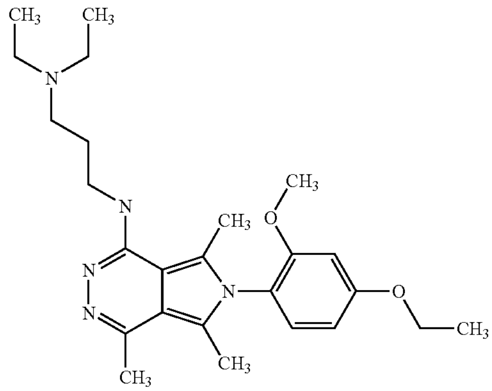 | 441 |
| Example 183 | 6-(4-ethoxy-2-methoxyphenyl)-N-(3-ethoxyphenyl)-4,5,7-trimethyl-6H-pyrrolo[3,4-d]pyridazin-1-amine | 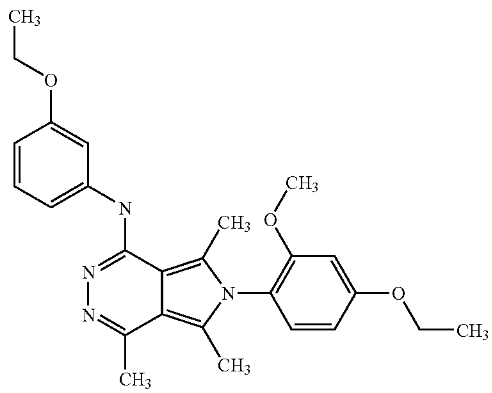 | 448 |
| Example 184 | 7-[6-(4-ethoxy-2-methoxyphenyl)-4,5,7-trimethyl-6H-pyrrolo[3,4-d]pyridazin-1-yl]-2-(trifluoromethyl)-5,6,7,8-tetrahydroimidazo[1,2-a]pyrazine | 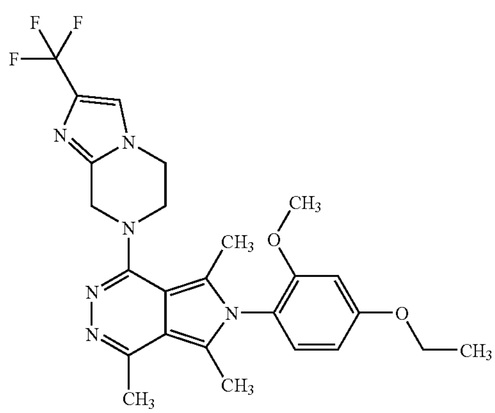 | 502 |
| Example 185 | N-(3-chloro-4-methoxyphenyl)-6-(4-ethoxy-2-methoxyphenyl)-4,5,7-trimethyl-6H-pyrrolo[3,4-d]pyridazin-1-amine | 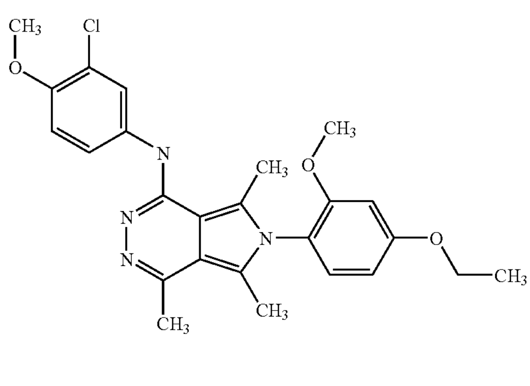 | 468 |

-continued

| Example | Name | Structure | MS (ESI) |
|---|---|---|---|
| Example 186 | 1-[4-(2,3-dihydro-1,4-benzodioxin-5-yl)piperazin-1-yl]-6-(4-ethoxy-2-methoxyphenyl)-4,5,7-trimethyl-6H-pyrrolo[3,4-d]pyridazine | 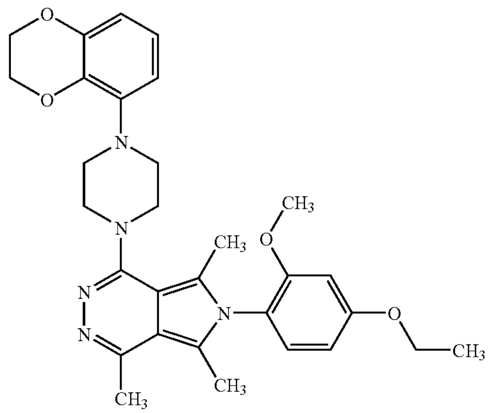 | 531 |
| Example 187 | 6-(4-ethoxy-2-methoxyphenyl)-4,5,7-trimethyl-N-[(6-methylpyridin-2-yl)methyl]-6H-pyrrolo[3,4-d]pyridazin-1-amine | 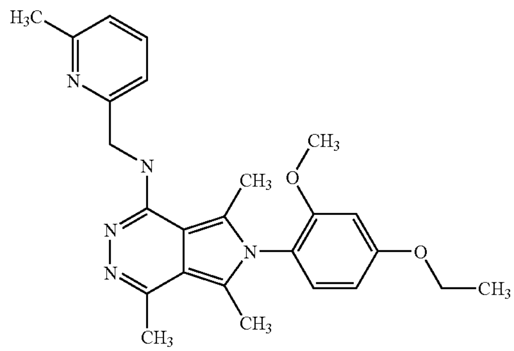 | 433 |
| Example 188 | 6-(4-ethoxy-2-methoxyphenyl)-N-(4-ethylphenyl)-4,5,7-trimethyl-6H-pyrrolo[3,4-d]pyridazin-1-amine | 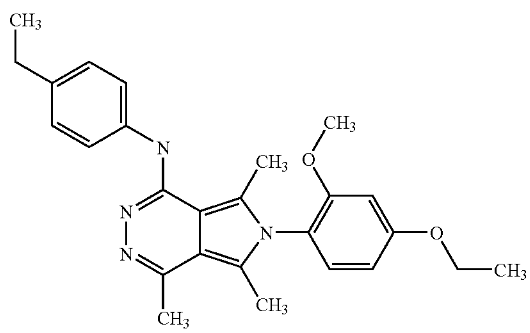 | 432 |
| Example 189 | 1-azetidin-1-yl-6-(4-ethoxy-2-methoxyphenyl)-4,5,7-trimethyl-6H-pyrrolo[3,4-d]pyridazine | 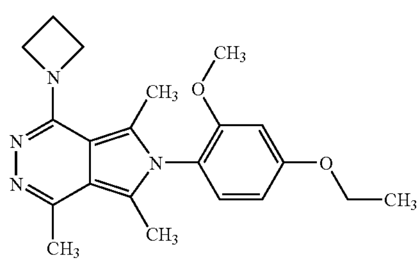 | 367 |

| Example | Name | Structure | MS (ESI) |
|---|---|---|---|
| Example 190 | N-(3,4-dimethylphenyl)-6-(4-ethoxy-2-methoxyphenyl)-4,5,7-trimethyl-6H-pyrrolo[3,4-d]pyridazin-1-amine | 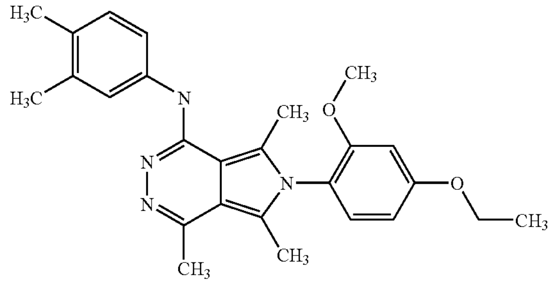 | 432 |
| Example 191 | N-(3,4-difluorobenzyl)-6-(4-ethoxy-2-methoxyphenyl)-4,5,7-trimethyl-6H-pyrrolo[3,4-d]pyridazin-1-amine | 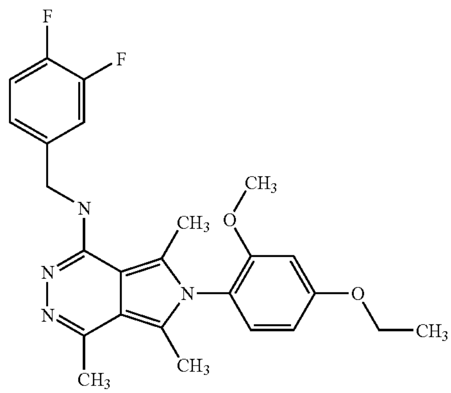 | 454 |
| Example 192 | 6-(4-ethoxyphenyl)-4,5,7-trimethyl-N-(tetrahydrofuran-2-ylmethyl)-6H-pyrrolo[3,4-d]pyridazin-1-amine | 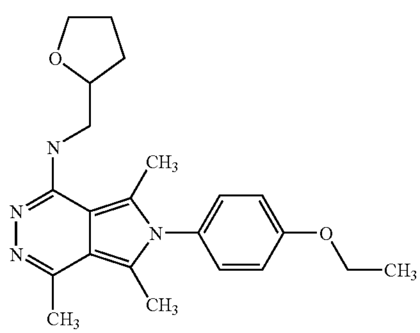 | 381 |
| Example 193 | 6-(4-ethoxy-2-methoxyphenyl)-1,5,7-trimethyl-4-morpholin-4-yl-6H-pyrrolo[3,4-d]pyridazine | 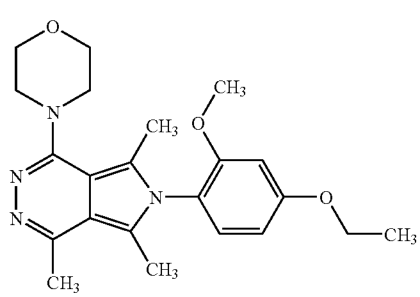 | 397 |

-continued

| Example | Name | Structure | MS (ESI) |
|---|---|---|---|
| Example 194 | 6-(4-ethoxy-2-methoxyphenyl)-4,5,7-trimethyl-N-{2-[4-(trifluoromethyl)phenyl]ethyl}-6H-pyrrolo[3,4-d]pyridazin-1-amine | 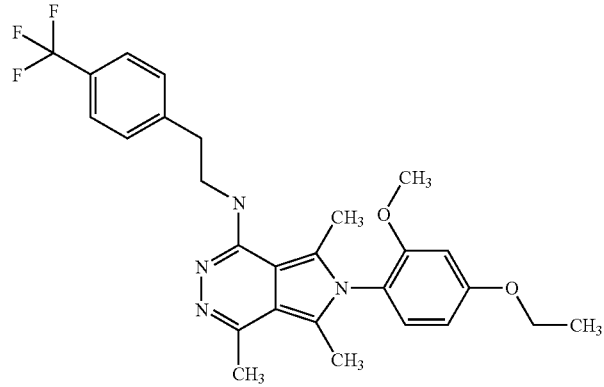 | 500 |
| Example 195 | 6-(4-ethoxy-2-methoxyphenyl)-4,5,7-trimethyl-N-(octahydro-2H-quinolizin-1-ylmethyl)-6H-pyrrolo[3,4-d]pyridazin-1-amine | 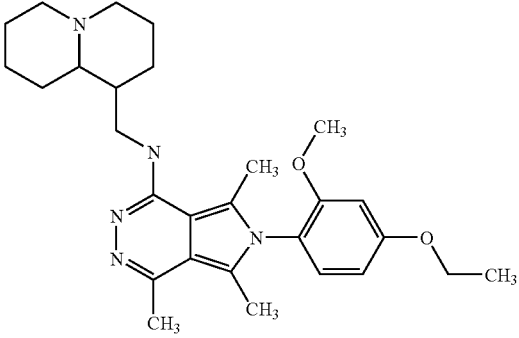 | 479 |
| Example 196 | N-(3-chlorobenzyl)-6-(4-ethoxy-2-methoxyphenyl)-4,5,7-trimethyl-6H-pyrrolo[3,4-d]pyridazin-1-amine | 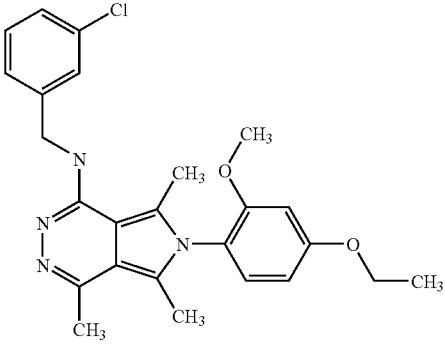 | 452 |
| Example 197 | 6-(4-ethoxy-2-methoxyphenyl)-N-[2-(2-methoxyphenyl)ethyl]-4,5,7-trimethyl-6H-pyrrolo[3,4-d]pyridazin-1-amine | 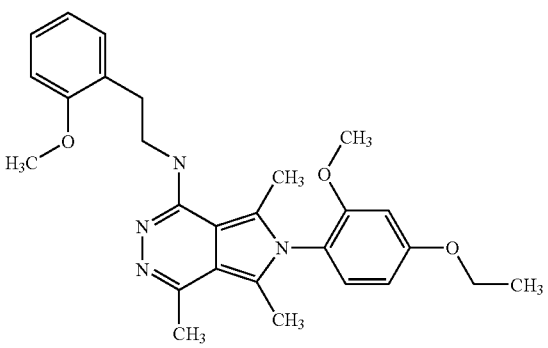 | 462 |

-continued

| Example | Name | Structure | MS (ESI) |
|---|---|---|---|
| Example 198 | N-(3-bromo-4-methylphenyl)-6-(4-ethoxy-2-methoxyphenyl)-4,5,7-trimethyl-6H-pyrrolo[3,4-d]pyridazin-1-amine | 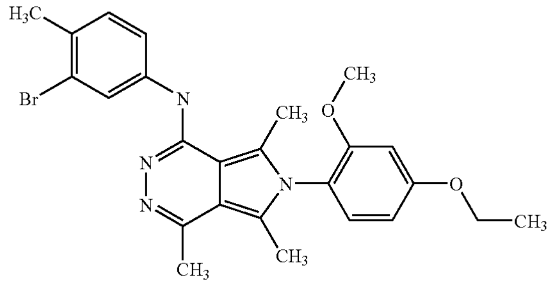 | 496 |
| Example 199 | 6-(4-ethoxy-2-methoxyphenyl)-4,5,7-trimethyl-N-[3-(2-methylpiperidin-1-yl)propyl]-6H-pyrrolo[3,4-d]pyridazin-1-amine | 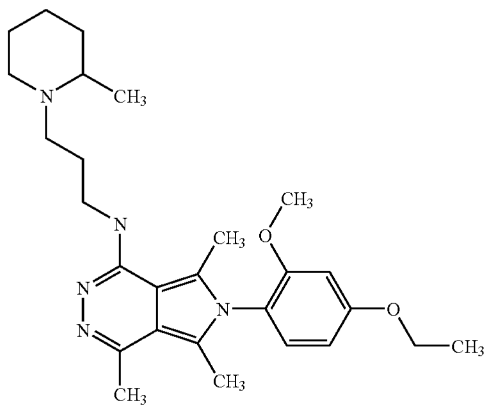 | 467 |
| Example 200 | 2-[6-(4-ethoxy-2-methoxyphenyl)-4,5,7-trimethyl-6H-pyrrolo[3,4-d]pyridazin-1-yl]-2,3,4,9-tetrahydro-1H-beta-carboline | 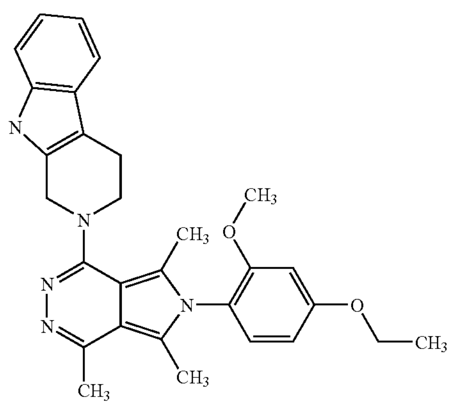 | 483 |
| Example 201 | N-(2,3-dihydro-1H-inden-1-yl)-6-(4-ethoxyphenyl)-4,5,7-trimethyl-6H-pyrrolo[3,4-d]pyridazin-1-amine | 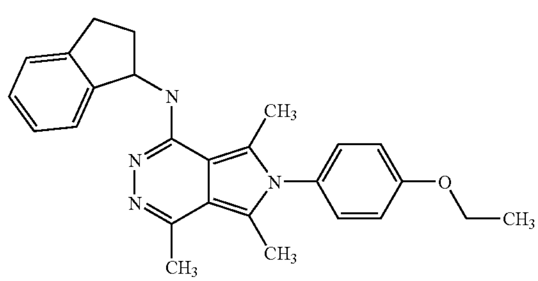 | 414 |

-continued

| Example | Name | Structure | MS (ESI) |
|---|---|---|---|
| Example 202 | N-(sec-butyl)-6-(4-ethoxy-2-methoxyphenyl)-4,5,7-trimethyl-6H-pyrrolo[3,4-d]pyridazin-1-amine | 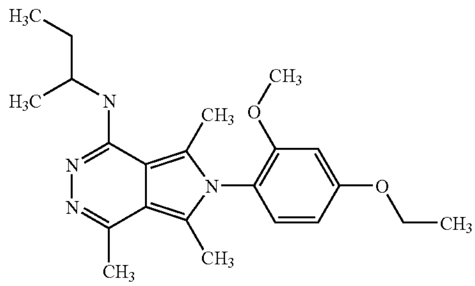 | 384 |
| Example 203 | N-(3,4-dichlorobenzyl)-6-(4-ethoxy-2-methoxyphenyl)-4,5,7-trimethyl-6H-pyrrolo[3,4-d]pyridazin-1-amine | 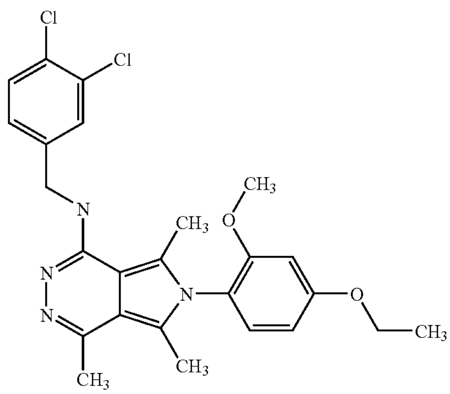 | 486 |
| Example 204 | 3-{4-[6-(4-ethoxy-2-methoxyphenyl)-4,5,7-trimethyl-6H-pyrrolo[3,4-d]pyridazin-1-yl]piperazin-1-yl}phenyl | 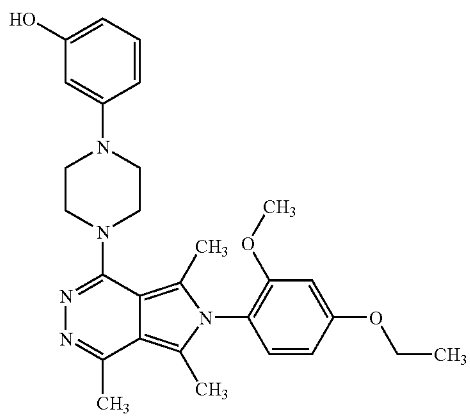 | 489 |
| Example 205 | 6-(4-ethoxy-2-methoxyphenyl)-1,5,7-trimethyl-4-[(1S,5R)-1,3,3-trimethyl-6-azabicyclo[3.2.1]oct-6-yl]-6H-pyrrolo[3,4-d]pyridazine | Chiral | 464 |

-continued

| Example | Name | Structure | MS (ESI) |
|---|---|---|---|
| Example 206 | N-[3-(benzyloxy)phenyl]-6-(4-ethoxy-2-methoxyphenyl)-4,5,7-trimethyl-6H-pyrrolo[3,4-d]pyridazin-1-amine | 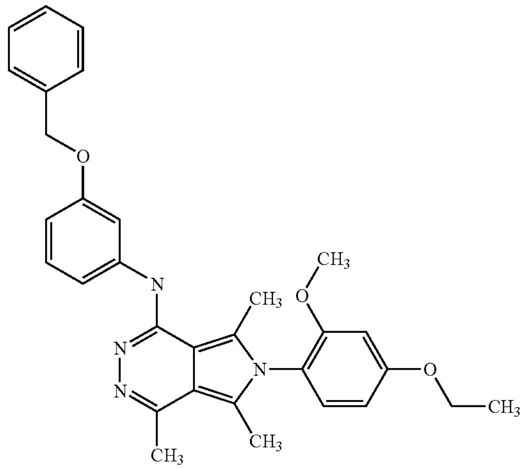 | 510 |
| Example 207 | 6-(4-ethoxyphenyl)-N-1H-indazol-5-yl-4,5,7-trimethyl-6H-pyrrolo[3,4-d]pyridazin-1-aminium chloride | 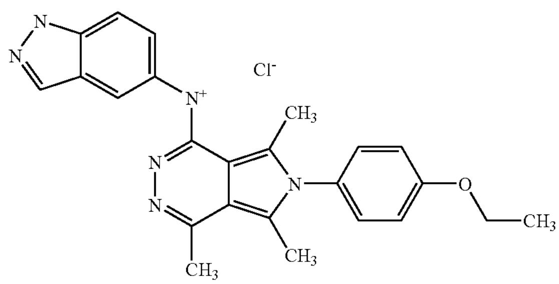 | 450 |
| Example 208 | 6-(4-ethoxy-2-methoxyphenyl)-4,5,7-trimethyl-N-[(1-piperidin-1-ylcyolohexyl)methyl]-6H-pyrrolo[3,4-d]pyridazin-1-amine | 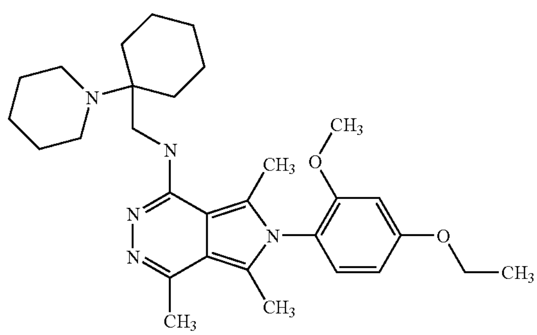 | 507 |
| Example 209 | N-butyl-6-(4-ethoxyphenyl)-4,5,7-trimethyl-6H-pyrrolo[3,4-d]pyridazin-1-amine | 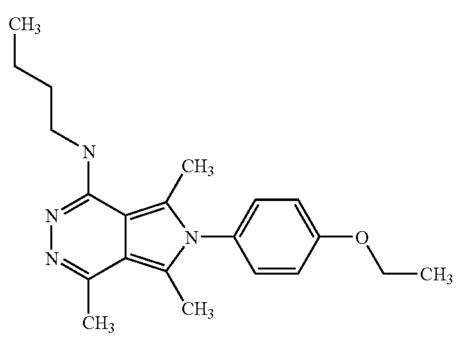 | 353 |

-continued

| Example | Name | Structure | MS (ESI) |
|---|---|---|---|
| Example 210 | 6-(4-ethoxyphenyl)-4,5,7-trimethyl-N-(quinolin-8-ylmethyl)-6H-pyrrolo[3,4-d]pyridazin-1-amine | 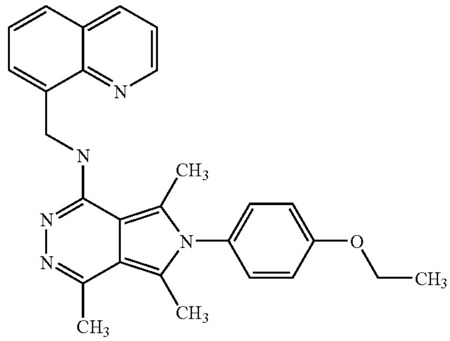 | 439 |
| Example 211 | 6-(4-ethoxy-2-methoxyphenyl)-N-(4-isopropylphenyl)-4,5,7-trimethyl-6H-pyrrolo[3,4-d]pyridazin-1-amine | 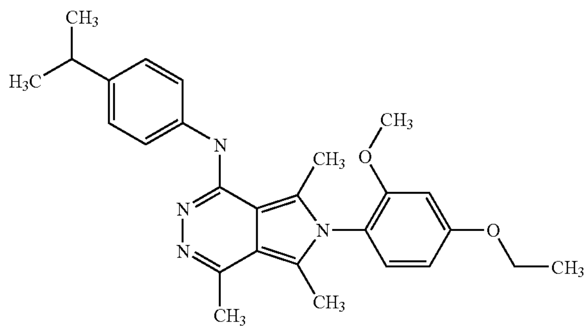 | 446 |
| Example 212 | 6-(4-ethoxy-2-methoxyphenyl)-4,5,7-trimethyl-N-[4-(trifluoromethyl)benzyl]-6H-pyrrolo[3,4-d]pyridazin-1-amine | 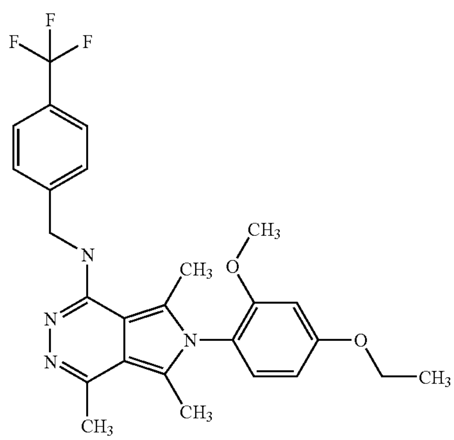 | 486 |
| Example 213 | 6-(4-ethoxyphenyl)-N-[(1-ethyl-1H-pyrazol-4-yl)methyl]-4,5,7-trimethyl-6H-pyrrolo[3,4-d]pyridazin-1-amine | 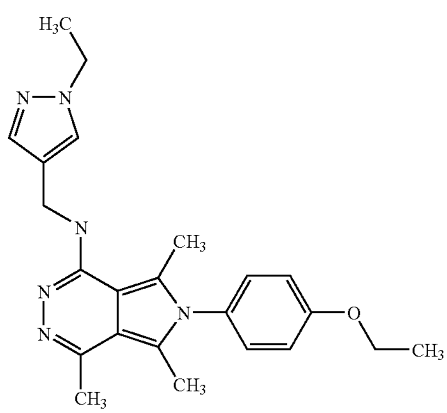 | 406 |

| Example | Name | Structure | MS (ESI) |
|---|---|---|---|
| Example 214 | N-[2-(4-chlorophenyl)ethyl]-6-(4-ethoxy-2-methoxyphenyl)-4,5,7-trimethyl-6H-pyrrolo[3,4-d]pyridazin-1-amine | 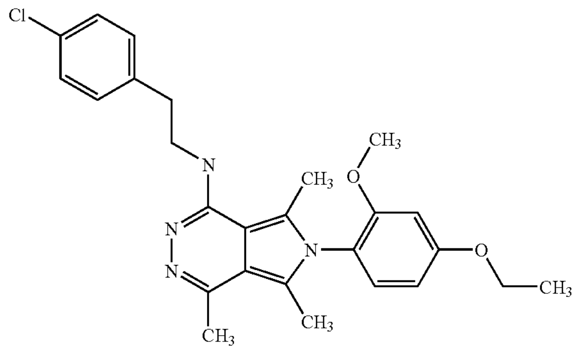 | 466 |
| Example 215 | N-(4-chlorobenzyl)-6-(4-ethoxyphenyl)-4,5,7-trimethyl-6H-pyrrolo[3,4-d]pyridazin-1-amine | 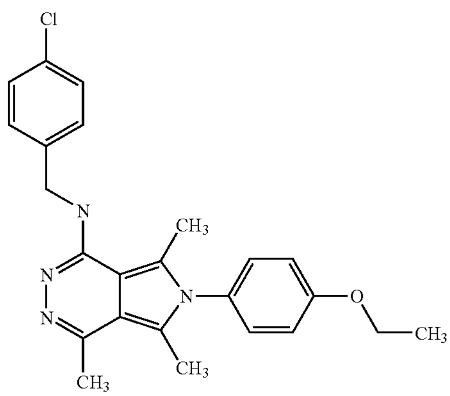 | 422 |
| Example 216 | 1-[4-(2,5-dimethylphenyl)piperazin-1-yl]-6-(4-ethoxy-2-methoxyphenyl)-4,5,7-trimethyl-6H-pyrrolo[3,4-d]pyridazine | 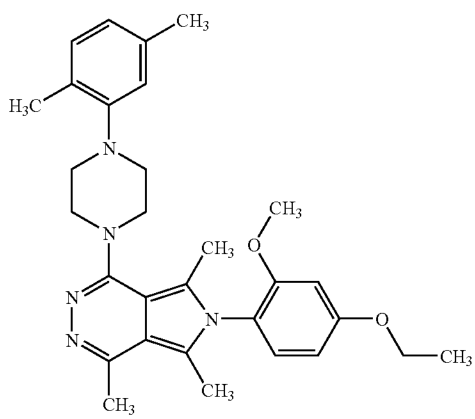 | 501 |
| Example 217 | 1-(4-benzylpiperazin-1-yl)-6-(4-ethoxy-2-methoxyphenyl)-4,5,7-trimethyl-6H-pyrrolo[3,4-d]pyridazine | 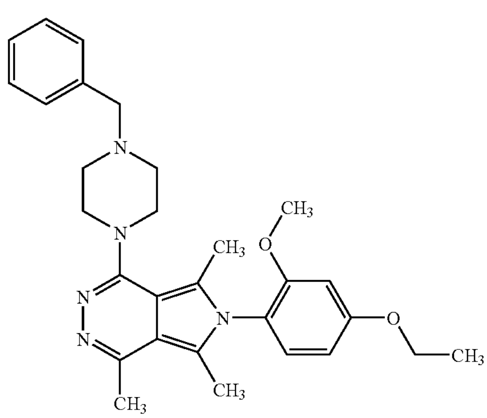 | 487 |

| Example | Name | Structure | MS (ESI) |
|---|---|---|---|
| Example 218 | 6-(4-ethoxyphenyl)-N-isopropyl-4,5,7-trimethyl-6H-pyrrolo[3,4-d]pyridazin-1-amine | 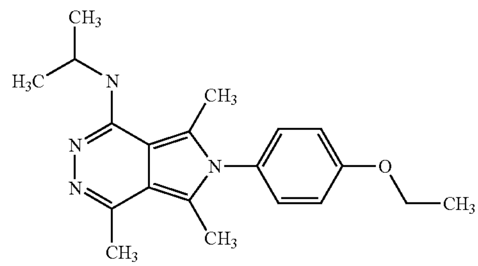 | 339 |
| Example 219 | 6-(4-ethoxyphenyl)-4,5,7-trimethyl-N-[2-(tetrahydro-2H-pyran-2-yl)ethyl]-6H-pyrrolo[3,4-d]pyridazin-1-amine | 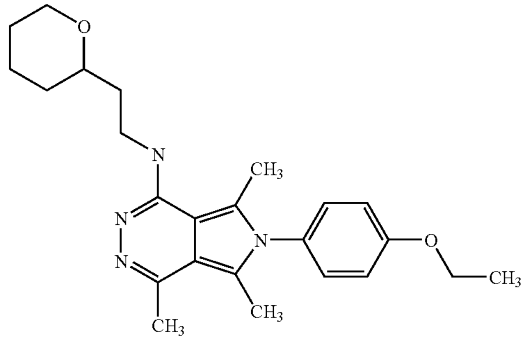 | 410 |
| Example 220 | N-(3-chloro-4-morpholin-4-ylphenyl)-6-(4-ethoxy-2-methoxyphenyl)-4,5,7-trimethyl-6H-pyrrolo[3,4-d]pyridazin-1-amine | 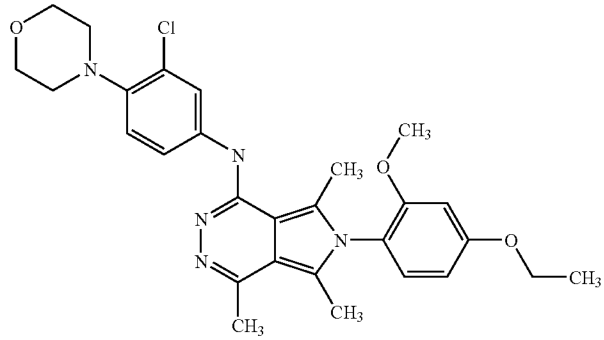 | 523 |
| Example 221 | N-[(3-cyclopropyl-1H-pyrazol-5-yl)methyl]-6-(4-ethoxyphenyl)-4,5,7-trimethyl-6H-pyrrolo[3,4-d]pyridazin-1-amine | 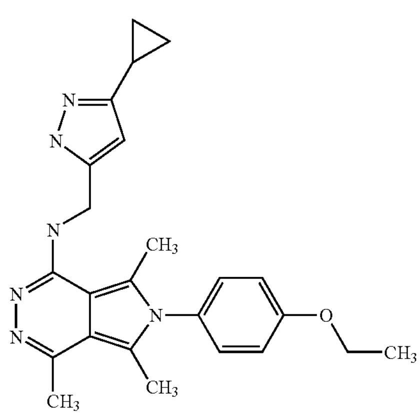 | 418 |

-continued

| Example | Name | Structure | MS (ESI) |
|---|---|---|---|
| Example 222 | 6-(4-ethoxy-2-methoxyphenyl)-4,5,7-trimethyl-N-[(2-phenyl-1,3-thiazol-4-yl)methyl]-6H-pyrrolo[3,4-d]pyridazin-1-amine | 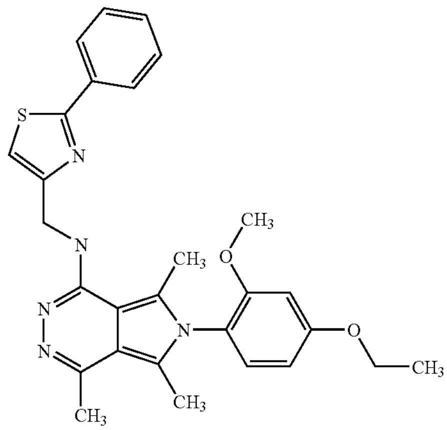 | 501 |
| Example 223 | 6-(4-ethoxyphenyl)-4,5,7-trimethyl-N-[(1-methyl-1H-pyrazol-4-yl)methyl]-6H-pyrrolo[3,4-d]pyridazin-1-amine | 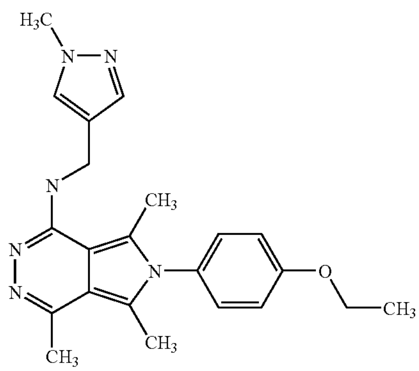 | 391 |
| Example 224 | 6-(4-ethoxy-2-methoxyphenyl)-N-(isoquinolin-5-ylmethyl)-4,5,7-trimethyl-6H-pyrrolo[3,4-d]pyridazin-1-amine | 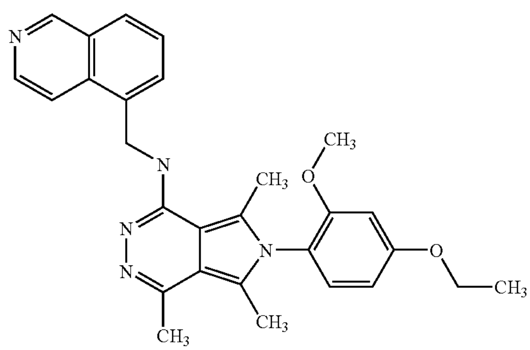 | 469 |
| Example 225 | 6-(4-ethoxy-2-methoxyphenyl)-1,5,7-trimethyl-4-[2-(phenoxymethyl)morpholin-4-yl]-6H-pyrrolo[3,4-d]pyridazine | 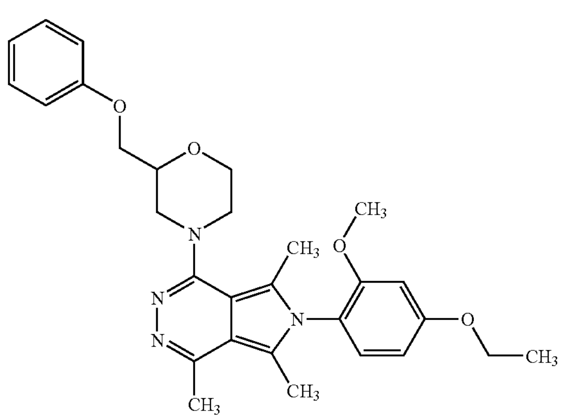 | 504 |

-continued

| Example | Name | Structure | MS (ESI) |
|---|---|---|---|
| Example 226 | 6-(4-ethoxyphenyl)-N-(1H-indol-4-ylmethyl)-4,5,7-trimethyl-6H-pyrrolo[3,4-d]pyridazin-1-amine | 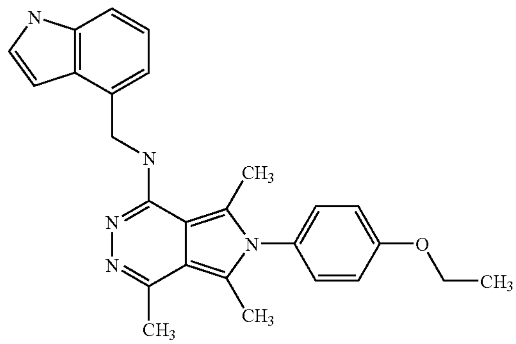 | 427 |
| Example 227 | N-(2,2-diphenylethyl)-6-(4-ethoxy-2-methoxyphenyl)-4,5,7-trimethyl-6H-pyrrolo[3,4-d]pyridazin-1-amine | 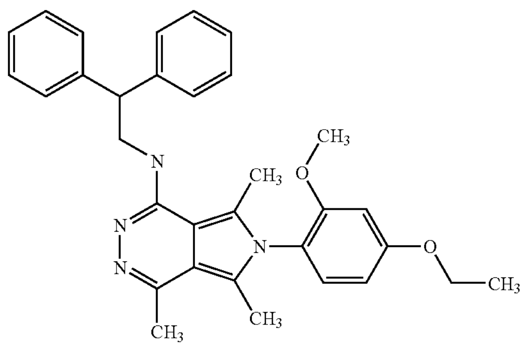 | 508 |
| Example 228 | N-(4-tert-butylphenyl)-6-(4-ethoxy-2-methoxyphenyl)-4,5,7-trimethyl-6H-pyrrolo[3,4-d]pyridazin-1-amine | 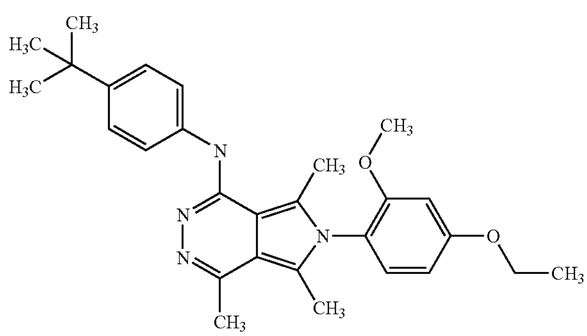 | 460 |
| Example 229 | N'-[6-(4-ethoxy-2-methoxyphenyl)-4,5,7-trimethyl-6H-pyrrolo[3,4-d]pyridazin-1-yl]-N,N-dimethylethane-1,2-diamine | 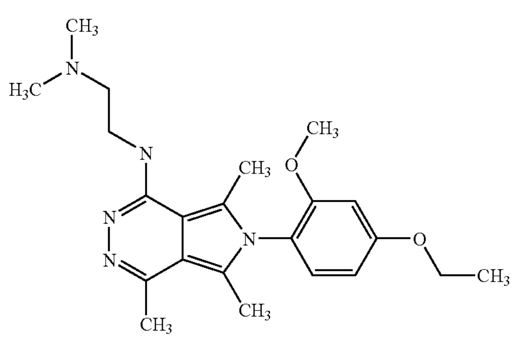 | 399 |

-continued

| Example | Name | Structure | MS (ESI) |
|---|---|---|---|
| Example 230 | 6-(4-ethoxyphenyl)-N-[2-(3-methoxyphenyl)ethyl]-4,5,7-trimethyl-6H-pyrrolo[3,4-d]pyridazin-1-amine | 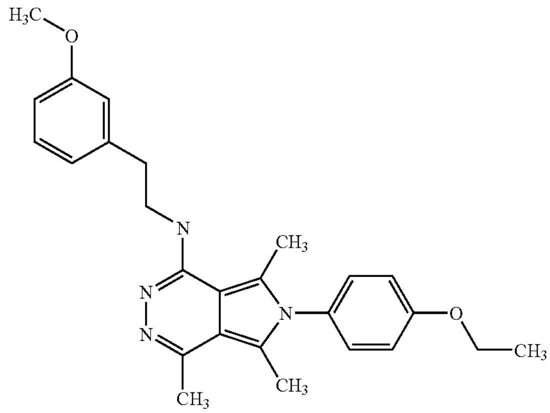 | 432 |
| Example 231 | 6-(4-ethoxyphenyl)-N-(2-methoxybenzyl)-4,5,7-trimethyl-6H-pyrrolo[3,4-d]pyridazin-1-amine | 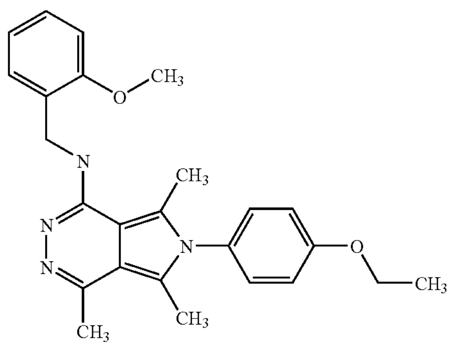 | 418 |
| Example 232 | 2-(2-{[6-(4-ethoxy-2-methoxyphenyl)-4,5,7-trimethyl-6H-pyrrolo[3,4-d]pyridazin-1-yl]amino}ethyl)quinazolin-4(3H)-one | 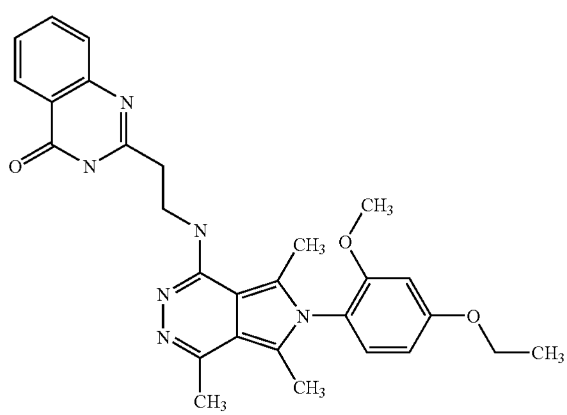 | 500 |
| Example 233 | 6-(4-ethoxy-2-methoxyphenyl)-4,5,7-trimethyl-6H-pyrrolo[3,4-d]pyridazin-1-amine | 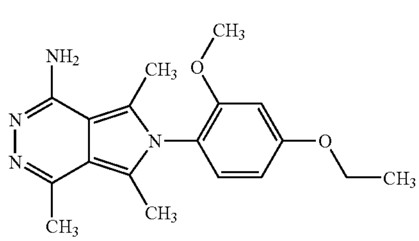 | 327 |

-continued

| Example | Name | Structure | MS (ESI) |
|---|---|---|---|
| Example 234 | 6-(4-ethoxy-2-methoxyphenyl)-1,5,7-trimethyl-4-(4-pyridin-2-ylpiperazin-1-yl)-6H-pyrrolo[3,4-d]pyridazine | 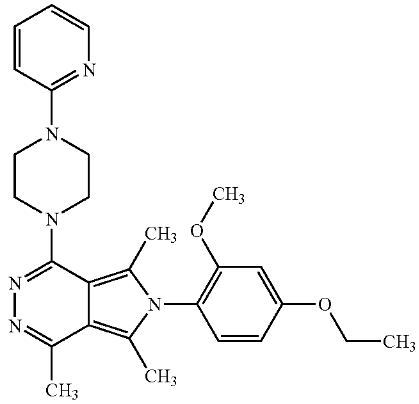 | 474 |
| Example 235 | 6-(4-ethoxy-2-methoxyphenyl)-N-(4-fluorobenzyl)-4,5,7-trimethyl-6H-pyrrolo[3,4-d]pyridazin-1-amine | 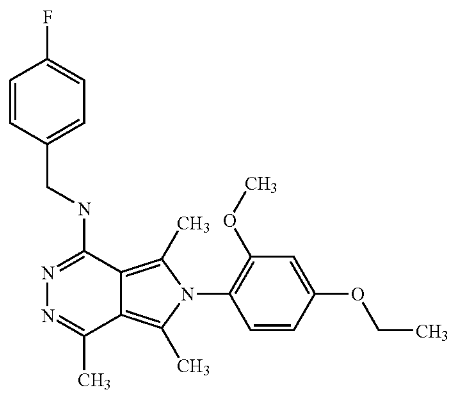 | 436 |
| Example 236 | 1-[(2R,6S)-2,6-dimethylmorpholin-4-yl]-6-(4-ethoxy-2-methoxyphenyl)-4,5,7-trimethyl-6H-pyrrolo[3,4-d]pyridazine | 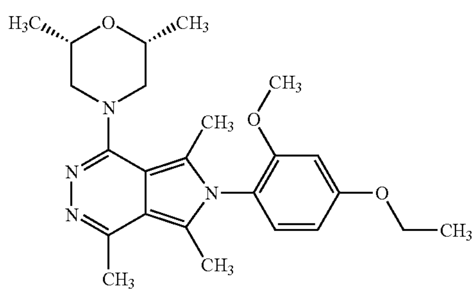 | 426 |
| Example 237 | 1-(3,5-dimethylpiperidin-1-yl)-6-(4-ethoxy-2-methoxyphenyl)-4,5,7-trimethyl-6H-pyrrolo[3,4-d]pyridazine | 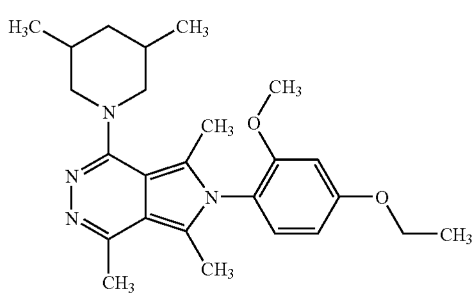 | 424 |

-continued

| Example | Name | Structure | MS (ESI) |
|---|---|---|---|
| Example 238 | 6-(4-ethoxy-2-methoxyphenyl)-4,5,7-trimethyl-N-(1-naphthylmethyl)-6H-pyrrolo[3,4-d]pyridazin-1-amine | 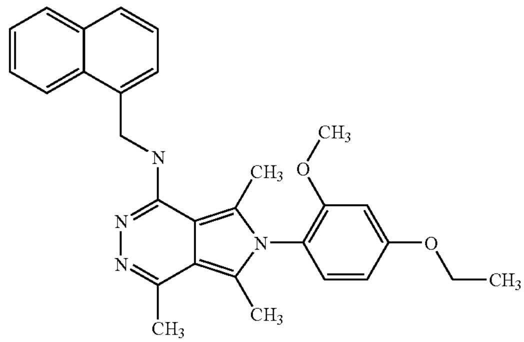 | 468 |
| Example 239 | 4-[6-(4-ethoxy-2-methoxyphenyl)-4,5,7-trimethyl-6H-pyrrolo[3,4-d]pyridazin-1-yl]piperazine-1-carbaldehyde | 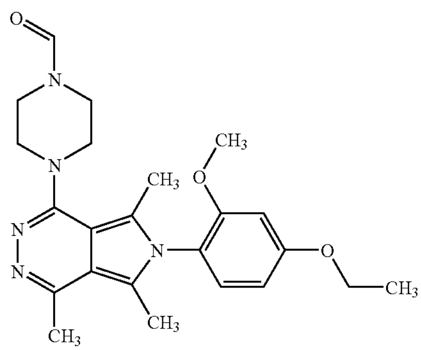 | 425 |
| Example 240 | 6-(4-ethoxyphenyl)-4,5,7-trimethyl-N-[(6-methylpyridin-2-yl)methyl]-6H-pyrrolo[3,4-d]pyridazin-1-amine | 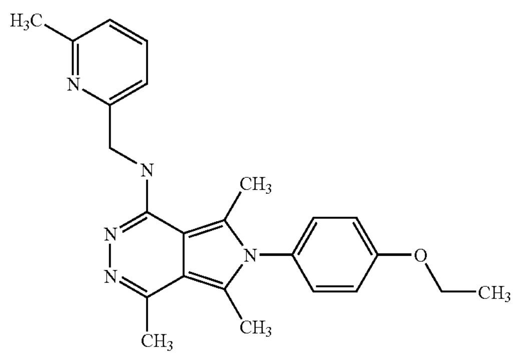 | 403 |
| Example 241 | 6-(4-ethoxyphenyl)-4,5,7-trimethyl-N-(2-methylbutyl)-6H-pyrrolo[3,4-d]pyridazin-1-amine | 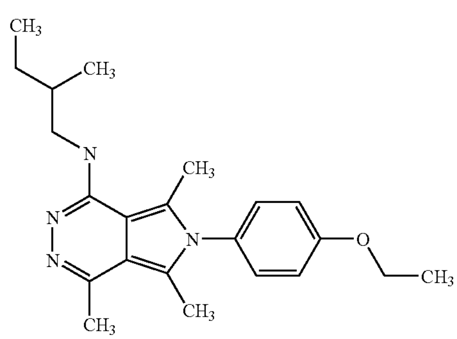 | 368 |

| Example | Name | Structure | MS (ESI) |
|---|---|---|---|
| Example 242 | 6-(4-ethoxyphenyl)-4,5,7-trimethyl-N-(pyridin-4-ylmethyl)-6H-pyrrolo[3,4-d]pyridazin-1-amine | 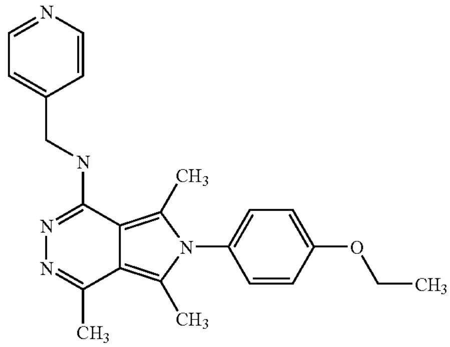 | 388 |
| Example 243 | (3aR,9bR)-2-[6-(4-ethoxyphenyl)-4,5,7-trimethyl-6H-pyrrolo[3,4-d]pyridazin-1-yl]-2,3,3a,4,5,9b-hexahydro-1H-benzo[e]isoindole | 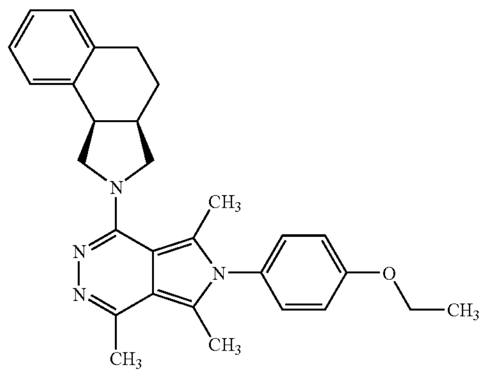 | 454 |
| Example 244 | 1-{4-[2-(4-chlorophenyl)ethyl]piperidin-1-yl}-6-(4-ethoxy-2-methoxyphenyl)-4,5,7-trimethyl-6H-pyrrolo[3,4-d]pyridazine | 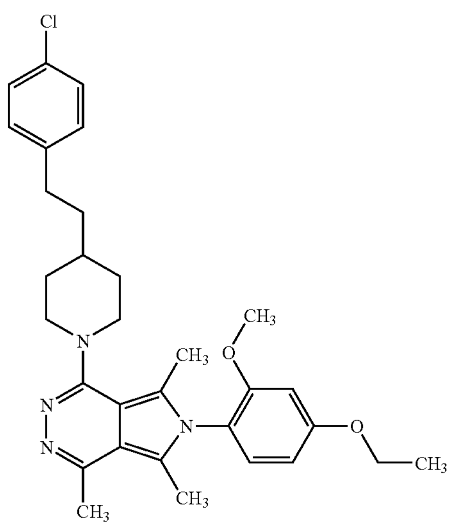 | 534 |
| Example 245 | 6-(4-ethoxy-2-methoxyphenyl)-4,5,7-trimethyl-N-[(1-morpholin-4-ylcyclohexyl)methyl]-6H-pyrrolo[3,4-d]pyridazin-1-amine | 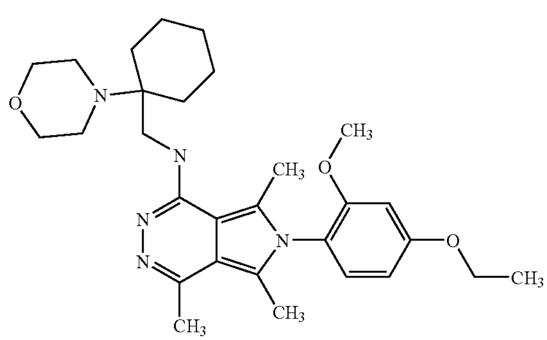 | 509 |

-continued

| Example | Name | Structure | MS (ESI) |
|---|---|---|---|
| Example 246 | 6-(4-ethoxy-2-methoxyphenyl)-1,5,7-trimethyl-4-(4-methylpiperidin-1-yl)-6H-pyrrolo[3,4-d]pyridazine | 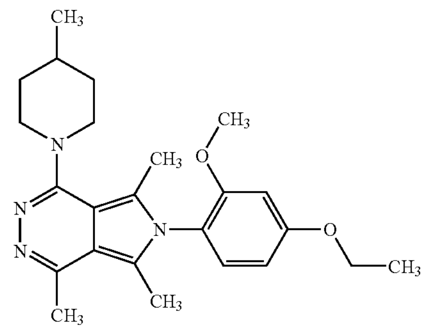 | 410 |
| Example 247 | N-(2,4-dichlorobenzyl)-6-(4-ethoxy-2-methoxyphenyl)-4,5,7-trimethyl-6H-pyrrolo[3,4-d]pyridazin-1-amine | 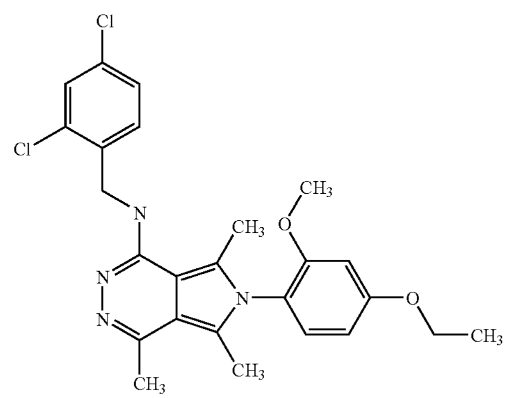 | 486 |
| Example 248 | 6-(4-ethoxyphenyl)-4,5,7-trimethyl-N-(3-pyridin-3-ylpropyl)-6H-pyrrolo[3,4-d]pyridazin-1-amine | 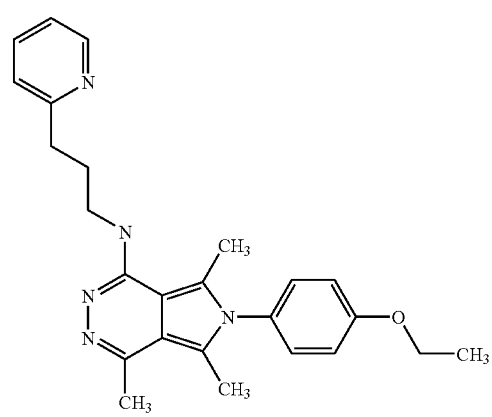 | 417 |
| Example 249 | 6-(4-ethoxy-2-methoxyphenyl)-1,5,7-trimethyl-4-(4-phenylpiperazin-1-yl)-6H-pyrrolo[3,4-d]pyridazine | 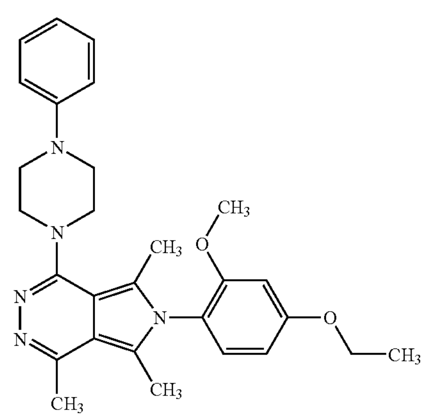 | 473 |

-continued

| Example | Name | Structure | MS (ESI) |
|---|---|---|---|
| Example 250 | ethyl 1-[6-(4-ethoxy-2-methoxyphenyl)-4,5,7-trimethyl-6H-pyrrolo[3,4-d]pyridazin-1-yl]piperidine-4-carboxylate | 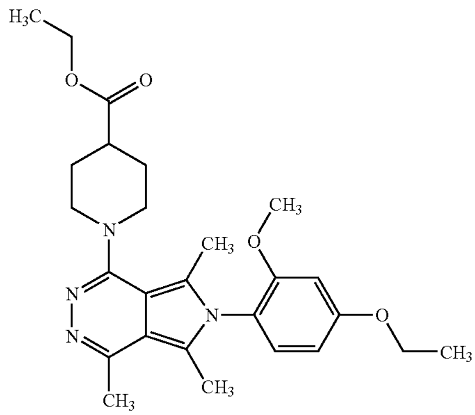 | 468 |
| Example 251 | N-(2,3-dihydro-1H-inden-5-yl)-6-(4-ethoxy-2-methoxyphenyl)-4,5,7-trimethyl-6H-pyrrolo[3,4-d]pyridazin-1-amine | 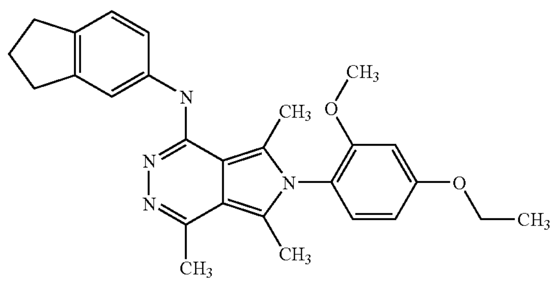 | 444 |
| Example 252 | 6-(4-ethoxy-2-methoxyphenyl)-1-[4-(2-fluorophenyl)piperazin-1-yl]-4,5,7-trimethyl-6H-pyrrolo[3,4-d]pyridazine | 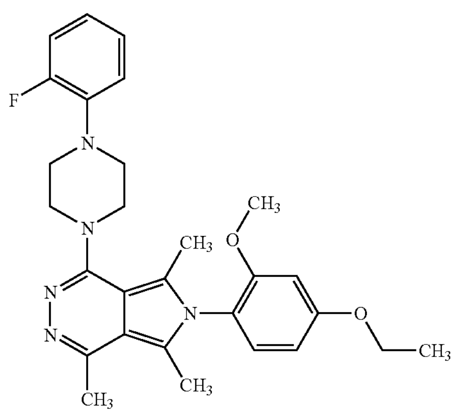 | 491 |
| Example 253 | 6-(4-ethoxyphenyl)-N-(4-fluorobenzyl)-4,5,7-trimethyl-6H-pyrrolo[3,4-d]pyridazin-1-amine | 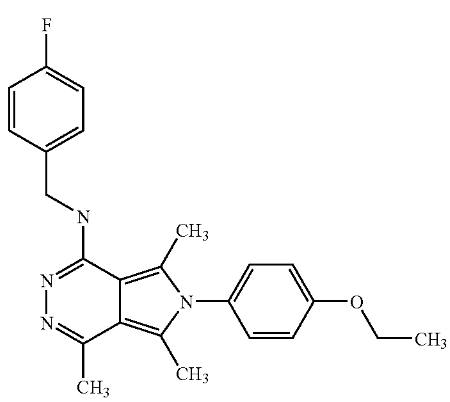 | 405 |

-continued

| Example | Name | Structure | MS (ESI) |
|---|---|---|---|
| Example 254 | 6-(4-ethoxy-2-methoxyphenyl)-1,5,7-trimethyl-4-[3-[methyl-4-(4-methylphenyl)piperazin-1-yl]-6H-pyrrolo[3,4-d]pyridazine | 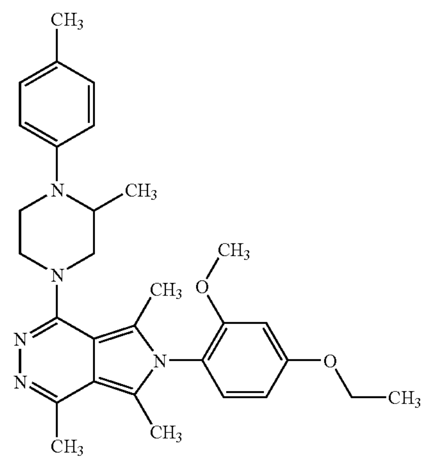 | 501 |
| Example 255 | 6-(4-ethoxy-2-methoxyphenyl)-1-[4-(2-methoxyphenyl)piperazin-1-yl]-4,5,7-trimethyl-6H-pyrrolo[3,4-d]pyridazine | 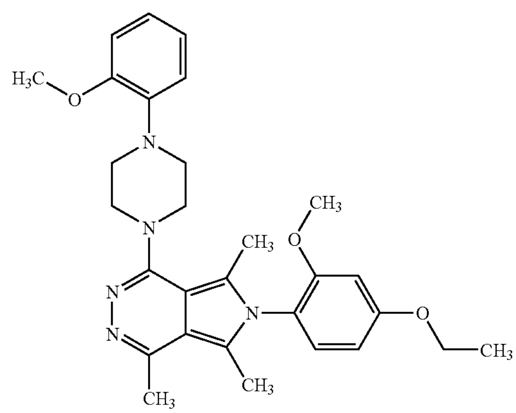 | 503 |
| Example 256 | 2-[6-(4-ethoxy-2-methoxyphenyl)-4,5,7-trimethyl-6H-pyrrolo[3,4-d]pyridazin-1-yl]-1,2,3,4-tetrahydroisoquinoline | 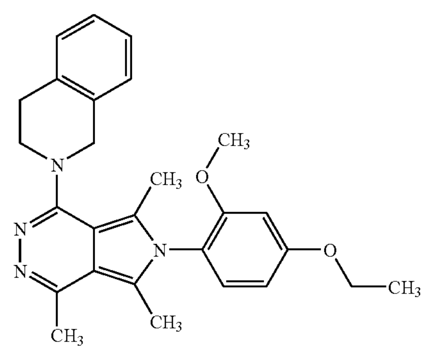 | 444 |

-continued

| Example | Name | Structure | MS (ESI) |
|---|---|---|---|
| Example 257 | 1-(4-{4-[6-(4-ethoxy-2-methoxyphenyl)-4,5,7-trimethyl-6H-pyrrolo[3,4-d]pyridazin-1-yl]piperazin-1-yl}phenyl)ethanone | 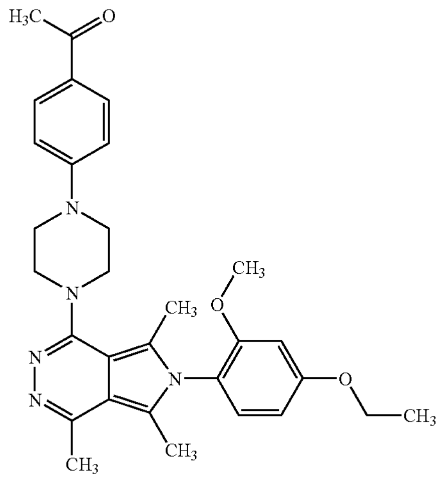 | 515 |
| Example 258 | 6-(4-ethoxy-2-methoxyphenyl)-4,5,7-trimethyl-N-(4-methylcyclohexyl)-6H-pyrrolo[3,4-d]pyridazin-1-amine | 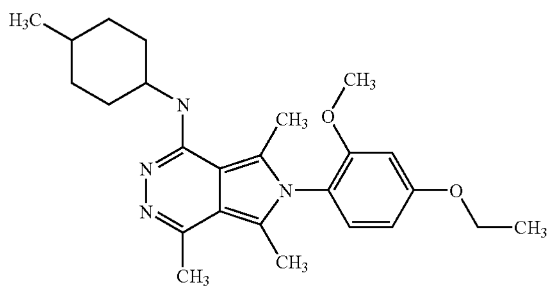 | 424 |
| Example 259 | N-(3,3-diphenylpropyl)-6-(4-ethoxy-2-methoxyphenyl)-4,5,7-trimethyl-6H-pyrrolo[3,4-d]pyridazin-1-amine | 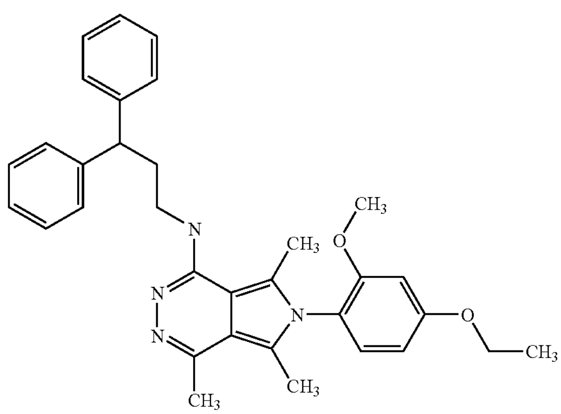 | 522 |
| Example 260 | 6-(4-ethoxyphenyl)-4,5,7-trimethyl-N-[2-(1,3-thiazol-2-yl)ethyl]-6H-pyrrolo[3,4-d]pyridazin-1-amine | 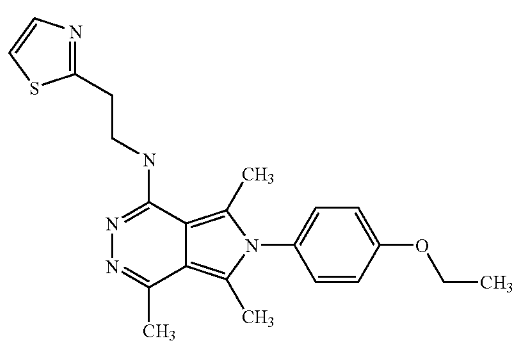 | 409 |

-continued

| Example | Name | Structure | MS (ESI) |
|---|---|---|---|
| Example 261 | 6-(4-ethoxy-2-methoxyphenyl)-4,5,7-trimethyl-N-[2-(3-phenylpyrrolidin-1-yl)ethyl]-6H-pyrrolo[3,4-d]pyridazin-1-amine | 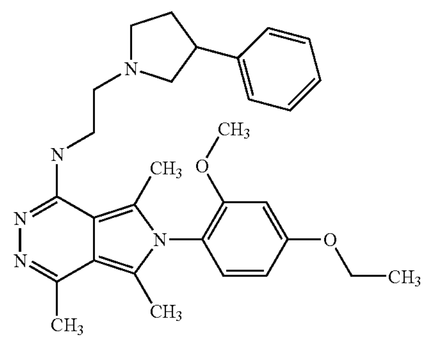 | 501 |
| Example 262 | 6-(4-ethoxy-2-methoxyphenyl)-N-isobutyl-4,5,7-trimethyl-6H-pyrrolo[3,4-d]pyridazin-1-amine | 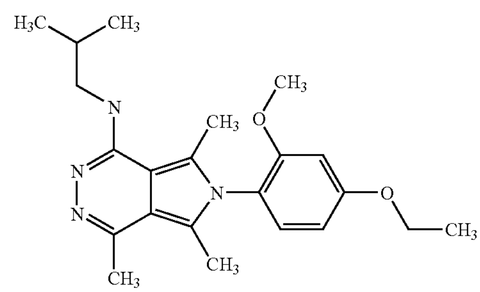 | 384 |
| Example 263 | 1-[4-(1,3-benzodioxol-5-ylmethyl)piperazin-1-yl]-6-(4-ethoxy-2-methoxyphenyl)-4,5,7-trimethyl-6H-pyrrolo[3,4-d]pyridazine | 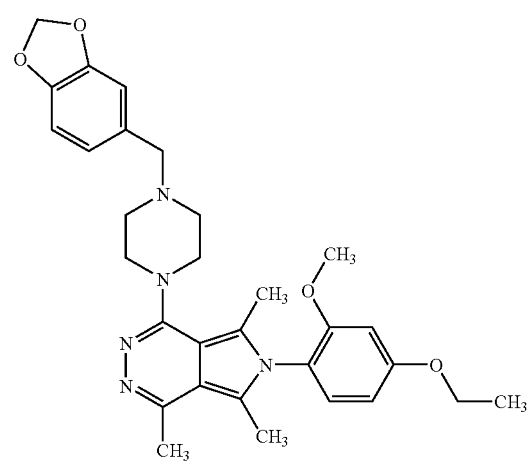 | 531 |
| Example 264 | 4-(4-chlorophenyl)-1-[6-(4-ethoxy-2-methoxyphenyl)-4,5,7-trimethyl-6H-pyrrolo[3,4-d]pyridazin-1-yl]piperidin-4-ol | 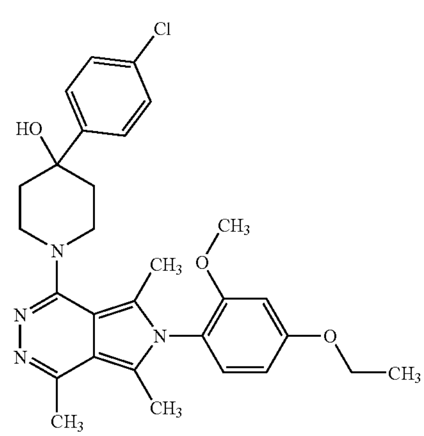 | 522 |

| Example | Name | Structure | MS (ESI) |
|---|---|---|---|
| Example 265 | 6-(4-ethoxy-2-methoxyphenyl)-1-[4-(4-fluorophenyl)piperazin-1-yl]-4,5,7-trimethyl-6H-pyrrolo[3,4-d]pyridazine | 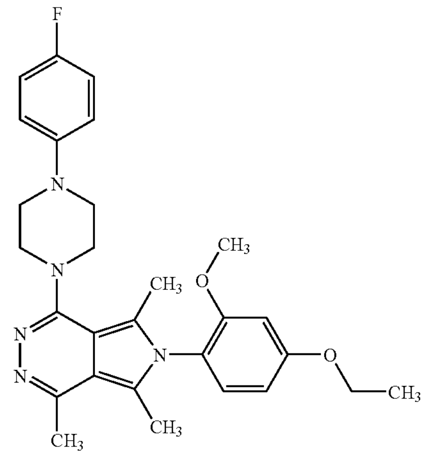 | 491 |
| Example 266 | 1-[4-(4-chlorophenyl)piperazin-1-yl]-6-(4-ethoxy-2-methoxyphenyl)-4,5,7-trimethyl-6H-pyrrolo[3,4-d]pyridazine | 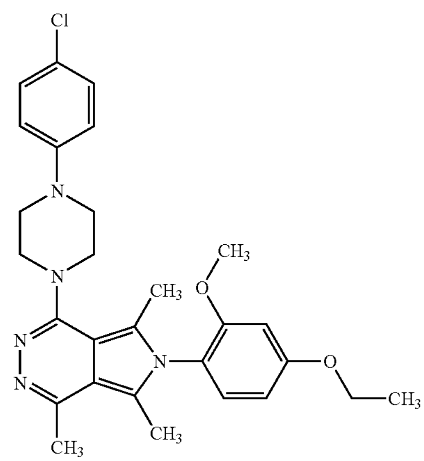 | 507 |
| Example 267 | 6-(4-ethoxyphenyl)-N-[2-(4-methoxyphenyl)ethyl]-4,5,7-trimethyl-6H-pyrrolo[3,4-d]pyridazin-1-amine | 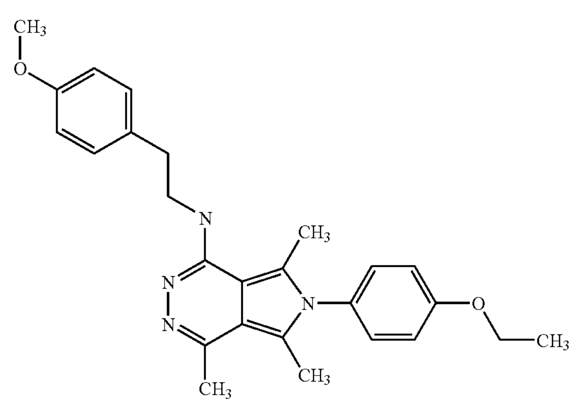 | 432 |

-continued

| Example | Name | Structure | MS (ESI) |
|---|---|---|---|
| Example 268 | N-(1H-benzimidazol-2-ylmethyl)-6-(4-ethoxyphenyl)-4,5,7-trimethyl-6H-pyrrolo[3,4-d]pyridazin-1-amine | 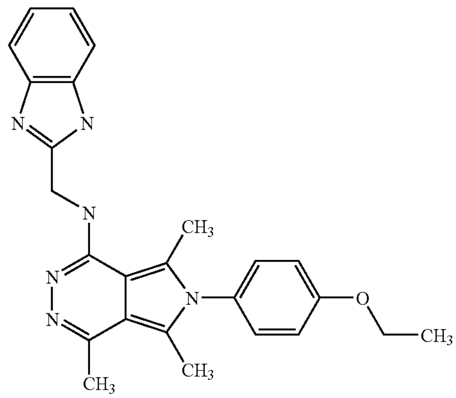 | 428 |
| Example 269 | 1-[6-(4-ethoxy-2-methoxyphenyl)-4,5,7-trimethyl-6H-pyrrolo[3,4-d]pyridazin-1-yl]-4-[3-(trifluoromethyl)phenyl]piperidin-4-ol | 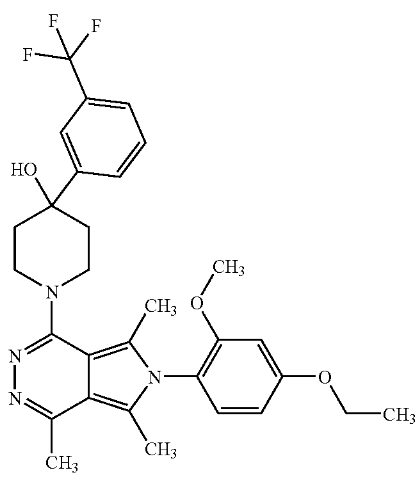 | 556 |
| Example 270 | ethyl 1-[6-(4-ethoxy-2-methoxyphenyl)-4,5,7-trimethyl-6H-pyrrolo[3,4-d]pyridazin-1-yl]piperidine-3-carboxylate | 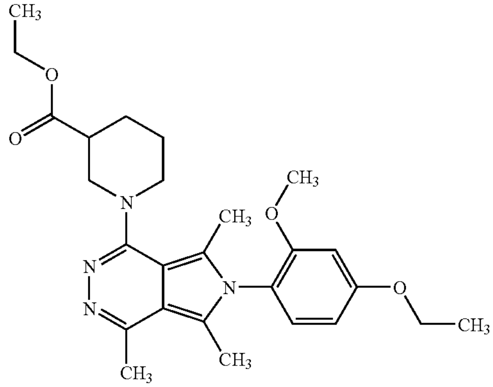 | 468 |

-continued

| Example | Name | Structure | MS (ESI) |
|---|---|---|---|
| Example 271 | 6-(4-ethoxyphenyl)-4,5,7-trimethyl-N-(pyridin-3-ylmethyl)-6H-pyrrolo[3,4-d]pyridazin-1-amine | 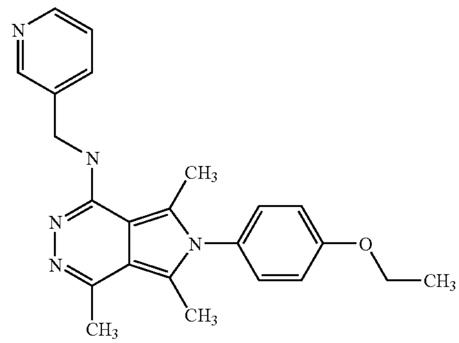 | 388 |
| Example 272 | N-(3,4-difluorobenzyl)-6-(4-ethoxyphenyl)-4,5,7-trimethyl-6H-pyrrolo[3,4-d]pyridazin-1-amine | 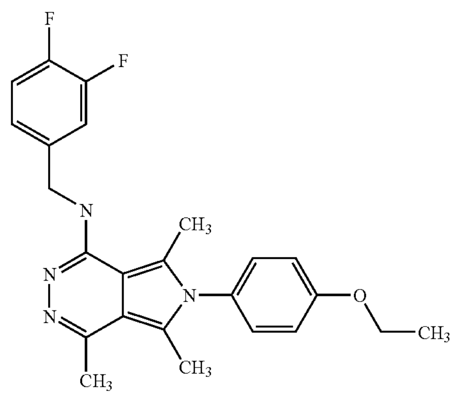 | 423 |
| Example 273 | 6-(4-ethoxyphenyl)-N-(3-fluorobenzyl)-4,5,7-trimethyl-6H-pyrrolo[3,4-d]pyridazin-1-amine | 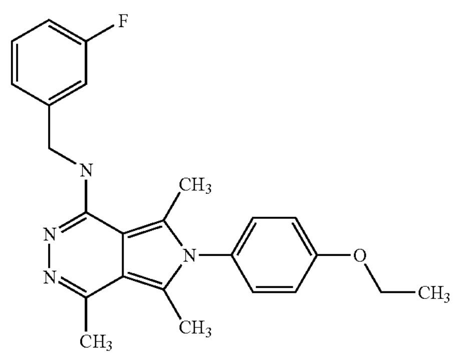 | 405 |
| Example 274 | 6-(4-ethoxy-2-methoxyphenyl)-1,5,7-trimethyl-4-[3-methyl-4-(3-methylphenyl)piperazin-1-yl]-6H-pyrrolo[3,4-d]pyridazine | 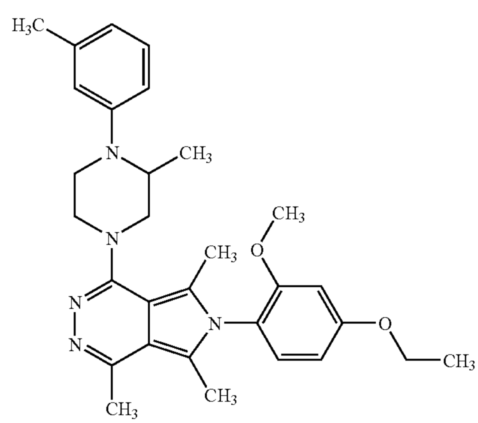 | 501 |

| Example | Name | Structure | MS (ESI) |
|---|---|---|---|
| Example 275 | 6-(4-ethoxy-2-methoxyphenyl)-1,5,7-trimethyl-4-{4-[(2E)-3-phenylprop-2-en-1-yl]piperazin-1-yl}-6H-pyrrolo[3,4-d]pyridazine | 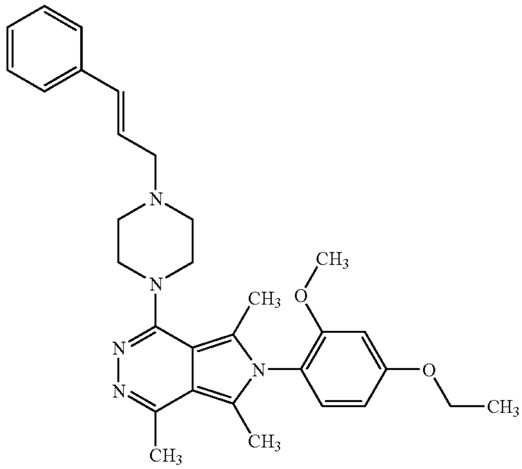 | 513 |
| Example 276 | 6-(4-ethoxyphenyl)-4,5,7-trimethyl-N-(pyrazolo[1,5-a]pyridin-7-ylmethyl)-6H-pyrrolo[3,4-d]pyridazin-1-amine | 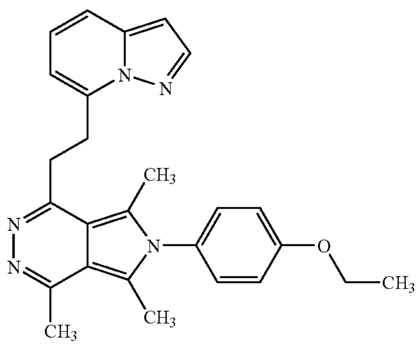 | 428 |
| Example 277 | 6-(4-ethoxyphenyl)-4,5,7-trimethyl-N-(pyrazolo[1,5-a]pyridin-7-ylmethyl)-6H-pyrrolo[3,4-d]pyridazin-1-amine | 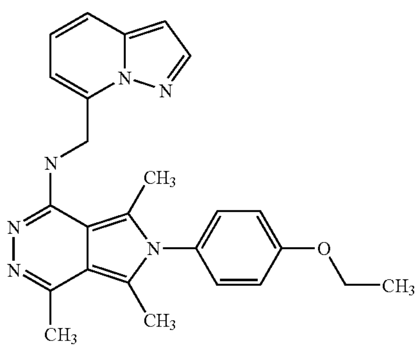 | 428 |
| Example 278 | N-[2-(4-chlorophenyl)ethyl]-6-(4-ethoxyphenyl)-4,5,7-trimethyl-6H-pyrrolo[3,4-d]pyridazin-1-amine | 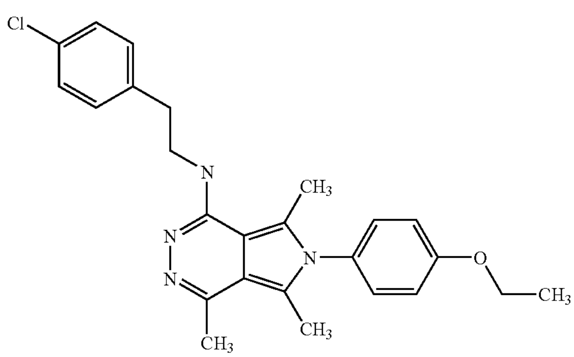 | 436 |

-continued

| Example | Name | Structure | MS (ESI) |
|---|---|---|---|
| Example 279 | 1-[4-(3,4-dimethylphenyl)piperazin-1-yl]-6-(4-ethoxy-2-methoxyphenyl)-4,5,7-trimethyl-6H-pyrrolo[3,4-d]pyridazine | 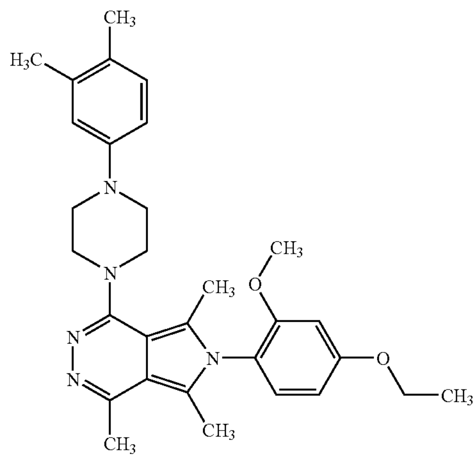 | 501 |
| Example 280 | 6-(4-ethoxyphenyl)-4,5,7-trimethyl-N-(1-phenylethyl)-6H-pyrrolo[3,4-d]pyridazin-1-amine | 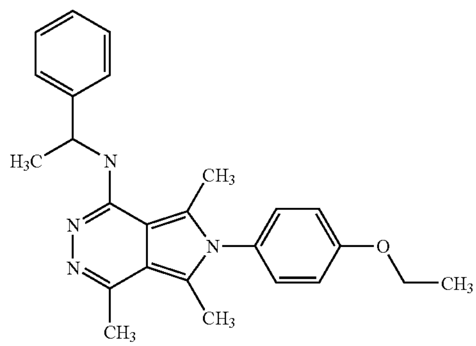 | 402 |
| Example 281 | N-[2-(2,4-dichlorophenyl)ethyl]-6-(4-ethoxy-2-methoxyphenyl)-4,5,7-trimethyl-6H-pyrrolo[3,4-d]pyridazin-1-amine | 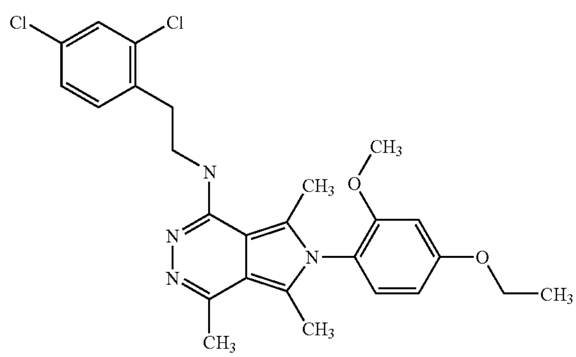 | 500 |
| Example 282 | N-(3,4-dimethoxyphenyl)-6-(4-ethoxyphenyl)-4,5,7-trimethyl-6H-pyrrolo[3,4-d]pyridazin-1-amine | 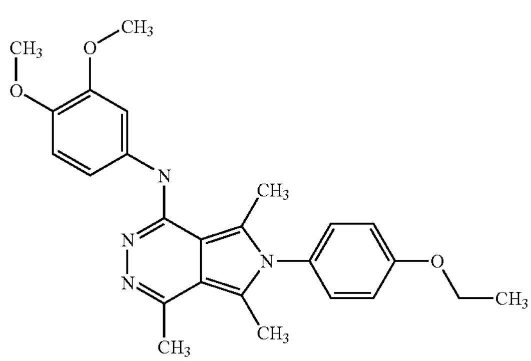 | 434 |

-continued

| Example | Name | Structure | MS (ESI) |
|---|---|---|---|
| Example 283 | 2-[6-(4-ethoxyphenyl)-4,5,7-trimethyl-6H-pyrrolo[3,4-d]pyridazin-1-yl]-2,3,4,9-tetrahydro-1H-beta-carboline | 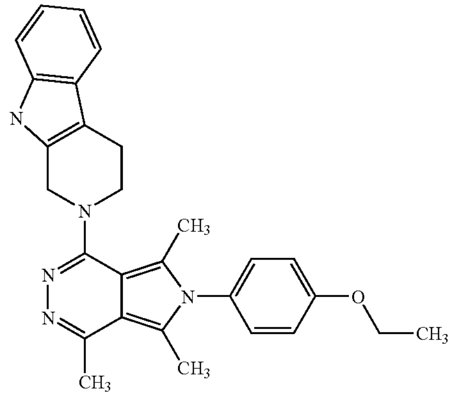 | 453 |
| Example 284 | 8-(4-ethoxy-2-methoxyphenyl)-4,5,7-trimethyl-N-(2-pyrrolidin-1-ylethyl)-6H-pyrrolo[3,4-d]pyridazin-1-amine | 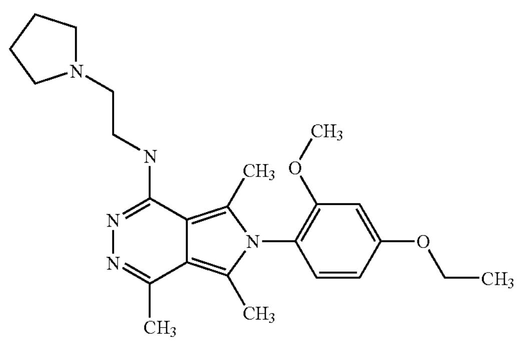 | 425 |
| Example 285 | 6-(4-ethoxyphenyl)-N-isobutyl-4,5,7-trimethyl-6H-pyrrolo[3,4-d]pylidazin-1-amine | 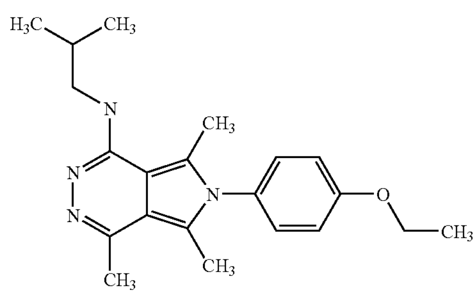 | 353 |
| Example 286 | 8-[6-(4-ethoxy-2-methoxyphenyl)-4,5,7-trimethyl-6H-pyrrolo[3,4-d]pyridazin-1-yl]-1,4-dioxa-8-azaspiro[4.5]decane | 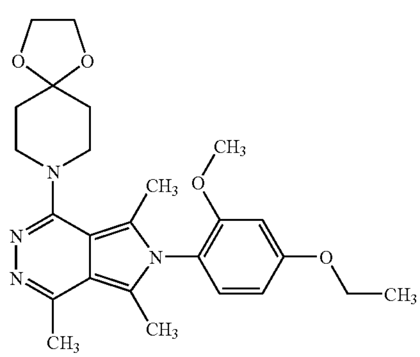 | 454 |

-continued

| Example | Name | Structure | MS (ESI) |
|---|---|---|---|
| Example 287 | 2-({[6-(4-ethoxyphenyl)-4,5,7-trimethyl-6H-pyrrolo[3,4-d]pyridazin-1-yl]amino}methyl)quinazolin-4(3H)-one | 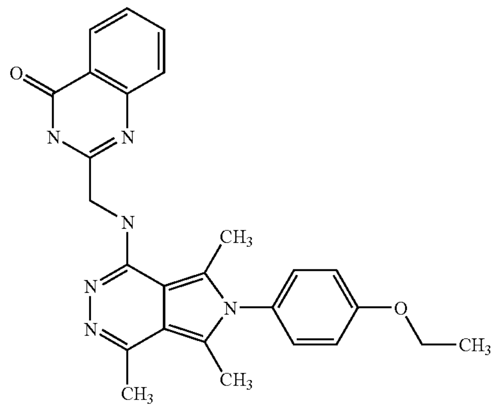 | 456 |
| Example 288 | 1-[4-(2,4-dimethylphenyl)piperazin-1-yl]-6-(4-ethoxy-2-methoxyphenyl)-4,5,7-trimethyl-6H-pyrrolo[3,4-d]pyridazine | 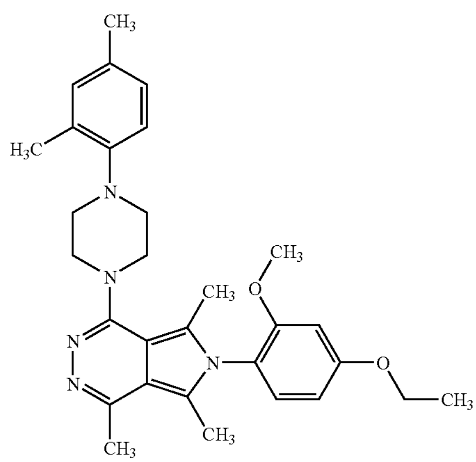 | 501 |
| Example 289 | 6-(4-ethoxyphenyl)-4,5,7-trimethyl-N-(2-phenylethyl)-6H-pyrrolo[3,4-d]pyridazin-1-amine | 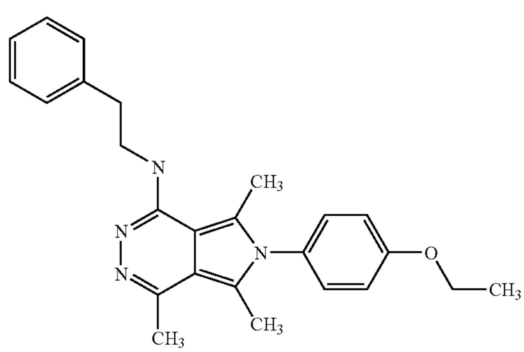 | 402 |

| Example | Name | Structure | MS (ESI) |
|---|---|---|---|
| Example 290 | 1-(3,3-diphenylpyrrolidin-1-yl)-6-(4-ethoxyphenyl)-4,5,7-trimethyl-6H-pyrrolo[3,4-d]pyridazine | 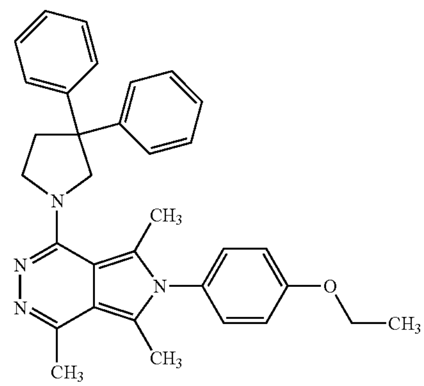 | 504 |
| Example 291 | N-{1-[6-(4-ethoxyphenyl)-4,5,7-trimethyl-6H-pyrrolo[3,4-d]pyridazin-1-yl]pyrrolidin-3-yl}acetamide | 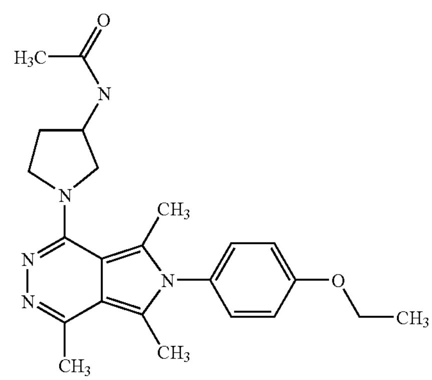 | 409 |
| Example 292 | 6-(4-ethoxy-2-methoxyphenyl)-1-(4-ethylpiperazin-1-yl)-4,5,7-trimethyl-6H-pyrrolo[3,4-d]pyridazine | 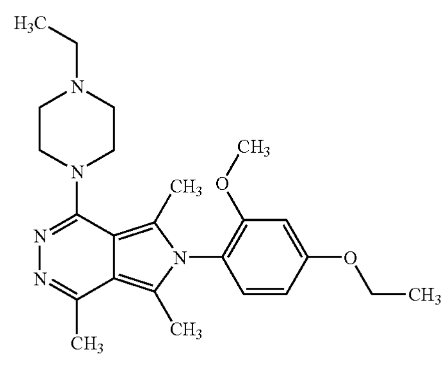 | 425 |
| Example 293 | N-cyclopentyl-6-(4-ethoxyphenyl)-4,5,7-trimethyl-6H-pyrrolo[3,4-d]pyridazin-1-amine | 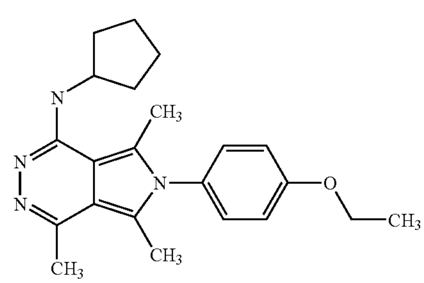 | 365 |

| Example | Name | Structure | MS (ESI) |
|---|---|---|---|
| Example 294 | 6-(4-ethoxy-2-methoxyphenyl)-1,5,7-trimethyl-4-piperidin-1-yl-6H-pyrrolo[3,4-d]pyridazine | 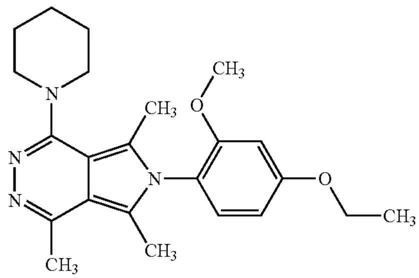 | 396 |
| Example 295 | N-(1-benzothien-2-ylmethyl)-6-(4-ethoxyphenyl)-4,5,7-trimethyl-6H-pyrrolo[3,4-d]pyridazin-1-amine | 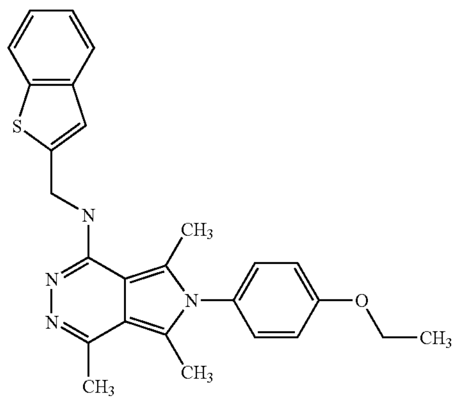 | 444 |
| Example 296 | N'-[6-(4-ethoxy-2-methoxyphenyl)-4,5,7-trimethyl-6H-pyrrolo[3,4-d]pyridazin-1-yl]-N,N-diethylethane-1,2-diamine | 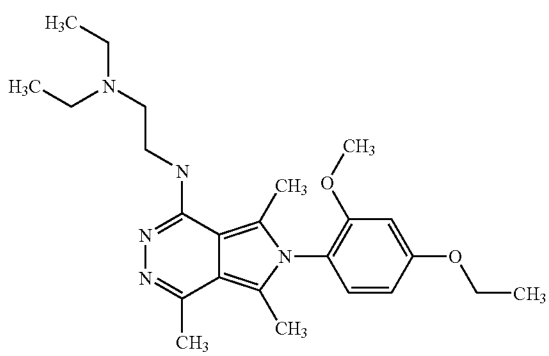 | 427 |
| Example 297 | 1'-[6-(4-ethoxy-2-methoxyphenyl)-4,5,7-trimethyl-6H-pyrrolo[3,4-d]pyridazin-1-yl]-1,4'-bipiperidine | 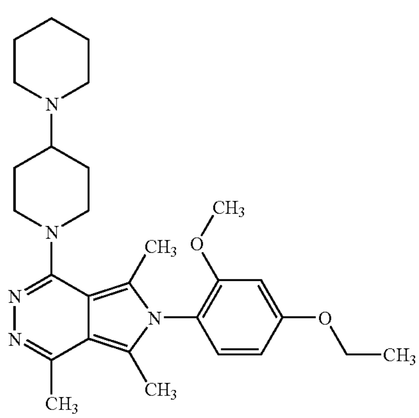 | 479 |

-continued

| Example | Name | Structure | MS (ESI) |
|---|---|---|---|
| Example 298 | 6-(4-ethoxyphenyl)-4,5,7-trimethyl-N-(3-phenylpropyl)-6H-pyrrolo[3,4-d]pyridazin-1-amine | 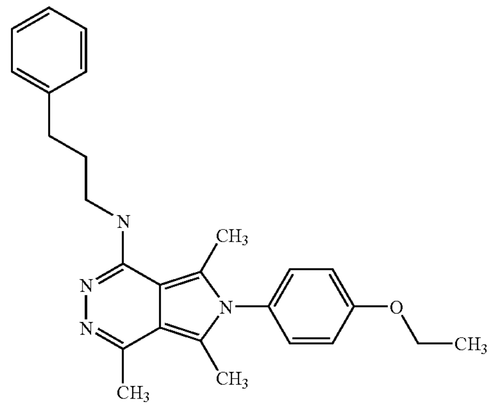 | 416 |
| Example 299 | 6-(4-ethoxyphenyl)-4,5,7-trimethyl-N-(2-morpholin-4-ylethyl)-6H-pyrrolo[3,4-d]pyridazin-1-amine | 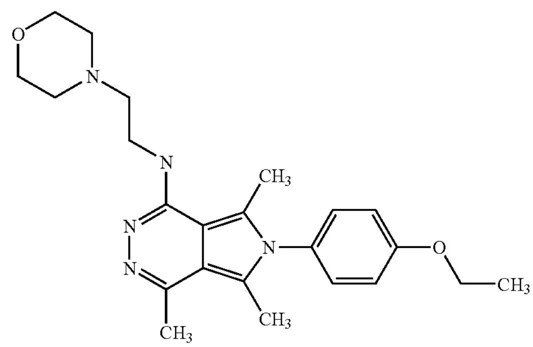 | 411 |
| Example 300 | N'-[6-(4-ethoxyphenyl)-4,5,7-trimethyl-6H-pyrrolo[3,4-d]pyridazin-1-yl]-N,N-diethylethane-1,2-diamine | 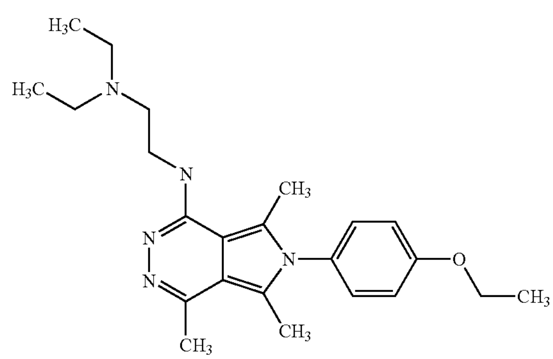 | 397 |
| Example 301 | N-(1,3-dihydro-2-benzofuran-5-yl)-6-(4-ethoxyphenyl)-4,5,7-trimethyl-6H-pyrrolo[3,4-d]pyridazin-1-amine | 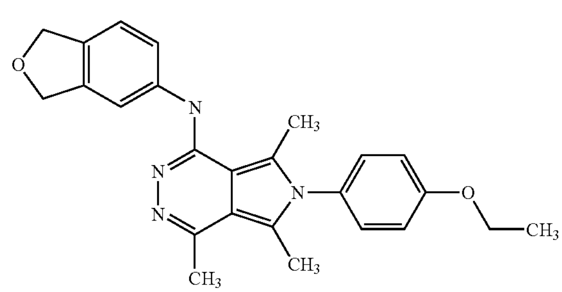 | 416 |

-continued

| Example | Name | Structure | MS (ESI) |
|---|---|---|---|
| Example 302 | 6-(4-ethoxyphenyl)-4,5,7-trimethyl-N-(1,2,3,4-tetrahydronaphthalen-1-yl)-6H-pyrrolo[3,4-d]pyridazin-1-amine | 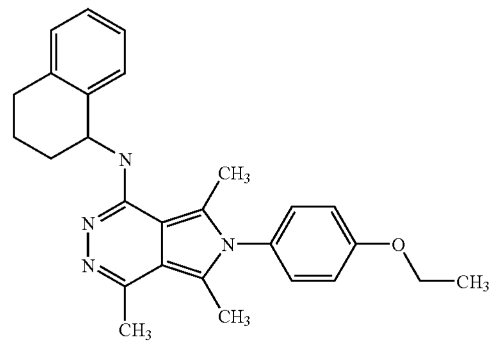 | 428 |
| Example 303 | 6-(4-ethoxyphenyl)-4,5,7-trimethyl-N-[2-(trifluoromethyl)benzyl]-6H-pyrrolo[3,4-d]pyridazin-1-amine | 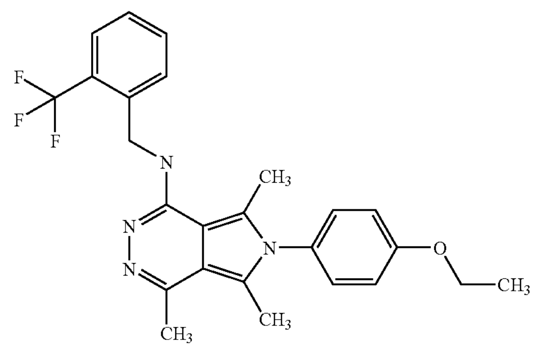 | 455 |
| Example 304 | 6-(4-ethoxyphenyl)-4,5,7-trimethyl-N-[(2-phenyl-1,3-thiazol-4-yl)methyl]-6H-pyrrolo[3,4-d]pyridazin-1-amine | 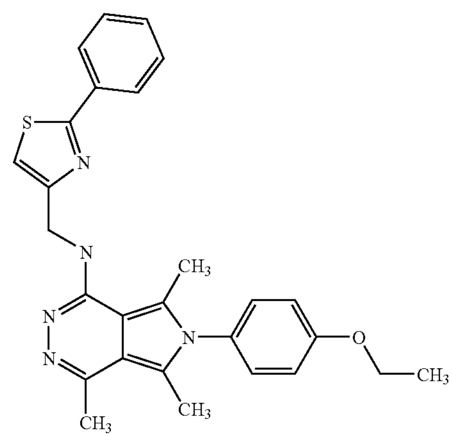 | 471 |
| Example 305 | 2-(2-{[6-(4-ethoxyphenyl)-4,5,7-trimethyl-6H-pyrrolo[3,4-d]pyridazin-1-yl]amino}ethyl)quinazolin-4(3H)-one | 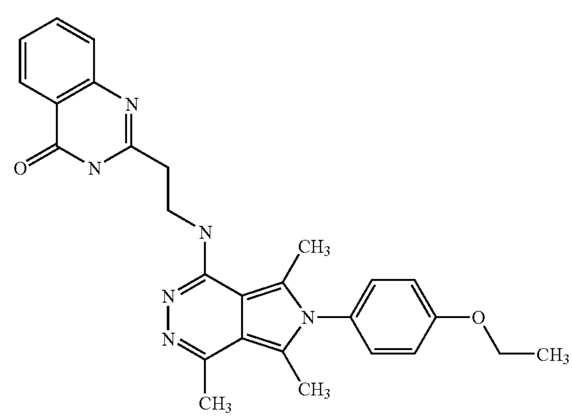 | 470 |

| Example | Name | Structure | MS (ESI) |
|---|---|---|---|
| Example 306 | 6-(4-ethoxyphenyl)-4,5,7-trimethyl-N-(4-phenylbutyl)-6H-pyrrolo[3,4-d]pyridazin-1-amine | 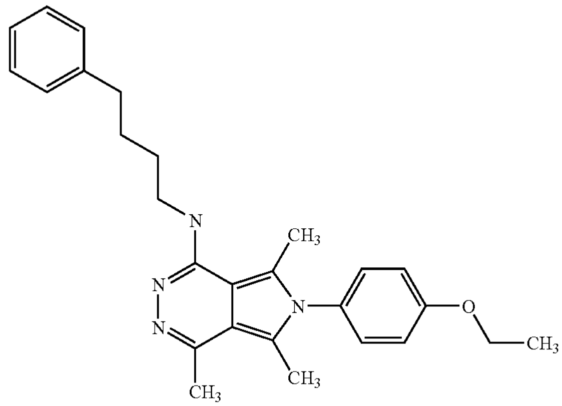 | 430 |
| Example 307 | 6-(4-ethoxyphenyl)-N,4,5,7-tetramethyl-N-(2-pyridin-2-ylethyl)-6H-pyrrolo[3,4-d]pyridazin-1-amine | 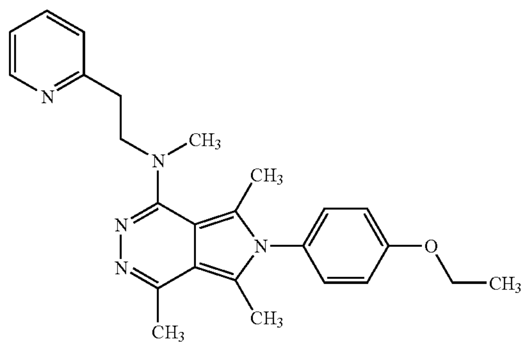 | 417 |
| Example 308 | 6-(4-ethoxyphenyl)-1,5,7-trimethyl-4-pyrrolidin-1-yl-6H-pyrrolo[3,4-d]pyridazine | 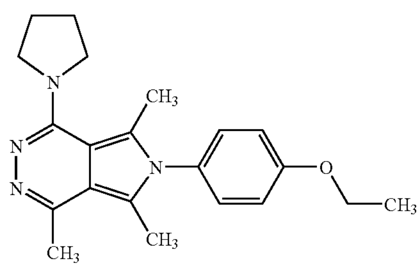 | 351 |
| Example 309 | 1-[6-(4-ethoxy-2-methoxyphenyl)-4,5,7-trimethyl-6H-pyrrolo[3,4-d[pyridazin-1-yl]-N,N-diethylpiperidine-3-carboxamide | 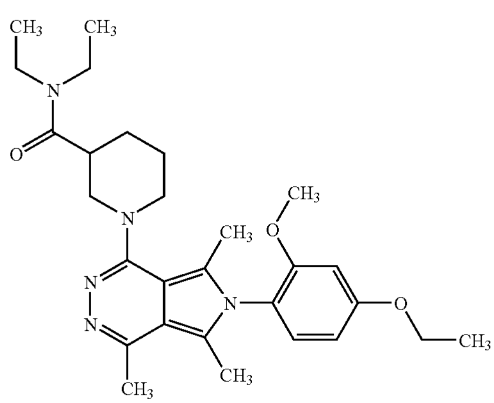 | 495 |

-continued

| Example | Name | Structure | MS (ESI) |
|---|---|---|---|
| Example 310 | N-(2,3-dimethylcyclohexyl)-6-(4-ethoxyphenyl)-4,5,7-trimethyl-6H-pyrrolo[3,4-d]pyridazin-1-amine | 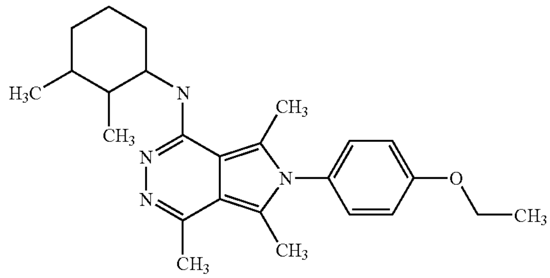 | 408 |
| Example 311 | 6-(4-ethoxyphenyl)-N-(2-methoxyethyl)-4,5,7-trimethyl-6H-pyrrolo[3,4-d]pyridazin-1-amine | 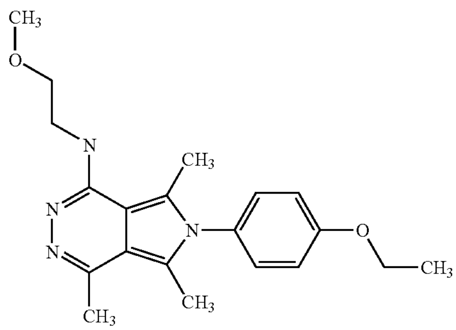 | 355 |
| Example 312 | N-(2,3-dihydro-1H-inden-5-yl)-6-(4-ethoxyphenyl)-4,5,7-trimethyl-6H-pyrrolo[3,4-d]pyridazin-1-amine | 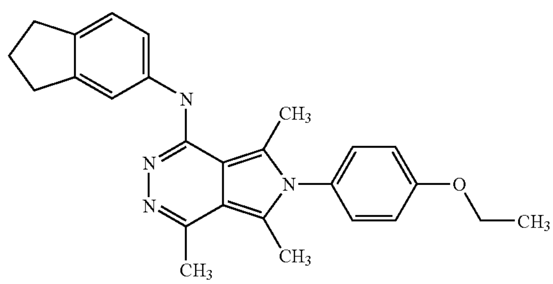 | 414 |
| Example 313 | N-(2,4-dichlorobenzyl)-6-(4-ethoxyphenyl)-4,5,7-trimethyl-6H-pyrrolo[3,4-d]pyridazin-1-amine | 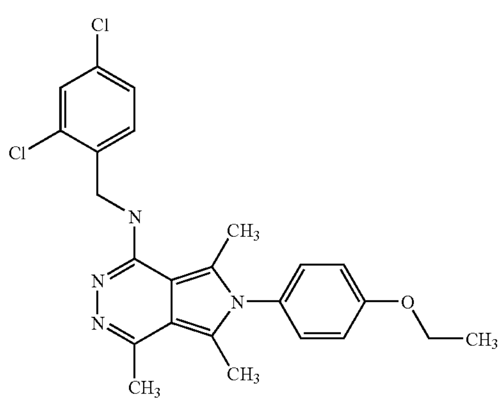 | 456 |

-continued
| Example | Name | Structure | MS (ESI) |
|---|---|---|---|
| Example 314 | N-1,3-benzodioxol-5-yl-6-(4-ethoxyphenyl)-4,5,7-trimethyl-6H-pyrrolo[3,4-d]pyridazin-1-amine | 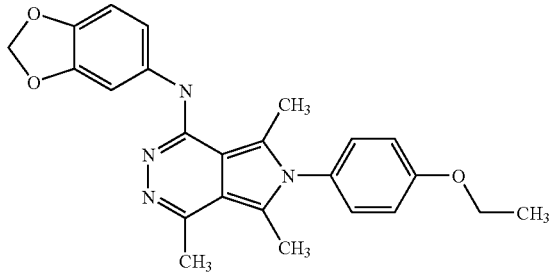 | 417 |
| Example 315 | 6-(4-ethoxyphenyl)-N-(4-methoxyphenyl)-4,5,7-trimethyl-6H-pyrrolo[3,4-d]pyridazin-1-amine | 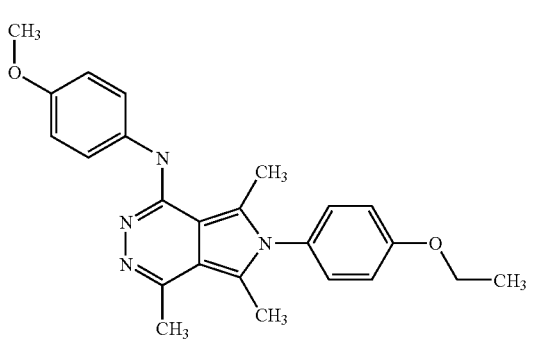 | 404 |
| Example 316 | 6-(4-ethoxyphenyl)-1,5,7-trimethyl-4-piperidin-1-yl-6H-pyrrolo[3,4-d]pyridazine | 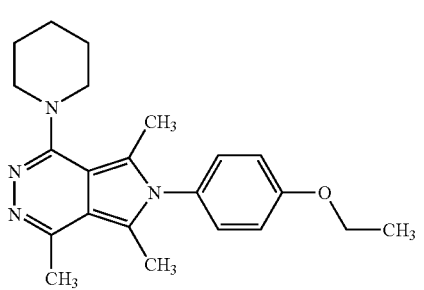 | 365 |
| Example 317 | N-(1,3-dimethylbutyl)-6-(4-ethoxy-2-methoxyphenyl)-4,5,7-trimethyl-6H-pyrrolo[3,4-d]pyridazin-1-amine | 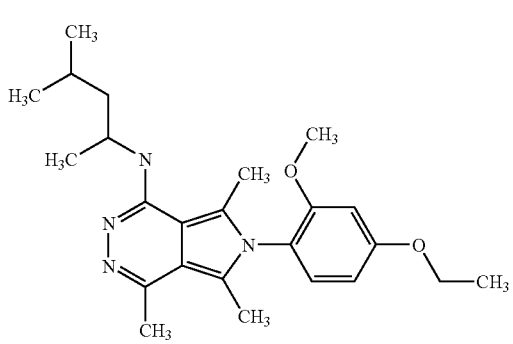 | 412 |

-continued

| Example | Name | Structure | MS (ESI) |
|---|---|---|---|
| Example 318 | 1-[4-(3,4-dichlorophenyl)piperazin-1-yl]-6-(4-ethoxy-2-methoxyphenyl)-4,5,7-trimethyl-6H-pyrrolo[3,4-d]pyridazine | 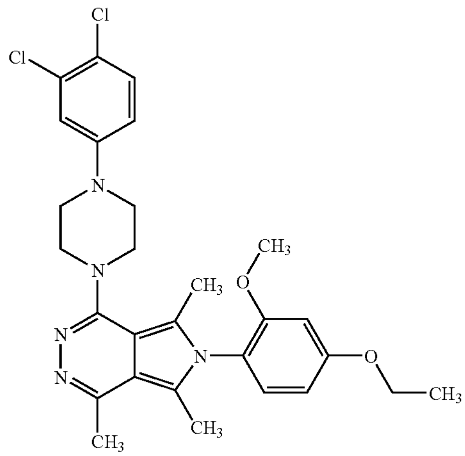 | 541 |
| Example 319 | 6-(4-ethoxyphenyl)-4,5,7-trimethyl-N-[4-(methylthio)phenyl]-6H-pyrrolo[3,4-d]pyridazin-1-amine | 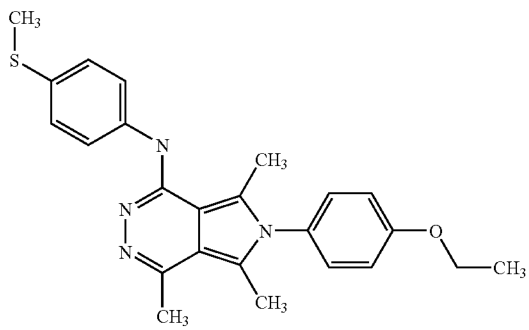 | 420 |
| Example 320 | 6-(4-ethoxyphenyl)-N-(3-methoxybenzyl)-4,5,7-trimethyl-6H-pyrrolo[3,4-d]pyridazin-1-amine | 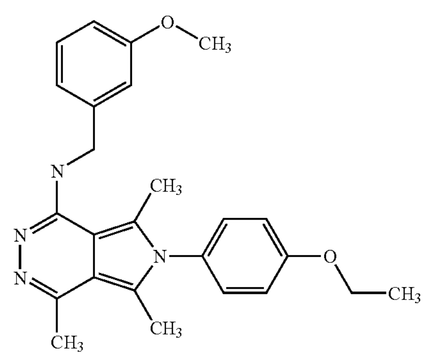 | 418 |
| Example 321 | 1-(4-cyclohexylpiperazin-1-yl)-6-(4-ethoxy-2-methoxyphenyl)-4,5,7-trimethyl-6H-pyrrolo[3,4-d]pyridazine | 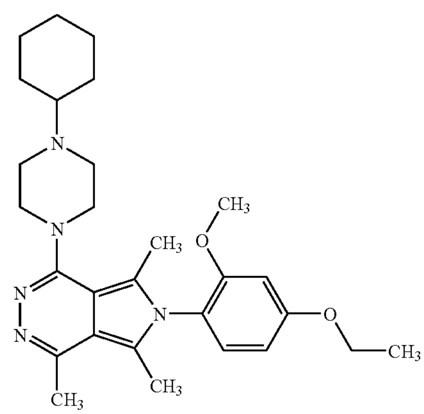 | 479 |

-continued

| Example | Name | Structure | MS (ESI) |
|---|---|---|---|
| Example 322 | 1-(4-benzylpiperazin-1-yl)-6-(4-ethoxyphenyl)-4,5,7-trimethyl-6H-pyrrolo[3,4-d]pyridazine | 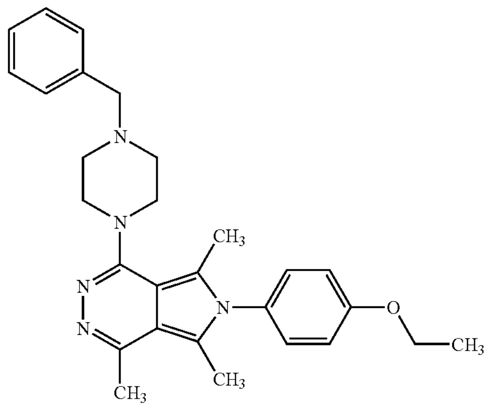 | 457 |
| Example 323 | 6-(4-ethoxyphenyl)-1,5,7-trimethyl-4-(4-phenylazepan-1-yl)-6H-pyrrolo[3,4-d]pyridazine | 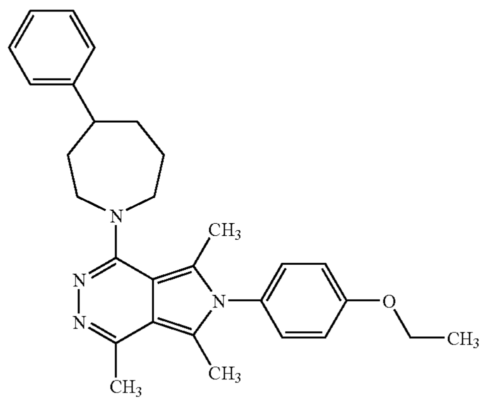 | 456 |
| Example 324 | 6-(4-ethoxyphenyl)-N-(isoquinolin-8-ylmethyl)-4,5,7-trimethyl-6H-pyrrolo[3,4-d]pyridazin-1-amine | 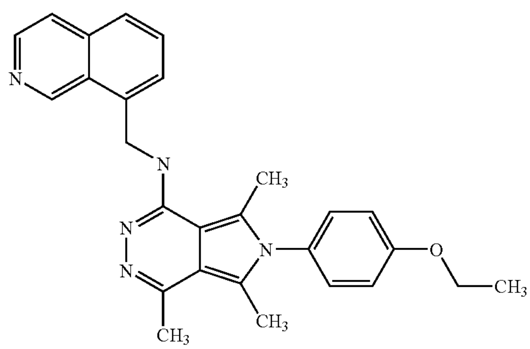 | 439 |
| Example 325 | N-(2-ethoxybenzyl)-6-(4-ethoxyphenyl)-4,5,7-trimethyl-6H-pyrrolo[3,4-d]pyridazin-1-amine | 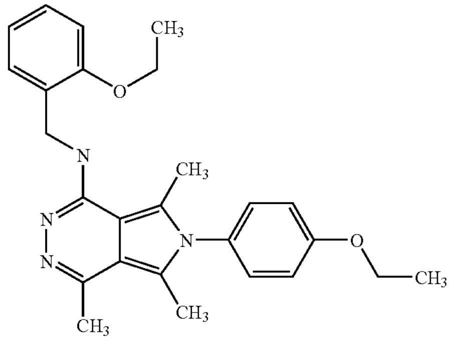 | 432 |

-continued

| Example | Name | Structure | MS (ESI) |
|---|---|---|---|
| Example 326 | N-(1,3-dimethylbutyl)-6-(4-ethoxyphenyl)-4,5,7-trimethyl-6H-pyrrolo[3,4-d]pyridazin-1-amine | 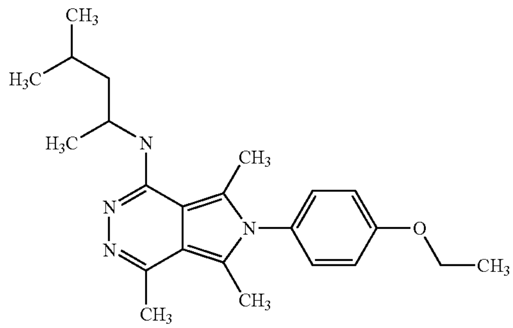 | 382 |
| Example 327 | 6-(4-ethoxyphenyl)-N-(3-fluoro-4-methylphenyl)-4,5,7-trimethyl-6H-pyrrolo[3,4-d]pyridazin-1-amine | 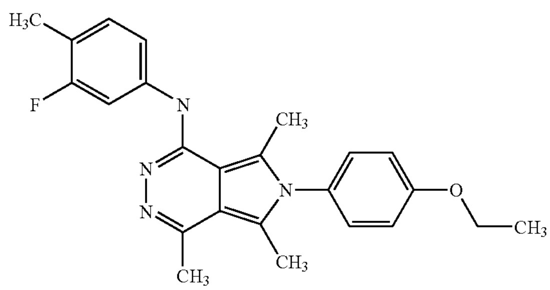 | 405 |
| Example 328 | N-[6-(4-ethoxyphenyl)-4,5,7-trimethyl-6H-pyrrolo[3,4-d]pyridazin-1-yl]-1H-1,2,3-benzotriazol-5-amine | 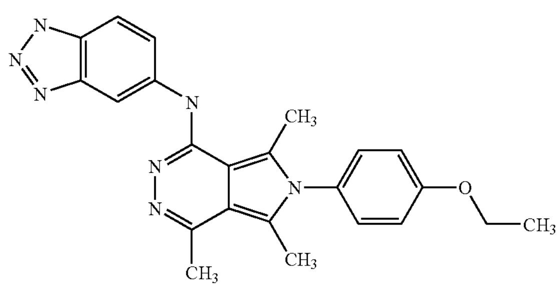 | 414 |
| Example 329 | 6-(4-ethoxyphenyl)-N-(4-methoxyphenyl)-4,5,7-trimethyl-6H-pyrrolo[3,4-d]pyridazin-1-amine | 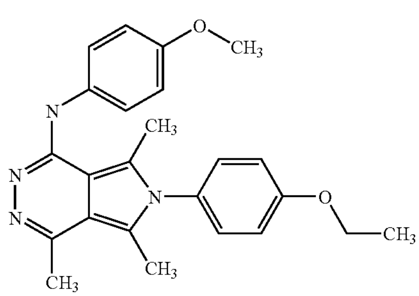 | 404 |

-continued

| Example | Name | Structure | MS (ESI) |
|---|---|---|---|
| Example 330 | N-(3,3-diphenylpropyl)-6-(4-ethoxyphenyl)-4,5,7-trimethyl-6H-pyrrolo[3,4-d]pyridazin-1-amine | 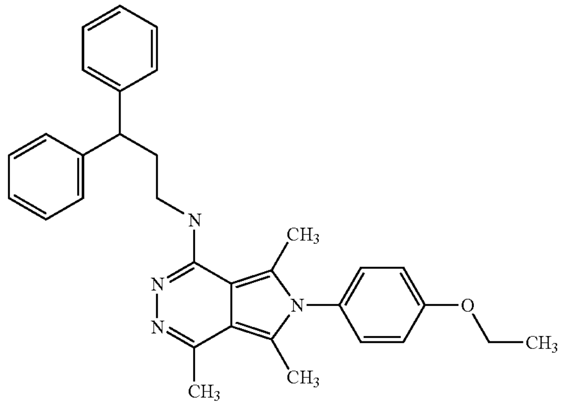 | 492 |
| Example 331 | 6-(4-ethoxyphenyl)-1,5,7-trimethyl-4-(4-methylpiperidin-1-yl)-6H-pyrrolo[3,4-d]pyridazine | 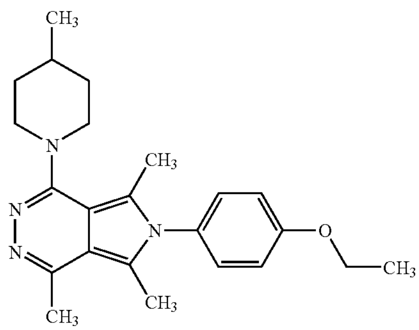 | 380 |
| Example 332 | 2-[6-(4-ethoxyphenyl)-4,5,7-trimethyl-6H-pyrrolo[3,4-d]pyridazin-1-yl]-1,2,3,4-tetrahydroisoquinoline | 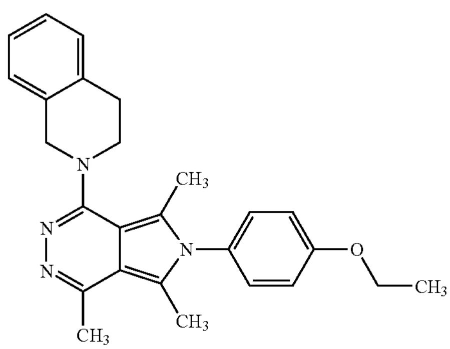 | 414 |
| Example 333 | N'-[6-(4-ethoxyphenyl)-4,5,7-trimethyl-6H-pyrrolo[3,4-d]pyridazin-1-yl]-N,N-dimethylethane-1,2-diamine | Chiral | 368 |

-continued

| Example | Name | Structure | MS (ESI) |
|---|---|---|---|
| Example 334 | 6-(4-ethoxyphenyl)-1,5,7-trimethyl-4-[(1S,5R)-1,3,3-trimethyl-6-azabicyclo[3.2.1]oct-6-yl]-6H-pyrrolo[3,4-d]pyridazine | 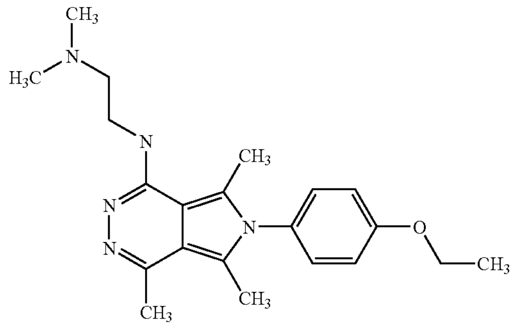 | 434 |
| Example 335 | 1'-[6-(4-ethoxyphenyl)-4,5,7-trimethyl-6H-pyrrolo[3,4-d]pyridazin-1-yl]-1,4'-bipiperidine | 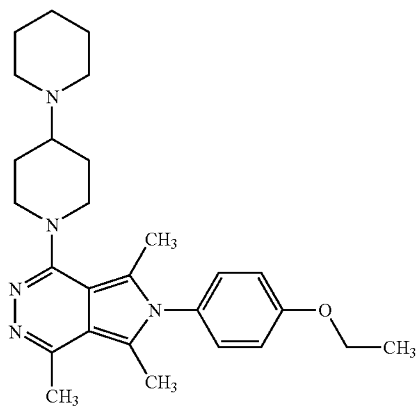 | 449 |
| Example 336 | 6-(4-ethoxyphenyl)-1,5,7-trimethyl-4-(4-phenylpiperazin-1-yl)-6H-pyrrolo[3,4-d]pyridazine | 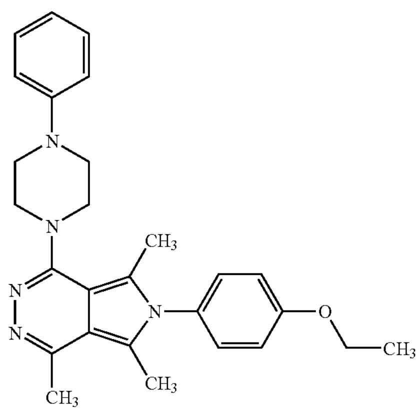 | 443 |
| Example 337 | 6-(4-ethoxyphenyl)-1,5,7-trimethyl-4-(4-pyridin-2-ylpiperazin-1-yl)-6H-pyrrolo[3,4-d]pyridazine | 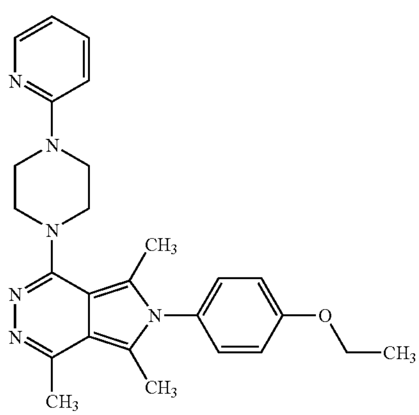 | 444 |

-continued

| Example | Name | Structure | MS (ESI) |
|---|---|---|---|
| Example 338 | 1-[4-(1,3-benzodioxol-5-ylmethyl)piperazin-1-yl]-6-(4-ethoxyphenyl)-4,5,7-trimethyl-6H-pyrrolo[3,4-d]pyridazine | 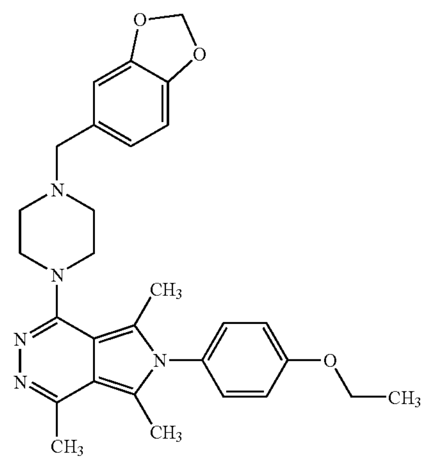 | 501 |
| Example 339 | 6-(4-ethoxyphenyl)-N-(4-isopropylphenyl)-4,5,7-trimethyl-6H-pyrrolo[3,4-d]pyridazin-1-amine | 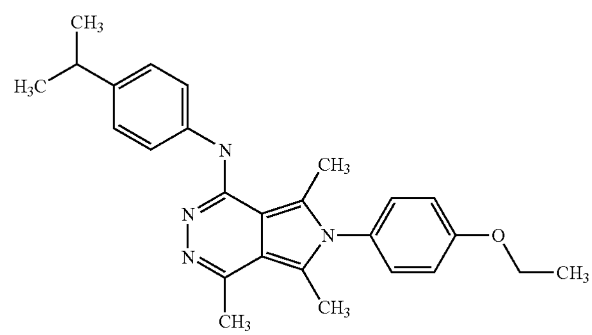 | 416 |
| Example 340 | 1-[4-(3,4-dimethylphenyl)piperazin-1-yl]-6-(4-ethoxyphenyl)-4,5,7-trimethyl-6H-pyrrolo[3,4-d]pyridazine | 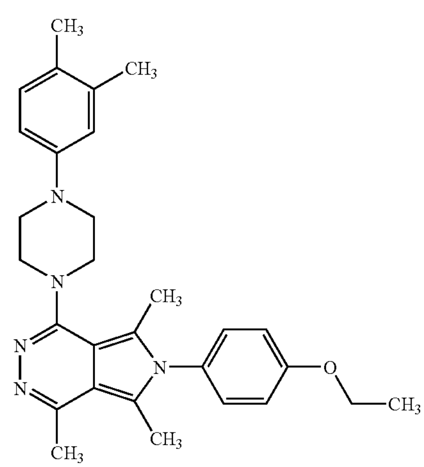 | 471 |

-continued

| Example | Name | Structure | MS (ESI) |
| --- | --- | --- | --- |
| Example 341 | 6-(4-ethoxyphenyl)-4,5,7-trimethyl-N-[3-(2-methylpiperidin-1-yl)propyl]-6H-pyrrolo[3,4-d]pyridazin-1-amine | 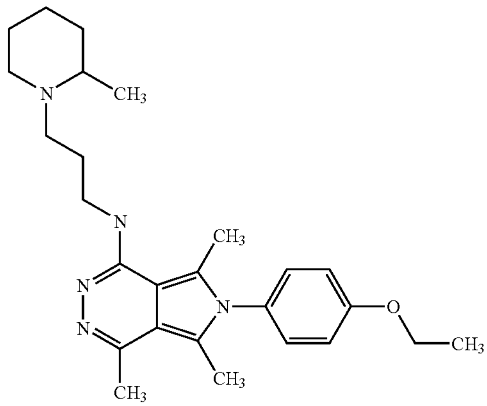 | 437 |
| Example 342 | N-(1-benzylpiperidin-4-yl)-6-(4-ethoxyphenyl)-4,5,7-trimethyl-6H-pyrrolo[3,4-d]pyridazin-1-amine | 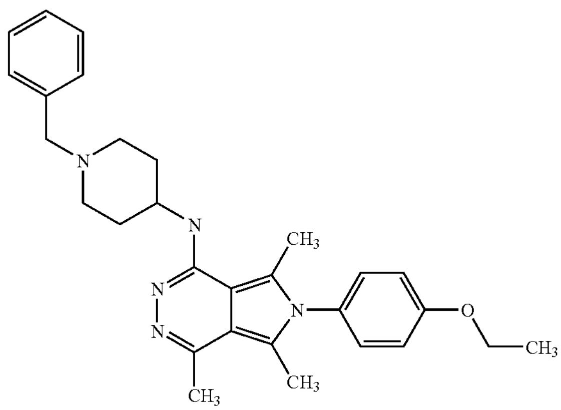 | 471 |
| Example 343 | N-(3-chloro-4-morpholin-4-ylphenyl)-6-(4-ethoxyphenyl)-4,5,7-trimethyl-6H-pyrrolo[3,4-d]pyridazin-1-amine | 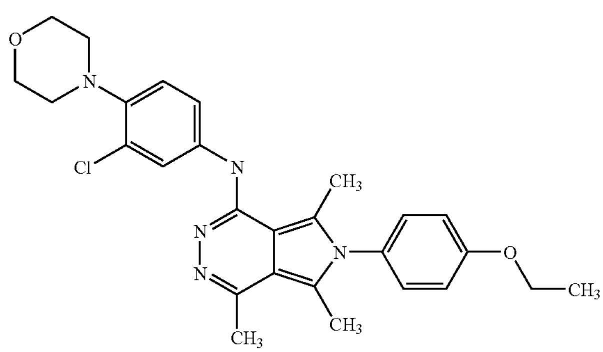 | 493 |

-continued

| Example | Name | Structure | MS (ESI) |
|---|---|---|---|
| Example 344 | 6-(4-ethoxyphenyl)-1-[4-(4-fluorophenyl)piperazin-1-yl]-4,5,7-trimethyl-6H-pyrrolo[3,4-d]pyridazine | 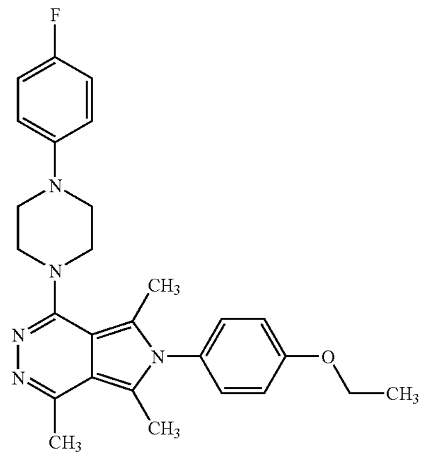 | 461 |
| Example 345 | 1-(3,5-dimethylpiperidin-1-yl)-6-(4-ethoxyphenyl)-4,5,7-trimethyl-6H-pyrrolo[3,4-d]pyridazine | 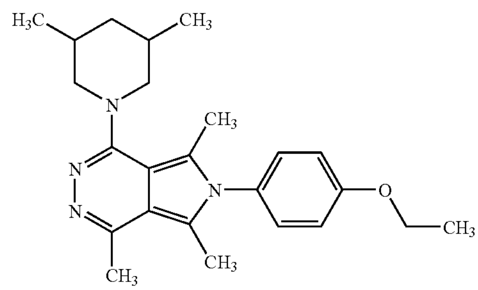 | 394 |
| Example 346 | 6-(4-ethoxyphenyl)-N-(4-methoxybenzyl)-4,5,7-trimethyl-6H-pyrrolo[3,4-d]pyridazin-1-amine | 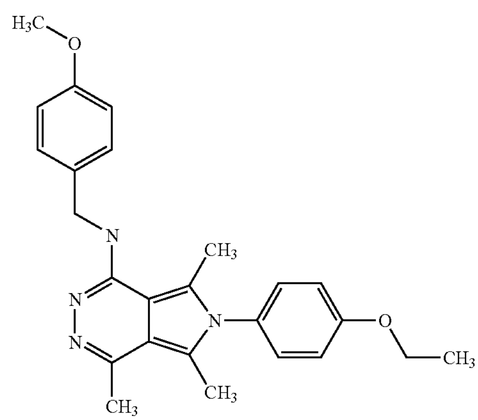 | 418 |
| Example 347 | 6-(4-ethoxyphenyl)-1-[4-(2-methoxyphenyl)piperazin-1-yl]-4,5,7-trimethyl-6H-pyrrolo[3,4-d]pyridazine | 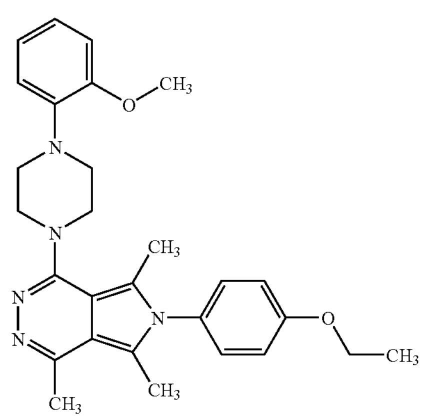 | 473 |

-continued

| Example | Name | Structure | MS (ESI) |
| --- | --- | --- | --- |
| Example 348 | N'-[6-(4-ethoxyphenyl)-4,5,7-trimethyl-6H-pyrrolo[3,4-d]pyridazin-1-yl]-N,N-diethylpropane-1,3-diamine | 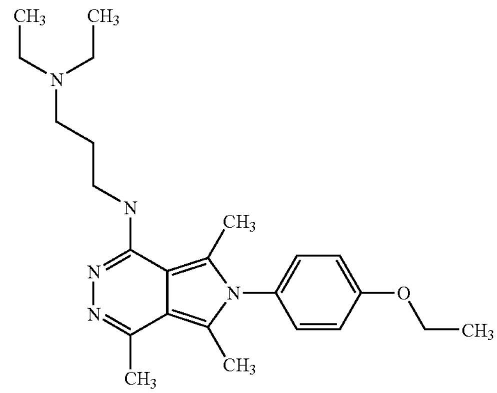 | 411 |
| Example 349 | 6-(4-ethoxyphenyl)-1-[4-(2-fluorophenyl)piperazin-1-yl]-4,5,7-trimethyl-6H-pyrrolo[3,4-d]pyridazine | 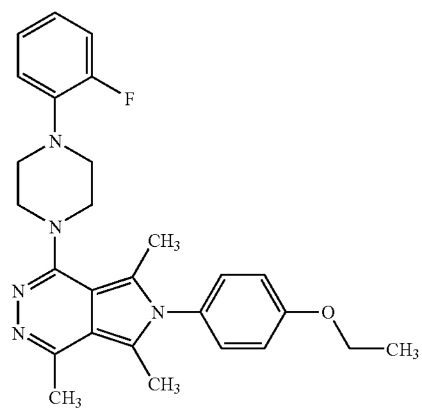 | 461 |
| Example 350 | N-benzyl-6-(4-ethoxyphenyl)-N,4,5,7-tetramethyl-6H-pyrrolo[3,4-d]pyridazin-1-amine | 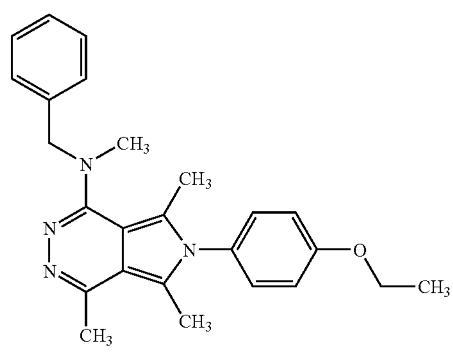 | 402 |

-continued

| Example | Name | Structure | MS (ESI) |
|---|---|---|---|
| Example 351 | 1-{4-[2-(4-chlorophenyl)ethyl]piperidin-1-yl]-6-(4-ethoxyphenyl)-4,5,7-trimethyl-6H-pyrrolo[3,4-d]pyridazine | 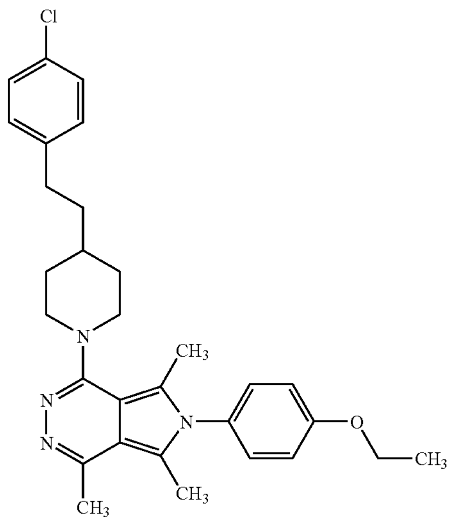 | 504 |
| Example 352 | N~4~-[6-(4-ethoxyphenyl)-4,5,7-trimethyl-6H-pyrrolo[3,4-d]pyridazin-1-yl]-N~1~,N~1~-diethylpentane-1,4-diamine | 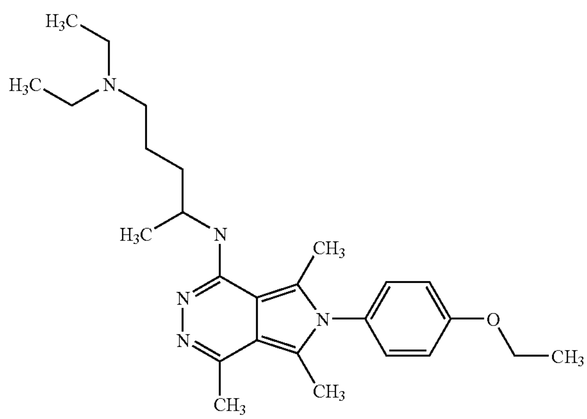 | 439 |
| Example 353 | 6-(4-ethoxyphenyl)-4,5,7-trimethyl-N-[4-(trifluoromethyl)benzyl]-6H-pyrrolo[3,4-d]pyridazin-1-amine | 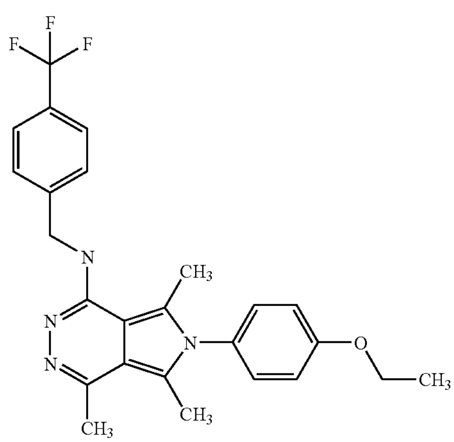 | 455 |

-continued

| Example | Name | Structure | MS (ESI) |
|---|---|---|---|
| Example 354 | 1-[6-(4-ethoxyphenyl)-4,5,7-trimethyl-6H-pyrrolo[3,4-d]pyridazin-1-yl]-4-[3-(trifluoromethyl)phenyl]piperidin-4-ol | 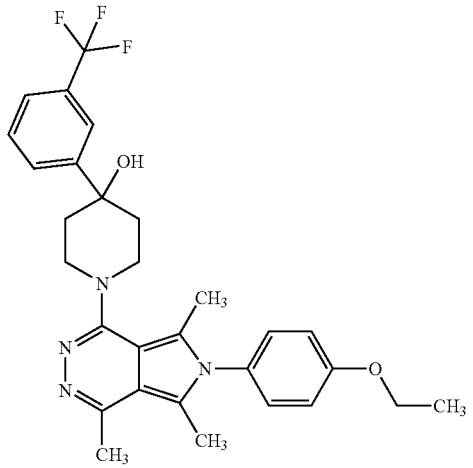 | 526 |
| Example 355 | N-[3,5-bis(trifluoromethyl)benzyl]-6-(4-ethoxyphenyl)-4,5,7-trimethyl-6H-pyrrolo[3,4-d]pyridazin-1-amine | 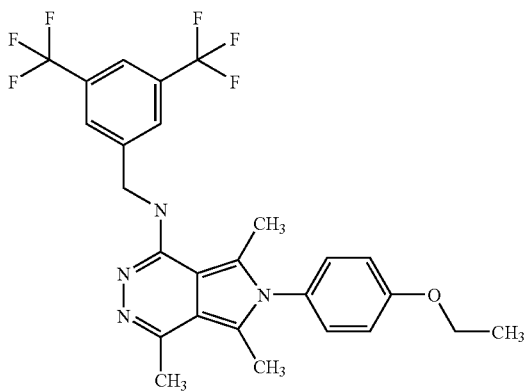 | 523 |
| Example 356 | 6-(4-ethoxyphenyl)-4,5,7-trimethyl-N-[2-(1-methylpyrrolidin-2-yl)ethyl]-6H-pyrrolo[3,4-d]pyridazin-1-amine | 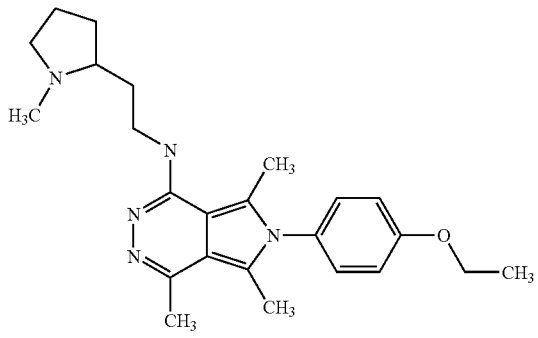 | 409 |
| Example 357 | 6-(4-ethoxyphenyl)-1,5,7-trimethyl-4-morpholin-4-yl-6H-pyrrolo[3,4-d]pyridazine | 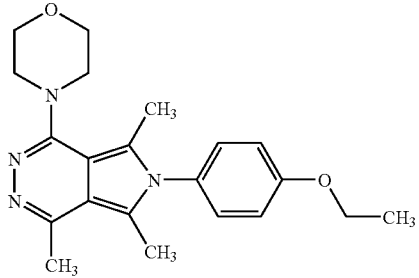 | 367 |

-continued

| Example | Name | Structure | MS (ESI) |
|---|---|---|---|
| Example 358 | 6-(4-ethoxyphenyl)-1-[4-(2-furoyl)piperazin-1-yl]-4,5,7-trimethyl-6H-pyrrolo[3,4-d]pyridazine | 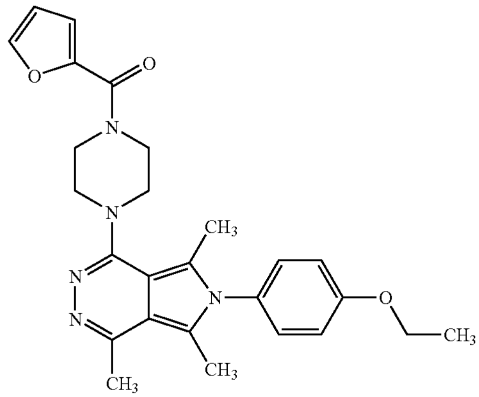 | 461 |
| Example 359 | 4-[6-(4-ethoxyphenyl)-4,5,7-trimethyl-6H-pyrrolo[3,4-d]pyridazin-1-yl]piperazine-1-carbaldehyde | 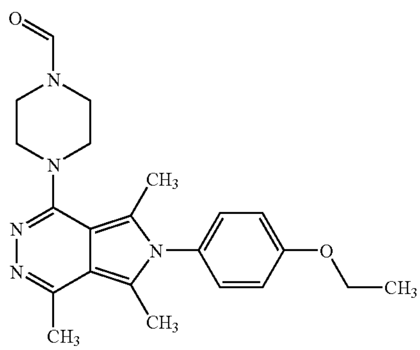 | 394 |
| Example 360 | 6-(4-ethoxyphenyl)-1,5,7-trimethyl-4-(4-methylpiperazin-1-yl)-6H-pyrrolo[3,4-d]pyridazine | 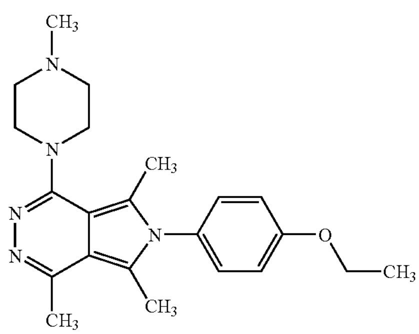 | 381 |
| Example 361 | 1-[(2R,6S)-2,6-dimethylmorpholin-4-yl]-6-(4-ethoxyphenyl)-4,5,7-trimethyl-6H-pyrrolo[3,4-d]pyridazine | 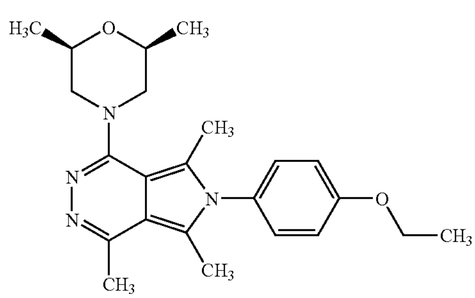 | 396 |

-continued

| Example | Name | Structure | MS (ESI) |
|---|---|---|---|
| Example 362 | 6-(4-ethoxyphenyl)-4,5,7-trimethyl-N-(pyridin-2-ylmethyl)-6H-pyrrolo[3,4-d]pyridazin-1-amine | 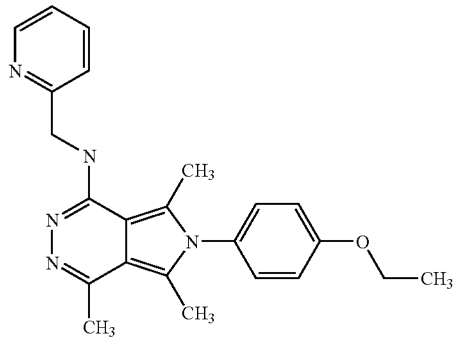 | 388 |
| Example 363 | 6-(4-ethoxyphenyl)-4,5,7-trimethyl-N-(2-pyrrolidin-1-ylethyl)-6H-pyrrolo[3,4-d]pyridazin-1-amine | 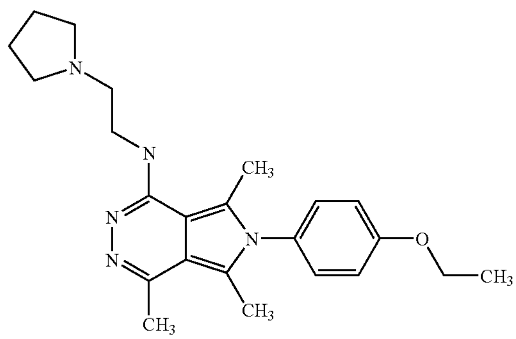 | 395 |
| Example 364 | 1-[6-(4-ethoxyphenyl)-4,5,7-trimethyl-6H-pyrrolo[3,4-d]pyridazin-1-yl]-N,N-diethylpiperidine-3-carboxamide | 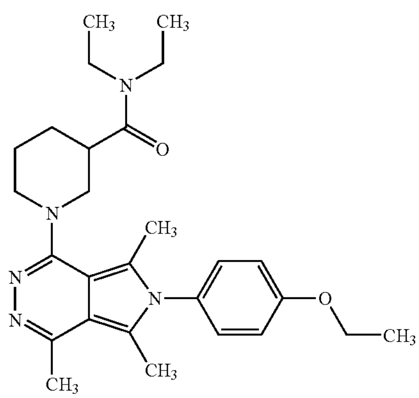 | 465 |
| Example 365 | N-[6-(4-ethoxyphenyl)-4,5,7-trimethyl-6H-pyrrolo[3,4-d]pyridazin-1-yl]-N-ethyl-N',N'-dimethylethane-1,2-diamine | 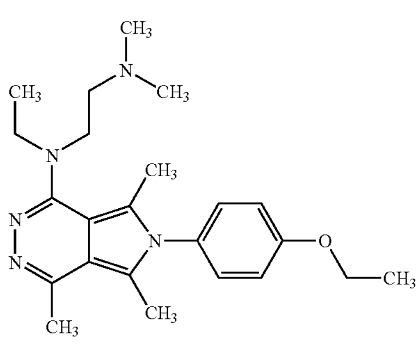 | 397 |

| Example | Name | Structure | MS (ESI) |
|---|---|---|---|
| Example 366 | 6-(4-ethoxyphenyl)-1,5,7-trimethyl-4-(4-methylpiperazin-1-yl)-6H-pyrrolo[3,4-d]pyridazine | 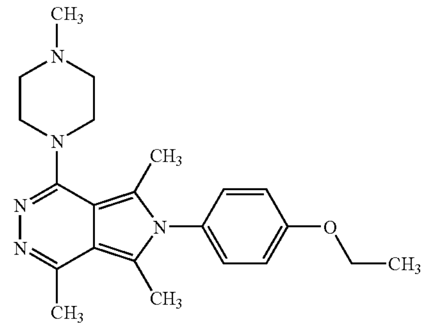 | 381 |
| Example 367 | 6-(4-ethoxy-2-methoxyphenyl)-4,5,7-trimethyl-6H-pyrrolo[3,4-d]pyridazin-1-amine | 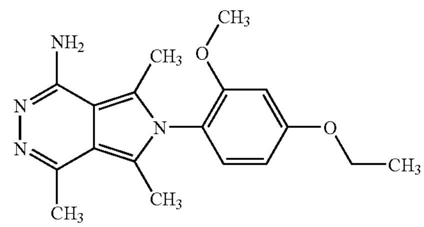 | 327 |

EXAMPLE 368

6-(4-ethoxyphenyl)-1-hydrazino-4,5,7-trimethyl-6H-pyrrolo[3,4-d]pyridazine

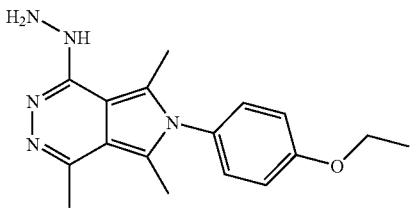

Utilizing the general procedure outlined in EXAMPLE 85, 1-chloro-6-(4-ethoxyphenyl)-4,5,7-trimethyl-6H-pyrrolo[3,4-d]pyridazine and hydrazine (0.10 mL, 0.32 mmol) reacted to give 6-(4-ethoxyphenyl)-1-hydrazino-4,5,7-trimethyl-6H-pyrrolo[3,4-d]pyridazine: $^1$H NMR (CDCl$_3$, 500 MHz) δ 7.03-7.11 (m, 4H), 4.12 (q, 2H), 2.43 (s, 3H), 2.36 (s, 3H), 2.28 (s, 3H), 1.69 (s, 2H), 1.50 (t, 3H); MS (ESI) 312 (M+H)$^+$.

EXAMPLE 369

6-(4-ethoxyphenyl)-1-methoxy-4,5,7-trimethyl-6H-pyrrolo[3,4-d]pyridazine

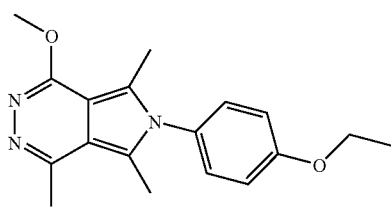

A solution of 1-chloro-6-(4-ethoxyphenyl)-4,5,7-trimethyl-6H-pyrrolo[3,4-d]pyridazine (EXAMPLE 85) (100 mg, 0.32 mmol) and MeOH (5 mL) was treated with a solution of NaOMe (freshly prepared from MeOH (5 mL) and sodium metal (22 mg, 0.96 mmol)). The resulting mixture was placed in a resealable reaction vessel and heated at 100° C. for 12 h. The reaction was allowed to cool to rt, and poured into ice water (100 mL) to give 6-(4-ethoxyphenyl)-1-methoxy-4,5,7-trimethyl-6H-pyrrolo[3,4-d]pyridazine: $^1$H NMR (CDCl$_3$, 500 MHz) δ 7.11-7.25 (m, 4H), 4.16 (q, 2H), 2.71 (s, 3H), 2.40 (s, 3H), 2.38 (s, 3H), 1.43-1.46 (t, 3H); MS (ESI) 312 (M+H)$^+$.

EXAMPLE 370

6-(4-ethoxyphenyl)-2,4,5,7-tetramethyl-2,6-dihydro-1H-pyrrolo[3,4-d]pyridazin-1-one

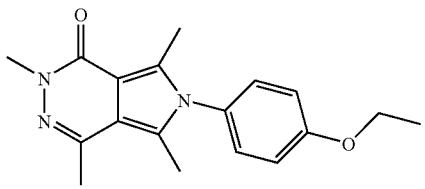

A solution of ethyl-4-acetyl-1-(4-ethoxyphenyl)-2,5-dimethyl-1H-pyrrole-3-carboxylate (prepared as in EXAMPLE 85) (70 mg, 0.20 mmol) and MeOH (5 mL) in a resealable reaction vessel was mixed with methylhydrazine (0.032 mL, 0.60 mmol) and AcOH (~3 drops). The vessel was sealed and heated at 70° C. for 12 h. The resulting slurry was allowed to cool to rt and poured into ice water (50 mL). The resulting white solid was filtered and dried under vacuum for 8 h to give 6-(4-ethoxyphenyl)-2,4,5,7-tetramethyl-2,6-dihydro-1H-pyrrolo[3,4-d]pyridazin-1-one: $^1$H NMR (CDCl$_3$, 500 MHz) δ 7.00-7.26 (m, 4H), 4.10 (q, 2H), 3.71 (s, 3H), 2.49 (s, 3H), 2.45 (s, 3H), 2.30 (s, 3H), 1.48 (t, 3H); MS (ESI) 312 (M+H)$^+$.

EXAMPLE 371

6-(4-ethoxyphenyl)-5-phenyl-1,4,7-trimethyl-6H-pyrrolo[3,4-d]pyridazine

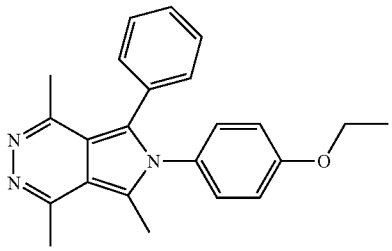

To a solution of 1-phenyl-1,4-pentanedione (1.06g, 6.0 mmol) and toluene (50 mL) was added p-phenetidine (0.78 mL, 6.0 mmol) and 5 drops of glacial acetic acid. The mixture was heated at reflux overnight. After cooling to rt, the mixture was concentrated in vacuo and purified by flash chromatography on silica gel (15-25% EtOAc/hexanes) to give 1-(p-ethoxyphenyl)-5-methyl-2-phenyl-pyrrole as a yellow solid: $^1$H NMR (CDCl$_3$, 500 MHz) δ 7.17-7.13 (m, 2H), 7.10-7.05 (m, 5H), 6.89-6.84 (m, 2H), 6.35 (d, 1H), 6.08 (d, 1H), 4.04 (q, 2H), 2.13 (s, 3H), 1.44 (t, 3H); MS (ESI) 278 (M+H)$^+$.

Acetyl chloride (0.36 mL, 5.0 mmol) and SnCl$_4$ (5.0 mL of a 1.0 M solution in CH$_2$Cl$_2$, 5.0 mmol) were added dropwise to a stirring solution of 1-(p-ethoxyphenyl)-5-methyl-2-phenyl-pyrrole (554 mg, 2.0 mmol) and toluene (10 mL) at 0° C. The mixture was warmed to rt and then heated at 50° C. overnight. Following cooling to rt, the mixture was diluted with 1N NaOH (50 mL), extracted with EtOAc (100 mL), the organic layer washed with brine, dried (MgSO$_4$), filtered, concentrated in vacuo, and purified by flash chromatography on silica gel (0-30% EtOAc/hexanes). The resulting diacetylpyrrole was dissolved in EtOH (10 mL) and hydrazine (0.5 mL) and the mixture was heated at 50° C. for 2h. The mixture was cooled to rt and poured into ice water (50 mL). The resulting solid was filtered to give 6-(4-ethoxyphenyl)-5-phenyl-1,4,7-trimethyl-6H-pyrrolo[3,4-d]pyridazine as a white solid: $^1$H NMR (CDCl$_3$, 500 MHz) δ 7.26-7.23 (m, 3H), 7.16-7.13 (m, 2H), 7.00-6.97 (m, 2H), 6.84-6.81 (m, 2H), 3.99 (q, 2H), 2.87 (s, 3H), 2.53 (s, 3H), 2.27 (s, 3H), 1.40 (t, 3H); MS (M+H)$^+$ 358.58.

Other variations or modifications, which will be obvious to those skilled in the art, are within the scope and teachings of this invention. This invention is not to be limited except as set forth in the following claims.

What is claimed is:

1. A method of binding the α$_2$δ subunit of voltage gated calcium channels comprising a step of administering to a patient in need thereof an effective amount of a compound represented by Formula (I) selected from:

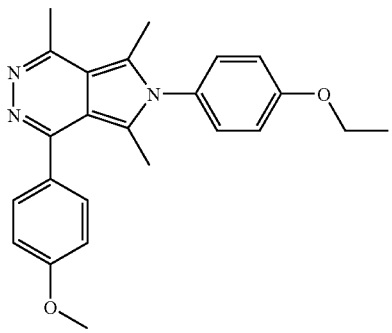

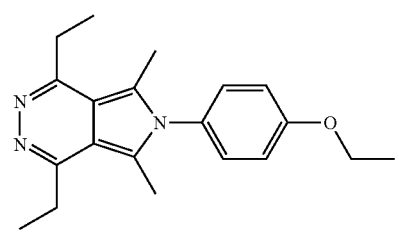

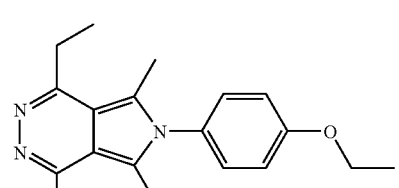

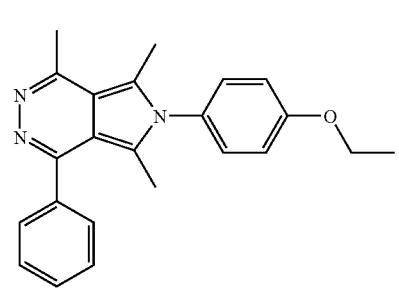

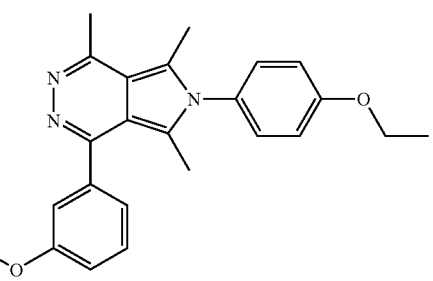

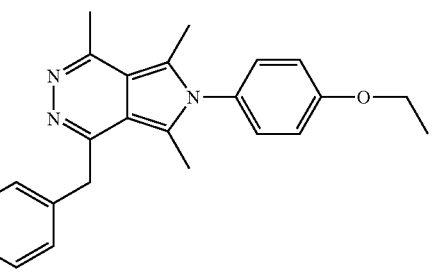

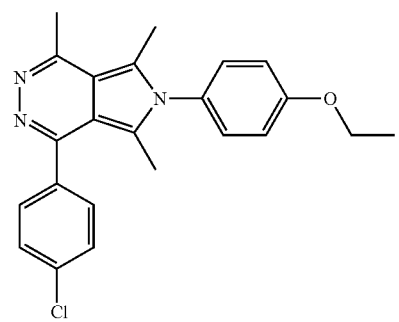

225
-continued
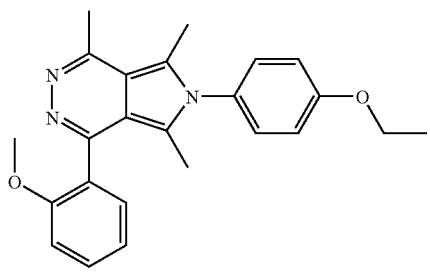
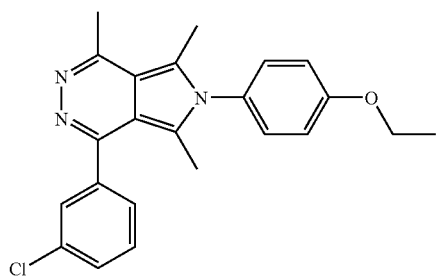
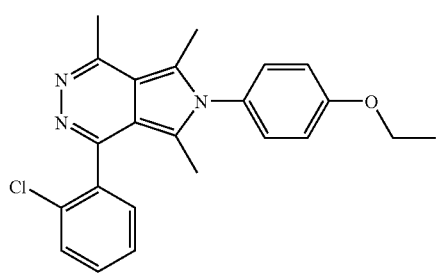
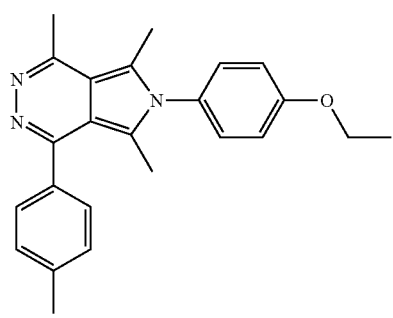
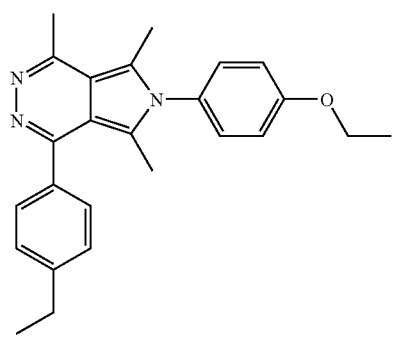
226
-continued
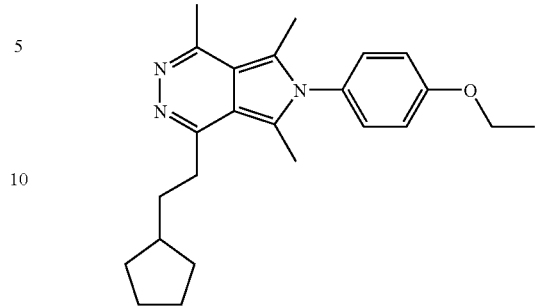
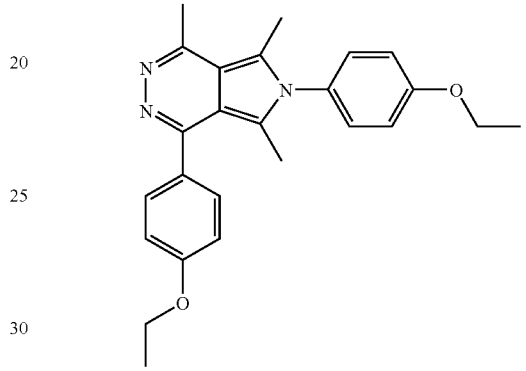
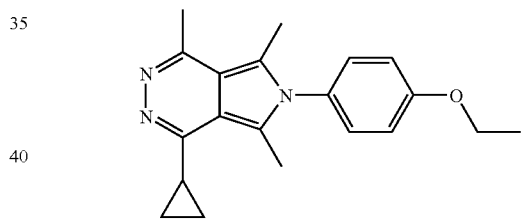
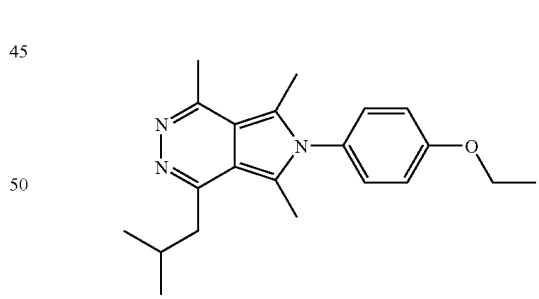
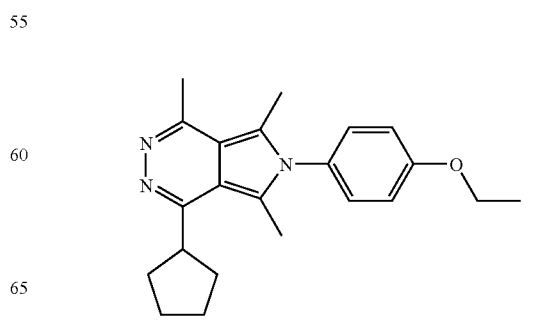

227
-continued
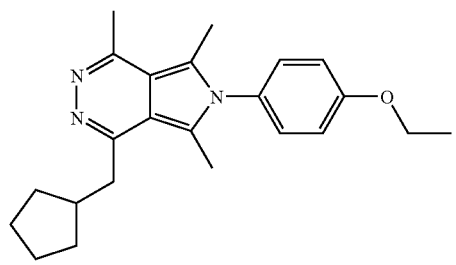
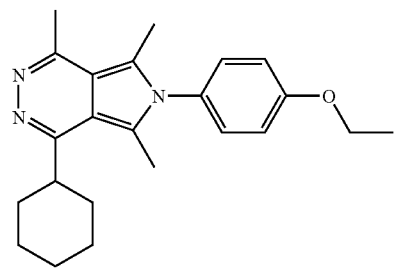
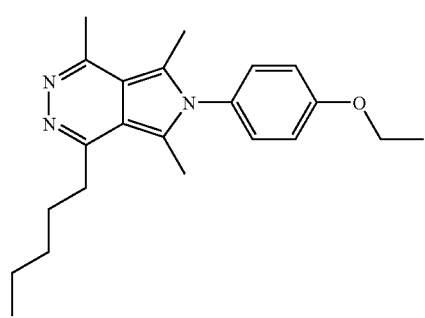
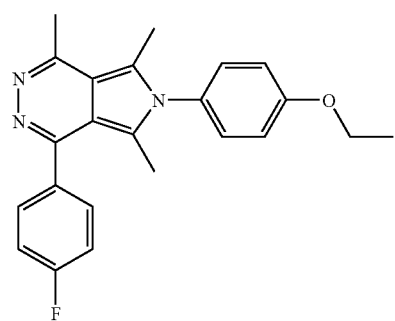
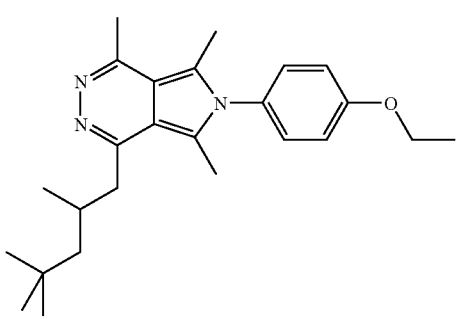
228
-continued
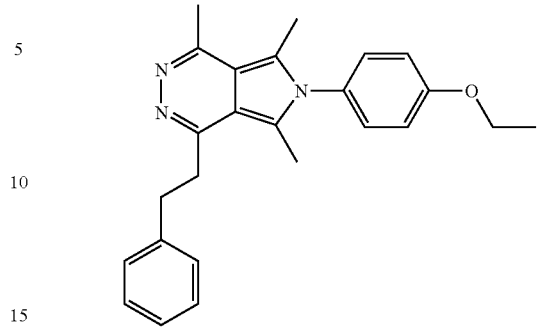
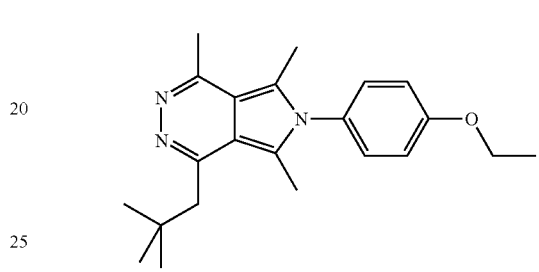
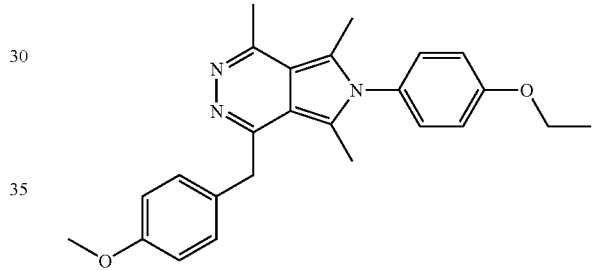
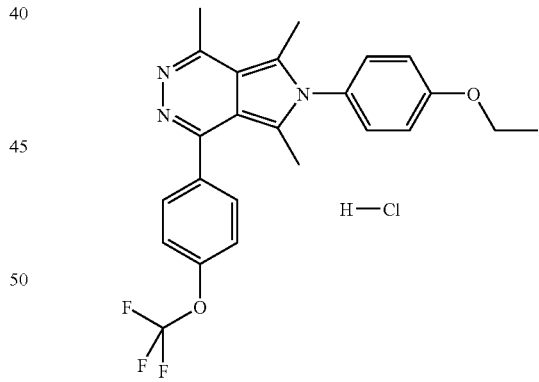
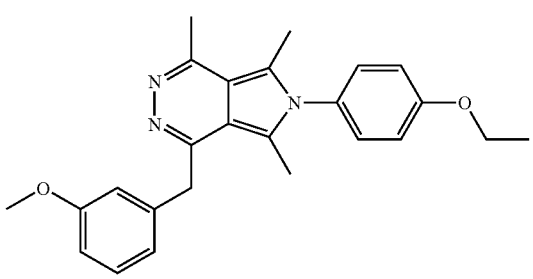

229
-continued
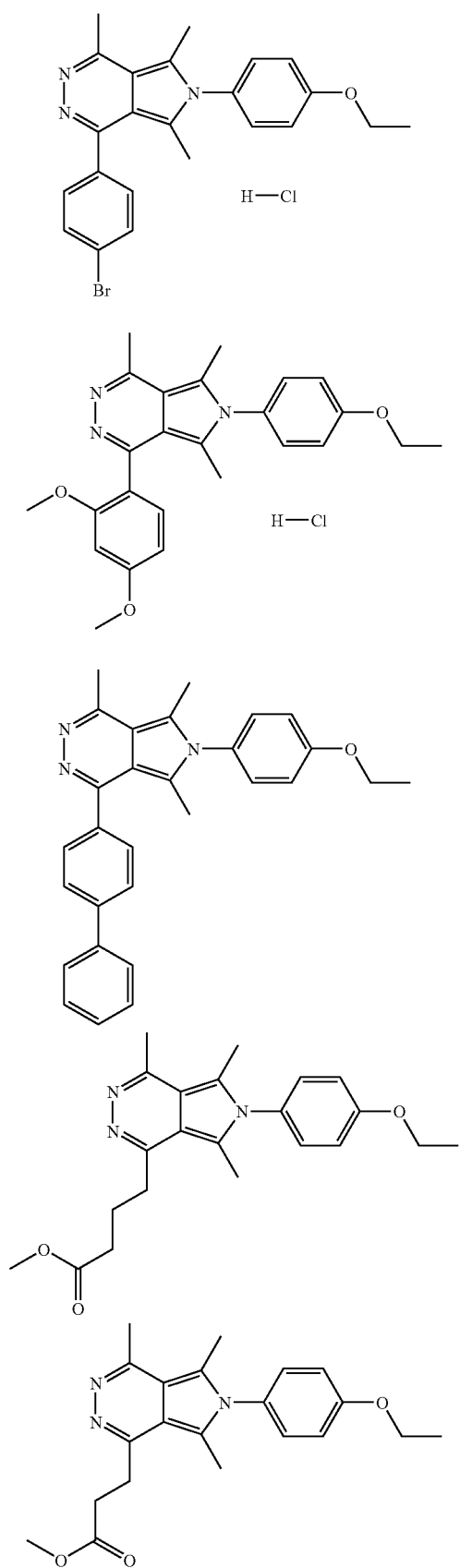
230
-continued
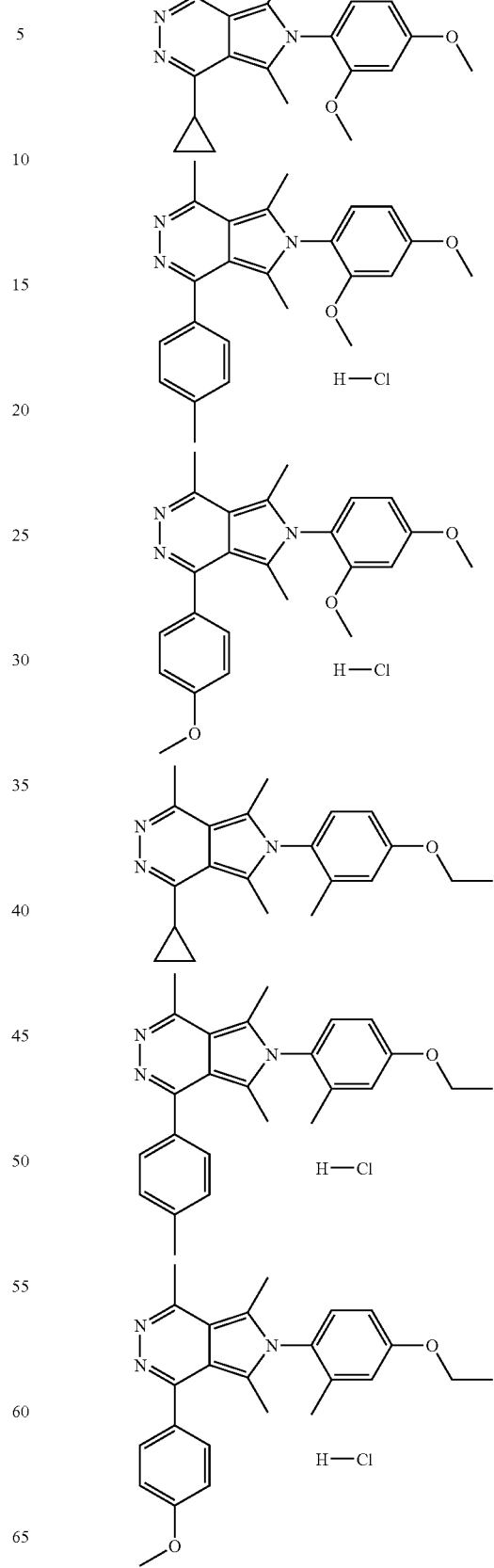

231
-continued
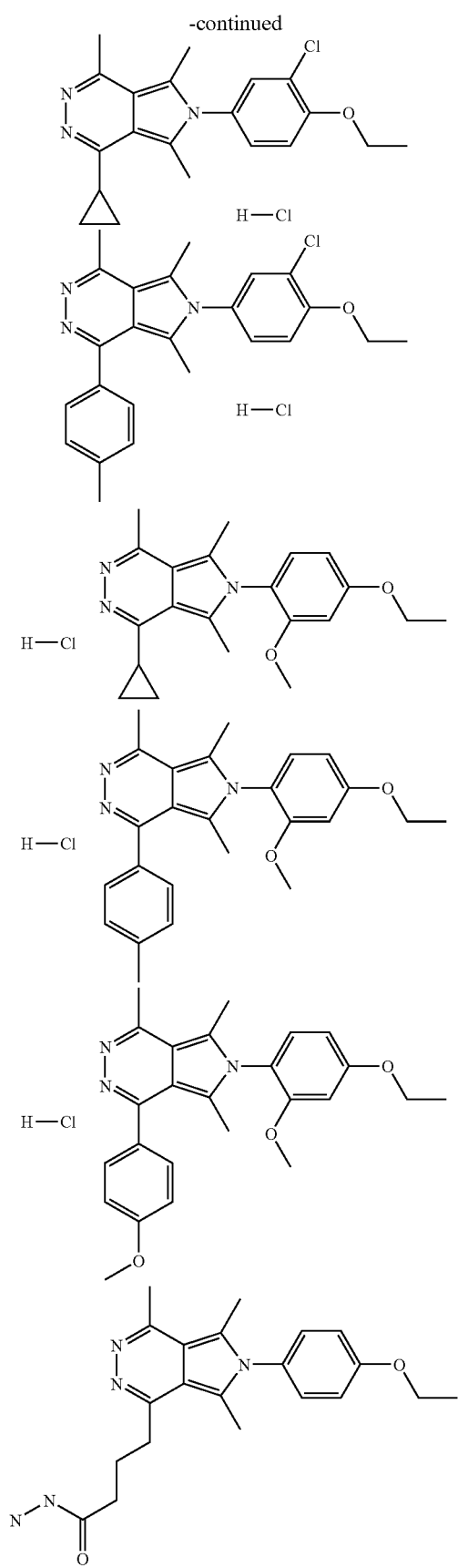
232
-continued
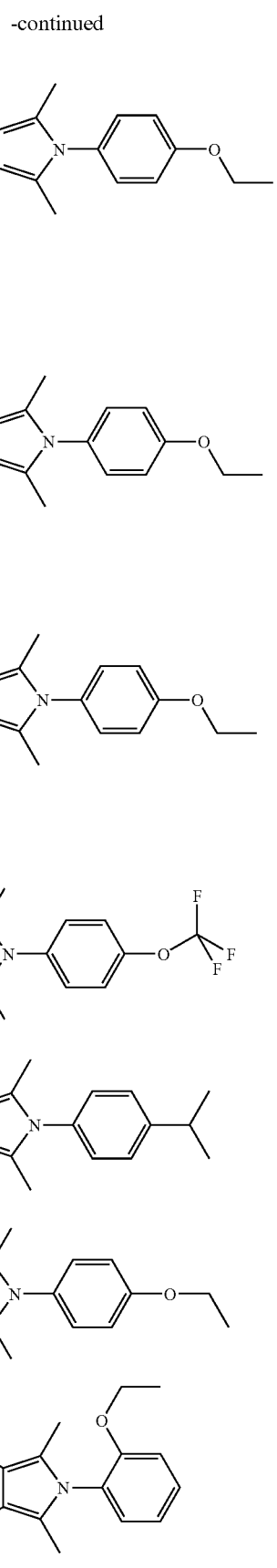

233
-continued
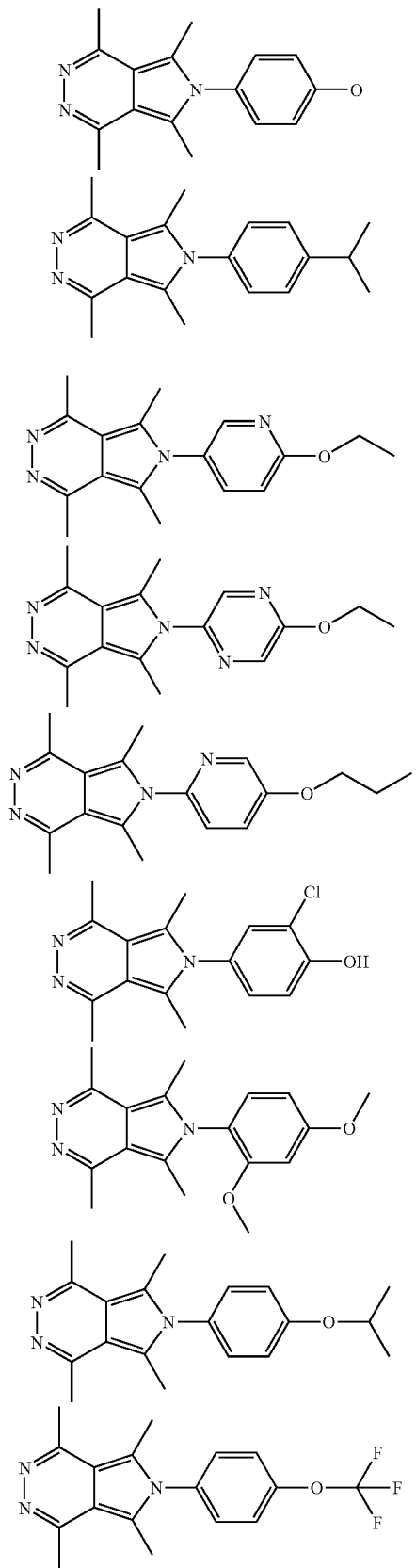
234
-continued
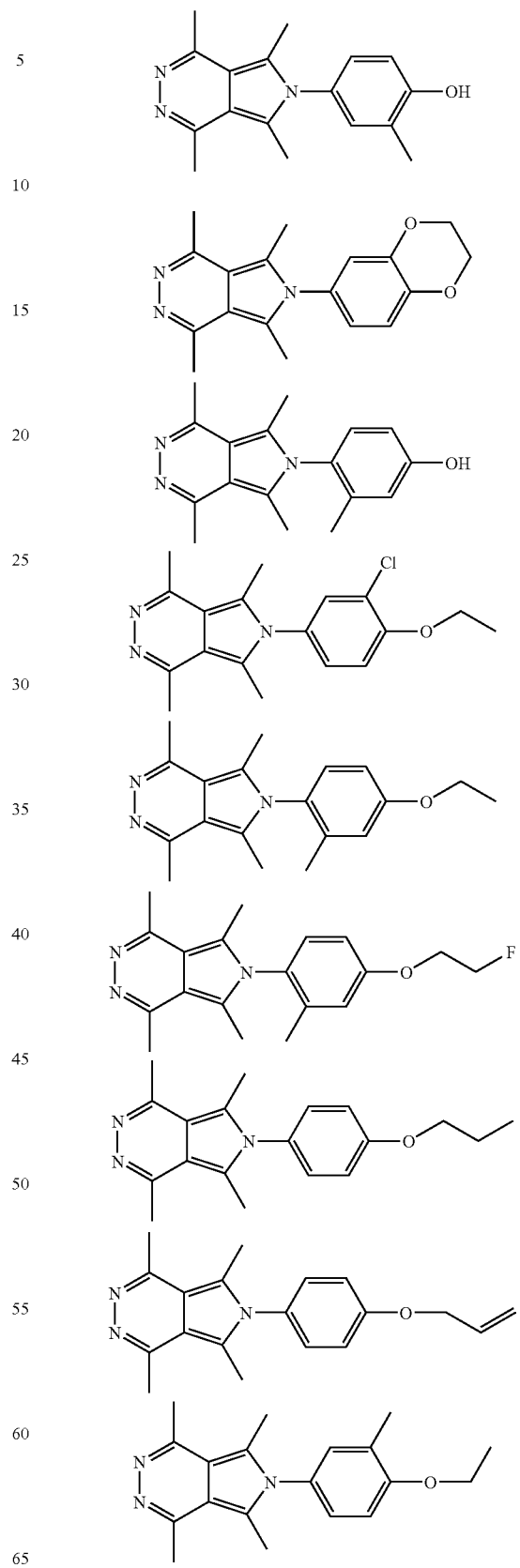

235
-continued
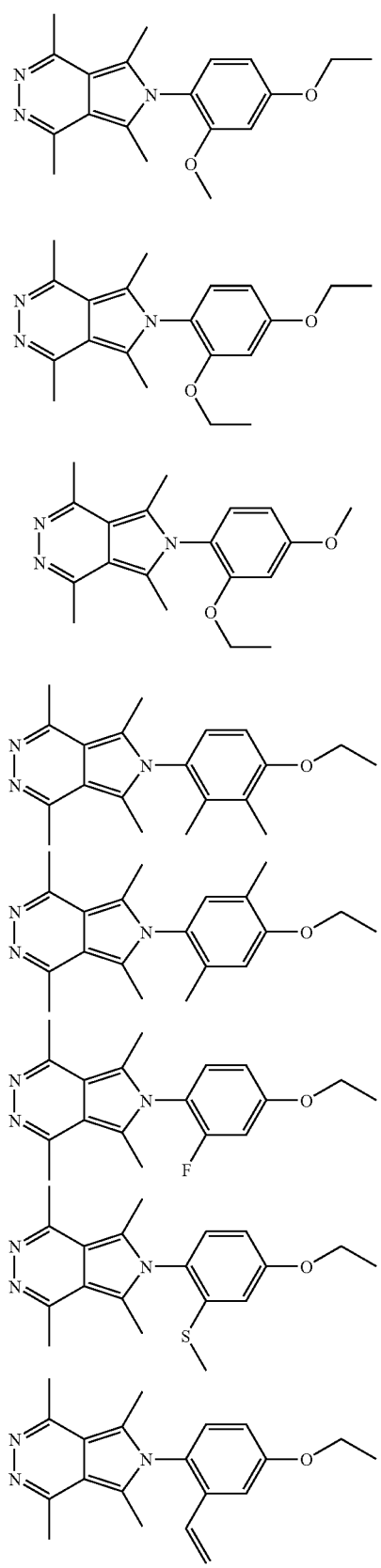
236
-continued
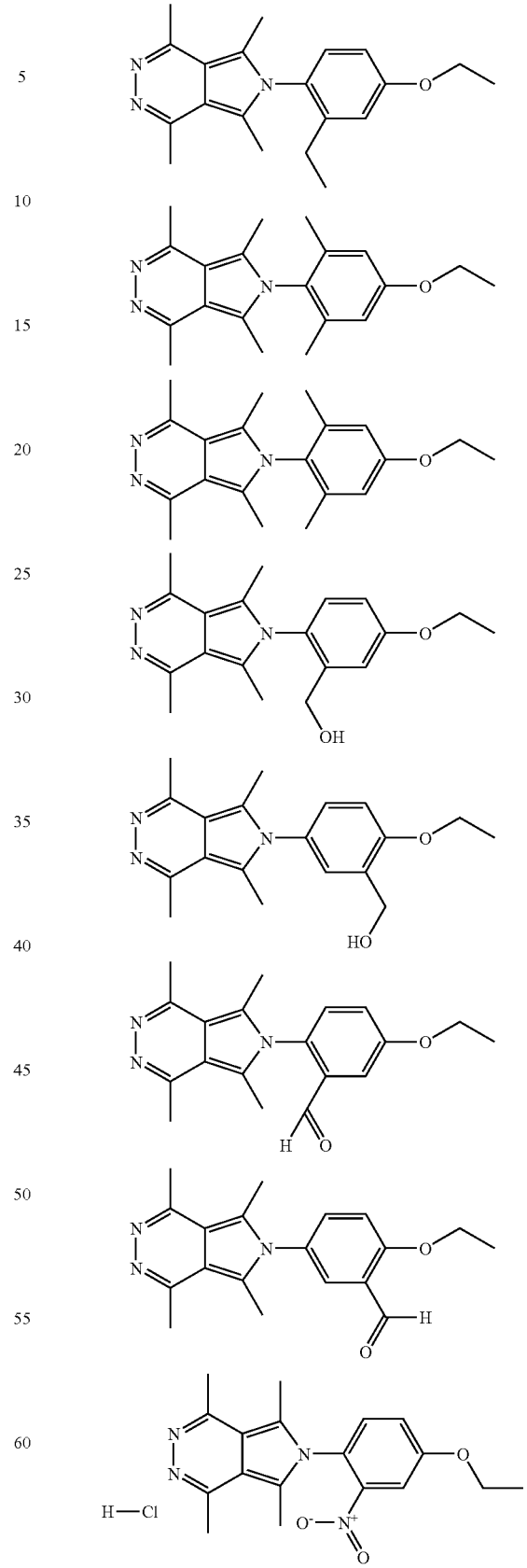

237
-continued
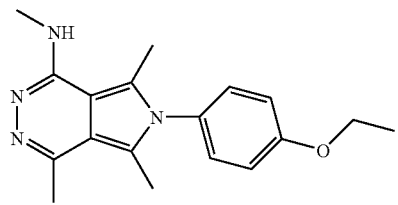
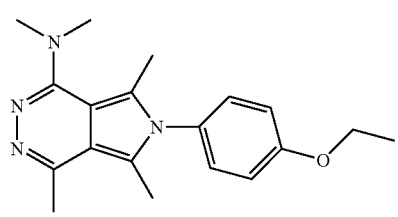
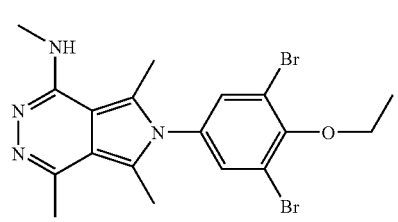
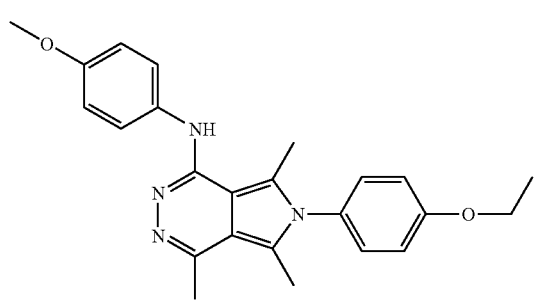
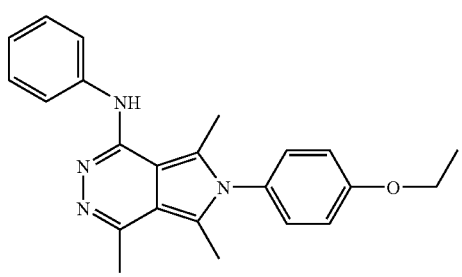
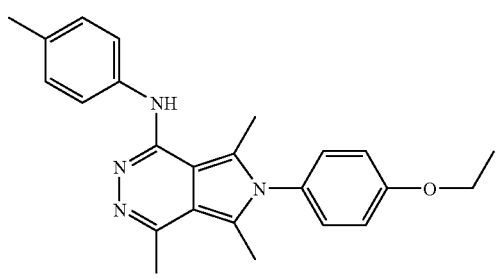
238
-continued
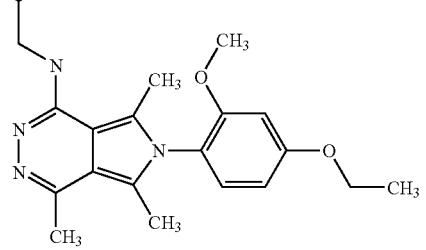
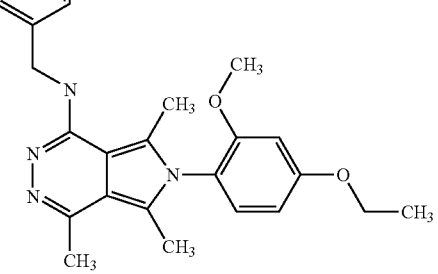
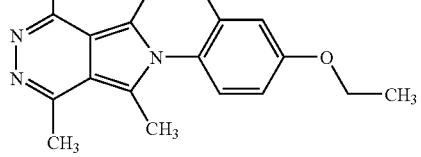
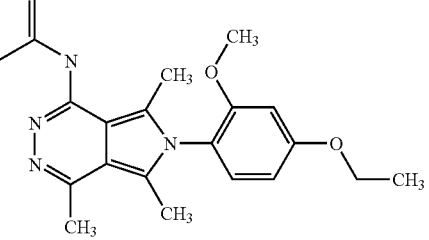

239
-continued
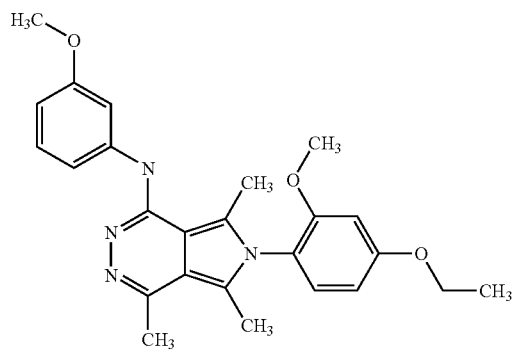
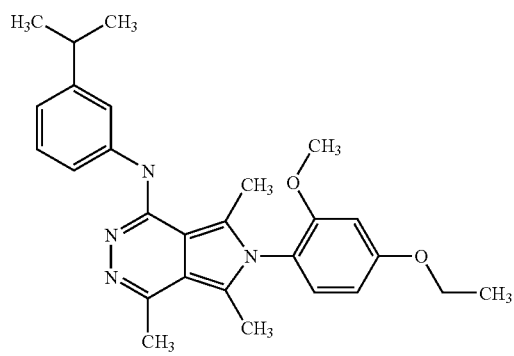
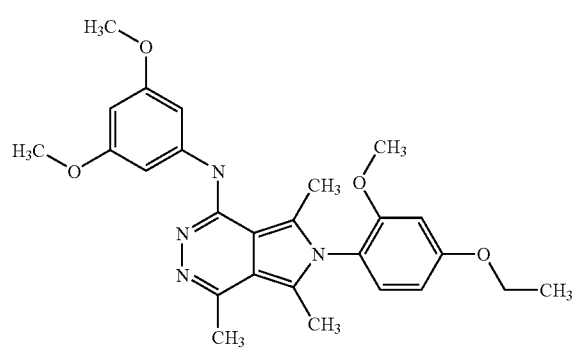
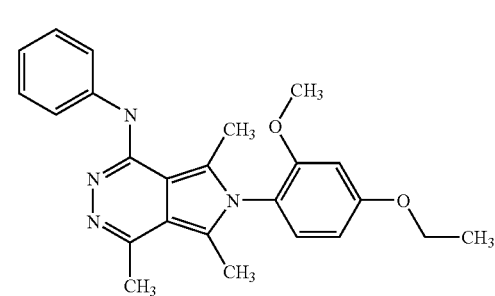
240
-continued
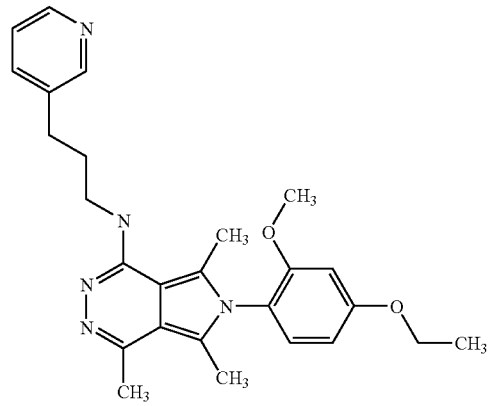
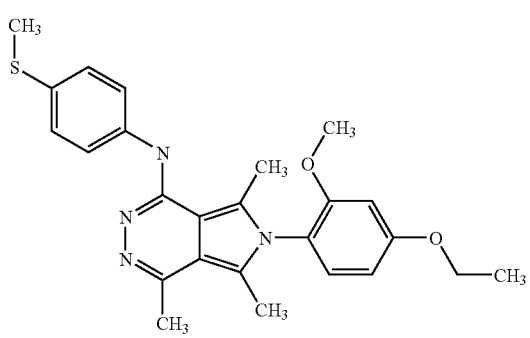

241
-continued
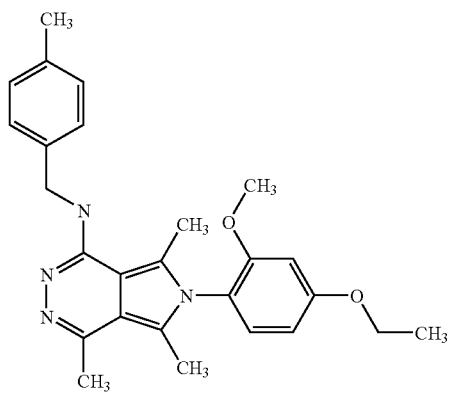
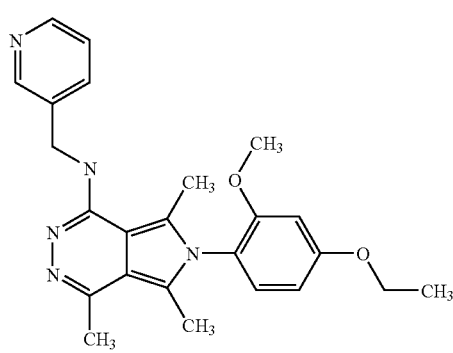
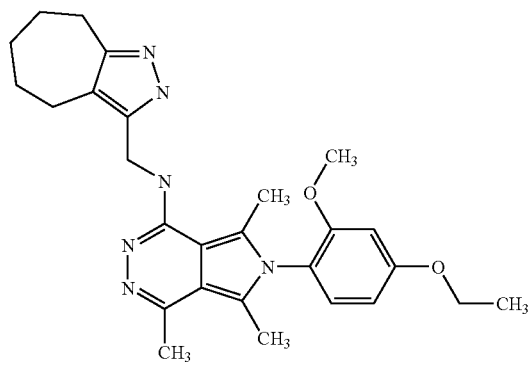
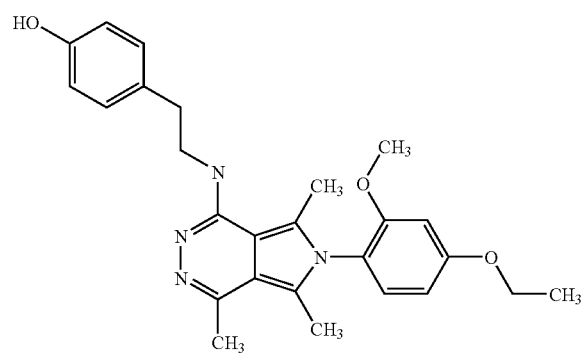
242
-continued
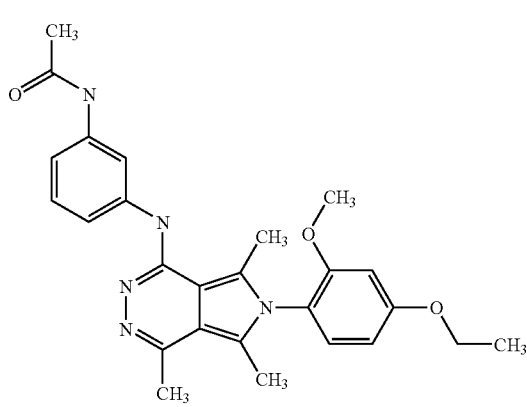
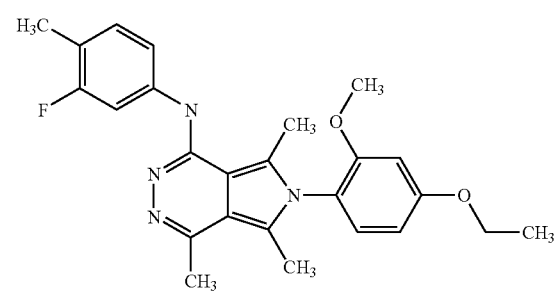
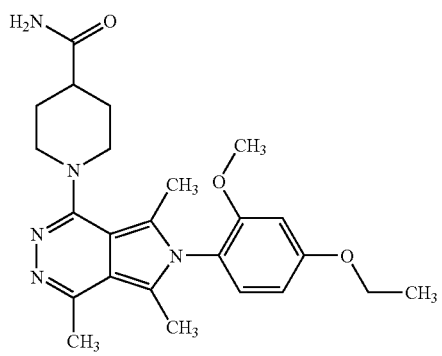
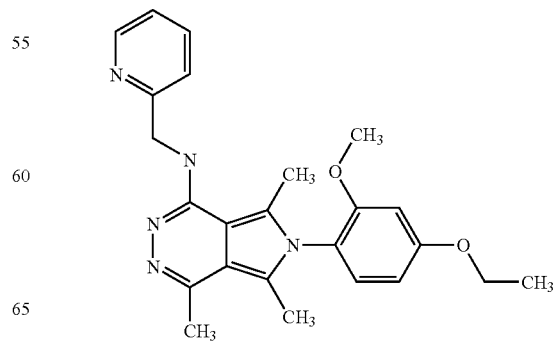

243
-continued
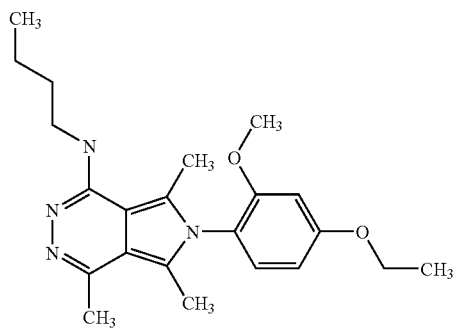
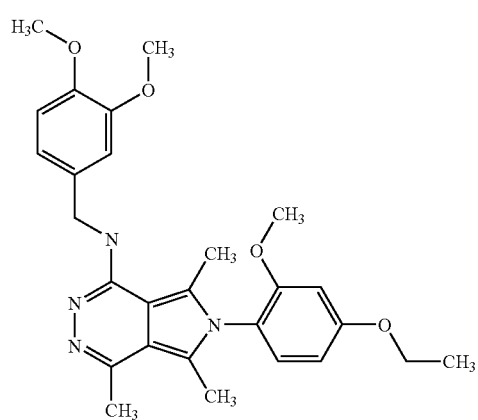
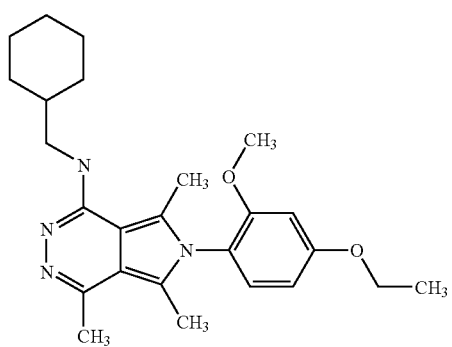
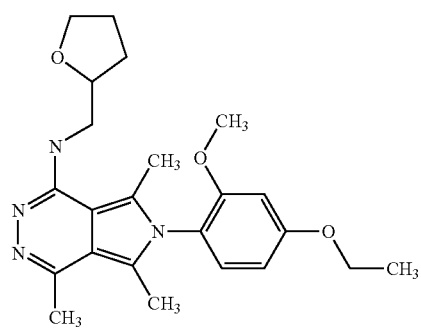
244
-continued
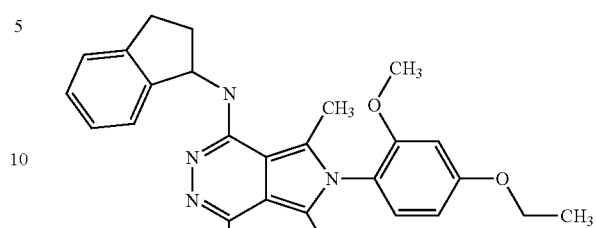
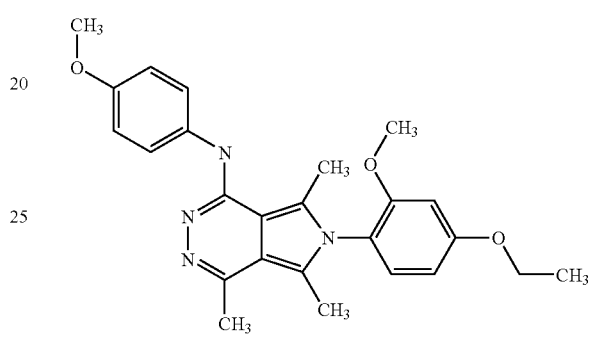
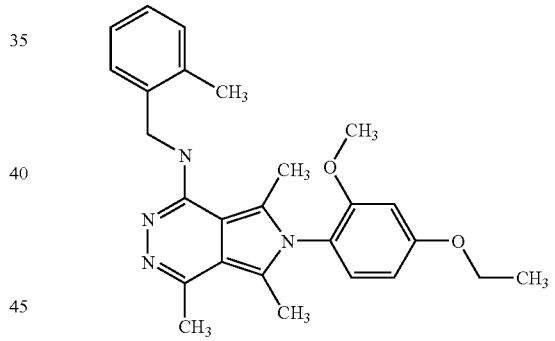
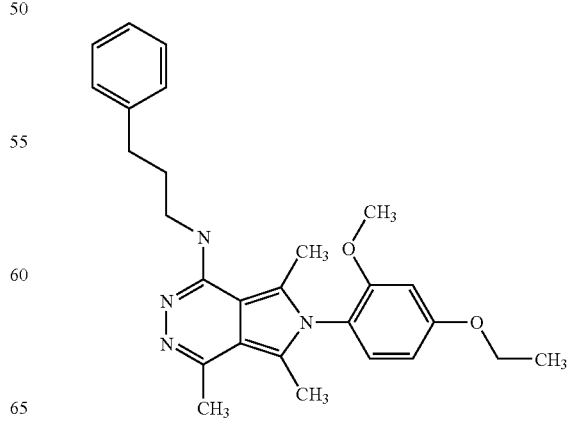

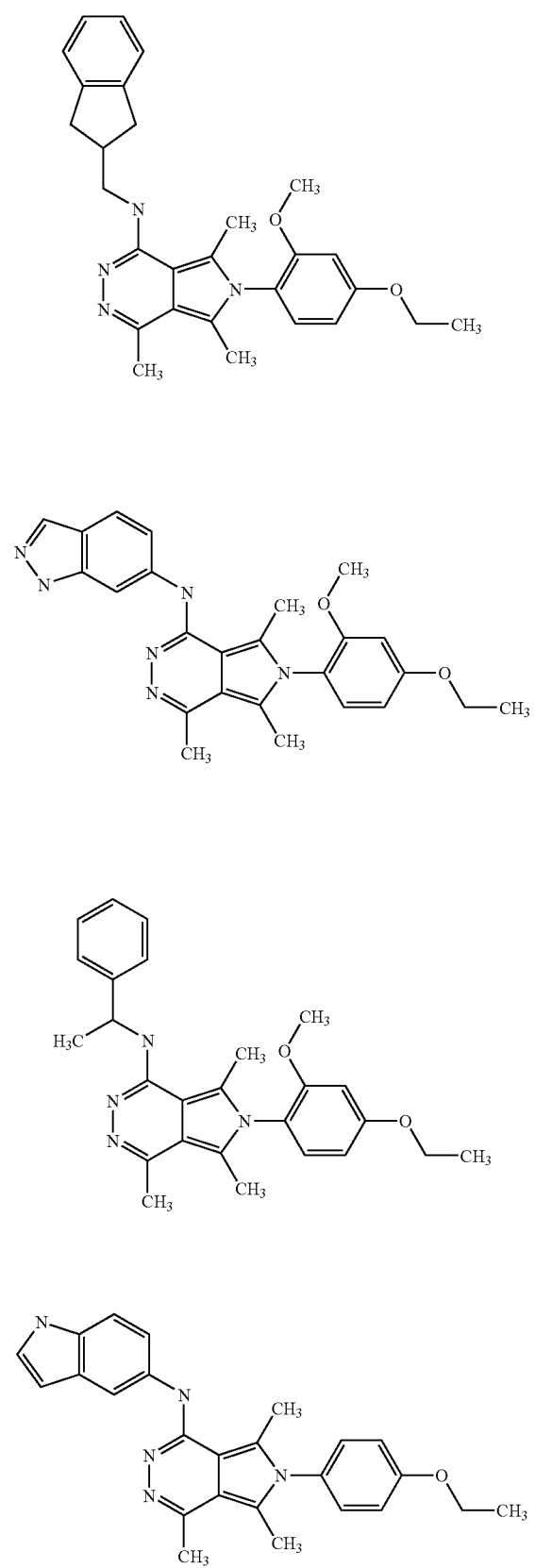
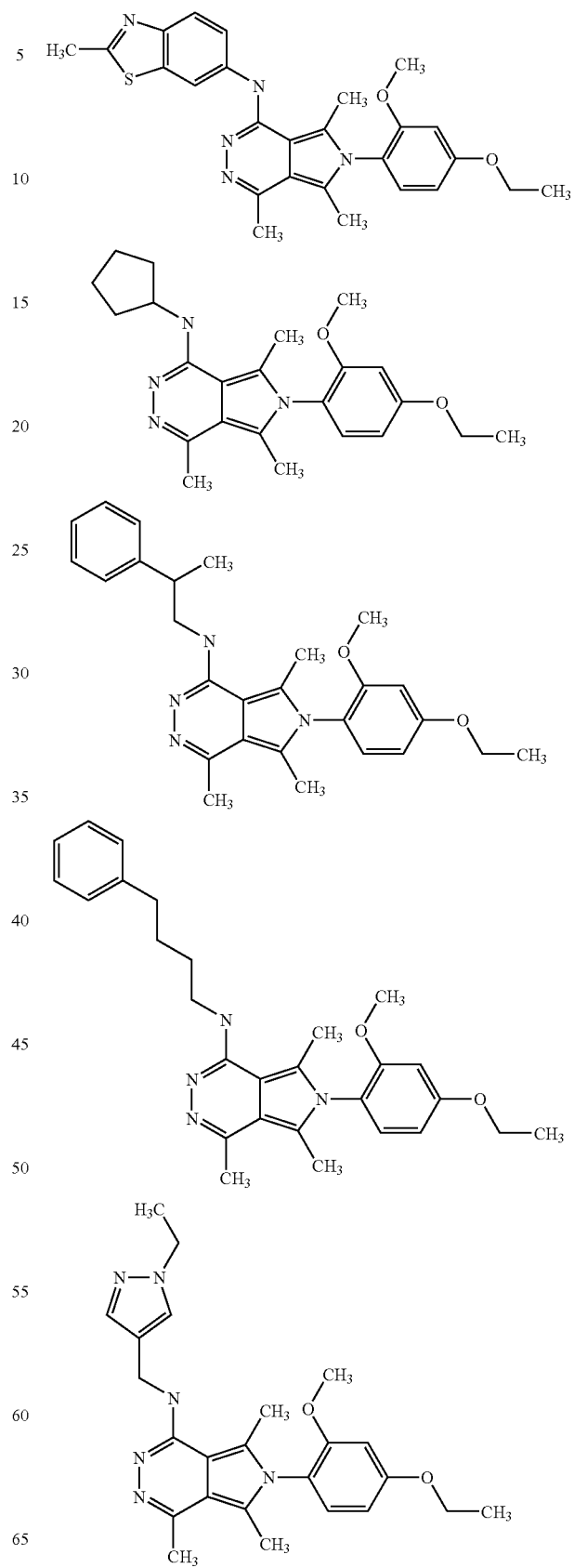

247 248
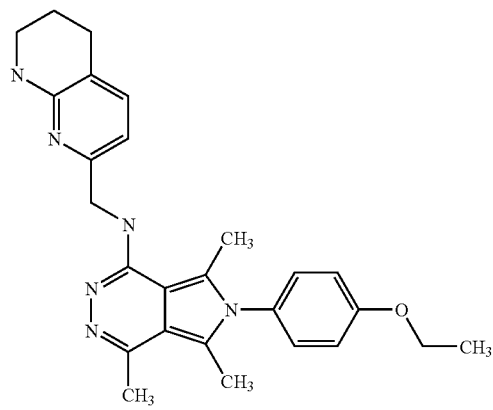
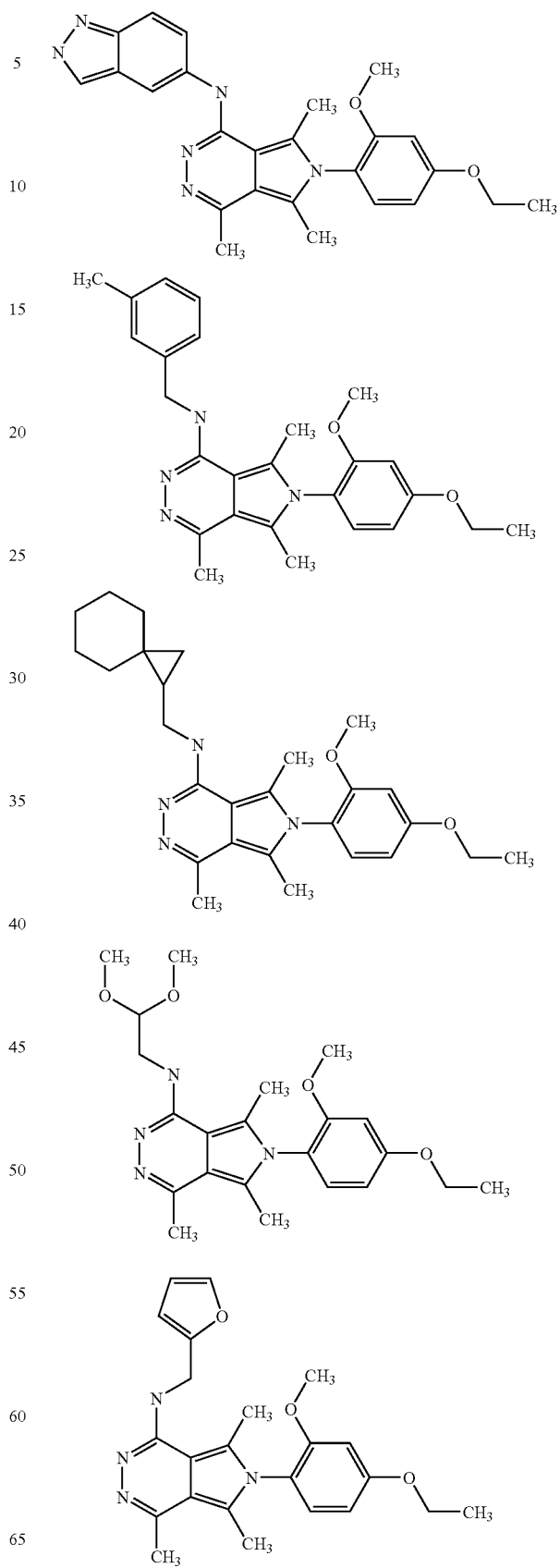

249
-continued
250
-continued
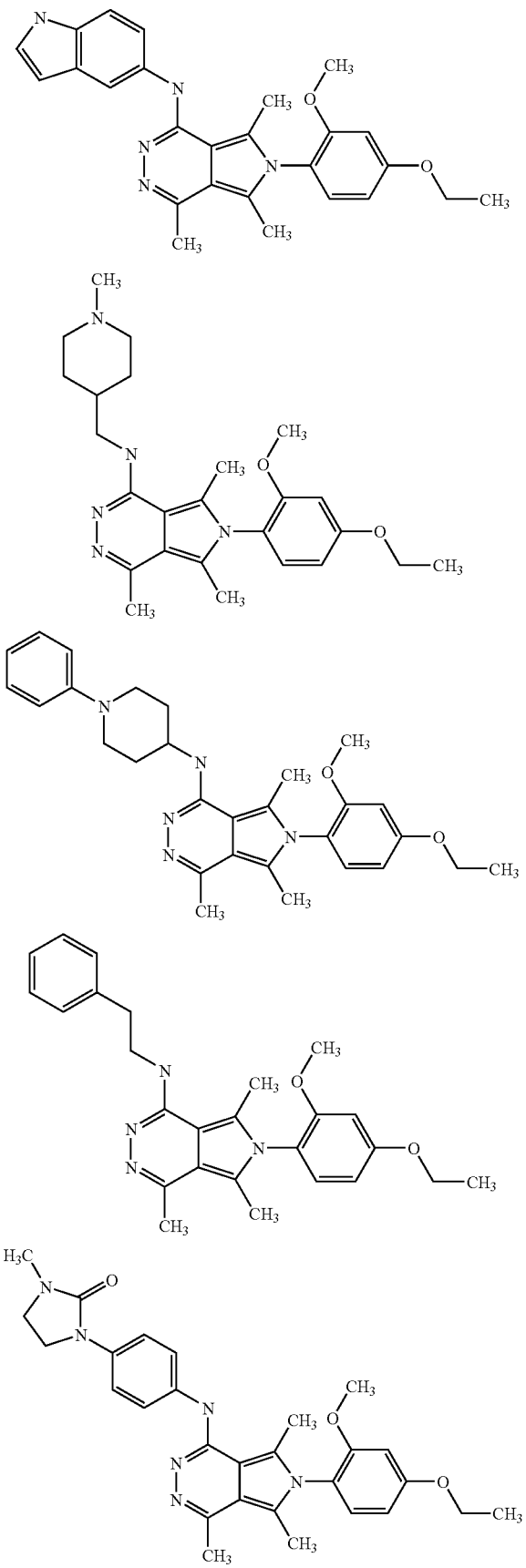
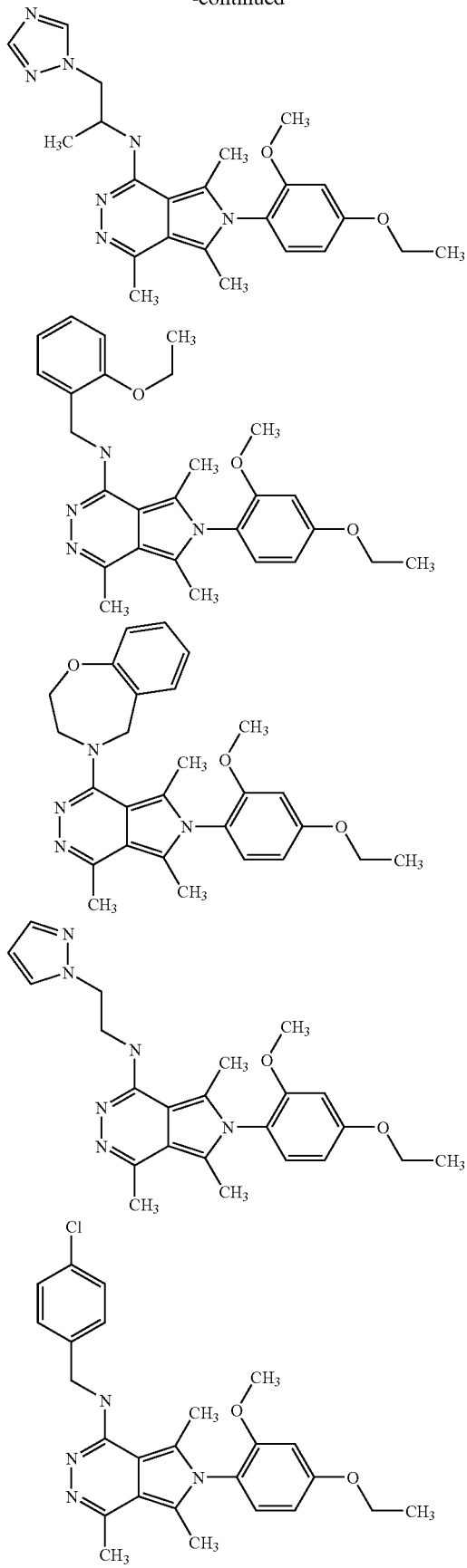

251
-continued
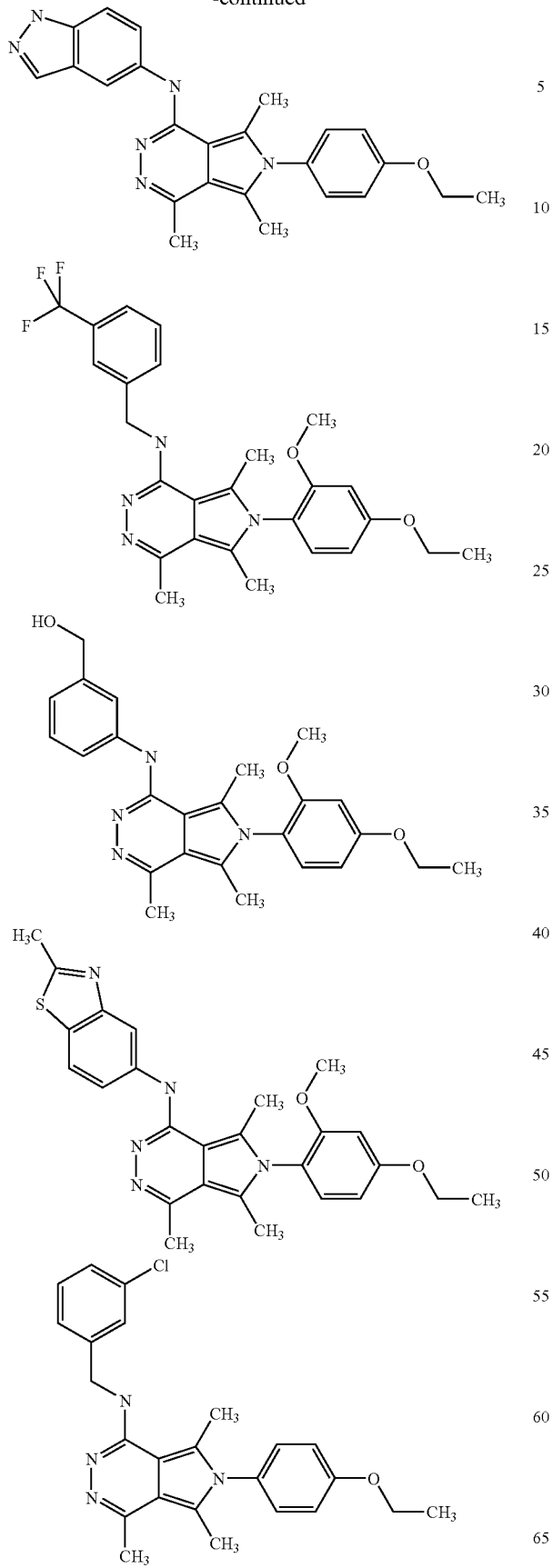
252
-continued
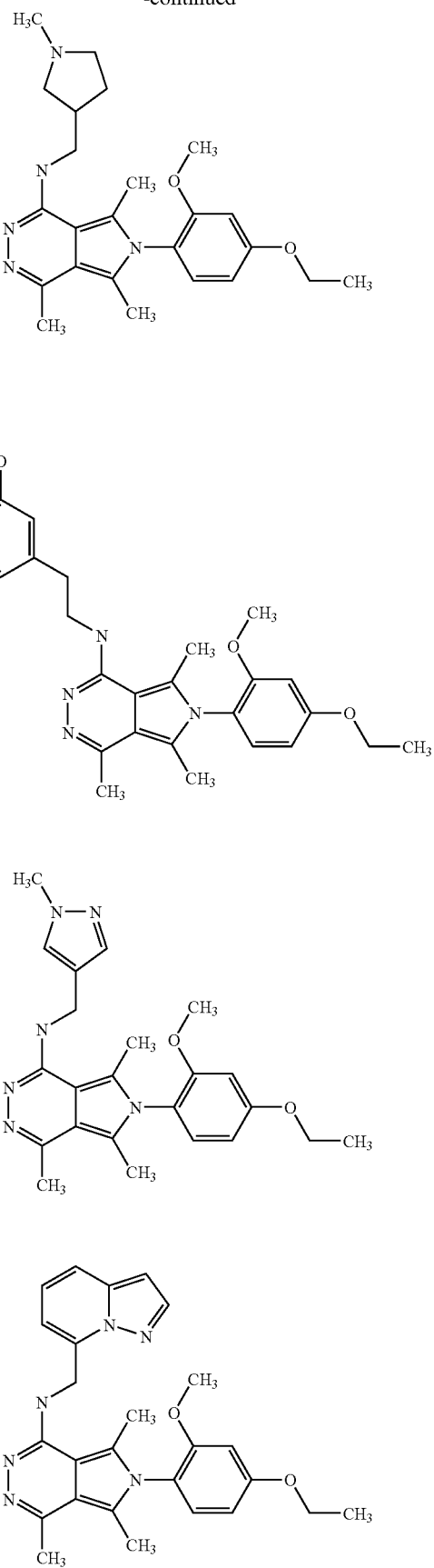

253
-continued
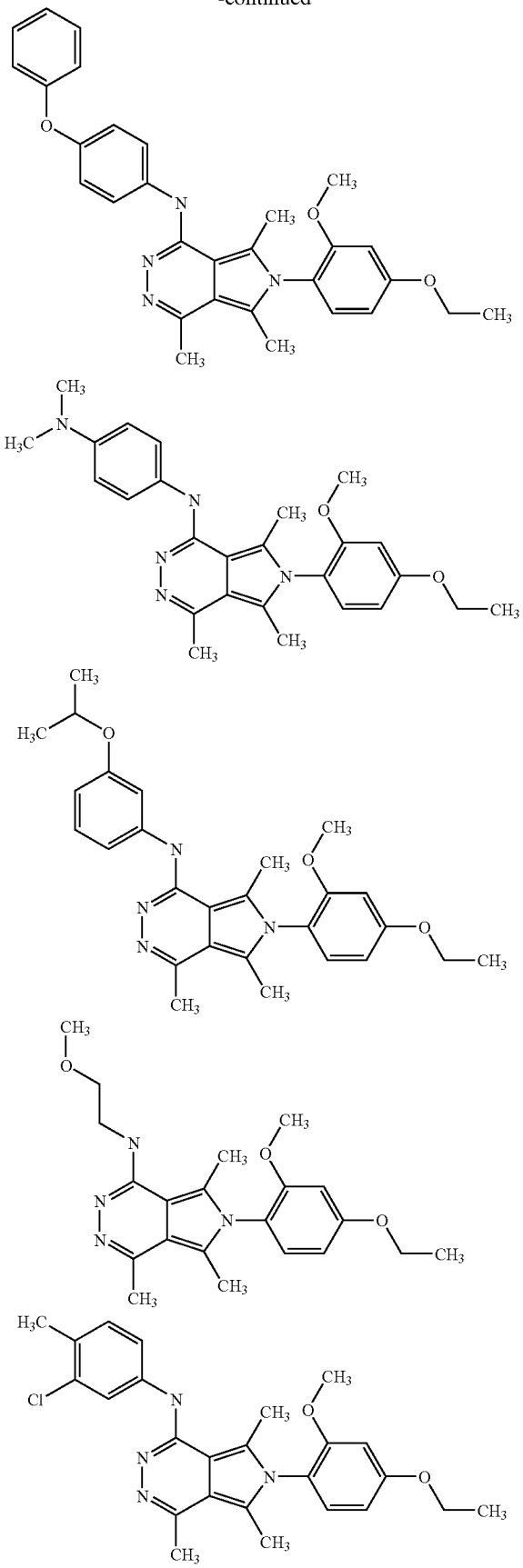
254
-continued
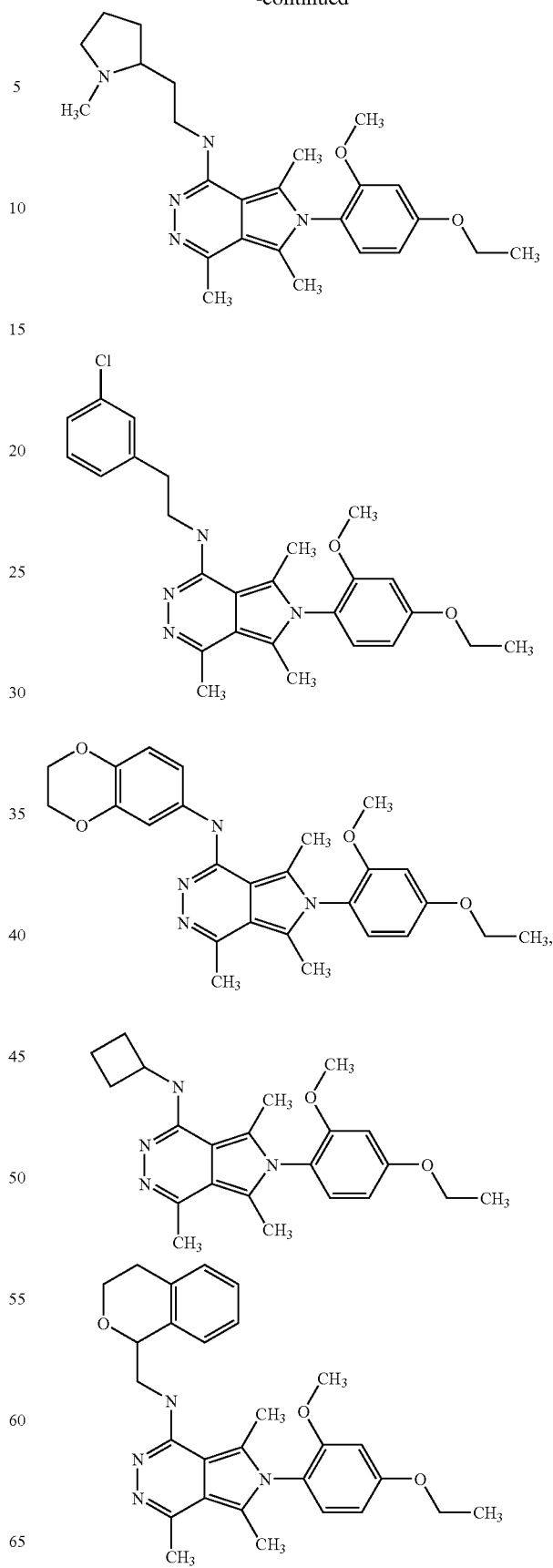

255
-continued
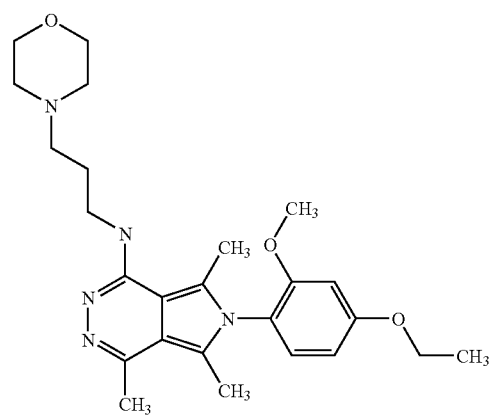
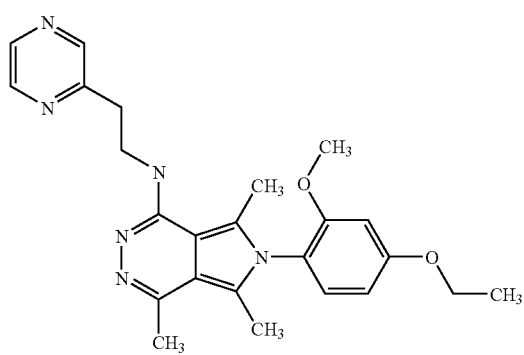
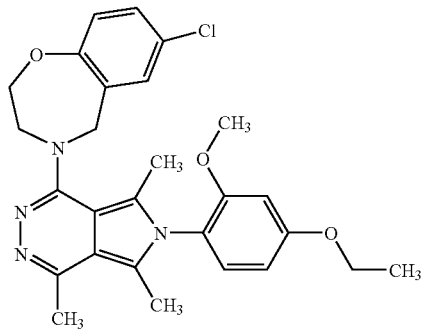
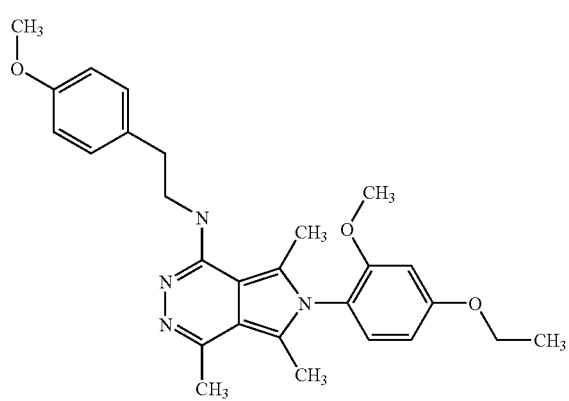
256
-continued
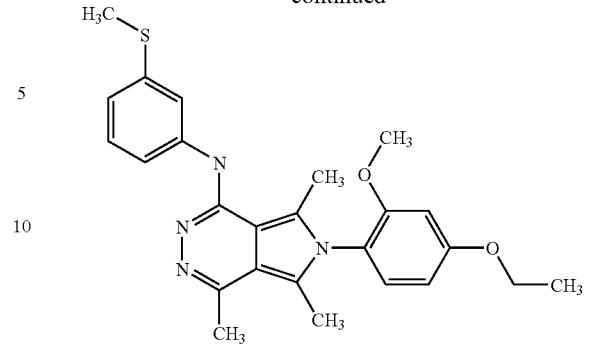
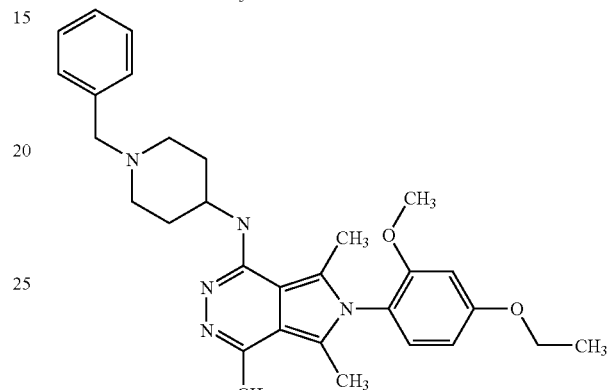
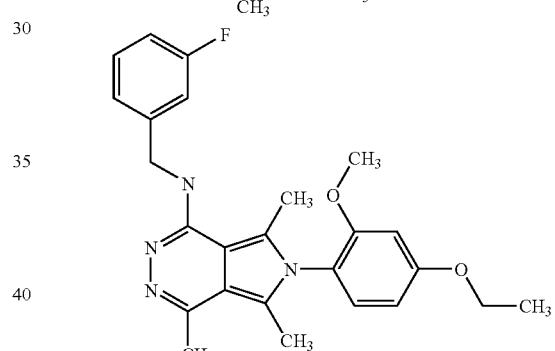
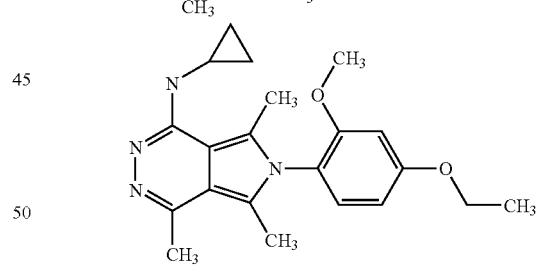
Chiral
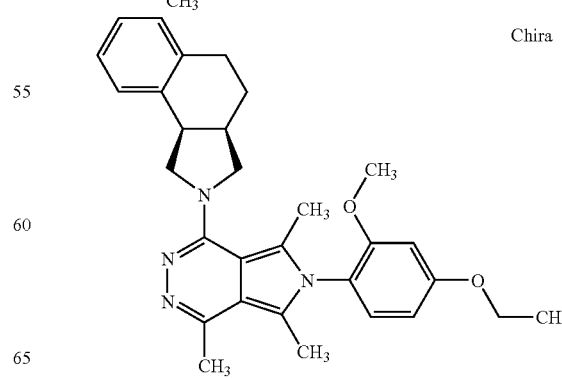

-continued
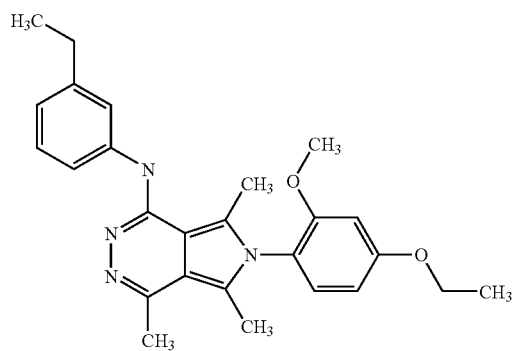
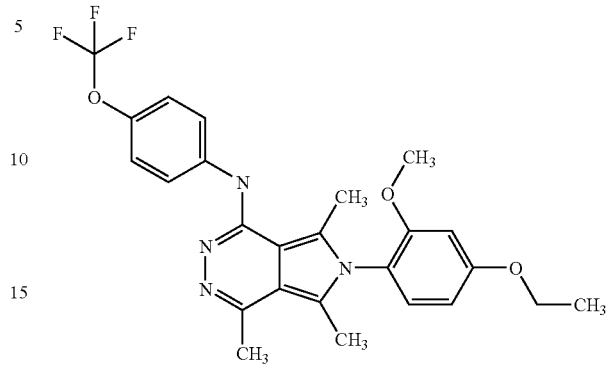
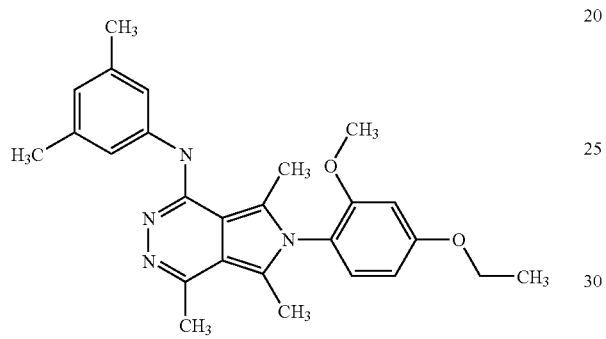
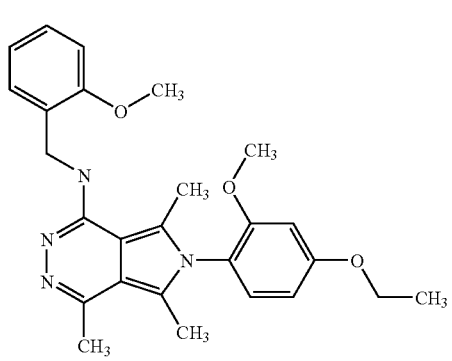
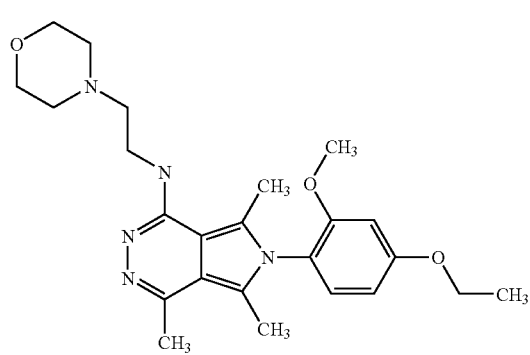
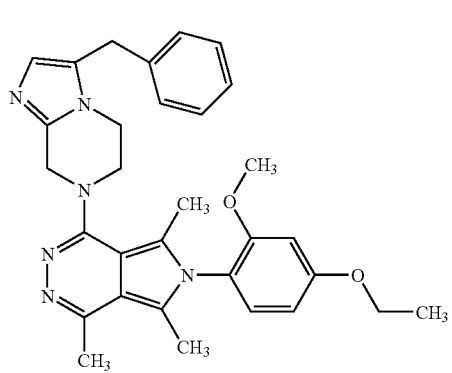
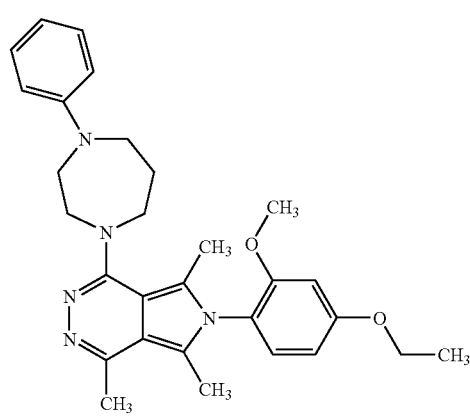
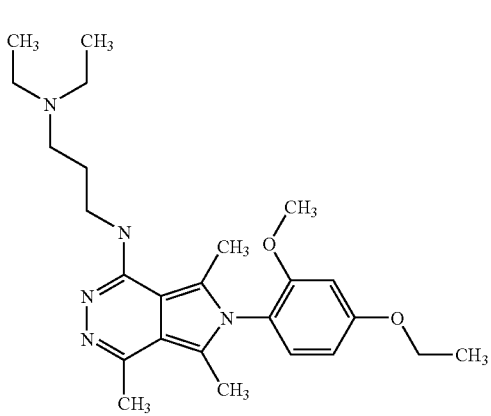

-continued
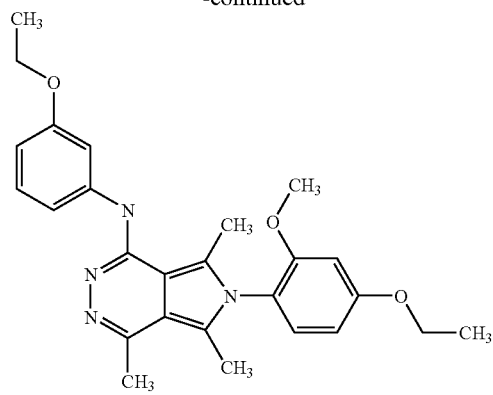
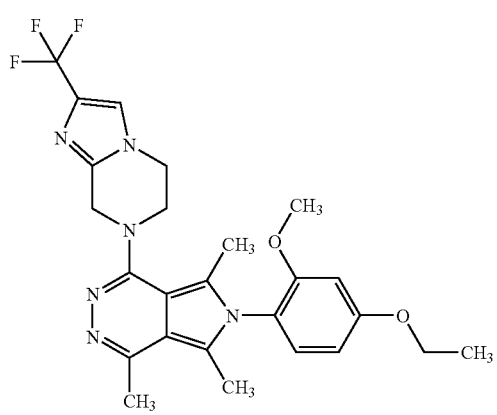
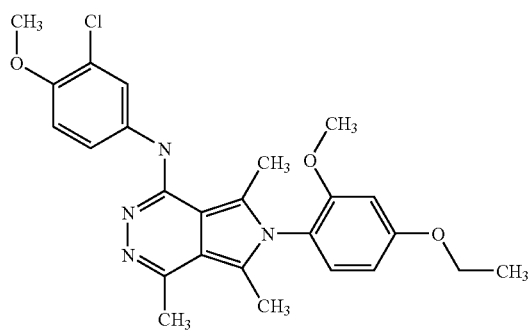
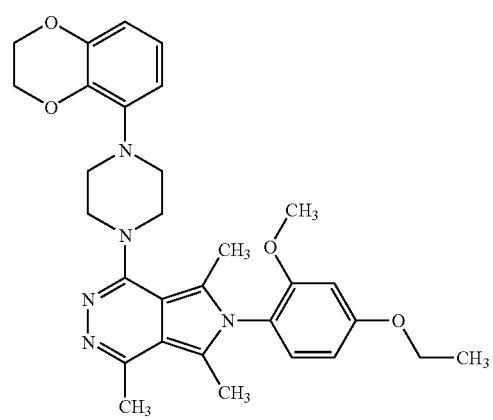
-continued
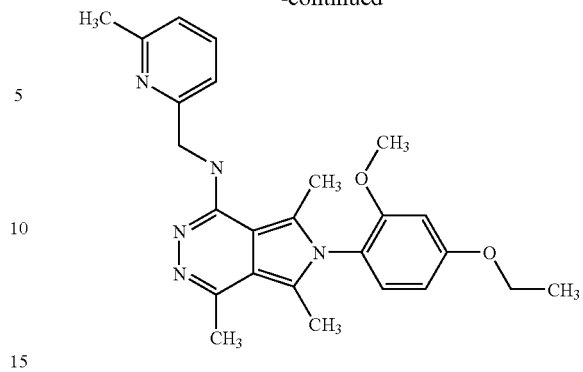
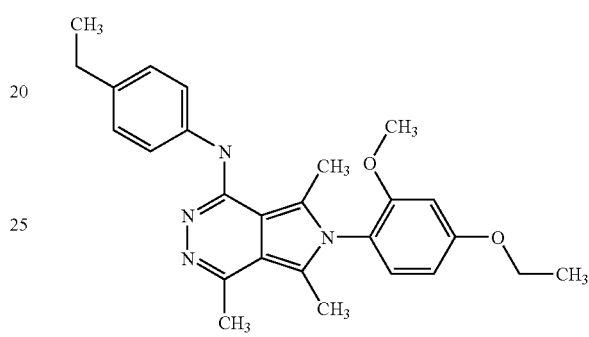
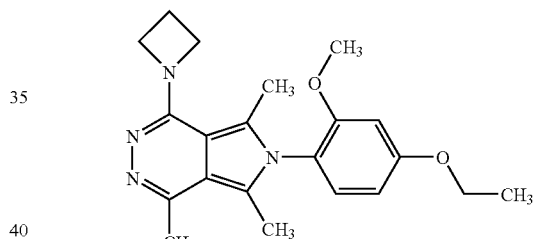
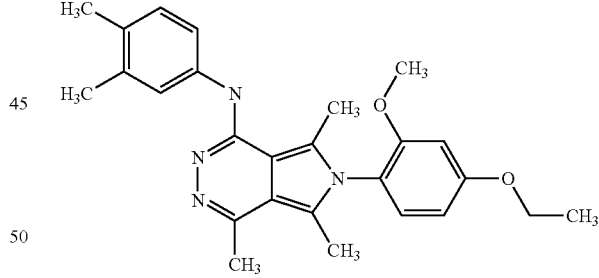
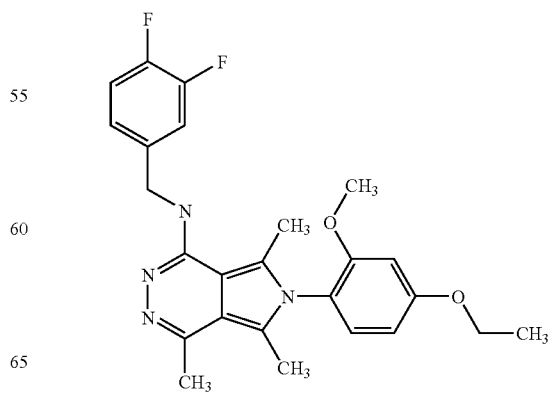

261
-continued
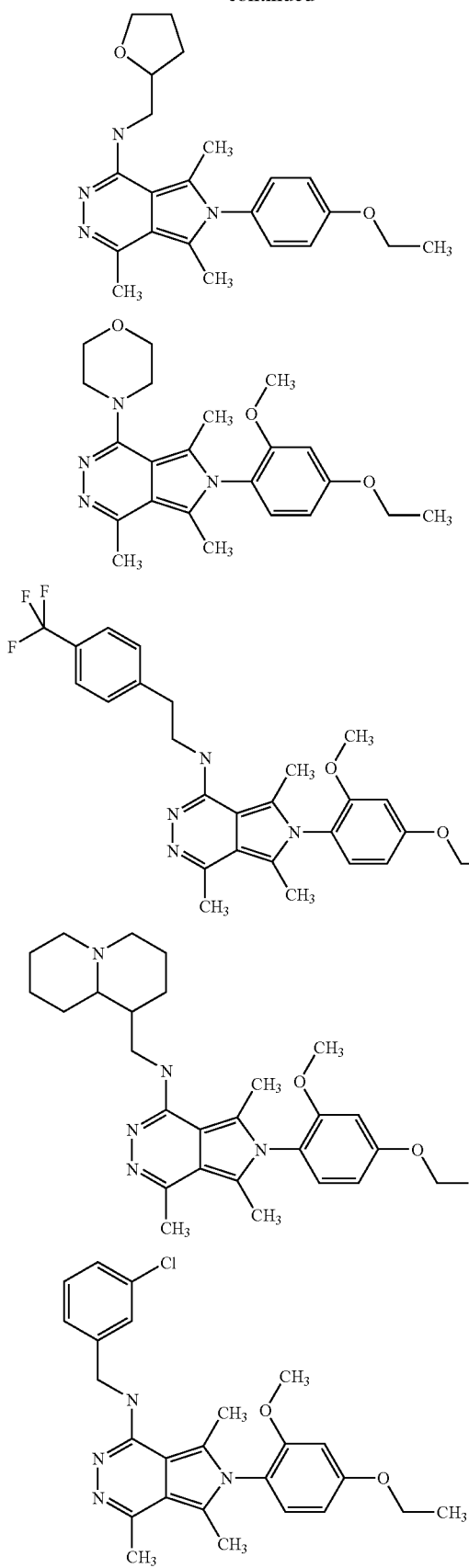
262
-continued
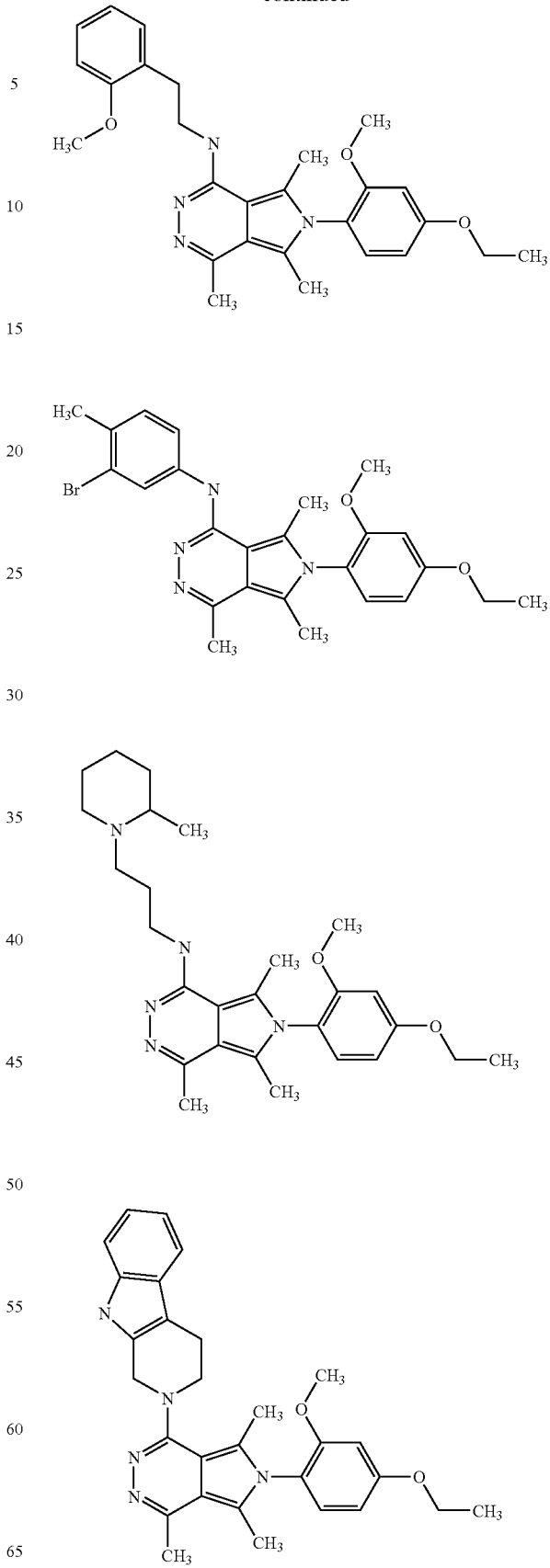

263
-continued
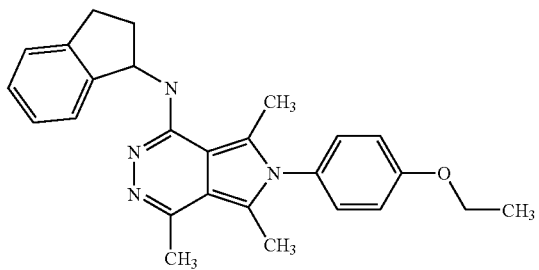
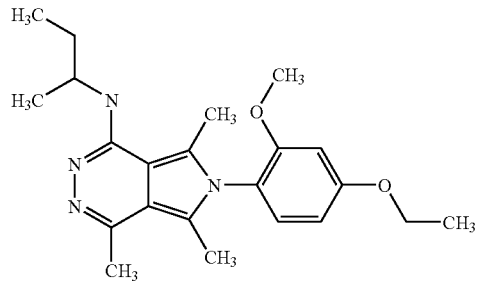
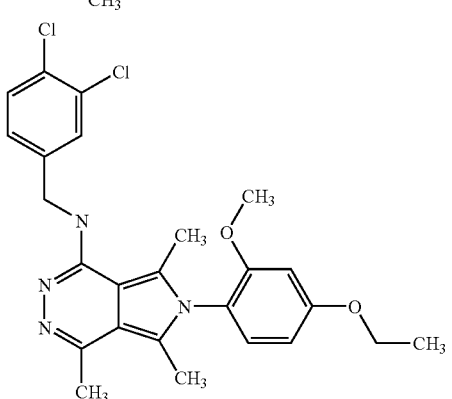
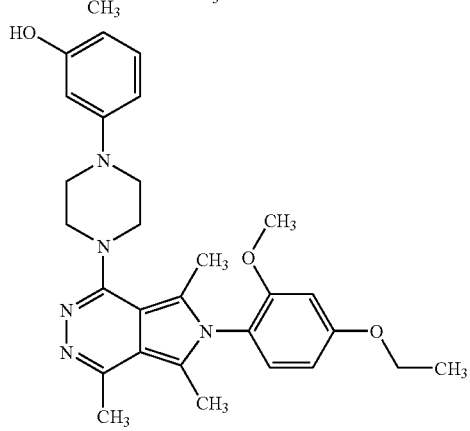
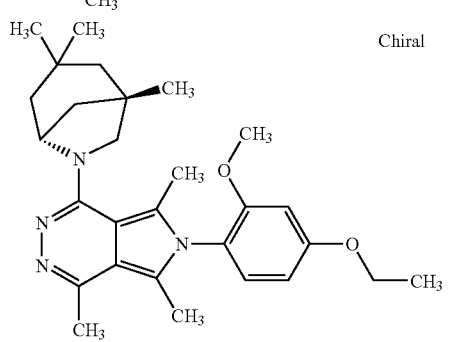
264
-continued
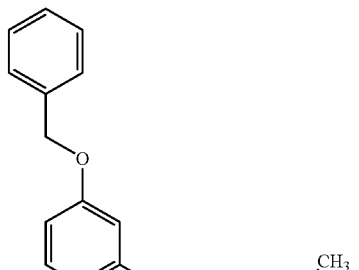
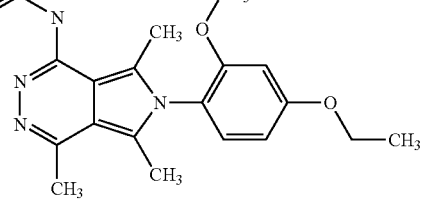
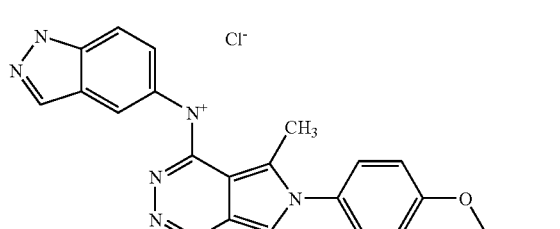
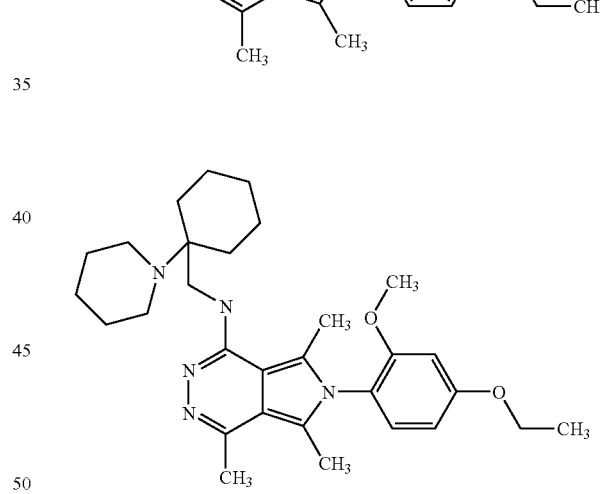
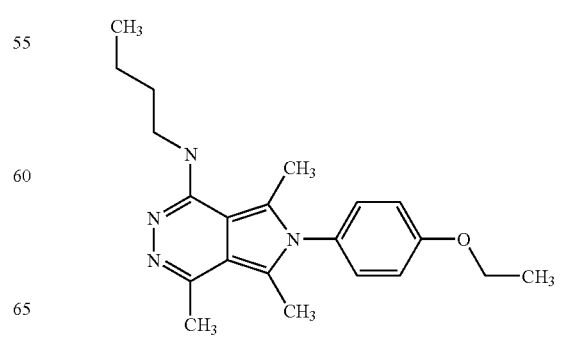

265
-continued
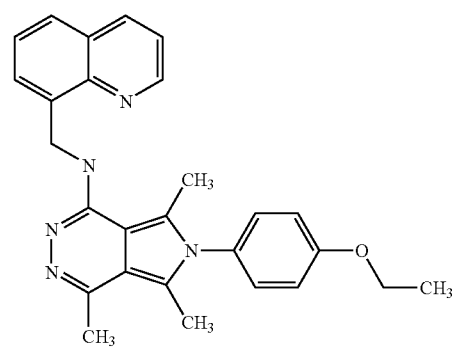
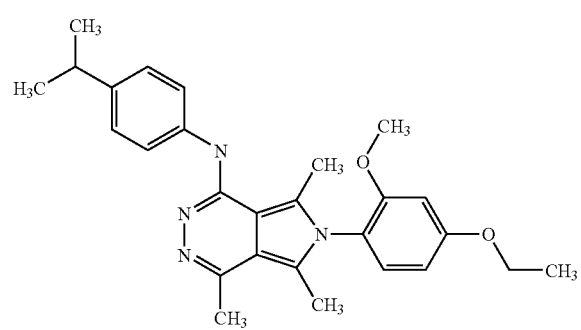
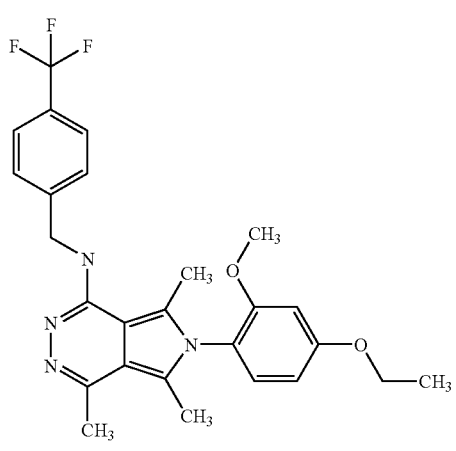
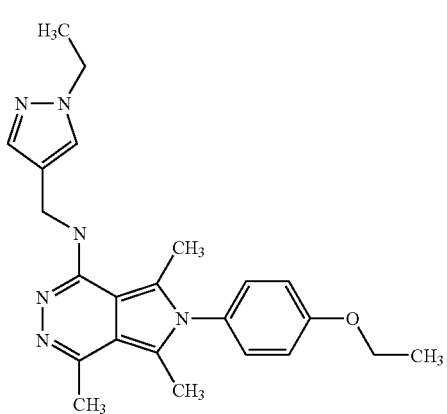
266
-continued
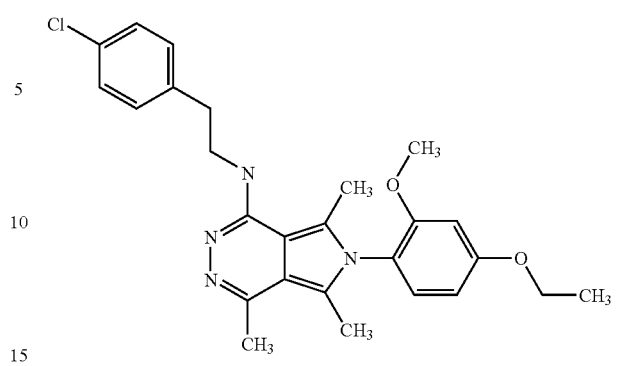
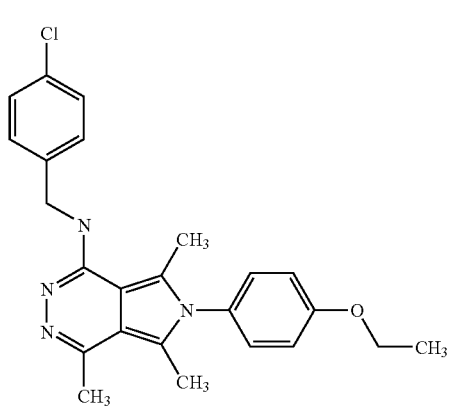
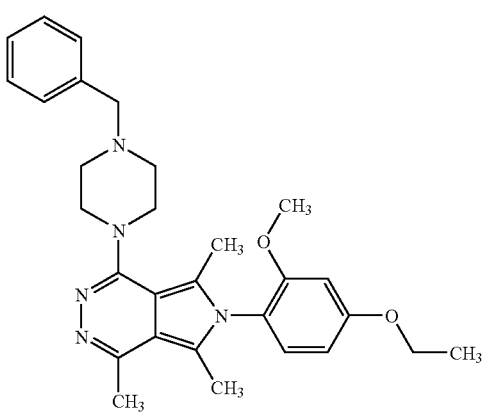

267
-continued
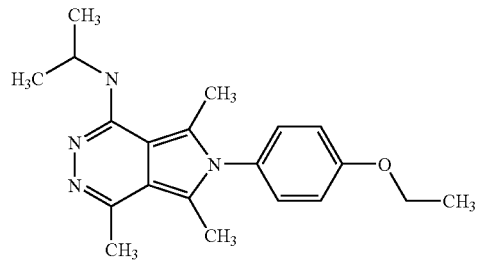
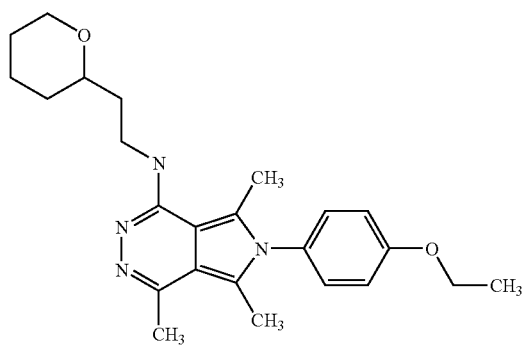
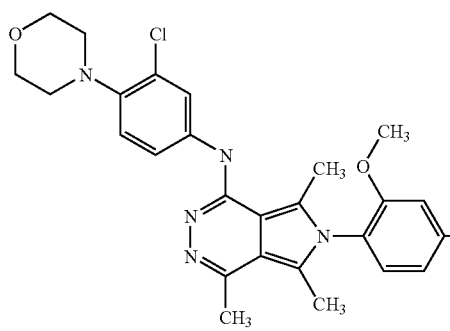
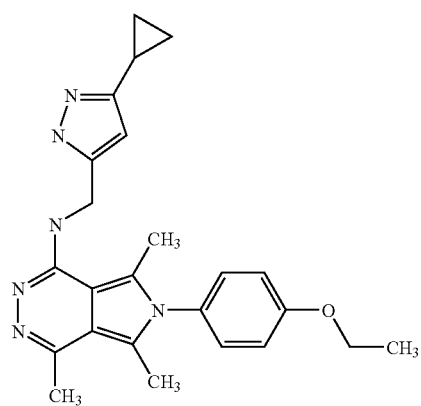
268
-continued
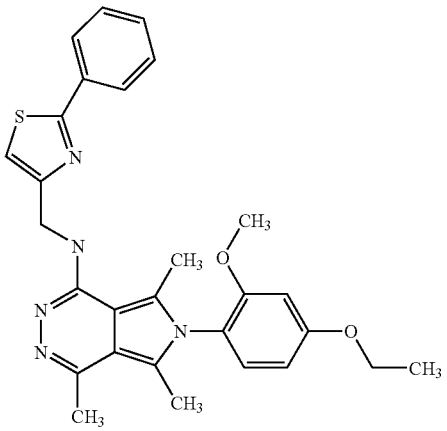
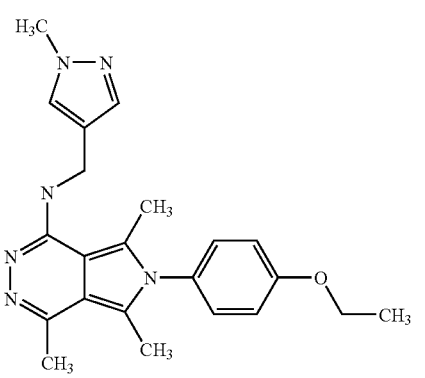
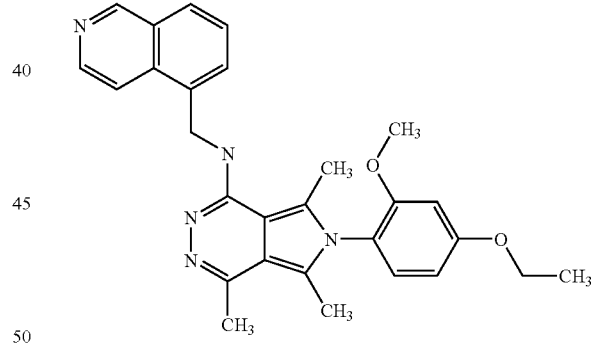
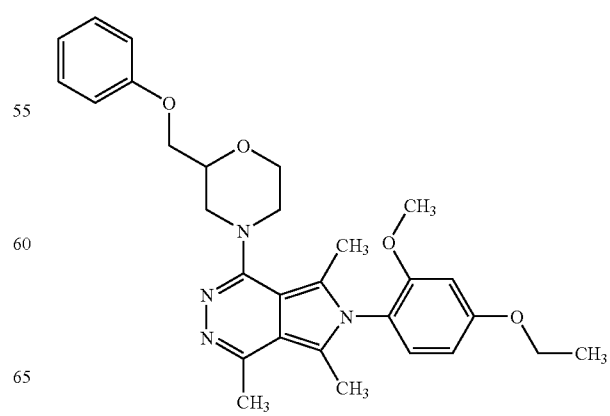

269
-continued
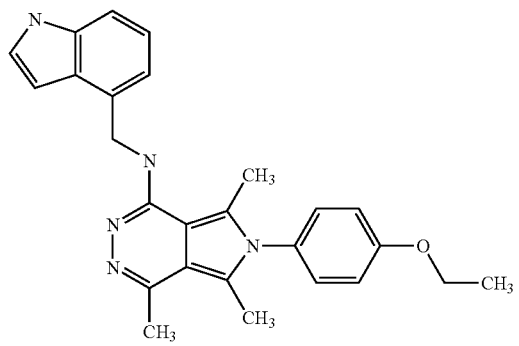
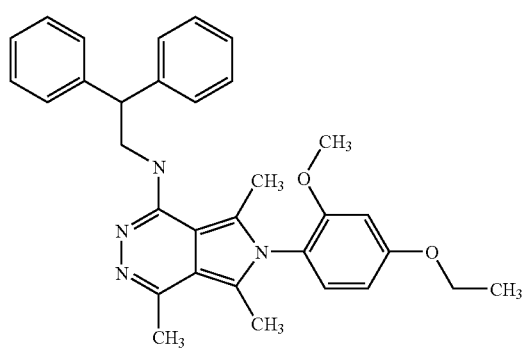
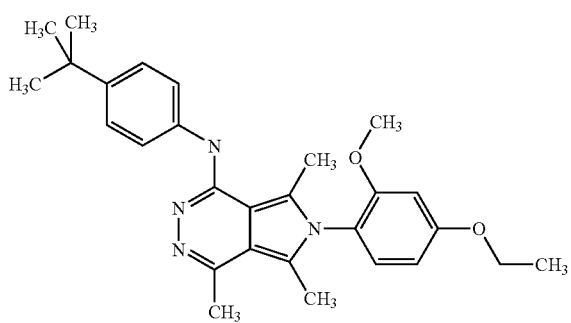
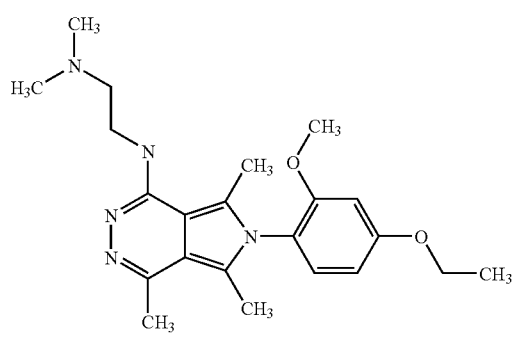
270
-continued
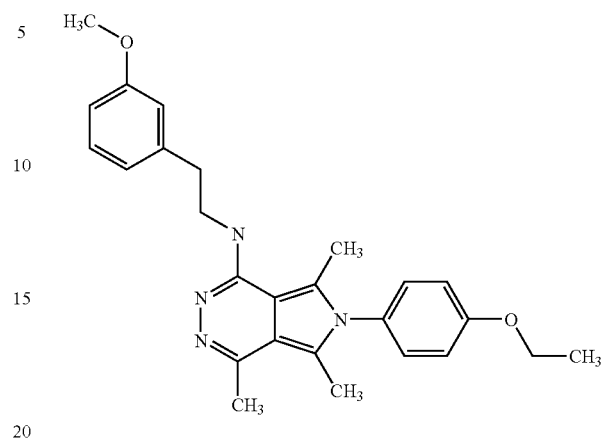
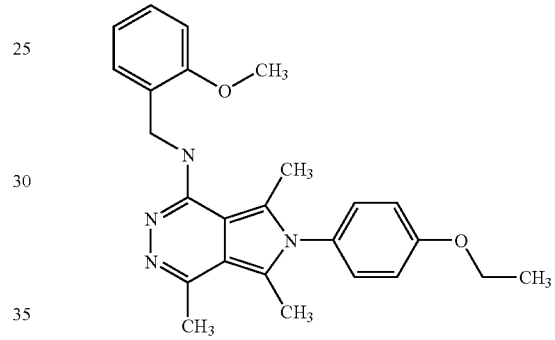
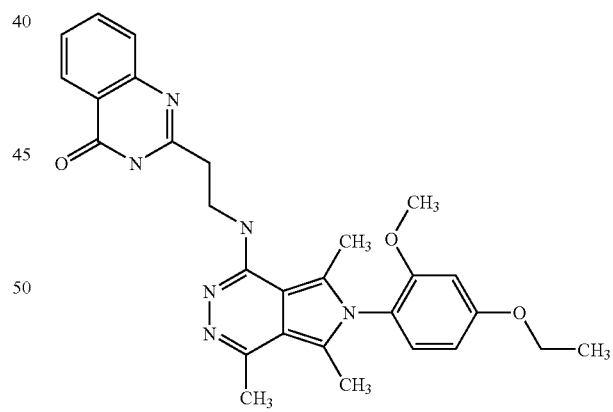
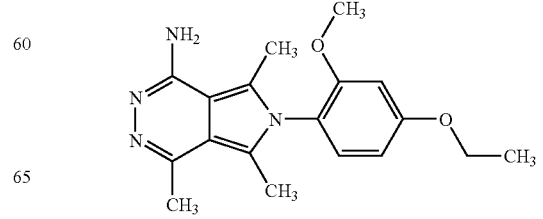

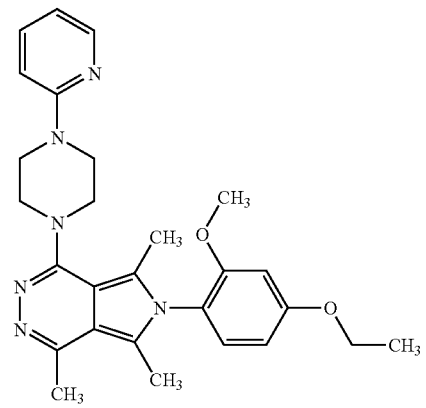
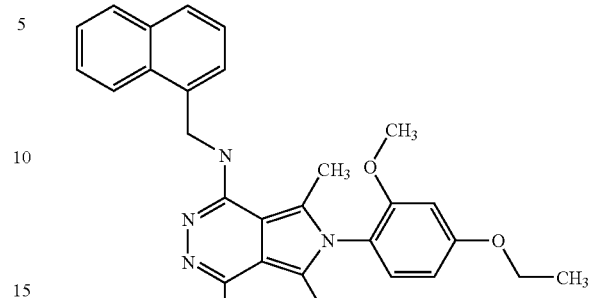
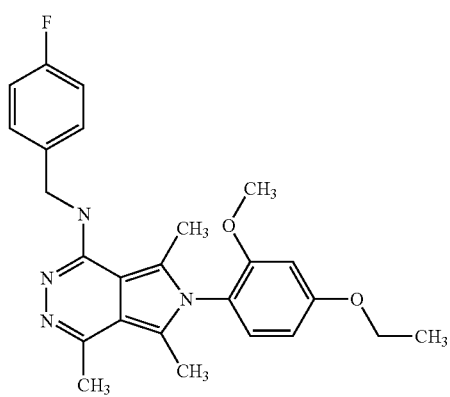
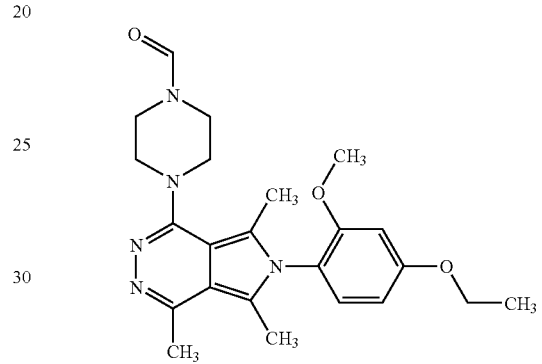
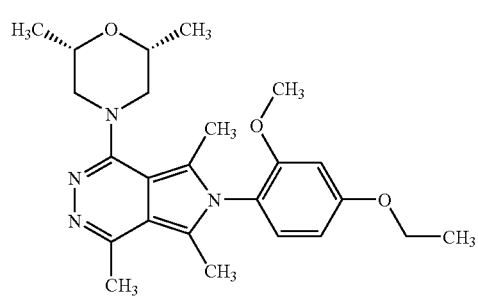
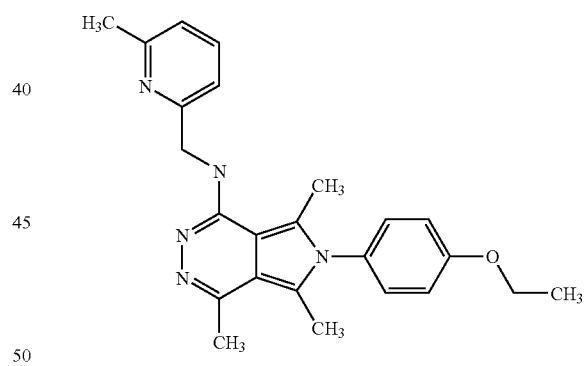
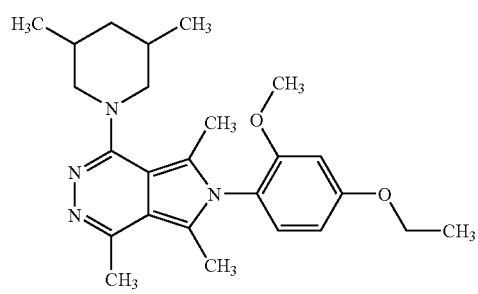
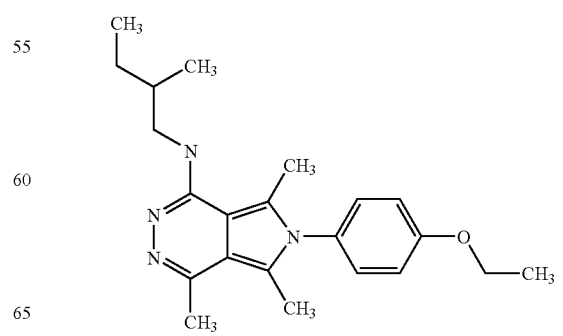

-continued
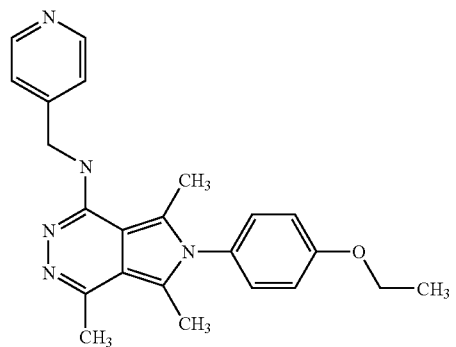
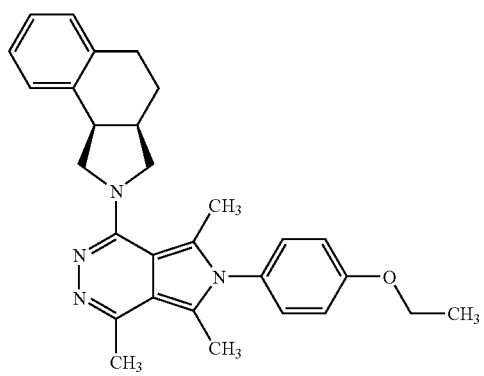
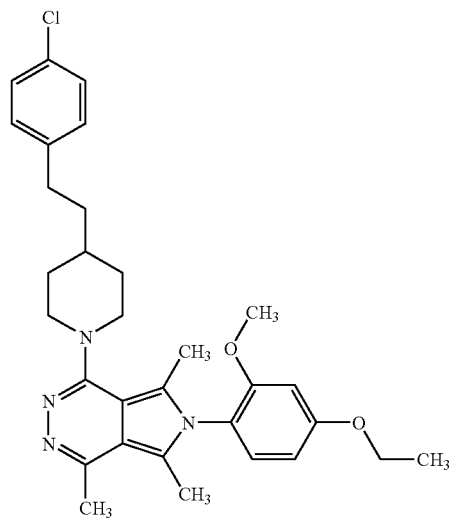
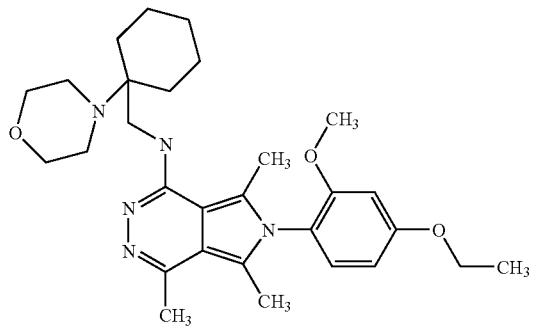
-continued
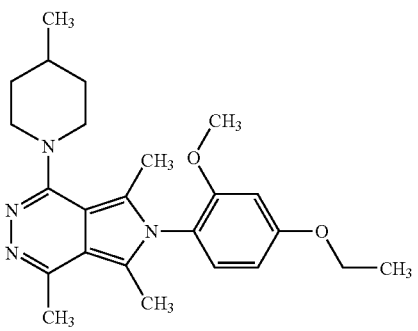
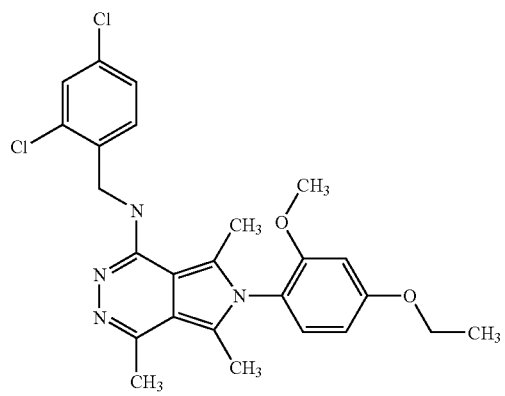
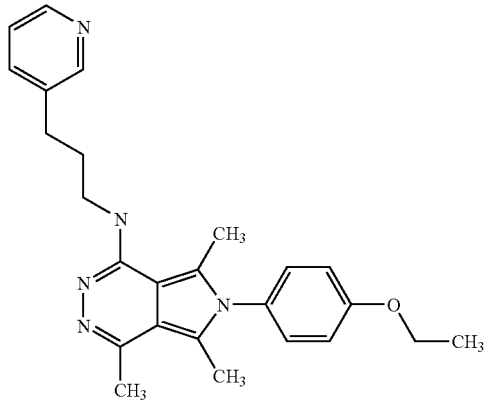
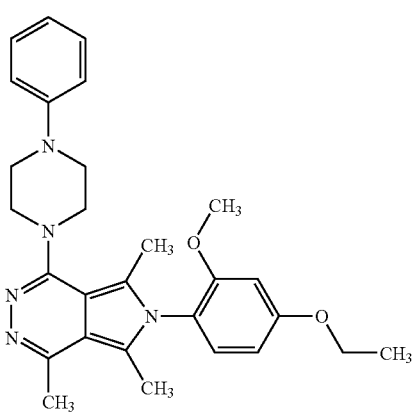

275
-continued
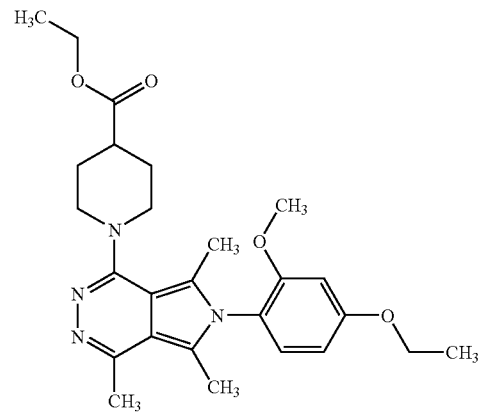
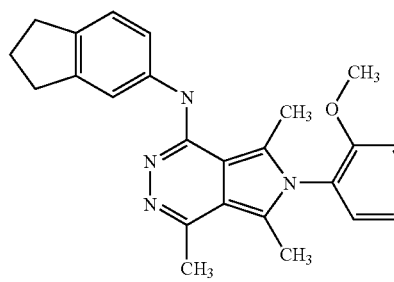
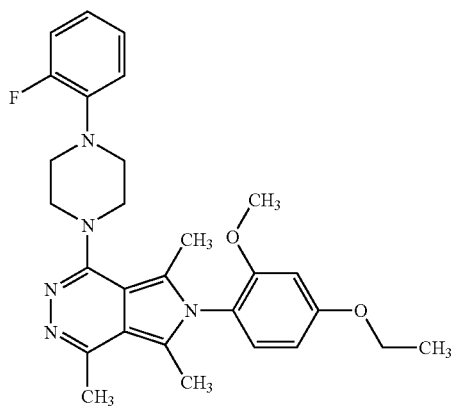
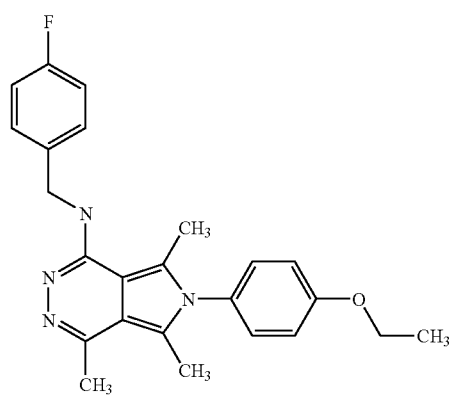
276
-continued
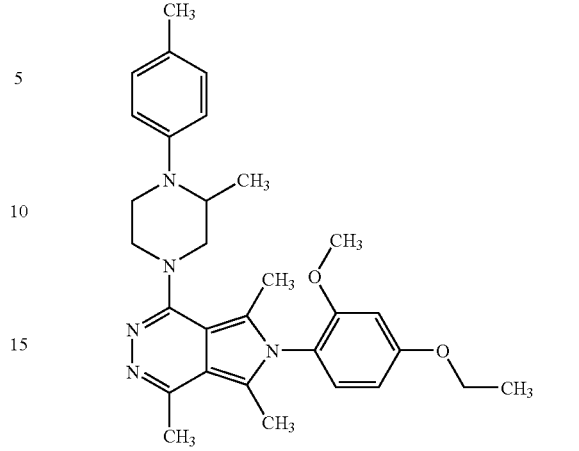
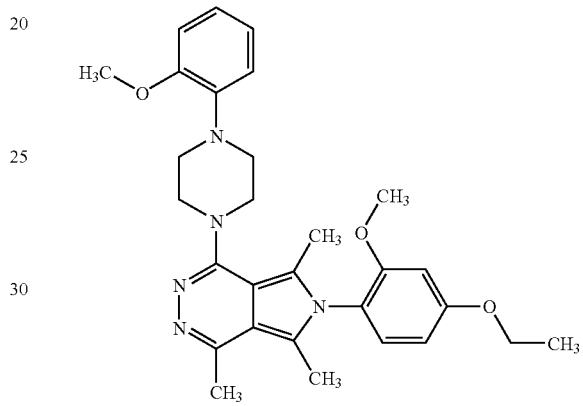
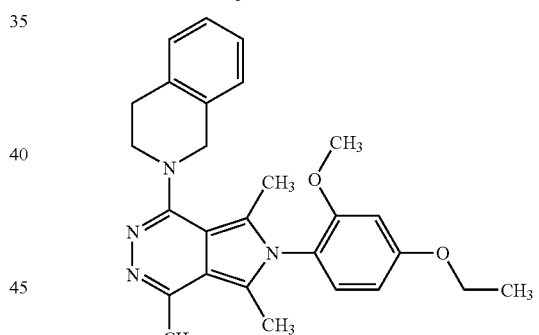
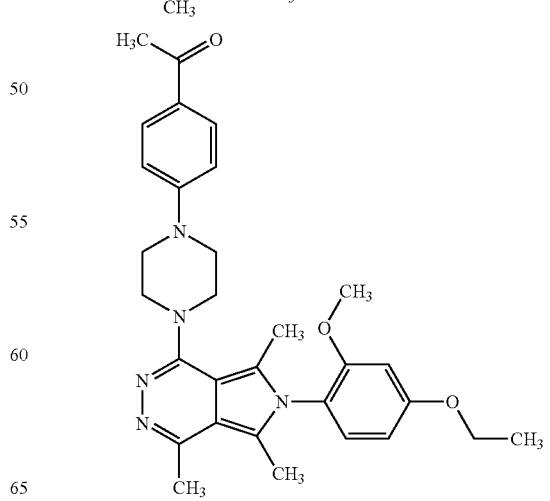

277
-continued
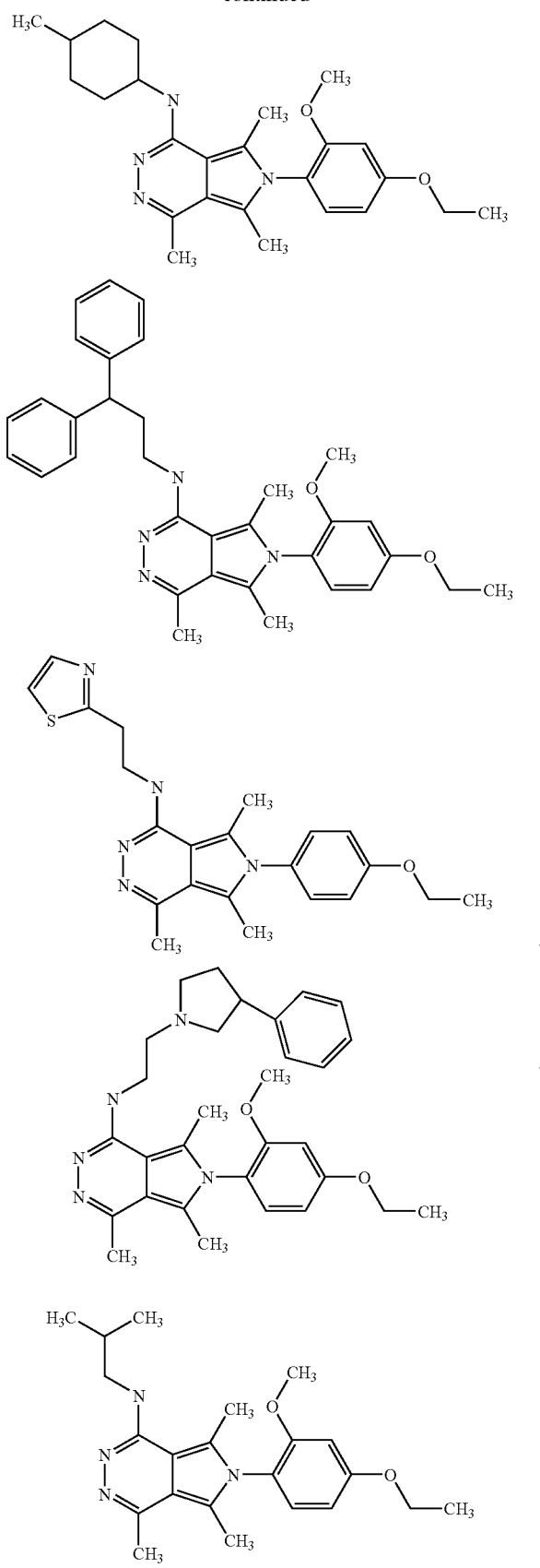
278
-continued
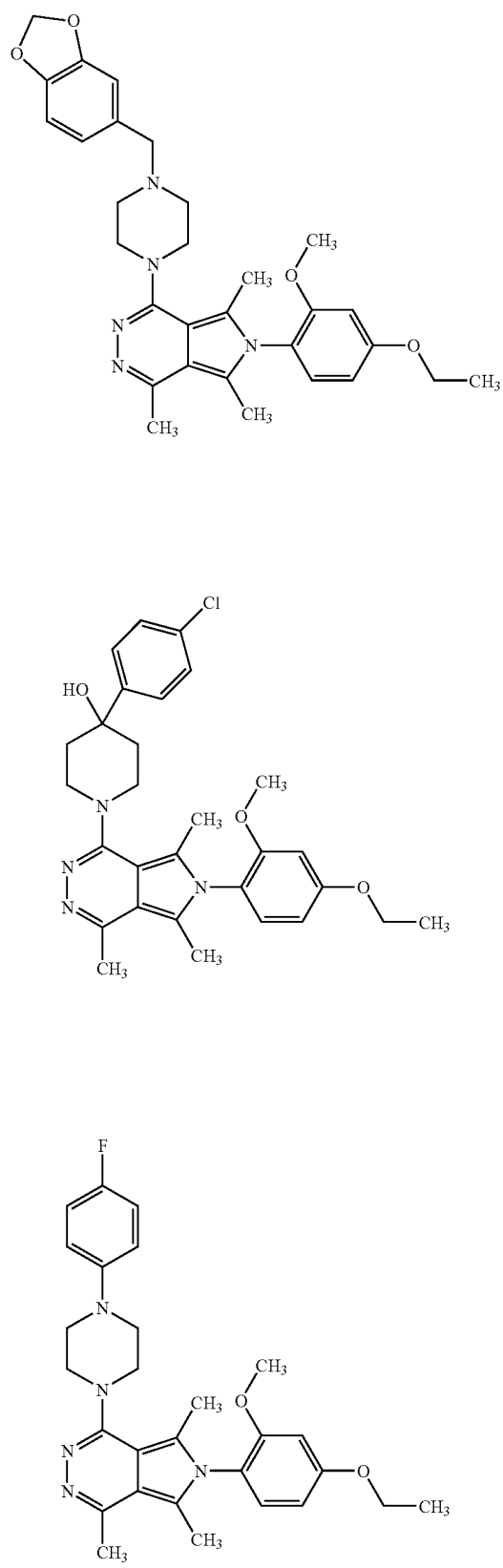

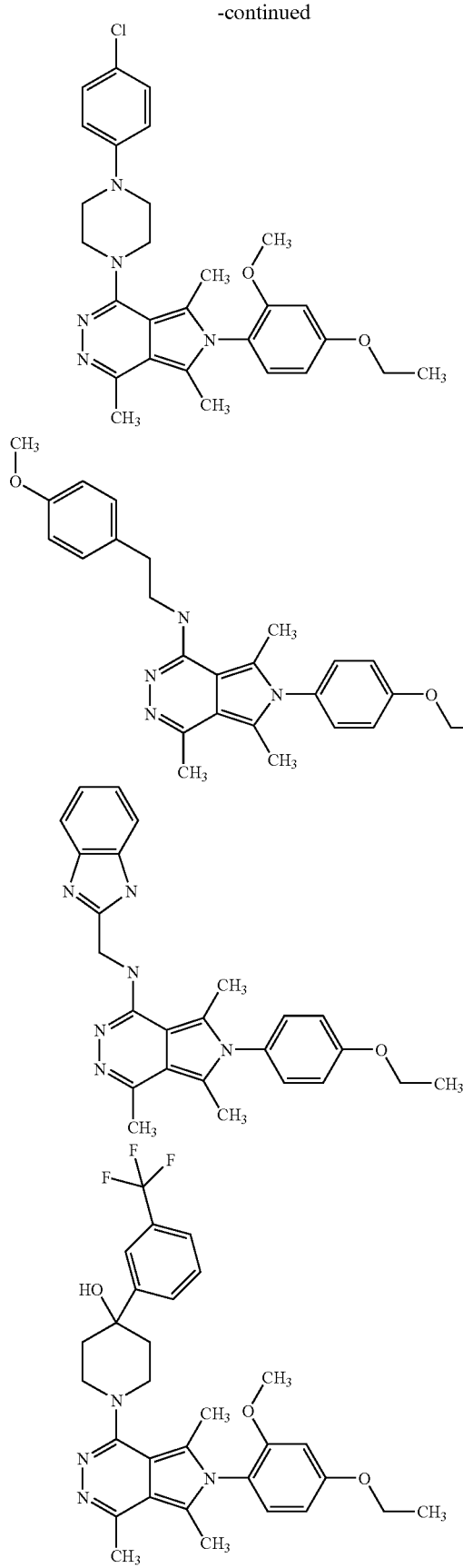
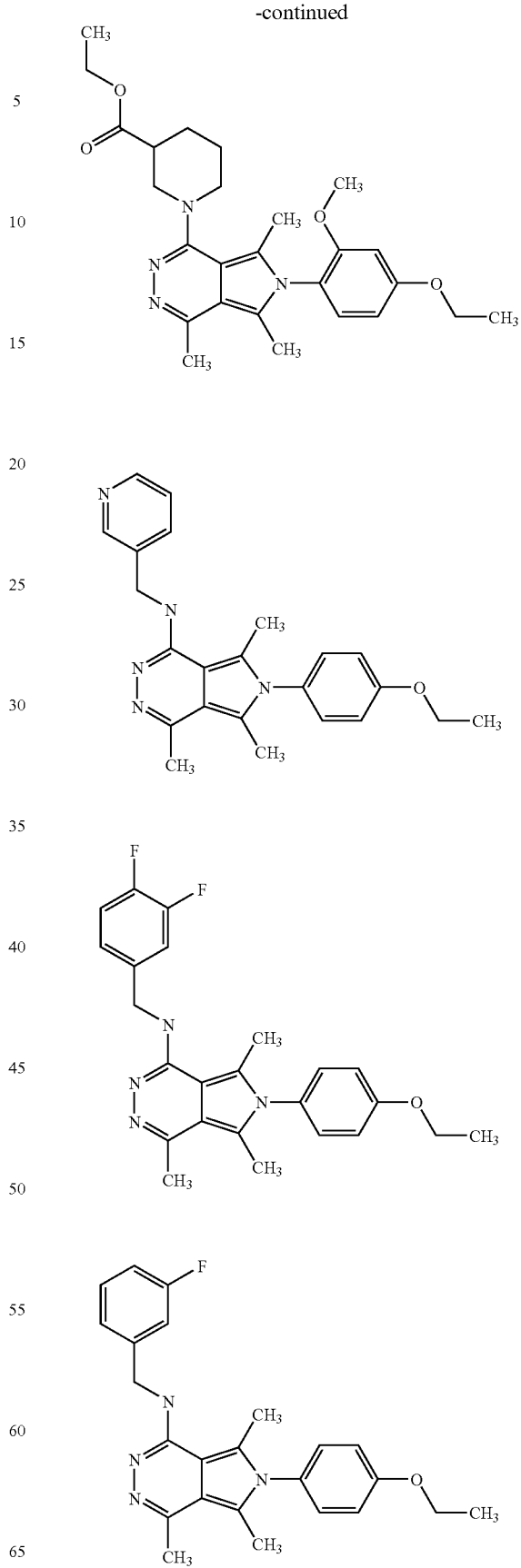

-continued
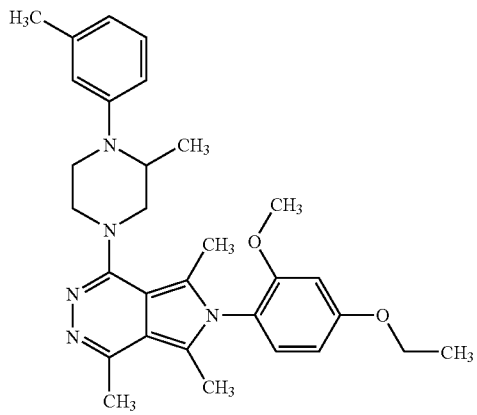
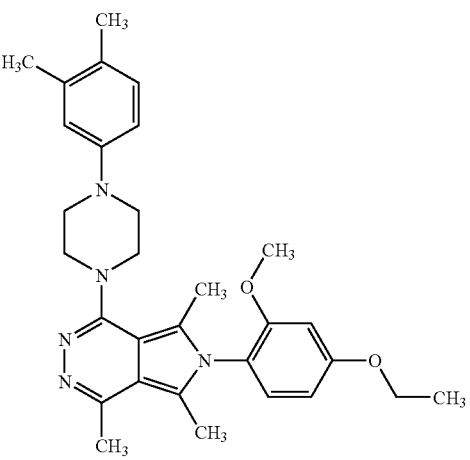
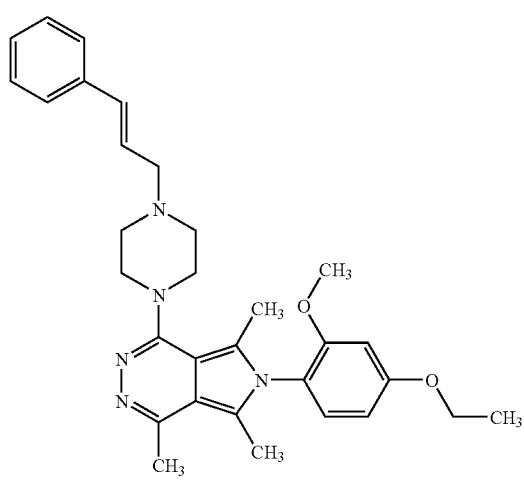
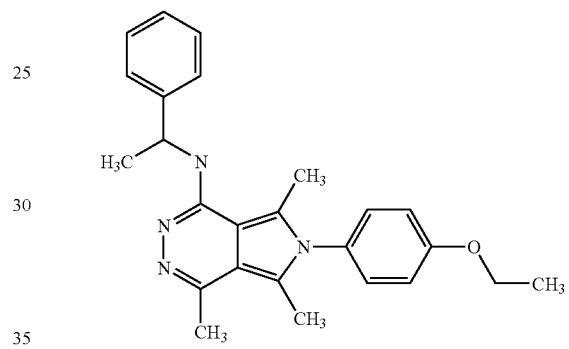
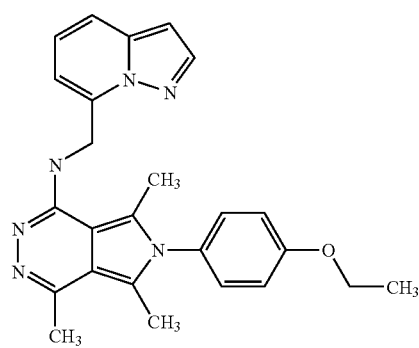
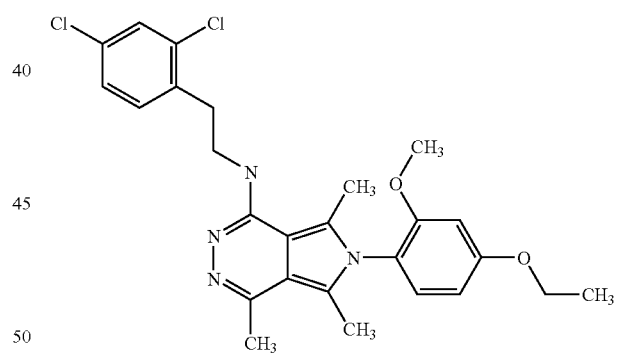
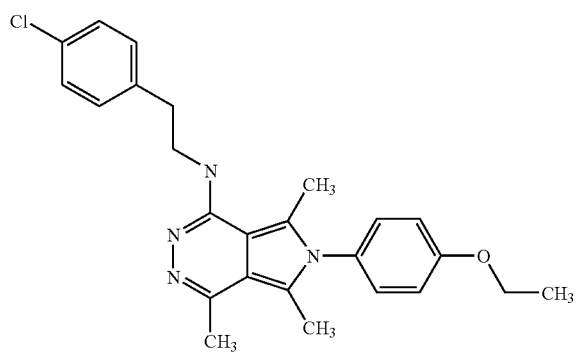
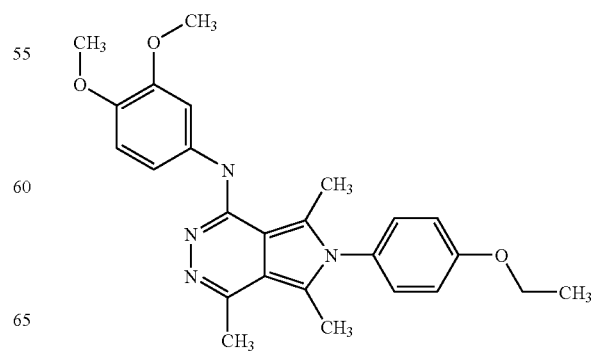

283
-continued
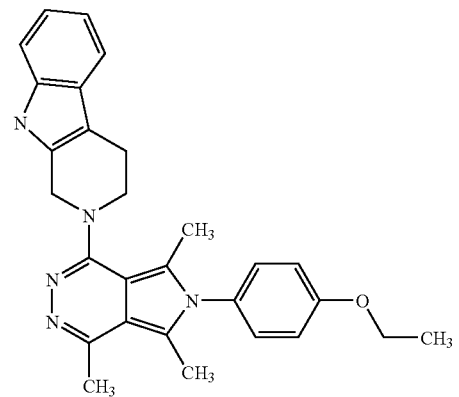
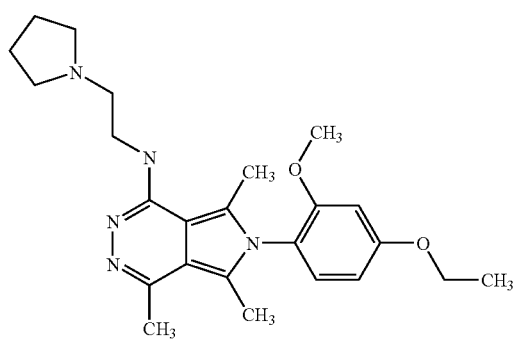
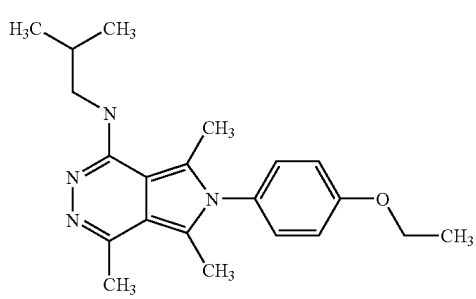
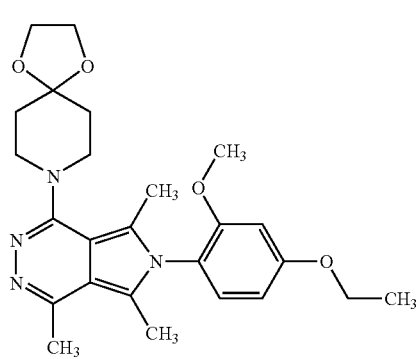
284
-continued
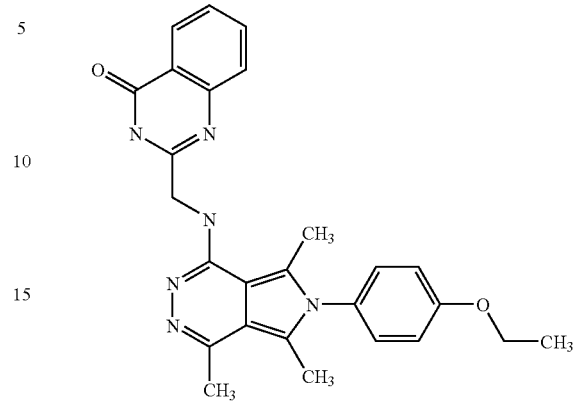
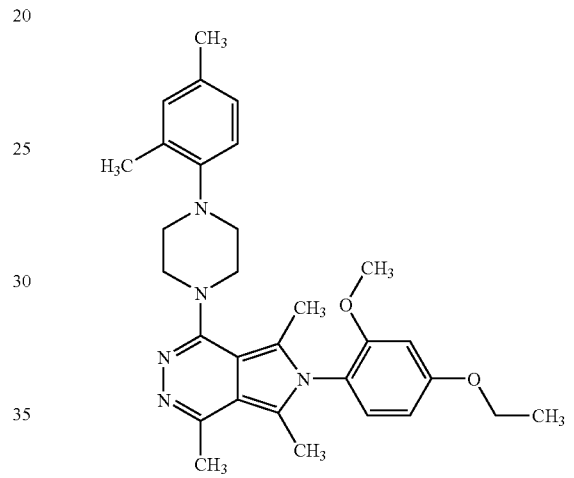
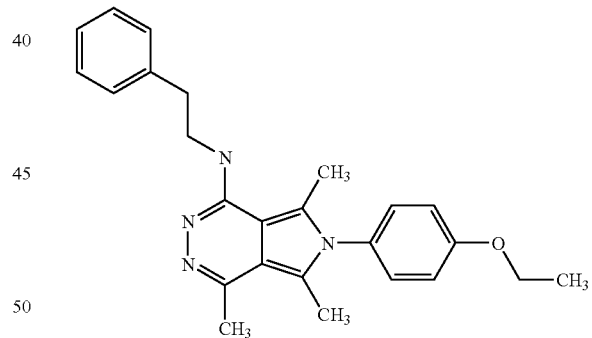
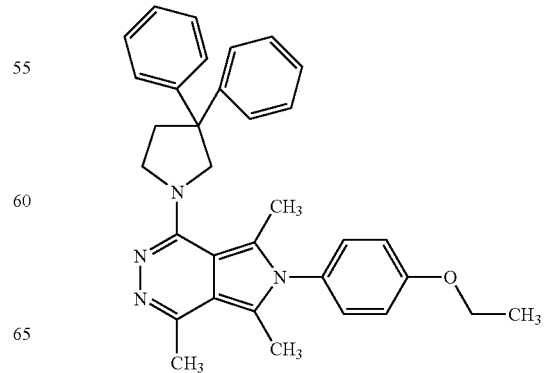

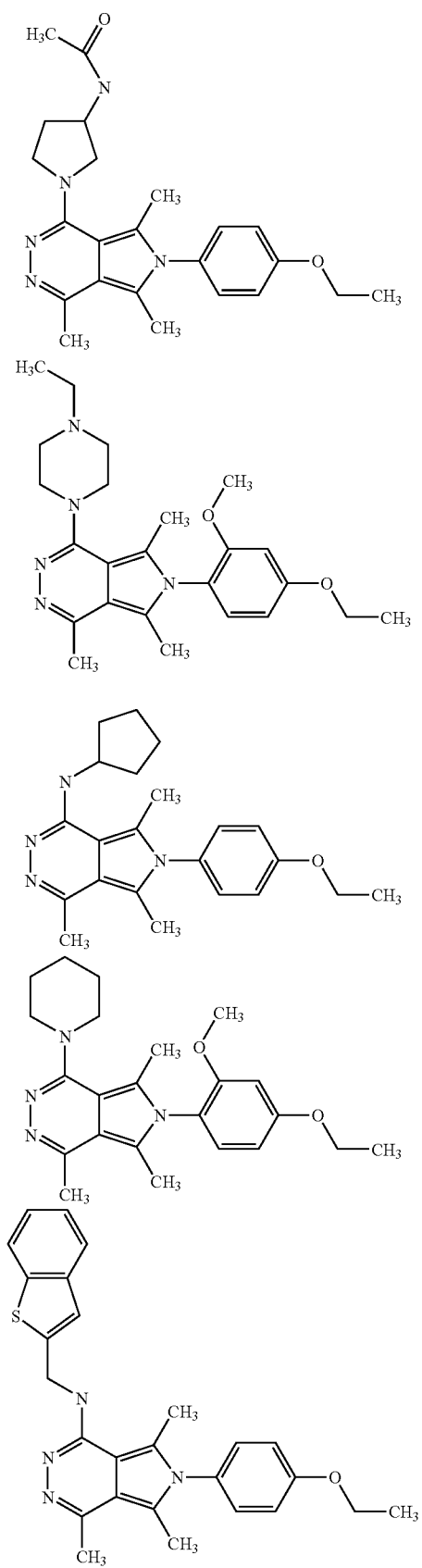
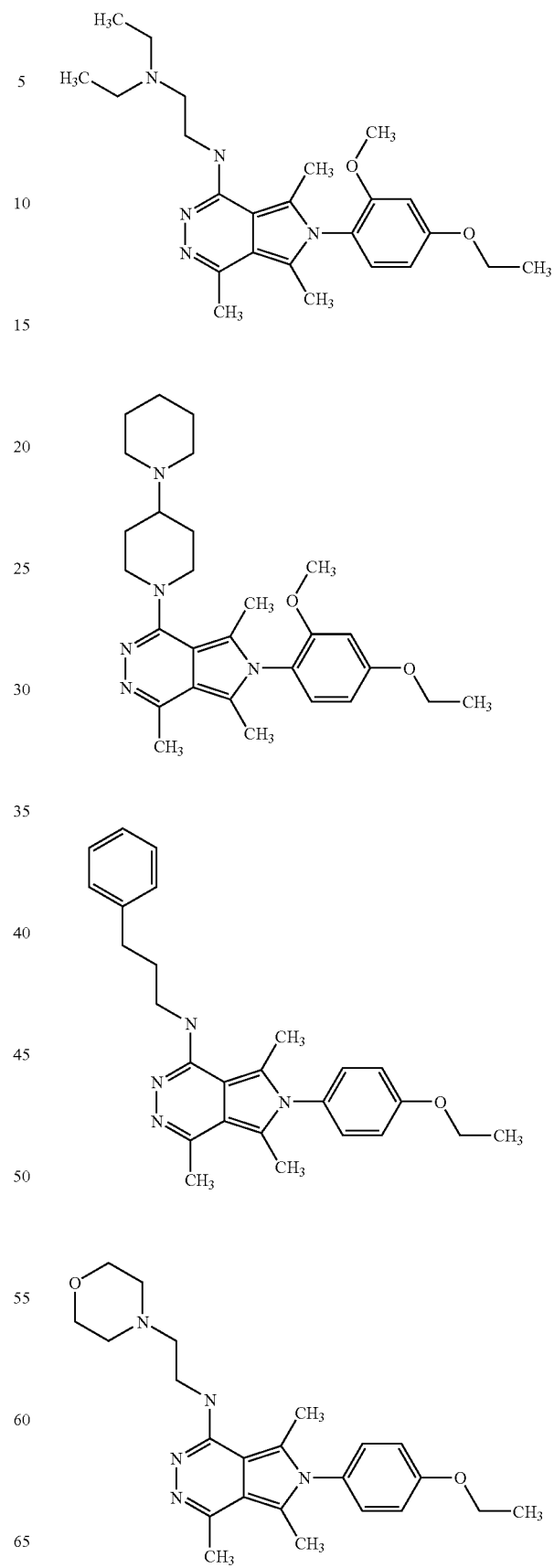

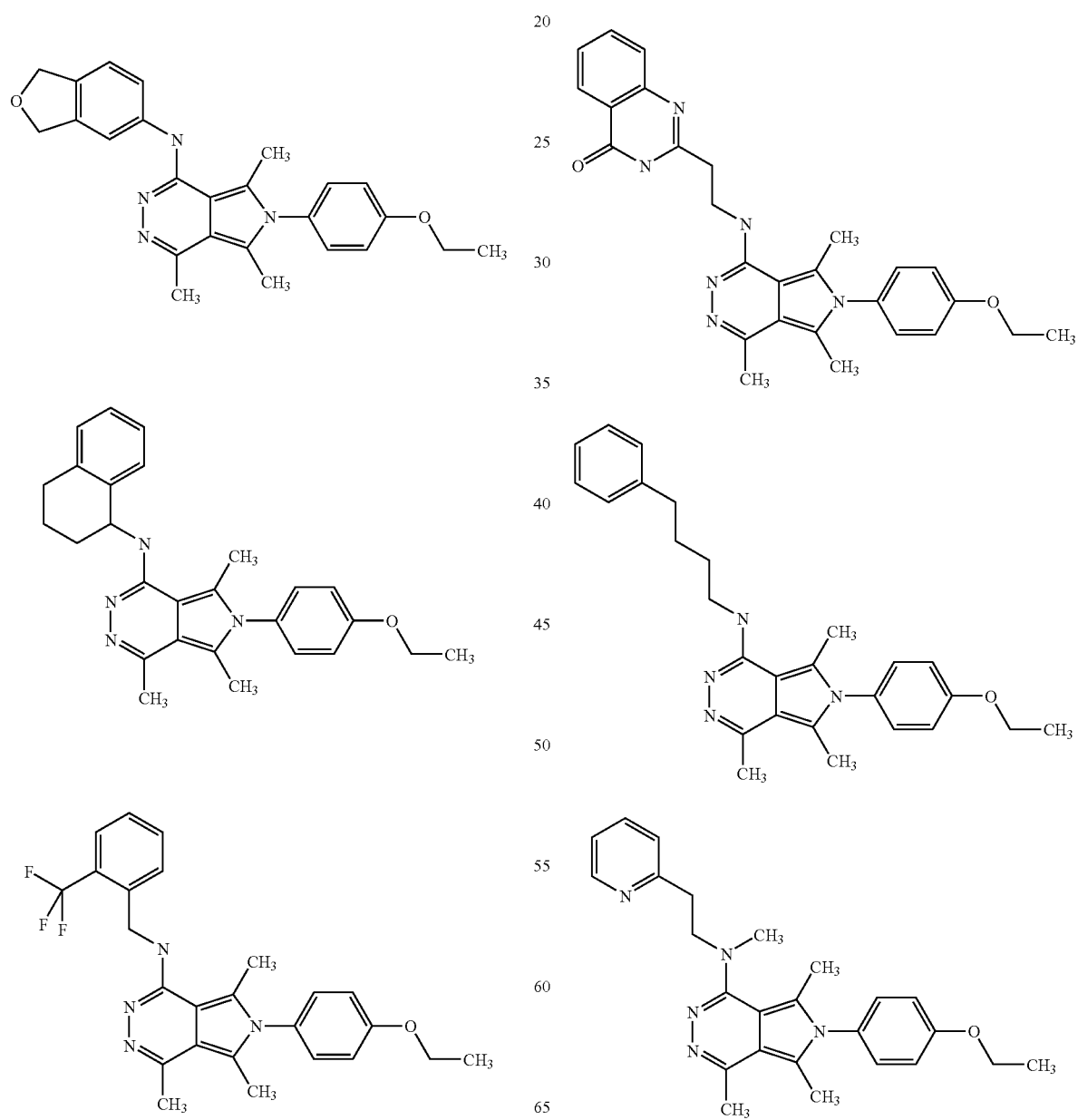

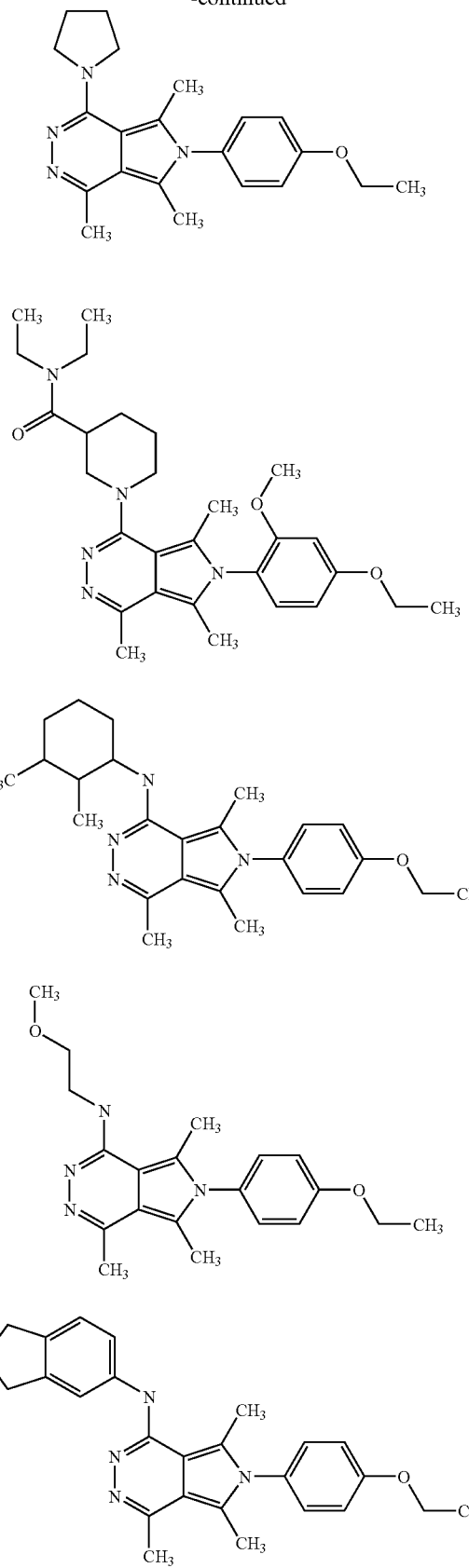
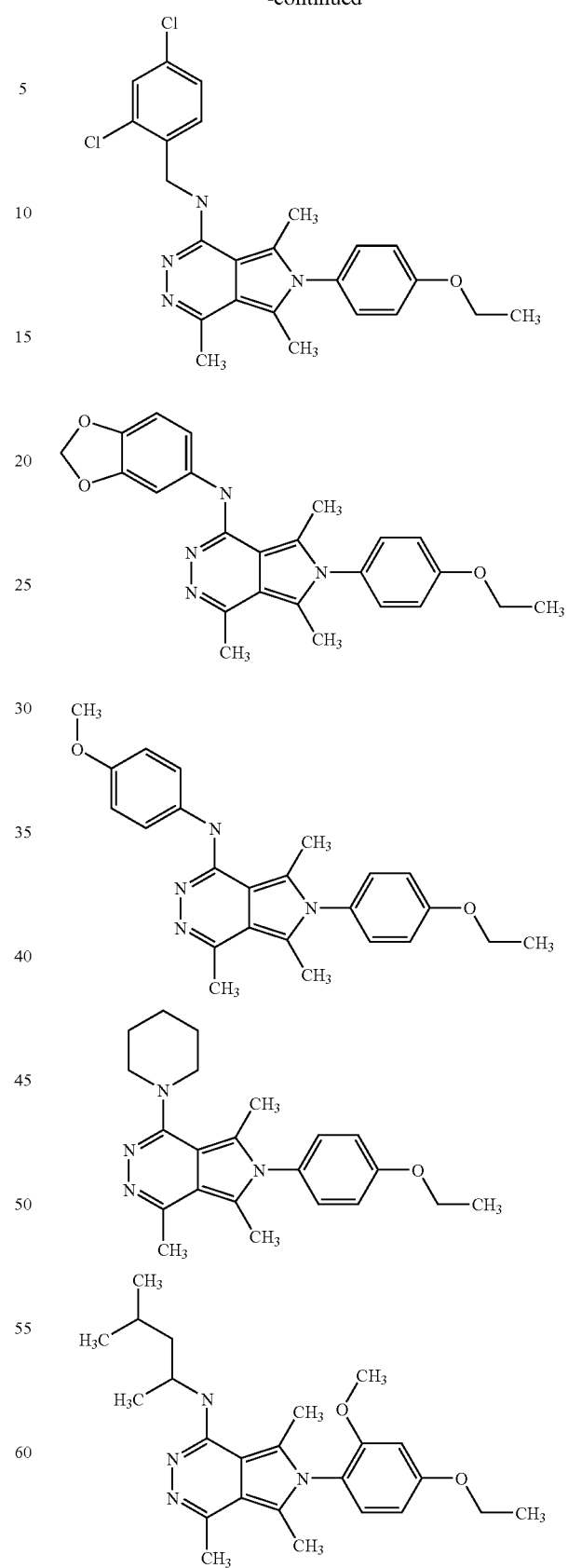

291
-continued
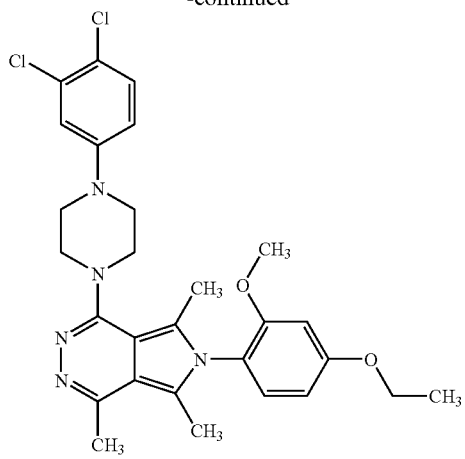
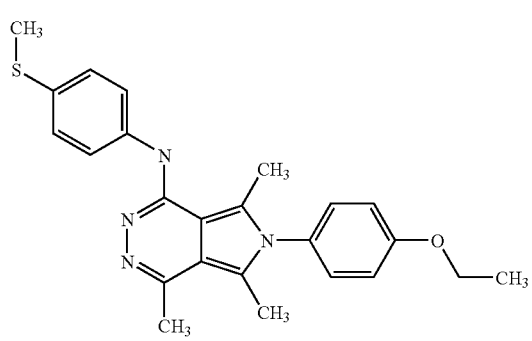
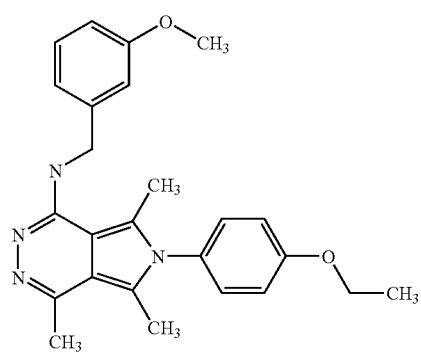
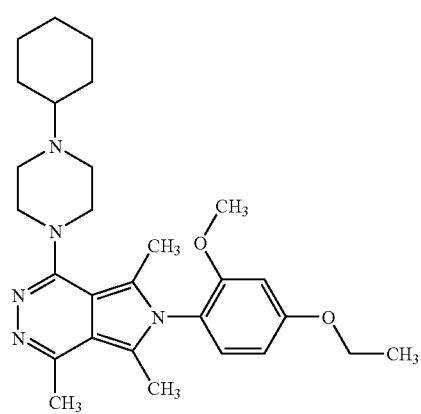
292
-continued
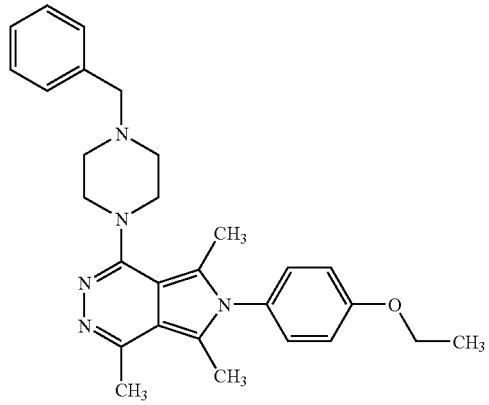
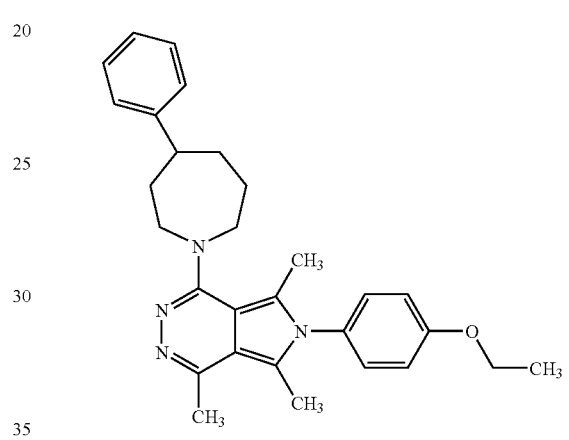
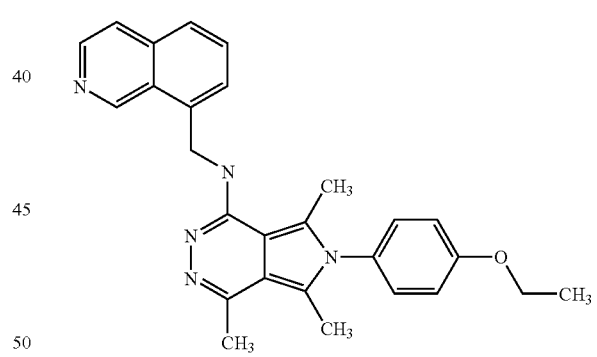
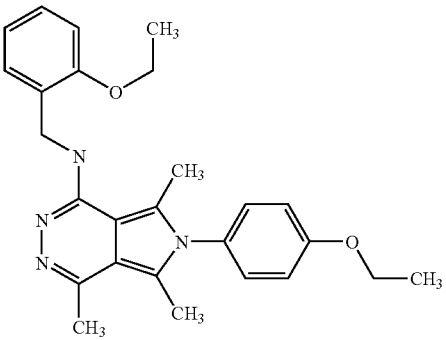

293
-continued
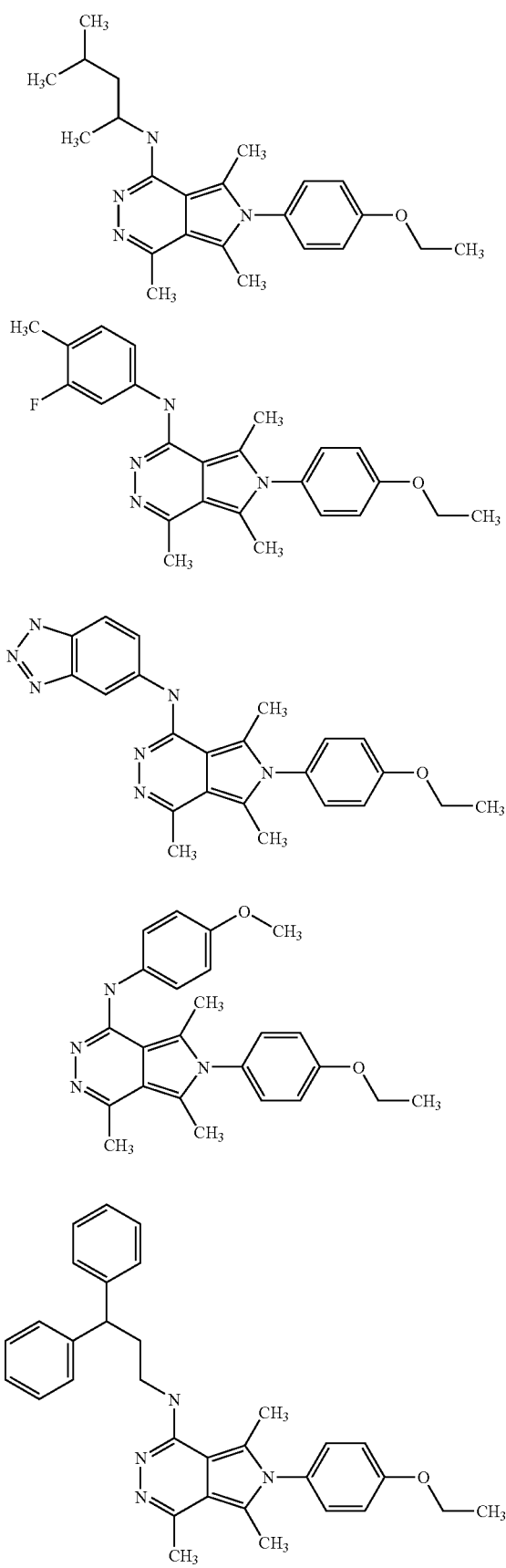
294
-continued
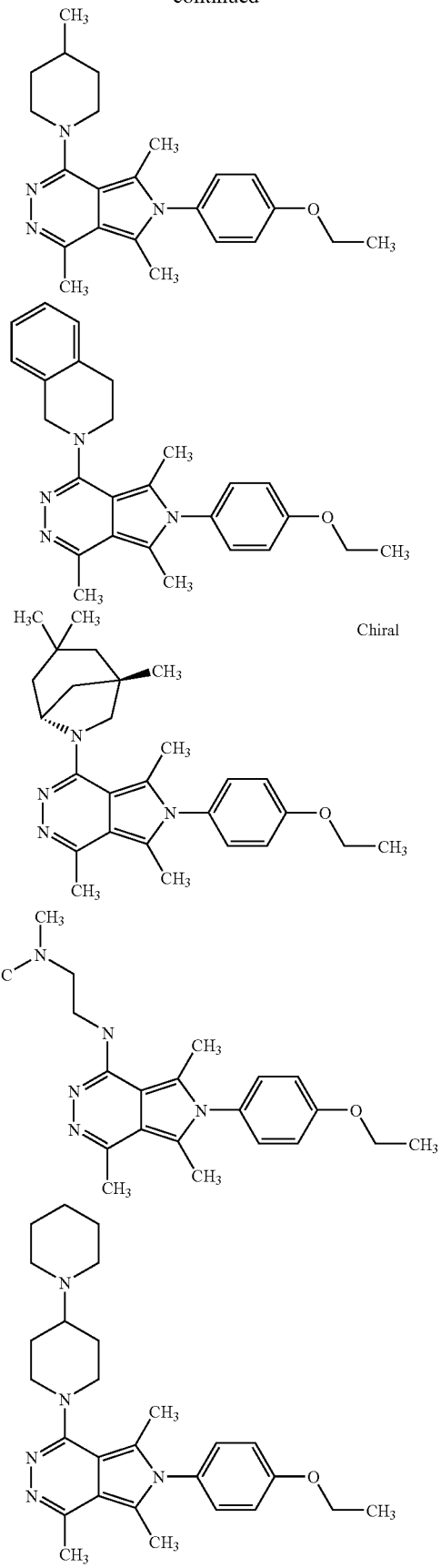

295
-continued
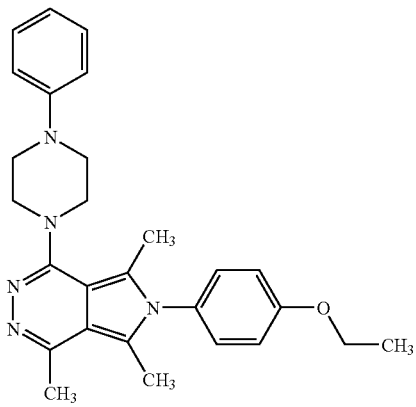
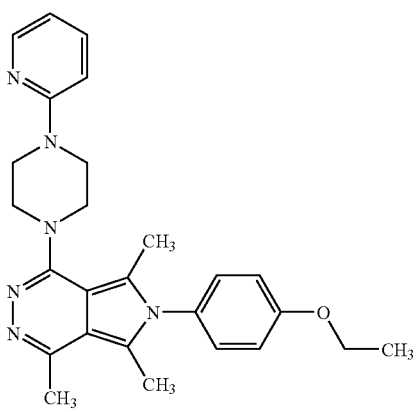
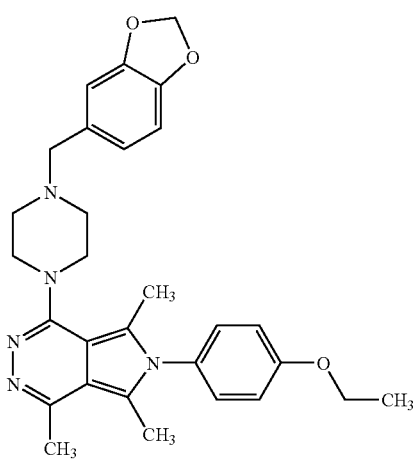
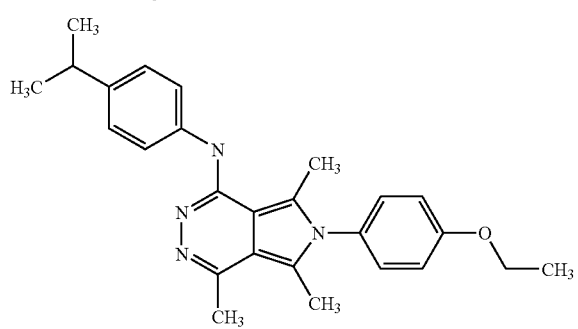
296
-continued
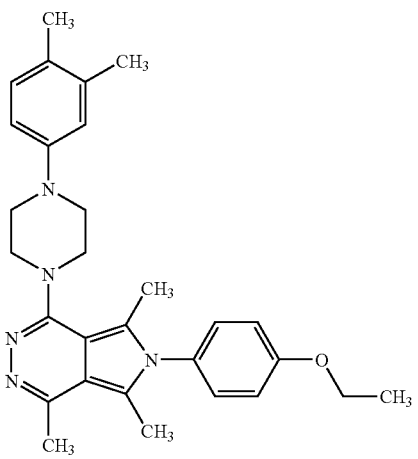
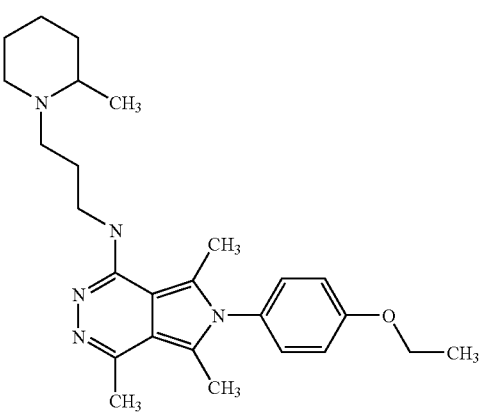
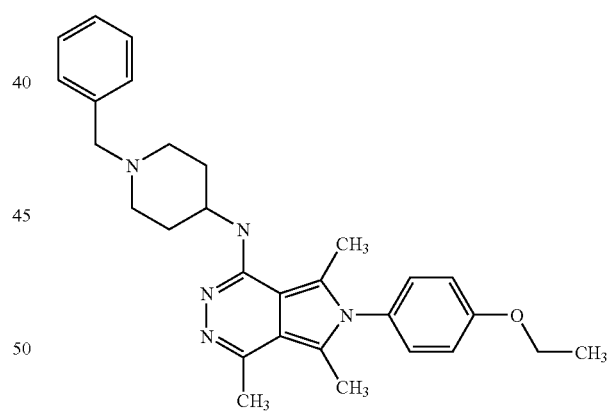
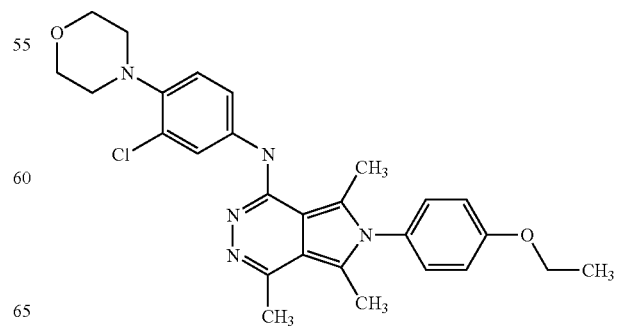

297
-continued
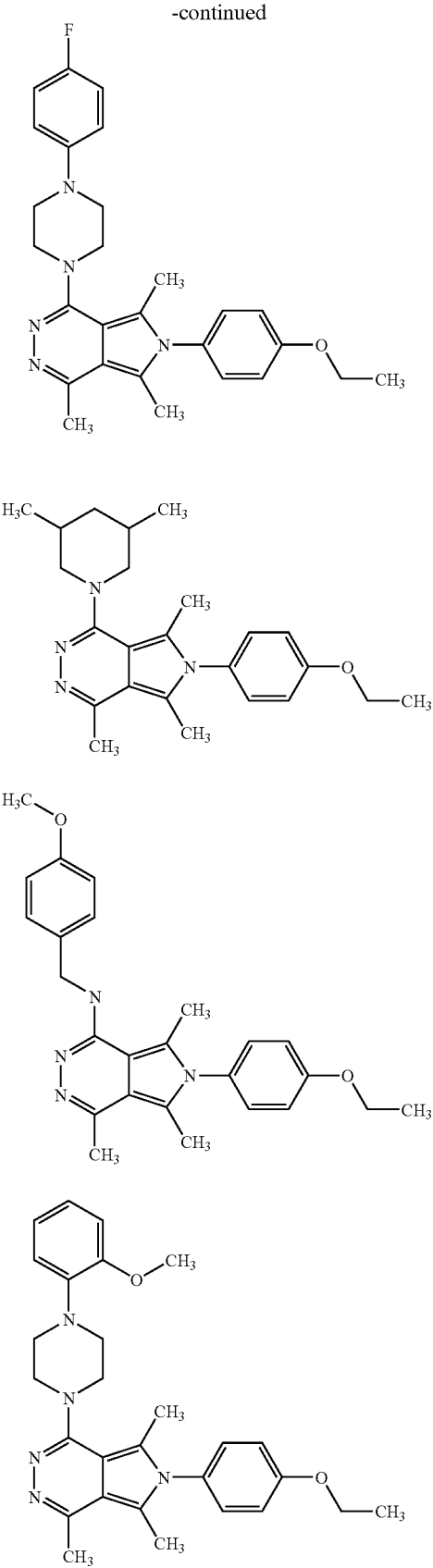
298
-continued
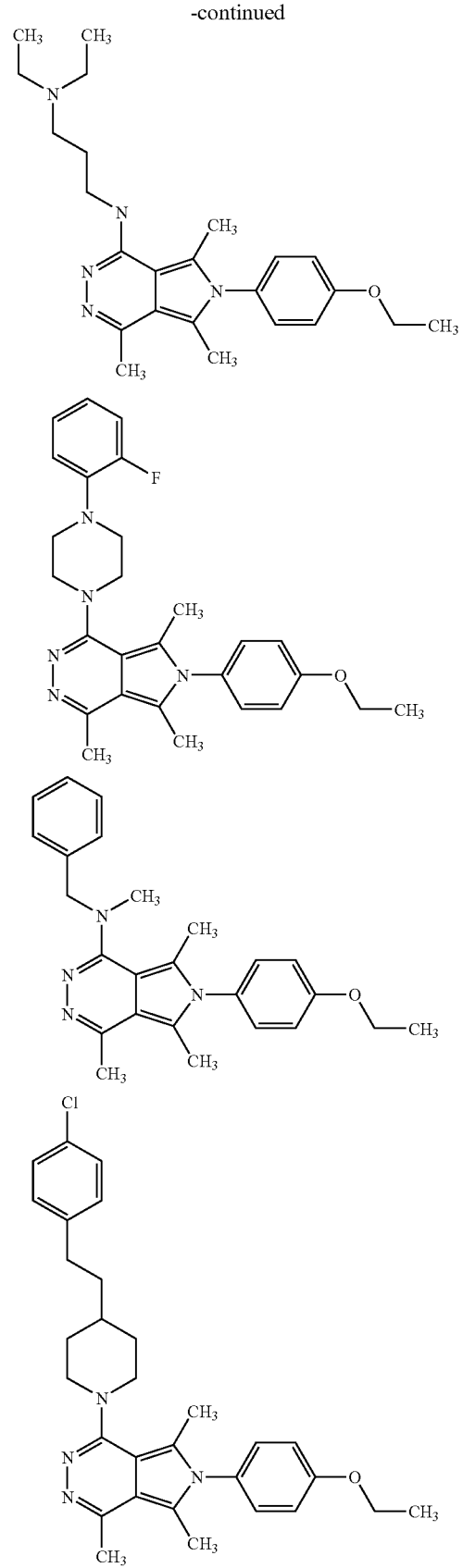

299
-continued
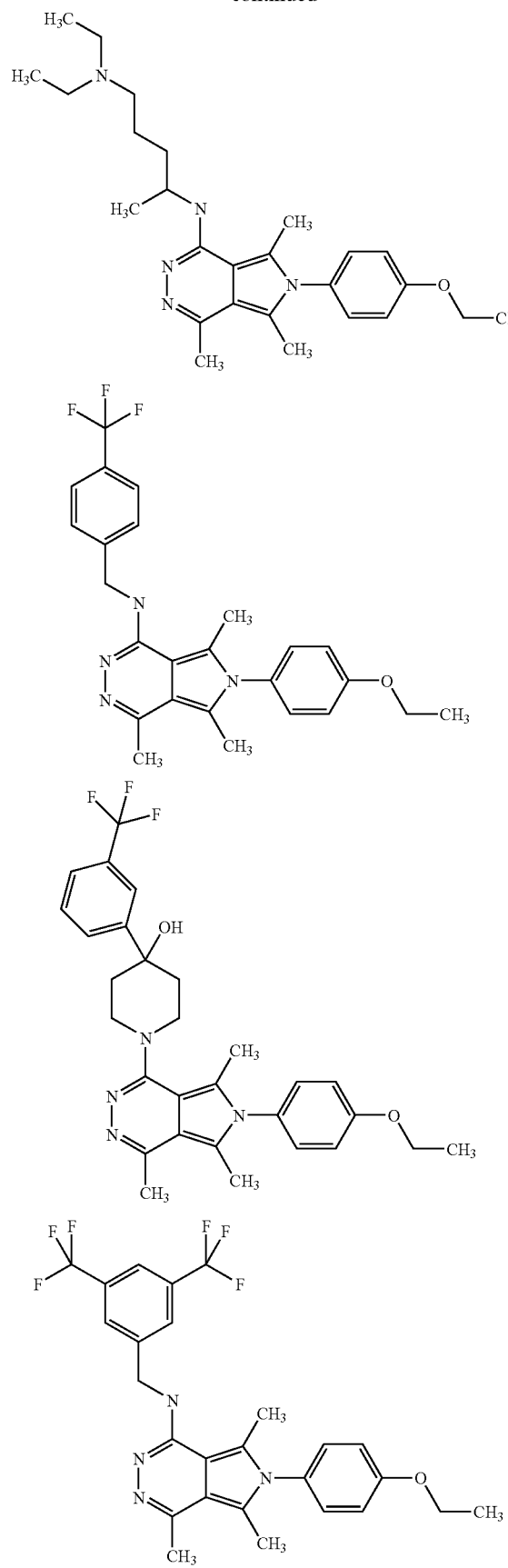
300
-continued
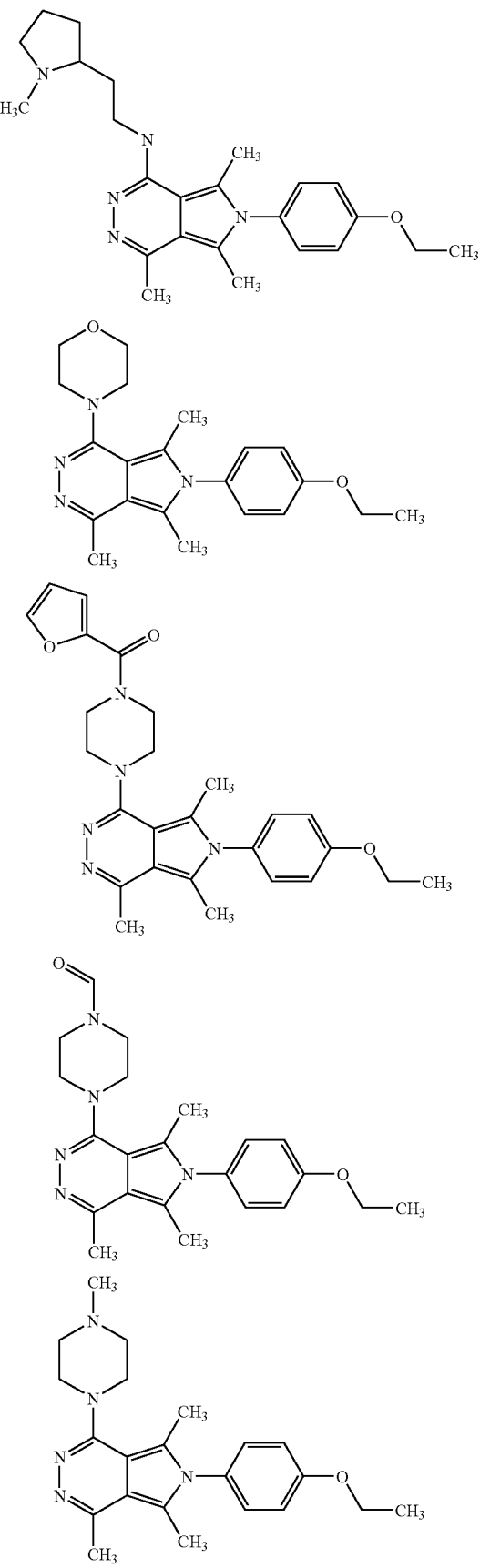

301
-continued
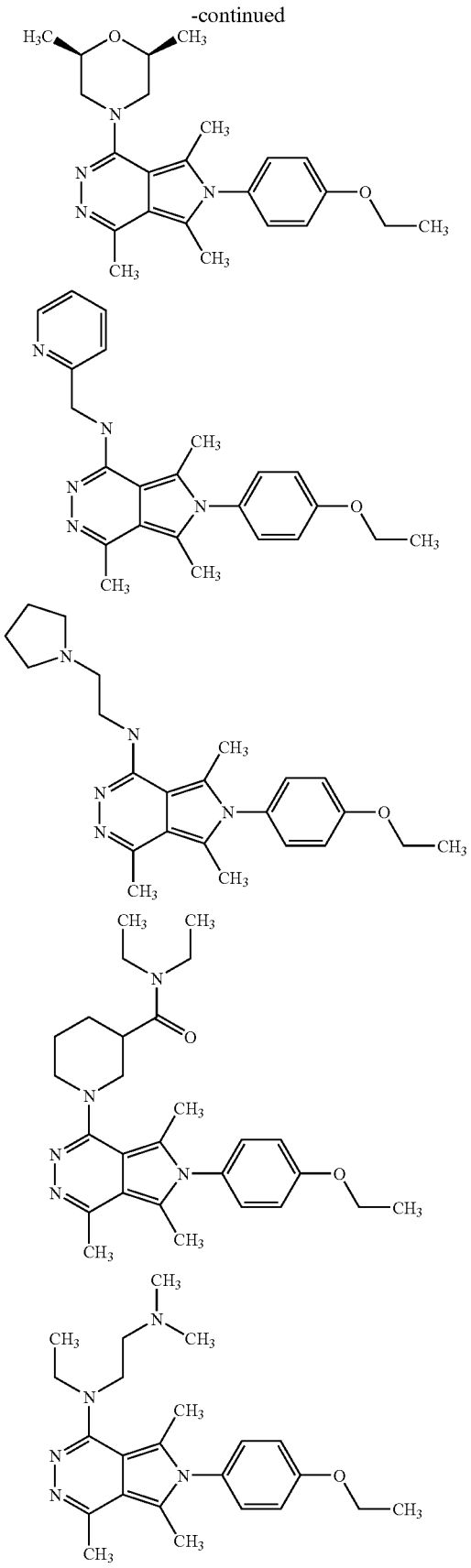
302
-continued
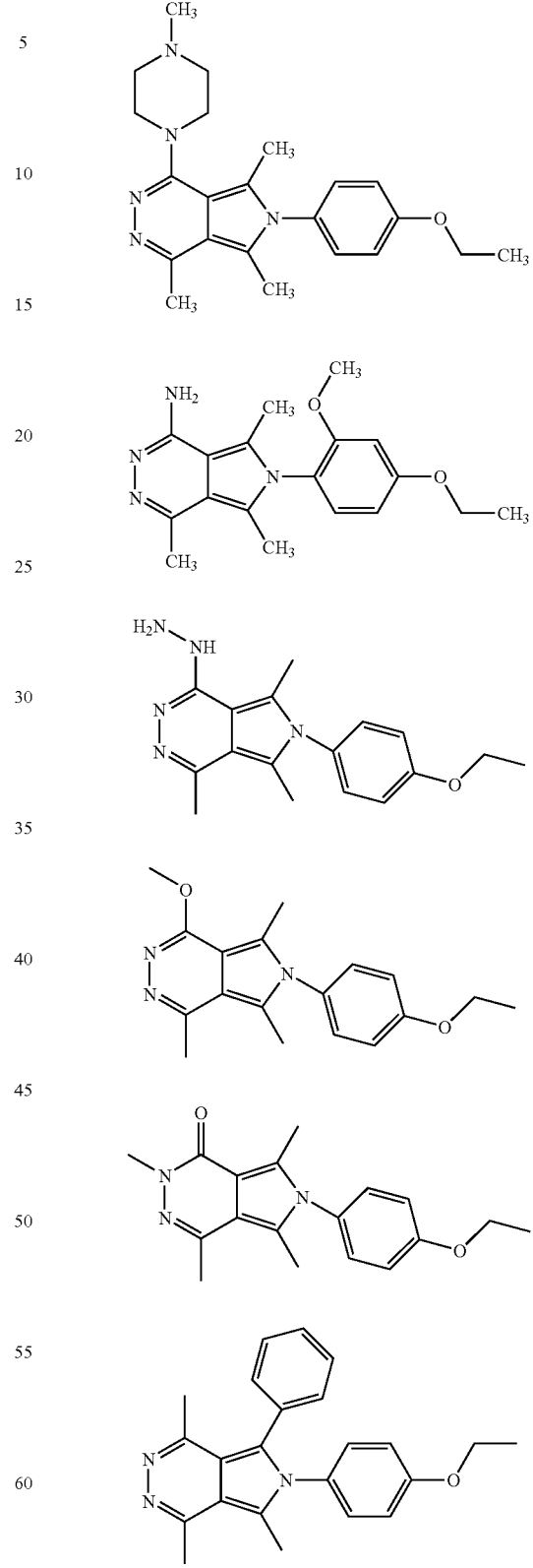
or a pharmaceutically acceptable salt thereof.

2. A compound selected from:
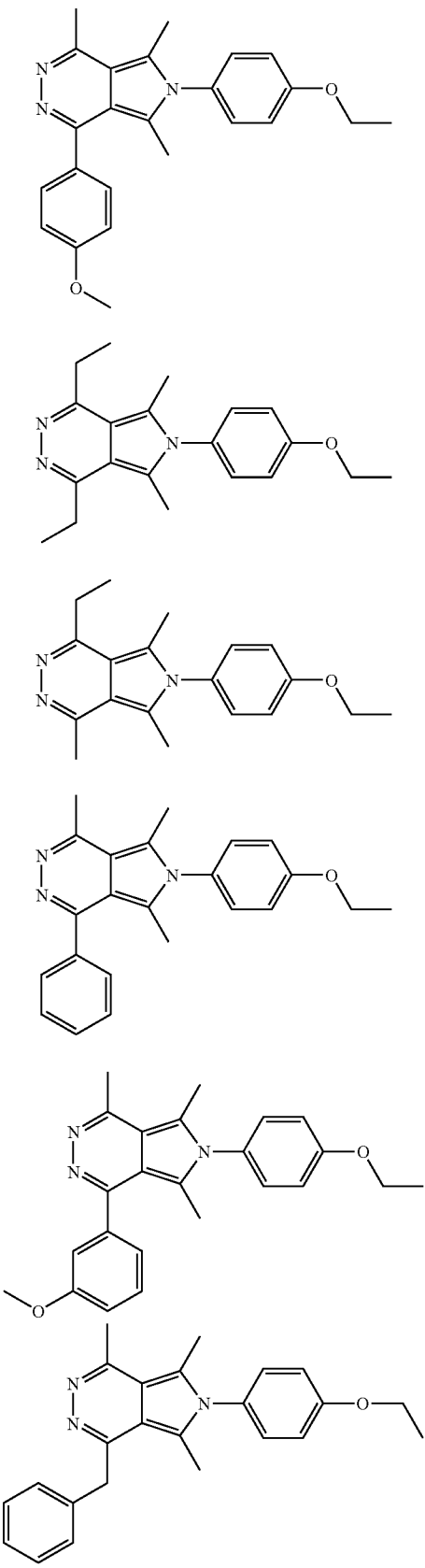
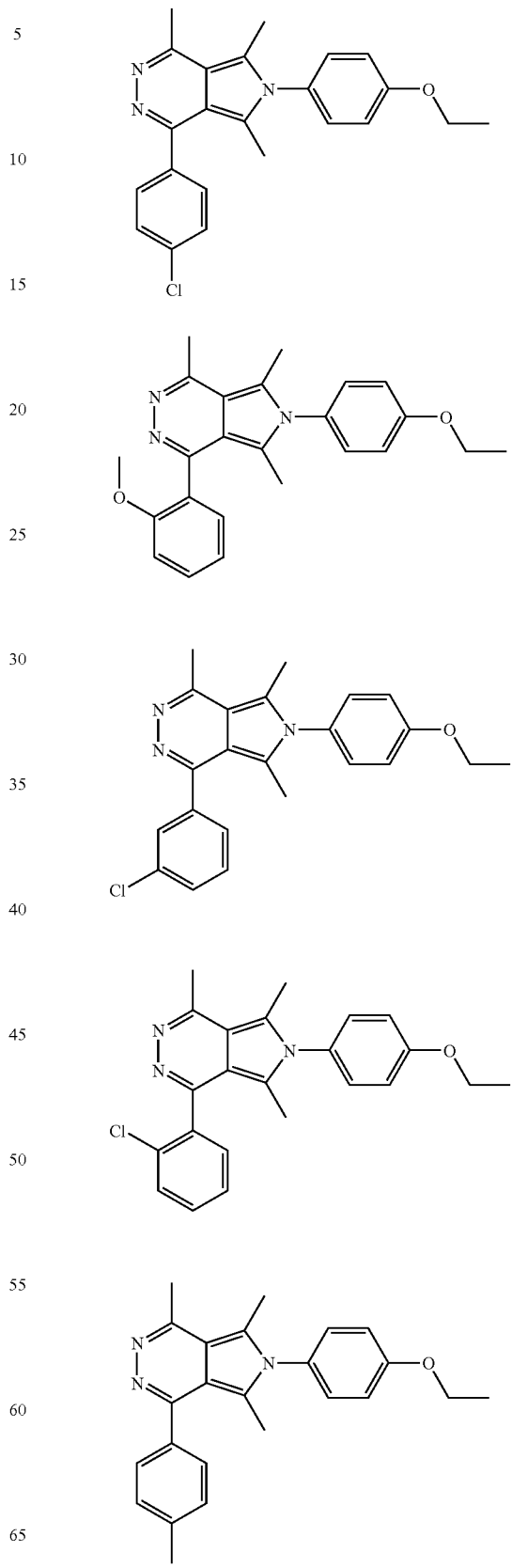

-continued
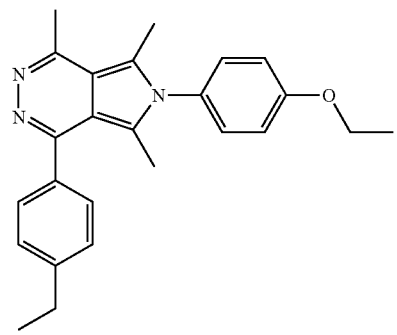
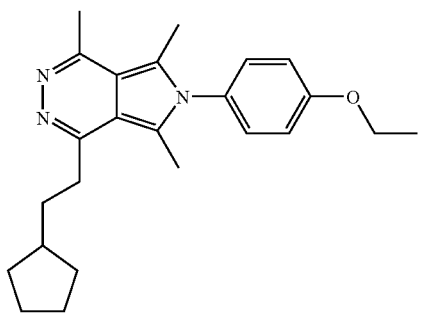
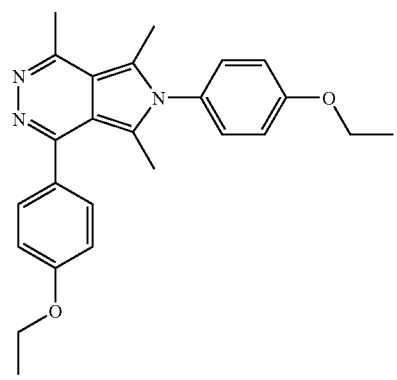
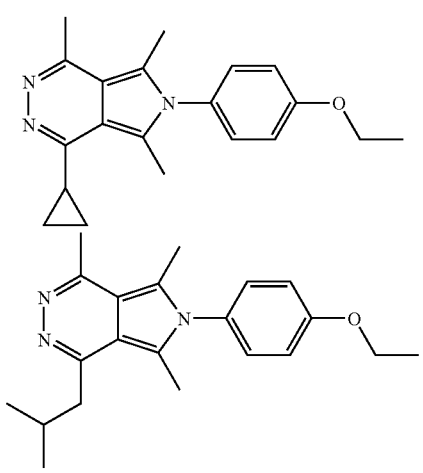
-continued
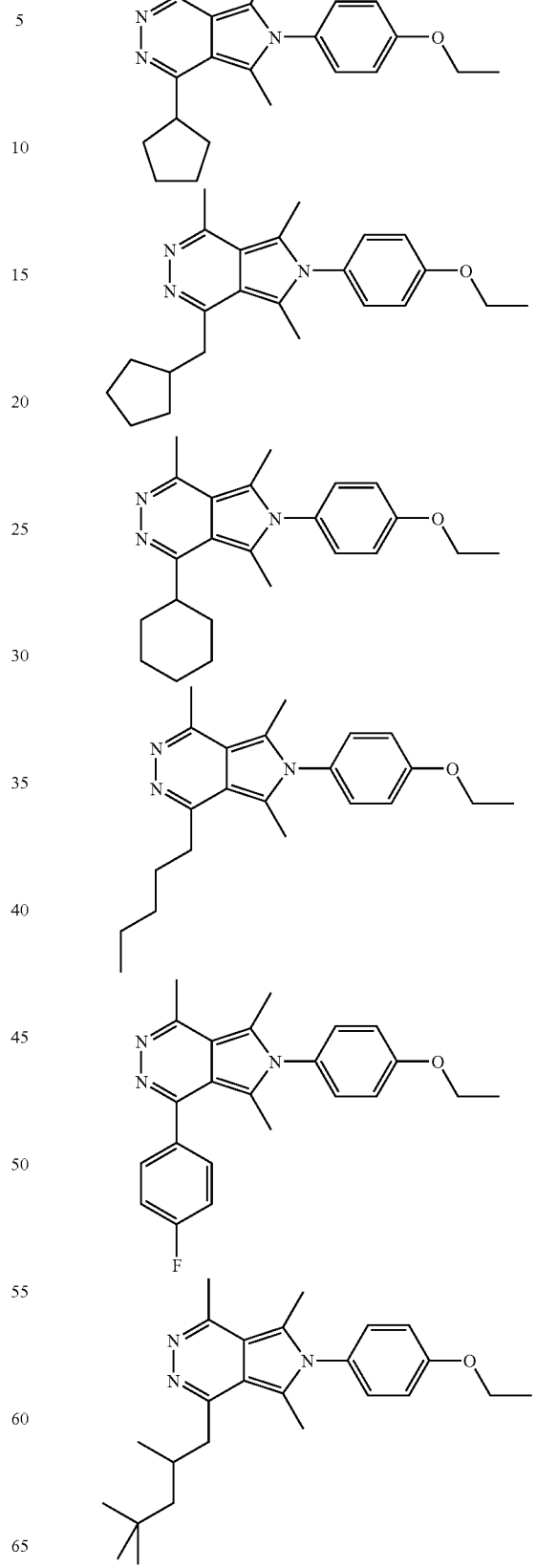

-continued
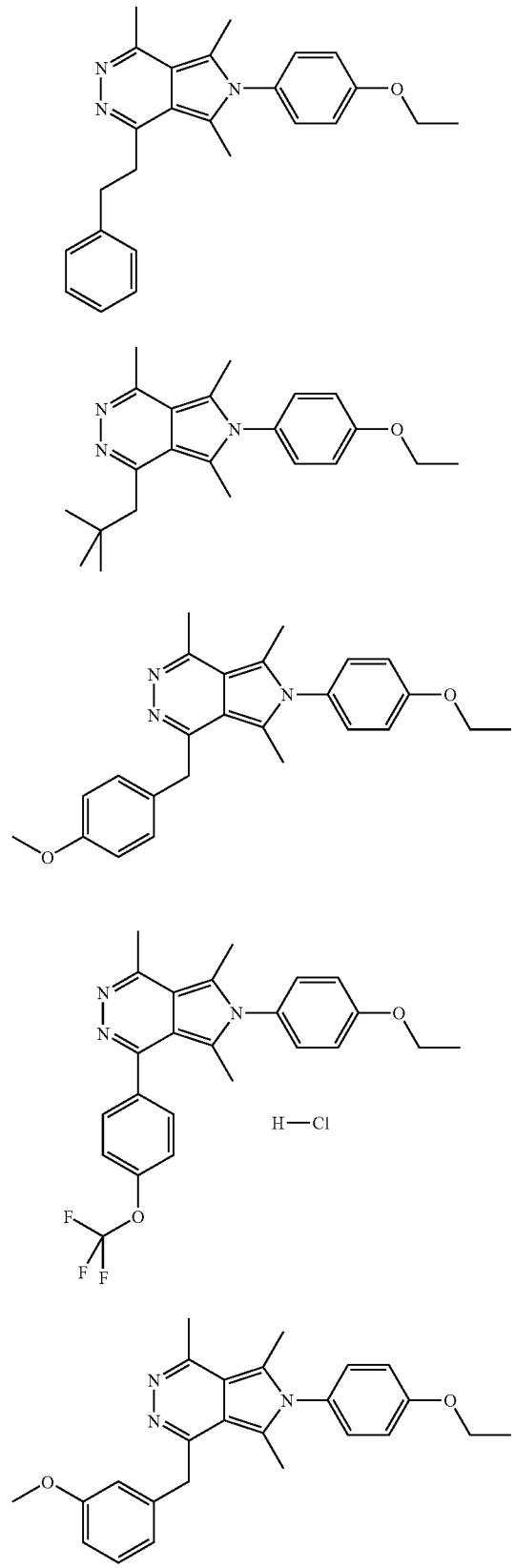
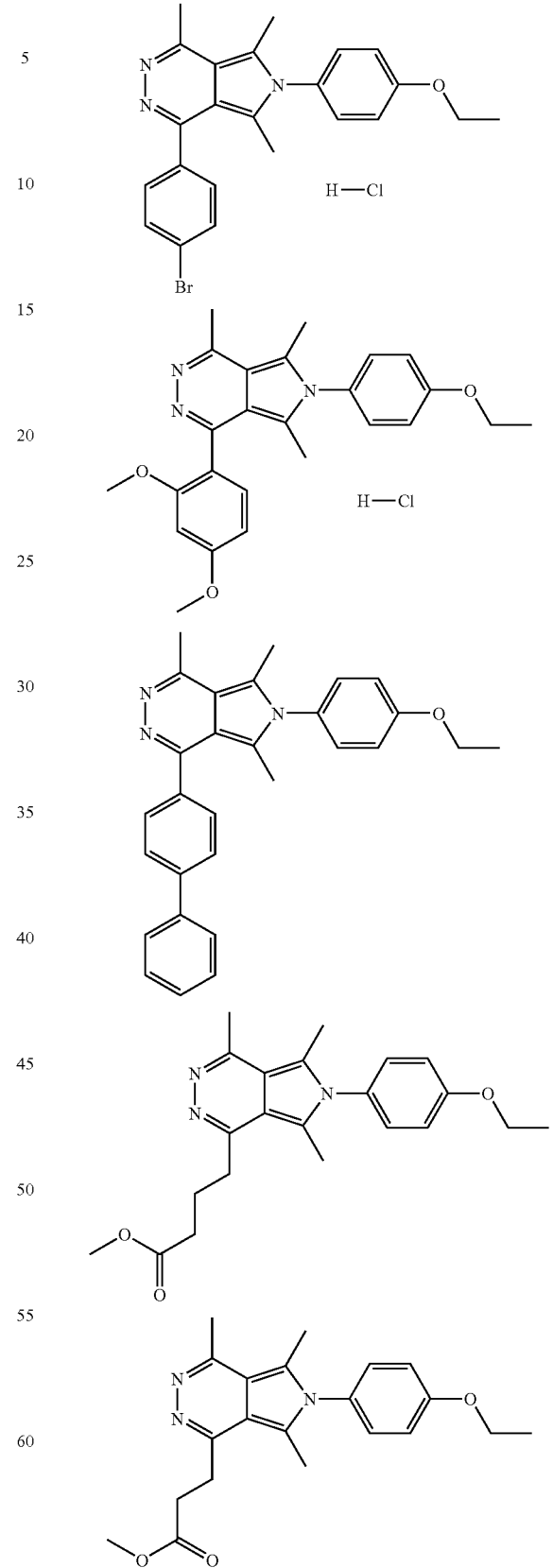

309
-continued
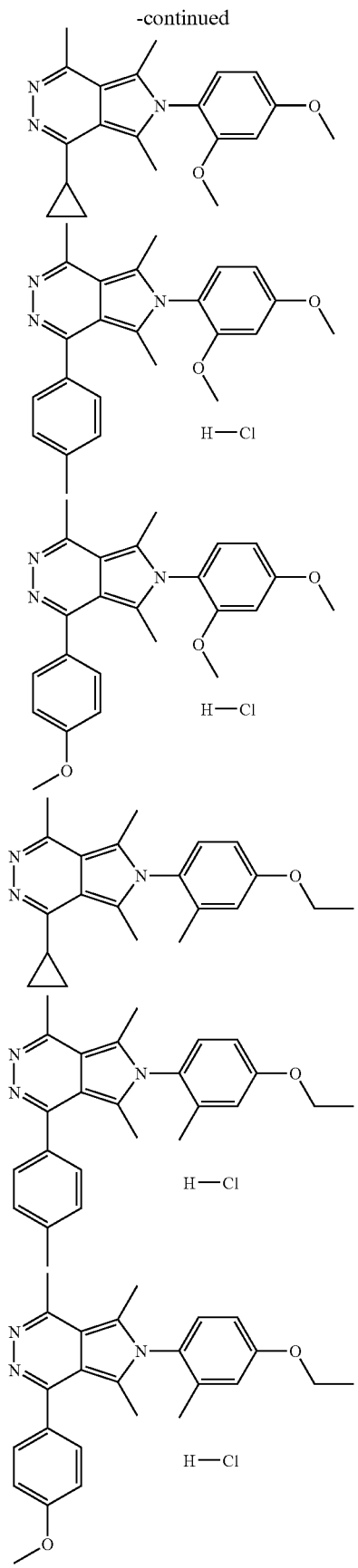
310
-continued
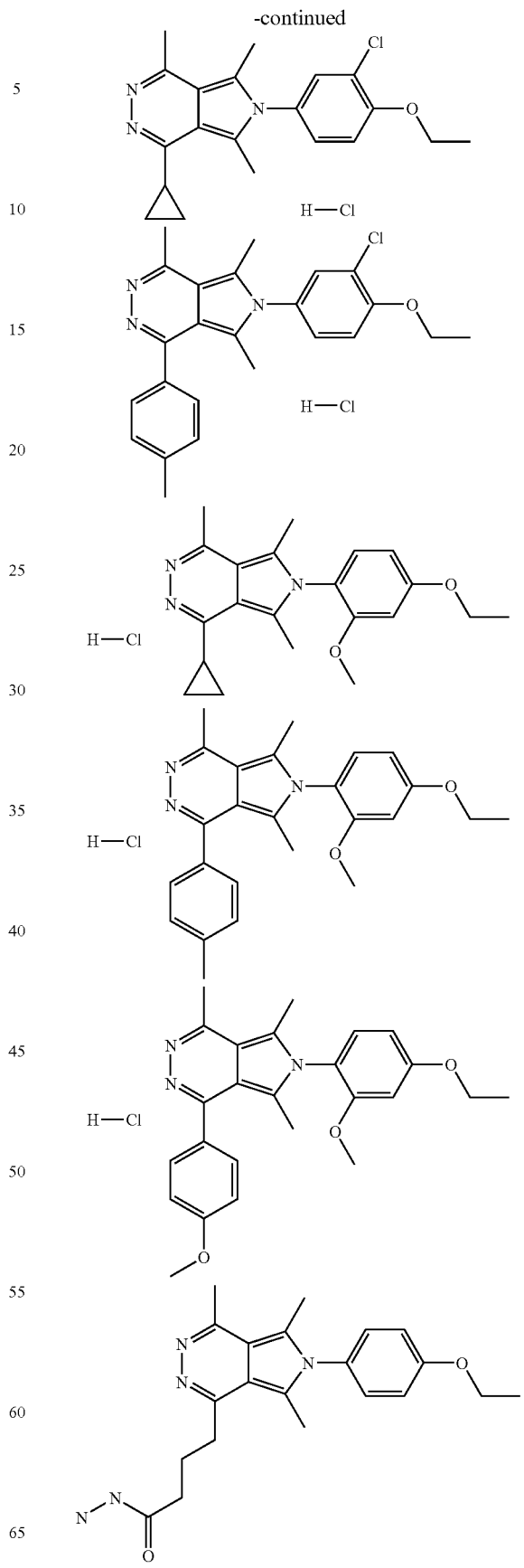

311
-continued
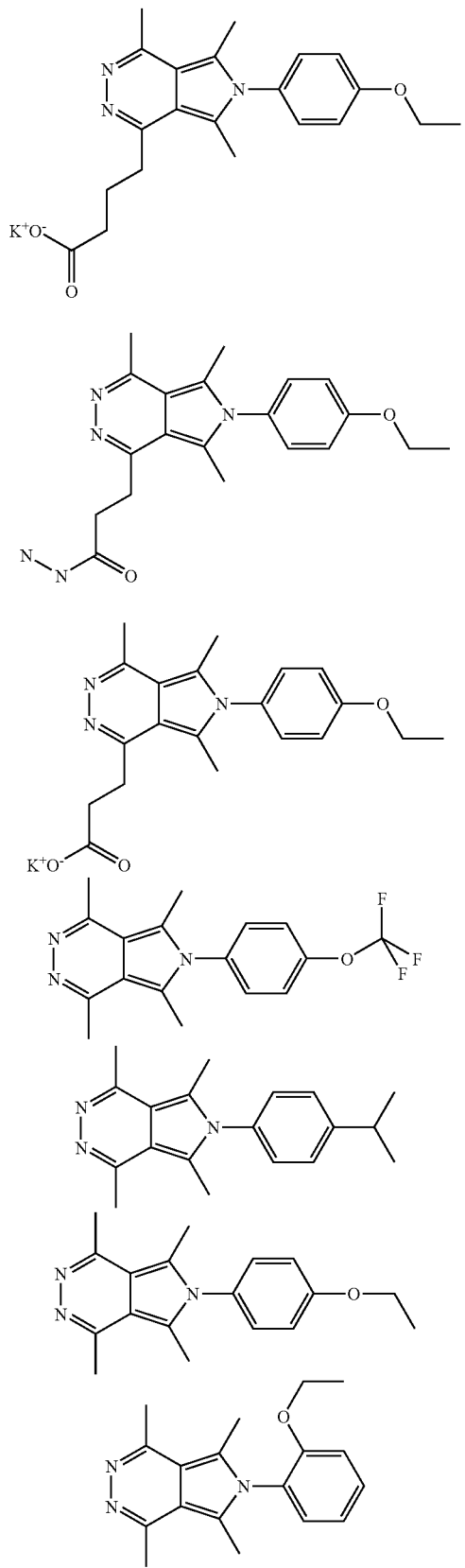
312
-continued
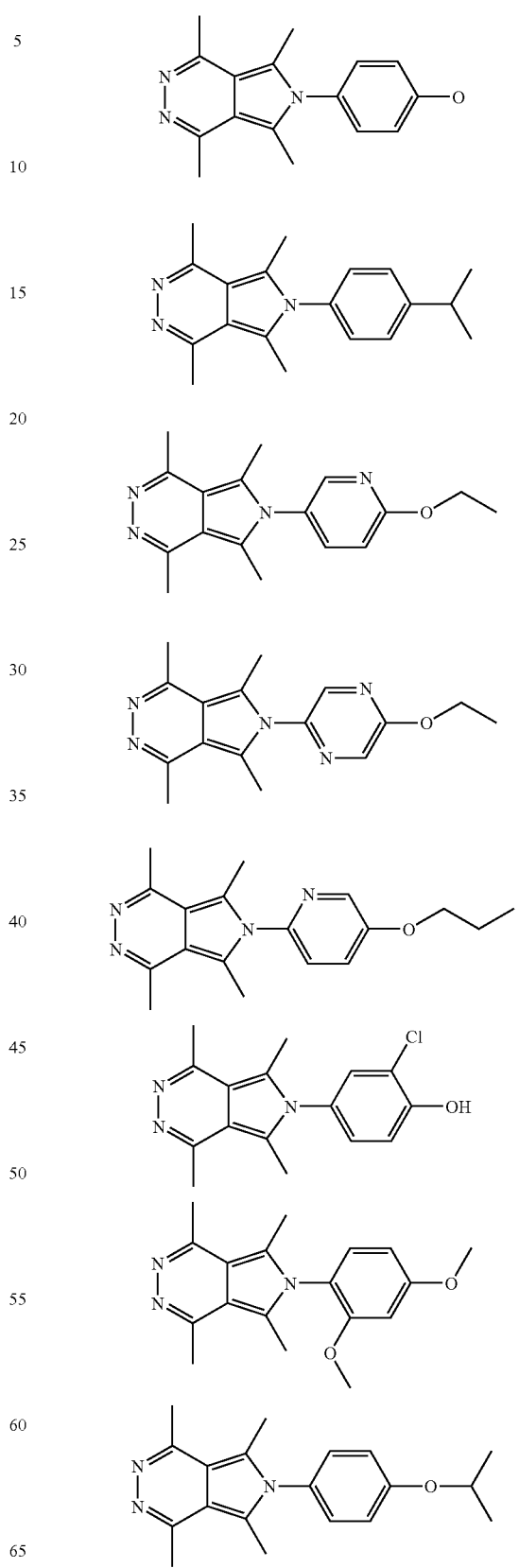

313
-continued
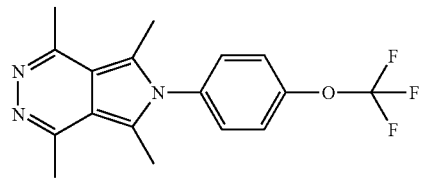
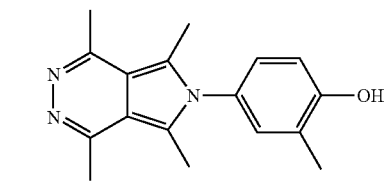
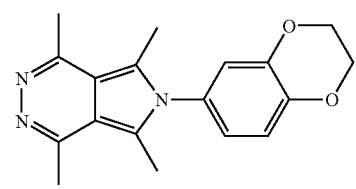
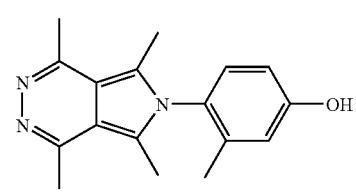
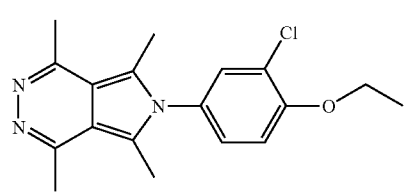
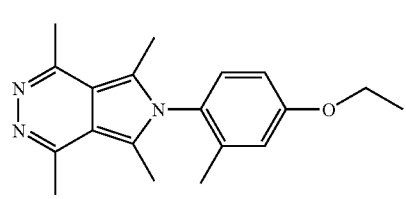
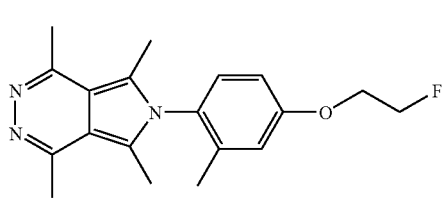
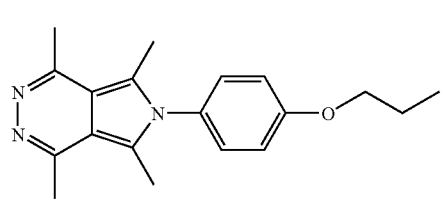
314
-continued
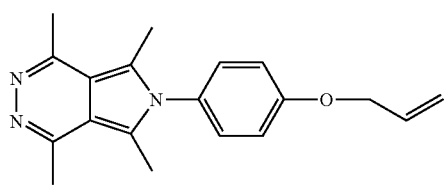
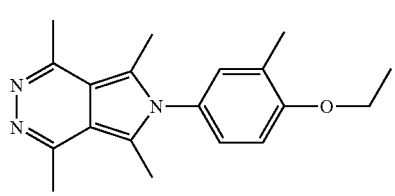
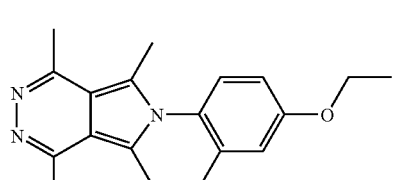
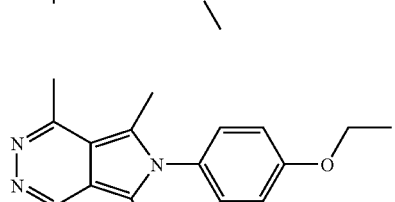
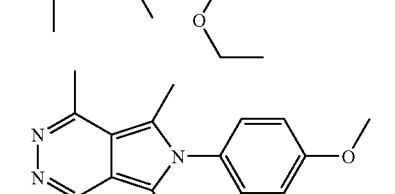
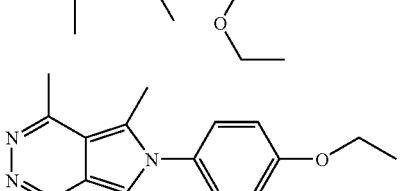
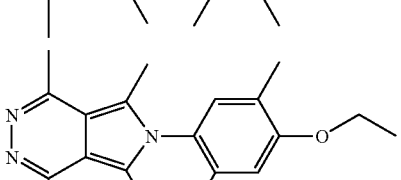
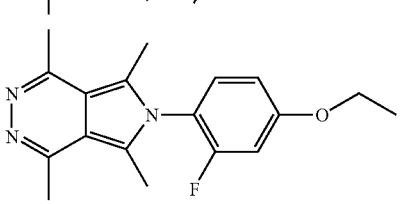

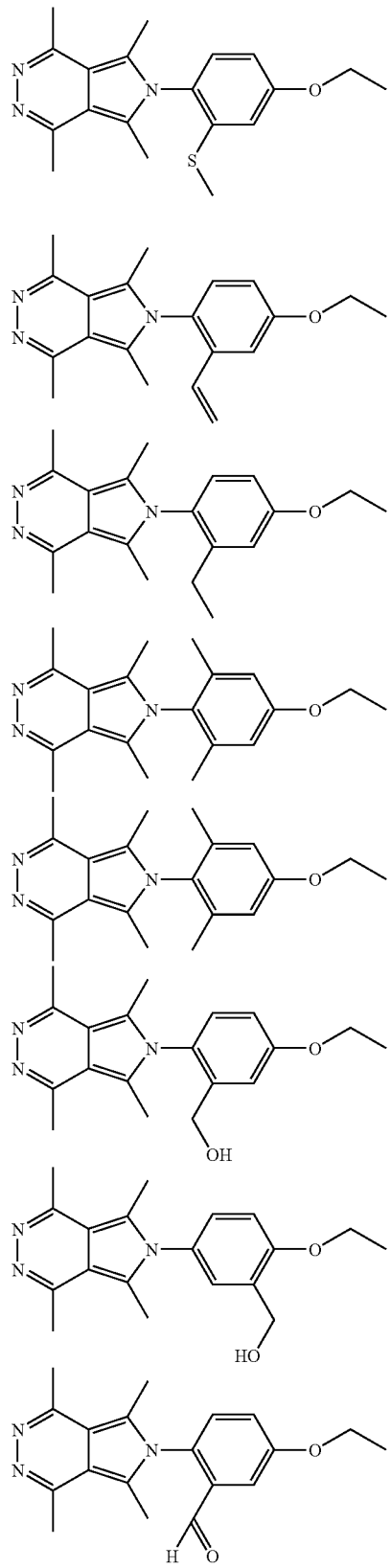
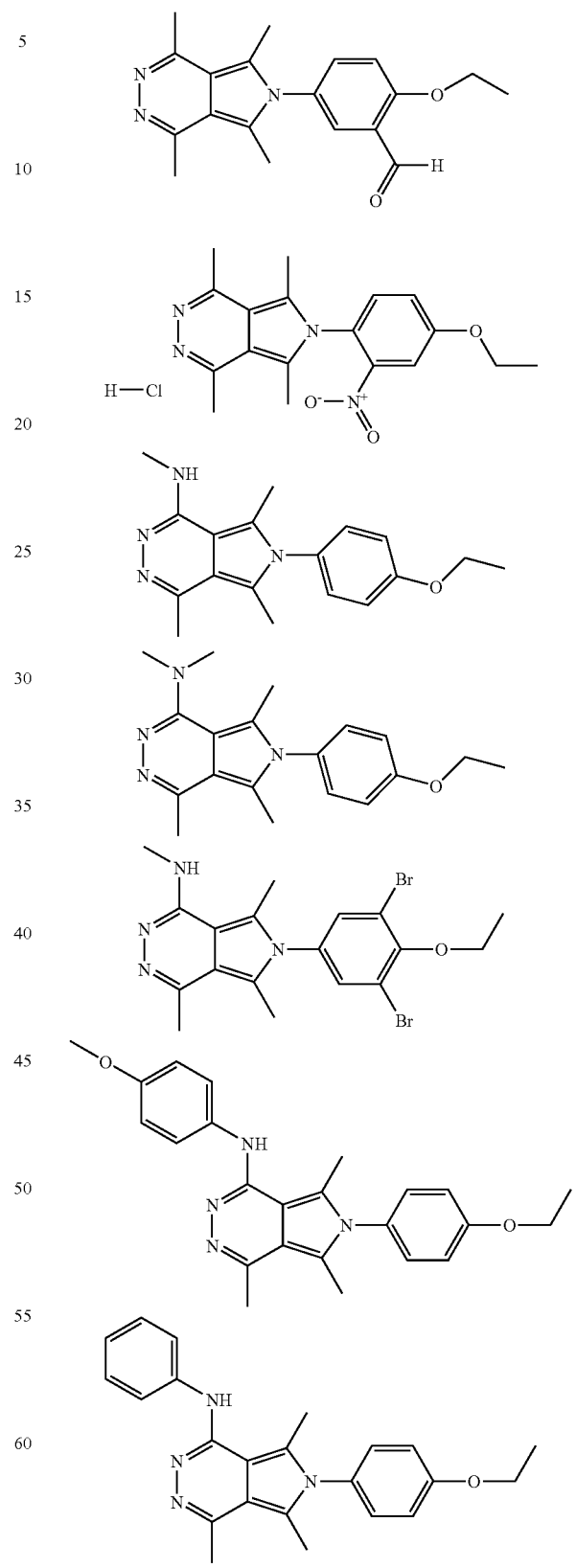

317
-continued
318
-continued
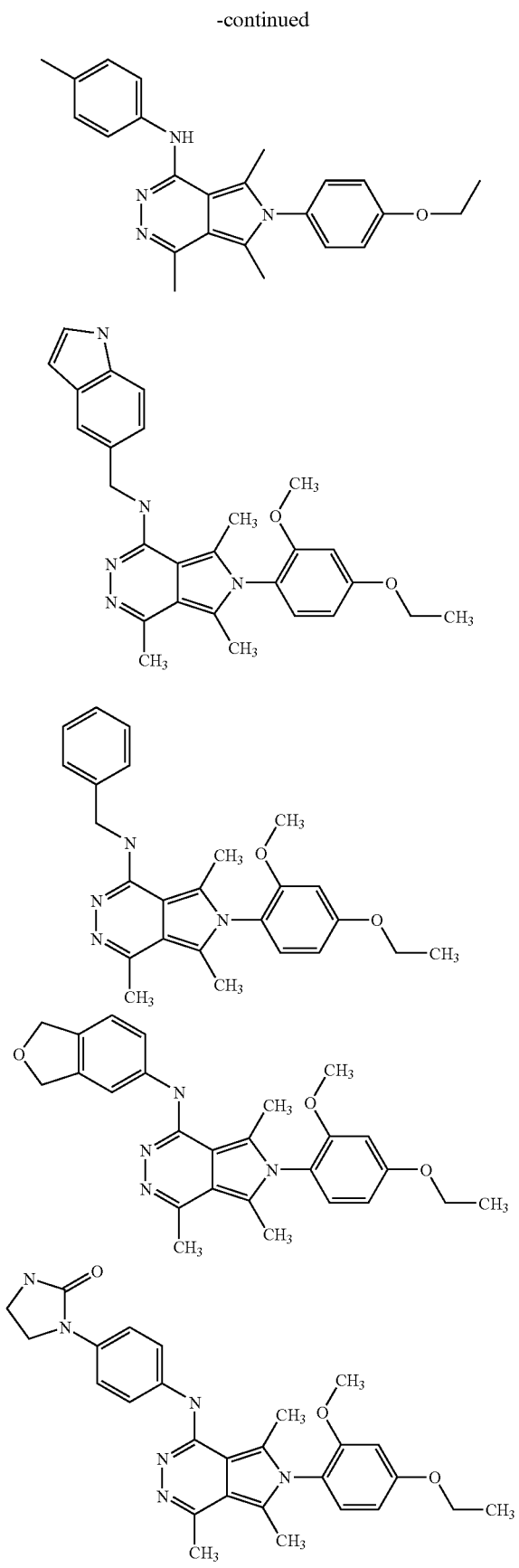
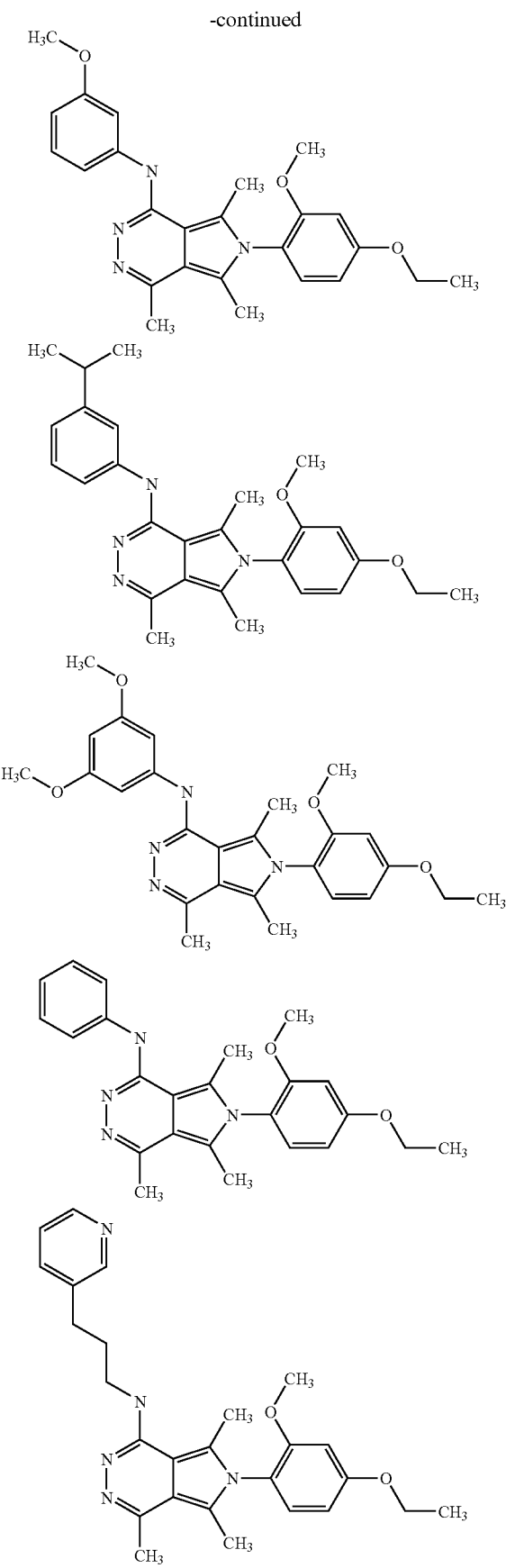

319
-continued
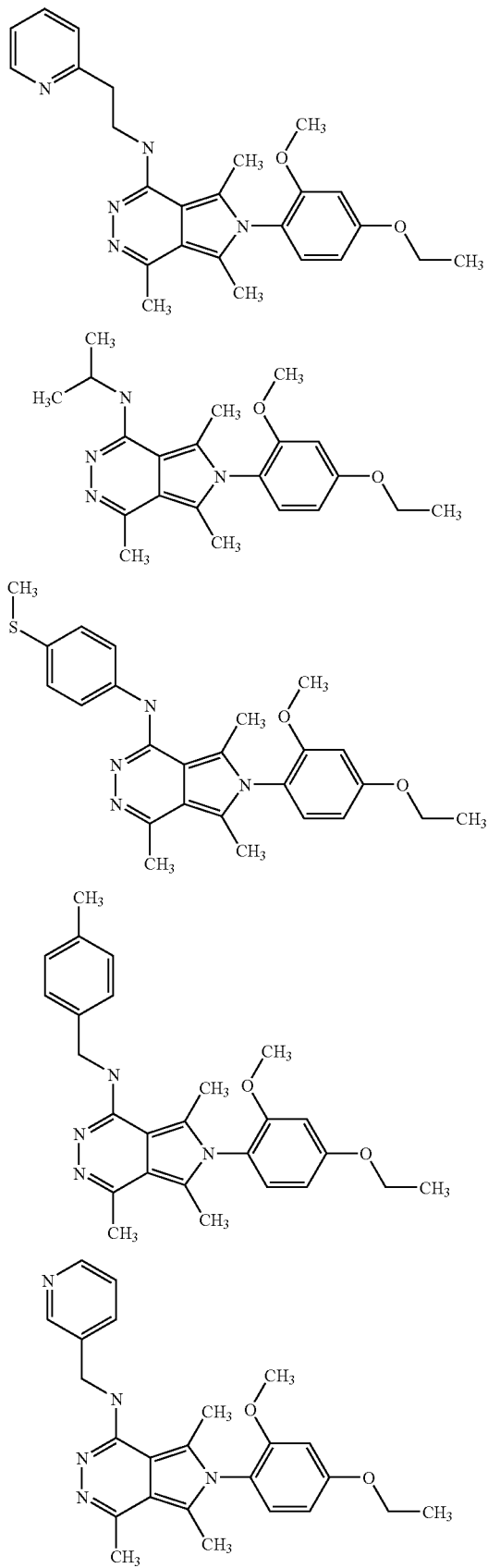
320
-continued
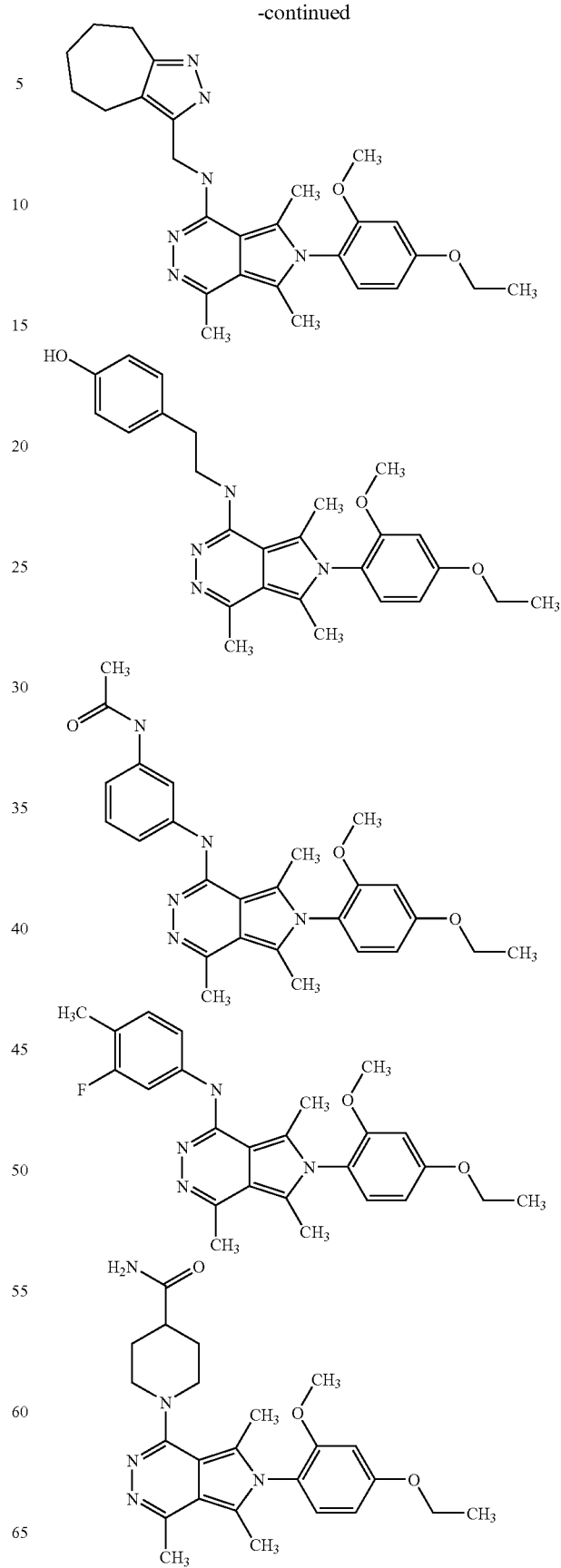

321
-continued
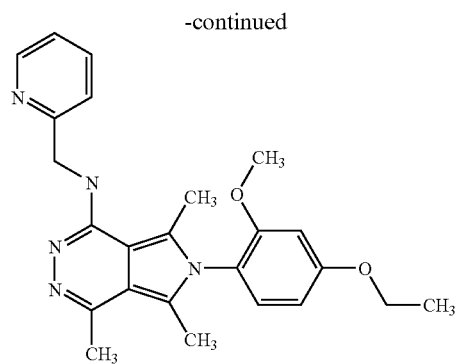
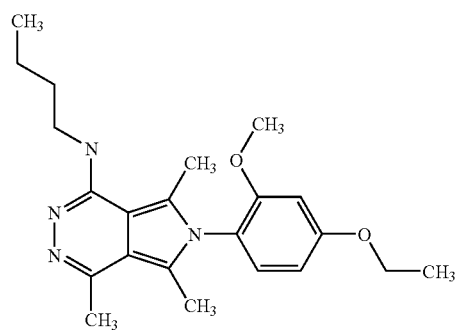
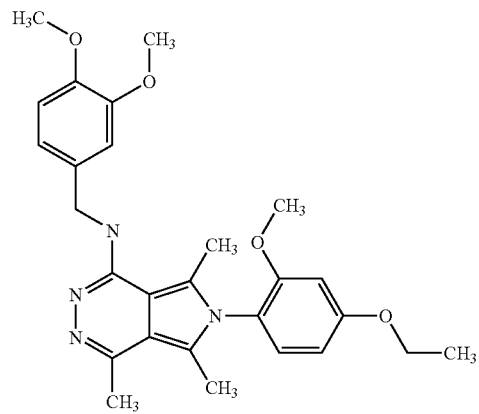
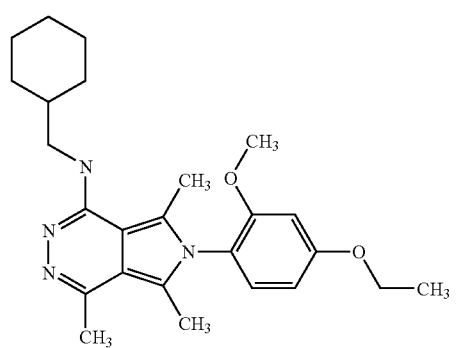
322
-continued
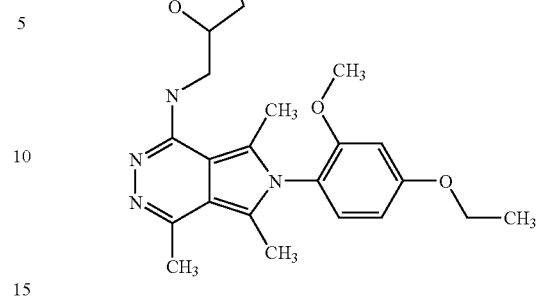
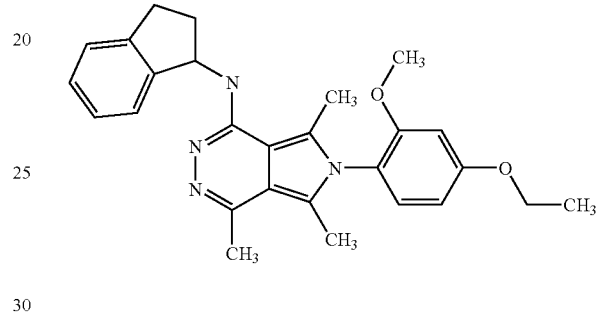
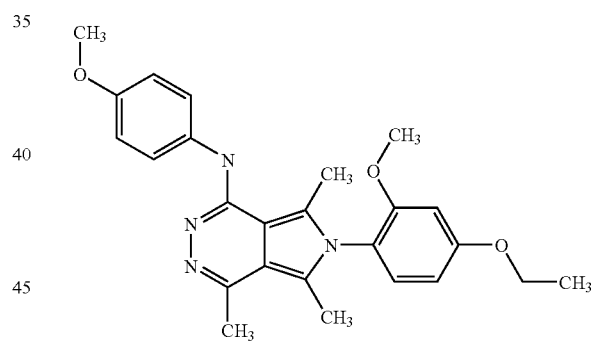
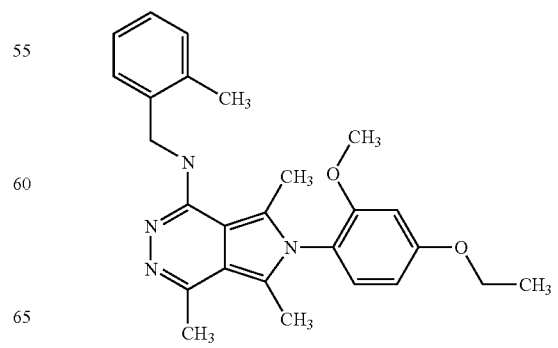

323
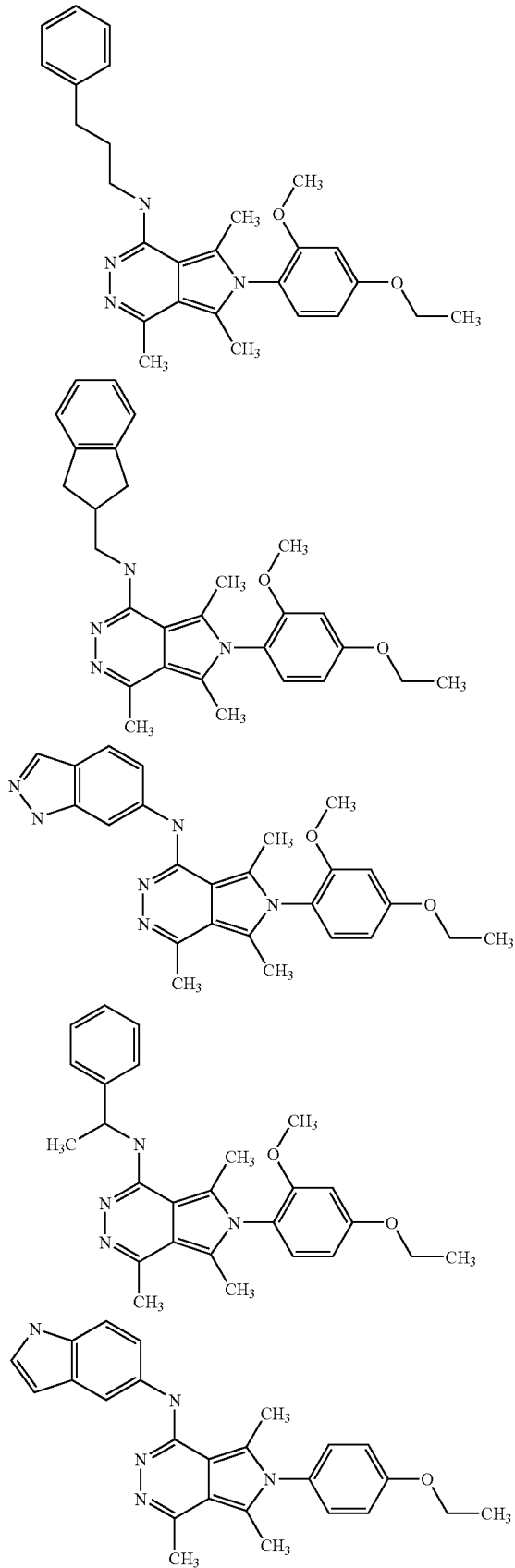
324
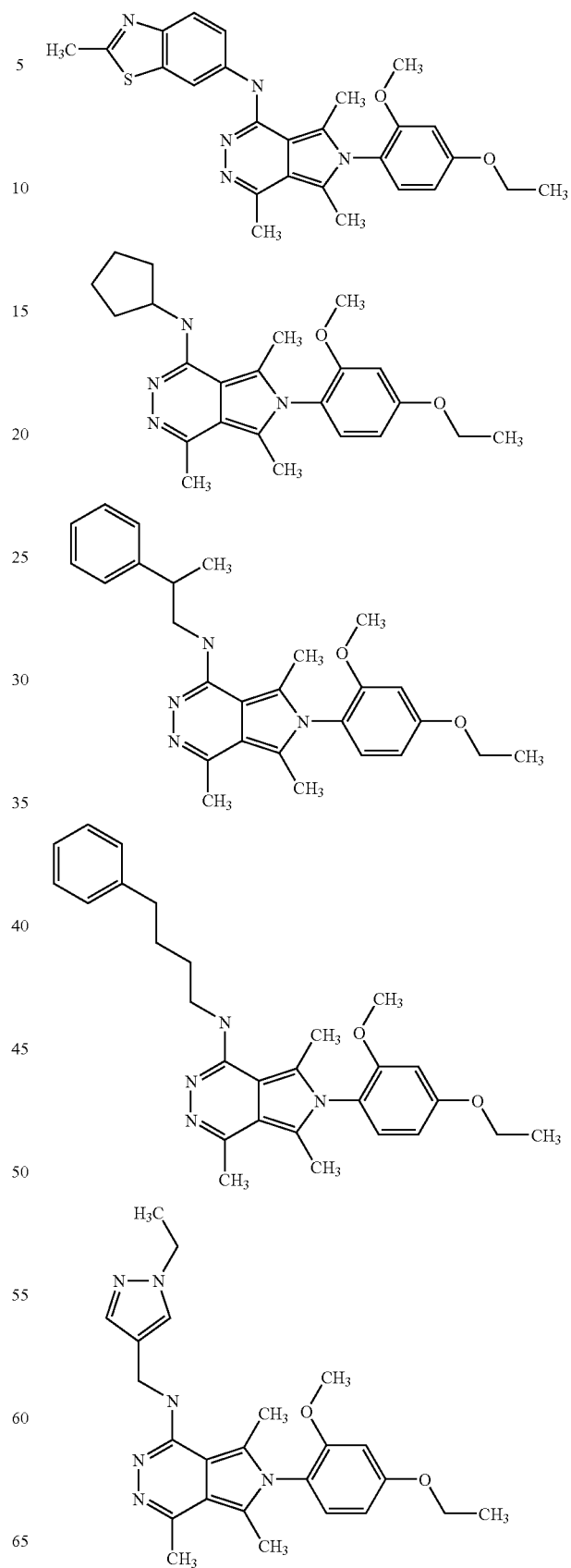

325
-continued
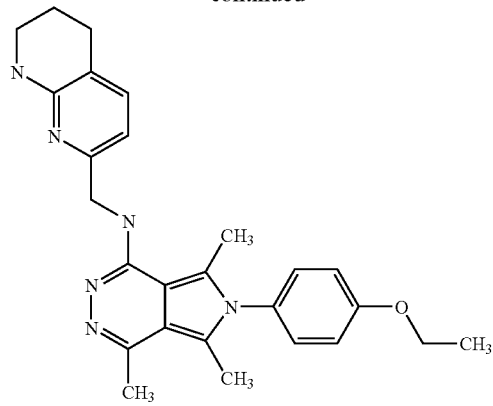
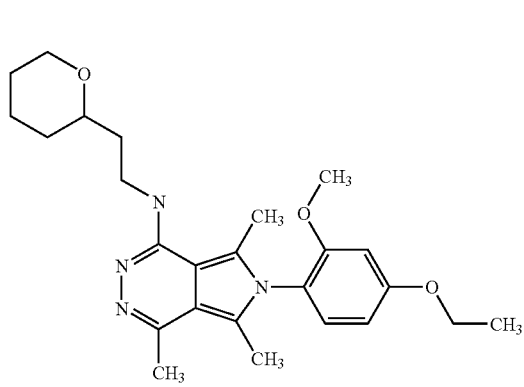
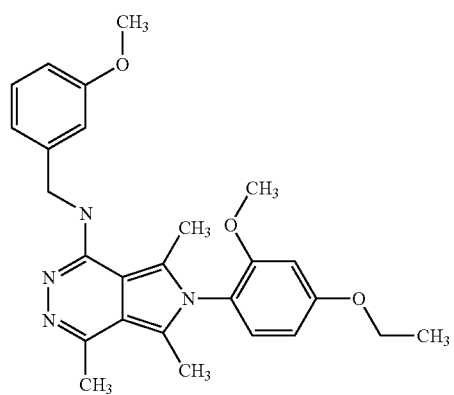
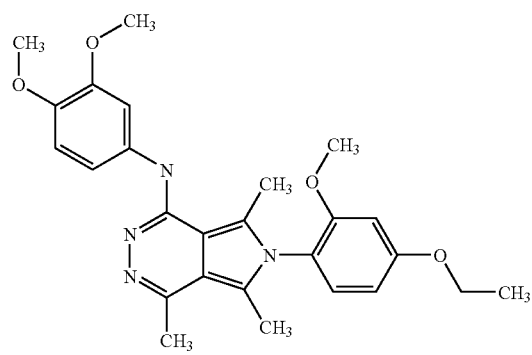
326
-continued
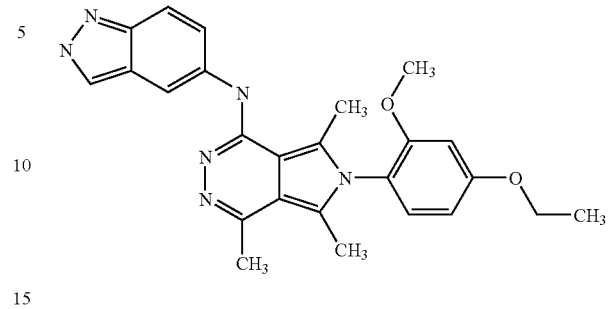
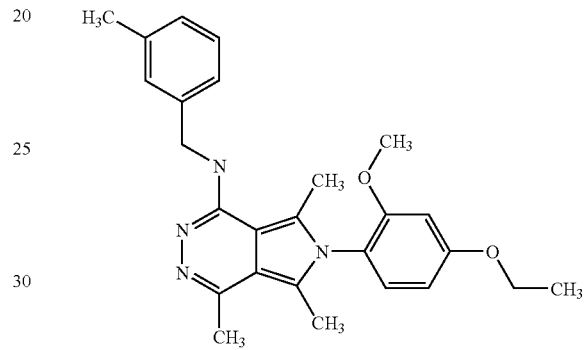
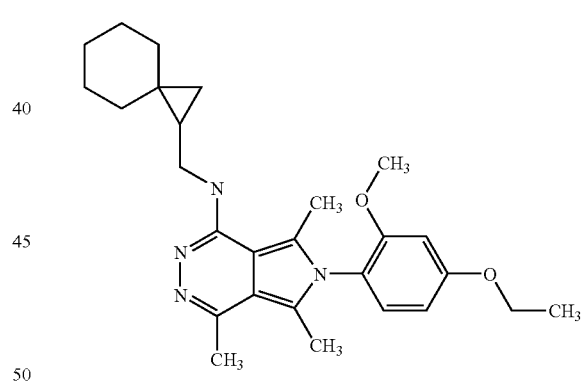
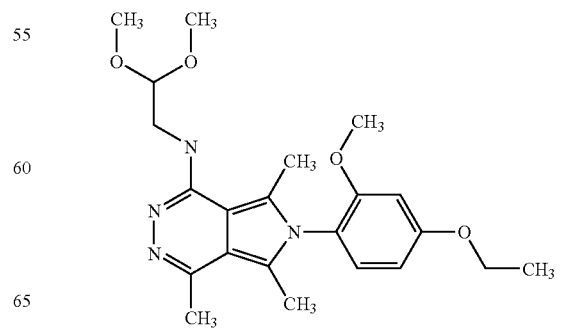

327
-continued
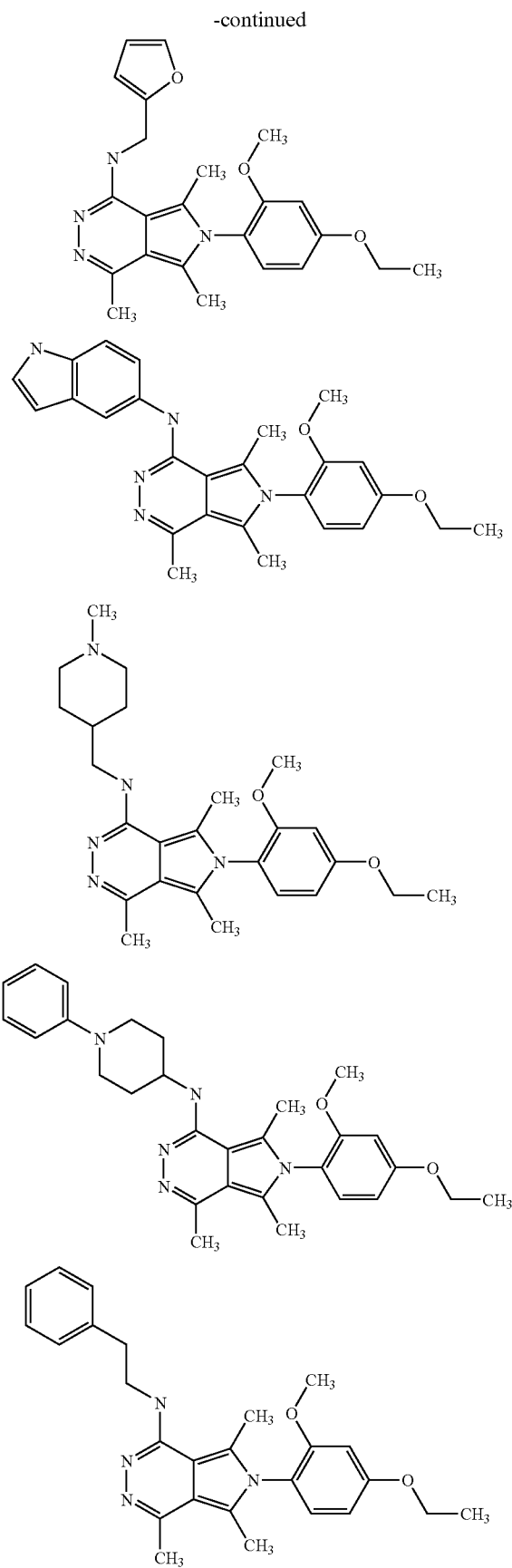
328
-continued
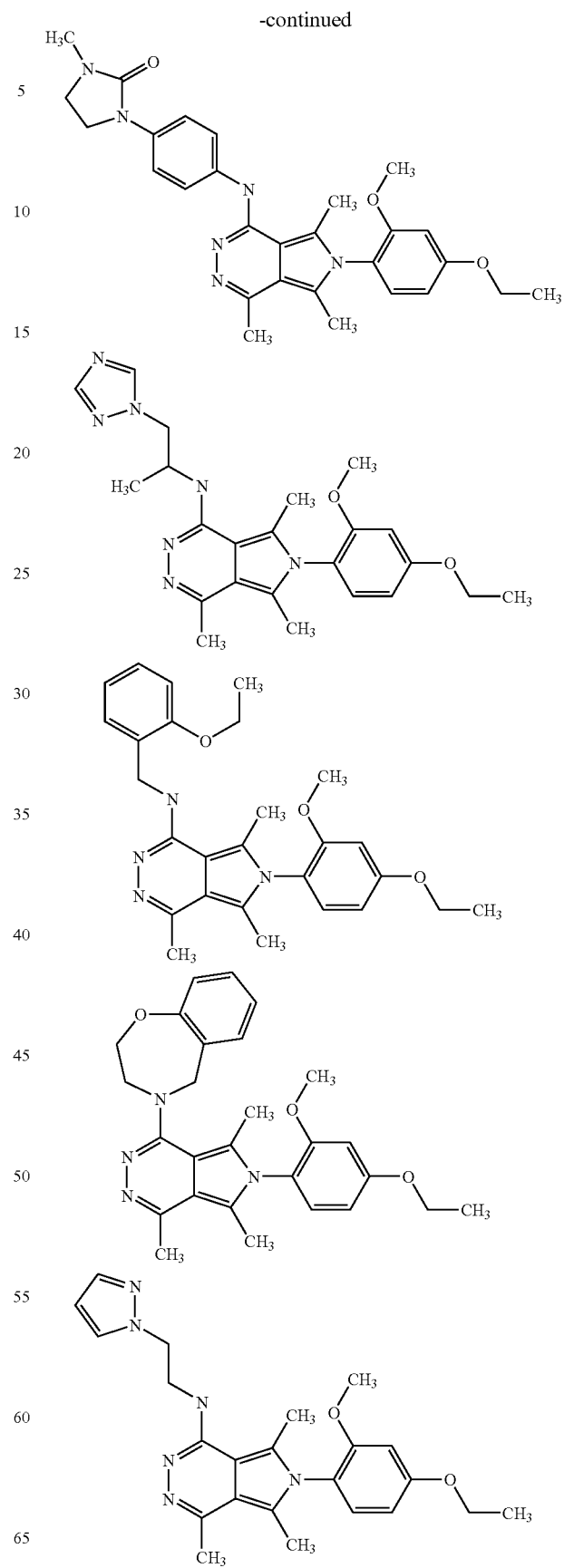

-continued
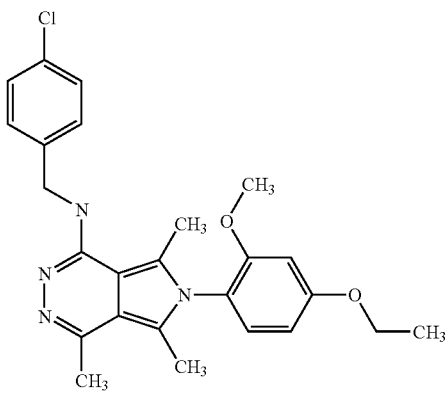
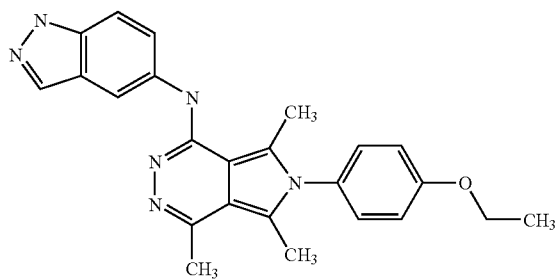
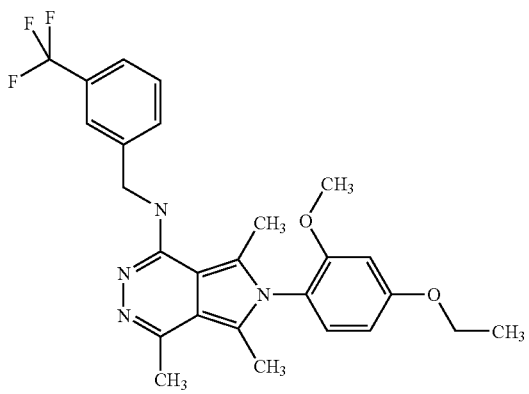
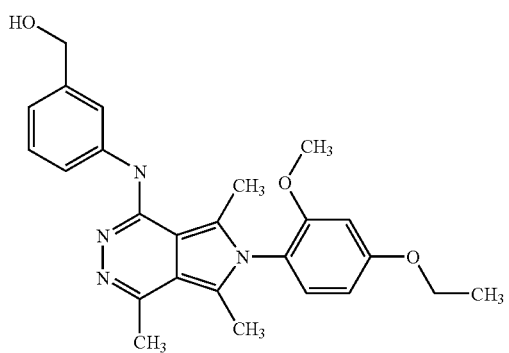
-continued
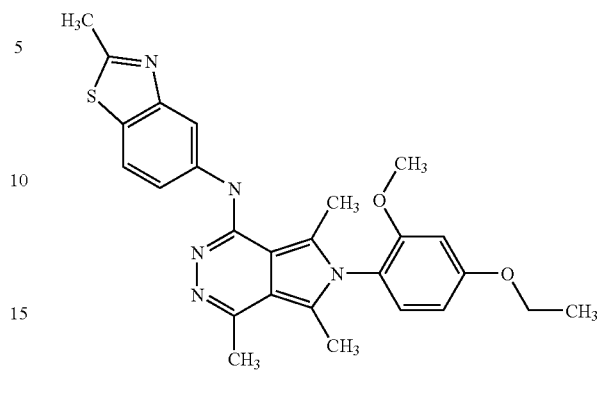
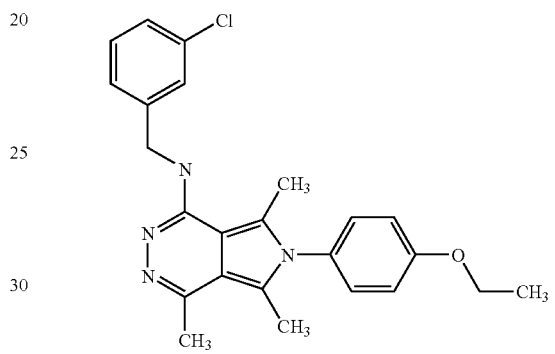
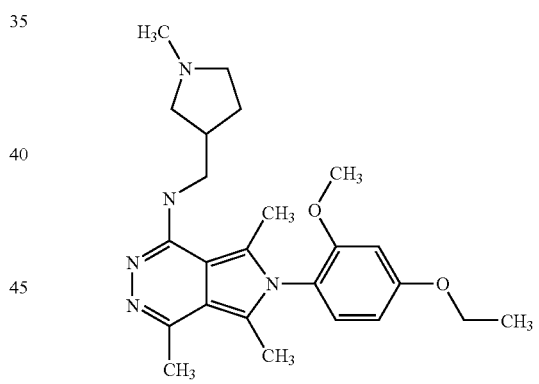
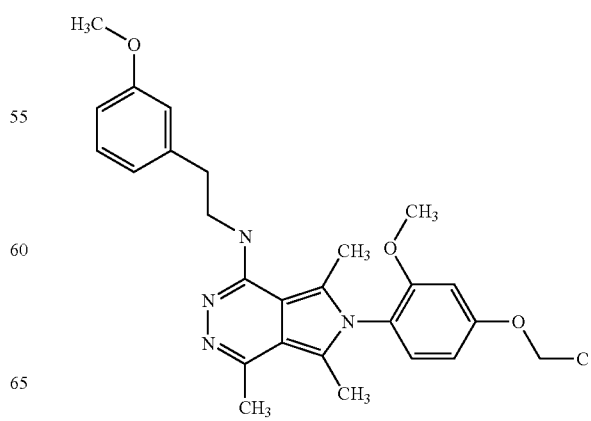

331
-continued
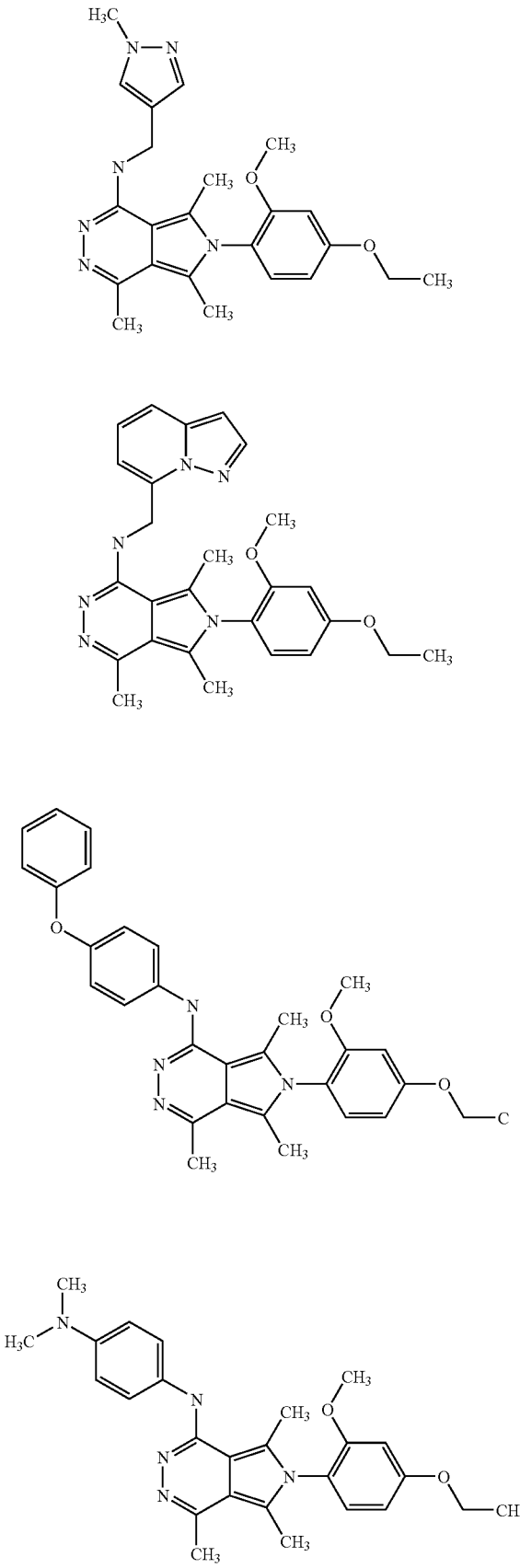
332
-continued
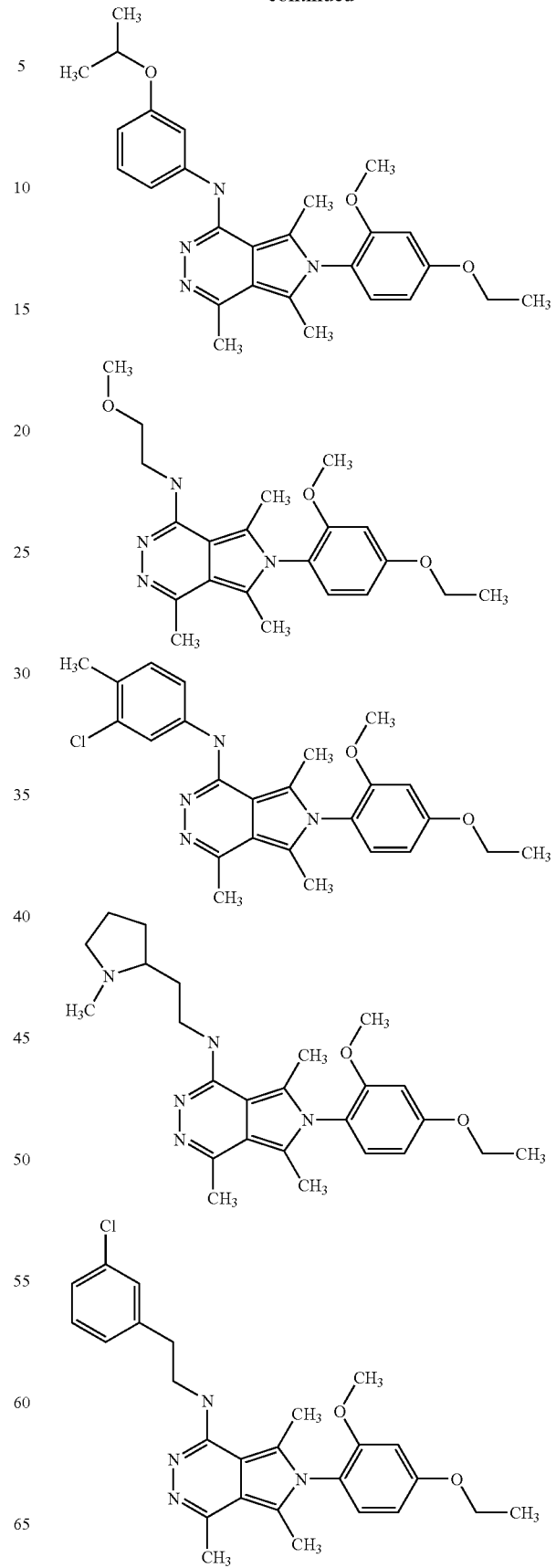

-continued
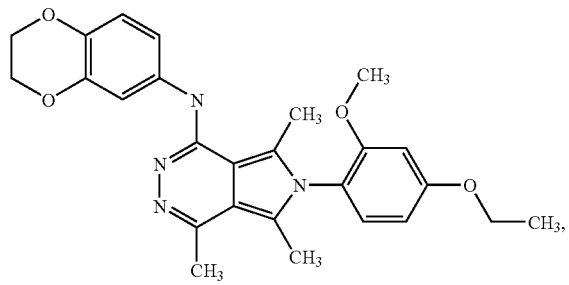
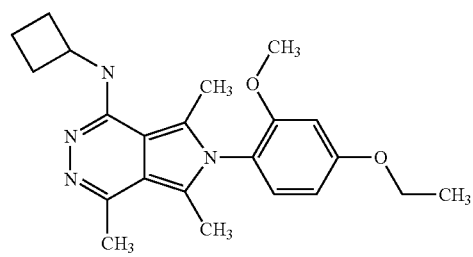
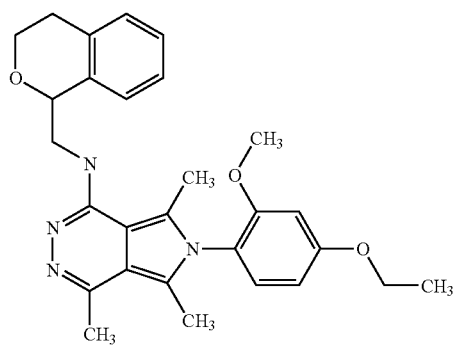
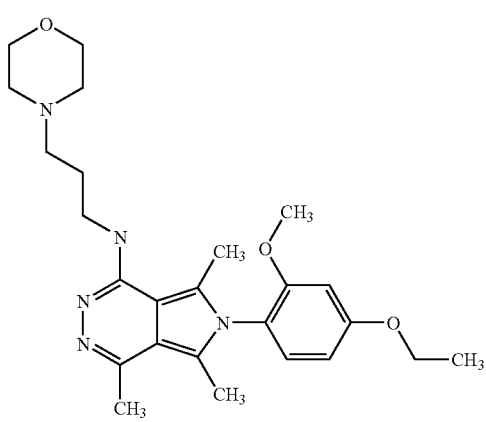
-continued
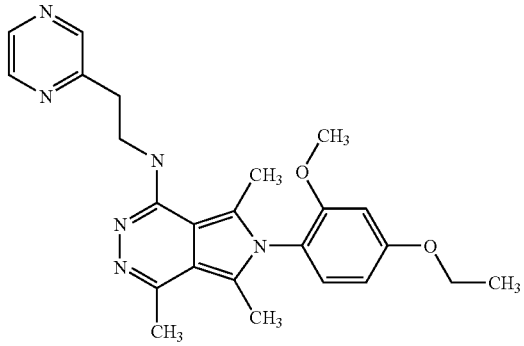
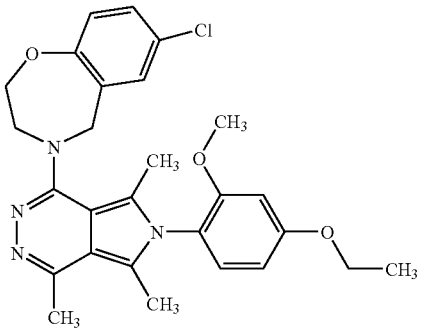
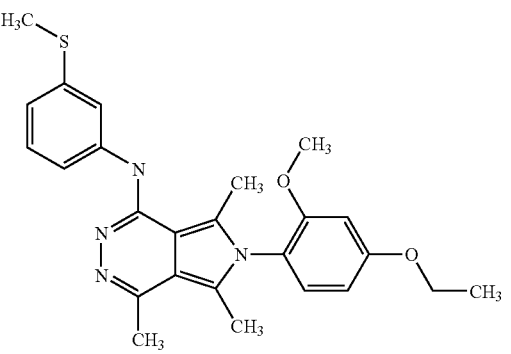

335
-continued
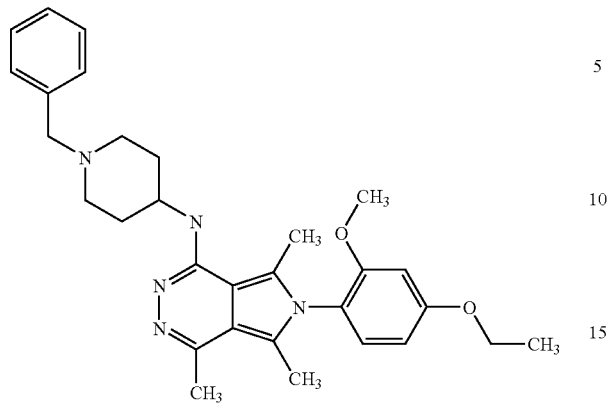
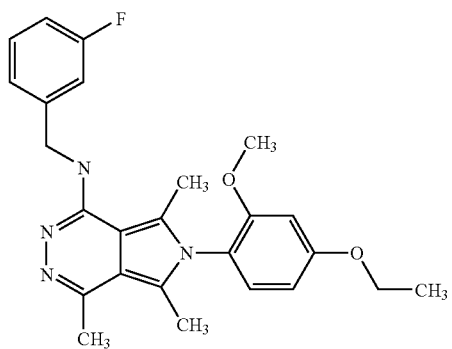
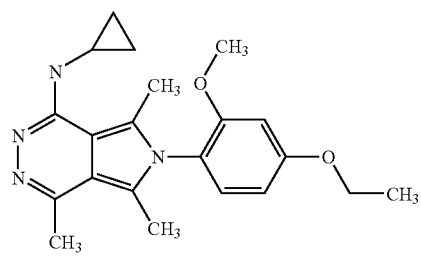
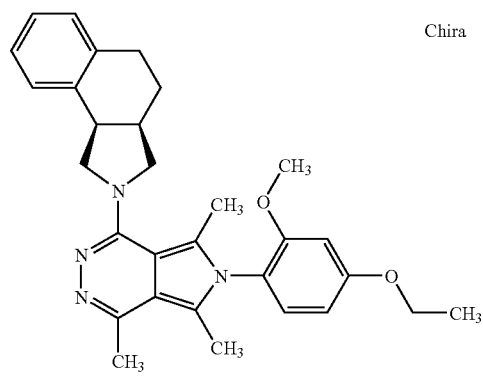
336
-continued
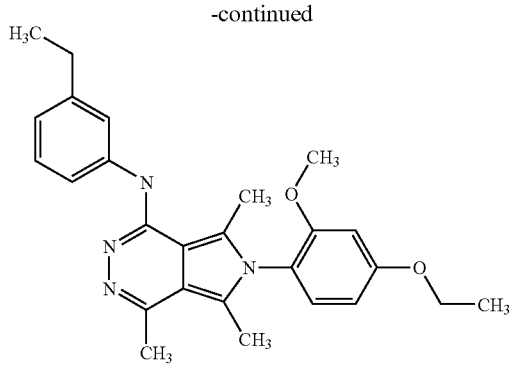
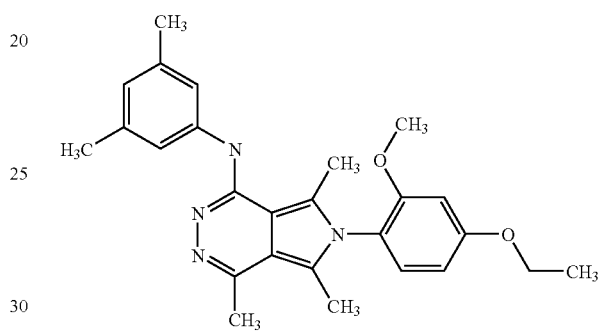
Chiral
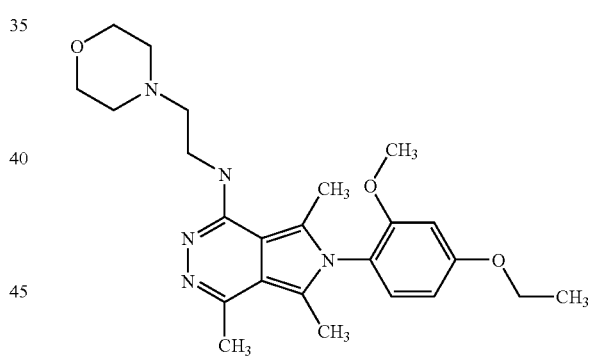
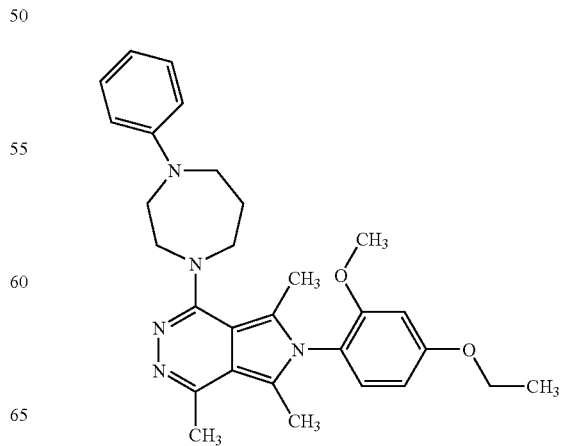

337
-continued
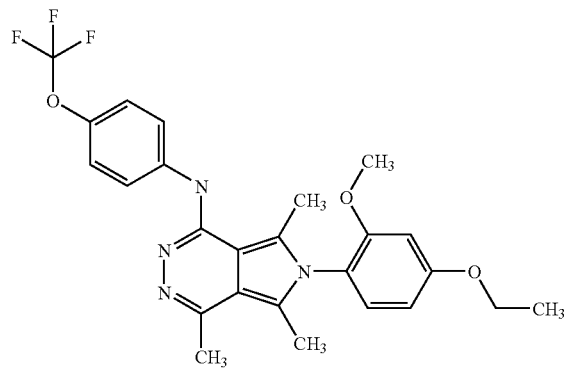
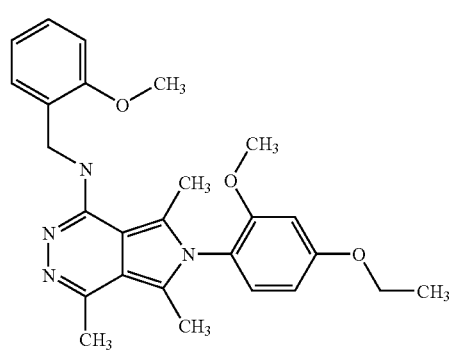
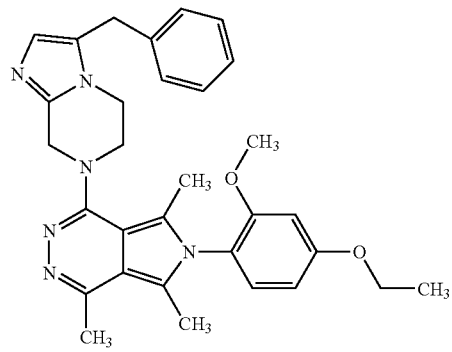
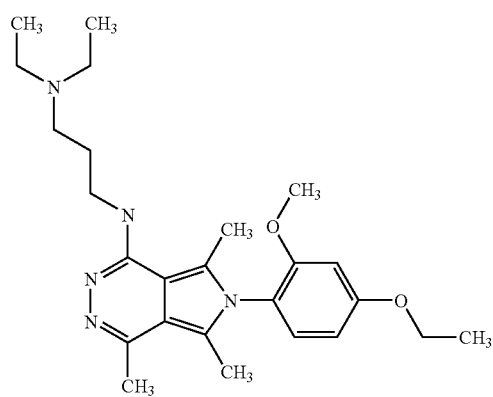
338
-continued
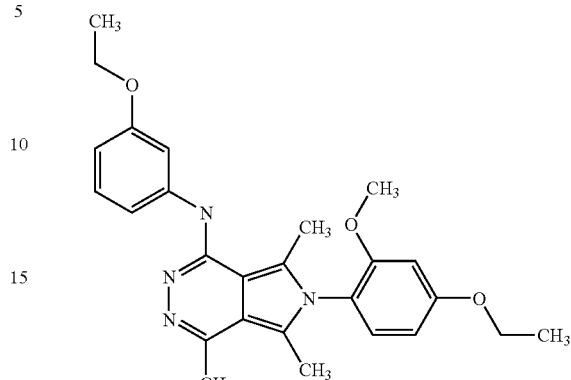
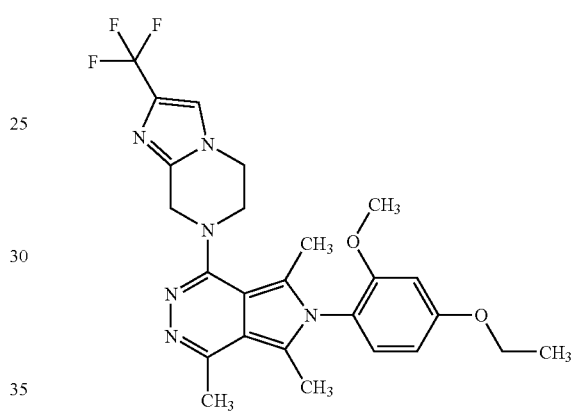
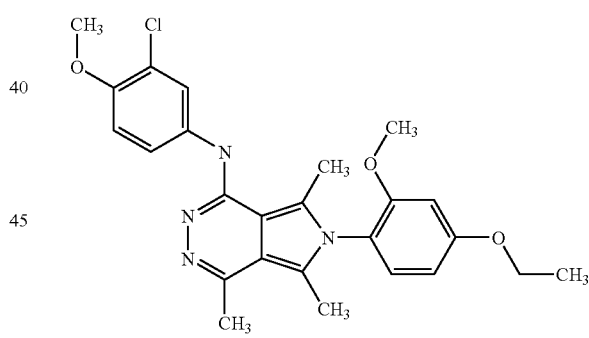
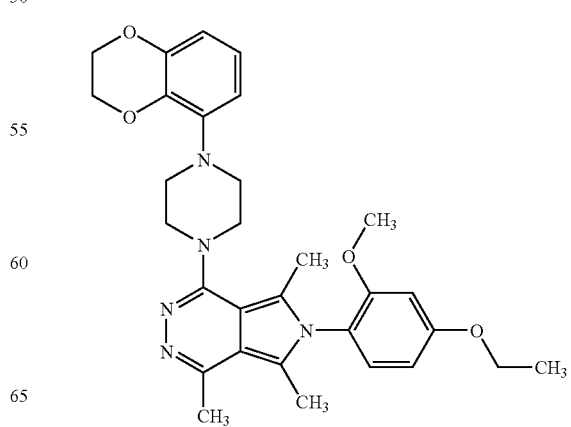

-continued
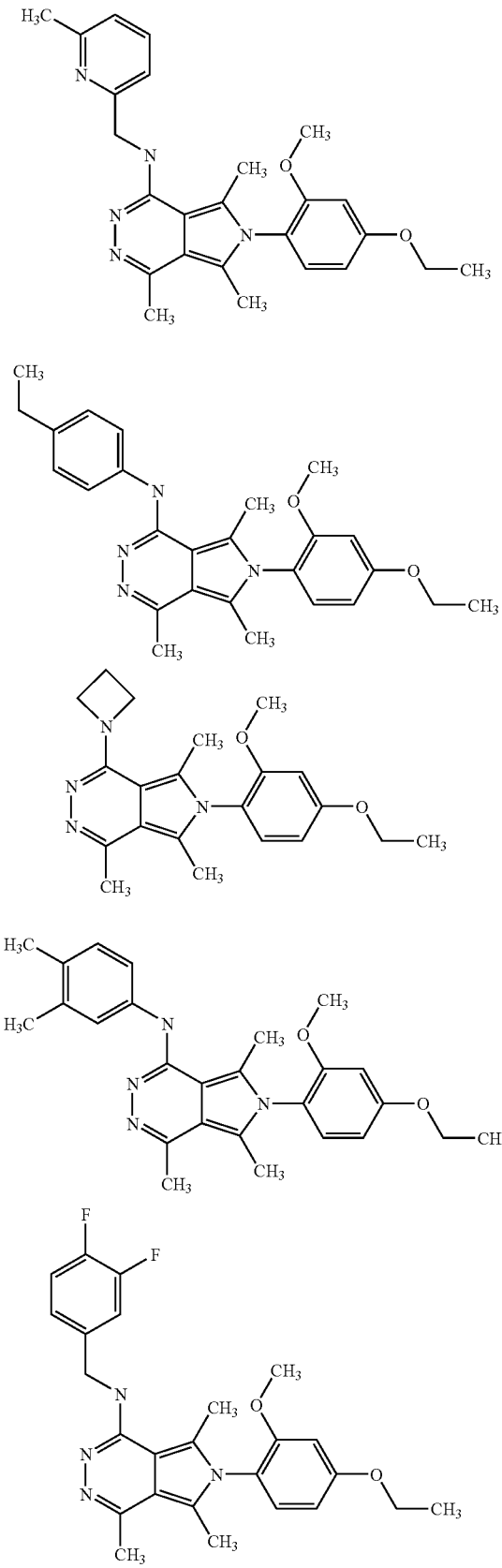
-continued
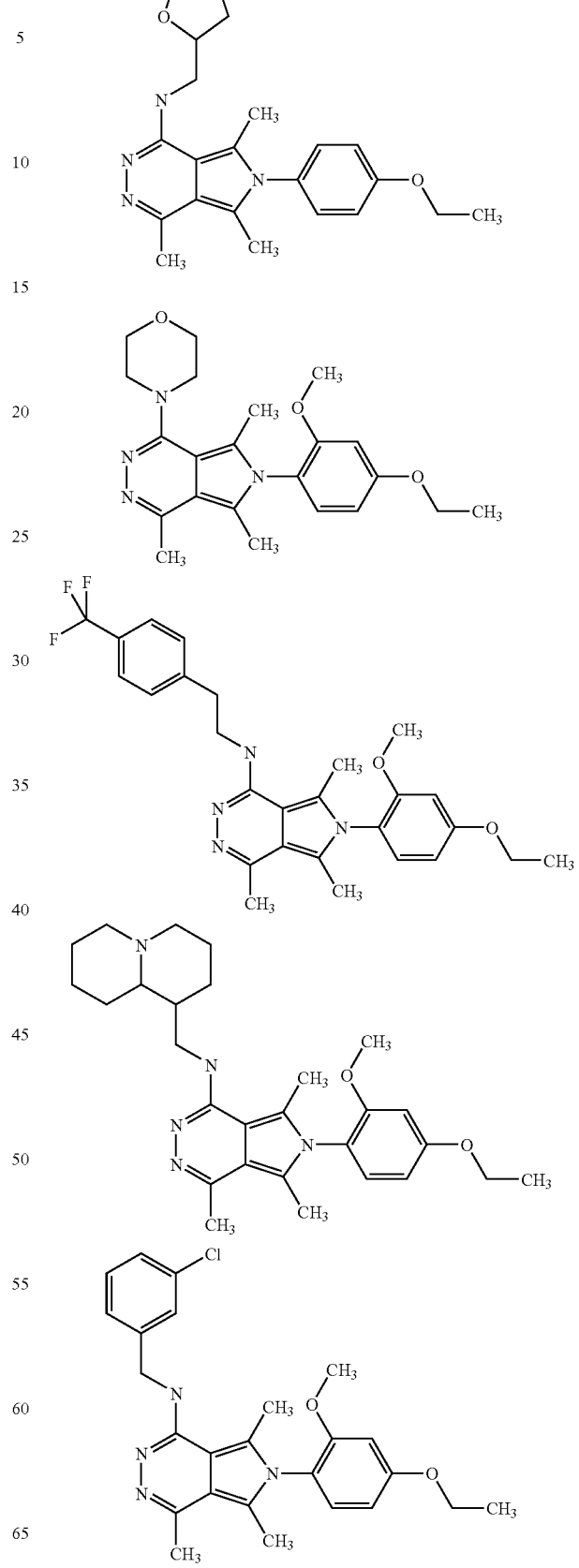

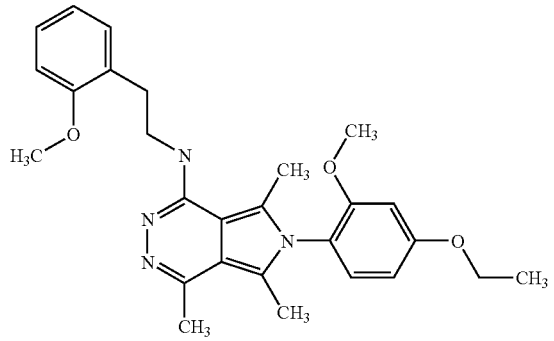
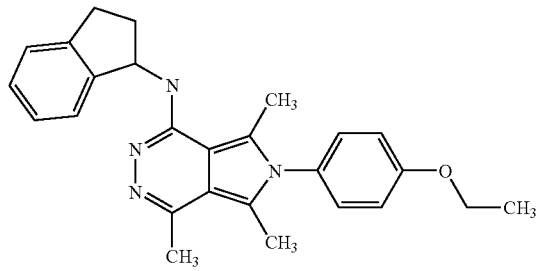
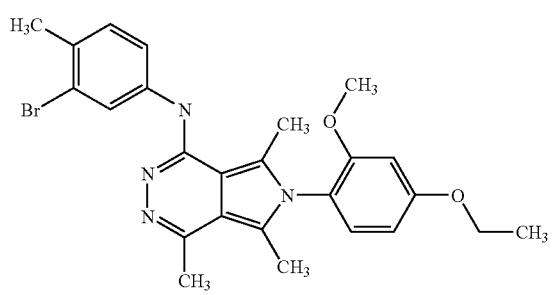
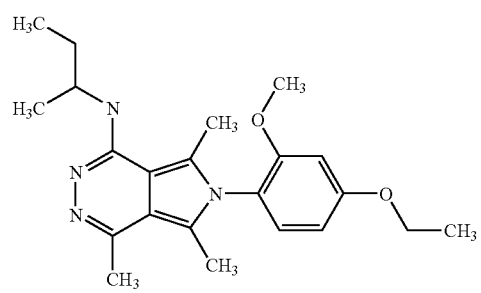
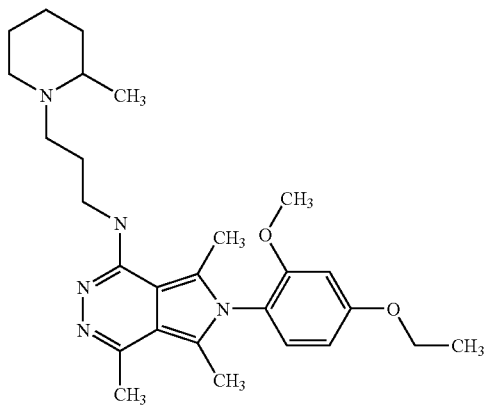
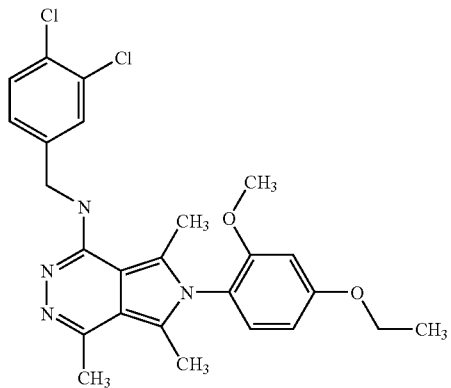
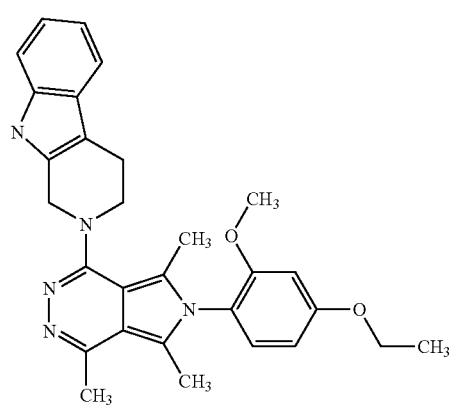
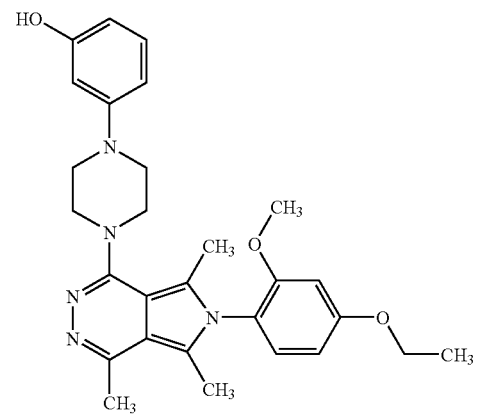

343
-continued
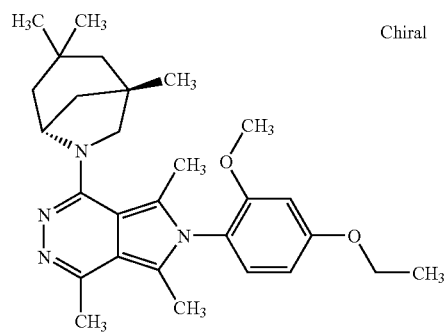
Chiral
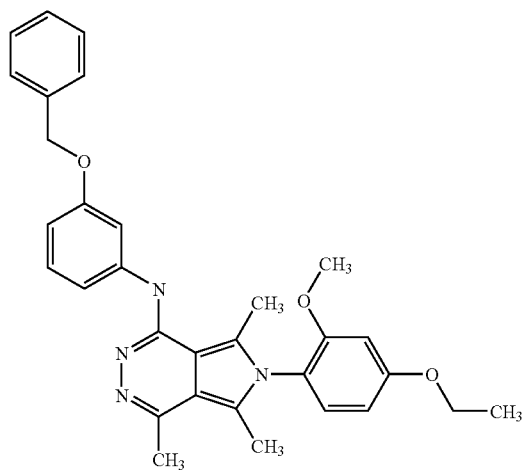
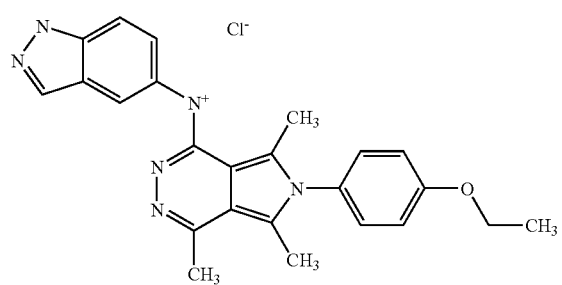
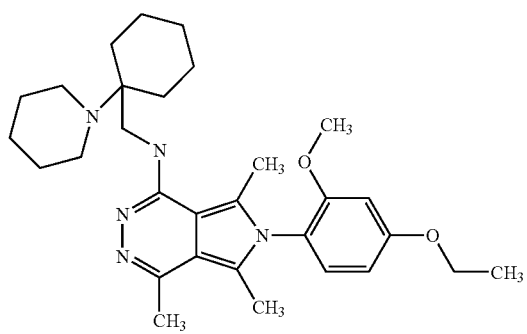
344
-continued
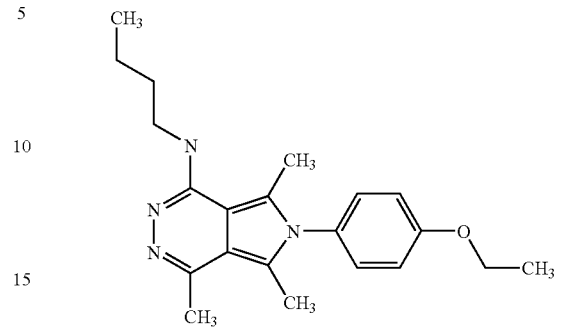
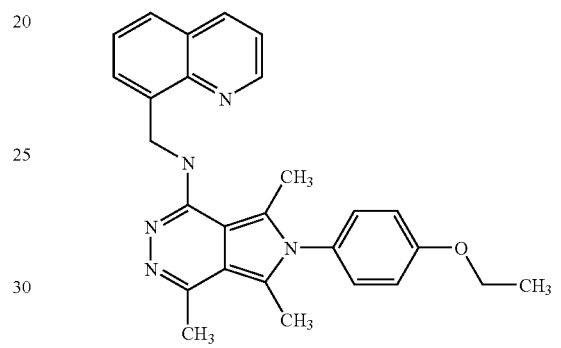
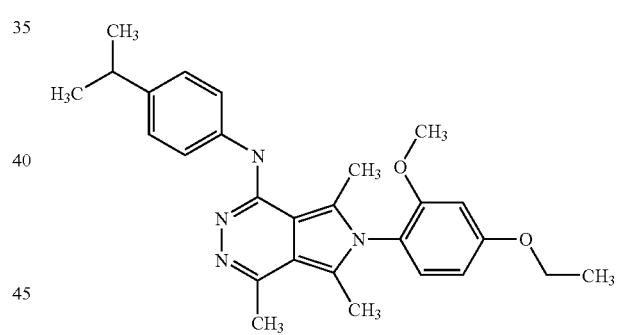
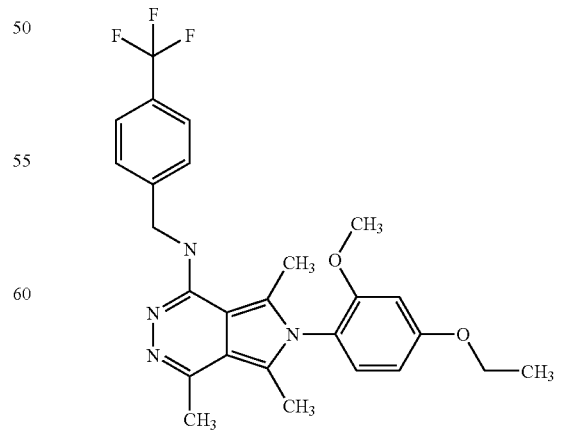

-continued
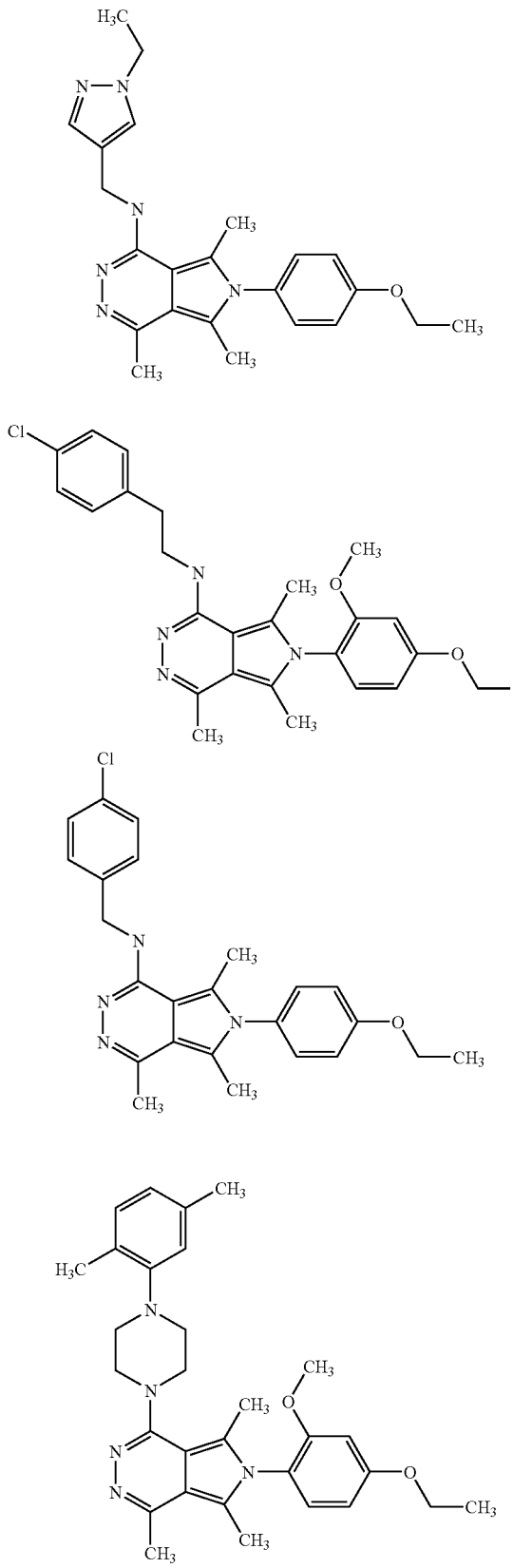
-continued
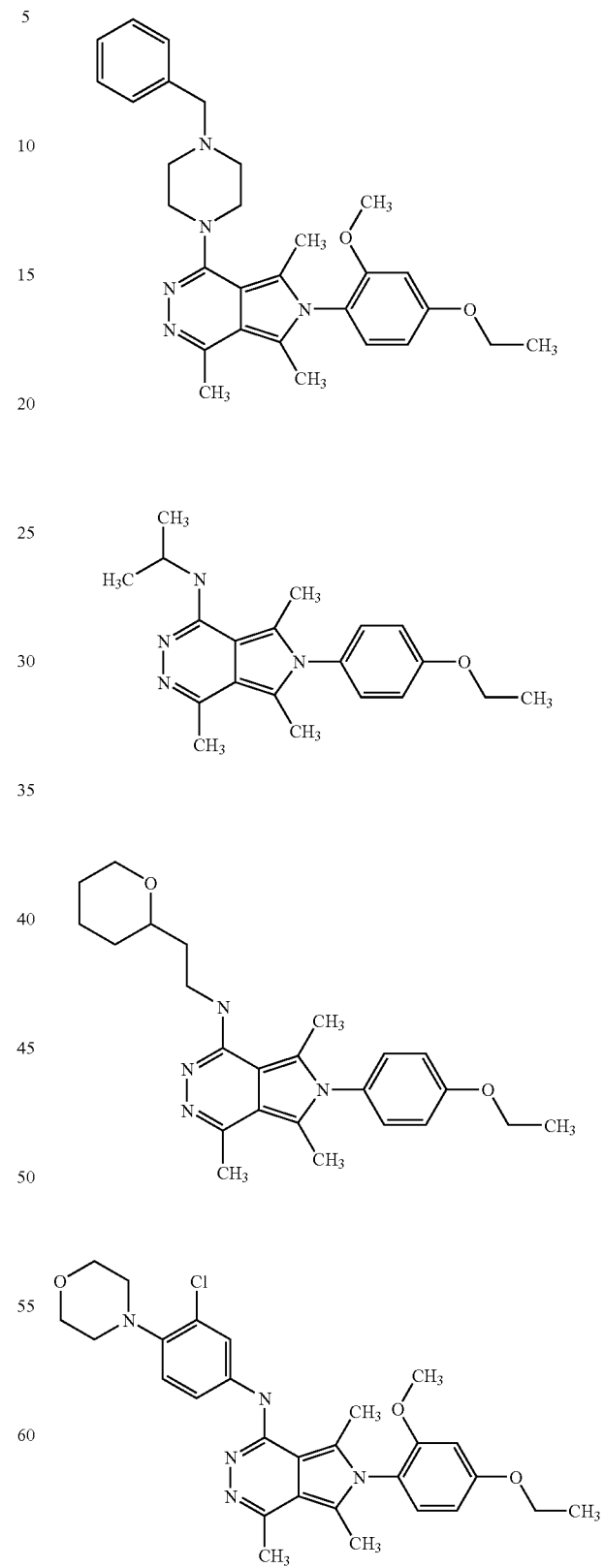

-continued
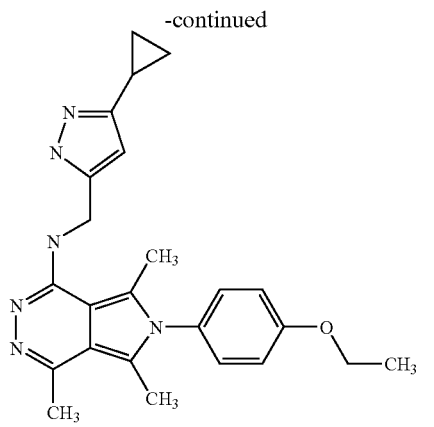
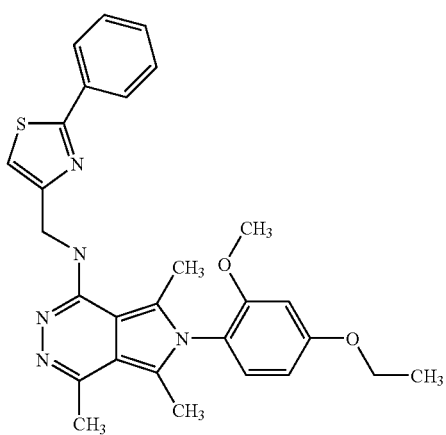
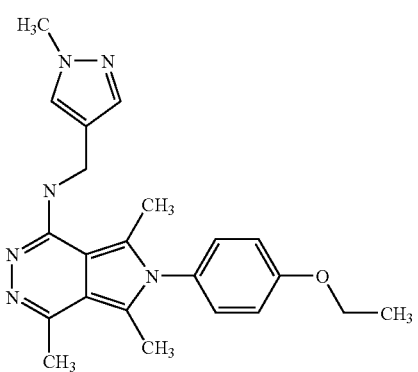
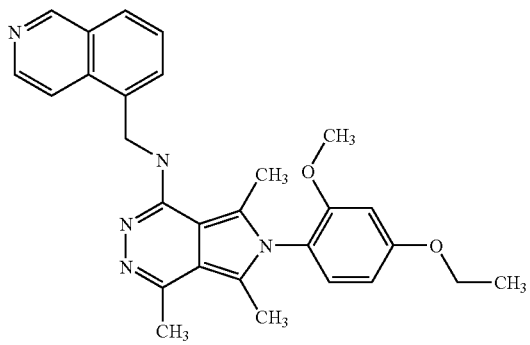
-continued
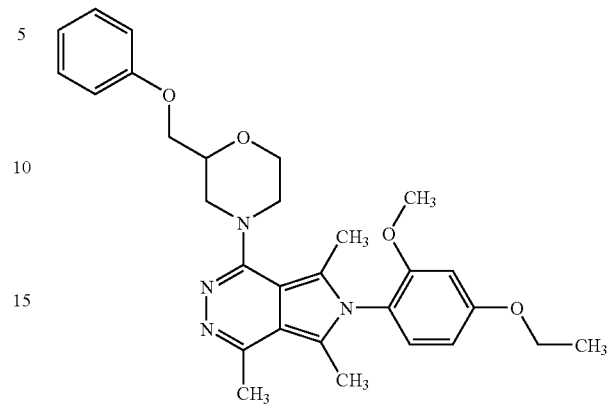
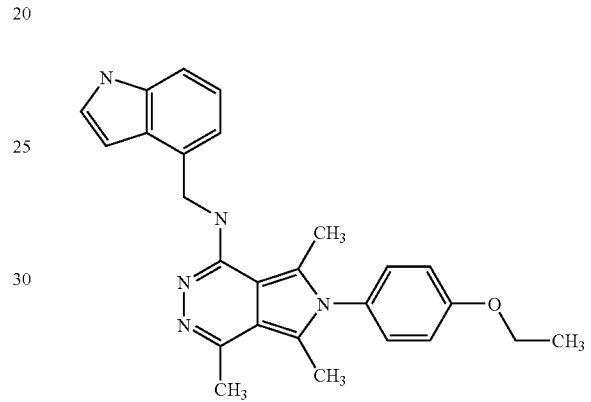
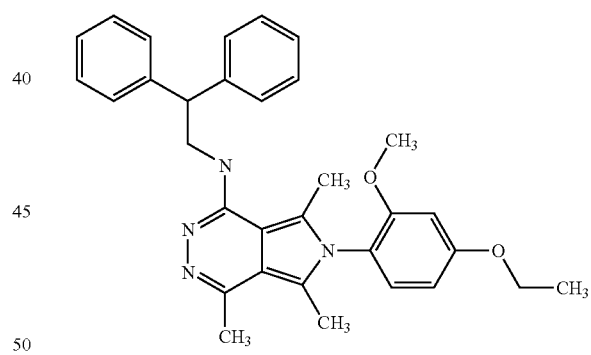
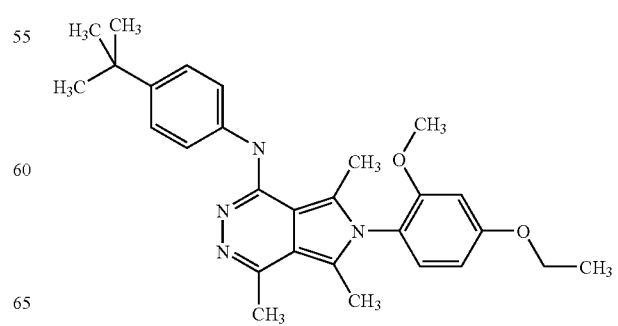

349
-continued
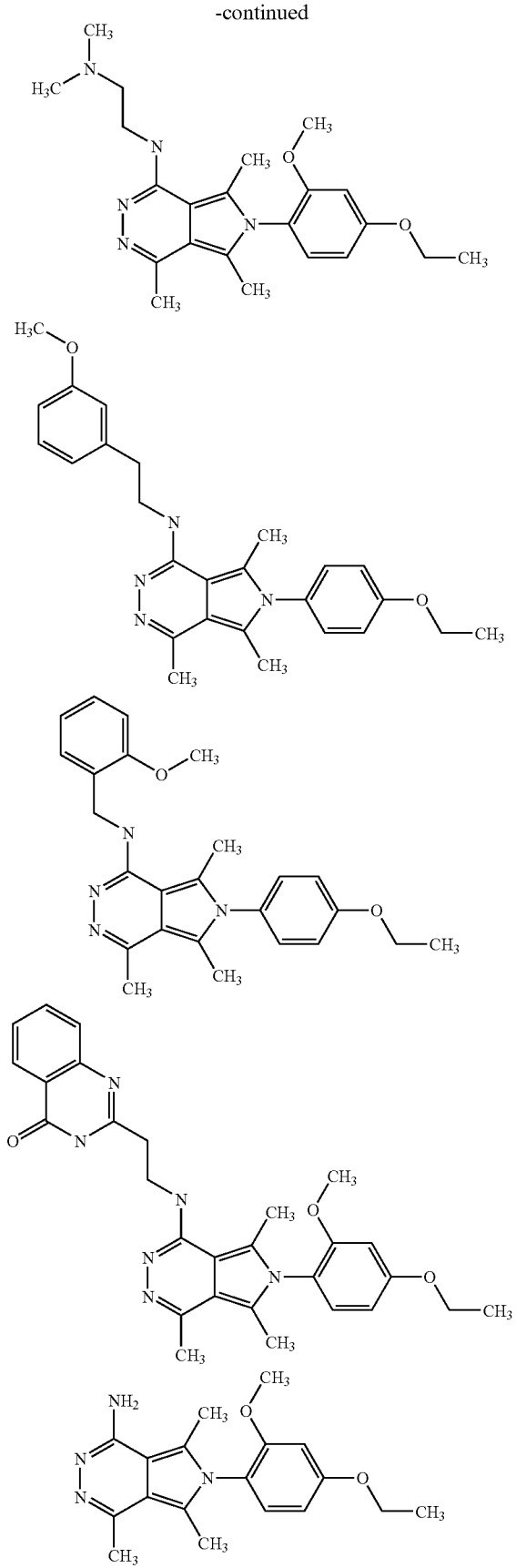
350
-continued
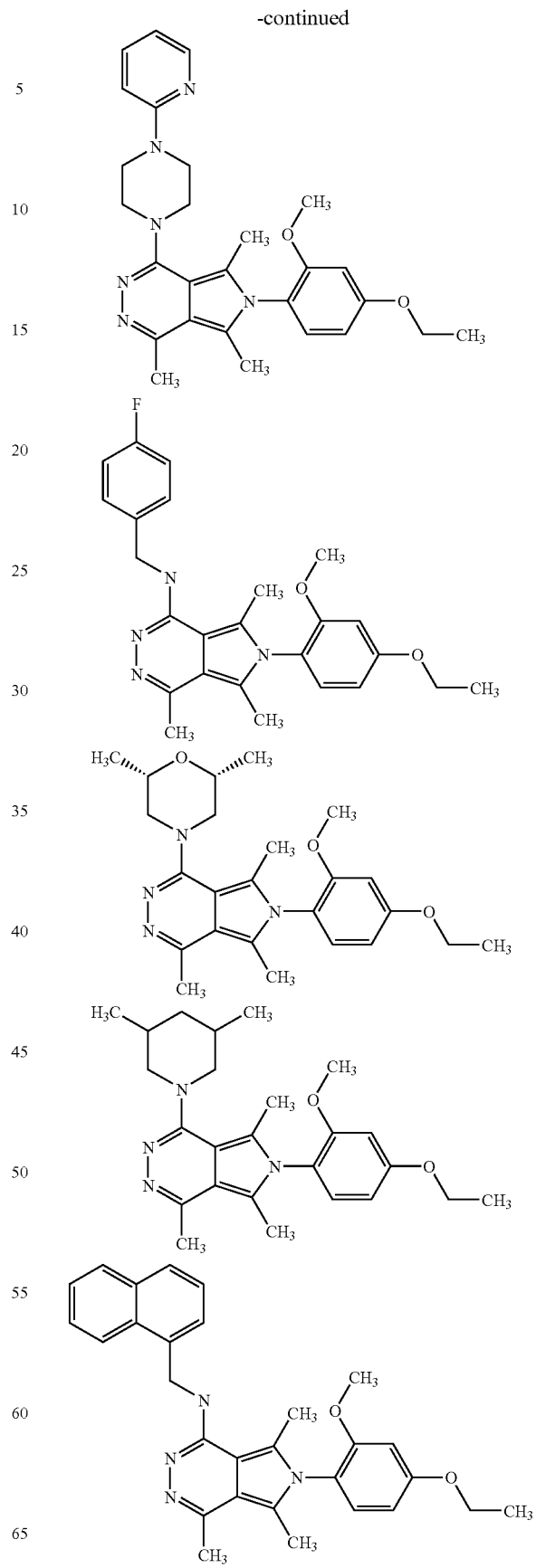

351
-continued
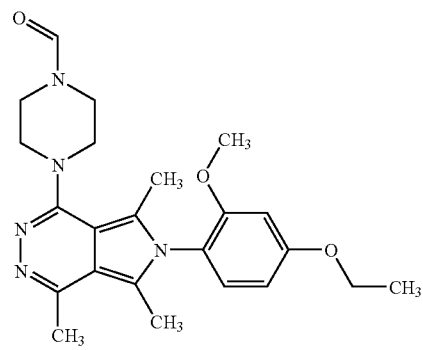
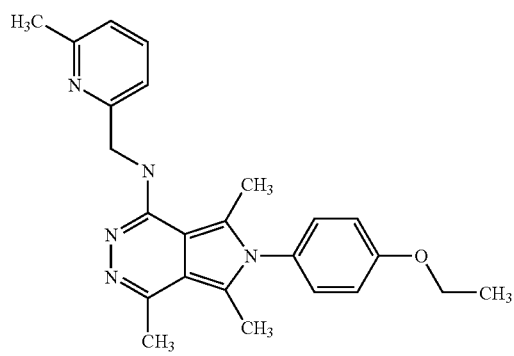
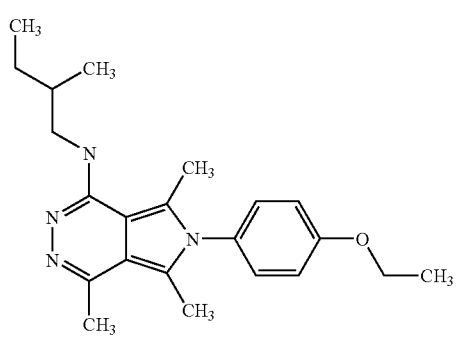
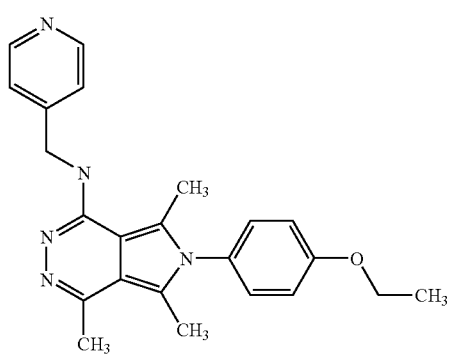
352
-continued
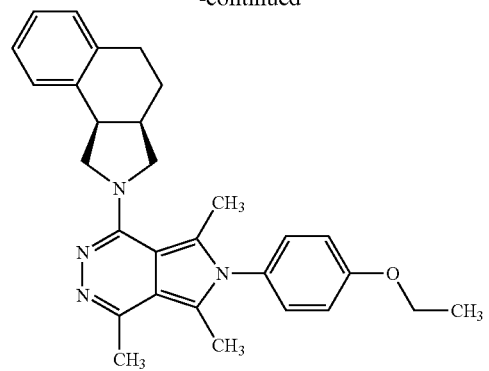
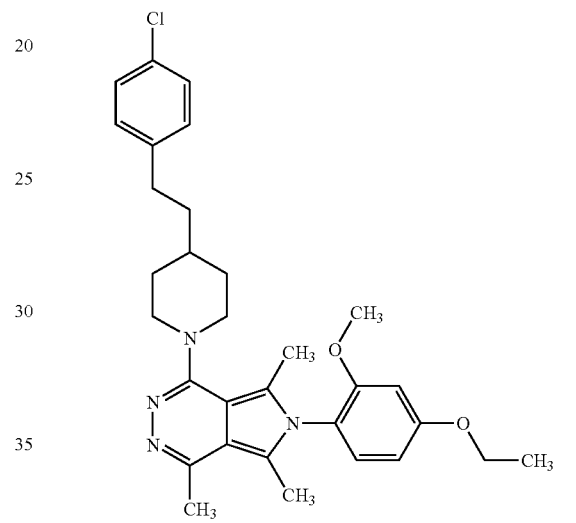
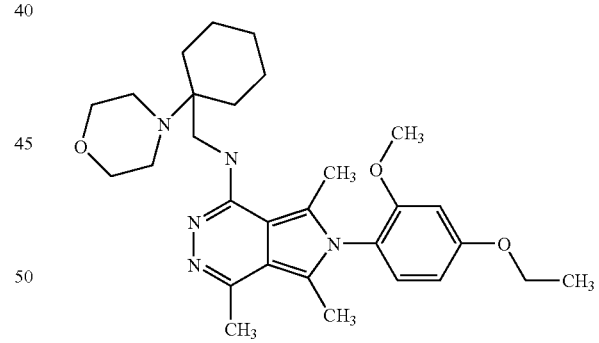
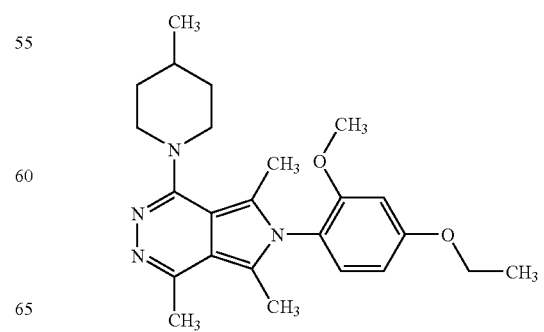

353
-continued
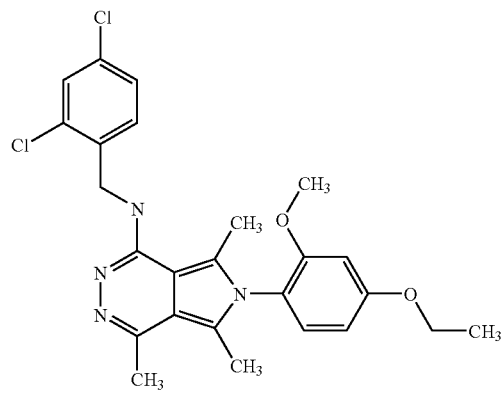
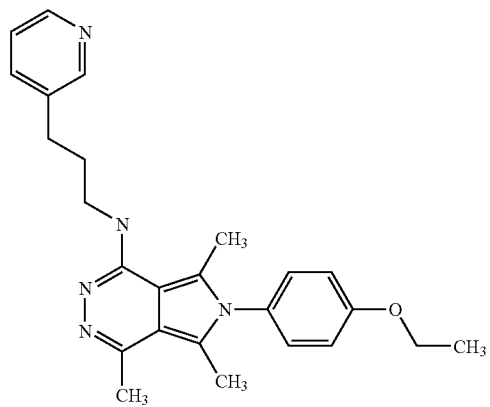
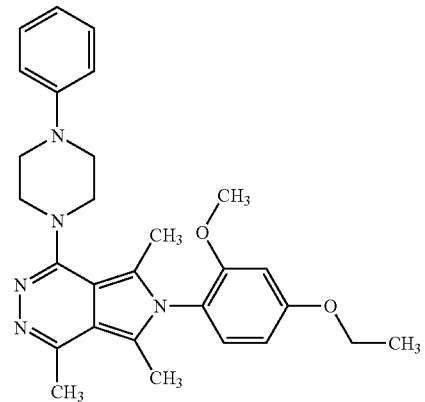
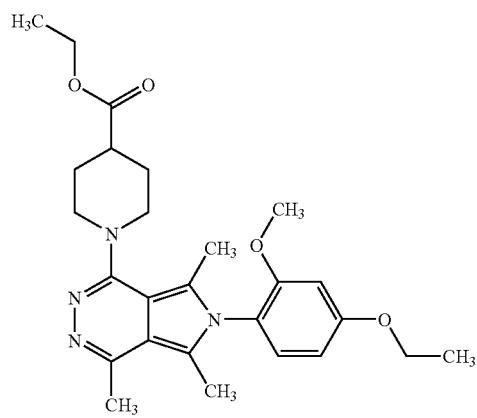
354
-continued
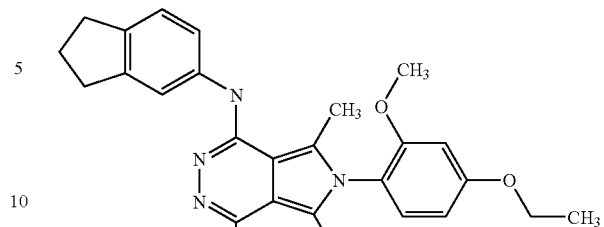
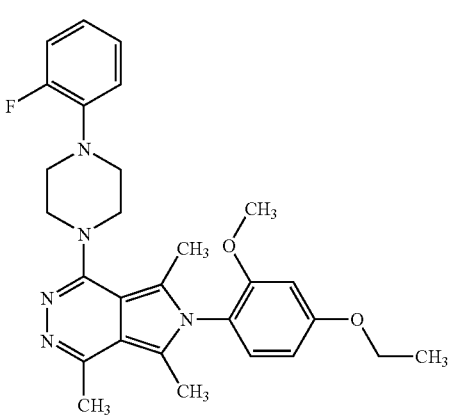
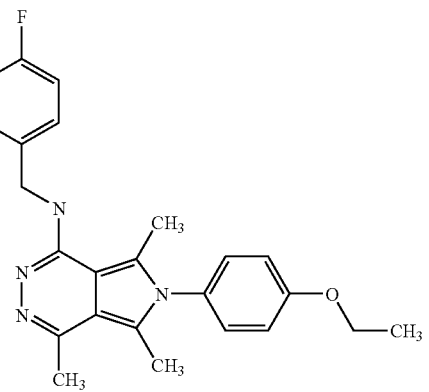
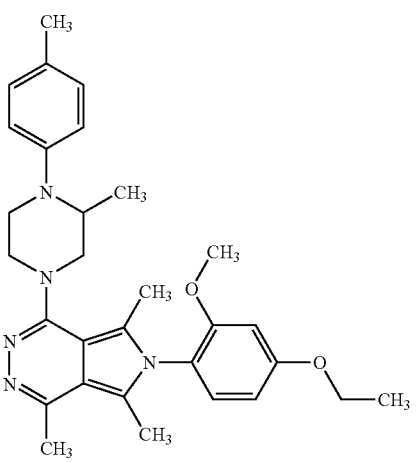

-continued
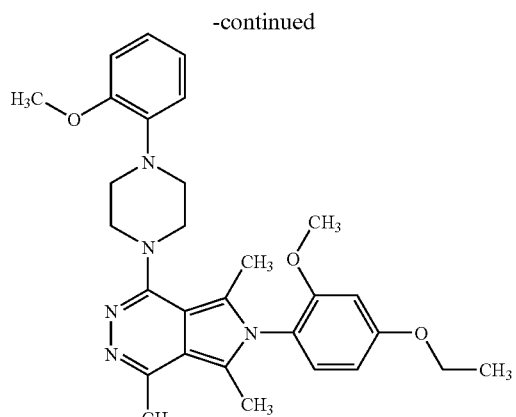
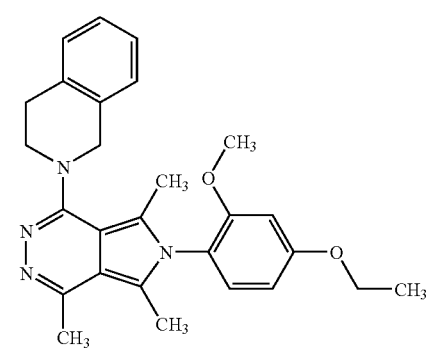
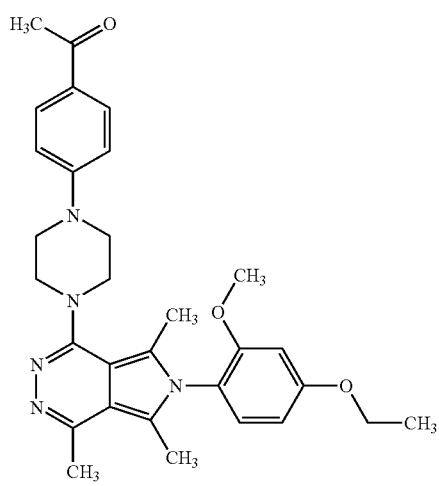
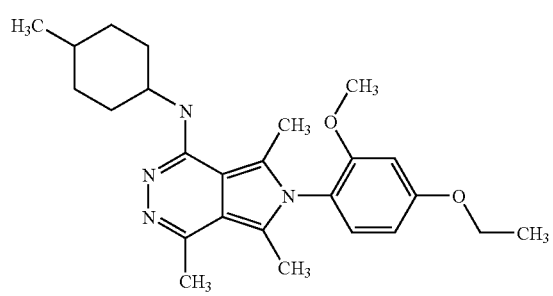
-continued
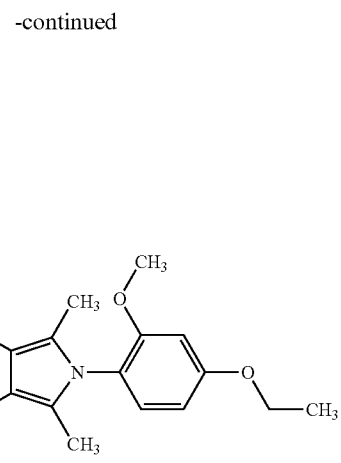
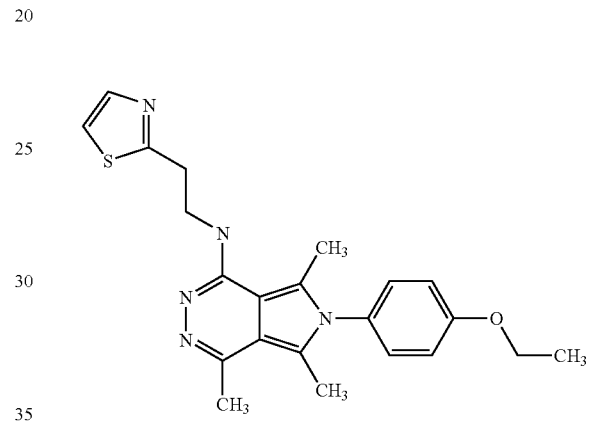
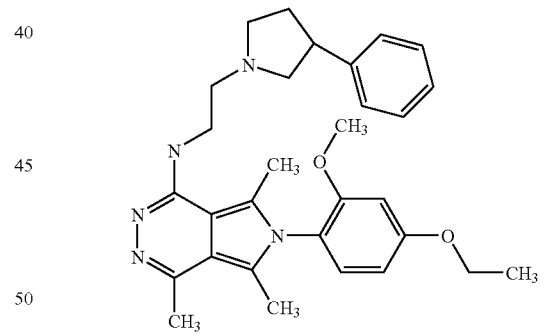
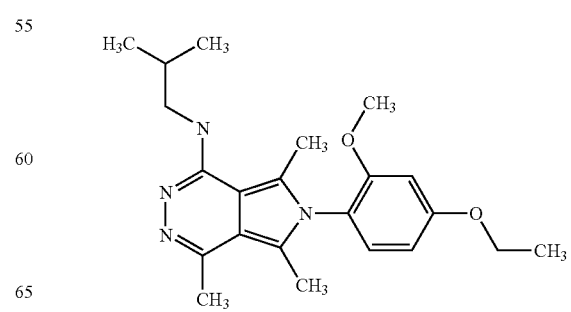

357
-continued
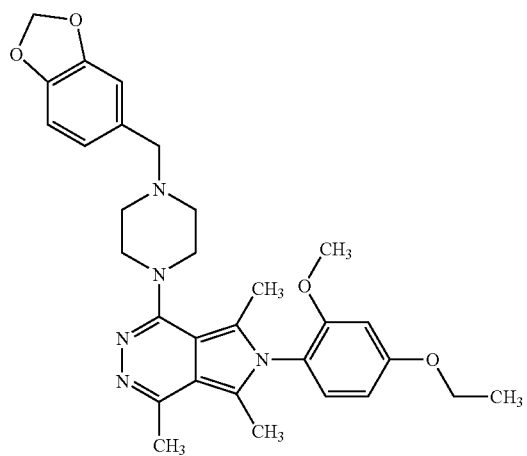
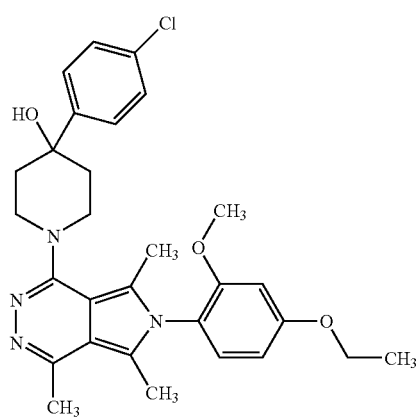
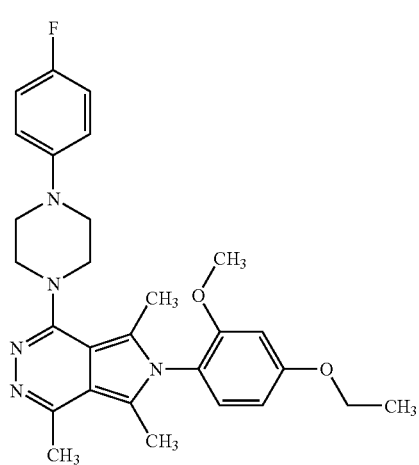
358
-continued
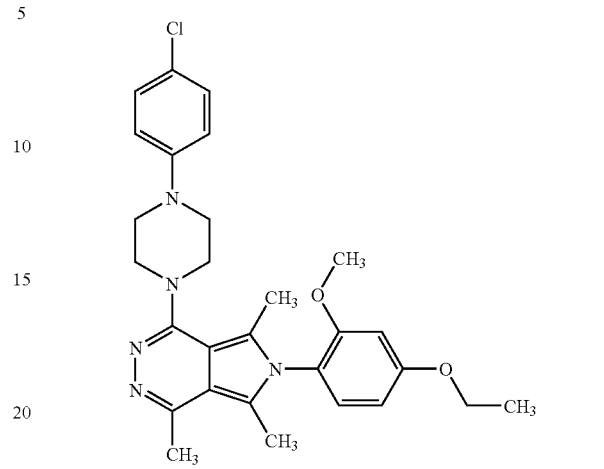
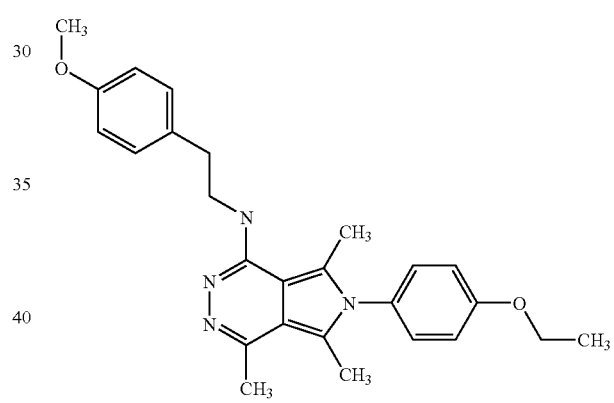
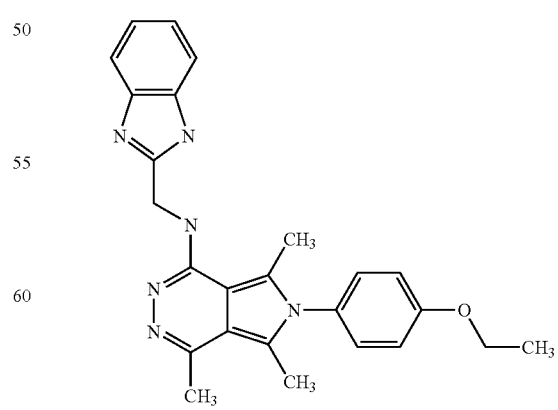

359                                                360
-continued                                       -continued
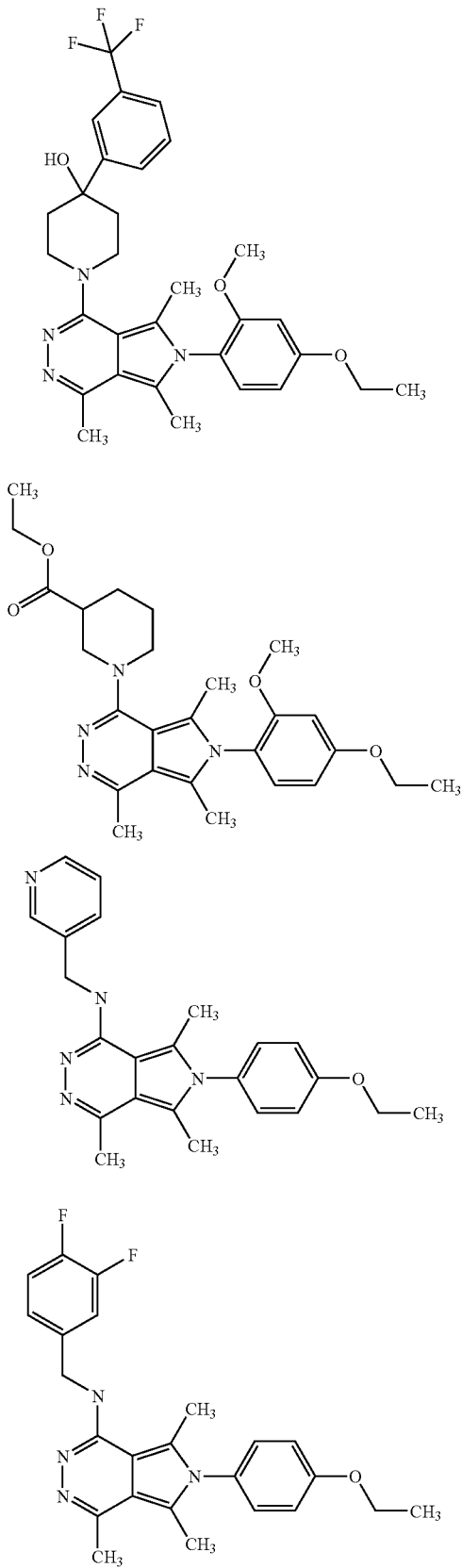
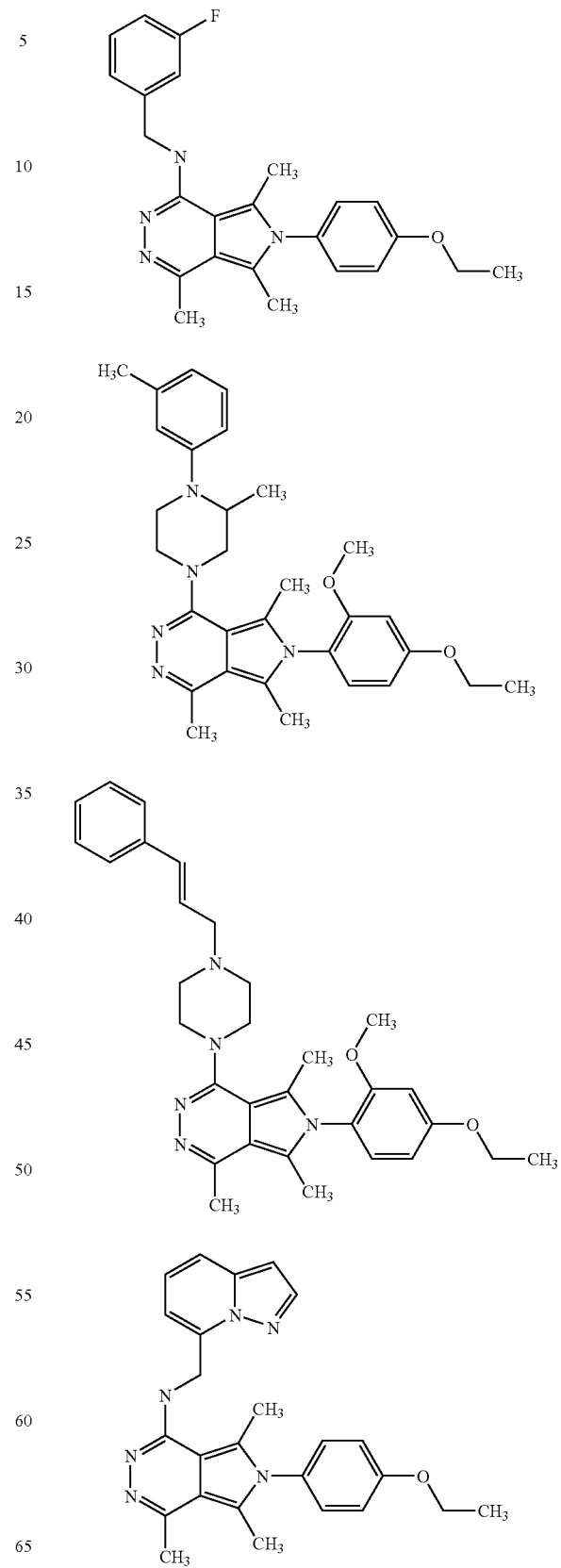

-continued
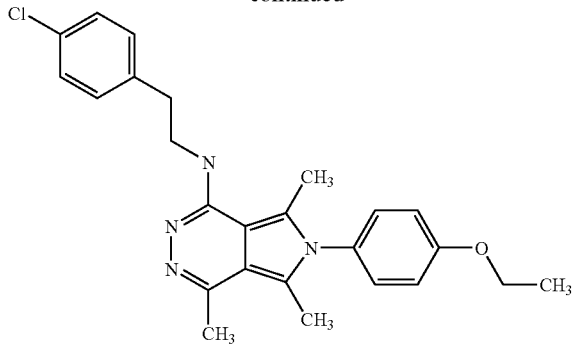
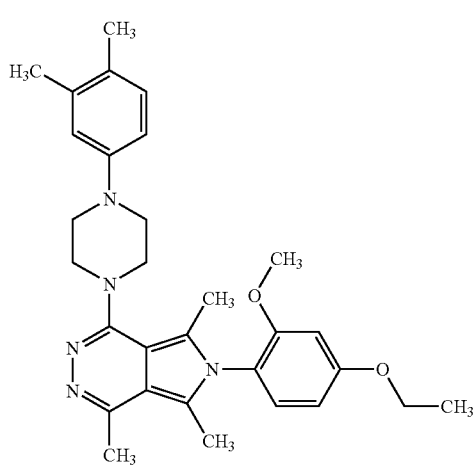
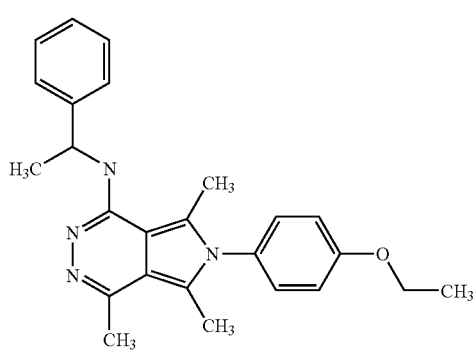
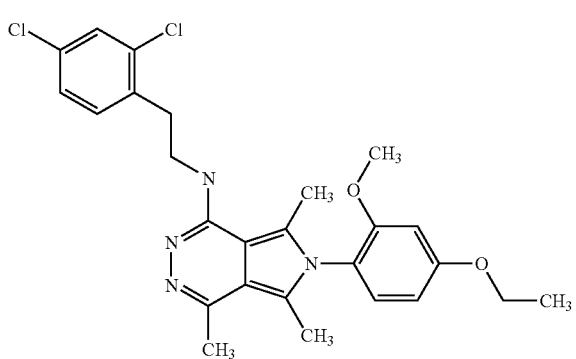
-continued
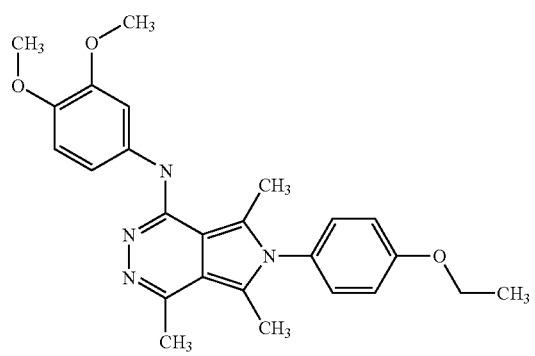
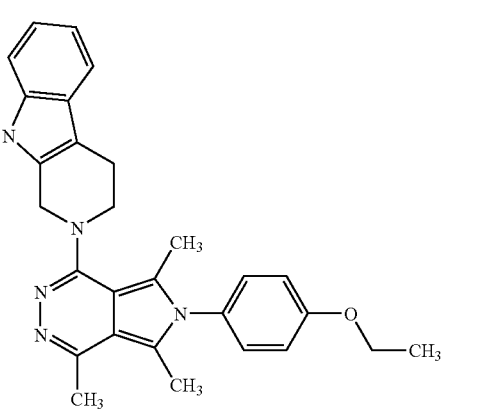
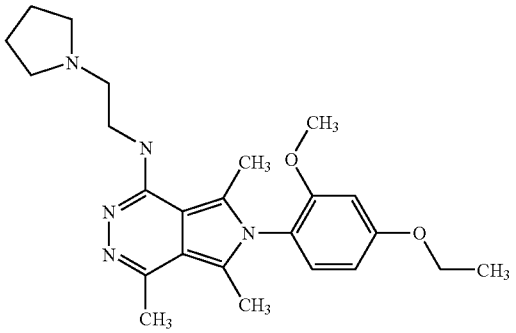
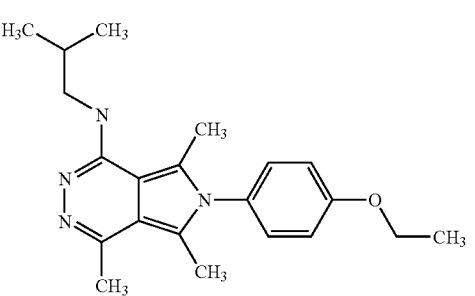

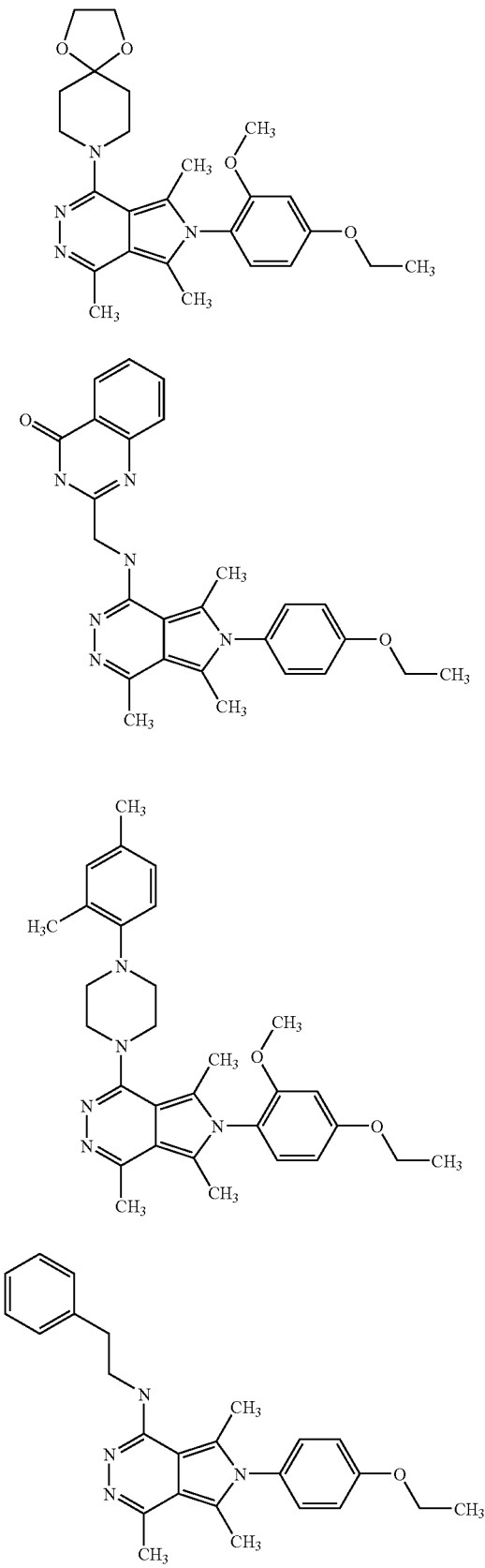
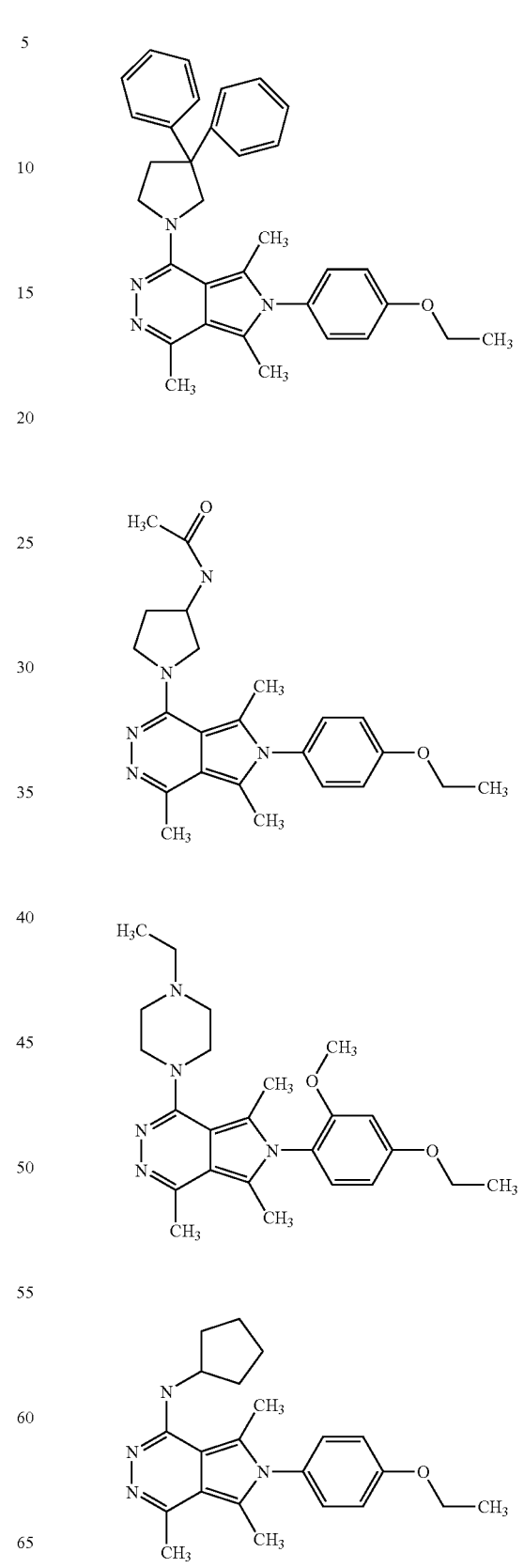

365
-continued
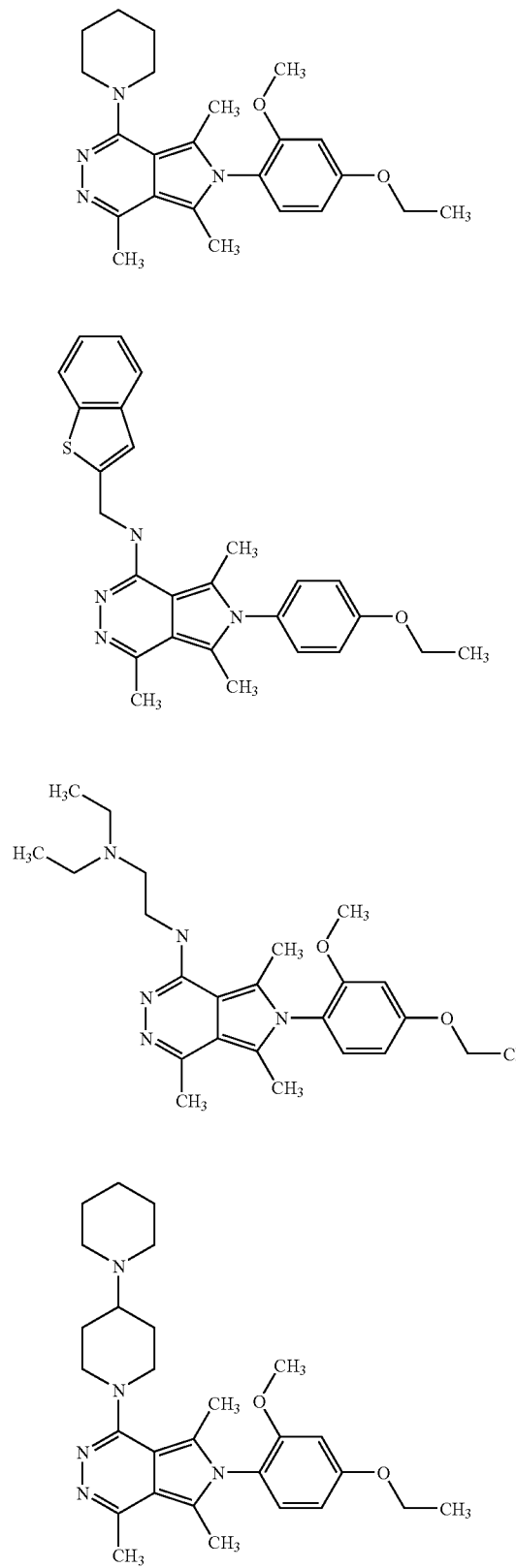
366
-continued
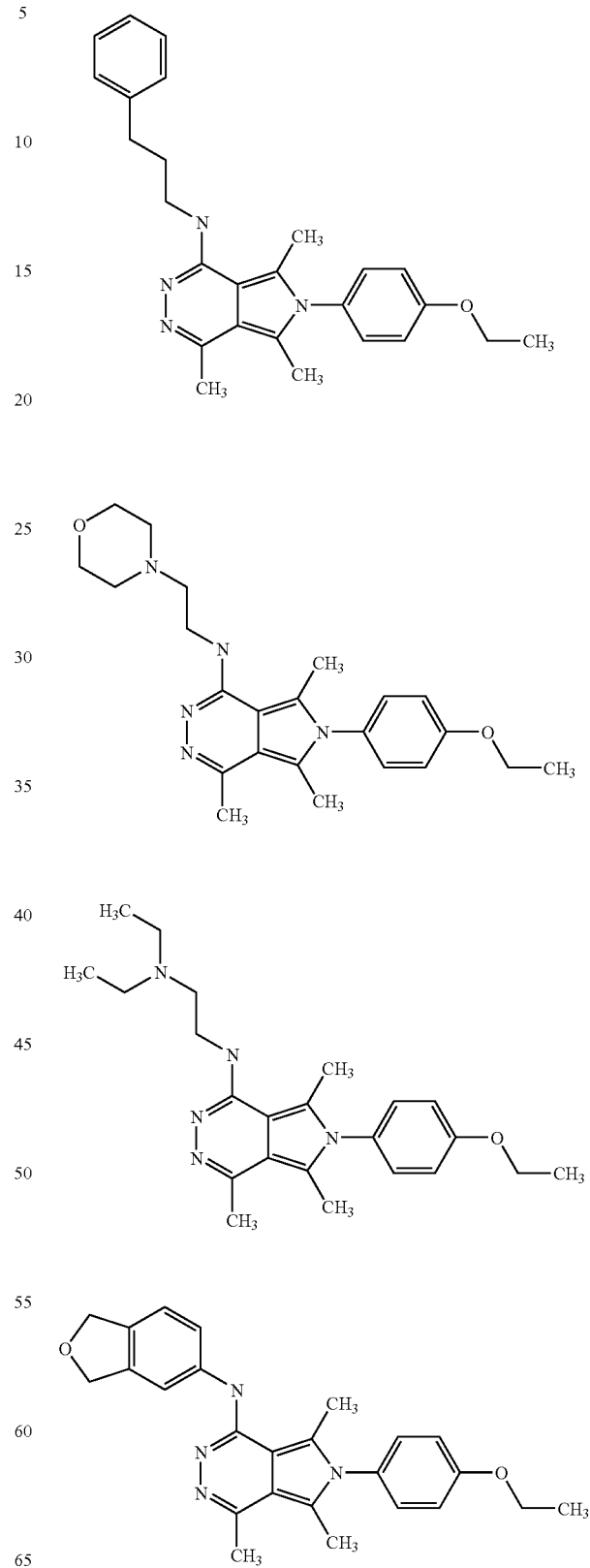

367
-continued
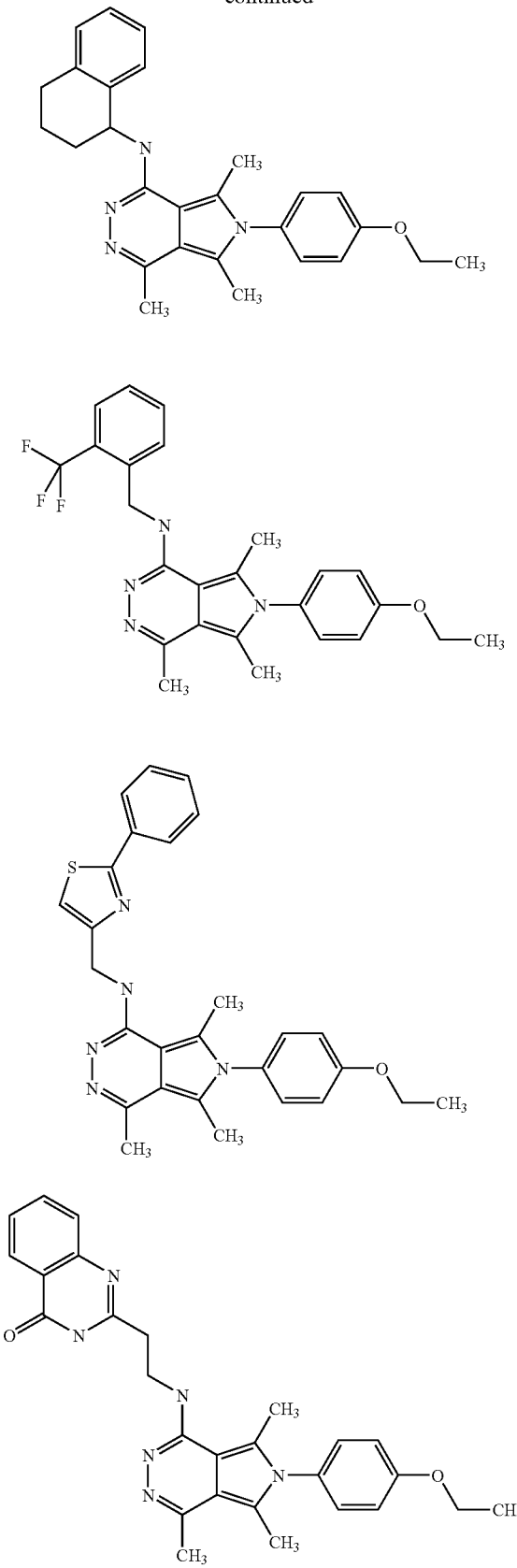
368
-continued
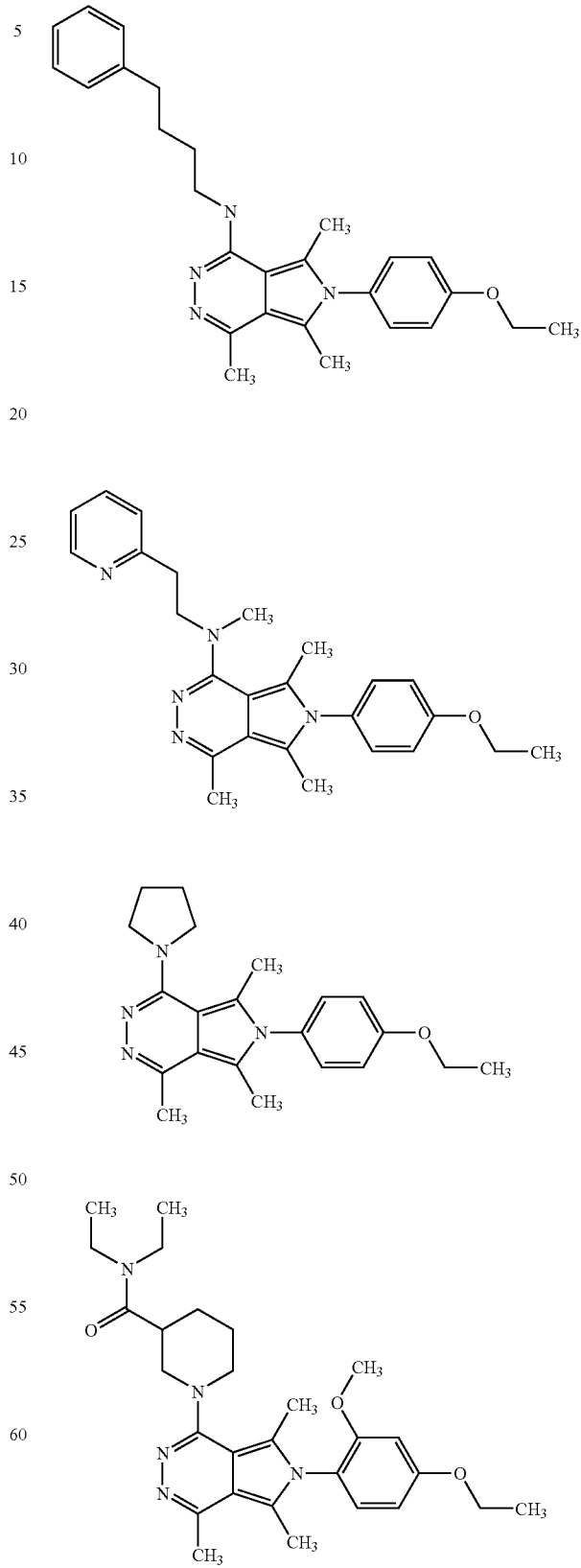

369                                    370
-continued                             -continued
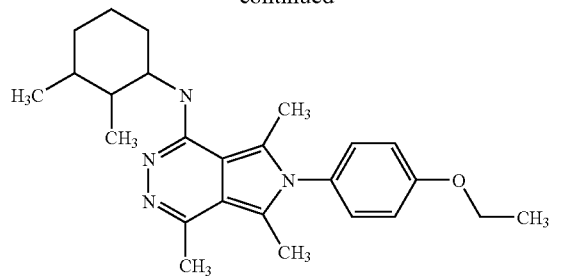
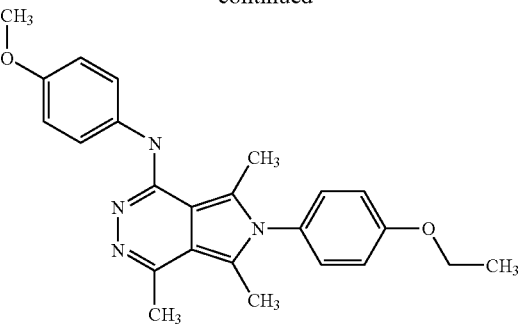
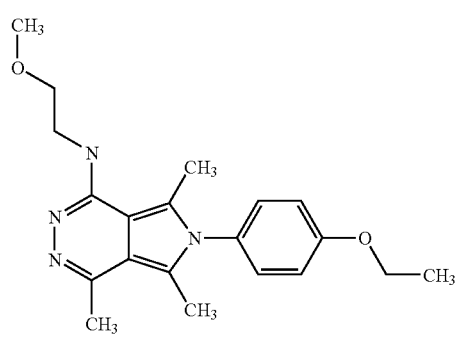
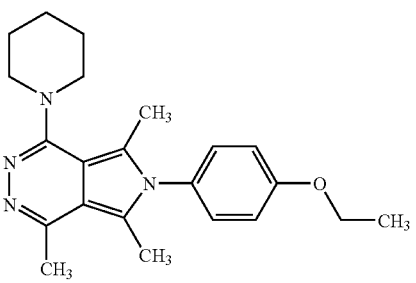
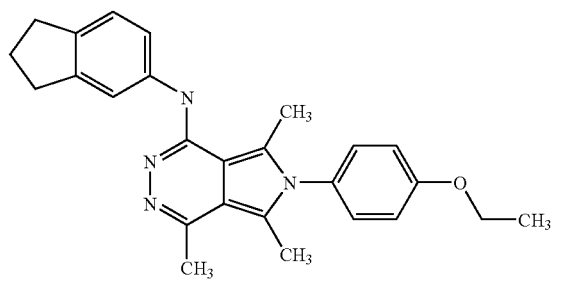
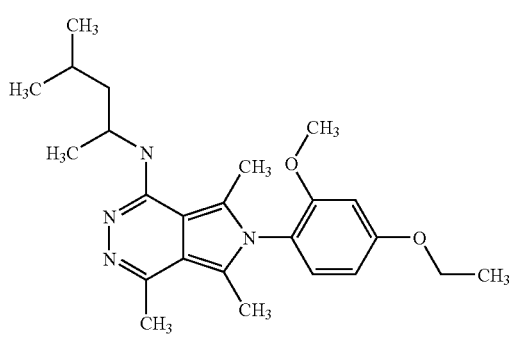
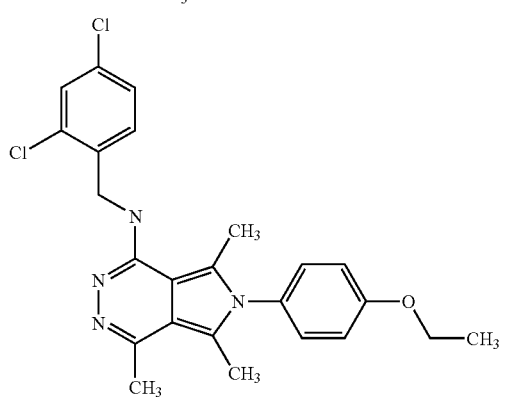
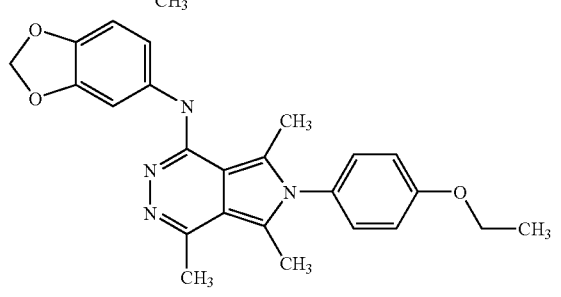
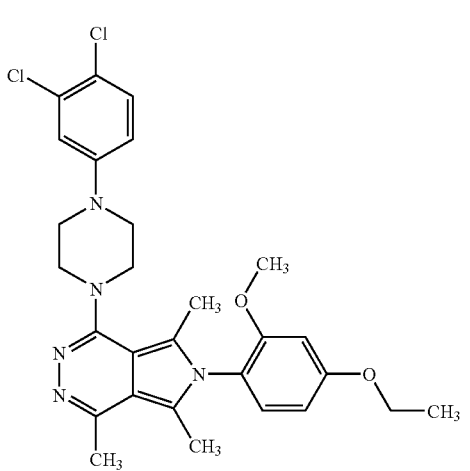

-continued
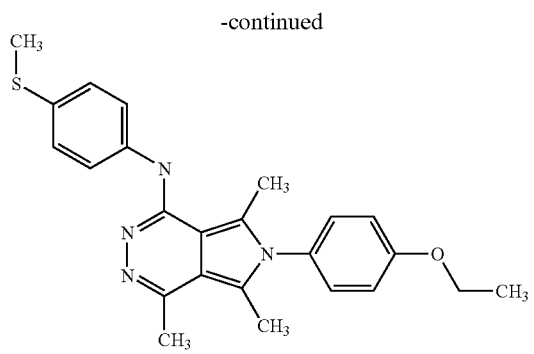
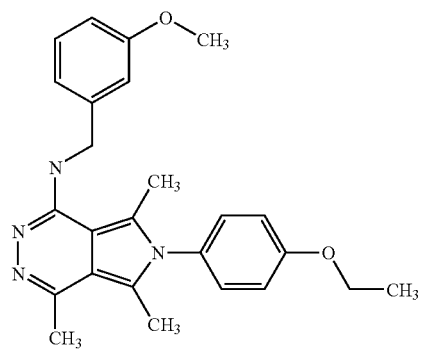
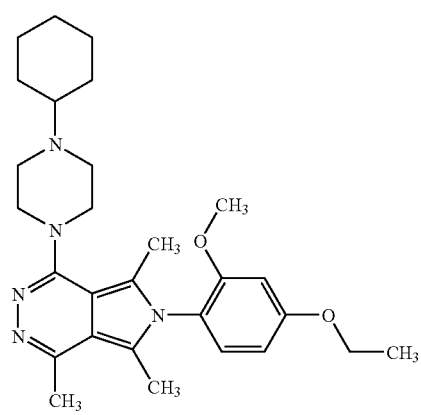
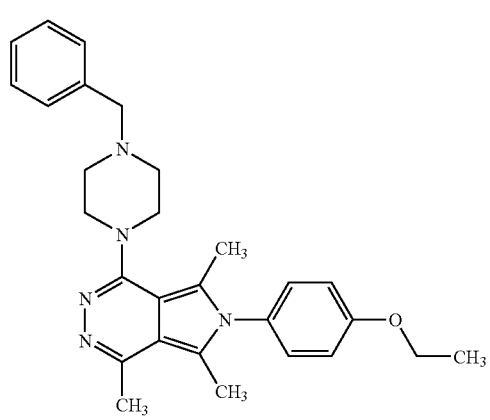
-continued
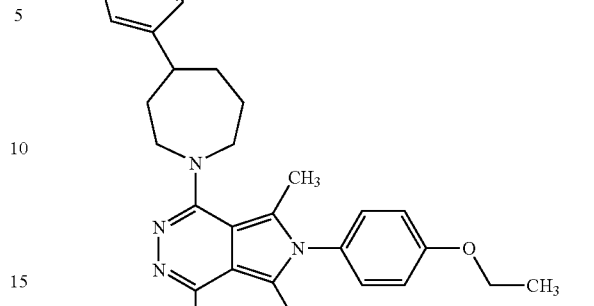
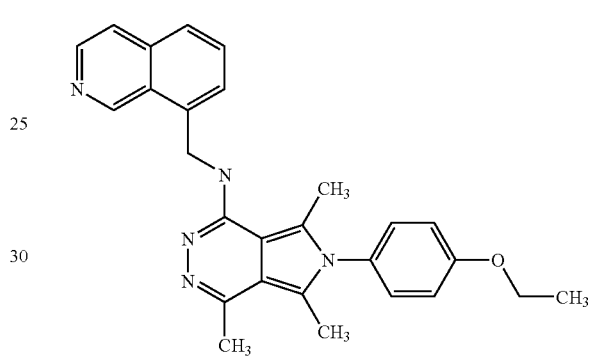
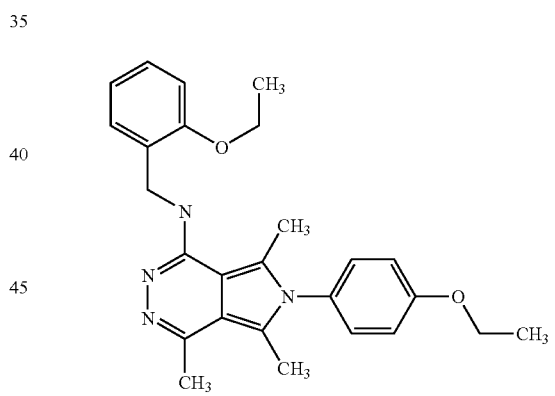
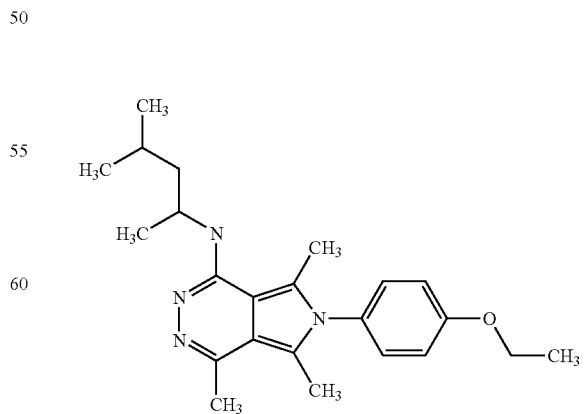

-continued
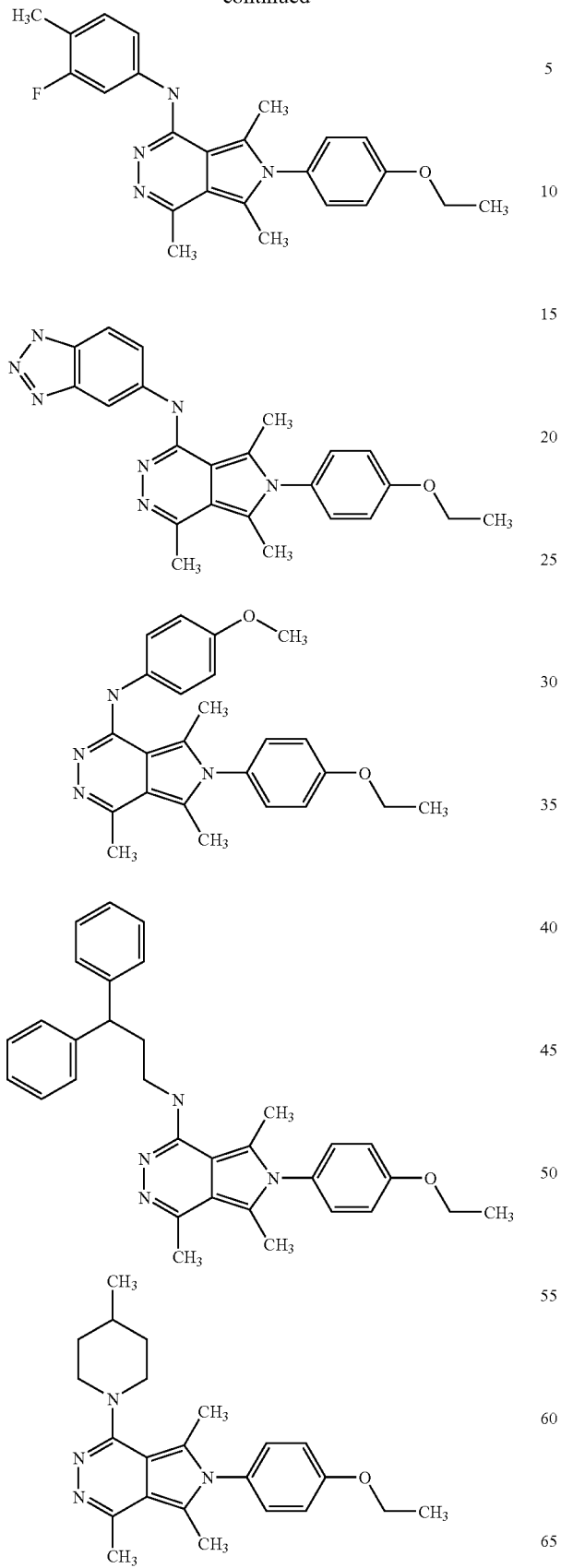
-continued
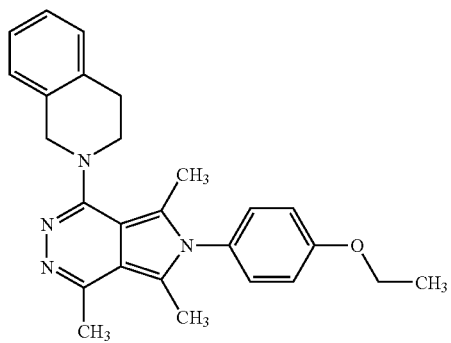
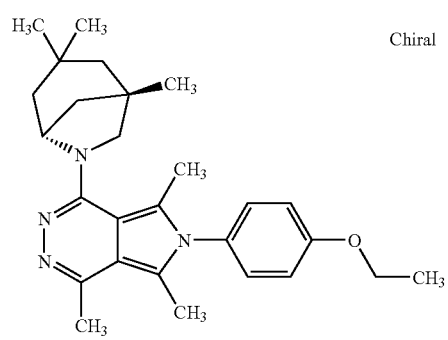
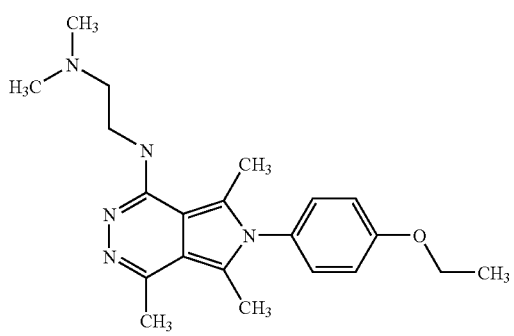
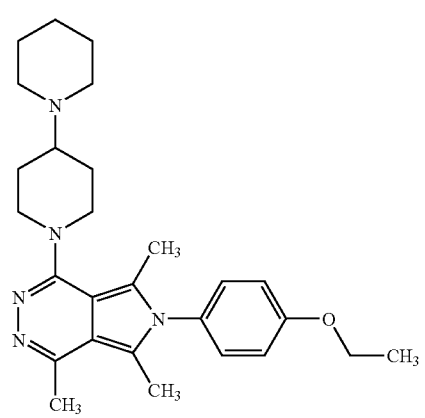

375
-continued
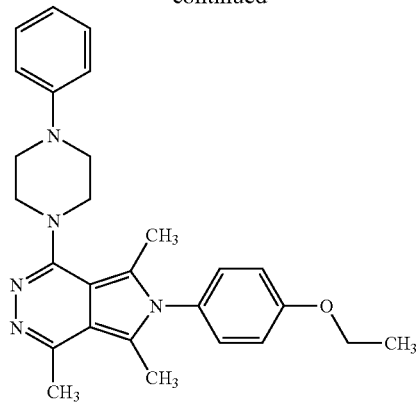
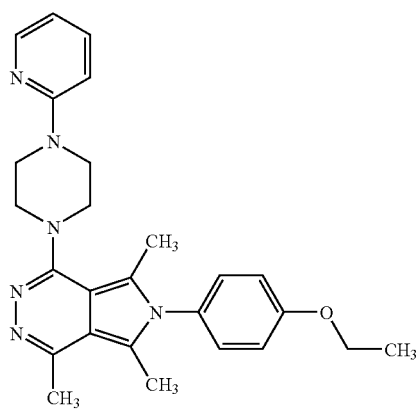
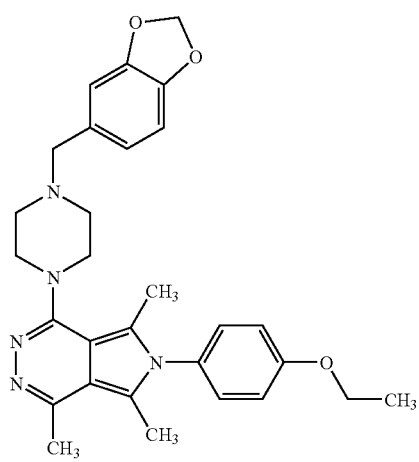
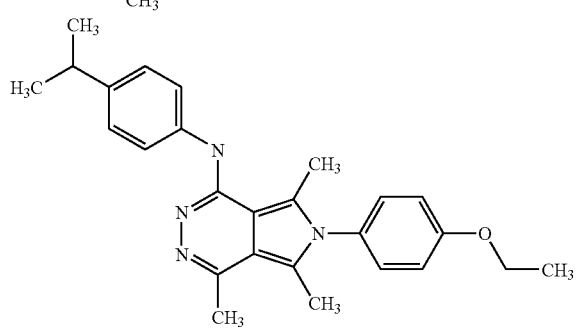
376
-continued
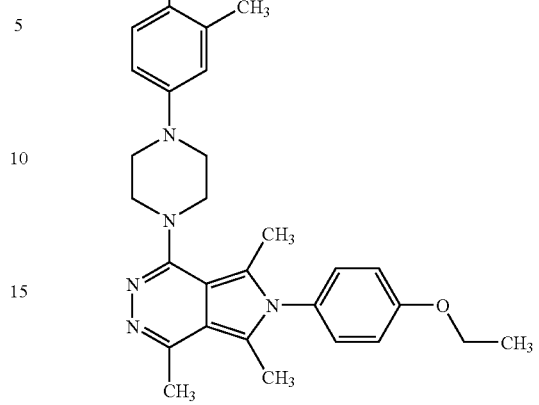
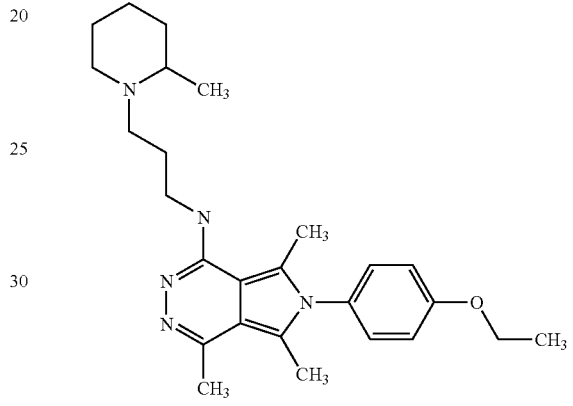
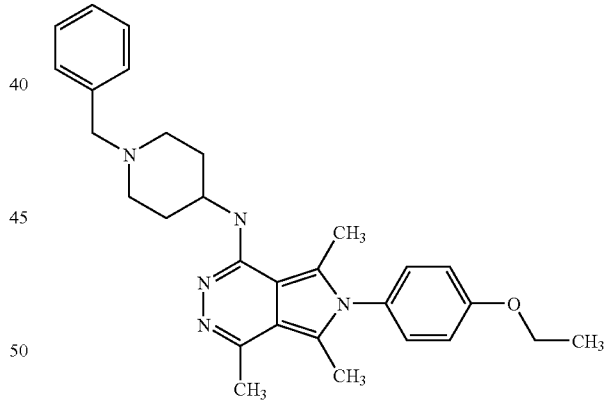
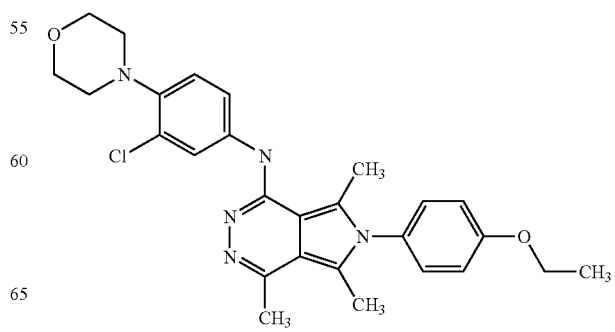

377
-continued
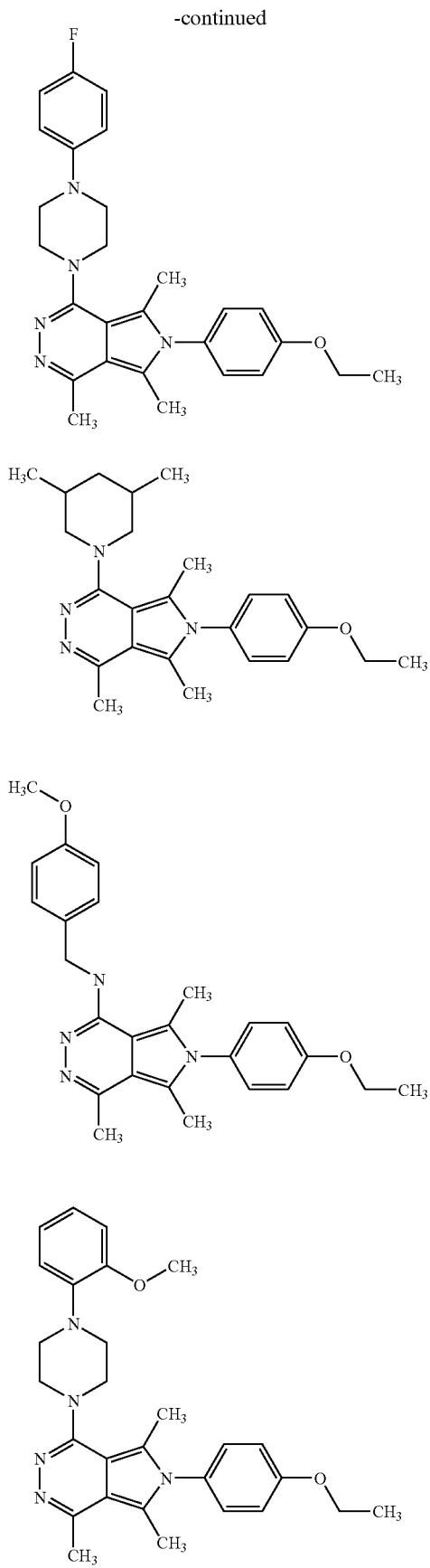
378
-continued
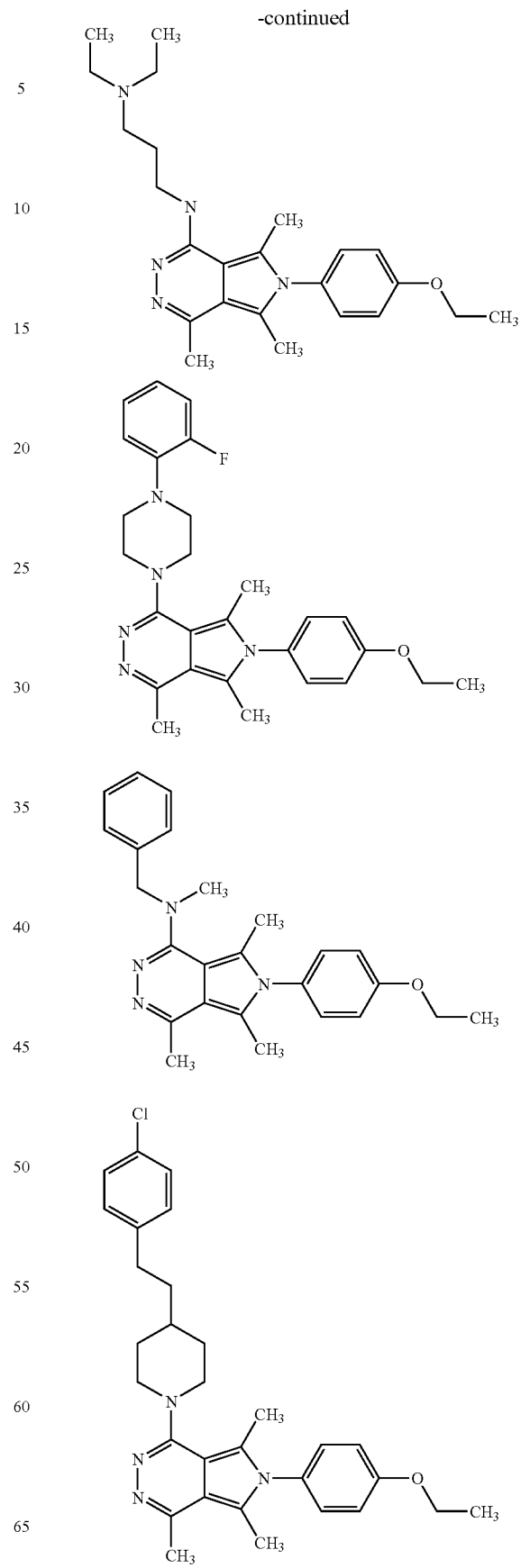

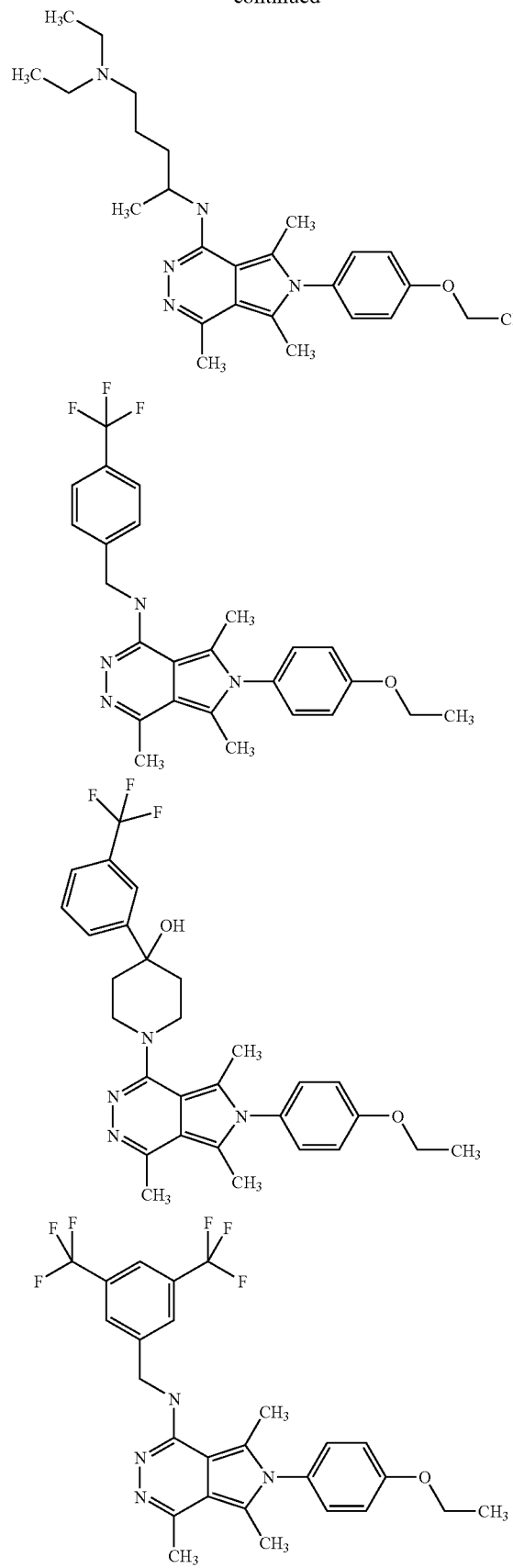
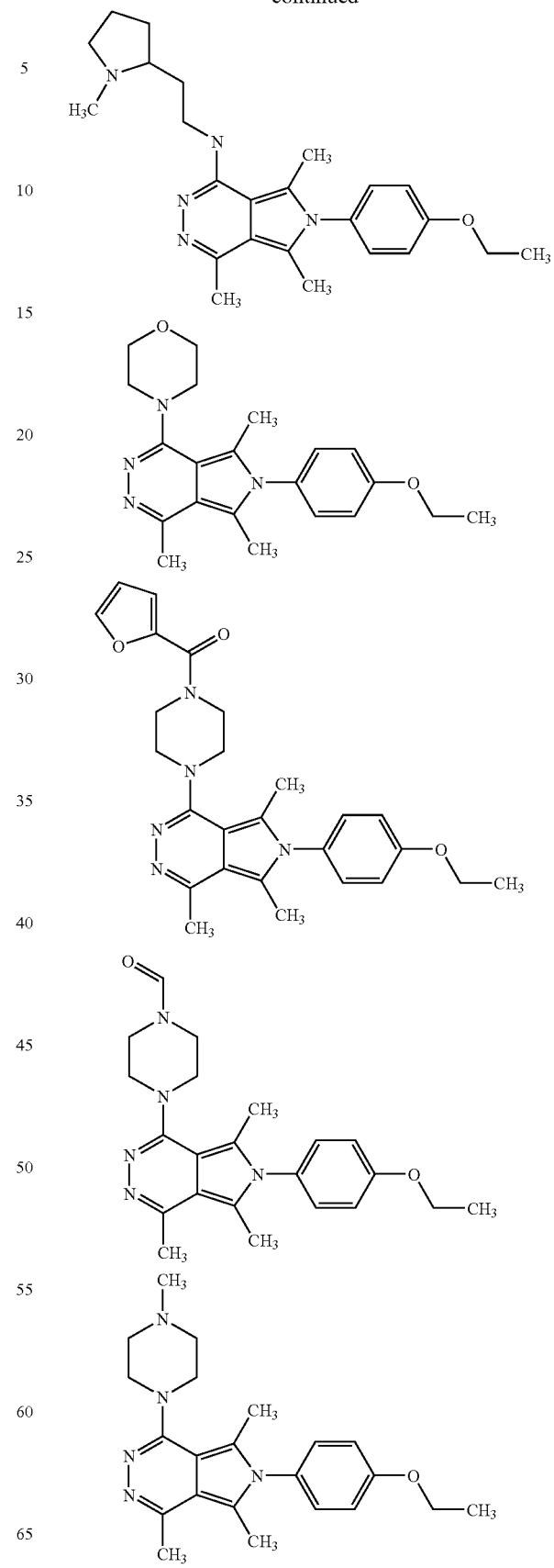

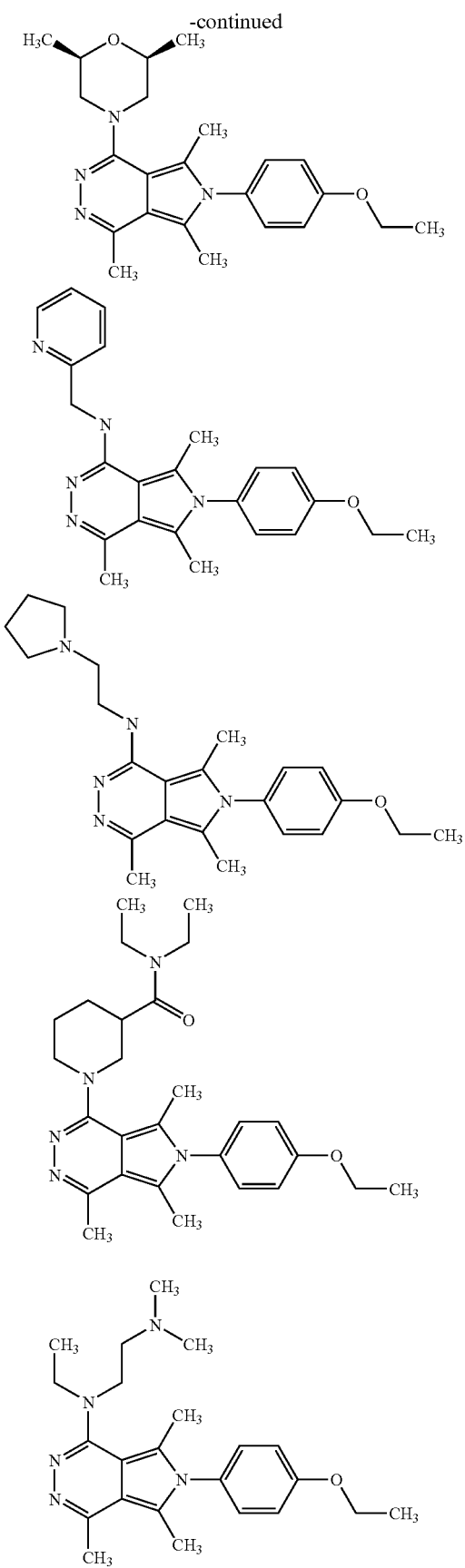
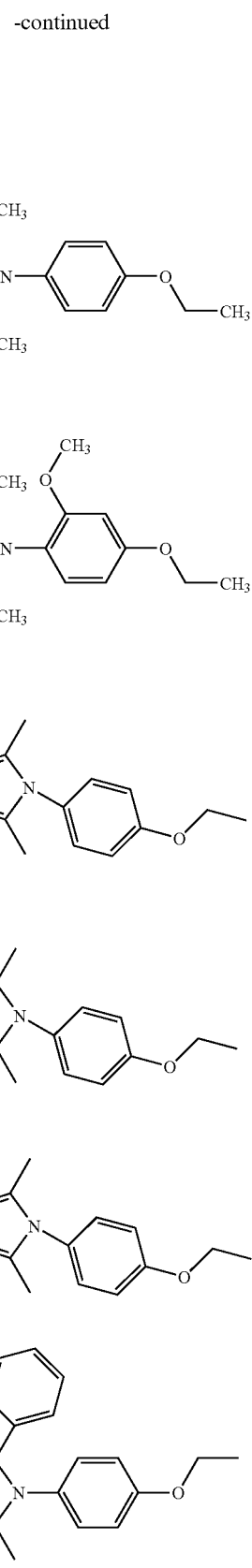
or a pharmaceutically acceptable salt thereof.

3. A compound represented by Formula (I):

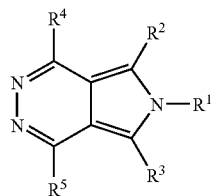

or a pharmaceutically acceptable salt thereof, wherein
$R^1$ is —$C_{0-6}$alkyl-aryl, —$C_{0-6}$alkyl-heteroaryl, —$C_{0-6}$alkyl-$C_{3-6}$cycloalkyl, or —$C_{0-6}$alkyl-hetero$C_{3-7}$cycloalkyl, optionally substituted with 1-6 independent halogen, —CN, $NO_2$, —$C_{1-6}$alkyl, —$C_{0-6}$alkyl-$C_{3-6}$cycloalkyl, —$C_{0-6}$alkyl-hetero$C_{3-7}$cycloalkyl, —$OR^6$, —$NR^6R^7$, —$C(=NR^6)NR^7R^8$, —$N(—NR^{88}R^6)NR^7R^8$, —$NR^6COR^7$, —$NR^6CO_2R^7$, —$NR^6SO_2R^{88}$, —$NR^6CONR^7R^8$, —$SR^{88}$, —$SOR^{88}$, —$SO_2R^{88}$, —$SO_2NR^6R^7$, —$COR^6$, —$CO_2R^6$, —$CONR^6R^7$, —$C(=NR^6)R^7$, or —$C(=NOR^6)R^7$ substituents;

$R^{2,}$ and $R^{3,}$ each independently is —$C_{1-6}$alkyl, —$C_{0-6}$alkyl-aryl, —$C_{0-6}$alkyl-heteroaryl, —$C_{0-6}$alkyl-$C_{3-6}$cycloalkyl, or —$C^{0-6}$alkyl-hetero$C_{3-7}$cycloalkyl, optionally substituted with 1-6 independent halogen, —CN, $NO_2$, —$C_{1-6}$alkyl, —$OR^6$, —$NR^6R^7$, —$C(=NR^6)NR^7R^8$, —$N(—NR^{88}R^6)NR^7R^8$, —$NR^6COR^7$, —$NR^6CO_2R^7$, —$NR^6SO_2R^{88}$, —$NR^6CONR^7R^8$, —$SR^{88}$, —$SOR^{88}$, —$SO_2R^{88}$, —$SO_2NR^6R^7$, —$COR^6$, —$CO_2R^6$, —$CONR^6R^7$, —$C(=NR^6)R^7$, or —$C(=NOR^6)R^7$ substituents;

$R^4$, and $R^5$ each independently is —$C_{0-6}$alkyl, —$C_{0-6}$alkyl-aryl, —$C_{0-6}$alkyl-heteroaryl, —$C_{0-6}$alkyl-$C_{3-6}$cycloalkyl, or —$C_{0-6}$alkyl-hetero $C_{3-7}$cycloalkyl, optionally substituted with 1-6 independent halogen, —CN, $NO_2$, —$C_{1-6}$alkyl, —$OR^6$, —$NR^6R^7$, —$C(=NR^6)NR^7R^8$, —$N(—NR^{88}R^6)NR^7R^8$, —$NR^6COR^7$, —$NR^6CO_2R^7$, —$NR^6SO_2R^{88}$, —$NR^6CONR^7R^8$, —$SR^{88}$, —$SOR^{88}$, —$SO_2R^{88}$, —$SO_2NR^6R^7$, —$COR^6$, —$CO_2R^6$, —$CONR^6R^7$, —$C(=NR^6)R^7$, or —$C(=NOR^6)R^7$ substituents; and $R^6$, $R^7$, $R^8$, and $R^{88}$ each independently is —$C_{0-6}$alkyl, —$C_{3-7}$cycloalkyl, heteroaryl, or aryl; optionally substituted with 1-5 independent halogen, —CN, —$C_{1-6}$alkyl, —O($C_{0-6}$alkyl), —O($C_{3-7}$cycloalkyl), —O(aryl), —N($C_{0-6}$alkyl)($C_{0-6}$alkyl), —N($C_{0-6}$alkyl)($C_{3-7}$cycloalkyl), or —N($C_{0-6}$alkyl)(aryl) substituents, wherein when the carbon atom in —$C_{0-6}$alkyl equals "0" then no alkyl is present; provided that the compound is not
6-methyl-6H-pyrrolo[3,4-d]pyridazine,
1,4,5,7-tetramethyl-6-phenyl-6H-pyrrolo[3,4-d]pyridazine,
1,4,5-trimethyl-6,7-diphenyl-6H-pyrrolo[3,4-d]pyridazine,
5,7-dimethyl-1,4,6-triphenyl-6H-pyrrolo[3,4-d]pyridazine,
5-methyl-1,4,6,7-tetraphenyl-6H-pyrrolo[3,4-d]pyridazine,
1,4-bis-(4-methoxy-phenyl)-5,7-dimethyl-6-phenyl-6H-pyrrolo[3,4-d]pyridazine,
1,4-bis-(4-methoxy-phenyl)-5-methyl-6,7-diphenyl-6H-pyrrolo[3,4-d]pyridazine,
1,4-diethyl-5,7-dimethyl-6-phenyl-6H-pyrrolo[3,4-d]pyridazine,
1,4,5,7-tetramethyl-6H-pyrrolo[3,4-d]pyridazine,
N-(1,4,5,7-tetramethyl-pyrrolo[3,4-d]pyridazin-6-yl)-benzamide,
1,4,5,7-tetramethyl-pyrrolo[3,4-d]pyridazin-6-ylamine picrate,
1,4,5,7-tetramethyl-pyrrolo[3,4-d]pyridazin-6-ylamine,
5,7-dimethyl-6-phenyl-6H-pyrrolo[3,4-d]pyridazine,
5,7-dimethyl-2-phenacyl-6H-pyrrolo[3,4-d]pyridazinium bromide,
2-(2-methoxycarbonylvinyl)-5,7-dimethyl-6H-pyrrolo[3,4-d]pyridazinium tetrafloroborate
5,7-diphenyl-6H-pyrrolo[3,4-d]pyridazine,
5,6,7-trimethyl-6H-pyrrolo[3,4-d]pyridazine,
1,4-diphenyl-7,8,9,10-tetrahydro-pyridazino[4,5-a]indolizine,
5-methyl-1,4-diphenyl-7,8,9,10-tetrahydro-pyridazino[4,5-a]indolizine,
6-benzyl-1,4-diphenyl-5-p-tolyl-6H-pyrrolo[3,4-d]pyridazine,
6-benzyl-5-(2-chloro-phenyl)-1,4-diphenyl-6H-pyrrolo[3,4-d]pyridazine,
1,4,5,6,7-pentaphenyl-6H-pyrrolo[3,4-d]pyridazine,
6,7,10,11-tetraphenyl-pyridazino[4',5':3,4]pyrrolo[1,2-a]quinoxaline,
11-(4-nitro-phenyl)-6,7,10-triphenyl-pyridazino[4',5':3,4]pyrrolo[1,2-a]quinoxaline,
6-benzyl-1,4,5-triphenyl-6H-pyrrolo[3,4-d]pyridazine,
9,12-diphenyl-pyridazino[4', 5':3,4]pyrrolo[2, 1-a]isoquinoline,
5-methylsulfanyl-1,4,6,7-tetraphenyl-6H-pyrrolo[3,4-d]pyridazine,
1,4,6,7-tetraphenyl-6H-pyrrolo[3,4-d]pyridazine-5-carboxylic acid ethyl ester,
7,10-diphenyl-pyridazino[4',5':3,4]pyrrolo[1,2-a]quinoline,
11,14-diphenyl-pyridazino[4',5':3,4]pyrrolo[1,2-f]phenanthridine,
1-oxo-7-oxy-6b,11b-dihydro(pyridazino[4',5'-c]-pyrrolo)[2.1-c]benzoxazine-1,4,
10-methyl-1,4-diphenyl-8,9-dihydro-7H-benzo(ef)pyridazino[4,5-a]cycl[3.3.2]azine,
11-methyl-1,4-diphenyl-7,8,9,10-tetrahydrocyclohepta(ef)pyridazino[4,5-a]cycl[3.3.2]azine,
1,4-dichloro-5,6,7-trimethyl-6H-pyrrolo[3,4-d]pyridazine,
1-chloro-4-ethoxy-5,6,7-trimethyl-6H-pyrrolo[3,4-d]pyridazine,
1-chloro-5,6,7-trimethyl-6H-pyrrolo[3,4-d]pyridazinium chloride,
1-ethoxy-2,5,6,7-tetramethyl-6H-pyrrolo[3,4-d]pyridazinium tetrafluoroborate,
1-ethoxy-5,6,7-trimethyl-2H,6H-pyrrolo[3,4-d]pyridazinium tetrafluoroborate,
1-ethoxy-3-ethyl-5,6,7-trimethyl-6H-pyrrolo[3,4-d]pyridazinium tetrafluoroborate,
1-ethoxy-5,6,7-trimethyl-6H-pyrrolo[3,4-d]pyridazine,
5-cyano-1,4-dimethylpyridazino[4,5-a]indolizine,
1,4-dimethyl-6-phenyl-2,3,8a-triaza-fluorene-9-carbonitrile,
6-benzolyl-1,4-dimethyl-2,3,8a-triaza-fluorene-9-carbonitrile,
6-benzyl-1,4-diphenyl-2,3,8a-triaza-fluorene-9-carbonitrile,
1,4,6-trimethyl-2,3,8a-triaza-fluorene-9-carbonitrile,
5-cyano-1,4-diphenylpyridazino[4,5-a]indolizine,
6-methyl-1,4-diphenyl-2,3,8a-triaza-fluorene-9-carbonitrile, 6-benzoyl-1,4-diphenyl-2,3,8a-triaza-fluorene-9-carbonitrile,
1,4,6-triphenyl-2,3,8a-triaza-fluorene-9-carbonitrile,
5,7-dimethyl-1,4-diphenyl-2,3,8a-triaza-fluorene-9-carbonitrile,
9,12-diphenyl-pyridazino[4',5':3,4]pyrrolo[2,1-a]isoquinoline-8-carbonitrile,
dimethyl 3,12,13,17-tetramethyl-$7^2,7^3$-diazabenzo[g]porphyrin-2,18-dipropionate,
5,6-dihydro-2,3-dimethoxypyridazino[4',5':3,4]pyrrolo[2,1-a]isochinolin-9-ol,
5,6-dihydro-2,3-dimethoxypyridazino[4',5':3,4]pyrrolo[2,1-a]isochinolin-9-ol-hydrochloride,
3-methyl-6,9-diphenylthiazolo[3',2':1,2]pyrrolo[3,4d]pyridine, or
1,4-diphenylpyridazino[4',5':3,4]pyrrolo[2,1-b]benzothiazole; and
is not selected from the following table:

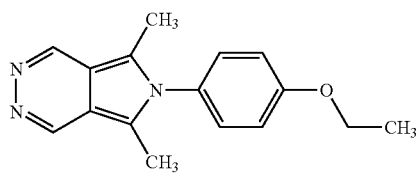

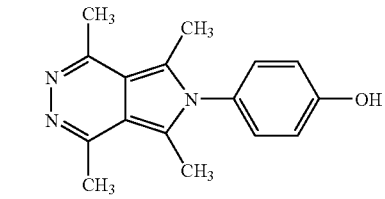

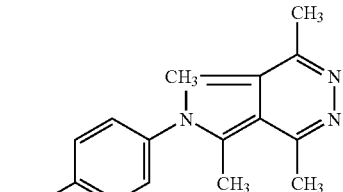

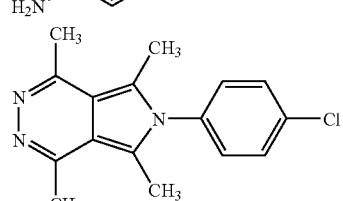

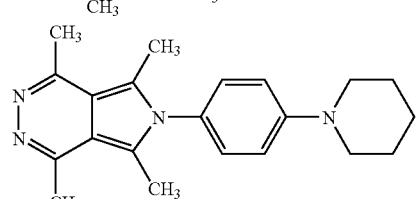

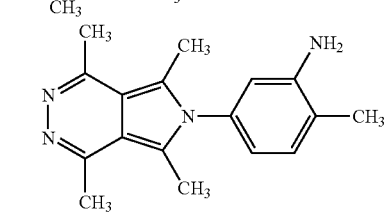

-continued

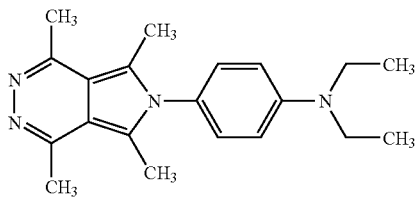

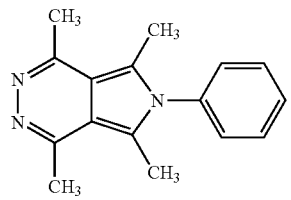

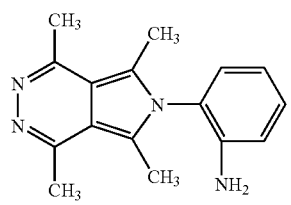

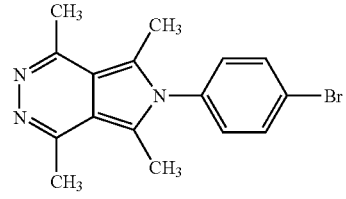

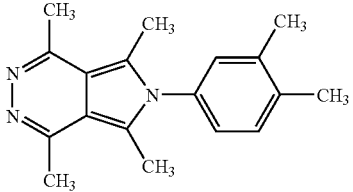

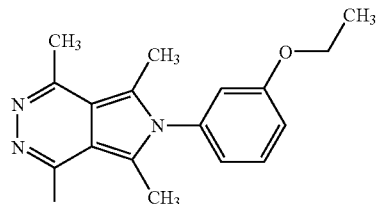

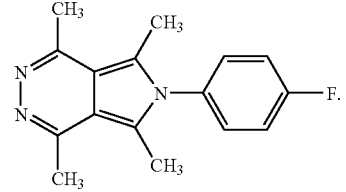

* * * * *